(12) United States Patent
Faaberg et al.

(10) Patent No.: US 10,294,459 B2
(45) Date of Patent: May 21, 2019

(54) PRRS VIRUSES, INFECTIOUS CLONES, MUTANTS THEREOF AND METHODS OF USE

(71) Applicant: Regents of the University of Minnesota, Minneapolis, MN (US)

(72) Inventors: Kay Faaberg, Ames, IA (US); Jun Han, Hershey, PA (US); Gongping Liu, St. Paul, MN (US); Yue Wang, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/794,647

(22) Filed: Jul. 8, 2015

(65) Prior Publication Data

US 2017/0130207 A1   May 11, 2017

Related U.S. Application Data

(63) Continuation of application No. 13/276,671, filed on Oct. 19, 2011, now Pat. No. 9,080,143, which is a continuation of application No. 11/922,798, filed as application No. PCT/US2006/024355 on Jun. 23, 2006, now Pat. No. 8,110,390.

(60) Provisional application No. 60/694,021, filed on Jun. 24, 2005.

(51) Int. Cl.
 *C12N 7/00* (2006.01)
 *C07K 14/005* (2006.01)

(52) U.S. Cl.
 CPC ............. *C12N 7/00* (2013.01); *C07K 14/005* (2013.01); *C12N 2770/10021* (2013.01); *C12N 2770/10022* (2013.01); *C12N 2770/10043* (2013.01)

(58) Field of Classification Search
 None
 See application file for complete search history.

(56) References Cited

U.S. PATENT DOCUMENTS

2017/0130207 A1*  5/2017  Faaberg ............... C07K 14/005

FOREIGN PATENT DOCUMENTS

EP    1018557 A2   12/1998

OTHER PUBLICATIONS

Genbank locus accession No. DQ176019, identified as porcine respiratory and reproductive syndrome virus isolate MN184A, submitted Jun. 1, 2006.*
Genbank locus accession No. DQ176020, identified as porcine respiratory and reproductive syndrome virus isolate MN184B, submitted Jun. 1, 2006.*
Johnson et al (Veterinary Immunology and Immunopathology 102: 233-247, 2004).*
Fang Y et al: "Heterogeneity in Nsp2of European-like porcine reproductive and respistory syndrome virsus isolated in the United States" Virus Research, Mar. 15, 2004, vol. 100, No. 2, p. 229-235, Neatherlands.
Nielsen HS et al: "Genomic characterization of two Chinese isolates of Porcine respiratory and reproductive syndrome virus" Archives of Virology, vol. 149, No. 7, p. 1341-1351, Jul. 2004.
Shen S et al: "Determination of the complete Nucleotide Sequence of a Vaccine Strain of Porcine Reproductive and Respiratory Syndrome Virus and Indentification of the NSP2 Gene with a Unique Insertion" Archives of Virology, vol. 145, No. 5, p. 871-883, Jan. 2000, NY.

* cited by examiner

*Primary Examiner* — Shanon A. Foley
(74) *Attorney, Agent, or Firm* — Davis, Brown, Koehn, Shors & Roberts, P.C.

(57) ABSTRACT

This disclosure provides isolated infectious polynucleotides, such as infectious clones, having a nucleotide sequence with identity to PRRS viruses such as VR-2332, Lelystad, or others, and optionally further including a deletion in a region of ORF1 that encodes the nsp2 polypeptide.

8 Claims, 92 Drawing Sheets

Specification includes a Sequence Listing.

```
>VR-V5.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTGGCCTTCACAGCCCCTGGGTGTGGTGTTTCTATGCGGGTCGAACGCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGTGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGGTTGAGCCTAACACGTC
GCCATTGGCTGACAAGGAAGAAAAAATTTTTCCGGTTTGGCAGTCACAAGTGGTACGGCGCTGGAAAGAGAGCAAGAAAG
CACGCTCTTGTGCGACTGCTACAGTCGCTGGCCGCGCTTTGTCCGTTCGTGAAACCCGGCAGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAACGGTGAGCATTGGACTGTCACTGTGACCTCCTTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGGCTCTGGCCGAAATGTCTGGCGATTCCGAT
CGTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTCAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCAGCACCCCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCGTTGTCCAGCGTGAGAATCACACGCCCAAAATACTCAGCTCAAGCCATCATCGACTCGGGCGGGC
CCTGCAGTGCGCATCTCCAAGAGGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTAGATGGCAGGTTAAAGTTCCTCCCAAAAATGATACTCGAGACACCGCCGGCCCTATCCGTGTGAGT
TTGTGATGATGCCTCACACGCCCTGCACCTTCCGTAGGTGCGGAGAGCGACCTTACCATTGGCTCAGTTGCTACTGAAGAT
GTTCCACGGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGCACATCAGCTCCGTCCGCAGGCA
```

TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCAGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCGGGAAACACTGGGATCGAT
GGCACGCTCTGGGATTTTGAGTCCGAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTCCAGAATACAAGGTTTGGAGACATACCTTACAAAACCCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTAGCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAAACAGTATTGCGGGAAGAAGAAGACTAGGACCATACTCGGC
ACCAATAACTTCATGGCACTAGCCCACCGAGCAGTGTTGAGTGGTGTTACCCAGGGCTTCATGAAAAGGCGTTTAACTC
GCCCATGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGACAGGTGGCCTGTC
GTCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCCGTCTATTCGGACGACCTCGTGCTGTATGCCGAGTCTCCTCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGGGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGCCCCGGCCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCGTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAAGTCGCCGCGGATTA
GTCTCTGTCAGGCCTGGAATTAGGGGAAATGAAGTTGGACTACAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCTCACCCGGTGCTGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCTCCCGCACCGGTCCGTG
GGTTCGCATCCTAGCCGGCGGTTGGTGTCCTGGCAAGAATTCCTTCCTAGATGAAGCAGCGTATTGCAATCAGCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGCAGGTTTGGACAGAATATCTGTGATGCCATTCA
GCCAGATTACAGGGACAAACTCATGTCCATGGTCAACACAACCGTGTGACCTACGTGGAAAAACCTGTCAGGTATGGGC
AGGTCCTCACCCCCTACCAACAGGGACCGAGAGGACGACGCCATCACTATTGACTCCAGTCAAGGCGCCAGATTCGATGTG
GTTACATTGCATTTGCCCACTAAAGATTCAGTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGCAGCTGATCGTGCTGGATAGAAATAACAAAGAATGCACGGTTGCTCAGGCTCTAGGCAACGGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTAACACAGTTTGCTAAACTCCAGTAGAACTTGCACCTC
ACTGGCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG

*Fig. 1B-4*

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGCCCCGCCCTTTGCAACAGGAGAGTCGTCGGGTCCACCCACTGGGGGGCTGACCTCGCGG
TCACCCCTTATGATTACGGCGCTAAAATTATCCTGTCTAGCGCGTACCATGGTGAAATGCCCCCGGATACAAAATTCTG
GCGTGCGCGGAGTTCTCGTTGGATCACCCAGTTAAGTACAAACATACCTGGGGGTTTGAATCGGATACAGCGTATCTGTA
TGAGTTCACCGGAAACGGTGAGGACTGGGAGGATTACAATGATGCCGTTTCGTGCCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTCGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCAGCCGGCAAGC
AGCCACAGAGATCTACGAACCCGGTAGGTCTCTTTGGTGCACGATAGGGTATGACCGATGTGGGGAGGACGATCATGACG
AGCTAGGGTTTATGATACCCGCCTGGCCTCTCCAGCGAAGCCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAGATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGTGACAGATGAGAATTATTTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTCTTGCTGTGCTCGCCAACGCCAGCAACGACAGCAGCTCCCATCTACAGCTGATTTACAACT
TGACGCTATCTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTGTTCACGGCGGTAYGTCCTAAGTAGCATCTACGCGGTCTGTGCCCTGGCTGCGTTGACTTGCTTCGTCA
TTAGGTTTGCAGAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGTGTACTCAGCCAT
AGAAACCTGGAAATTCATCACCTCCAGATGCCGTTTGTGCTTGCTAGGCCGCAAGTACATTCTGGCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCTTCGTGTTGGGTGGCAGAAAGCTCTTAAACAGGGAGTGGTAAACCT
TGTCAAATATGCCAAATAAACAACGGCAAGCAGCAGAAGAGAAAGAAGGGGGATGGCCAGCCAGTCAATCAGCTGTGCCAG
ATGCTGGGTAAGATCATCACTCAGCAAAACAGTCCAGAGGCAAGGGACGGGAAAGAAAAATAAGAAGAAAACCCGGA
GAAGCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCAGCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC
```

Fig. 1B-5

ATCTCAGTGTTTGAATTGGAAGAATGTGTGGTGAATGGCACTGATTGACATTGTGCCTCTAAGTCACCTATTCAATTAGG
GCGACCGTGTGGGGTGAGATTTAATTGGCGAGAACCATGCGGCCGAAATTAAAAAAAAAAAAAAAAAAAAAAAAAAAAA
AAAAAAAAAAAAAAAAA

*Fig. 1C-1*

>V8-V567475A_seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCGACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGCAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTCACACTGTCCCTGAAGGCAACTGCTGGTGGAGCTTGTTTGACTTGCTTCGACTGGAAGTTCAGAA
CAAAGAAATTCGCCATCCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGGCTTTGTCCGTTCGTGAAACCGGCAGCCTAAGGAGCACGAGGTT
GCCGGCGCCAACAAGGCTGAGCACCTCAAACACTACTCCCCGCCTGCCGAAGGGAATTGTGGTTGGACTGCATTCCGC
CATCGCCAACCGGATGGTGAATTCAAATTTGAAACCACCCTTCCCGAAAGAGTGAGACCTCCAGATGACTGGGCTACTG
ACGAGGATCTTGTGAATGCCATCCAAATCCTCAGACTCCCTGCCGGCCTTAGACAGGAACGGTGCTTGTACTAGCGCAAG
TACGTACTTAAGCTGGAAGGTGAGCATTGGACTGTCACTGTGACCCCCTGGGATGTCCCCTTCTTTGCTCCCTCTTGAATG
TGTTCAGGGCTGTTGTGGGGCAAGGGCGGTCTTGGTTCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTCGGCTTCTCCGGTCACCACCGTGTGGACTGTTTCGCATTCTTTGCCCGTCACAGCGGAGGGAATCACCCTGACCA
AGTGCGCTTAGGGAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATCTTGTGCTCCCTGGGGTTGAGGCGGCAACCCAGAC
GATCAAGCTGCCCCAGGTCAACCAGTGCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCACGGCCCACACTGCC
ACGCCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACGCCCTCCGCCA
AAAGTTCAGCCTCGAAAAACGAAGCCTGTCAAGAGCTTGCCGGAGAGAAAGCCTGTCCCGGCCCCGGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCCGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTCTGTCTCGACCGGTGACACCTTGAGTGAGCC
GATCCTGTGCCCGCACCGCGTAAGTTTCAGCAGGTGAAAAGATTGAGTTCGGCGGCGGCAATCCACCGTACCAGG
ACGAGCCCCTGGATTTGTCTGCTTCCTCACAGACTGAATATGAGGCCTCTCCCCAGCACCGCCGCAGACGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGTGGACATGCTGACTTGGCGCAACACGTCTGTTTACCA
GGCGATTTGCACCTTAGATGGCAGGTTAAAGTTCCTCCCAAAAAATGATACTCGAGACACCGCCGCCCTATCCGTGTGAGT
TTCTGATGATGCCTCACACGCCTGCACCTTCCGTAGGTGCGGAGAGCGACCTTACCATTGGCTCAGTTGCTACTGAAGAT
GTTCCACGCATCCTCGAGAAAATAGAAAATCTCGGCCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAATAGTCAAATTTCACAACCGGACCTTCACCCTGGGACCTGTGAATTTAAAAGTGGCCAGTGAGGTTGAGCTAAAAGA
CGCCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAACACTGGGATCGAT
GGCACGCTCTGGGATTTTGAGTCCGAAGCCACTAAAGAGGAAGTCGCACTCAGTGCGCAAATAATACAGGCTTGTGACAT
TACGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCGGTGACTGATGGGCCGCTCCGTCTTGGCCACGACCATGCCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAGAAACTGGCAAACTGTCAKCCCTTGTACTCTTAAGAAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAGGCGTTTAACTC
GCCCATCGCCCTCGGAAAGAACAAGTTTAAGGAGCTACAGAACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCTGGCGACCCGATCACCTCTGTGTCTAACACCATTTATAGTTTGGTGATCTATGCACAGCATATGGTGCTTAGTTACT
TCAAAAGTCGGTCACCCCCATGGCCTTCTGTTCTTACAACACCAGCTAAAGTTTGAGGACATGCTCAAGGTTCAACCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGACTATGATCCTGAATGGTTTGAAGAACTTGT
AGTTGGAATAGCGCAGTGCGCCCGCAAGGACGGCTACAGCTTTCCCGGCACGCCGTTCTTCATGCCATGTGGGAAAAAC
TCAGGTCCAATTATGAGGGGAAGAAGTCGAGAGTGTGCGGGTACTGCGGGGCCCCGGCCCGTACGCTACTGCCTGTGGC
CTCGACGTCTGCATTTACCACACCCACTTCCACCAGGATTGTCCAGTCACAATCTGGTGTGGCCATCCAGCGGGTTCTGG
TTCTTGTAGTGAGTGCAAATCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGGCTGCAATTCCCCGTCCCCTCCCGCACCGGTCCGTG
GGTTCGCATCCTAGCCGGCGGTTGGTGCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGAGCTACGTGGAAAAACCTGTCAGGTATGGGC
AGGTCCTCACCCCCTACCACAGGGACGGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACGCTAT
CTTTGTGTATGACCCACACAGGCAGCTGCAGGGCTTGTTTGATCTTCCTGCAAAAGGCACGCCCGTCAACCTCGCAGTGC
ACTGCCGACGGGCAGCTGATCGTGCTGGATAGAAATAACAAAGAATGCACGGTTGCTCAGGCTCTAGGCAACGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAATGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGGACTACCGTT
GGAGGATCGTCATCATGTCACCTCCAGATACCTCCCGCGCGTCCTTCCCAAGGAATCAGTTGCGGTAGTCGGGGTTTCAAG
```

*Fig. 1C-4*

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCGGCCCTTTGCAACAGGAGAGTCGTCGGGTCCACCCACTGGGGGCTGACCTCGCGG
TCACCCCTTATGATTACGGCGCTAAAATTATCCTGTCTAGCGCGTACCATGGTGAAATGCCCCGCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGAGGACGATCATGACG
AGCTAGGGTTTATGATACCGCTGGCCTCTCCAGCGAAGCCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTCTTTCAGACCTATT
ACCAACATCAAGTCGACGGCGGCAATTGGTTTCACCTAGAATGGCTTCGTCCCTTCTTTTCCTCGTGGTTGGTTTAAAT
GTCTCTTGGTTTCTCAGGCGTTCGCCTGCAAACCATGTTTCAGTCGAGTCTTCAAATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGGGACAGATGAGAATTATCTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGCTGTTGCTCGCGATTGCTTTCTTTGTG
GTGTATCGTGCCGTTCTGTCTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGAGTCGCTTTAGTCACTGTGTCTAC
CGCCGGGTTTGTTCACGGGCGGTATGTCCTAAGTAGCATCTACGCGGTCTGTGCCCTGGCTGCCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAACGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGCCGCAAGTACATTCGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAAGGGGGATGGCCAGCCAGTCAATCAGCTGTGCCAG
ATGCTGGGTAAGATCATCACTCAGCAAAACCAGTCCAGAGGCAAGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGCTGGCATTCTTGAGGC
```

Fig. 1C-5

ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAA
AAAAAAAAAAAAAAAACCC

Fig. 1D-1

```
>V8-V6.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGCCCCTCG
TGGCGGGGATGAAGTGAAATTTTGAAGCTGTCCCCGGGGAGTTGAAGTTGATTGCGAACCGGCTCCGCACCTCCTTCCCGC
CCCACCACACAGTGGACATGTCTAAGTTGGCCTTCACAGCCCTGGGTGTGGTGTTTCTATGCGGGTCGAACGCCAACAC
GGCTGCCTTCCCGCTGACACTGTCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGCGGGAGAACCCAGCTACTCTGGGTTGAGGACCTCCTCAGAATAAGGGTTGAGCCTAACACGTC
GCCATTGGCTGACAAGGAAGAAAAATTTTCCGGTTTGGCAGTCACAAGTGGTACGGCGCTGGAAAGAGAGCAAGAAAAG
CACGCTCTTGTGCGACTGCTACAGTCGCTGGGCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGGCATCCAAATCCTGAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTTCCGTGGTGCAACAAATCTTGAAGAATGCTTGGCCAGGCTTGAG
AAAGCGCGCCGCCACGCGTAATCGACACCTCCTTTGATTGGGATGTTGTGCTCAAAAGTCCTTGGACAACAACTCGGTCC
GATCAAGCTGCCCCAGGTCAAGGCAGTGCTCGTGCTCTGCCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAGGGTTGTTCGAGAAGAATATGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAACAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGCAGTAGAGGGGCATGAAGCTGAGGAAACCCTGAGTGAAATCTCGGACATGTCGGGTAACATTAAAGCTGCGTCCGT
GTCATCAAGCAGCTCCTTGTCCAGCGTCAGAATCACACGCGCAAAATACTCAGCTCAAGCCATCATCGACTCGGGCGGGC
CCTGCAGTGGCATCTCCAAGAGCTAAAGGAAACATGCCTTAGTGTCATGCGCGAGGCATGTGATGCGACTAAGCTTGAT
GACCCTGCTACGCAGGAATGGCTTTCTCGCATGTGGGATCGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCCTCACACGCCTGCACCTTCCGTAGGTGCGGAGAGCGACCTTACCATTGGCTCAGTTGCTACTGAAGAT
GTTCCAGGCATCCTCGAGAAAATAGAAAATGTCGGCGAGATGGCCAACCAGGGACCCTTGGCCTTCTCGGAGGATAAACC
GGTAGATGACCAACTTGTCAACGACCCCCGGATATCGTCGCGGAGGCCTGACGAGAGCACATCAGCTCCGTCCGCAGGCA
```

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGGATGGGCCCCGCCCTTTGCAACAGGAGAGTCGTCGGGTCCACCCACTGGGGGGCTGACCTCGCGG
TCACCCCTTATGATTACGGCGCTAAAATTATCCTGTCTAGCGCGTACCATGGTGAAATGCCCCCGGATACAAAATTCTG
GCGTGCGCGGAGTTCTCGTTGGATGACCCACTTAAGTACAAACATACCTGGGGGTTTGAATCGGATACAGCGTATCTGTA
TTGAGTTCACCGGAAACGGTGAGGACTGGGACGGATTACAATGATGCGTTTCGTGCGCGCCAGGAAGGGAAAATTTATAAGG
CCACTGCCACCAGCTTGAAGTTTTATTTTCCCCCGGGGCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGGCATTTTGTTTGGCTTCACCATCGCCGGTTGGCTGGTGGTCTTTTGCATCAGATTGGTTTGCT
CCGCGATACTCCGTACGCGCCCTGCGATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAGGTGTCAAGCCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTGGC
CTCCCGGCTGCCCATGCTACACAACCTGCGCATGACAGGGTCAAATGTAACGATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCAGCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTAAAT
GTCTCTTGGTTTCTCAGGCGTTCGCCTGCAAACCATGTTCAGTTCGAGTCTTGCAGATATTAAGACCAACACCACCGCA
GCGGCAAGCTTTGCTGTCCTCCAAGACATCAGTTGCCTTAGGCATCGCGACTCGGCCTCTGAGGCGCATTCGCAAAATCCC
TCAGTGCCGTACGGCGATAGGGACACCCGTGTATGTTACCATCACAGCCAATGTGACAGATGAGAATTATTTACATTCTT
CTGATCTCCTCATGCTTTCTTCTTGCCTTTTCTATGCTTCTGAGATGAGTGAAAAGGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTTTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGGGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTGATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCGGCGTCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAATAACAACGGCAAGCAGCAGAAGAGAAAGAAGGGGGATGGCCAGCCAGTCAATCAGCTGTGCCAG
ATGCTGGGTAAGATCATCGCTCAGCAAAACCAGTCCAGAGGCAAGGGACCGGGAAAGAAAAATAAGAAGAAAAACCCGGA
GAAGCCCCATTTTCTCTCAGCGACTGAAGATGATGTGCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCTGATCCGCGTCACAGCATCACCCTCAGCATGATGGGCTGGCATTCTTGAGGC
```

*Fig. 1D-5*

ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAA
AAAAAAAAAAAAAAAA

*Fig. 1E-1*

```
>MN184A_DQ176819.seq
-ATGACGTATAGGTGTTGCTCTATGCCACGACATTTGTATTGTCAGGAGCTGTGACCACTGGCACAGCCAAAGCTTGCT
GCACAGAAACACCCTTCTGTGACGGCCTCCTTCAGGGGAGTTTAGGGGTTTATCCCTAGCACCTTGTTTCTGGAGTTGCA
CTGCTTTACGGTCTCTCCACCCCTTTAACCATGTCTGGGATTCTTGATCGGTGCACGTGCACCCCAATGCCAGGGTGTT
TATGGCAGAGGGCCAAGTCTACTGCACACGATGTCTCAGTGCACGGTCCCTCCTTCCCTGAATCTCCAAGTCCCTGAGC
TCGGAGTGTTGGGCTTGTTTATAGGCCCGAAGAGCCGCTCCGGTGGACGTTGCCACGCGCATTCCCCACTGTTGAGTGC
TCCCCTGCTGGGGCTTGTTGGCTTTCTGCAATTTTTCCAATTGCACGAATGACCAGTGGAAACCTGAACTTTCAACAAAG
ATTAGTGCGGGTCGCAGCTGAGCTTTACAAAGCCGGCTGCCTCACCCCTATAGTCCTAAAGAATCTACAAGTCTATGAAC
GGGGTTGCCGATGGTACCCCATCGTTGGACCTGTCCCTGGAGTTGCCGTTTTCGCCAACTCCCTACATGTGAGTGATAGA
CCTTTCCCAGGGGTACTCACGTGCTAACCAACCTGCCGCTCCCGCAGAGACCTAAGCCTGAAGATTTTTGCCCCTTTGA
GTGTGCTATGGCTGMCCTCTATGAYATTGGTCATGACGCCGTTATGTTCGTGGCCGAAGGGAGAGTCTCCTGGGCTCCGC
GTGGTGGGGAAAAGGAAAATTTGAAACTGTTCCGGAGGAGTTGAGGTTGATTGCAGAGCAACTTTATACCTCCTTCCCG
CCCCAGCACGTGGTGGACATGTCGAAATTCACCTTTACGGCCCCTGAGTGTGGTGCTTCCATGCGAGTCGAACGCCATTA
TGCTGCCTCCCCGCCGGGACTGTCCCTGACGGCAATTGCTGGTGGAGTTTGTTTAGCTCGCTCCCATTGGAAATCCAGT
ACAAAGAAATTCGCCACGCCACCCAATTTGGCTATCAAACTAAGCATGGCGTTGCTGGCAAGTACCTACAGCGGAGGCTG
CAAGTTAATGGTCTCCGAGCAGTGGTTGACTCGAATGGACCTATCGTCATACAGTACTTCTCTGTTAAGGAGAGCTGGAT
CCGCCACGTGAAACTGGCGGAAGAGTTTGACTACCCTGGGTTTGAGGATCTCCTCAGGATAAGAGTCGAGCCCAACACGT
TGCCATTGTCCAACAAGGACGAGAAAATCTTCCGGTTTGGTGGGTGCAAGTGGTACGGTGCTGGGAAGAGGGCAAGGAGG
GCACGTGCAAGTGCAGTCACCGCAGTCGCCGGTCACGCTCCGCCTACTCGTGAAACCCAGCAAGCCAAGAAACACGAGGC
TGCTAGTGCCAACAAGGCTGAGCTTCTTGAACGCTACTCCCGCCTGCTGAAGGGAATTGCGGCTGGCACTGTATTTCCG
CCATCGCCAATCGGATGGTAAATTCTAAGTTTGAAGACTGCCTTCCGGAAAGAGTGAGATCCCCAGAAGAGTGGGCTACT
GATGAGGATCCTTGTGAATACTATCAARATCCTCAGGCTCCCYGCCGGCCTTAAGCAGGAACGGCGCCTGTGCAAGCGCCAA
GTACATCCTTAAGCTGGAAGGTGAGCACTGGACTGTTTCAGTGATTCCCGGAATGYCCCCTTCCTTGCTCCCCCTTGAAT
GCGTTCAGGGTTGCTGTGAGCATAAGGGTAATCTTGGTTCTCCGAACGCGGTCGGGGTTTTTGGATTCGACCCTGCCAGC
CTTGACCGACTTGCTGGGGTGATGCACCTGCCCAGCAGTGCCATCCCAGCCGCTCTGGCCGAGTTGTCTGGCGACCTTGA
TCGTCCAACTTCCCCGGCCGCCACTGTGTGGACTGTCTCGCAGTTTTATGCTCGTCATAGTGGAGGRGAGCATCCTGATC
AAAAGTGTTTAAAAAAAATTATCAGTCTCTGTGAGGTGATCGAGAGTTGTTGCTGTTCTCGAACAAAACTAACCGGGTC
ACCCCGGAAGAGGTCACAGCAAAGATTGATCTGTACCTTTTTGGTGCAGCAAGTCTTGAAGAATGCTTGGCCAGGCTTGA
RAAAGCTCGCCCGCCAAGCGTATTARACACCTCCTTTGATTGGGATGTTGTGCTCCCTGGTGTTGGGRCGGCTGCTCAAG
CAGCAAAACTGCGCCCTCACCAACCAGCGTCACGCTCTAGCCACTGTTGTGACYCAAAGGTCTTTGCCGAAATTTCAACCT
CGAAAAGCGGAGTCTGTCAAGAGCTACCAGAGAGCAGCCCACTCCCTGCCCCGCGCAAAAAGATTAGTGCCAGGTGTGG
TAGTCCGATTTCATTGGGCGGCAATCTCCCTGACAGCCAGGAAGACTTGGCCGGTGGTTCCTTTGATTTCCCAACCCTAC
CTGAGTTGGTGGTAAGCTCGAGTGAGTCTGTGCCTGTCCCTGCACCGCGCAGGGTTGTGTCCCGATTAGTGTCGTCTCCG
ATAGTGTCGACCCCTGTGCCCGCACCACGACGTGGGCTTCCGCAGGTGGAGGGAATGAAATTTGGCGGCAGTGACTCTAGC
GTGCCAGGACGAGCCCCTCGATTTGTCTGCGTCCTCGCAGACTGAATATGAGGCGTCCCCCTTGGCATTGCCGCTGAGTG
AGGATGTCCTGGCGGTGGAGAGCGAGAAGTTGAAGAAGTCCTGAGCGGAATATCGGGCATGTCAGATGACATCAGGTTG
GCGCCCGTGTCATCAAGTAGCTCCTGTCAAGCATAGAGATCACACGTCCAAAGTACTCAGCTCAAGCCATCATTAACTC
AGGTGGGCCCTGTTGTGGGCACCTCCAGGAGGTGAAAGAGAAATACCTTAATGTGATGCGTGAGGCATGTGATGCGACCA
AGCTTGATGACCCTGCCACGCAAGAATGGCTTTCCCGTATGTGGGATAGGGTAGACATGCTAACCTGCCGCAACACGTCC
ATTTTCAGGCGCCCTTTCACCTTCGCTGACAAGTTTAAGTCCCTCCCGAAGATGATACTCGAAACACCGCCGCCCTACCC
TTGTGGCTTTGTGATGATGCCCCGCACGCCTGCGACCTTCTGTAGGTGCGGAGAGCGACCTCACCGTTGGCTCAGTTGCTA
CTGAAGATGTCCCGCGCATTCTCGGGAAGGTACAAGGTGTTGGCGAAACGACCGACCAGGGACCCTTGGCACTCTTCGCA
GATGAATTGGCAGATGACCAACCTGCTAGAGAACCCCGGACACAAACCCCTCCTGCAACGCGCAGGTGGCGCCGGCTTAGT
TTTGGATTCTGGAGGGTCGCCGGAGCTCACTGACCTGCCGCTTCCARACGGTACAGACGCGGGCGGAGGGGGGACCGTTAC
ACACGGTCAAGAAGAAAGCTGAGAGGTGCTTTGACCAGCTGAGCCGTCGGGTTTTTGACATTGTCTCCCATCTCCCTGTC
TTCTTCTCACGCCTTTCAAGCCTGACAGTCACTACTCTTCGGGTGACTGGAGTTTTGCAGCTTTTACTTTATTGTGCCT
CTTTCTATGTACAGTTACCCGGCCTTTGGTGTTGCTCCCCTATTGGGTGTATTTCTGGGTCTTCTCGGCGCGTTCGCA
TGGGGTTTTTGGCTGCTGGTTGGCTTTCGCTGTTGGTTTGTTCAAGCCTGCACCCGACCAGTCGGTGCTGCTTGTGAG
```

```
GGATTGATGGCACGCTCTGGGATTTTGAGTCCGTAGCCACTAAAGAGGAAGTCGCACTTAGTGCACAAATAATACAGGCT
TGTGGCATTAGGCGTGGCGATGCTCCTGAGATTGGCCTCCCTTACAAGCTGCACCCTGTTAGGGACAACCCTGAACGTGT
AAAAGGGGTTTTGAAAAACACAAGGTTTGGACACATACCTTACAAGACCCCTAGCGACACTGGGAGCCCAGTACATGCGG
CCGCCTGCCTTACGCCTAATGCCACCCCGGTGACTGATGGCGCTCCGTCTTGGCCACGACTATGCCCTCCGGTTTGAG
TTGTATCTGCCGACCATTCCAGCGTCTGTCCTTGATTACCTTGATTCCAGGCCAGACTGCCCTAAACAGTTGACGGAGCA
CGGGTGTGAAAATGCTGCATTGAGAGACCTCTCCAAATATGACTTGTCCACCCAAGGTTTTGTTTTGCCCGGAGTCCTCC
GCCTCGTGCGGAAATACTTGTTTGCCCACGTGGGCAAGTGCCCACCTGTCCATCGGCCCTCCACCTACCCGGCCAAGAAT
TCCATGGCTGGAATAAACGGGAATAGGCTTCCCGACCAAGGACATTCAGAGCATCCCTGAGATCGACGTTCTGTGTGCACA
GGCTGTACGAGAGAACTGGCAGACCGTTACCCCTTCCACCCTCAAGAAGCAGTATTGCGGGAAGAAGAAAACCAGGACCA
TACTCGGTACCAATAACTTCATTGCGCTGGCCCACCGGGCAGCACTGAGTGGTGTCACCCAGGGCTTCATGAAAAGGCG
TTTAACTCGCCCATCGCCCTCGGGAAGAACAAATTCAAGGAGCTACAGACTCCGGTCCTGGCAGATGTCTTGAGGCTGA
TCTTGCCTCTTGCCGATCGGTCCACTCCCGCGATTGTCCGCTGGTTTGCCGCCCATCCTCCTTTATGAACTTGCCTGCGCTG
AGGAGCACCTACCGTCGTATGTGCTGAATTGCTGCCATGACCTATTGGTCACGCAGTCCGGTGCGGTGACTAAGAGAGGT
GGCCTGTCATCTGGTGATCCGATCACCTCTGTATCCAACACCATTTACAGTCTGGTAATTTATGCGCAGCACATGGTGCT
CAGTTACTTCAAAAGTGGTCACCCACATGGTCTCCTGTATCTCCAGGACCAGCTAAAGTTTGAGGACATGCTTAAGGTTC
AGCCCCTGATGTCTACTCGGATGATCTTGTGCTGTATGCCGAGTCCCCACCATGCCAAACTACCACTGGTGGGTTGAG
CATCTGAACTTGATGCTAGGGTTTCAGACGGACCCAAAGAAGACAACCATTACTGACTCGCCATCTTTTCTGGGCTGTAG
GATAATGAATGGGCGTCAGCTAGTCCCAAACCGTGACAGGATTCTCGCAGCTCTTGCCTACCACATGAAGGCGAATAATG
TTTCTGAGTACTACGCCTCCGCTGCTGCAATACTCATGGACAGTTGTGCTTGTCTGGAGTACGACCCTGAATGGTTTGAA
GAACTTGTGGTTGGAATGGCGCTATGCGCCCGCAAGGACGGCTATAGCTTCCCCGGCCCGCCGTTCTTCTTATCCATGTG
GGAGAAACTTAAGTCCAATTATGAGGGGAAGAAGTCAAGGGTATGTGGGTACTGCGGAGCTTCGGCCCCGTATGCCACTG
CCTGTGGTCTTGACGTCTGTGTTTACCACACTCACTTTCACCAGCATTGTCCAGTCATAATCTGGTGTGGCCACCCTGCA
GGTTCCAGGTCCTGTGATGAGTGCAAATCCCCCATAGGGAAAGGCACAAGCCCTCTGGATGAGGTTTTGAGACAAGTCCC
GTATAAGCCTCCACGGACCGTCCTCATGCATGTGGAGCAGGGCCTCACCCCCCTTGACCCAGGCAGATATCACACCCGCC
GTGGGTTGGTTGCCGTTAGGCGCGGGATCAGGGGAAATGAAGTTGACCTACCAGATGGTGATTATGCTAGCACCGCCTTA
CTCGCAACCTGTAAAGAGATCAACATGGTTGCTGTTGCTTCTAATGTGTTGGCGCAGCAGATTTATCATCGGTCCACCCGG
TGCTGGGAAAACATACTGGCTCCTTCAACAGGTCCAGGATCGTGATGTCATATACACACCGACCCATCAGACCATGCTTG
ACATGATCAAAGCTTTAGGGACGTGCCGGTTTAACGTCCCGGCAGGCACAACGCTGCAATTCCCCGTCCCTCCCGGACC
GGTCCGTGGGTTCGCATCCTGGCCGGCGGGTGGTGTCCTGGCAAAAACTCCTTCCTGGACGAAGCTGCGTATTGTAATCA
TCTTGATGTCTTGAGGCTTCCTTAGCAAAACCACTCTCACCTGTTTGGGGGACTTCAAACAACTCCACCCAGTGGGTTTTG
ATTCTCATTGCTATGTCTTTGACATTATGCCCTCAGACTCAATTGAAGACCATCTGGAGATTTGGACAGAACATCTCTGAT
GCCATCCAACCAGACTACAGAGACAAGCTTATGTCCATGGTCAACACAACTCGTGTAACTTATGTGGAAAAACCTGTCAA
ATATGGGCAAGTCCTCACCCCTTACCATAGGGACCGAGAGGATAGCGCCATTACCATTGACTCCAGTCAAGGCGCCACAT
TTGATGTGGTTACACTGCATTTGCCCACGAAAGATTCACTCAACAAACAAAGGGCCCTTGTTGCTATTACCAGGGCAAGA
CATGCCATCTTTGTGTATGACCCATATAGGCAACTGCAGAGCCTATTTGATCTTCCTGCAAAAAGCACGCCCGTCAACTT
GGCCGTGCACCACGATGGGCAACTGATTGTGCTAGATAGAAATAACAAAGAATGCACGGTTGCCCAAGCTCTGGGTAATG
GTGACAAATTTAGGGCCACAGACAAGCGCGTTGTGGATTCTCTCCGCGCCATTTGTGCTGACCTAGAAGGGTCGAGCTCT
CCACTCCCCAAGGTTGCACATAATTGGGGGTTTTATTTCTCACCTGATTTGATACAGTTTGCCAAGCTTCCAATAGAACT
TGCGCCACACTCGCCAGTAGTGACGACCCAAGCAATAAAAACTGGCCAGATCGGCTGGTTGCCAGCCTACGCCCTATTC
ACAAACATAGCCGTGCGTGTATCGGTGCCGGCTATATGGTGGGCCCCTCGGTGTTTTTAGGCACCCCTGGGGTTCTGTCA
TACTATCTTACAAAATTTGTTAAGGGCGAGGCTCAAGTGCTTCCGGAAACGGTCTTCAGTACCGGCCGAATTGAGGTGGA
TTGCCGGAATATCTTGACGACCGGGAGCGGGAAGTTGCAGCGTCCCTCCCACACGCCTTTATCGGCGACGTCAAAGGCA
CTACCGTCGGAGGGTGTCATCACATCACCTCCAAATACCTTCCGCGCTTCCTCCCCAAGGAATCAGTTGCCGTAGTCGGG
GTTTCAAGCCCCGGAAAAGCAGCGAAAGCACTGTGTACATTGACAGATGTGTACCTCCCAGACCTTGAAGCTTACCTCCA
TCCTAAGACCCTGTCCAAGTGCTGGAAAAATGATGTTGGACTTCAAAGAAGTTCGGCTGATGGTCTGGAAGGACAAGACGG
CCTATTTCCAACTCGAAGGTCGCCATTTCACCTGGTATCAACTTGCTAGCTATGCCCTCGTACATCCCGTGTTCCTTTAAAC
TCCACGGTGTACCTGGACCCCTGCATGGCCCCGCCCTTTGCAACAGAAAAGTTGTTGGGTCCACTCATTGGGAGCTGA
CCTCGCAGTCACCCCTTATGATTATGGGGCAAGAATTATTTTGTCTAGTGCGTACCATGGTGAGATGCCTCCTGGGTACA
```

Fig. 1E-4

AGATTCTGGCGTGCGCGGAGTTCTCGCTGGACGACCCAGTCAGATACAAGCACACTTGGGGGTTTGAGTCGGATACAGCG
TACTTGTACGAGTTCACTGGAAACGGTGAGGACTGGGAGGATTATAACGACGCGTTTCGTGCGCGACAGAAAGGAAAGAT
TTACAAGGCCACTGCCACCAGCCTGAAGTTCCATTTTCCTCCGGGTCATACCGTTGAACCAACTTTGGGCCTAGACTGAA
ATGAAATGGGGCTGTGCAGAGCCTATTTGATAAAATTGGCCAACTGTTTGTGGACGCTTTCACGGAGTTCTTGGTGTCC
ATTGTTGATATCATCATATTTTTGGCCATTTTGTTCGGCTTCACAATCGCCGGTTGGCTGGTGGTCTTTTGCATCAGATT
GGTTTGCTCCGCGATACTCCGTTCGCGCTCTGCCGTTCACCCTGAGCAATTACAGAAGATCCTATGAGGCATTTCTCTCC
CAGTGCCGGACGGAYATTCCCACCTGGGAACTAAACATCCCTTGGGGATGCTCTGGCACCACAAGGTGTCGACCCTAAT
TGATGAAATGGTGTCGCGTCGAATGTACCGCATCATGGAACAAGCAGGGCAGGCTGCCTGGAAACAGGTGGTGACCGAGG
CAACGTTGTCTCGTATTAGTAGCTTGGATGTGGTGGCTCATTTCCAGCACCTTGCCGCCATAGAAGCCGAGACTTGTAAA
TACTTCGCCTCCGGCTGCCAATGCTGCACAACCTGCGCATGACAGGGTCAAATGTAACCATAGTGTATAATAGCTCTCT
AGAACAGGTGTTTGCTGTTTCCCGACCCTCAGTTCCCGGCCAAAGCTTCATGATTTTCGGCAATGGCTAATAGCTGTGC
ATTCCTCCATATTCTCTTCTGTGGCGGCTTCCTGTACCCTTTTCGTCGTGCTGTGGTTGCGGCTTCCAATAATACGTACT
GTTTTGGTTTCCACTGGTTAGGGGCAATTTTTCCTTCGAGCTCACAGTGAACTACACGGTGTGCCTCCCTGCCTCACC
CGGCAGGCGGCCGCAGAGATCTACGAACCTAGTGGGTCTCTTTGGTGCAGGATAGGGCACGATCGATGCTCGGAGGACGA
TCACGACGAGCTAGGATTCTGGTGCCGCCTGGCCTCTCCAGCGAAGCCACTTGACCAGTGTTTACGCCTGGTTGGCGT
TCTTCTCCTTCAGTTACACGGCCCAGTTTCACCCCGAGATATTCGGGATAGGGAATGTGAGTAAAGTTTATGTTGACATC
AAGCATCAATTTATTTGCGCTGTTCATGACGGGCAAAACACCACCTTGCCTCGCCATGACAACGTCTCAGCCGTGTTCCA
GACTTATTACCAGCATCAGGTCGACGGCGGCAATTGGTTTCACCTGGAATGGCTGCGCCCCTTCTTCTCCTCCTGGTTGG
TTTTGAACGTCTCTTGGTTTCTCAGGCGTTCGCCTGTAAGCCGTGTTTCAGTTCGAGTCTCTCAGACATTAAGACCAACA
CCACCGCAGCTGCAGGCTTTGCTGTCCTCCAAGACATCAGTTGTCTTAGGCATGGCCACTCGTCCTCTGAGGCGACTCGC
AAAAGCCGTCAATGTCGCACGGGATAGGAACGCCGTATACATTACTGTCACAGCCAATGTAACAGATGAGAATTATTT
GCATTCCTCTGACCTTCTCATGCTTTCCTCTTGCCGTTTCTACGCTTCCGAGATGAGTGAAAACGGGATTTGAAGTGATAT
TTGGCAATGTGTCAGGCATAGTGGCTGTGTGTGTCAACTTTACCAGCTATGTCCAACATGTCAAGGAGTTCACCCAGCGC
TCCTTGGTGGTTGACCATGTGCGGTTACTTCATTTTATGACAGCTGAGACTATGAGGTGGGCGACCGTTTTAGCCTGTCT
TTTTGCCATTCTGTTGGCCATTTGAATGTTCAGATATGTTGGGGAAATGCTTGACCGCGGGCTATTGCTCGCAATTGCTT
TTTTTGTGGTGTATCGTGCCGTTCTGTCTTGCTGCGCTCGTCAACGCCGACAGCAACAGCAGCTCCCATTTACAGTTGAT
TTATAAMTTAACGATATGTGAGCTGAATGGCACAGACTGGCTGAACAATCATTTTAGTTGGGCAGTGGAGACTTTCGTTA
TCTTTCCTGTGTTGACTCATATTGTTCCTACGGCGCCCTCACTACCAGCCACCTCCTTGACACGGTCGGCCTGATCACT
GTGTCCACCGCCGGATACTGCCATAAGCGGTATGTCTTGAGTAGCATCTATGCTGTCTGCGCCCTGGCTGCGCTGATTTG
CTTCGTCATCAGGTTGACGAAAAATTGTATGTCCTGGCGCTACTCATGTACCAGATATACCAACTTTCTTCTGGACACCA
AGGGCAGACTCTATCGCTGGCGTCACCCGTCACTCATAGAGAAAAGGGGTAAAATTGAGGTTGGAGGTGACCTGATCGAC
CTCAAGAGAGTTGTGCTTGATGGTTCCGCGGCAACCCCTGTAACCAAAGTTTCAGCGGAACAATGGGGTCGTCCTTAGAC
GACTTCTGCAATGACAGCACGGCTCCACAAAAGGTGATCTTGGCATTTTCTATCACCTACACACCAGTGATGATATATGC
CCTAAAGGTGAGTCGTGGCCGGCTGCTAGGGCTTTTACACCTTTTGATTTTTTAAACTGTGCTTTTACCTTCGGGTATA
TGACATTTGTGCACTTTCAGAGCACAAACAGAGTTGCACTCACTATGGGAGCAGTAGTCGCGCTCCTTTGGGGGTGTAC
TCAGCTATAGAAACCTGGAAATTCATCACTTCCAGATGCCGTTTGTGCTTGCTAGGCCGCAAGTACATTCTGGCCCCTGC
CCACCACGTTGAGAGTGCCGCAGGCTTTCATCCGATTGCGGCAAGTGATAACCACGGATTTGTCGTCGGCGTCCCGGTT
CCACTACGGTTAACGGCACATTGGTGCCCGGGTTGAAAAGCCTCGTGTTGGGTGGCAGAAGAGCTGTCAAACGGGGAGTG
GTAAACCTCGTTAAATATGCCAAATAACAACGGCAGGCAGCAGAAGAAAAAGAAAGGGGACGGCCAGCCAGTCAATCAGC
TGTGCCAAATGTTGGGCAGGATCATCGCCCAGCAAAACCAGTCCAGAGGCTAAGGGACCGGGGAAGAAAAGTAAGAAGAAA
AGCCCGGAGAAGCCCCATTTCCTCTCGCGACTGAAGATGACGTTAGACATCACTTCACCCCTAGTGAGCGGCAATTGTG
TCTGTCGTCAATCCAGACTGCCTTTAACCAAGGCGCTGGAACTTGTACCCTGTCGGATTCAGGGAGAATAAGTTACGCTG
TGGAGTTTAGTTTGCCTACGCATCATACTGTGCGCCTAATTCGCGTCACAGCATCACCCTCAGCATGATGAGCTGGCATT
CTTGAGACATCCAGTGTTTGAATTGGAAGGATGTGTGGTGAATGGCACTGATTGATATTGTGCCTYTAAGTCACCTATT
CAATTAGGGGACCGTATGGGGTAATATTTAATTGGCGTGAACCATGCGGCCGAAATT

*Fig. 1F-1*

```
>MN3848_DQ176020.seq
ATGACGTATAGCTGTTGGCTCTATGCCACGACATTTGTATTGTCAGGAGCTGTGACCACTGGCACAGCCCAAAGCTTGCT
GCACAGAAACACCCTTCTGTGACGGCCTCCTTCAGGGGAGTTTAGGGGTTTGTCCCTAGCACCTGTTTCTGGAGTTGCA
CTGCTTTACGGTCTCTCCACCCCTTTAACCATGTCTGGATTCTTGATCGGTGCACGTGCACCCCCAATGCCAGGGTGTT
TATGGCAGAGGGCCAAGTCTACTGCACACGATGTCTCAGTGCACGGTCCCTCCTTCCCCTGAATCTCCAAGTCTCTGAGC
TCGGAGTGTTGGGCTTGTTTATAGGCCTGAAGAGCCGCTCCGGTGGACGTTGCCACGCGCATTCCCACTGTTGAGTGC
TCCCCTGCTGGGCTTGTTGGCTTTCTGCAATTTTTCCAATTGCACGAATGACCAGTGGAAACCTGAACTTTCAACAAAG
ATTAGTGCGGGTCGCAGCTGAGCTTTACAAAGCCGGCTGCCTCACCCCTACAGTCCTAAAGAGTCTACAAGTCTATGAAC
GGGGTTGCCGCTGGTACCCCATCGTTGGACCTGTCCCTGGAGTTGCCGTTTTCGCCAACTCCCTACATGTGAGTGATAGA
CCTTTCCCACGTGCTACTCACGTGCTAACCAACCTGCCGCTCCCGCAGAGACCTAAGCCTGAAGATTTTTGCCCCTTTGA
GTGTGCTATGGCTGCCGTCTATGACATTGGTCATGACGCCTTATGTTCGTGGCCGAAGGGAGACTCTCTTGGGCTCCGC
GTGGTGGGGAAAAAGGAAAATTTGAAACTGTTCCCGAGGAGTTGGGGTTGATTGCAGAGCAACTTTATACCTCCTTCCCG
CCCCACCACTTGGTGGACATGTCGAAATTCACCTTTACGGCCCCTGAGTGTGGTGCTTCCATGCGAGTCGAACGCCAGTA
TGGCTGCCTCCCGCTGGCACTCGTCCCTGACGGCAATTGCTGGTGGAGCTTGTTTAGCTCGCTCCCATTGGAAGTCCAGT
ATAAAGAAATTCGCTACGCCACCCAATTTGGCTATCAAACTAAGCATGGCGTTGCTGGCAAGTACCTACAGCGGAGGCTG
CAAATTAATGGTCTCCGAGCAGTCGTTGACTCGAATGGACCCATCGTCATACAGTACTTCTCTGTTAAGGAGAGCTGGAT
CCGCCACGTGAAACTGGCGGAAGAGTTTGACTACCCTGGGTTTGAGGATCTCCTCAGGATAAGAGTCGAGCCCAACACGT
TGCCATTGTCCAACAAGGACGAGAAAATCTTCCGGTTTGGTGGGTGCAAGTGGTACGGTGCTGGGAAGAGGGCAAGGAGG
GCACGTGCAAGTGCAGTCACCGCAGTCGCCGGTCACGGCTCCGCCTACTCGTGAAACCCAGCAAGCCAAGAAACACGAAGC
TGCTAGTGCCAACAAGGCTGAGCTTCTTGAACGCTACTCCCCGCCTGCTGAAGGGAATTGCGGCTGCCACTGTATCTCCG
CCATCGCCAACCGGATGGTAATTCYAARTTTGAAACYRCCCTTCCCGAAAGAGTGAGACCTCCAGATGACTGGGCYACT
GACGAGGATCTTGTGAATGCCATCCAAATCCTCAGACTCCCTGCGGCCTTAGACAGGAACGGTGCTTGTACTAGCGCCAA
GTACGTACTTAAGCTGGAAGGTGAGCATGGACTGTCACTGTGACCCCTGGGATGTCCCCTTCTTTGCTCCCTCTTGAAT
GTGTTCAGGGCTGTTGTGGGCACAAGGGCGGYCTTGGTTCCCAGATGCAGTCGAGGTCTCCGGATTTGACCCTGCCTGC
CTTGACCGGCTGGCTGAGGTGATGCACCTGCCTAGCAGTGCTATCCCAGCCGCTCTGGCCGAAATGTCTGGCGATTCCGA
TCGTTCGGCTTCTCCGGTCACCACGTGTGGACTGTTTCGCAGTTCTTTGCCCGTCACAGCGGAGGGAATCACCCTGACC
AAGTGCGCTTAGGGAAATTATCAGCCTTTGTCAGGTGATTGAGGACTGCTGCTGTTCCCAGAACAAAACCAACCGGGTC
ACCCCGGAGGAGGTCGGCAGCAAAGATTGAYCAGTACCTTTTTGGTGCAGCAAGTCTTGAAGAATGCTTGGCCAGGCTTGA
RAAAGCTCGCCCGCCAAGCGTATTARACACCTCCTTTGATTGGGATGTTGTGCTCCCTGGTGTCGGGGCGGCTGCTCAAG
CAGCAAAACTGCCCCTCACCAACCAGCGTCACGCTCTAGCCACTGTTGTGACTCAAAGGTCTTTGCCGAAATTTCAACCT
CGAAAAGCGGAGTCTGTCAAGAGCCTACCAGAGAGCAGGCCCCTCCCTGCCCCGCGCAAAAAGATTGGGTCCAGGTGTGG
TAGTCCGATTTCATTGGGCGGCAATCTCCCTGACAGCCGGGAAGACTTGGCCGGTGGTTCCTTTGATTTCCCAACCCTAC
CTGAGTTGGTGGCAAGCTCGAGCGAGCCTGTGCCTGCCCCTGCCACCGCGCAGGGTTGTGTCCCGATTAGTGTCGTCTCCG
ATAGTGTCGACCCCTGTGCCGGCACCACGACGTGGGCTTCGGCAGGTGGAGGGGAATGAATTTGGCGGCGGTGACTCTAGC
GTGCCAGGACGAGCCCCTCGATTTGTCTGCGTCCTCGGCAGACTGAATATGAGGCGTCCCCCTTGGCATTGCCGCTGAGTG
AGGATGTCCTGCCGGTGGAGAGACGAGAAGTTGAAGAAGTCCTGAGCGGAATATCGGGCATGCCAGATGACATCAGGTTG
GCGCCCGTGTCATCAAGTAGCTCCCTGTCAAGCATAGAGATCACACGTCCAAAGTACTCAGCTCAAGCCATCATTAACTC
AGGTGGGCCCTGTTGTGGGCACCTCCAGGAGGTAAAAGAAAATACCTTAATGTGATGCGTGAGGCATGTGATGCGACCA
AGCTTGATGACCCTGCCACGCAAGAATGGCTTTCCCGCATGTGGGATAGGGTAGACATGCTAACCTGGCGCAACACGTCC
ATTTTTCAGGCGCCTTTCACCTTTGGCTGACAAGTTTAAGACCCTCCCGAAGATGATACTCGAAACACCGGCGCCCTACCC
TTGTGGGTTTGTGATGATGCCCCGGACGGCCTGGACCTTCTGTAGGTGCGGAGAGCGGACCTCACCGTTGGCTCAGTTGCTA
CTGAGGATGTCCCGCGCATTCTCGGGAATGTACAAGGTGTTGGCGAAACGACCGACCAGGGACCTTGGCACCGCTTCGCA
GACGAATTGGCAGATGACCAACTTGCTAGAGAACCCCGGACACAAACCCTCCTGCAAGCACAGGTGGCGCCGGCTTGGT
TTCGGATTCTGGAAGGTCGCCGGAGCTCACTGACCTGCCGCTTTCAAACGGTACAGACGCGGGCGGAGGGGGCCGTTAC
ACACGGTCAAGAAGAAAGCTGAGAGGTGCTTTGACCAGCTGAGCCGTCGGGTTTTTGACATTGTCTCCCATCTCCCTGTT
TTCTTCTCACGCCTTTTCAAGCCTGACAGTCACTACTCTTCGGGTGACTGGAGTTTTGCAGCTTTTACTTTATTGTGCCT
CTTTCTATGTTACAGTTACCCAGCCTTTGGTGTTGCTCCCTATTGGGTGTATTTCTGGGTCTTCTCGGGCGTTCGCA
TGGGGTTTTTGGCTGCTGGTTGGCTTTCGCTGTTGGTTTGTTCAAGCCTGCACCCGACCCAGTCGGTGCTGCTTGTGAG
```

*Fig. 1F-2*

```
TTTGATTCGCCAGAGTGTAGAGACATCCTTCATTCTTTTGAGCTTCTGCAACCTTGGGACCCTGTTCGCAGCCTTGTGGT
GGGGCCCGTCGGTCTCGGTCTTGCCATTATTGGCAGGTTACTGGGCGGGGCACGCTACGTCTCGCTGCTTTTGCTTAGGC
TTGGCATCGTTTCAGACTGTATCTTGGCTGGAGCTTATGTGCTTTCGCAAGGTAGGTGTAAAAAGTGTTGGGGATCTTGT
ATAAGAACTGCTCCCAGTGAGGTCGCCTTCAATGTGTTTCCCTTCACACGTGCAACCAGATCGTCACTTGTCGACCTGTG
CGACCGGTTTTGTGCGCCCAAGGGCATGGACCCCATCTTCCTCGCCACTGGATGGCGCGGATGTTGGTCCGGCCAGAGCC
CCATTGAGCAACCCACTGAGAAACCCATTGCGTTCGCCCAGTTGGATGAAAAGAAAATCACGGCAAGGACTGTGGTTGCC
CAACCTTATGACCCCAACCAAGCTGTGAAGTGCTTACGAGTCTTGCAGGCGGGTGGGGCGATGGTGGCTGAGGCGGTTCC
AAAAGTGGTTAAGGTCTCTGCTGTCCCATTTCGAGCCCCCTTCTTCCCCGCCGGAGTGAAAGTTGATCCTGAATGCAGGG
TCGTGGTTGACCCAGACACCTTCACAACTGCTCTCCGGTCCGGCTACTCCACCACAAACCTCATTCTTGGTATGGGGGAT
TTTGCCCAACTGAATGGGTGAAAATCAGACAAATTTCCAAGCCTTCAGGAGGTGGTCCATACCTCATGGCGGCCTTACA
TGTCGCTTGCTCGATGGCCTTGCACATGCTCGTTGGGATTTATGTTACCGCGGTGGGTTCTTGTGGTTCTGGCACTAACG
ATCCGTGGTGCACTAACCCGTTTGCCGTCCCTGTCTACGGGCCTGGCTCTCTTTGCACGTCCAGGTTGTGCATCTCCCAG
CATGGCCTTACTCTGCCTTTAACAGCGCTTGTGGCGGGGTTTGGCATTCAGGAAGTTGCTTTGGTTGTTTAATCTTTAC
TTCCATCGGGGGTATGGCTCACAGGTTGAGCTGCAAGGCCGATGTGCTGTGTATTCTGCTTGCAATTGCCAGCTATGTTT
GGGTACCCTTCACCTGGTTGCTTTGTGTGTTTCCTTGCTGGTTGCGCTGGTTTTCTTTGCATCCCCTGACCATTCTATGG
TTGGTGTTTTCTTGATTTCTGTGAACATGCCCTCAGGAATCTTGGCTTTAGTGTTGTTGATCTCTCTCTGGCTCCTTGG
TGCTATACCAATGTCGCTGGCCTTGTCACCCCTTATGACATTCACCATTACACCAACGGCCCCGCGGCGTTGCCGCCT
TGGCCACTGCCCCGGATGGGACCTATTTGGCTGCTGTCCGCCGGCTGCGTTGACTGGCCGCACCATGCTGTTTACCCCG
TCTCAACTTGGGTCACTCCTTGACGGCGCCTTTAGAAGCCAAAAGCCTTCACTGAATACCGTCAATGTGGTTGGGTCCTC
CATGGGCTCCGGCGGGGTGTTCACCATTGACGGGAAAATTAAGTGCGTGACCGCCGCACATATCCTCACGGGTAACTCTG
CTAGGGTCTCTGGGGTTGGCTTCAATCARATGTTGGATTTTGATGTAAAAGGGGATTTTGCCATAGCCGATTGTCCGGGT
TGGCAGGGAGTCGCTCCCAAGTCCCAGTTCTGCAAGGATGGGTGGACTGGCCGCGCTTATTGGCTAACGTCCTCTGGCGT
CGAACCCGGCGTCATTGGTAGGGGATTCGCCTTTTGTTTCACCGCGTGCGGCGATTCCGGGTCCCCAGTGATCACCGAGG
CCGGACAGCTTGTCGGAGTCCACACGGGATCARAGTGAATTCTTYGCYGGRCGTAGGGTCCCGCTYGGTGAYGTGAAGGTCGG
AATGTCGCACCCAYCAAYTAAGYGAATTRAGTGAATTCTTYGCYGGRCGTAGGGTCCCGCTYGGTGAYGTGAAGGTCGG
CAGCCACATAATTAAAAGACATAAGCGAGGTGCCTTCAGATCTTTGTGCCTTGCTTGCTGCCAAACCTGAACTGGAAGGAG
GCCTCTCCACCGTCCAACTTCTTTGTGTGTTTTTTCTCCTGTCGAGAATGATGGGACATGCCTGGACGCCCTTGGTTGCT
GTGAGTTTCTTTATTTTGAATGAGGTTCTCCCAGCCGTCCTGGTCCGGAGTGTTTCTCCTTTGGAATGTTTGTGCTATC
CTGGCTCACGCCATGGTCTGCCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCTCGGATGATGGTTGTGACCTCACCAGTCCCAGTGATCACGTGTGGTCTCGTGCA
CCTACTTGCCATCATTTGTACTTGTTTAAGTACCGTGGCCTGCACCATATCCTTGTTGGCGATGGAGTGTTCTCTGCGG
CTTTCTTCTTGAGATACTTTCCCGAGGGAAAAGTTGACGGAAGGGGTGTCGCAATCCTGCGGAATGAATCATGAGTCTCTG
ACTGGTGCCCTCGCTATGAGACTCAATGACGAGGACTTGGATTTCCTTATCAAATGGACTGGATTTAAGTGCTTTGTTTC
TGCGTCCAACATGAGGAATGCAGGGGGTCARTTTATCGAGGCYGCCTATGCGAAAGCGATCAGGGTGGAACTTGCCCAGT
TAGTGCAGGTCGACAAGGTTCGGGGTGTTTAGCCAAACTTGAAGCTTTTGCTGACACCGTGGCGCCCCATCTTTCACCC
GGCGACATTGTTGTTCTTGGTCATACGCCCGTTGGCAGCATCTTTGACTTAAAGATTGCAATGCCAAGCACACCCT
ACAAGCCATCGAGACCAGAGTCCTTGCTGGGTCCAGGATGACCGTGGCGCGTGTCGTTGATCCGACTCCCGCGCCGCCAC
CCGTACCCGTGCCCGTTCCTGTCCCACCGAAAGTTTTAGAGAACGGCCCCAGTGCCTGGGGGATGAAGACCGCCTGAAC
AAAAAGAAGCGGCGCAAGATGGAAGCCGTTGGCATTTACGTTATGGCGGGAAAAAGTACCAGAAATTTTGGGATAAGAA
TTCTGGTGATGTGTTCTATGAGGAAGTCCACGACAACACAGATGCGTGGGAATGCCTTAGAGCTGACGACCCCGCCGACT
TGGATCCTGAGAGGGGACCTTGTGTGGACACGTCACCATAGAGAATAGGCCTTACCATGTTTATGCCTCCCGTCTGGT
AGGAAGTTCCTGGTCCTGCCGACCCAGAGAATGGGAAAGCCCAGTGGGAAGCTGCAAAGCTTTCCATGGAGCAGGCCCT
TGGTATGATGAACGTTGACGGCGAGCTGACCGCCAAAGAACTGGAGAAATTGAAGAGAATAATTGACAAACTCCAGGCC
TGACTAAGGAGCAGTGTTTAAACTGTTAGCCGCCAGCGGCTTGACCCGCTGTGGTCGCGGCGGCTTGGTTATTACTGAGA
CAGCGGTAAAATAGTCAGATTCCACAATCGGACCTTCACCCTGGGCCTGTGAATTTGAAAGTGGCCAGCGAAGTTGAG
TTGAAAGACGCCGTCGAGCACAACCAACACCCGGTGCAAGACCCAGTTGACGGTGGCGTTGTGCTCCTGCGCTCTGCAGT
TCCTTCGCTTATAGACGGTCTTGATCTCCGGTGCCGACGCATCTCCCCAGTTGCTCGCCCATCACGGGCCAGGAAACACTG
```

AGATTCTGGCGTGCGCGGAGTTCTCGCTGGACGACCCAGTCACATACAAGCACACTTGGGGGTTTGAGTCGGATACAGCG
TACTTGTACGAGTTCACTGGAAACGGTGAGGACTGGGAGGATTATAACGACGCGTTTCGTGCGCGACAGAAAGGAAAGAT
TTACAAGGCCACTGCCACCAGCCTGAAGTTCCATTTTCCTCCGGGTCATACCGTTGAACCAACTTTGGGCTTAGACTGAA
ATGAAATGGGGGCTGTGCAGAGCCTATTTGATAAAATTGGCCAACTGTTTGTGACGCTTTCACGGAGTTCTTGGTATCC
ATTGTTGATATCATCATATTTTTGGCCATTTTGTTCGGCTTCACAATCGCCGGTTGGCTGGTGGTCTTTTGCATCAGATT
GGTTGCTCCGCGATACTCCGTTCGCGCTCTGCCGTTCACCCTGAGCAATTACAGAAGATCCTATGAGGCATTTCTCTCC
CAGTGCCGGACGGACATTCCCACCTGGGGAACTAAACATCCCTTGGGGATGCTCTGGCACCACAAGGTGTCGACCCTAAT
TGATGAAATGGTGTCGCGTCGAATGTACCGCACCATGGAACAAGCAGGGCAGGCTGCCTGGAGACAGGTGGTGACCGAGG
CAACGTTGTCTCGTATTAGTAACTTGGATGTGGTGGCTCATTTCCAGCACCTTGCCGCATAGAAGCCGAGACTTGTAAA
TACTTGGCCTCCCGGCTGCCAATGCTGCACAACCTGCGCATGACAGGGTCAAATGTAACCATAGTGTATAATAGCTCTCT
AGAACAGGTGTTTGCTATTTTCCCGACCCTCGATTCCCGGCCAAAGCTTCATGATTTTCGGCAATGGCTAATAGCTGTGC
ATTCCTCCATATTCTCTTCTGTTGCGGCTTCCTGTACCCTTTTCGTCGTGCTGTGGTTGCGGCTTCCAATAATACGTACT
GTTTTTGGTTCCACTGGTCAGGGGCAATTTTTCCTTCGAGCTCACAGTGAACTACACGGTGTGTCCTCCCTGCCTCACC
CGGCAGGCGGCCGCAGAGATCTACGAACCTGTGGGTCTCTTTGGTGCAGGATAGGGCACGATCGATGCTCGGAGGACGA
TCACGACGAGCTAGGATTTCTGGTGCCGCCTGGCCTCTCCAGCGAAGGCCACTTGACCAGTGTTTACGCCTGGTTGGCGT
TCTTGTCCTTCAGTTACACGGCCCAGTTTCACCCCGAGATATTCGGAATAGGGAATGTGAGCCAAGTTATGTTGACATC
AAGCATCAATTTATTTGTGCTGTTCATGACGGGCAAAACACCACCTTGCCTCGCCATGACAACGTCTCAGCCGTGTTCCA
GACTTATTACCAGCATCAGGTCGACGGCGGCAATTGGTTTCACCTGGAATGGCTGCGCCCCTTCTTCTCCTCCTGGTTGG
TTTTGAACGTCTCTTGGTTTCTCAGGCGTTCGCCTGTAAGCCGTGTTTCAGTTCGAGTCTTTCAGACATTAAGACCAACA
CCACCGCAGCTGCAGGCTTTGCTGTCCTCCAAGACATCAGCTGTCTTAGGCATGGCCACTCGTCCTCTGAGGCGACTCGC
AAAGGCCGCCAATGCCGCACGGCGATAGGAACGCCCGTATACATTACTGTCACAGCCAATGTAACAGATGAGAATTATTT
GCATTCCTCTGACCTTCTCATGCTTTCCTCTTGCCTTTTCTACGCGTTCCGAGATGAGTGAAAAGGGATTTGAGGTGATAT
TTGGCAATGTGTCAGGCATAGTGGCTGTGTGTGTCAACTTTACCAGCTATGTCCAACATGTTAAGGAGTTCACCCAGCGC
TCCTTGGTGGTTGACCATGTGCGGTTACTTCATTTTGTGACACCTGAGACTATGAGGTGGGCGACCGTTTTAGCCTGTCT
TTTTGCCATTCTGTTGGCCATTTGAATGTTCAGATATGTTGGGGAAATGCTTGACCGCGGCTATTGCTCGCAATTGCCT
TTTTTGTGGTGTATCGTGCCGTTCTGTCTTGCTGCGCTCGTCAACGCCAGCAGCAACAGCAGCTCCCACTTACAGTTGAT
TTATAACTTAACGATATGTGAGCTGAATGGCACAGACTGGCTGAATGATCATTTTAGTTGGGCAGTGGAGACTTTCGTTA
TCTTTCCTGTGTTGACTCACATTGTTTCCTACGGCGCCCTCACTACCAGCCACTTCCTTGACACGGTCGGCCTGATCACT
GTGTCCACCGCCGGATACTACCATGCGCGGTATGTCTTCAGTAGCATCTATGCCGTCTGCGCCCTGGCTGCGCTGATTTG
CTTCGTCATCAGGTTGACGAAAAATTGTATGTCCTGGCCCTACTCATGTACCAGATATACCAACTTTCTTCTGGACACCA
AGGGCAGACTCTATCGCTGCCGGTCACCCGTCATCATAGAGAAAAGGGGTAAAATTGAGGTTGGAGGTGACCTGATCGAC
CTCAAGAGAGTTGTGCTTGATGGCTGCGCGGCAACCCCTGTAACCAAAGTTTCAGCGGAACAATGGGGTCGTCCTTAGAC
GACTTCTGCAATGACAGCACGGCTCCACAAAAGGTGATCTTGGCATTTCTATCACCTACACTCCAGTGATGATATATGC
CCTAAAGGTGAGTCCGTGCCCGGCTGCTAGGCTTTTACACCTTTTGATTTTCTAAACTGTGCTTTTACCTTCGGGTATA
TGACATTTGTGCACTTTCAGAGCACAAACAGAGTTGCACTCACTATGGGAGCAGTAGTCGCGCTCCTTTGGGGGGTGTAC
TCAGCTATAGAAACCTGGAAATTCATCACTTCCAGATGCCGTTTGTGCTTGCTAGGCCGCAAGTACATTCTGGCCCCTGC
CCACCACGTTGACAGTGCCGCAGGGCTTTCATCCGATTGCGGCAAGTGATAACCACGCATTTGTCGTCCGGCGTCCCGGTT
CCACTACGGTTAACGGCACATTGGTTCCGGGTTGAAAAGCCTCGTGTTGGGTGGCAGAAGAGCTGTCAAACGGGGAGTG
GTAAACCTCGTTAAATATGCCAAATAACAACGGCAGGCAGCAGAAGAAGAAGAAAGGGACGGCCAGCCAGTCAATCAGC
TGTGCCAAATGTTGGGCAGGATCATCGCCCAGCAAAACCAGTCCAGAGGTAAGGGACCGGGGAAGAAAAGTAAGAAGAAA
AGCCTGGAGAAGCCCCATTTTCCTCTCGCGACTGAAGATGACGTTAGACATCACTTCACCCCTAGTGACGGCAATTGTG
TCTGTCGTCAATCCAGACTGCCTTTAACCAAGGCGCTGGAACTTGTACCCTGTCGGATTCAGGGAGAATAAGTTACACTG
GGGAGTTTAGTTTGCCTACGCATCATACTGTGCGCCTAATTCGCGTCACAGCATCACCCTCAGCATGATGAGCTGGCATT
CTTGAGACATCCAGTGTTTGAATTGGAAGGATGTGTGGTGAATGGCACTGATTGATATTGTGCCTYTAAGTCACCTATT
CAATTAGGGCGACCGTATGGGGTAATATTTAATTGGCGTGAACCATGCGGCCGAAAYT

Fig. 1G-1

```
>V7-Nsp2d324-494.seq
ATGACGTATAGGTGTTGCCTCTATGCCTTGGCATTTGTATTGTCAGGAGCTGTGACCATTGGCACAGCCCAAAACTTGCT
GCACAGAAACACCCTTCTGTGATAGCCTCCTTGAGGGGAGCTTAGGGTTTGTCCCTAGCACCTTGCTTCCGGAGTTGCAC
TGCTTTACGGTCTCTCCACCCCTTTAACCATGTCTGGGATACTGATCGGTGCACGTGTACCCCCAATGCCAGGGTGTTT
ATGCCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCTGAAGAGCCACTCCGCTGGACGTTGCCACGTGCATTCCCCACTGTTGAGTGCT
CCCCCGCCGGGGCCTGCTGGCTTTCTGCAATCTTTCCAATCGGACGAATGACCAGTGGAAACCTGAACTTCCAACAAAGA
ATGGTACGGGTCGCAGCTGAGCTTTACACAGCCGGCCAGCTCACCCCTGCAGTCTTGAAGGCTCTACAAGTTATGAACG
GGGTTGCTGCTGGTACCCCATTGTTGGACCTGTCCCTGGAGTGGCCGTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGCCTACTGTCTATGACATTGGTCATGACGCCGTCATGTATGTGGCCGAAAGGAAAGTCTCCTGGGCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTCTATGCGGGTCGAACGCCAACAC
GGCTGCCTTCCCGCTGACACTGTCCCTGAAGCCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAACAAAAAATTTTCCGGTTTGGCAGTGCACAAGTGGTACGGCGTCTGGAAAGAGACGAAGAAAAAG
CACGCTCTTGTGCGACTGCTACAGTGGCTGGCGGGCTTTGTCCGTTCGTGAAACCCGGCAGGCCAAGGAGCACGAGGTT
GCCGGCGCCAACAAGCTGAGCACCTCAAACACTACTCCCGCCTGCCGAAGGGAATTGTGGTTGGCACTGCATTTCCGC
CATCGCCAAGCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGCACAAGGGCGGTCTTGGTTGCCCAGATGCAGTCGAGGTCTCCGGATTTGACCCTGCCTGCC
TTGACCGCCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTTATCAGCCGTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGCTCAACCAGTGTCGTGCTCTGGTCCCTGTTGTGACTCAAAAGTCCTTGCCAAAAGTTCAGCCTC
GAAAAACGAAGCCTGTCAAGAGCTTGCCGGAGAGAAAGCCTGTCCCCGCCCCGCGCAGGAAGGTTGGGTCCGATTGTGGC
AGCCCGGTTTCATTAGGCCGCGATGTCCCTAACAGTTGGGAAGATTTGGCTGTTAGTAGCCCCTTTGATCTCCCGACCCC
ACCTGAGCCGGCCAACACCCTTCAAGTGAGCTGGTGATTGTGTCCTCACCGCAATGCATCTTCAGGCCGGCGACACCCTTGA
GTGAGCCGGCTCCAATTCCCGACCCTCGCGGAACTGTGTCTCGACCGGTGACACCCTTGAGTGAGCCGATCCCTGTGCCC
GGACCGCGCGTAAGTTTCAGCAGGTGAAAAGATTGAGTTCGGCGGCGGCAATCCCACCGTACCAGGACGAGCCCTGGA
TTTGTCTGCTTCCTCACAGACTGAATATGAGGCCTCTCCCCCAGCACCGCCGGCAGAGCGGGGGCGTTCTGGGAGTAGAGG
GGCATGAAGCTGAGGAAACCCTGAGTGAAATCTCGGACATGTCGGGTAACATTAAACCTGCGTCCGTGTCATCAAGCAGC
TCCTTGTCCAGCGTGAGAATCACACGCCCAAAATACTCAGCTCAAGCCATCATCGACTCGGGCGGGCCTGCAGTGGGCA
TCTCCAAGAGGTAAAGGAAACATGCCTTAGTGTCATGCCGCGAGGCATGTGATGCGACTAAGCTTGATGACCCTGCTACGC
AGGAATGGCTTTCTCGCCATGTGGATCGGGTGGACATGCTGACTTGGCGCAACACGTCTGTTTACCAGGCCGATTTGCACC
TTAGATGGCAGGTTAAAGTTCCTCCCAAAAATGATACTCGAGACACCGCCGCCCTATCCGTGTGAGTTTGTGATGATGCC
TCACGCGCTGCACCTTCCGTAGGTGCGGAGAGCGACCTTACCATTGGCTCAGTTGCTACTGAAGATGTTCCACGCATCC
TCGAGAAAATAGAAATGTCGGCGAGATGGCCAACCAGGGACCCTTGGCCTTCTCCGAGGATAAACCGGTAGATGACCAA
CTTGTCAACGACCCCCGGATATCGTCGCCGGAGGCCTGACGAGAGCACATCAGCTCCGTCCGCAGGCAGGTGGCGCCGG
CCTCTTTTACCGGATTTGCCGCCTTCAGATGGCGCGGATGCGGACGGGGGGGGCCGTTTCGGACGGTAAAAAGAAAAGCTG
AAAGGCTCTTTGACCAACTGAGCCGTCAGGTTTTGACCTCGTCTCCCATCTCCCTGTTTTCTTCTCACGCCTTTTCTAC
CCTGGCGGTGGTTATTCTCCGGGTGATTGGGTTTTGCAGCTTTTACTCTATTGTGCCTCTTTTTATGTTACAGTTACCC
AGCCTTTGGTATTGCTCCCCTCTTGGGTGTGTTTCTGGGTCTTCTCGGCGCGTTCGAATGGGGGTTTTGGCTGCTGGT
TGGCTTTTGCTGTTGGTCTGTTCAAGCCTGTGTCCGACCCAGTCGGCGCTGCTTGTGAGTTTGACTCGCCAGAGTGTAGA
AACATCCTTCATTCTTTTGAGCTTCTCAAACCTTGGGACCCTGTTCGCAGCCTTGTTGTGGGCCCCGTCGGTCTCGGTCT
```

```
CCACTCCGGTGACTGATGGGCGCTCGGTCTTGGCCACGACCATGCCCCCCGGGTTTGAGTTATATGTACCGACCATACCA
GCGTCTGTCCTTGATTACCTTGACTCTAGGCCTGACTGCCCTAAACAGCTCACAGAGCACGGCTGCGAAGATGCCGCACT
GAAAGACCTCTCTAAATATGACTTGTCCALCCAAGGCTTTGTTTTACCTGGAGTTCTTCGCCTTGTGCGGAAATACCTGT
TTGCCCATCTAGGTAAGTGGCCACCCGTTCATCGGCCTTCTACTTACCCTGCTAAGAATTCTATGGCTGGAATAAATGGG
AACAGGTTCCCAACCTAAGGACATTCAGAGCGTCCCTGAAATCGACGTTCTGTGCGCACAGGCTGTGCGAGAAAACTGGCA
AACTGTCACCCCTTGTACTCTTAAGAAACAGTATTGCGGGAAGAAGAAGACTAGGACCATACTCGGCACCAATAACTTCA
TCGCACTAGCCCACCGAGCAGTGTTGAGTGGTGTTACCCAGGGCTTCATGAAAAAGCCGTTTAACTCGCCCATCGCCCTC
GGAAAGAACAAGTTTAAGGAGCTACAGACTCCGGTCCTGGGCAGGTGCCCTTGAAGCTGATCTCGCATCCTGCGATCGATC
CACGCCTGCAATTGTCCGCTGGTTTGCGGCCAACCTTCTTTATGAACTTGCCTGTGCTGAAGAGCATCTACCGTCGTACG
TGCTGAACTGCTGCCACGACTTACTGGTCACGCAGTCGGCGCTAGTGACTAAGAGAGGTGGCCTGTCGTCTGCGACCCG
ATCACCTCTGTGTCTAACCACCATTTATAGTTGGGTGATCTATGCACAGCATATGGTGCTTAGTTACTTCAAAAGTGGTCA
CCCCCATGGCCTTCTGTTCTTACAAGACCAGCTAAGTTTGAGGACATGCTCAAGGTTCAACCCCTGATCGTCTATTCGG
ACGACCTCGTGCTGTATGCCGAGTCTCCCACCATGCCAAACTATCACTGGTGGGTTGAACATCTGAATTTGATGCTGGGG
TTTCAGACGGACCCAAAGAAGACAGCAATAACAGACTCGCCATCATTTCTAGGCTGTAGAATAATAAATGGGCGCCAGCT
AGTCCCCAACCCGTGACAGGATCCTGCGCGCCCTCGCCTATCACATGAAGGCGAGTAATGTTTCTGAATACTATGCCTCAG
CGGCTGCAATACTCATGGACAGCTGTGCTTGTTGGAGTATGATCCTGAATGGTTTGAAGAACTTGTAGTTGGAATAGCG
CAGTGCGCCGCAAGGACGGCTACAGCTTTCCCGGCACGCCGTTCTTCATGTCCATGTGGGAAAAACTCAGGTCCAATTA
TGAGGGGAAGAAGTCGAGAGTGTGCGGGTACTGCGGGGCCCTGGCCCCGTACGCTACTGCCTGTGGCCTCGACGTCTGCA
TTTACCACACCCACTTCCACCAGCATTGTCCAGTCACAATCTGGTGTGGCCATCCAGCGGGTTCTGGTTCTTGTAGTGAG
TGCAAATCCCTGTAGGGAAAGGCACAAGCCCTTTAGACGAGGGTGCTGGAACAAGTCCCGTATAAGCCCCCACGGACCGT
TATCATGCATGTGGAGCAGGGTCTCACCCCCCTTGATCCAGGTAGATACCAAACTCGCCGCGATTAGTCTCTGTCAGGC
GTGGAATTAGGGGAAATGAAGTTGGACTACCAGACGGTGATTATGCTAGCACCGCCTTGCTCCCTACCTGCAAAGAGATC
AACATGGTCGCTGTCGCTTCCAATGTATTGCGCAGCAGGTTCATCATCGGCCCACCCGGTGCTGGGAAAACATACTGGCT
CCTTCAACAGGTCCAGGATGGTGATGTTATTTACACACCAACTCACCAGACCATGCTTGACATGATTAGGGCTTGGGGA
CGTGCCGGTTCAACGTCCCGGCAGGCACAACGCTGCAATTCCCCGTCCCCTCCCGCACCGGTCCGTGGGTTCGCATCCTA
GCCGGCGGTTGGTGTCCTGGCAAGAATTCCTTCCTAGATGAAGCAGCGTATTGCAATCACCTTGATGTTTTGAGGCTTCT
TAGTAAAACTACCCTCACCTGTCTAGGAGACTTCAAGCAACTCCACCCAGTGGGTTTGATTCTCATTGCTATGTTTTTG
ACATCATGCCTCAAACTCAACTGAAGACCATCTGGAGGTTGGACAGAATATCTGTGATGCCATTCAGCCAGATTACAGG
GACAAACTCATGTCCATGGTCAACACAACCCGTGTCACCTACGTGCAAAAACCTGTCAGGTATGGGCAGGTCCTCACCCC
CTACCACAGGGACCGAGAGGACGACGCCATCACTATTGACTCCAGTCAAGGCGCCACATTCGATGTGGTTACATTGCATT
TGCCCACTAAAGATTCACTCAACAGGCAAAGAGCCCTTGTTGCTATCACCAGGGCAAGACACGCTATCTTTGTGTATGAC
CCACACAGGCAGCTGCAGGGCTTGTTTGATCTTCCTGCAAAAGGCACGCCCGTCAACCTCGCAGTGCACTGCGACGGGCA
GCTGATCGTGCTGGATAGAAATAACAAAGAATGCACGGTTGCTCAGGCTCTAGGCAACGGGGATAAATTTAGGGCCACAG
ACAAGGGTGTTGTAGATTCTCTCCGCGCCATTTGTGCTGATCTAGAAGGGTCGAGCTCTCCGCTCCCAAGGTCGCACAC
AACTTCGGATTTTATTTCTCACCTGATTTAACACAGTTTGCTAAACTCCCAGTAGAACTTGCACCTCACTGGCCGGTGGT
GTCAACCCAGAACAATGAAAAGTGGCGGATCGGCTGGTTGCCAGCCTTCGCCCTATCCATAAATACAGCCGCGCGTGCA
TCGGTGCCGGCTATATGGTGGGCCCTTCGGTGTTTCTAGGCACTCCTGGGGTCGTGTCATACTATCTGCAAAAATTTGTT
AAGGGCGGGGCTCAAGTGCTTCCTGGAGACGGTTTTCAGCACCGGCCGAATTGAGGTAGACTGCCGGGAATATCTTGATGA
TCGGGAGCGAGAACTTGCTGCGTCCCTCCCACACGGCTTTCATTGGCCACCGTCAAAGGCACTACCGTTGGAGGATGTCATC
ATGTCACCTCCAGATACCTCCGCGCGTCCTTCCTAAGGAATCAGTTGCGGTAGTCGGGGTTCAAGCCCCGGAAAAGCC
GCGAAAGCATTGTGCACACTGACAGATGTGTACCTCCCAGATCTTGAAGCCTATCTCCACCCGGAGACCCAGTGCAAGTG
CTGGAAAATGATGTTGGACTTCAAAGAAGTTGACTAATGGTCTGGAAAGACAAAACAGCCTATTTCCAACTTGAAGGTC
GCTATTTCACCTGGTATCAGCTTGCCAGCTATGCCTCGTACATCCGTGTTCCGTCAACTCTACGGTGTACTTGGACCCC
TGCATGGGCCCCAGCCCTTTGCAACAGGAGAGTCGTCGGGTCCACCCACTGGGGGCTGACCTCGCGGTCACCCCTTATGA
TTACGGCGCTAAAATTATCCTGTCTAGCGCGTACCACCTGGGGGTTTGAACCCCGGATACAAAATTCTGGCGTGCGCGGAGT
TCTCGTTGGATGACCCAGTTAAGTACAAACATACCTGGGGGTTTGAATCGGATACAGCGTATCTGTATGAGTTCACCGGA
AACGGTGAGGACTGGGAGGATTACAATGATGCGTTTCGTGCGCGCCAGGAAGGGAAAATTTATAAGGCCACTGCCACCAG
CTTGAAGTTTTATTTTCCCCCGGGCCCTGTCATTGAACCAACTTTAGGCCTGAATTGAAATGAAATGGGGTCCATGCAAA
GCCTTTTTGACAAAATTGGCCAACTTTTTTGTGGATGCTTTCCACGGAGTTCTTGGTGTCCATTGTTGATATCATTATATTT
TTGGCCATTTGTTTGGCTTGAGCATCGGCGGTTGGCTGGTGGTCTTTTGCATCAGATTGGTTTGCTCGCGGATACTCCG
```

*Fig. 1G-4*

```
TAGGCGCCTGCCATTCACTCTGAGCAATTACAGAAGATCTTATGAGGCCTTTCTTTCCCAGTGCCAAGTGGACATTCCC
ACCTGGGAACTAAACATCCTTTGGGGATGCTTTGGCACCATAAGGTGTCAACCCTGATTCATGAAATGGTGTCGCGTCG
AATGTACCGCATCATGGAAAAGCAGGGCAGGCTGCCTGGAAACAGGTGGTGAGCGAGGCTACGCTGTCTCGGATTAGTA
GTTTGCATGTGGTCGCTCATTTTCAGCATCTAGCCGCCATTGAAGCCGAGACCTGTAAATATTTGGGCTCCCGGCTGCCC
ATGCTACACAACCTCCGCATGACAGGGTCAAATGTAACCATAGTGTATAATAGCACTTTTGAATCAGGTGTTTGCTATTTT
TCCAACCCCTGGTTCCCGGCCAAAGCTTCATGATTTTCAGCAATGGTTAATAGCTGTACATTCCTCCATATTTTCCTCTG
TTGCAGCTTCTTGTACTCTTTTTGTTGTGCTGTGGTTGCGGGTTCCAATACTACGTACTGTTTTTGGTTTCCGCTGGTTA
GGGGCAATTTTTCTTTCGAACTCACAGTGAATTACACGGTGTGTCCACCTTGCCTCACCCGGCAAGCAGCCACAGAGATC
TACGAACCCGGTAGGTCTCTTTGGTGCAGGATAGGGTATGACCGATGTGGGGAGGACGATCATGACGAGCTAGGGTTTAT
GATACCGCCTGCCCTCTCCAGCGAAGGCCACTTGACTGGTGTTTACGCCTGGTTGGCGTTCTTGTCCTTCAGCTACACGG
CCCAGTTCCATCCCGAGATATTCGGGATAGGCAATGTGAGTCGACTTTATGTTGACATCAAACATCAACTCATCTGCGCC
GAACATGACGGGCAGAACACCACCTTGCCTCGTCATGACAACATTTCAGCCGTGTTTCAGACCTATTACCAACATCAAGT
CGACGTCGGCAATTGGTTTCACCTAGAATGGCTTCGTCCCTTCTTTTCCTCGTGGTTGGTTTTAAATGCTCTTGGTTTC
TCAGGCGTTCGCCTGCAAACCATGTTTCAGTTCGAGTCTTGCAGATATTAAGGACCAACACCACCGCAGCGGCAAGCTTTG
CTGTCCTCCAAGACATCAGTTGCCTTAGGCATCGCGACTCGGCCTCTGAGGCGGATTCGCAAAATCCCTCAGTGCCGTACG
GCGATAGGGACACCCGTGTATGTTACCATCACAGCCAATGTGACAGATGAGAATTATTTACATTCTTCTGATCTCCTCAT
GCTTTCTTCTTGCCTTTTCTATGCTTCTGAGATGAGTGAAAAGGGATTTAAGGTGGTATTTGGCAATGTGTCAGGCATCG
TGCTGTGTGTGTCAATTTTACCAGCTACGTCCAACATGTCAAGGAGTTTACCCAACGCTCCCTGGTGGTCGACCATGTG
CGGTTGCTCCATTTCATGACACCTGAGACCATGAGGTGGGCAACTGTTTTAGCCTGTCTTTTTGCCATTCTGTTGGCAAT
TTGAATGTTAAGTATGTTGGAGAAATGCTTGACCGCCGGCTGTTGCTCGCGATTGCTTTCTTTGTGGTGTATCGTGCCG
TTCTGTTTTGCTGTGCTCGCCAACGCCAGCAACGACAGCAGCTCCCATCTACAGCTGATTTACAACTTGACGCTATGTGA
GCTGAATGCACAGATTGGCTAGCTAACAAATTTGATTGGGCAGTGGAGAGTTTTGTCATCTTTCCCGTTTGACTCACA
TTGTCTCCCTATGGTGCCTCACTACCAGCCATTTCCTTGACACAGTCGCTTTAGTCACTGTGTCTACCGCCGGGTTTGTT
CACGGGCGGTATGTCCTAAGTAGCATCTACGCGGTCTGTGCCCTGGCTGCCGTTGACTTGCTTCGTCATTAGGTTTGCAAA
GAATTGCATGCCTGGCGCTACGCCGTGTACCAGATATACCAACTTTCTTCTGGACACTAAGGCCAGACTCTATCGTTGGC
GGTCGCCTGTCATCATAGAGAAAAGGGCAAAGTTGAGGTCGAAGGTCATCTGATCGACCTCAAAAGAGTTGTGCTTGAT
GGCTCCGTGGCAACCCCTATAACCAGAGTTTCAGCGGAACAATGGGGTCGTCCTTAGATGACTTCTGTCACGATAGCACG
GCTCCACAAAAGGTGCTTTTGGCGTTTTCTATTACCTACACGCCAGTGATGATATATGCCCTAAAGGTGAGTCGCGGCCG
ACTGCTAGGGCTTCTGCACCTTTTGATCTTCCTGAATTGTGCTTTCACCTTCGGGTACATGACTTCGCGCACTTTCAGA
GTACAAATAAGCTCGCGCTCACTATGGGAGCAGTAGTTGCACTCCTTTGGGGGGTGTACTCAGGCATAGAAACCTGGAAA
TTCATCACCTCCAGATGCCGTTTGTGCTTGCTAGGCCGCAAGTACATTCTGGCCCCTGCCCACCACGTTGAAAGTGCCGC
AGGCTTTCATCCGATTGCGGCAAATGATAACCACGCATTTGTCGTCCGGCGTCCCGGCTCCACTACGGTCAACGGCACAT
TGGTGCCCGGGTTAAAAAGCCTCGTGTTGGGTGGCAGAAAAGCTGTTAAACAGGGAGTGGTAAACCTTGTCAAATATGCC
AAATAACAACGGCAAGCAGCAGAAGAGAAAGAAGGGGGATGGCCAGCCAGTCAATCAGCTGTGCCAGATGCTGGGTAAGA
TCATCGCTCAGCAAACCAGTCCAGAGGCAAGGGACCGGGAAAGAAAATAAGAAGAAAAACCGGAGAAGCCCCATTTT
CCTCTAGCGACTGAAGATGATGTCAGACATCACTTTACCCCTAGTGAGCGGCAATTGTGTCTGTCGTCAATCCAGACCGC
CTTTAATCAAGGCGCTGGGACTTGCACCCTGTCAGATTCAGGGAGGATAAGTTACACTGTGGAGTTTAGTTTGCCTACGC
ATCATACTGTGCGCCTGATCCGCGTCACAGCATCACCCTCAGCATGATGGGCTGGCATTCTTGAGGCATCTCAGTGTTTG
AATTGGAAGAATGTGTGGTGAATGGCACTGATTGACATTGTGCCTCTAAGTCACCTATTCAATTACGGCGACCGTGTGGG
GCTGAGATTTAATTGGCGAGAACCATGCGGCCGAAATTAAAAAAAA
```

TTCATCGGCCTTCTACTTACCCTGCTAAGAATTCTATGGCTGGAATAAATGGGAACAGGTTCCCAACCAAGGACATTCAG
AGCGTCCCTGAAATCGACGTTCTGTGCGCACAGGCTGTGCGAGAAAACTGGCAAACTGTCACCCCTTGTACTCTTAAGAA
ACAGTATTGCGGGAAGAAGAAGACTAGGACCATACTCGGCACCAATAACTTCATCGCACTAGCCCACCGAGCAGTGTTGA
GTGGTGTTACCCAGGGCTTCATGAAAAGGCGTTTAACTCGCCCATCGCCCTCGGAAAGAACAAGTTTAAGGAGCTACAG
ACTCCGGTCCTGGGCAGGTGCCTTGAAGCTGATCTCGCATCCTGCGATCGATCCACGCCTGCAATTGTCCGCTGGTTTGC
CGCCAACCTTCTTTATGAACTTGCCTGTGCTGAAGAGGATCTAGCGTCGTACGTGCTGAACTGCTGCCACGACTTACTGG
TCACGCAGTCCGGCGCAGTGACTAAGAGAGGTGGCCTGTCGTCTGGGCGACCCGATCACCTCTGTGTCTAACACCATTTAT
AGTTTGGTGATCTATGCACAGCATATGGTGCTTAGTTACTTCAAAAGTGGTCACCCCATGGCCTTCTGTTCTTACAAGA
CCAGCTAAAGTTTGAGGACATGCTCAAGGTTCAACCCCTGATCGTCTATTCGGACGACCTCGTGCTGTATGCCGACTCTC
CCACCATGCCAAACTATCACTGGTGGGTTGAACATCTGAATTTGATGCTGGGGTTTCAGACGGACCCAAAGAAGACAGCA
ATAACAGACTCGCCATCATTTCTAGGCTGTAGAATAATAAATGGGCGCCAGCTAGTCCCCAACCGTGACAGGATCCTCGC
GGCCCTCGCCTATCACATGAAGGCGAGTAATGTTTCTGAATACTATGCCTCAGCGGCTGCAATACTCATGGACAGCTGTG
CTTGTTTGGAGTATGATCCTGAATGGTTTGAAGAACTTGTAGTTGGAATAGCGCAGTGCGCCTGCAAGGACGGCTACAGC
TTTCCCGGCACGCCGTCTTCATGTCCATGTGGAAAAACTCAGGTCCAATTATGAGGGAAGAAGTCGAGAGTGTGCGG
GTACTGCGGGGCCCCGGCCCCGTACGCTACTGCCTGTGGCCTCGACGTCTGCATTTACCACACCCACTTCCACCAGCATT
GTCCAGTCACAATCTGGTGTGGCCATGCAGCGGGTTCTGGTTCTTGTAGTGAGTGCAAATCCCCTGTAGGGAAAGGCACA
AGCCCTTTAGACGAGGTGCTGGAACAAGTCCCGTATAAGCCCCCACGGACCGTTATCATGCATGTGGAGCAGGGTCTCAC
CCCCCCTTGATCCAGGTAGATACCAAACTGCCGCGGATTAGTCTCTGTCAGGCGTGGAATTACGGGAAATGAAGTTGGAC
TACCAGACGGTGATTATGCTAGCACCGCCTTGCTCCCTACCTGCAAAGAGATCAACATGGTCGCTGTCGCTTCCAATGTA
TTGCGCAGCAGGTTCATCATCGGCCCACCCGGTGCTGGGAAAACATACTGGCTCCTTCAACAGGTCCAGGATGGTGATGT
TATTTACACACCAACTCACCAGACCATGCTTGACATGATTAGGGCTTGGGGACGTGCCGGTTCAACGTCCCGGCAGGCA
CAACGCTGCAATTCCCCGTCCCTCCCGCACCGGTCCGTGGGTTCGCATCCTAGCCGGCGGTTGGTGTCCTGGCAAGAAT
TCCTTCCTAGATGAAGCAGCGTATTGCAATCACCTTGATGTTTGAGGCTTCTTAGTAAAACTACCCTCACCTGTCTAGG
AGACTTCAAGCAACTCCACCCAGTGGGTTTTGATTCTCATTGCTATGTTTTGACATCATGCCTCAAACTCAACTGAAGA
CCATCTGGAGGTTTGGACAGAATATCTGTGATGCCATTCAGCCAGATTACAGGGACAAACTCATGTCCATGGTCAACACA
ACCCGTGTGACCTACGTGGAAAAACCTGTCAGGTATGGCCAGGTCCTCACCCCCTACCACAGGGACCGAGAGGACGACGC
CATCACTATTGACTCCAGTCAAGGCGCCACATTCGATGTGGTTACATTGCATTTGCCCACTAAAGATTCACTCAACAGGC
AAAGAGCCCTTGTTGCTATCACCAGGGCAAGACACGCTATCTTTGTGTATGACCCACACAGGCAGCTGCAGGGCTTGTTT
GATCTTCCTGCAAAAGGCACGCCGTCAACCTCGCAGTGCACTGCGACGGGCAGCTGATCGTGCTGGATAGAAATAACAA
AGAATGCACGGTTGCTCAGGCTCTAGGCAACGGGGATAAATTTAGGGCCACAGACAAGCCGTGTTGTAGATTCTCTCCGCG
CCATTTGTGCTGATCTAGAAGGGGTCGAGCTCTCCGCTCCCAAGGTCGCACACAACTTGGGATTTTATTTCTCACCTGAT
TTAACACAGTTGCTAAACTCCAGTAGAACTTGCACCTCACTGGCCCGTGGTGTCAACCCAGAACAATGAAAAGTGGCC
GGATCGGCTGGTTGCTAGCCTTGCCCTATCCATAAATACAGCCGCGCGTGCATCGGTGCCGGCTATATGGTGGGCCCTT
CGGTGTTCTAGGCACTCCTGGGGTCGTGTCATACTATCTCACAAAATTTGTTAAGGGCGGGGCTCAAGTGCTTCCGGAG
ACGGTTTTCAGCACCGGCCGAATTGAGGTAGACTGCCGGGAATATCTTGATGATCGGGAGCGAGAAGTTGCTGCGTCCCT
CCCACACGCTTTCATTGGCGACGTCAAAGGCACTACCGTTGGAGGATGTCATCATGTCACCTCCAGATACCTCCCGCGCG
TCCTTCCCAAGGAATCAGTTGCGGTAGTCGGGGTTTCAAGCCCCGGAAAAGCCGCGAAAGCATTGTGCACACTGACAGAT
GTGTACCTCCCAGATCTTGAAGCCTATCTCCACCCGGAGACCCAGTCCAAGTGCTGGAAAATGATGTTGGACTTCAAAGA
AGTTCGACTAATGGTCTGAAAGACAAAACAGCCGTATTTCAACTTGAAGGTCGCTATTTCACCTGGTATCAGCTTGCCA
GCTATGCCTCGTACATCCGTGTTCCGTCAACTCTACGGTGTACTTGGACCCCTGCATGGGCCCGGCCCTTTGCAACAGG
AGAGTCGTCGGGTCCACCCACTGGGGGCTGACCTCGCGGTCACCCCTTATGATTACGGCGCTAAAATTATCCTGTCTAG
CGCGTACCATGGTGAAATGCCCCCCGGATACAAAATTCTGGCGTGCGCGGAGTTCTCGTTGGATGACCCAGTTAAGTACA
AACATACCTGGGCGTTTGAATCGGATACAGCGGTATCTGTATGAGTTCACCGGAAACGGTGAGGACTGGGAGGATTACAAT
GATGCCTTTCGTCGCGCGCCAGGAAGGGAAAATTTATAAGGCCACTGCCACCAGCTTGAAGTTTTATTTTCCCCGGGCCC
TGTCATTGAACCAACTTTAGGCCTGAATTGAAATGAAATGGGGTCCATGCAAAGCCTTTTTGACAAAATTGGCCAACTTT
TTGTGGATGCTTTCACGGAGTTCTTGGTGTCCATTGTTGATATCATTATATTTTTGGCCATTTGTTTGGCTTCACCATC
GCCGGTTGGCTGGTGGTCTTTTGCATCAGATTGGTTTGCTCCGCGATACTCCGTACGCGCCCTGCCATTGACTCTGAGCA
ATTACAGAACATCTTATGAGGCCTTTCTTTCCCAGTGCCAAGTGGACATTCCCACCTGGGGAACTAAACATCCTTTGGGG
ATGCTTTGGCACCATAAGGTGTCAACCCTGATTGATGAAATGGTGTCGCGTCAATGTACTGCATCATGGAAAAAGCAGG
GCAGGCTGCCTGGAAACAGGTGGTGAGCGAGGCTACGCTGTCTCGCATTAGTAGTTTGGATGTGGTGCTCATTTTCAGC

*Fig. 1H-4*

ATCTAGCCGCCATTGAAGCCGAGACCTGTAAATATTTGGCCTCCCGGCTGCCCATGCTACACAACCTGCGCATGACAGGG
TCAAATGTAACCATAGTGTATAATAGCACTTTGAATCAGGTGTTTGCTATTTTTCCAACCCCTGGTTCCCGGCCAAAGCT
TCATGATTTTCAGCAATGGTTAATAGCTGTACATTCCTCCATATTTTCCTCTGTTGCAGCTTCTTGTACTCTTTTGTTG
TGCTGTGGTTGCGGGTTCCAATACTACGTACTGTTTTTGGTTCCGCTGGTTAGGGGCAATTTTTCTTTCGAACTCACAG
TGAATTACACGGTGTGTCCACCTTGCCTCACCGGCAAGCAGCCACAGAGATCTACGAACCCGGTAGGTCTCTTTGGTGC
AGGATAGGGTATGACCGATGTGGGGATGACGATCATGACGAGCTAGGGTTTATGATACCGCCTGGCCTCTCCAGCGAAGC
CCACTTGACTGGTGTTTACGCCTGGTTGGCGTTCTTGTCCTTCAGCTACACGGCCCAGTTCCATCCGAGATATTCGGGA
TAGGGAATGTGAGTCGAGTTTATGTTGACATCAAACATCAACTCATCTGCGCCGAACATGACGGGCAGAACACCACCTTC
CCTCGTCATGACAACATTTCAGCCGTGTTTCAGACCTATTACCAACATCAAGTCGACGGCGGCAATTGGTTTCACCTAGA
ATGCCTTCGTCCCTTCTTTTCCTCGTCGTTGGTTTTAAATGTCTCTTGGTTTCTCAGGCGTTCGCCTGCAAACCATGTTT
CAGTTCGAGTCTTCCAGATATTAAGATCAACAGCACTGCAGCGGCAAGCTTTGCTGTCCTCCAAGACATCAGTTGCCTTA
GGCATCGCGACTCCGCCCTCTGAGGCGATTCGCAAAATCCCTCAGTGCCGTACGGCGATAGGGACACCGCTGTATGTTACC
ATCACAGCCAATGTGACAGATGAGAATTATTTACATTCTTCTGATCCCTCATGCTTTCTTCTTGCCTTTTCTATGCTTC
TGAGATGAGTGAAAAGGGATTTAAGGTGGTATTTGGCAATGTGTCAGGCATCGTGGCTGTGTGTGTCAATTTTACCAGCT
ACGTCCAACATGTCAAGGAGTTTACCCAACGCTCCCTGGTGGTCGACCATGTGGGGTTGCTCCATTTCATGACACCTGAG
ACCATGAGGTGGGCAACTGTTTTAGCCTGTCTTTTGCCATTCTGTTGGCAATTTGAATGTTTAAGTATGTTGGACAAAT
GCTTGACCGCGGGCTGTTGCTCGCGATTGCTTTCTTTGTGGGTGTATCGTGCCGTTCTGTTTTGCTGTGCTCGCCAACGCC
AGCAAGCACAGCAGCTCCCATCTACAGCTGATTTACAACTTGACGCTATGTGAGCTGAATGGCACAGATTGGCTAGCTAA
CAAATTTGATTGGGCAGTGGAGAGTTTTGTCATCTTTCCCGTTTTGACTCACATTGTCTCCTATGGTGCCCTCACTACCA
GCCATTTCCTTGACACAGTCGCTTTAGTCACTGTGTCTACCGCCGGGTTTGTTCACGGGCGGTATGTCCTAAGTAGCATC
TACGCGGTCTGTGCCCTGGCTGCGTTGACTTGCTTCGTCATTAGGTTTGCAAAGAATTGCATGTCCTGGCGCTACGGCGTG
TACCAGATATACCAACTTTCTTCCGACACTAAGGGCAGACTCTATCGTTGGCGGTCGCCTGTCATCATAGAGAAAAGGG
GCAAAGTTGAGGTCGAAGGTCATCTGATCGACCTCAAAAGAGTTGTGCTTGATGGCTCCGTGGCAACCCCTATAACCAGA
GTTTCAGCGGAACAATGGGGTCGTCCTTAGATGACTTCTGTCACGATAGCACGGCTCCACAAAAGGTGCTTTTGGCGTTT
TCTATTACCTACACGGCCAGTGATGATATATGCCCTAAAGGTGAGTCGCGGCCGACTGCTAGGGCTTCTGCACCTTTTGAT
CTTCCTGAATTGTGCTTTCACCTTCGGTACATGACTTTCGCGCACTTTCAGAGTACAAATAAGGTCGCGCCTCACTATGG
GAGCAGTAGTTGCACTCCTTTTGGGCGGTGTACTCAGCCATAGAAACCTGAAATTCATCACCTCCAGATGCCGTTTGTGC
TTGCTAGGCCGCAAGTACATTCTGGCCCCTGCCCACCACGTTGAAAGTGCCGCAGGCTTTCATCCGATTGCGGCAAATGA
TAACCACGCATTTGTCGTCCGGCGTCCCGGCTCCACTACGGTCAACGGCACATTGGTGCCCGGGTTAAAAAGCCTCGTGT
TGGGTGGCAGAAAAGCTGTTAAACAGGGAGTGGTAAACCTTGTCAAATATGCCAAATAACAACGGCAAGCAGCAGAAGAG
AAAGAAGGGGGATGGCCAGCCAGTCAATCAGCTGTGCCAGATGCTGGGTAAGATCATCGCTCAGCAAAACCAGTCCAGAG
GCAAGGGACCGGGAAAGAAAAATAAGAAGAAAAACCCGGAGAAGCCCCATTTTCCTCTAGCGACTGAAGATGATGTCAGA
CATCACTTTACCCCTAGTGAGCGGCAATTGTGTCTGTCGTCAATCCAGACCGCCTTTAATCAAGGCGCTGGGACTTGCAC
CCTGTCAGATTCAGGGAGGATAAGTTACACTGTTGAGTTTAGTTTGCCTACGCATCATACTGTGCGCCTGATCCGCGTCA
CAGCATCACCCTCAGCATGATGGGCTGCATTCTTGAGGCATCTCAGTGTTTGAATTGGAAGAATGTGTGGTGAATGGCA
CTGATTGACATTGTGCCTCTAAGTCACCTATTCAATTAGGGCGACCGTGTGGGGGTGAGATTTAATTGCGAGAACCATG
CGGCCGAAATTAAAAAAAA

*Fig. 11-1*

>V7-Nsp2d543-632.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTGCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTGCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCACACGCCCAAAATACTCAGCTCAAGCCATCATCGACTCGGGCGGGCCCTGCAGTGGGCATCTCCAAGAGGTAAAGG
AAACATGCCTTAGTGTCATGCGCGAGGCATGTGATGCGACTAAGCTTGATGACCCTGCTACGCAGGAATGGCTTTCTCGC
ATGTGGGATCGGGTGGACATGCTGACTTGGCGCAACACGTCTGTTTACCAGGCGATTTGCACCTTAGATGGCAGGTTAAA
GTTCCTCCCAAAAATGATACTCGAGACACCGCCGCCCTATCCGTGTGAGTTTGTGATGATGCCTCACACGCCTGCACCTT
CCGTAGGTGCGGAGAGCGACCTTACCATTGGCTCAGTTGCTACTGAAGATGTTCCACGCATCCTCGAGAAAATAGAAAAT
GTCGGCGAGATGGCCAACCAGGGACCCTTGGCCTTCTCCGAGGATAAACCGGTAGATGACCAACTTGTCAACGACCCCCG
GATATCGTCGCCGAGGCCTGACGAGAGCACATCAGCTCCGTCCGCAGGCACAGGTGGCGCCGGCTCTTTTACCGATTTGC
CGCCTTCAGATGGCGCGGATGCGGACGGGGGGCGGCCGTTTCGGACGGTAAAAAGAAAAGCTGAAAGGCTCTTTGACCAA
CTGAGCCGTCAGGTTTTTGACCTCGTCTCCCATCTCCCTGTTTTCTTCTCACGCCTTTTCTACCCTGGCGGTGGTTATTC
TCCGGGTGATTGGGGTTTTGCAGCTTTTACTCTATTGTGCCTCTTTTTATGTTACAGTTACCCAGCCTTTGGTATTGCTC
CCCTCTTGGGTGTGTTTTCTGGGTCTTCTCGGCGCGTTCGAATGGGGGTTTTTGGCTGCTGGTTGGCTTTTGCTGTTGGT
CTGTTCAAGCCTGTGTCCGACCCAGTCGGCGCTGCTTGTGAGTTTGACTCGCCAGAGTGTAGAAACATCCTTCATTCTTT

*Fig. 11-2*

```
TGAGCTTCTCAAACCTTGGGACCCTGTTCGCAGCCTTGTTGTGGGCCCGTCGGTCTGGTCTTGCCATTCTTGGCAGGT
TACTGGCCGGGGCACGCTGCATCTGGCACTTTTTGCTTAGGCTTGGCATTGTTGCAGACTGTATCTTGGCTGGAGCTTAC
GTGCTTTCTCAAGGTAGGTGTAAAAAGTGCTGGGGATCTTGTATAAGAACTGCTCCCAATGAGGTCGCTTTTAACGTGTT
TCCTTTCACACGTGCGACCAGGTCGTCACTTATCGACCTGTGCGATCGGTTTTGTGCGCCAAAAGGAATGGACCCCATTT
TTCTCGCCACTGGGTGGGCGGGTGCTGGGCCGGCCGAAGCCCCATTGAGCAACCCTCTGAAAAACCCATCGCGTTTGCC
CAGTTGGATGAAAAGAAGATTACGGCTAGGACTGTGGTCGCCCAGCGCTTATGACCCCAACCAAGCCGTAAAGTGCTTGCG
GGTATTGCAGGCGGTGGGCGATGGTGCTAAGGCGGTCCCAAAAGTGGTCAAGGTTTCCGCTGTTCCATTCCGAGCCC
CCTTCTTCCCACTGGAGTGAAAGTTGACCCTGATTGCACGGTCGTGGTTCACCCTGACACTTTCACTGCAGCTCTCCGG
TCTGGCTACTCCACCACAAACCTCGTCCTTGGTGTGGGGACTTTGCCCAGCTGAATGGATTAAAAATCAGGCAAATTTC
CAAGCCTTCAGGGGGAGGCCCACATCTCATGGCTGCCCTGCATGTTGCCTGCTTGATGGCTCTGCACATGCTTGCTGGGA
TTTATGTGACTGCGGTGGTTCTTGCGGCACCGGCACGAACGACCCGTGGTGCGCTAACCCGTTGCCGTCCCTGGCTAC
GGACCTGGCTCTCTCTGCACGTCCAGATTGTGCATTTCCCAACACGGCCTTAGCCTGCCCTTGACAGCACTTGTGGCGGG
ATTCGGTATTCAAGAAATTGCCTTGGTCGTTTTGATTTTTGTTTCCATCGGAGGCATGGCTCATAGGTTGAGCTGTAAGG
CTGACATGCTGTGTGTCTTGCCTTGCAATTGCCAGCTATGTTTGGGTACCTCTTACCTGGTTGCTTGTGTGTTTCCTTGC
TGGTTGCGCTGTTTTTCTTTGCACCCCCTCACCATCCTATGGTTGGTGTTTTTCTTGATTTCTGTGAATATGCCTTCAGG
AATCTTGGCCATGCTGTTGTTGGTTTCTCTTTGGCTTCTTGGTCGTTATACTAATGTTGCTGGCCTTGTCACCCCCTACG
ACATTCATCATTACACCAGTGGCCCCCGCGGTGTTGCCGCCTTGGCTACCGGACCAGATGGGACCTACTTGGCCGCTGTC
CGCCGCGCTGCGTTGACTGGCCGCACCATGCTGTTTACCCCGTCCCAGCTTGGGTCTCTTCTTGAGGGTGCTTTCAGAAC
TCGAAAGCCCTCACTGAACACCGTAATGTGATCGGGTCCTCCATGGGCTCTGGCGGGGTGTTTACCATCGACGGGAAAG
TCAAGTGCGTAACTGCCGCACATGTCCTTAGGGGCAATTCAGCTCGGGTTTCCGGGGTCGGCTTCAATCAAATGCTTGAC
TTTGACGTAAAGGGAGATTCGCTATAGCTGATTGCCCGAATTGGCAGGGCTGCCCCCAAGACCCAATTCTGCACGGA
TGGATGGACTGGCCGTGCTATTGGCTAACATCCTCTGGCGTCGAACCCGGCGTCATTGGAAAAGGATTCGCCTTCTGCT
TCACCGCATGTGGCGATTCCGGGTCCCCAGTGATCACCGAGGCCGGTGAGCTTGTCGGCGTTCACACGGGATCGAATAAA
CAAGGGGGGGGCATTGTTACGCGCCCCTCAGGCCAGTTTTGTAATGTGGCACCCATCAAGCTAAGCGAATTAAGTGAATT
CTTTGCTGGGCTAAGGTCCCGCTCGGTGATGTGAAGGTCGGCAGCCACATAATTAAAGACATAAGCGAGGTGCCTTCAG
ATCTTTGTGCCTTGCTTGCTGCCAAACCTGAACTGGAAGGAGGCCTCTCCACCGTCCAACTTCTTTGTGTGTTTTTCTC
CTGTGGAGAATGATGGGACATGCCTGGACGCCCTTGGTTGCTGTGAGTTTCTTTATTTTGAATGAGGTTCTCCCAGCCGT
CCTGGTCCGGAGTGTTTCTCCTTTGGAATGTTTGTGCTATCCTGGCTCACGCCATGGTCTGCGCAAGTTCTGATGATCA
GGCTTCTGACAGCAGCTCTTAACAGGAACAGATGGTCACTTGCCTTTTTCAGCCTCGGTGCAGTGACCGGTTTTGTCGCA
GATCTTGCGGCCACTCAGGGGCATCCGTTGCAGGCAGTGATGAATTTGAGCACCTATGCATTCCTGCCTCGGATGATGGT
TGTGACCTCACCAGTCCCAGTGATCACGTGTGGTGTCGTCGACCTACTTGCCATCATTTTGTACTTGTTTAAGTACCGTG
GCCTGCACCATATCCTTGTTGCCGATGGAGTGTTCTCTGCCGCTTTCTTCTTGAGATACTTTGCCGAGGGAAAGTTGAGG
GAAGGGGTGTCGCAATCCTCCGGAATGAATCATGAGTCTCTGACTGGTGCCCTCGCTATGCAGACTCAATGACGAGGACTT
GGATTTCCTTATGAAATGGACTGATTTTAAGTGCTTTGTTTCTGCGTCCAACATGAGGAATGCAGCGGGTCAATTTATCG
AGGCTGCCTATGCTAAAGCACTTAGAGTAGAACTGGCCCAGTTGGTGCAGGTTGATAAAGTTCGAGGTACTTGGCCAAA
CTTGAAGCTTTTGCTGATACCGTGGCACCTCAACTCTCGCCCGGTGACATTGTTGTCGCTCTCGGCCACACGCCTGTTGG
CAGTATCTTCGACCTAAAGGTTGGTAGCACCAAGCATACCCTCCAAGCCATTGAGACCAGAGTCCTTGCTGGGTCCAAAA
TGACCGTGGGCGCCGTCGTCGACCCGACCCCCACGCCCCCACCCGCACCCGTGCCCATCCCCTCCCACCGAAAGTTCTG
GAGAATGCCCCAACGCTTGGGGGATGAGGACCGTTTGAATAAGAAGAGAGGCGCAGGATGGAAGCCCTCGGCATCTA
TGTTATGGGCGGGAAAAAATACCAGAAATTTTGGGACAAGAATTCCGGTGATGTGTTTATGAGGAGGTCCATAATAACA
CAGATGAGTGGGAGTGTCTCAGAGTTGGCGACCCTGCCGACTTTGACCCTGAGAAGGGAACTCTGTGTGGACATGTCACC
ATTGAAAACAAGGCTTACCATGTTTACACCTCCCCATCTGGTAAGAAGTTCTTGGTCCCCGTCAACCCAGAGAATGGAAG
AGTCCAATGGGAAGCTGCAAAGCTTTCCGTGGAGCAGGCCCTAGGTATGATGAATGTCGACGGCGAACTGACTGCCAAAG
AACTGGAGAAACTGAAAAGAATAATTGACAAACTCCAGGGCCTGACTAAGGAGCAGTGTTTAAACTGCTAGCCGCCAGCG
ACTTGACCCGCTGTCGTCGCGGCGGCTTGGTTGTTACTGAAACAGCGGTAAAAATAGTCAAATTTCACACCGGACCTTC
ACCCTGGGACCTGTGAATTTAAAAGTCGGCCAGTGAGGTTCAGCTAAAAGACGCCGGTTGAGCACAACCAACACCCGGTTGC
GAGACCGATCGATGGTGGAGTTGTGCTCCTGCGTTCCGCGGTTCCTTGGCTTATAGACGTCTTGATCTCCGGTGCTGATG
CATCTCCCAAGTTACTTGCCCATCACGGGCCGGAAACACTGGGATCGATGGCACGCTCTGGGATTTTGAGTCCGAAGCC
ACTAAAGAGGAAGTCTCCACTCAGTGCGCAAATAATACAGGCTTGTGACATTAGGCGCGGCGACGCTCCTGAAATTGGTCT
CCCTTACAAGCTGTACCCTGTTAGGGGGTAACCCTGAGCGGGTGAAAGGAGTTCTGCAGAATACAAGGTTTGGAGACATAC
```

CTTCACCATCGCCGGTTGGCTGGTGGTCTTTTTGCATCAGATTGGTTTGCTCCGCGATACTCCGTACGCGCCCTGCCATTC
ACTCTGAGCAATTACAGAAGATCTTATGAGGCCTTTCTTTCCCAGTGCCAAGTGGACATTCCCACCTGGGGAACTAAACA
TCCTTTGGGGATGCTTTGGCACCATAAGGTGTCAACCCTGATTGATGAAATGGTGTCGCGTCGAATGTACCGCATCATGG
AAAAAGCAGGGCATGCTGCCTGGAAACAGGTGGTCAGCGAGGCTACGCTGTCTCGCATTAGTAGTTTGGATGTGGTGGCT
CATTTTCAGCATCTAGCCGCCATTGAAGCCGAGACCTGTAAATATTTGGCCTCCCGGCTGCCCATGCTACACAACCTGCG
CATGACAGGGTCAAATGTAACCATAGTGTATAATAGCACTTTGAATCAGGTGTTTGCTATTTTTCCAACCCCTGGTTCCC
GGCCAAAGCTTCATGATTTTCAGCAATGGTTAATAGCTGTACATTCCTCCATATTTTCCTCTGTTGCAGCTTCTTGTACT
CTTTTTGTTGTGCTGTGGTTGCGGGTTCCAAATACTACGTACTGTTTTGGTTTCCGCTGGTTAGGGGCAATTTTCTTTC
GAACTCACAGTGAATTACACGGTGTGTCCACCTTGCCTCACCGGCAAGCAGCCACAGAGATCTACGAACCCGGTAGGTC
TCTTTGGTGCAGGATAGGGTATGACGGATGTGGGGAGGACGATCATGACGAGCTAGGGTTTATGATACGGCCTGGCCTCT
CCAGCGAAGGCCACTTGACTGGTGTTACGCCTGGTTGGCGTTCTTGTCCTTCAGCTACACGGCCCAGTTCCATCCCGAG
ATATTCGGGATAGGGAATGTGAGTCGAGTTTATGTTGACATCAAACATCAACTCATCTGCGCCGAACATGACGGGCAGAA
CACCACCTTGCCTCGTCATGACAACATTTCAGCCGTGTTTCAGACCTATTACCAACATCAAGTCGACGGCGGCAATTGGT
TTCACCTAGAATGGCTCGTCCCTTCTTTTCCTCGTGGTTGGTTTAAATGTCTCTTGGTTTCTCAGGCGTTCGCCTGCA
AACCATGCTTCAGTTCGAGTCTTGCAGATATTAAGACCAACACCACCGCAGCGGCAAGCTTTGCTGTCCTCGAAGACATC
AGTTGCCTTAGGCATCGCGACTCGGCCTCTGAGGCGATTCGCAAAATCCCTCAGTGCCGTACGGCGATAGGGACACCCGT
GTATGTTACCATCACAGCCAATGTGACAGATGAGAATTATTTACATTCTTCTGATCTCCTCATGCTTTCTTCTTGCCTTT
TCTATGCTTCTGAGATGAGTGAAAAGGGATTTAAGGTGGTATTTGGCAATGTGTCAGGCATCGTGGCTGTGTGTGTCAAT
TTTACCAGCTACGTCCAACATGTCAAGGAGTTTACCCAACGCTCCCTGGTGGTCGACCATCTGCGGTTGCTCCATTTCAT
GACACCTGAGACCATGAGGTGGGCAACTGTTTTAGCCTGTCTTTTTGCCATTCTGTTGGCAATTTGAATGTTTAAGTATG
TTGGAGAAATGCTTGACCGCGGGCTGTTGCTCGCGATTGCTTTCTTTGTGGTGTATCGTGCCGTTCTGTTTTGCTGTGCT
CGCCAACGCCAGCAACGAACCACGCAGCCTCCCATCTACAGCTGATTTACAACTTGACGCTATGTGAGCTGAATGGCACAGATT
GGCTAGCTAACAAATTTGATTGGGCAGTGGAGAGTTTTGTCATCTTTCCCGTTTTGACTCACATTGTCTCCTATGGTGCC
CTCACTACCAGCCATTTCCTTGACACAGTCCCTTTAGTCACTGTGTCTACCGCCGGGTTTGTTCACGGCGGTATGTCCT
AAGTAGCATCTACGCGGTCTGTGCCCTGGCTGCGTTGACTTGCTTCGTCATTAGGTTTGCAAAGAATTGCATGTCCTGCC
GCTACGCGTGTACCAGATATACCAACTTTCTTCTGGACACTAAGGGCAGACTCTATCGTTGCCGGTCGCCTGTCATCATA
GAGAAAAGGGGCAAAGTTGAGGTCGAAGGTCATCTGATCGACCTCAAAAGAGTTGTGCTTGATGGCTCCGTGGCAACCCC
TATAACCAGAGTTTCAGCGGAACAATGGGGTCGTCCTTAGATGACTTCTGTCACGATAGCACGGCTCCACAAAAGGTGCT
TTTGGCGTTTTCTATTACCTACACGCCAGTGATGATATATGCCCTAAAGGTGAGTCGCGGCCGACTGCTAGGGCTTCTGC
ACCTTTTGATCTTCCTGAATTGTGCTTTCACCTTCGGGTACATGACTTTCGCGCACTTTCAGAGTACAAATAAGGTCGCG
CTCACTATGGGAGCAGTAGTTGCACTCCTTTGGGGGGTGTACTCAGCCATAGAAACCTGCAAATTCATCACCTCCAGATG
CCGTTTGTGCTTGCTAGGCCGCAAGTACATTCTGGCCCCTGCCCACCACGTTGAAAGTGCCGCAGGCTTTCATCCGATTG
CGGCAAATGATAACCACGCCATTTGTCGTCCGGCGTCCCGGCTCCACTACGGTCAACGGCACATTGGTGCCCGGGTTAAAA
AGCCTCGTGTTGGGTGGCAGAAAAGCTGTTAAACAGGGAGTGGTAAACCTTGTCAAATATGCCAAATAACAACGGCAAGC
AGCAGAAGAGAAAGAAGGGGATGCCCAGCCAGTCAATCAGCTGTGCCAGATGCTGGGTAAGATCATCGCTCAGCAAAAC
CAGTCCAGAGGCAAGGGACCGGGAAAGAAAAATAAGAAGAAAAACCCGGAGAAGCCCCATTTTCCTCTAGCGACTGAAGA
TGATGTCAGACATCACTTTACCCCTAGTGAGCGGCAATTGTGTCTGTCGTCAATCCAGACCGCCTTTAATCAAGGCGCTG
GGACTTGCACCCTGTCAGATTCAGGGAGGATAAGTTACACTGTGGAGTTTAGTTTGCCTACGCATCATACTGTGGCCTG
ATCGCGTCACAGCATCACCCTCAGCATCATGGGCTGGCATTCTTGAGGCATCTCAGTGTTTGAATTGGAAGAATGTGTG
GTGAATGGCACTGATTGACATTGTGCCTCTAAGTCACCTATTCAATTAGGGCGACCGTGTGGGGTGAGATTTAATTGGC
GAGAACCATGCGGCCGAAATTAAAAAAAA

TGTTTTCTGGGTCTTCTCGGCGGGTTCGAATGGGGGTTTTTGGCTGCTGGTTGGCTTTTGCTGTTGGTCTGTTCAAGCCT
GTGTCCGACCCAGTCGGCGCTGCTTGTGAGTTTGACTCGCCAGAGTGTAGAAACATCCTTCATTCTTTTGAGCTTCTCAA
ACCTTGGGACCCTGTTCGCAGCCTTGTTGTGGGCCCCGTCGGTCTCGGTCTTGCCATTCTTGGCAGGTTACTGGGCGGGG
CAGCCTGCATCTGGCACTTTTTGCTTAGGCTTGGCATTGTTGCAGACTGTATCTTGGCTGGAGCTTACGTGCTTTCTGAA
GGTAGGTGTAAAAAGTGCTGGGGATCTTGTATAAGAACTGCTCCCAATGAGGTCGCTTTTAACGTGTTTCCTTTCACACG
TCCGACCAGGTCGTCACTTATCGACCTGTGCGATCGGTTTTGTGCGCCAAAAGGAATGGACCCCATTTTTCTCGCCACTG
GGTGGCGCGGGTGCTGGGCCGGCCGAAGCCCCATTGAGCAACCCTCTGAAAAACCCATCGCGTTTGCCCAGTTGGATGAA
AAGAAGATTACGGCTAGGACTGTGGTCGCCCAGCCTTATGACCCCAACCAAGCCGTAAAGTGCTTGCGGGTATTGCAGGC
GGGTGGGGCGATGGTGGCTAAGGCGGTCCCAAAAGTGGTCAAGGTTTCCGCTGTTCCATTCCGAGCCCCTTCTTTCCCA
CTGGAGTGAAAGTTGACCCTGATTGCAGGGTCGTCGTTGACCCTGACACTTTCACTGCAGCTCTCCGGTCTGGCTACTCC
ACCACAAACCTCGTCCTTGGTGTGGGGGACTTTGCCCAGCTGAATGGATTAAAAATCAGGCAAATTTCCAAGCCTTCAGG
GGGAGGCCCACATCTCATGGCTGCCCTGCATGTTGCCTGCTCGATGGCTCTGCACATGCTTGCTGGGATTTATGTGACTG
CGGTGGGTTCTTGCGGCACCGGCACCAACGACCCGTGGTGCGCTAACCCGTTTGCCGTCCCTGGCTACGGACCTGGCTCT
CTCTGCACGTCCAGATTGTGCATTTCCCAACACGGCCTTACCCTGCCCTTGACAGCACTTGTGGCGGGATTCGGTATTCA
AGAAATTGCCTTGGTCGTTTTGATTTTTGTTTCCATCGGAGGCATGGCTCATAGGTTGAGCTGTAAGGCTGACATGCTGT
GTGTCTTGCTTGCAATTGCCAGCTATGTTTGGGTACCTCTTACCTGGTTGCTTTGTGTGTTTCCTTGCTGGTTGCGCTGT
TTTTCTTTGCACCCCCTCACCATCCTATGGCTTGGTGTTTTTCTTGATTTCTGTGAATATGCCTTCAGGAATCTTGGCCAT
GGTGTTGTTGGTTTCTCTTTGGCTTCTTGGTCGTTATACTAATGTTGCTGGCCTTGTCACCCCCTACGACATTCATCATT
ACACCAGTGGCCCCGCGGTGTTGCCGCCTTGGCTACCGCACCAGATGGGACCTACTTGGCCGCTGTCCGCCGCGCTGCG
TTGACTGGCCGGCACCATGCTGTTTACCCCGTCCCAGCTTGGGTCTCTTCTTGAGGGTGCTTTCAGAACTCGAAAGCCCTC
ACTGAACACCGTCAATGTGATCGGGTCCTCCATGGCTCTGGCGGGTGTTTACCATCGACGGGAAAGTCAAGTGCGTAA
CTGCCGCACATGTCCTTACGGGCAATTCAGCTCGGGTTCCGGGGTCGGCTTCAATCAAATGCTTGACTTTGACGTAAAG
GGAGATTTCGCTATAGCTGATTGCCCGAATTGGCAAGGGGCTGCCCCCAAGACCCAATTCTGCACGGATGGATGGACTGG
CCGTGCCTATTGGCTAACATCCTCTGGCGTCGAACCCGGCGTCATTGGAAAAGGATTCGCCTTCTGCTTCACCGCATGTG
GCGATTCCGGGTCCCCAGTGATCACCGAGGCCGGTGAGCTTGTCGGCGTTCACACGGGATCGAATAAACAAGGGGGGGC
ATTGTTACGCGCCCCTCAGGCCAGTTTTGTAATGTGGCACCCATCAAGCTAAGCGAATTAAGTGAATTCTTTGCTGGGCC
TAAGGTCCCGCTCGGTGATGTGAAGGTCGGCAGCCACATAATTAAAGACATAAGCGAGGTGCCTTCAGATCTTTGTGCCT
TGCTTGCTGCCAAACCTGAACTGGAAGGAGGCCTCTCCACCGTCCAACTTCTTTGTGTGTTTTTCTCCTGTGGAGAATG
ATGGGACATGCCTGGACGCCCTTGGTTGCTGTGAGTTCTTTATTTTGAATGAGGTTCTCCCAGCCGTCCTGGTCCGGAG
TGTTTTCTCCTTTGGAATGTTTGTGCTATCCTGGCTCACGCCATGGTCTGCGCAAGTTCTGATGATCAGGCTTCTGACAG
CAGCTCTTAACAGGAACAGATGTCACTTGCCTTTTTTAGCCTCGGTGCAGTGACCGGTTTTGTCGCAGATCTTGCGGCC
ACTCAGGGCATCCGTTGCAGGCAGTGATGAATTTGAGCACCTATGCATTCCTGCCTCGGATGATGGTTGTGACCTCACC
AGTCCAGTGATCACGTGTGGTGTCGTGCACCTACTTGCCATCATTTTGTACTTGTTTAAGTACCGTGGCCTGCACCATA
TCCTTGTTGGCGATGGAGTGTTCTCTGCGGCTTTCTTCTTGAGATACTTTGCCGAGGGAAAGTTGAGGGAAGGGGTGTCG
CAATCCTGCGGAATGAATCATGAGTCTCTGACTGGTGCCCTCGCTATGAGACTCAATGACGAGGACTTGGATTTCCTTAT
GAAATGGACTGATTTTAAGTGCTTTGTTTCTGCGTCCAACATGAGGAATGCAGCGGGTCAATTTATGAGGCTGCCTATG
CTAAAGCACTTAGAGTAGAACTGGCCCAGTTGGTCAGGTTGATAAAGTTCGAGGTACTTTGGCCAAACTTGAAGCTTTT
GCTGATACCGTGGCACCTCAACTCTCGCCCGGTGACATTGTTGTCGCTCTCGGCCACACGCCTGTTGGCAGTATCTTCGA
CCTAAAGGTTGGTAGCACCAAGCATACCCTCCAAGCCATTGAGACCAGAGTCCTTGCTGGGTCCAAAATGACCGTGGCGC
GCGTCGTCGACCCGACCCCCACGCCCCACCCGCACCCGTGCCCATCCCCCTCCCACCGAAAGTTCTGGAGAATGGCCCC
AACGCTTGGGGGATGAGGACCGTTTGAATAAGAAGAAGAGGCGCAGGATGGAAGCCCTCGGCATCTATGTTATGGGCGG
GAAAAATACCAGAAATTTTGGGACAAGAATTCCGGTGATGTGTTTTATGAGGAGGTCCATAATAACACAGATGAGTGGG
AGTGTCTCAGAGTTGGCGACCCTGCCGACTTTGACCCTGAGAAGGGAACTCTGTGTGGACATGTCACCATTGAAAACAAG
GCTTACCATGTTTACACCTCCCCATCTGGTAAGAAGTTCTTGGTCCCCGTCAACCCAGAGAATGGAAGAGTCCAATGGA
AGCTGCAAAGCTTTCCGTGGAGCAGGCCCTAGGTATGATGAATGTCGACGGCGAACTGACTGCCAAAGAACTGGAGAAAC
TGAAAAGAATAATTGACAAACTCCAGGGCCTGACTAAGGAGCAGTGTTTAAACTGCTAGCCGCCAGCGACTTGACCCGCT
GTGGTCGCGGCGGCTTGGTTCTTACTGAAACAGCGGTAAAAATAGTCAAATTTCACAACCGGACCTTCACCCTGGGACCT
GTGAATTTAAAAGTGGCCAGTGAGGTTGAGCTAAAAGACGCGGTTGAGCACAACCAACACCCGGTTGCGAGACCGATCGA

*Fig. 1J-3*

```
TGGTGGAGTTGTGCTCCTGCGTTCCGCGGTTCCTTCGCTTATAGACGTCTTGATCTCCGGTGCTGATGCATCTCCCAAGT
TACTTGCCCATCACGGGCCGGGAAACACTGGGATCGATGGCACGCTCTGGGATTTTGAGTCCGAAGCCACTAAGAGGAA
GTCGCACTCAGTGCGCAAATAATACAGGCTTGTGACATTAGCGCGGCGACGCTCCTGAAATTGGTCTCCCTTACAAGCT
GTACCCTGTTAGGGGTAACCCTGAGCGGGTGAAAGGAGTTCTGCAGAATACAAGGTTTGGAGACATACCTTACAAAACCC
CCAGTGACACTGGAAGCCCAGTGCACGCGGCTGCCTGCCTTACGCCCAACGCCACTCCGGTGACTGATGGGCGCTCCGTC
TTGGCCACGACCATGCCCCCCGGGTTTGAGTTATATGTACCGACCATACCAGCGTCTGTCCTTGATTACCTTGACTCTAG
GCCTGACTGCCCTAAACAGCTGACAGAGCACGGCTGCGAAGATGCCGCACTGAAAGACCCTCTCTAAATATGACTTGTCCA
CCCAAGGCTTTGTTTTAGCTGGAGTTCTTCGCCTTGTGCGGAAATACCCTGTTTGCCCATGTAGGTAAGTGCCCACCCGTT
CATCGGCCTTCTACTTACCCTGCTAAGAATTCTATGGCTGGAATAAATGGGAACAGGTTCCCAACCAAGGACATTCAGAG
CGTCCCTGAAATCGACGTTCTGTGCGCACAGGCTGTGCAGAAAACTGGCAAACTGTCACCCCTTGTACTCTTAAGAAAC
AGTATTGCGGGAAGAAGAAGACTAGGACCATACTCGGCACCAATAACTTCATCGCACTAGCCCACCGAGCAGTGTTGAGT
GGTGTTACCCAGGGCTTCATGAAAAAGGCGTTTAACTCGCCCATCGCCCTCGGAAAGAACAAGTTTAAGGAGCTACAGAC
TCCGGTCCTGGGCAGGTGCCTTGAAGCTGATCTCGCATCCTGCGATCGATCCACGCCTGCAATTGTCCGCTGGTTGCCG
CCAACCTTCTTTATGAACTTGCCTGTGCTGAAGAGCATCTACCGTCGTACGTGCTGAACTGCTGCCACGACTTACTGGTC
ACGCAGTCCGGCGCAGTGACTAAGAGAGGTGGCCTGTCGTCTGGCGACCGATCACCTCTGTGTCTAACACCATTTATAG
TTTGGTGATCTATGCACAGCATATGGTGCTTAGTTACTTCAAAAGTGGTCACCCCATGGCCTTCTGTTCTTACAAGACC
AGCTAAAGTTTGAGGACATGCTCAAGGTTCAACCCCTGATCGTCTATTCGGACGACCTCGTGCTGTATGCCGAGTCTCCC
ACCATGCCAAACTATCACTGGTGGGTTGAACATCTGAATTTGATGCTGGGGTTTCAGAGGGACCGAAAGAAGACAGCAAT
AACAGACTCGCCATCATTTCTAGGCTGTAGAATAATAAATGGGCGCCAGCTAGTCCCGAACCGTGACAGGATCCTCGCGG
CCCTCGCCTATCACATGAAGGCGAGTAATGTTTCTGAATACTATGCCTCAGCGGCGTGCAATACTCATGGACAGCTGTGCT
TGTTTGGAGTATGATCCTGAATGGTTTGAAGAACTTGTAGTTGGAATAGCGCAGTGCGCCTGCAAGGACGGCTACAGCTT
TCCCGGCACGCCGTTCTTCATGTCCATGTGGGAAAAACTCAGGTCCAATTATGAGGGGAAGAAGTCGAGAGTGTGCGGGT
ACTGCGGGGCCCGGCCCCGTACGCTACTGCCTGTGGCCTCGACGTCTGCATTTACCACACCCACTTCCACCAGCATTGT
CCAGTCACAATCTGGTGTGGCCATCCAGCGGGTTCTGGTTCTTGTAGTGAGTGCAAATCCCCTGTAGGGAAAGGCACAAG
GCCTTTAGACGAGGTGCTGGAACAAGTCCCGTATAAGCCCCCACGGACCGTATCATGCATGTGGAGCAGGGTCTCACCC
CCCTTGATCCAGGTAGATACCAAACTGCCGCGGATTAGTCTCTGTCAGGCGTGGAATTAGGGGAAATGAAGTTGGACTA
CCAGACGGTGATTATGCTAGCACCGCCTTGCTCCCTACCTGCAAAGAGATCAACATGGTCGCTGTGCTTCCAATGTATT
GGCAGCAGGTTCATCATCGGCCCACCCGGTGCTGGGAAAACATACTGGCTCCTTCAACAGGTCCAGGATGGTGATGTTA
TTTACACACCAACTCACCAGACCATGCTTGACATGATTAGGGCTTTGGGGACGTGCCGGTTCAACGTCCCGGCAGGCACA
ACGCTGCAATTCCCCGTCCCTCCCGCACCGGTCCGTGGGTTCGCATCCTAGCCGGCGGTTGGTGTCCTGGCAAGAATTC
CTTCCTAGATGAAGCAGGGTATTGCAATCACCTTGATGTTTGAGGCTTCTTAGTAAAACTACCCTCACCTGTCTAGGAG
ACTTCAAGCAACTCCACCCAGTGGGTTTTGATTCTCATTGCTATGTTTTTGACATCATGCCTCAAACTCAACTGAAGACC
ATCTGGAGGTTTGGACAGAATATCTGTGATGCCATTCAGCAGGTTACAGGGACAAACTCATGTCCATGGTCAACACAAC
CCGTGTGACCTACGTGGAAAACCTGTCAGGTATGGGCAGGTCCTCACCCCCTACCACAGGGACCGAGAGGACGACGCCA
TCACTATTGACTCCAGTCAAGGCGCCACATTCGATGTGGTTACATTGCATTTGCCCACTAAAGATTCACTCAACAGGCAA
AGAGCCCTTGTTGCTATCACCAGGGCAAGACACGCTATCTTTGTGTATGACCCACACAGGCAGCTGCAGGGCTTGTTTGA
TCTTCCTGCAAAAGGCACGCCCGTCAACCTCGCAGTGCTACTGCGACGGGCAGCTGATCGTGCTGGATAGAAATAACAAAG
AATGCACGGTTGCTCAGGCTCTAGGCAACGGGGATAAATTTAGGGCCACAGACAAGCGTGTTGTAGATTCTCTCCGCGCC
ATTTGTGCTGATCTAGAAGGGTCGAGCTCTCCGCTCCTCAAGGTCGCACACAACTTGGGATTTTATTTCTCACCTGATTT
AACACAGTTTGCTAAACTCCCAGTAGAACTTGCACCTCACTGGCCCGTGGTGTCAACCCAGAACAATGAAAAGTGGCCGG
ATCGGCTGGTTGCCAGCCTTCGCCCTATCCATAAATACAGCCGCGCGTGCATCGGTGCCGGCTATATGGTGGGCCCTTCG
GTGTTTCTAGGCACTCCTGGGGTCGTGTCATACTATCTCACAAAATTTGTTAAGGGCGGGGCTCAAGTGCTTCCGGAGAC
GGTTTTCAGCACCGGCCGAATTGAGGTAGACTGCCGGAATATCTTGATGATCGGGAGCGAGAAGTTGCTGCGTCCCTCC
CACACGCTTTCATTGGCGACGTCAAAGGCACTACCGTTGGAGGATGTCATCATGTCACCTCCAGATACCTCCGGCGCGTC
CTTCCCAAGGAATCAGTTGCGGTAGTCGGGGTTTCAAGCCCCGGAAAAGCCGCGAAAGCATTGTCCACACTGACAGATGT
GTACCTCCAGATCTTGAAGCCTATCTCCCACCCGGAGACCCAGTCCAAGTGCTGGAAAATGATGTTGGACTTCAAAGAAG
TTCGACTAATGGTCTGGAAAGACAAAACAGCCTATTTCCAACTTGAAGGTCGCTATTTCACCTGGTATCAGCTTGCCAGC
TATGCCTCGTACATCCGTGTTCCCGTCAACTCTACGGTGTACTTGGACCCCTGCATGGGCCCGCCCTTTGCAACAGGAG
```

*Fig. 11-4*

```
AGTCGTCGGGTCCACCCACTGGGGGCTGACCTCGCGGTCACCCCTTATGATTACGGCGCTAAAATTATCCTGTCTAGCG
CGTACCATGGTGAAATGCCCCCCGGATACAAAATTCTGGCGTGCGCGGAGTTCTCGTTGGATGACCCAGTTAAGTACAAA
CATACCTGGGGGTTTGAATCGGATACAGCGTATCTGTATGAGTTCACCGGAAACGGTGAGGACTGGGAGGATTACAATGA
TGCGTTTCGTCGCGCCAGGAAGGGAAAATTTATAAGGCCACTCCCACCAGCTTGAAGTTTTATTTTCCCCCGGGCCCTG
TCATTGAACCAACTTTAGGCCTGAATTGAAATGAAATGGGGTCCATGCAAAGCCTTTTTGACAAAATTGGCCAACTTTTT
GTGGATGCTTTCACGGAGTTCTTGGTGTCCATTGTTGATATCATTATATTTTTGGCCATTTTGTTTGGCTTCACCATCGC
CGGTTGGCTGGTGGTCTTTTGCATCAGATTGGTTTGCTCCGCGATACTCCGTACGCGCCCTGCCATTCACTCTGAGCAAT
TACAGAAGATCTTATGAGGCCTTTCTTTCCCAGTGCCAAGTGGACATTCCCACCTGGGGAACTAAACATCCTTTGGGGAT
GCTTTGGCACCATAAGGTGTCAACCCCTGATTGATGAAATGGTGTCGCGTCGAATGTACCGCATCATGGAAAAAGCAGGGC
AGGCTGCCTGGAAACAGGTGGTGAGCGAGGCTACGCTGTCTCGCATTAGTAGTTTGGATGTGGTGGCTCATTTTCAGCAT
CTAGCCGCCATTGAAGCCGAGACCTGTAAATATTTGGCCTCCCGGCTGCCCATGCTACACAACCTGCGCATGACAGGGTC
AAATGTAACCATAGTGTATAATAGCACTTTGAATCAGGTGTTTGCTATTTTTCCAACCCCTGGTTCCCGGCCAAAGCTTC
ATGATTTTCAGCAATGGTTAATAGCTGTAGATTCCTCCATATTTTCCTCTGTTGCAGCTTCTTGTACTCTTTTTGTTGTG
CTGTGGTTGCGGGTTCCAATACTACGTACTGTTTTTGGTTTCCGCTGGTTAGGGCAATTTTTCTTTCGAACTCACAGTG
AATTACACGGTGTGTCCACCTTGCCCTCACCCGGCAAGCAGCCACAGAGATCTACGAACCCGGTAGGTCTCTTTGGTGCAG
GATAGGGTATGACCGATGTGGGAGGACGATCATGACGAGCTAGGGTTTATGATACCGCCTGGCCTCTCCAGCGAAGGCC
ACTTGACTGGTGTTTACGCCTGGTTGGCGTTCTTGTCCTTCAGCTACACGGCCCAGTTCCATCCCGAGATATTCGGGATA
GGGAATGTGAGTCGAGTTTATGTTGACATCAAACATCAACTCATCTGCGCCGAACATGACGGGCAGAACACCACCTTGCC
TCGTCATGACAACATTTCAGCCGTGTTTCAGACCTATTACCAACATCAAGTCGACGGCGGCAATTGGTTTCACCTAGAAT
GGCTTCGTCCCTTCTTTTCCTCGTGGTTGGTTTTAAATGTCTCTTGGTTTCTCAGGCGTTCGCCTGCAAACCATGTTTCA
GTTCGAGTCTTGCAGATATTAAGACCAACACCACCGCAGCGGCAAGCTTTGCTGTCCTCCAAGACATCAGTTGCCTTAGG
CATCGCGACTCGGCCTCTGAGGCGATTCGCAAAATCCCTCAGTGCCGTACGGCGATAGGGACACCCGTGTATGTTACCAT
CACAGCCAATGTGACAGATGAGAATTATTTACATTCTTCTGATCTCCTCATGCTTTCTTCTTGCCTTTTCTATGCTTCTG
AGATGAGTGAAAAGGGATTTAAGGTGGTATTTGGCAATGTGTCAGGCATCGTGGCTGTGTGTGTCAATTTTACCAGCTAC
GTCCAACATGTCAAGGAGTTTACCCAACGCTCCCTGGTGGTCGACCATGTGCGGTTGCTCCATTTCATGACACCTGAGAC
CATGAGGTGGGCAACTGTTTTAGCCTGTCTTTTTGCCATTCTGTTGGCAATTTGAATGTTTAAGTATGTTGGAGAAATGC
TTGACCGCGGGCTGTTGCTCGCGATTGCTTTCTTTGTGGTGTATCGTGCCGTTCTGTTTTGCTGTGCTCGCCAACGCCAG
CAACGACAGCAGCTCCCATCTACAGCTGATTACAAACTTGACGCTATGTGAGCTGAATGGCACAGATTGGCTAGCTAACA
AATTTGATTGGGCAGTGGAGAGTTTTGTCATCTTTCCCGTTTTGACTCACATTGTCTCCTATGGTGCCCTCACTACCAGC
CATTTCTTGACACAGTCGCTTTAGTCACTGTGTCTACCGCCGGGTTTGTTCACGGGCGGTATGTCCTAAGTAGCATCTA
CGCGGTCTGTGCCCTGGCTGCGTTGACTTGCTTCGTCATTAGGTTTGCAAAGAATTGCATGTCCTGGCGCTACGCGTGTA
CCAGATATACCAACTTTCTTCTGGACACTAAGGGCAGACTCTATCGTTGGCGGTCGCCTGTCATCATAGAGAAAGGGGC
AAAGTTGAGGTCGAAGGTCATCTGATCGACCTCAAAAGAGTTGTGCTTGATGGCTCCGTGGCAACCCCTATAACCAGAGT
TTCAGCGGAACAATGGGGTCGTCCTTAGATGACTTCTGTCACGATAGCACGGCTCCACAAAAGGTGCTTTTGGCGTTTC
TATTACCTACACGCCAGTGATGATATGCCCTAAAGGTGAGTCGCGGCCGACTGCTAGGGCTTCTGCACCTTTTGATCT
TCCTGAATTGTGCTTTCACCTTCGGGTACATGACTTTCGCGCACTTTCAGAGTACAAATAAGGTCGCGCTCACTATGGA
GCAGTAGTTGCACTCCTTTGGGGGTGTACTCAGCCATAGAAACCTGGAAATTCATCACCTCCAGATGCCGTTTGTGCTT
GCTAGGCCGCAAGTACATTCTGGCCCCTGCCCACCACGTTGAAAGTGCCGCAGGCTTTCATCCGATTGCGGCAAATGATA
ACCACGCCATTTGTCGTCCGGCCTCCCGGCTCCACTACGGTCAACGGCACATTGGTGCCCGGGTTAAAAAGCCTCGTGTTG
GGTGGCAGAAAAGCTCTTTAAACAGGGAGTGGTAAACCTTGTCAAATATGCCAAATAACAACGGCAAGCAGCAGAAGAGAA
AGAAGGGGATGGCCAGCCAGTCAATCAGCTGTGCCAGATGCTGGGTAAGATCATCGCTCAGCAAAACCAGTCCAGAGGC
AAGGGACCGGGAAAGAAAAATAAGAAGAAAAACCCGGAGAAGCCCCATTTTCCTCTAGCGACTGAAGATGATGTCAGACA
TCACTTTACCCCTAGTGAGCGGCAATTGTGTCTGTCGTCAATCCAGACCGCCTTTAATCAAGGCGCTGGGACTTGCACCC
TGTCAGATTCAGGGAGGATAAGTTACACTGTGGAGTTTAGTTTGCCTACGCATCATACTGTGCGCCTGATCCGCGTCACA
GCATCACCCTCAGCATGATGGGCTGGCATTCTTGAGGCATCTCAGTGTTTGAATTGGAAGAATGTGTGGTGAATGGCACT
GATTGACATTGTGCCTCTAAGTCACCTATTCAATTAGGGCGACCGTGTGGGGGTGAGATTTAATTGGCGAGAACCATGCG
GCCGAAATTAAAAAAAAA
```

*Fig. 1K-1*

```
>V7-Nop2d543-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGAGGGCCAAGTCTACTGCACACGATGCCTCAGTGCACGGTCTCTCCTTCCCCTGAACCTCCAGGTTTCTGAGCT
CGGGCTGCTAGGCCTATTCTACAGGCCCGAAGAGCCACTCCGGTGGACGTTGCCACGTGCATTCCCACTGTTGAGTGCT
CCCCCGCCGGGGCCTCCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAAGCTGCCGCTCCCGCAGAGACCCAAGGCTGAAGACTTTTGCCCCTTTGAG
TGTGCTATGGCTACTGTCTATGACATTGTCATGACGCCGTCATGTATGTGGCCGAAAGGAAAGTCTCCTGGGCCCCTCG
TGGCGGGGATGAAGTGAAATTTGAAGGCTGTCCCCGGGGAGTTGAAGTTGATTGCGAACCGGCTCCGCACCTCCTTCCCGC
CCCACCACACAGTGGACATGTCTAAGTTCGCCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGGTTAAGGAGAGTTGGATC
CGCCATTTGAACTGCGGCGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGGCAAGGAGCACGAGGTT
GCCGGCGCCAACAAGGCTGAGCACGTCAAACACTACTCCCCGCCTGCCGAAGGGAATGTGGTGCGACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGGTGAGCATTGGACTGTCACTGTGACCCCTGGGATGTCCCCTTCTTTGCTCCCTCTTGAATG
TGTTCAGGGCTGTTGTGGCACAAGGGCGGTCTTGGTTCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCACTGCCAACCGAGCCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGACCAGGTTGACCCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCGCGCAGGAAGGTTGG
GTCCGATTGTGGCAGCCCGGTTTCATTAGGCGGCGATGTCCCTAACAGTTGGGAAGATTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GTGTGAGTTTGTGATGATGCCTCACACGCCTGCACCTTCCGTAGGTGCGGAGAGCGACCTTACCATTGGCTCAGTTGCTA
CTGAAGATGTTGCACGCATCCTCGAGAAAATAGAAAATGTCGGCGAGATGGCCAACCAGGGACCCTTGGCCTTCTCCGAG
GATAAACCGGTAGATGACCAACTTGTCAACGACCCCTCGGATATCGTCGCGGAGGCCTGACGAGAGCACATCAGCTCCGTC
GGCAGGCACAGGTGGCGCGGCTCTTTTACCGATTTGCCGGCCTTCAGATGGCGCGGATGCGGACGGGGGGGGCCGTTTC
GGACGGTAAAAAGAAAAGCTGAAAGGCTCTTTGACCAACTGAGCCGTCAGGTTTTGACCTCGTCTCCCATCTCCCTGTT
TTCTTCTCACGCCTTTTCTACCCTGGCGGTGGTTATTCTCCGGGTCATTGGGGTTTTGCAGCTTTACTCTATTGTGCCT
CTTTTTATGTTACAGTTACCCAGCCTTTGGTATTGCTCCCTCTTGGGTGTGTTTCTGGGTCTTCTCGGCGCGTTCGAA
TGGGGGTTTTTGGCTGCTGGTTGGCTTTTGCTGTTGGTCTCGTTCAAGCCTGTGTCCGACCCAGTCGGCGCTGCTTGTAG
TTTGACTCGCCAGAGTGTAGAAACATCCTTCATTCTTTTGAGCTTCTCAAACCTTGGGACCCTGTTCGCAGCCTTGTTGT
GGGCCCCGTCGGTCTCGGTCTTGCCATTCTTGGCAGGTTACTGGGCGGGGCACGCTGCATCTGGCACTTTTTGCTTAGGC
```

GAAAGGAGTTCTGCAGAATACAAGGTTTGGAGACATACCTTACAAAACCCCCAGTGACACTGGAAGCCCAGTGCACGCGG
CTGCCTGCCTTACGCCCAACGCCACTCCGGTGACTGATGGGCGCTCCGTCTTGGCCACGACCATGCCCCCGGGTTTGAG
TTATATGTACCGACCATACCAGCGTCTGTCCTTGATTACCTTGACTCTAGGCCTGACTGCCCTAAACAGCTGACAGAGCA
CGGCTGCGAAGATGCCGCACTGAAAGACCTCTCTAAATATGACTTGTCCACCCAAGGCTTTGTTTTACCTGGAGTTCTTC
GCCTTGTGCGGAAATACCTGTTTGCCCATGTAGGTAAGTGCCCACCCGTTCATCGGCCTTCTACTTACCCTGCTAAGAAT
TCTATGGCTGGAATAAATGGGAACAGGTTCCCAACCAAGGACATTCAGAGCGTCCCTGAAATCGACGTTCTGTGCGCACA
GGCTGTGCGAGAAAACTGGCAAACTGTCACCCCTTGTACTCTTAAGAAACAGTATTGCGGGAAGAAGAAGACTAGGACCA
TACTCGGCACCAATAACTTCATCGCACTAGCCCACCGAGCAGTGTTGAGTGGTGTTACCCAGGGCTTCATGAAAAAGGCG
TTTAACTCGCCCATCGCCCTCGGAAAGAACAAGTTTAAGGAGCTACAGACTCCGGTCCTGGGCAGGTGCCTTGAAGCTGA
TCTCGCATCCTGCGATCGATCCACGCCTGCAATTGTCGGCTGGTTTGCCGCCAACCTTCTTTATGAACTTGCCTGTCCTG
AAGAGCATCTACCGTCCTACGTGCTGAACTGCTGCCACGACTTACTGGTCACGCAGTCCGGCGCAGTGACTAAGAGAGGT
GGCCTGTCGTCTGGCGACCTGATCACCTCTGTGTCTAACACCATTTATAGTTTGGTGATCTATGCACAGCATATGGTGCT
TAGTTACTTCAAAAGTGGTCACCCCCATGGCCTTCTGTTCTTACAAGACCAGCTAAAGTTTGAGGACATGCTCAAGGTTC
AACCCCTGATCGTCTATTCGGACGACCTCGTGCTGTATGCCGAGTCTCCCACCATGCCAAACTATCACTGGTGGGTTGAA
CATCTGAATTTGATGCTGGGGTTTCAGACGGACCCAAAGAAGACAGCAATAACAGACTCGCCATCATTTCTAGGCTGTAG
AATAATAAATGGGCGCCAGCTAGTCCCCAACCGTGACAGGATCCTCGCGGCCCTCGCTATCACATGAAGGCGAGTAATG
TTTCTGAATACTATGCCTCAGCGGCTGCAATACTCATGGACAGCTGTGCTTGTTTGGAGTATGATCCTGAATGGTTTGAA
GAACTTGTAGTTGGAATAGCGCAGTGCGCCGCAAGGACGGCTACAGCTTTCCCGGCACGCCGTTCTTCATGTCCATGTG
GGAAAAACTCAGGTCCAATTATGAGGGGAAGAAGTCGAGAGTGTGCGGGTACTGCGGGCCCCGGCCCGTACGCTACTG
CCTGTGGCCTCGACGTCTGCATTTACCACACCCACTTCCACCAGCATTGTCCAGTCACAATCTGGTGTGGCCATCCAGCG
GGTTCTGGTTCTTGTAGTGAGTGCAAATCCCCTGTAGGGAAAGGCACAAGCCCTTTAGACGAGGTGCTGGAACAAGTCCC
GTATAAGCCCCACGGACCGTTATCATGCATGTGGAGCAGGGTCTCACCCCCCCTTGATCCAGGTACATACCAAACTCGCC
GCGGATTAGTCTCTGTCAGGCGTGGAATTAGGGGAAATGAAGTTGGACTACCAGACGGTGATTATGCTAGCACCGCCTTG
CTCCCTACCTGCAAACAGATCAACATGGTCGCTCGTCGCTTCCAATGTATTGCGCAGCAGGTTCATCATCGGCCCACCGG
TGCTGGGAAAACATACTGGCTCCTTCAACAGGTCCAGGATGGTGATGTTATTTACACACCAACTCACCAGACCATGCTTG
ACATGATTAGGGCTTTGGGGACGCTGCCGGTTCAACGTCCGGCAGGCACAAGCGCTGCAATTCCCCGGTCCCCTCCCGCACC
GGTCCGTGGGTTCGCATCCTAGCCGGCGGTTGGTGTCCTGGCAACAATTCCTTCCTAGATGAAGCAGCGTATTGCAATCA
CCTTGATGTTTGAGGCTTCTTAGTAAAACTACCCTCACCTGTCTAGGAGACTTCAAGCAACTCCACCCAGTGGGTTTTG
ATTCTCATTGCTATGTTTTGACATCATGCCTCAAACTCAACTGAAGACCATCTGGAGGTTTGGACAGAATATCTGTGAT
GCCATTCAGCCAGATTACAGGGACAAACTCATGTCCATGGTCAACACAACCCGTGTGACCTACGTGGAAAAACCTGTCAG
GTATGGGCAGGTCCTCACCCCCTACCACAGGGACCGAGAGGACGACGCCATCACTATTGACTCCAGTCAAGGCGCCACAT
TCGATGTGGTTACATTGCATTTGCCCACTAAAGATTCACTCAACAGGCAAAGAGCCCTTGTTGCTATCACCAGGGCAAGA
CACGCTATCTTTGTGTATGACCCACACAGGCAGCTGCAGGGCTTGTTTGATCTTCCTGCAAAAGGCAGGCCCGTCAACCT
CGCAGTGCACTGCGACGGGCAGCTGATCGTGCTGGATAGAAATAACAAAGAATGCACGGTTGCTCAGGCTCTAGGCAACG
GGGATAAATTTAGGGCCACAGACAAGCCTGTTGTAGATTCTCTCCGCGCCATTTGTGCTGATCTAGAAGGGTCGAGCTCT
CCGCTCCCAAGGTCGCACACAACTTGGGATTTTATTTCTCACCTGATTTAACACAGTTTGCTAAACTCCCAGTAGAACT
TGCACCTCACTGGCCGTGGTGTCAACCCAGAACAATGAAAGTGGCCGGATCGGCTGGTTGCCAGCCTTCGCCCTATCC
ATAAATACAGCCGCGCTGCATCGGTGCCGGCTATATGGTGGGCGCCTTCGGTGTTTCTAGGCACTCCTGGGGTCGTGTCA
TACTATCTCACAAAATTTGTTAAGGGCGGGGCTCAACTGCTTCCGGAGACGGTTTTCAGCACCGGCCGAATTGAGGTAGA
CTGCCCGGAATATCTTGATGATCGGGAGCCAGAAGTTGCTGCGTCCCTCCCACACGCTTTCATTGCGACGTCAAAGGCA
CTACCGTGCGAGGATGTCATCATGTCACCTCCAGATACCTCCCGCGCGTCCTTCCCAAGGAATCAGTTGCGGTAGTCGGG
GTTTCAAGCCCCGGAAAGCCGCGAAAGCATTGTGCAGCACTGACAGATGTGTACCTCCCAGATCTTGAAGCCTATCTCCA
CCCGGAGACCCAGTCCAAGTGCTGGAAAATGATGTTGACTTCAAAGAAGTTCGACTAATGGTCTGGAAAGACAAAACAG
CCTATTCCAACTTGAAGGTCGCTATTTCACCTGGTATCAGCTTGCCAGCTATGCCTCGTACATCCGTGTTCCCGTCAAC
TCTACGGTGTACTTGGACCCCTGCATGGGCCCGCCCTTTGCAACAGGAGAGTCGTCGGGTCCACCCACTGGGGGCTGA
CCTCGCGGTCACCCCTTATGATTACGGCGCTAAAATTATCCTGTCTAGCGCGTACCATGGTGAAATGCCCCCGGATACA
AAATTCTGGCGTGCGCGGAGTTCTCGTTGGATGACCCAGTTAAGTACAAACATACCTGGGGGTTTGAATCGGATACAGCG
TATCTGTATGAGTTCACCGGAAACGGTGAGGACTGGGAGGATTACAATGATGCGTTCGTGCGCGGCCAGGAAGGGAAAAT

>V7-Nsp2d727-813.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCCGTTAAGGAGAGTTGGATC
CGCCATTTGAAACTGCCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTCATGCAGCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCTGGGGTTGAGGCGGCAACCCAGAC
GATCAAGCTGCCCAGGTCAACCAGTGTCGTGCTCTCGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCTAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTCCGGAGAGAAAGCCTGTCCCCGCCCCGCAGGAAGGTTGG
GTCCGATTGTGGCAGCCCCGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCAGCACCGCCGCAGAGCGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGCTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCAAAAATGATACTCGAGACACCGCCGCCCTATCCGTCTTTTA
CCGATTTGCTGCCTTCAGATGGCGCGGATGCGGACGGGGGGGGCCGTTTCGGACGGTAAAAAGAAAAGCTGAAAGGCTC
TTTGACCAACTGAGCCGTCAGGTTTTTGACCTGTCTCCCATCTCCCTGTTTCTTCTCACGCCTTTTCTACCCTGGCGG
TGGTTATTCTCCGGGTGATTGGGTTTTGCAGCTTTTACTCTATTGTGCCTCTTTTTATGTTACAGTTACCCAGCCTTTG
GTATTGCTCCCCTCTTTGGGTGTGTTTTCTGGGTCTTCTCGGCGCCGTTCGAATGGGGGTTTTTGGCTGCTGGTTGGCTTTT

```
TCCGAAGCCACTAAAGAGGAAGTCGCACTCAGTGCGCAAATAATACAGGCTTGTGACATTAGGCGCGGCGACGCTCCTGA
AATTGGTCTCCCTTACAAGCTGTACCCTGTTAGGGGTAACCCTGAGCGGGTGAAAGGAGTTCTGCAGAATACAAGGTTTG
GAGACATACCTTACAAAACCCCCAGTGACACTGGAAGCCCAGTGCACGCGGCTGCCTGCCTTACGCCCAACGCCACTCCG
GTGACTGATGGGCGCTCCGTCTTGGCCACGACCATGCCCCCCGGGTTTGAGTTATATGTACCGACCATACCAGCGTCTGT
CCTTGATTACCTTGACTCTAGGCCTGACTGCCCTAAACAGCTGACAGAGCACGGCTGCGAAGATGCCGCACTGAAAGACC
TCTCTAAATATGACTTGTCCACCCAAGGCTTTGTTTTACCTGGAGTTCTTCGCCTTGTGCGGAAATACCTGTTTGCCCAT
GTAGGTAAGTGCCCACCCGTTCATCGGCCTTCTACTTACCCTGCTAAGAATTCTATGGCTGGAATAAATGGGAACAGGTT
CCCAACCAAGGACATTCAGAGCGTCCCTGAAATCGACGTTCTGTGCGCACAGGCTGTGCGAGAAAACTGGCAAACTGTCA
CCCCTTGTACTCTTAAGAAACAGTATTGCGGGAAGAAGAAGACTAGGACCATACTCGGCACCAATAACTTCATCGCACTA
GCCCACCGAGCAGTGTTGAGTGGTGTTACCCAGGGCTTCATGAAAAAGGCGTTTAACTCGCCCATCGCCCTCGGAAAGAA
CAAGTTTAAGGAGCTACAGACTCCGGTCCTGGGCAGGTGCCTTGAAGCTGATCTCGCATCCTGCGATCGATCCACGCCTG
CAATTGTCCGCTGGTTTGCCGCCAACCTTCTTTATGAACTTGCCTGTGCTGAAGAGCATCACCGTCGTACGTGCTGAAC
TGCTGCCACGACTTACTGGTCACGCAGTCCGGCGCAGTGACTAAGAGAGGTGGCCTGTCGTCTGGCGACCCGATCACCTC
TGTGTCTAACACCATTTATAGTTTGGTGATCTATGCACAGCATATGGTGCTTAGTTACTTCAAAAGTGGTCACCCCCATG
GCCTTCTCTTCTTACAAGACCAGCTAAAGTTTGAGGACATGCTCAAGGTTCAACCCCTGATCGTCTATTCGGACGACCTC
GTGCTGTATGCCGAGTCTCCCACCATGCCAAACTATCACTGGTGGGTTGAACATCTGAATTTGATGCTGGGGTTTCAGAC
GGACCCAAAGAAGACAGCAATAACAGACTCGCCATCATTTCTAGGCTGTAGAATAATAAATGGGCGGCCAGCTAGTCCCA
ACCGTGACAGGATCCTCGCGGCCCTCGCCTATCACATGAAGGCGAGTAATGTTTCTGAATACTATGCCTCAGCGGCTGCA
ATACTCATGGACAGCTGTGCTTGTTTGGAGTATGATCCTGAATGGTTTGAAGACTTGTAGTTGGAATAGCGCAGTGCGC
CCGCAAGGACGGCTACAGCTTTCCCGGCACGCCGTTCTTCATGTCCATGTGGGAAAAACTCAGGTCCAATTATGAGGGGA
AGAAGTCGACAGTGTGCGGGTACTGCGGGGCCCCGGCCCGTCAGCGCTACTGCCTGTGGCCCTCGACGTCTGCATTTACCAC
ACCCACTTCCACCCAGCATTGTCCAGTCACAATCTGGTGGGCCATCCAGCGGGGTTCTGGTTCTTGTAGTGAGTGCAAATC
CCCTGTAGGGAAAGGCACAAGCCCTTTAGACGAGGTGCTGGAACAAGTCCCGTATAAGCCCCCACGGACCGTTATCATGC
ATGTGGAGCAGGGTCTCACCCCCCTTGATCCAGGTAGATACCAAACTGGCCGCGGATTAGTCTCTGTCAGGCGTGGAATT
AGGGGAAATGAAGTTGGACTACCAGACGGTGATTATGCTAGCACCGCCTTGCTCCCTACCTGCAAAGAGATCAACATGGT
CGCTGTCGCTTCCAATGTATTGCGCAGCAGGTTCATCATCGGCCCACCCGGTGCTGGGAAAACATACTGGCTCCTTCAAC
AGGTCCAGGATGGTGATGTTATTTACACACCAACTCACCAGACGATGCTTGACATGATTAGGGCTTTGGGGACGTGCCGG
TTCAACGTCCCGGCAGGCACAACGCTGCAATTCCCCGTCCCTCCCGCACCGGTCCGTGGGTTCGCATCCTAGCCGGCGG
TTCGTGTCCTGGCAAGAATTCCTTCCTAGATGAAGCAGCGTATTGCAATCACCTTGATGTTTTGAGGCTTCTTAGTAAAA
CTACCCTCACCTGTCTAGGAGACTTCAAGCAACTCCACCCAGTGGGTTTTGATTCTCATTGCTATGTTTTTGACATCATG
CCTCAAACTCAACTGAAGACCATCTGGAGGGTTTGGACAGAATATCTGTGATGCCATTCAGCCAGATTACAGGGACAAACT
CATGTCCATGGTCAACACAACCCGTGTGACCTACGTGGAAAAACCTGTCAGGTATGGGCAGGTCCTCACCCCCTACCACA
GGGACCGAGAGGACGACGCCATCACTATTGACTCCAGTCAAGGCGCCACATTCGATGTGGTTACATTGCATTTGCCCACT
AAAGATTCACTCAACAGGCAAAGAGCCCTTGTTGCTATCACCAGGGCAAGACACGCTATCTTTGTGTATGACCCACACAG
GCAGCTGCAGGGCTTGTTTGATCTTCCTGCAAAAGGCACGCCCGTCAACCTCGCAGTGGACTGCGACGGGCAGCTGATCG
TGCTGGATAGAAATAACAAAGAATGCACGGTTGCTCAGGCTCTAGGCAACGGGGATAAATTTAGGGCCACAGACAAGCGT
GTTGTAGATTCTCTCCCGCGCCATTTGTGCTGATCTAGAAGGGTCGAGCTCTCCGCTCCCAAGGTCGCACACAACTTGGG
ATTTTATTTCTCACCTGATTTAACACAGTTTGCTAAACTCCCAGTAGAACTTGCACCTCACTGGCCCGTGGTGTCAACCC
AGAACAATGAAAAGTGGCCGGATCGGCTGGTTGCCAGCCTTCGCCCTATCCATAAATACAGCCGCGCGTGCATCGGTGCC
GGCTATATGGTGGGCCCTTCGGTGTTTCTAGGCACTCCTGGGGTCGTGTCATACTATCTCAGAAATTTGTTAAGGGCGG
GGCTCAAGTCGTTCGGAGACGGTTTCAGCACCGGCCGAATTGAGGTAGACTGCGGGAATATCTTGATGATCGGGAGC
GAGAAGTTGCGTCCCTCCCACACGCTTTCATTGGCGACGTCAAAGGCACTACCGTTGGAGGATGTCATCATGTCACC
TCCAGATACCTCCCGCGCGTCCTTCCCAAGGAATCAGTTGCGGTAGTCGGGGTTTCAAGCGCCGGAAAGCCGCGAAAGC
ATTGTGCACACTGACAGATGTGTACCTCCCAGATCTTGAAGCCTATCTCCACCCGGAGACCCAGTCCAAGTGCTGGAAAA
TGATGTTGGACTTCAAGGAAGTTCGACTAATGGTCTGGAAAGACAAAACAGCCTATTTCCAACTTGAAGGTCGCTATTTC
AGCTGGTATCAGCCTTGCCCAGCTATGCCCTCGTACATCCGTGTTCCCGTCAACTCTACGGTGTACTTGGACCCCTGCATGGG
CCCGCCCTTTGCAACAGGAGAGTCGTCGGGTCCACCCACTGGGGGCTGACCTCGCGGTCACCCCTTATGATTACGGCG
CTAAAATTATCCTGTCTAGCGCGTACGATGGTGAAATGCCCCCGGATACAAAATTCTGGCGTGCGCGGAGTTCTCGTTG
GATGACCCAGTTAAGTACAAACATACCCTGGGGGTTTGAATCGGATACAGCGTATCTGTATGAGTTCACCGGAAACGGTGA
```

Fig. 1L-4

GGACTGGGAGGATTACAATGATGCGTTTCGTGCGCGCCAGGAAGGGAAAATTTATAAGGCCACTGCCACCAGCTTGAAGT
TTTATTTTCCCCGGGCCCTGTCATTGAACCAACTTTAGGCCTGAATTGAAATGAAATGGGGTCCATGCAAAGCCTTTTT
GACAAAATTGGCCAACTTTTTGTGGATGCTTTCACGGAGTTCTTGGTGTCCATTGTTCATATCATTATATTTTTGGCCAT
TTTGTTTGGCTTCACCATCGCCGGTTGGCTGGTGGTCTTTTGCATCAGATTGGTTTGCTCGGCGATACTCCGTACGCGCC
CTGCCATTCACTCTGAGCAATTACAGAAGATCTTATGAGGCCTTTCTTTCCCAGTGCCAAGTGGACATTCCCACCTGGGG
AACTAAACATCCTTTGGGGATGCTTTGGCACCATAAGGTGTCAACCCTGATTGATGAAATGGTGTCGCGTCGAATGTACC
GCATCATGGAAAAGCAGGGCAGGCTGCCTGGAAACAGGTGGTGAGCGAGGCTACGCTGTCTCGGCATTAGTAGTTTGGAT
GTGGTGGCTCATTTTCAGCATCTAGCCGCCATTGAAGCCGAGACCTGTAAATATTTGGCCTCCCGGCTGCCCATGCTACA
CAACCTGCGCATGACAGGGTCAAATGTAACCATAGTGTATAATAGCACTTTGAATCAGGTGTTTGCTATTTTTCCAACCC
CTGGTTCCCGGCCAAAGCTTCATGATTTTCAGCAATGGTTAATAGCTGTACATTCCTCCATATTTTCCTCTGTTGCAGCT
TCTTCGACTCTTTTGTGTGCTGTGGTTGCGGGTTCCAATACTACGTACTGTTTTGGTTCCGCTGGTTAGGGCAAT
TTTTCTTTCGAACTCACAGTGAATTACACGGTGTGTCCACCTTGCCTCACCGGCAAGCAGCCACAGAGATCTACGAACC
CGGTAGGTCTCTTTGGTGCAGGATAGGGTATGACCGATGTGGGGAGGACGATCATGACGAGCTAGGGTTTATGATACCGC
CTGGCCTCTCCAGCGAAGGCCACTTGACTGGTGTTACGCCTGGTTGGCGTTCTTGTCCTTCAGCTACACGGCCCAGTTC
CATCCCGAGTATTCGGGATAGGGAATGTGAGTCGAGTTTATGTTGACATCAAACATCAACTCATCTGCGCCGAACATGA
CGGGCAGAACACCACCTTGCCTCGTCATGACAACATTTCAGCCGTGTTTCAGACCCTATTACCAACATCAAGTCGACGGCG
GCAATTGGTTCACCTAGAATGGCTTCGTCCCTTCTTTTCCTCGTGGTTGGTTTTAAATGTCTCTTGGTTTCTCAGGCGT
TCGCCTGCAAACCATGTTTCAGTTCGAGTCTTGCAGATATTAAGACCAACACCACGGCAGCGGCAAGCTTTGCTGTCCTC
CAAGACATCAGTTGCCTTAGGCATGCCGACTGGGCCTCTGAGGCGATTCGCAAAATCCCTCAGTGCCGTACGGCGATAGG
GACACCCGTGTATGTTACCATCACAGCCAATGTGACAGATGAGAATTATTTACATTCTTCTGATCTCCTCATGCTTTCTT
CTTGCCTTTTCTATGCTTCGAGATGAGTGAAAAGGGATTTAAGGTGGTATTTGGCAATGTGTCAGGCATCGTGGCTGTG
TGTGTCAATTTTACCAGCTACGTCCAACATGTCAAGGAGTTTACCCAACGCTCCCTGGTGGTCGACCATGTGCGGTTGCT
CCATTTCATGACACCTGAGACCATGAGGTGGGCAACTGTTTTAGCCTGTCTTTTTGCCATTCTGTTGGCAATTTGAATGT
TTAAGTATGTTGGAGAAATGCTTGACCGCGGGCTGTTGCTCGCGATTGCTTTCTTTGTGGTGTATCGTGCCGTTCTGTTT
TGCTGTGCTCGCCAAGCCAGCAACGACAGCAGCTCCCATCTACAGCTGATTTACAACTTGACGCTATGTGAGCTGAATG
GCACAGATTGGCTAGCTAACAAATTTGATTGGGCAGTGGAGAGTTTTGTCATCTTTCCCGTTTTGACTCACATTGTCTCC
TATGGTGCCCTCACTACCAGCCATTTCCTTGACACAGTCGCTTTAGTCACTGTGTCTACCGCCGGGTTTGTTCACGGGCG
GTATGTCCTAAGTAGGCATCTACGCGGTCTGTGCCCTGGCTGCGTTGACTTGCTTCGTCATTAGGTTTGCAAAGAATTGCA
TGTCCTGGCGCTACGCGTGTACCAGATATACCAACTTTCTTCTGGACACTAAGGGCAGACTCTATCGTTGGCGGTCGCCT
GTCATCATAGAGAAAAGGGGCAAAGTTGAGGTCGAAGGTCATCTGATCGACCTCAAAAGAGTTGTGCTTGATGGCTCCGT
GGCAACCCCTATAACCAGAGTTTCAGCGGGAACAATGGGGTCGTCCTTAGATGACTTCTGTCACGATAGCACGGCTCCACA
AAAGGTGCTTTTGGCGTTTTCTATTACCTACACGCCAGTGATGATATATGCCCTAAAGGTGAGTCGCGGCCGACTGCTAG
GGCTTCTGCACCTTTTGATCTTCCTGAATTGTGCTTTCACTTCGGGTACATGACTTTCGCGCACTTTCAGAGTACAAAT
AAGGTGCGCTCACTATGGGAGCAGTAGTTGCACTCCTTTGGGGGTGTACTCAGCCATAGAAACCTGGAAATTCATCAC
CTCCAGATGCCGTTTGTGCTTGCTAGGCCGCAAGTACATTCTGGCCCCTGCCCACCACGTTCAGACTGCCGCAGGCTTTC
ATCCGATTGCGGCAAATGATAACCACGCATTTGTCGTCCGGCGTCCCGGCTCCACTACGGTCAACGGCACATTGGTGCCC
GGGTTAAAAAGCCTCGTGTTGGGTGGCAGAAAAGCTGTTAAACAGGGAGTGGTAAACCTTGTCAAATATGCCAAATAACA
ACGGCAAGCAGCAGAAGAGAAAGAAGGGGGATGCCCAGCCAGTCAATCAGCTGTGCCAGATGCTGGGTAAGATCATCGCT
CAGCAAAACCAGTCCAGAGGCAAGGGACCGGGAAAGAAAAATAAGAAGAAAAACCCGGACAAGCCCCATTTTCCTCTAGC
GACTGAAGATGATGTCAGACATCACTTTACCCCTAGTGACGGCAATTGTGTCTGTCGTCAATCCAGACCGCCTTTAATC
AAGGCGCTGGGACTTGCACCCTGTCAGATTCAGGGAGGATAAGTTACACTGTGGAGTTTAGTTTGCCTACGCATCATACT
GTGCGCCTGATCCGCGTCACAGCATCACCCTCAGCATGATGGGCTGGCATTCTTGAGGCATCTGAGTGTTTGAATTGGAA
GAATGTGTGGTGAATGGCACTGATTGACATTGTGCCTCTAAGTCACCTATTCAATTAGGGCGACCGTGTGGGGCTGAGAT
TTAATTGGCGAGAACCATGCGGCCGAAATTAAAAAAAA

Fig. 1M-1

```
>V7-Nsp2d324-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTCATCGGTGCACGTGTACCCCCAATGCCAGGGTGTTT
ATGGCGGAGCGCCAAGTCTACTGCACACGATGCCTCAGTGCACGGTCTCTCCTTCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCTGCTGGCTTTCTGCAATCTTTCCAATCGCACGAATGACCAGTGGAAACCTGAACTTCAACAAAGA
ATGGTACGGGTGCGAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGCCTACTGTCTATGACATTGGTCATGACGCCGTCATGTATGTGGCGAAAGGAAAGTCTCCTGGCCCCTCG
TGGCGGGGATGAAGTGAAATTTGAAGCTGTCCCCGGGGAGTTGAAGTTGATTGCGAACCGGCTCCCGCACCTCCTTCCCGC
CCCACCACACAGTGGACATGTCTAAGTTCGCCTTCACAGCCCTGCGTGTGGTGTTTCTATGCGGGTCGAACGCCAACAC
GGCTGCCTTCCCGCTGACACTGTCGCTGAAGGCAACTGCTGGTGGAGCTTGTTTGACTTGCTTCCACTGGAAGTTCAAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCGGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGGCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCCTTCCCGAAAGAGTGAGACCTCCAGATGACTGGGCTACTG
ACGAGGATCTTGTGAATGCCATCCAAATCCTCAGACTCCCTGCCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCCGGAGGAGGTCGCAGCAAAGATTGACCTGTACCTCCGTGGTGCAACAAATCTTGAAGAATGCTTGGCCAGGCTTGAG
AAAGCGCGGCCCGCCACGCGTAATCGACACCTCCTTTGATTGGGATGTTGTGCTCCCTGGGGTTGAGGCGGCAACCCAGAC
GATCAAGCTGCCCAGCGTCAACCAGTGTCGTGCTCTGGTCCTGTTGTGACTCAAAAGTCCTTGTGAGTTTGTGATGA
TGCCTCACACGCCTGCACCTTCCGTAGGTGCGGAGAAGCGACCTTACCATTGGCTCAGTTGCTACTGAAGATGTTCCACGC
ATCCTCGAGAAATAGAAAATGTCGGCGAGATGGCCAACCAGGCCCTTGGCCTTCTCCGAGGATAAACCGGTAGATGA
CCAACTTGTCAACGACCCCGGATATCGTCGCCGGAGGCCTGACGAGAGCACATCAGCTCCGTCCGCAGGGACAGGTGGCG
CCGGCTCTTTTACCGATTTGCCGCCTTCAGATGGCGCGGATGCGGACGGGGGGGGCCGTTTCGGACGGTAAAAAGAAAA
GCTGAAAGGCTCTTTGACCAACTGAGCCGTCAGGTTTTTGACCTCGTCTCCCATCTCCCTGTTTCTTCTCACGCCTTTT
CTACCCTGGCGGTGGTTATTCTCGGGGTGATTGGGGTTTTGCAGCTTTTACTCTATTGTGCCTCTTTTTATGTTACAGTT
ACCCAGCCTTTGGTATTGCTCCCCTCTTGGGTGTGTTTTCTGGGTCTTCTCGGCGCGTTCGAATGGGGGTTTTGGCTGC
TGGTTGGCTTTTGCTGTTGGTCTGTTCAAGCCTGTGTCCGACCCAGTCGGCGCTGCTTGTGAGTTTGACTCGCCAGAGTG
TAGAAACATCCTTCATTCTTTTGAGCTTCTCAAACCTTGGGACCCTGTTCGCAGCCTTGTTGTGGGCCCCGTCGGTCTCG
GTCTTGCCATTCTTGGCAGGTTACTGGGCGGGGCACGCTGCATCTGGCACTTTTTGCTTAGGCTTGGCATTGTGCAGAC
TGTATCTTGGCTGGAGCTTACGTGCTTTCTCAAGGTAGGTGTAAAAAGTGCTGGGGATCTTGTATAAGAACTGCTCCCAA
TGAGGTCGCTTTTAACGTGTTTCCTTTCACACGTGCGACCAGGTCGTCACTTATCGACCTGTGCGATCGGTTTTGTGCGC
CAAAAGGAATGGACCCATTTTTCTCGCCACTGGGTGCGCGGGTGCTGGGCCGGCCGAAGCCCCATTGAGCAACCCTCT
GAAAAACCCATCGCGTTTGCCCAGTTGGATGAAAAGAAGATTACGGCTAGGACTGTGGTCGCCCAGCCTTATGACCCCAA
CCAAGCCGTAAAGTGCTTGCGGGTATTGCAGGCGGGTGGGGCGATGGTGGCTAAGGCGGTCCCAAAAGTGGTCAAGGTTT
CCGCTGTTCCATTCCGAGCCCCCTTCTTTCCACTGGAGTGAAAGTTGACCCTGATTGCAGGGTCGTGGTTGACCCTGAC
ACTTTCACTGCAGCTCTCCGGTCTGGCTACTCCACCACAAACCTCGTCCTTGGTGTGGGGACTTTGCCCAGCTGAATGG
ATTAAAAATCAGGCAAATTTCCAAGCCTTCAGGGGGACGCCCACATCTCATGGCTGCCCTGCATGTTGCCTGCTCGATGG
CTCTGCACATGCTTGCTGGGATTTATGTGACTGCGGTGGTTCTTGCCGCACCGGCACCAACGACCGTGGTGCGCTAAC
```

GATCTACGAACCCGGTAGGTCTCTTTGGTGCAGGATAGGGTATGACCGATGTGGGAGGACGATCATGACGAGCTAGGGT
TTATGATACCGCCTGGCCTCTCCAGCGAAGGCCACTTGACTGGTGTTTACGCCTGGTTGGCGTTCTTGTCCTTCAGCTAC
ACGGCCCAGTTCATCCCGAGATATTCGGGATAGGGAATGTGAGTCGAGTTTATGTTGACATCAAACATCAACTCATCTG
CGCCGAACATGACGGGCAGAACACCACCTTGCCTCGTCATGACAACATTTCAGCCGTGTTTCAGACCTATTACCAACATC
AAGTCGACGGCGGCAATTGGTTTCACCTAGAATGGCTTCGTCCCTTCTTTTCCTCGTGGTTGGTTTTAAATGTCTCTTGG
TTTCTCAGGCGTTCCGCCTGCAAACCATGTTTCAGTTCGAGTCTTGCAGATATTAAGACCAACACCACCGCAGCGGCAAGC
TTTGCTGTCCTCCAAGACATCAGTTGCCTTAGGCATCGCCACTCGGCCTCTGAGGCGATTCGCAAAATCCCTCAGTGCCG
TACGGCGATAGGGACACCCGTGTATGTTACCATCACAGCCAATGTGACAGATGAGAATTATTTACATTCTTCTGATCTCC
TCATGCTTTCTTCTTGCCTTTTCTATGCTTCTGAGATGAGTGAAAAGGGATTTAAGGTGGTATTTGGCAATGTGTCAGGC
ATCGTGGCTGTGTGTGTCAATTTTACCAGCTACGTCCAACATGTCAAGGAGTTTACCCAACGCTCCTGCTGGTCGACCA
TGTGCGGTTGCTCCATTTCATGACACCTGAGACCATGAGGTGGGCAACTGTTTTAGCCTGTCTTTTTGCCATTCTGTTGG
CAATTTGAATGTTTAAGTATGTTGGAGAAATGCTTGACCGCGGGCTGTTGCTCGCGATTGCTTTCTTGTGGTGTATCGT
GCCGTTCTGTTTTGCTGTGCTCGCCAACGCCAGCAACGACAGCAGCTCCCATCTACAGCTGATTTACAACTTGACGCTAT
GTGAGCTGAATGGCACAGATTGGCTAGCTAACAAATTTGATTGGGCAGTGGAGAGTTTTGTCATCTTTCCCGTTTTGACT
CACATTGTCTCCTATGGTGCCCTCACTACCAGCCATTTCCTTGACACAGTCGCTTAGTCACTGTGTCTACCGCCGGGTT
TGTTCACGGGCGGTATGTCCTAAGTAGCATCTACGCGGTCTGTGCCCTGGCTGCGTTGACTTGCTTCGTCATTAGGGTTTG
CAAAGAATTGCATGTCCTGGCCGCTACGCGTGTACCAGATATACCAACTTTCTTCTGGACACTAAGGGCAGACTCTATCGT
TGGCGGTCGCCTGTCATCATAGAGAAAGGGGCAAAGTTGAGGTCGAAGGTCATCTGATCGACCTCAAAAGAGTTGTGCT
TGATGGCTCCGTGGCAACCCCTATAACCAGAGTTTCAGCGGAACAATGGGGTCGTCCTTAGATGACTTCTGTCACGATAG
CACGGCTCCACAAAAGGTGCTTTTGGCGTTTTCTATTACCTACACGCCAGTGATGATATATGCCCTAAAGGTGAGTCGCG
GCCGACTGCTAGGGCTTCTGCACCTTTTGATCTTCCTGAATTGTGCTTTCACCTTCGGGTACATGACTTTCGCGLACTTT
CAGAGTACAAATAAGGTCGCGCTCACTATGGGAGCAGTAGTTGCACTCCTTTGGGGGGTGTACTCAGCCATAGAAACCTG
GAAATTCATCACCTCCAGATGCCGTTTGTGCTTGCTAGGCCGCAAGTACATTCTGGCCCCTGCCCACCACGTTGAAAGTG
CCGCAGGCTTTCATCCGATTGCGGCAAATGATAACCACGCGATTTGTCGTCCGGCGTCCGGCTCCACTACGGTCAACGGC
ACATTGCTGCCCGGGTTAAAAAGCCTCGTGTTGGGTGGCAGAAAAGCTGTTAAACAGGGAGTGGTAAACCTTGTCAAATA
TGCCAAATAACAACGGCAAGCAGCAGAAGAGAAAGAAGGGGATGGCCAGCCAGTCAATCAGCTGTGCCAGATGCTGGGT
AAGATCATCGCTCAGCAAAACCAGTCCAGAGGCAAGGGACCGGGAAAGAAAATAAGAAGAAAAACCCGGAGAAGCCCCA
TTTTCCTCTAGCGACTGAAGATGGTGTCAGACATCAGTTTACCCCTAGTGAGCGGGAATTGTGTCTGTCGTCAATCCAGA
CCGCCTTTAATCAAGCCGCTGGGACTTGCACCCTCTCAGATTCAGGGAGGGTAAGTTACACTCTGGAGTTTAGTTTGCCT
ACGCATCATACTGTGCGCCTGATCCGCGTCACAGCATCACCCTCAGCATGATGGGCTGGCATTCTTGAGGCATCTCAGTG
TTTGAATTGGAAGAATGTGTGGTGAATGGCACTGATTGACATTGTGCCTCTAAGTCACCTATTCAATTAGGGCGACCGTG
TGGGGGTGAGATTTAATTGGCGAGAACCATGCCGCCGAAATTAAAAAAAA

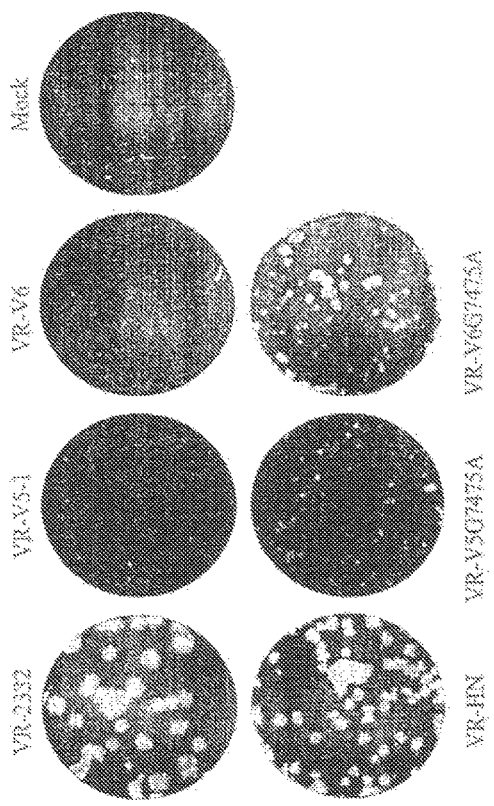
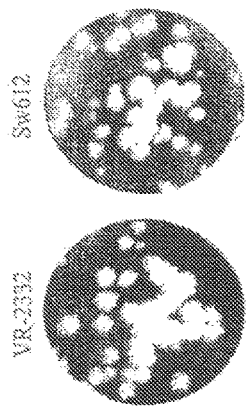
Fig. 5A
Fig. 5B

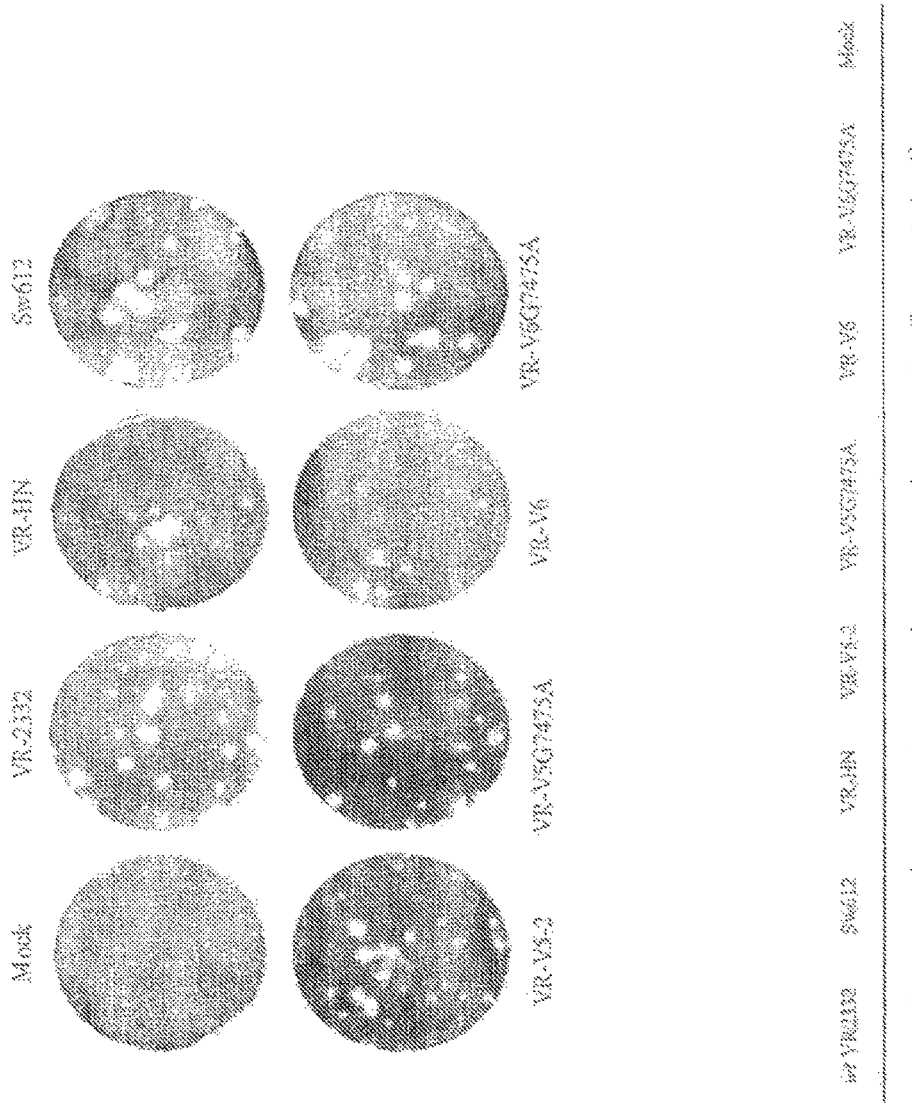

| | | |
|---|---|---|
| EuroPRRSV | IVDDRGGYHBWRSPIVVEKLGKADIDGSPVTIKHVTEGVKAQPLTRTSAEQW-EA | 201 |
| Lelystad | IVDDRGGYHBWRSPIVVEKLGKAEVDGMLVTIKHVTEGVKAQPLTRTSAEQW-EA | 201 |
| MN184A | LLDTRGRLYRWRSPVTIEKGKIEVGGDLIDLEKVTLDGSAATPVTKVSAEQWGRP | 200 |
| MN184B | LLDTKGRLYRWRSPVIVEKGRIEVGGDLEDLEKVTLDGSAATPVTKVSAEQWGRP | 200 |
| 98-3298 | LLDTKG Figure 11 (continued)

Figure 11 (continued)

| | | |
|---|---|---|
| EuroPRRSV | QVRGIRAVPDGPIHVEALSCSQSWIRHLTINDDVT-PGFVRLTSIRIVPNTEPTTS---QFRPGAHWTG | 219 |
| Lelystad | QVRGIRAVPDGPIHVEALSCVQSWIRHLTLDDDVT-PGFVRLTSLRIVPNTEPTTS---RIFPGAHWTG | 219 |
| MN184A | QVRGLRAVPSNGPTVIQFSVKESWIRHVKLAEEFDYPGFDLIRVEPNYLPLSNEDEKIFRGGCKWTG | 217 |
| MN184B | QIRGLRAVDSNGPTVIQFSVKESWIRHVKLAEEFDYPGFDLIRVEPNYXPLSNKDEKIFRGGCKWTG | 217 |
| Ingelvac | QVRGLRAVTDLNGPTVVQYFVKESWIRHLKLAGHPSYSGFEDLIETRVEPNTSPLADKEKIFRGSHWTG | 217 |
| VR-2332 | QVRGLRAVTDLNGPTVVQYFVKESWIRHLKLAGHPSYSGFEDLIETRVEPNTSPLADKEKIFRGSHWTG | 217 |
| PL97-1 | QVRGLRAVTDPMGPTVVQYFVKESWIRHLKLAGHPSYCGFEDLLIRVEPNTSPLADKEKIFRGSHWTG | 217 |
| HN1 | QVRGLRAVTDPMGPTVVQYFVKESWIRHLKLAGHPSYCGFEDLLIRVEPNTSPLADKEKIFRGSHWTG | 217 |
| 16244B | QVRGLRAVTDLNGPTVVQYFSVKESWIRHLKLAGHPSYSGFEDLLIRVEPNTSPLADKEZKIFRGSHWTG | 217 |
| PA-8 | QVRGLRAVTDSNGPTVVQCFSVKESWIRHLKLAEHPSYPGFEDLIIRVEPNTSPLADKEKIFRGNHWTG | 217 |
| SP | QVRGLRAVTDLNGPTVVQCFSVKESWIRHLKLAEHPSYPGFEDLIIRVEPNTSPLADKEKIFRGNHWTG | 217 |
| JA142 | QARGLRAVTDTDGPTVVQYFVKRGSWIRHFRLAGEPSLPGFEDLIIRVEPNTSELAEKDGKIFRGSHWTG | 217 |
| CH-1 | QVRGLRAVTDTDGPTVIQYFVKRSWIRHFRLAGEPSLPGFEDLIIRVEPNTSELAEKDGKIFRGSHWTG | 217 |
| P129 | QVRGLRAVTDTDGPTVIQYFVKESWIRHFRLAEHPSLPGFEDLIIRVEPNTSPLGGKGEKIFRGSHWTG | 217 |
| HB-2 | QINGLRAVTDTHGPTIQFSVKESWIRHLKLAQEPSLPGFEDLIIRVBSWIRSPLADEKIFRGSHWTG | 217 |
| HB-1 | QINGLRAVTDTHGPTVQFSVKESWIRHLKLAQEPSLPGFEDLIIRVEHSPLAGKNEKIFRGSHWTG | 217 |

| | | |
|---|---|---|
| MN184A | SRPLPAPRKEISRCGSPISLGGNLPDSQEDLAGG-SFDFPTLPELVVSSSESV----------------PV | 394 |
| MN184B | SRPLPAPRKKIGSRCGSPISLGGNLPDSREDLAGG-SFDFPTLPELVASSSEPV----------------PV | 394 |
| VR-2332 | RKPVPAPRRKVGSDCGSPVSLGGDVFNSWEDLAVSSPFDLPTPEPATDSSELVIVSSPQCIFRPATPLSEPAPI | 525 |
| Ingelvac | RKPVPAPRRKVGSDCGSPVSLGGDVFNSWEDLAVSSPFDLPTPEPEPATPSSELVIVSSPQCIFRPATPLSEPAPI | 525 |
| 01NP1.2 | RKPVPAPRRKVGSDCGSPVSLGGDVFNSWEDLAVSSPFDLTPEPEPATSSELVTVSSPQCIFRPATPLSEPAPI | 525 |
| PL97-1 | RKPVPAPRRKVGSDCGSPVSLGGDVFNSWEDLAVSSPFDLPTPPHPATPSSELVIVSSPQCIFRPATPLSEPAPI | 525 |
| SP | SKPVPAPRRKVPSDDCPTLSGMNLPDSWEDLAVGCPSDLPTSPEPVTPLSEPASVSAPRSFRPVKPLSEPVPV | 524 |
| PA-8 | RKPVPAPRRKVGSDCGSPVSLGGDVFNSWEDLAVSSPFDLPTPEPAIPSSELVIVSSPQCIFRPATPLSEPAPI | 525 |
| BJ-4 | RKPVPAPRRVGSDCGSPVSLGGDVFNSWEDLAVSSPFDLPTPEPFELATESSELVIVSSPQCIFRPATPLSEPAPI | 525 |
| HN1 | RKPVPAPRRVGSDCGGEVSIGGDVFNSWEDLAVSSPFDLPTPEPAIPSSELVIVSSPQCIFRPATPLSEPAPI | 525 |
| 10244B | RKPVPAPRRKVGSDCGSPVSLGGDVFNSWEDLAVSSPFDLPTPFHPATLSEELVIVSSPQCIFRPATPLSEPAPI | 525 |
| CH-1 | RKPVPAPRKVGSDCGSEILAGDNVFNCMEDFAVGGZLDFFTESEPMTPLSEPVLMPASQHIZRPVTPLSGPAPV | 525 |
| HB-2 | ----------GKSILAVGGPLMFSTPSELVTPLGPVLMPASQVSRPVTPLSEPAPV | 513 |
| P129 | MRPVPAPRRKVRSDF-----------GKSILAVGGPLMFSTPSELVTPLGPVLMPASQVSRPVTPLSEPAPV | 519 |
| JA142 | MKPVPAPRRVRSDYGSPILMGDNVFNGWEDSTVGGPILSAPSEPMTPLSEPVLI----SRPVTSLSVRAPV | 525 |
| HB-1 | MKPVPAPRKVRSDCGSPILMGDNVFDGREDITVGGPIDLSTFSEPMTPLSEPALMPALQYISRPVTSLSVLAPV | 525 |
| SPPRRS-01-48 | DKPVPAPRKVRSGGSPVLMGDNVFNGSBDITVGGPLNFPEPSEMPPMSEPVLIPALQRVPKLMPLDGSAPV | 423 |
| EuroPRRSV | -SSDSKRENMHNSREDEPLDISHPAPAAATTIVGEQTPDNPGSDASALPIAVRGFVPTGPILRHVEHCGTESGDS | 423 |
| Lelystad | -PLNSMKEMMRSREDEPLDISQPAPVAATIEREQTPDNPGSDAGALPATVRESVPTGEMLRHVEHCGTESGDS | 440 |
| | SPSDPMKEMMINSREDEPLDISQPAPASTTTVREQTPDMPGSDAGAI Figure 12 (continued)

Figure 12 (continued)

| | |
|---|---|
| MN184A | REVEEVLSGTSGMSDDIRLAPVSSSESLSSIEITRPKYSAQAIINSGGPCCGHLQEVKEKYLNVMREACDATKLD 544 |
| MN184B | REVEEVLSGISGMPDDIRLAPVSSSESLSSIEITRPKYSAQAIINSGGPCCGHLQEVKEKYLNVMREACDATKLD 544 |
| VR-2332 | HEAEETLSEISDMSGNIKPASVSSSSSLSSVRITRPKYSAQAIIDSGGPCSGHLQEVKETCLSVMREACDATKLD 675 |
| IngelVac | HEAEETLSEISDMSGNIKPASVSSSSSLSSVRITRPKYSAQAIIDSGGPCSGHLQEVKETCLSVMREACDATKLD 675 |
| 01NP1.2 | HEAEETLSEISDMSGNIKPASVSSSSSLSSVRITRPKYSAQAIIDSGGPCSGHLQEVKETCLSVMREACDATKLD 675 |
| PL97-1 | HEAEETLSEISDMSGNIKPASVSSSSSLSSVRITRPKYSAQAIIDSGGPCSGHLQEVEACLSVMREACDATKLD 675 |
| SP | REAEEILSGISDILDAIKDPASASSSSLSSVAITRPKYSAQAITRPKYSGHLQEVKETCISIMSILDVTKID 675 |
| PA-8 | HEAEETLSEISDMSGNIKPASVSSSSSLSSVRITRPKYSAQAIIDSGGPCSGHLQEVKETCLSVMREACDATKLD 675 |
| BJ-4 | HEAEETLSEISDMSGNIKPASVSSSSSLSSVRITRPKYSAQAIIDSGGPCSGHLQEVKETCLSVMREACDATKLD 675 |
| HN1 | HEAEETLSEISDMSGNIKPASVSSSSSLSSVRITRPKYSAQAIIDSGGPCSGHLQEVKETCLSVMREACDATKLD 675 |
| 16244B | HEAEETLSEISDMSGNIKPASVSSSSSLSSVETRPKYSAQAIIDSGGPCSGHLQGVKETCLSVMREACDATKLD 675 |
| CH-1 | QEAEEVISGISDILMDIINPAPVSSSSSLSSVKITRPKYSAQAIIDSGGPCSGHLQREKEACLSIRREAQDAAKLS 675 |
| HB-2 | QEAEEVLSGISDILDMTNPAPVSSESSSLSSVKITRPKYSAQAIIDSGGPCSGHLQKEKEACLRIMREAQDAARLG 863 |
| P129 | QEAEEVLSEISDILNDINPAPVSSESSSLSSVLSSVRITRPKYSAQAITDLGPPCSGHLQREMEACIRMEACDAAKLS 669 |
| JA142 | QEAEEVLSEISDTLMDINPAPVSSSSSSLSSVLSSVKITRPKHSAQAIIDSGGPCSGMLRREKEACLSIMREACDAAKLS 675 |
| HB-1 | QEAEEVLSEISDILMDISPAPTSPAPVSSSSSLSSVKITRPKYSAQAIIDSGGPCSGHLQKEACLSIMREACDASKLS 675 |
| SPPRRS-01-08 | DQTKDILVADAPVDLTTSNEALSAVDFSEFVELRREPHSAQALIDRGGPLADVHAKIKNRVYEQCLQACEPGSRA 569 |
| EuroPRRSV | DRITKDAPVVDAPVDLTTSNEALSIADPFEFAELKRDRFSKQALIDRGSPLADVHAKIKNRVYERCLQACEPGSRA 569 |
| Lelystad | DRITKDAPVVDAPVDLTTSNEALSVDPEFAELKRDRFSKQALIDRGDPLADVHAKIKNRVYEQCLQMCEPGSRA 580 |

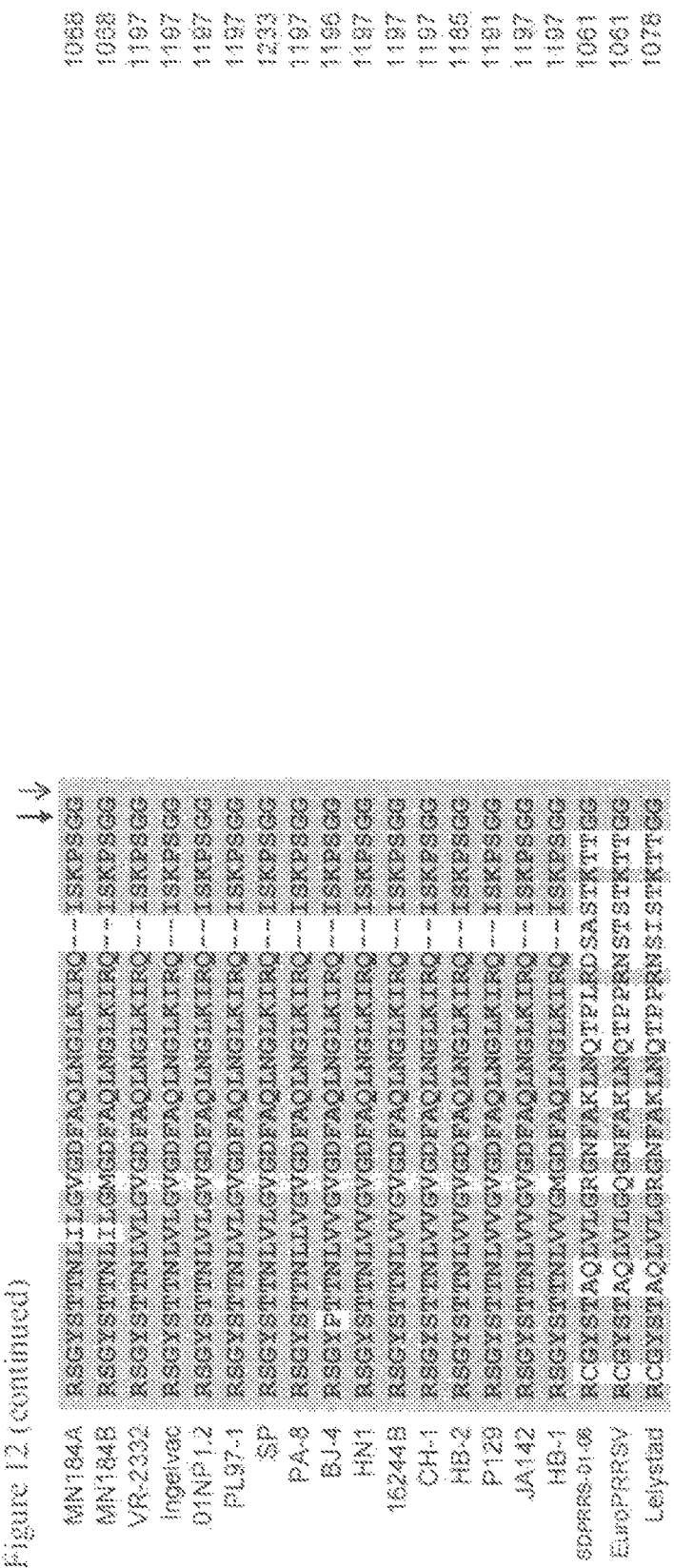

Fig. 13

| Base | Region | VR-2332 | V4 | V5 | VS-1-P3 | VS-2-P3 | VS Swine 612 | VSG7 475A | VSG7 475A-P3 | V6 | V6G 7475 A | V6G7 475A-P3 | VR-HN | MLV |
|---|---|---|---|---|---|---|---|---|---|---|---|---|---|---|
| -4 | | | | | | | T | | | | | | | |
| -3 | | | G | G | | T | | G | | G | G | | G | |
| -2 | | | G | G | | T | | G | | G | G | LO | G | |
| -1 | 5'UTR | | T | T | | T | | T | LO | T | T | T | T | T |
| 48 | | A | A | A | A | A | A | A | A | A | R (G/A) | A | A | |
| 102 | | A | A | A | A | A | G | A | A | A | A | A | A | A |
| 258 | | C | C | C | C | C | C | C | C | C | C | C | A | C |
| 309 | | A | G | G | G | G | G | G | G | G | G | G | A | A |
| 415 | NSP1 | T | T | T | - | Y (C/T) | T | T | - | T | T | - | T | T |
| 682 | | T | C | C | - | C | C | C | - | C | C | - | T | T |
| 794 | | G | G | G | - | G | G | G | - | G | G | - | G | A |
| 827 | | C | C | C | - | C | T | C | - | C | C | - | C | C |
| 1074 | | C | C | C | - | C | C | C | - | C | C | - | T | C |
| 1107 | | A | G | G | - | G | G | G | - | G | G | - | A | A |
| 1122 | NSP1b | A | A | A | - | R (G/A) | A | A | - | A | A | - | A | A |
| 1181 | | C | C | C | - | C | C | C | - | C | C | - | C | T |
| 1294 | | A | A | A | - | R (G/A) | A | A | - | A | A | - | A | A |
| 1379 | | C | C | C | - | C | T | C | - | C | C | - | C | C |
| 1595 | | C | A | C | - | C | C | C | - | C | C | - | C | C |
| 2192 | | C | C | C | - | C | C | C | - | C | C | - | C | T |
| 3040 | NSP2 | G | G | G | - | G | G | G | - | G | G | - | G | A |
| 3457 | | G | G | G | - | G | G | G | - | G | G | - | G | A |
| 3867 | | G | C | C | - | Y (C/T) | C | C | - | C | C | - | C | C |
| 4407 | | T | C | C | - | C | C | C | - | C | C | - | T | T |
| 4593 | NSP3 | A | G | G | - | G | G | G | - | G | G | - | A | A |
| 4681 | | T | G | G | - | G | G | G | - | G | G | - | G | G |

| Base | Region | VR-2332 | V4 | V5 | V5-1-P3 | V5-2-P3 | V5 Swine 682 | V5C7 475A | V5C7 475A-P3 | V6 | V6C7 7425 A | V6C7 475A-P3 | V6-HN | MLV |
|---|---|---|---|---|---|---|---|---|---|---|---|---|---|---|
| 4865 | | T | T | T | - | Y (C/T) | T | T | - | T | T | - | T | T |
| 4886 | | A | G | G | - | G | G | G | - | G | G | - | A | A |
| 5037 | | G | A | A | - | A | A | A | - | A | A | - | A | A |
| 5247 | | T | C | C | - | C | C | C | - | C | C | - | T | T |
| 5519 | | C | C | C | - | C | C | C | - | C | C | - | T | C |
| 5610 | | T | T | T | - | T | T | T | - | T | T | - | A | T |
| 6345 | NSP5 | A | A | A | - | A | A | A | - | A | A | - | A | T |
| 6624 | | C | T | T | - | T | T | T | - | T | T | - | C | T |
| 6853 | | G | G | G | - | G | G | G | - | G | G | - | A | G |
| 6866 | | T | T | T | T | T | T | T | T | T | T | T | C | T |
| 7183 | | A | A | A | A | A | A | A | A | A | A | R (G/A) | A | A |
| 7188 | | C | C | C | C | C | C | C | Y (C/T) | C | C | Y (C/T) | C | C |
| 7189 | NSP7 | C | C | C | C | C | C | C | C | C | C | Y (C/T) | C | C |
| 7213 | | C | C | C | C | C | C | C | M (A/C) | C | C | M (A/C) | C | C |
| 7329 | | G | A | A | A | A | A | A | A | A | A | A | G | G |
| 7425 | | A | G | G | G | G | A | A | A | G | A | A | A | A |
| 7434 | | T | C | C | C | C | C | C | C | C | C | C | C | T |
| 9220 | NSP9 | T | C | T | - | T | T | T | - | T | T | - | T | T |
| 9649 | | G | A | G | - | G | G | G | - | G | G | - | G | G |
| 9918 | | T | T | T | - | T | T | T | - | T | T | - | T | G |
| 9958 | | G | A | G | - | G | A | G | - | G | G | - | A | A |
| 10030 | | A | G | A | - | A | A | A | - | A | A | - | A | A |
| 10533 | | T | T | T | - | T | T | T | - | T | T | - | T | G |
| 10643 | NSP10 | T | T | T | - | T | T | T | - | T | T | - | C | T |
| 10697 | | T | C | T | - | T | T | T | - | T | T | - | C | C |
| 10739 | | C | T | C | - | C | C | C | - | C | C | - | C | C |
| 10781 | | G | A | G | - | G | G | G | - | G | G | - | A | A |
| 10913 | | T | C | T | - | T | T | T | - | T | T | - | C | C |
| 10985 | | C | C | C | - | C | C | C | - | C | C | - | C | T |
| 11053 | NSP11 | T | A | T | - | T | T | T | - | T | T | - | A | A |
| 11081 | | G | A | G | - | G | G | G | - | G | G | - | A | A |

| Base | Region | VR-2332 | V4 | V5 | V5-1-P3 | V5-2-P3 | V5-Swine 612 | VSG7 475A | VSG7 475A-P3 | V6 | V6G 7475 A | V6G7 475A-P3 | VR-BN | MLV |
|---|---|---|---|---|---|---|---|---|---|---|---|---|---|---|
| 15339 | | C | C | C | - | Y (T/C) | C | C | - | C | C | - | C | C |
| 15411 | | T | T | T | - | K (T/G) | V (G) | T | - | T | T | - | T | T |

| NT Position | AA Position | Region | VR-2332 | V4 | V5 | V5-1-P3 | V5-2-P3 | V5-Sw612 | V5G7 475A | V6 | V5G7 475A | VR-HN | MLV |
|---|---|---|---|---|---|---|---|---|---|---|---|---|---|
| 258 | 23 | | V | | | | | | | | | Silent | |
| 309 | 40 | NSP1α | Q | Silent | Silent | Silent | Silent | Silent | Silent | Silent | Silent | | |
| 642 | 151 | | P | Silent | Silent | - | Silent | Silent | Silent | Silent | Silent | | |
| 784 | 199 | | V | | | - | | | | | | | |
| 827 | 213 | | A | | | - | | V | | | | | |
| 1074 | 295 | NSP1β | Y | | | - | | | | | | Silent | |
| 1107 | 306 | | L | Silent | Silent | - | Silent | Silent | Silent | Silent | Silent | | |
| 1181 | 331 | | S | | | - | | | | | | | |
| 1379 | 397 | | A | | | - | | V | | | | | |
| 1595 | 469 | | A | D | | - | | | | | | | |
| 2192 | 668 | NSP2 | S | | | - | | | | | | | T |
| 3040 | 951 | | D | | | - | | | | | | | N |
| 3457 | 1090 | | D | | | - | | | | | | | N |
| 4407 | 1406 | | P | Silent | Silent | - | Silent | Silent | Silent | Silent | Silent | | |
| 4593 | 1468 | | Q | Silent | Silent | - | on | Silent | Silent | Silent | Silent | | |
| 4681 | 1498 | | S | A | A | - | S | A | A | A | A | | A |
| 4866 | 1559 | NSP3 | V | Silent | Silent | - | Silent | Silent | Silent | Silent | Silent | | |
| 5097 | 1636 | | R | Silent | Silent | - | Silent | Silent | Silent | Silent | Silent | Silent | Silent |
| 5247 | 1686 | | V | Silent | Silent | - | Silent | Silent | Silent | Silent | Silent | | |
| 5519 | 1777 | | T | | | - | | | | | | I | |
| 5610 | 1807 | | L | | | - | | | | | | Silent | |
| 6345 | 2052 | | P | | | - | | | | | | | Silent |
| 6674 | 2162 | NSP5 | P | T | T | - | T | T | T | T | T | | T |
| 6853 | 2222 | | D | | | - | | | | | | N | |
| 6966 | 2259 | | D | | | - | | | | | | Silent | |
| 7329 | 2380 | NSP7 | K | Silent | Silent | Silent | Silent | Silent | Silent | Silent | Silent | | |
| 7475 | 2429 | | E | G | G | G | G | | | G | | | |
| 7554 | 2455 | | V | Silent | Silent | Silent | Silent | Silent | Silent | Silent | Silent | Silent | |
| 9228 | 3011 | NSP9 | L | P | | - | | | | | | | |
| 9649 | 3134 | | G | E | | - | | | | | | | |
| 9918 | 3244 | | L | | | - | | | | | | | Silent |
| 9958 | 3257 | | G | E | | - | | E | | | | E | E |
| 10040 | 3284 | | V | Silent | | - | | | | | | | |
| 10533 | 3449 | | Y | | | - | | | | | | | H |
| 10643 | 3485 | NSP10 | V | | | - | | | | | | Silent | |
| 10697 | 3503 | | A | Silent | | - | | | | | | Silent | Silent |
| 10739 | 3517 | | H | Silent | | - | | | | | | | |
| 10781 | 3531 | | T | Silent | | - | | | | | | Silent | Silent |
| 10803 | 3539 | | C | R | | - | | | | | | Silent | R |
| 10893 | 3569 | | D | | | - | | | | | | | Silent |

| NT Position | AA Position | Region | VR-2332 | V4 | V5 | V5-1-P3 | V5-2-P3 | V5-Sw612 | V5G7 475A | V6 | V6G7 475A | VR-HN | MLV |
|---|---|---|---|---|---|---|---|---|---|---|---|---|---|
| 11055 | 3623 | NSP11 | S | T | | - | | | | | | T | T |
| 11081 | 3631 | | F | Silent | | - | | | | | | Silent | Silent |
| 11221 | 3678 | | G | E | | - | | E | | | | E | E |
| 11229 | 3681 | | V | | | - | | | | | | | I |
| 11259 | 3691 | | R | G | | - | | | | | | | |
| 11327 | 3738 | | H | Silent | | - | | | | | | | |
| 11329 | 3739 | | G | A | A | - | A | A | A | A | A | A | A |
| 11501 | 3771 | | E | Silent | | - | | | | | | | |
| 11666 | 3826 | NSP12 | F | Silent | | - | | | | | | Silent | Silent |
| 11744 | 3852 | | W | C | | - | | | | | | | |
| 11882 | 3898 | | K | Silent | | - | | | | | | | |
| 12076 | 2 | ORF2a/b | K | E | | - | | | | | | | |
| 12102 | 10/9 | | L/D | | | - | | | | | | | F/Y |
| 12153 | 37 | | P/I | F/V | | - | | | | | | | |
| 12432 | 120 | | K | Silent | | - | | | | | | | |
| 12501 | 143 | | D | E | | - | | | | | | | |
| 12600 | 176 | | G | | | - | | | | | | | Silent |
| 12943 | 83 | ORF3 | G | | | - | | | | | | | E |
| 12950 | 85 | | D | | | - | | | | | | | Silent |
| 12973 | 93 | | M | R | | - | | | | | | | |
| 13011 | 106 | | G | | | - | | | | | | S | S |
| 13825 | 13 | ORF5 | R | | | - | | | | | | | G |
| 13860 | 25 | | F | | L | - | L | L | L | | | | |
| 14238 | 151 | | R | | | - | | | | | | | G |
| 14336 | 183 | | G | | Silent | - | Silent | Silent | Silent | Silent | Silent | | |
| 14404 | 10 | ORF6 | H | | Silent | - | Silent | Silent | Silent | Silent | Silent | | |
| 14420 | 16 | | Q | | | - | | | | | | | E |
| 14686 | 104 | | L | | | - | | | | | | | |
| 14735 | 121 | | R | G | G | - | G | G | G | G | G | G | G |
| 14737 | 121 | | R | G | G | - | G | G | G | G | G | G | G |
| 14979 | 31 | ORF7 | A | T | T | - | T | T | T | | | | |

*Fig. 14* (Continued)

PRRS VIRUSES, INFECTIOUS CLONES, MUTANTS THEREOF AND METHODS OF USE

CONTINUING APPLICATION DATA

This application is a continuation of U.S. application Ser. No. 13/276,671, filed on Oct. 19, 2011, which issued as U.S. Pat. No. 9,080,143 on Jul. 14, 2015, which was a continuation of U.S. application Ser. No. 11/922,798, filed Sep. 12, 2008, which issued as U.S. Pat. No. 8,110,390 on Feb. 7, 2012 and was a U.S. National Stage Application of International Application No. PCT/US2006/024355, filed Jun. 23, 2006, now International Publication No. WO 2007/002321, which claims the benefit of U.S. Provisional Application Ser. No. 60/694,021, filed Jun. 24, 2005, all of which are incorporated by reference herein in their entirety.

BACKGROUND

Porcine reproductive and respiratory syndrome virus (PRRSV) is the causative agent of a disease characterized by respiratory disorders in young pigs and reproductive failure in sows (Benfield et al., *J. Vet. Diagn. Invest.,* 4:127-133 (1992); Collins et al., *J. Vet. Diagn. Invest.,* 4:117-126 (1992); Wensvoort et al., *Vet. Q.,* 13:121-130 (1991)) and is now endemic in most countries. The syndrome was first recognized as a "mystery swine disease" in the United States in 1987 and was discovered in Europe in 1990. The two prototype viral strains (Lelystad and VR-2332) differ in nucleotide sequence by approximately 40% and represent two distinct genotypes, referred to as European (EU or Type 1, Lelystad; Meulenberg et al., *Virology,* 192:62-72 (1993)) and North American (NA or Type 2, VR-2332; Nelsen et al., *J. Virol.,* 73:270-80 (1999)) strains (Fang et al., *Virus Res.,* 100:229-235 (2004); Mardassi et al., *J. Gen. Virol.,* 75:681-5 (1994); Meng et al., *Arch. Virol.,* 140:745-55 (1995); Ropp et al., *J. Virol.,* 78:3684-3703 (2004)). The disease has also been referred to as Wabash syndrome, mystery pig disease, porcine reproductive and respiratory syndrome, swine plague, porcine epidemic abortion and respiratory syndrome, blue abortion disease, blue ear disease, *abortus* blau, and seuchenhafter spatabort der schweine. The disease is characterized by reproductive failure in pregnant sows and respiratory problems in pigs of all ages. The disease has a significant negative impact on the swine industry.

PRRSV is an enveloped, positive-sense RNA virus belonging to the family Arteriviridae in the order Nidovirales (Cavanagh, *Arch. Virol.,* 142:629:633 (1997)). The PRRSV genome varies from 15.1-15.5 kb long (Meulenberg et al., *Virology,* 192:62-72 (1993); Nelsen et al., *J. Virol.,* 73:270-80 (1999)). The first 75% of the genome encodes the replicase polyprotein essential for virus replication and is comprised of two large open reading frames (ORFs) (1a and 1b) that are processed cotranslationally into smaller proteins by virally encoded proteases (Snijder et al., *J. Gen. Virol.,* 79:961-79 (1998)). The structural proteins are encoded by seven downstream ORFs and are translated from a 3'-coterminal nested set of subgenomic mRNAs (sgmRNA) (Meulenberg et al., *Virology,* 192:62-72 (1993); Pattnaik et al., *Cell,* 69:1011-1020 (1992)). In strain VR-2332, the coding region of the genome (15,411 bases) is flanked by 5' and 3' nontranslated regions of 189 and 151 nucleotides, respectively.

PRRSV strain VR-2332 has been well characterized in terms of its complete genome sequence (Pattnaik et al., *Cell,* 69:1011-1020 (1992)), the ability of PRRSV to constitutively produce defective subgenomic RNA species termed heteroclites (latin: uncommon forms) (Yuan et al., *Virology,* 275:158-169 (2000)); Yuan et al., *Virus Research,* 105:75-87 (2004)), and its growth properties in vitro as well as in vivo (Murtaugh et al., *Vet. Inununol. Innnunopathol.,* 102:105-349 (2004)). In addition, an infectious clone of this 15.4 kb NA PRRSV genome has been produced and examined for its ability to cause disease in swine (pVR-HN; Nielsen et al., *J. Virol.,* 77:3702-3711 (2003)).

PRRSV continues to cause significant economic losses throughout the world. Vaccines are available, but they are based on one PRRSV strain, and there is evidence that PRRSV strains vary at the antigenic and genetic levels. In addition, since the virus was identified in Europe and in the United States, new disease phenotypes have continued to emerge.

SUMMARY OF THE INVENTION

Prior reports had suggested that deletions and/or mutations of any strain of PRRS virus was often extremely detrimental to viral growth. Specifically, individual laboratories had made mutations in the 3' end of the virus, and the resultant virus was either unstable and quickly reverted back to wild-type sequence, or grew very poorly or not at all (Lee et al., *Virol.,* 331:47-62 (2005); Choi et al., *J. Virol.,* 80:723-736 (2006); Lee et al., *Virolog.,* 346:238-250 (2005)). Thus, in comparison of nucleotide sequences of European (Type 1 genotype) and VR-2332 (Type 2 genotype), where to make mutations in VR-2332 NSP2 that were not extremely detrimental was not known. However, alignment of the full genome sequences of new Type 2 PRRS viruses with VR-2332 began to provide insight as to where viable mutants could be made. Further deletion mutagenesis showed that the region between nsp2 amino acids 324-813 was not necessary for growth in vitro.

The present invention provides an isolated infectious polynucleotide having a nucleotide sequence with at least 88% identity to SEQ ID NO:1 and a deletion of at least 39 consecutive nucleotides selected from nucleotide 2062 to nucleotide 3864 of SEQ ID NO:1. Also provided is an isolated infectious polynucleotide having a nucleotide sequence with at least 88% identity to SEQ ID NO:14 and a deletion of at least 39 consecutive nucleotides selected from nucleotide 2061 to nucleotide 3545 of SEQ ID NO:14. The isolated polynucleotide may be present in a vector, in an isolated virus particle, present in a cell, or a combination thereof. When present in a vector an RNA polymerase promoter may be operably linked to the polynucleotide. The isolated polynucleotide may by an RNA. The isolated polynucleotide may include 2 or more deletions, and each deletion may be independently at least 37 consecutive nucleotides. The isolated polynucleotide may further include an exogenous polynucleotide present in the deletion, and the exogenous polynucleotide may encode a polypeptide, such as a detectable marker.

The present invention also provides an isolated polynucleotide having a nucleotide sequence with at least 88% identity to SEQ ID NO:1 and at least one deletion of at least 39 consecutive nucleotides selected from nucleotide 2062 to nucleotide 3864 of SEQ ID NO:1, and wherein the polynucleotide replicates and produces infectious virus particles when introduced into a cell. Also provided is an isolated polynucleotide having a nucleotide sequence with at least 88% identity to SEQ ID NO:14 and at least one deletion of at least 39 consecutive nucleotides selected from nucleotide 2061 to nucleotide 3545 of SEQ ID NO:14, wherein the polynucleotide replicates and produces infectious virus particles when introduced into a cell. The isolated polynucleotide may be present in a vector, in an isolated virus particle, present in a cell, or a combination thereof. When present in a vector an RNA polymerase promoter may be operably linked to the polynucleotide. The isolated polynucleotide may be an RNA. The isolated polynucleotide may include 2 or more deletions, and each deletion may be independently at least 37 consecutive nucleotides. The isolated polynucleotide may further include an exogenous polynucleotide present in the deletion, and the exogenous polynucleotide may encode a polypeptide, such as a detectable marker.

The present invention further provides an infectious clone having a polynucleotide with a nucleotide sequence having at least 88% identity to SEQ ID NO:1 and at least one deletion of at least 39 consecutive nucleotides selected from nucleotide 2062 to nucleotide 3864 of SEQ ID NO:1. Also provided is an infectious clone having a polynucleotide with a nucleotide sequence having at least 88% identity to SEQ ID NO:14 and at least one deletion of at least 39 consecutive nucleotides selected from nucleotide 2061 to nucleotide 3545 of SEQ ID NO:14. The infectious clone may be present in a cell. An RNA polymerase promoter may be operably linked to the polynucleotide. The infectious clone may include 2 or more deletions, and wherein each deletion is independently at least 37 consecutive nucleotides. The isolated polynucleotide may further include an exogenous polynucleotide present in the deletion, and the exogenous polynucleotide may encode a polypeptide, such as a detectable marker.

Also provided by the present invention is an isolated infectious polynucleotide comprising a nucleotide sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, and an nsp2 polypeptide encoded by an infectious polynucleotide comprising a nucleotide sequence SEQ ID NO:7, SEQ ID NO:8, SEQ ID NO:9, SEQ ID NO:10, SEQ ID NO:11, SEQ ID NO:12, or SEQ ID NO:13.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE FIGURES

Figure 1A-2:
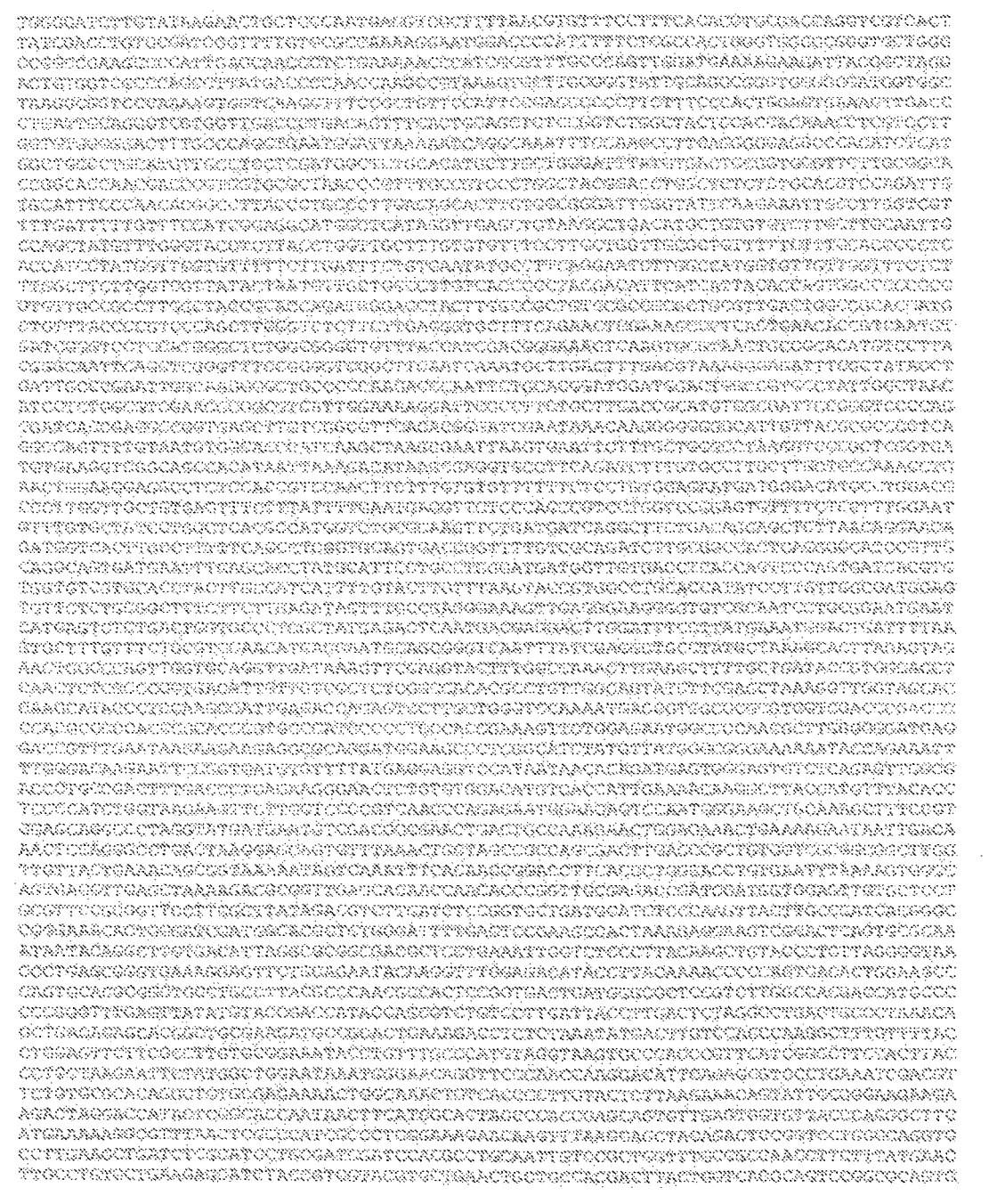
Figure 1A-3:
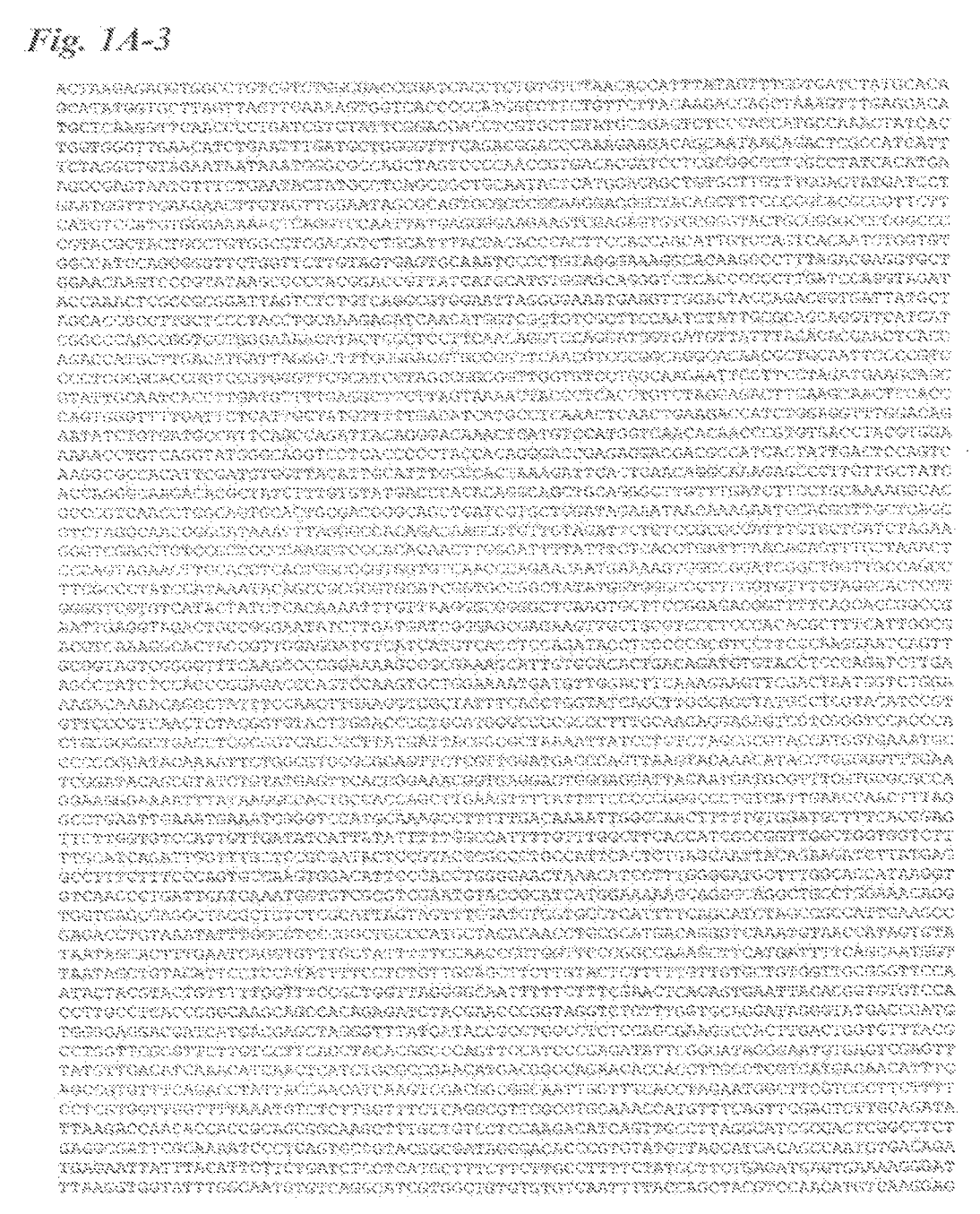
Figure 1A-4:
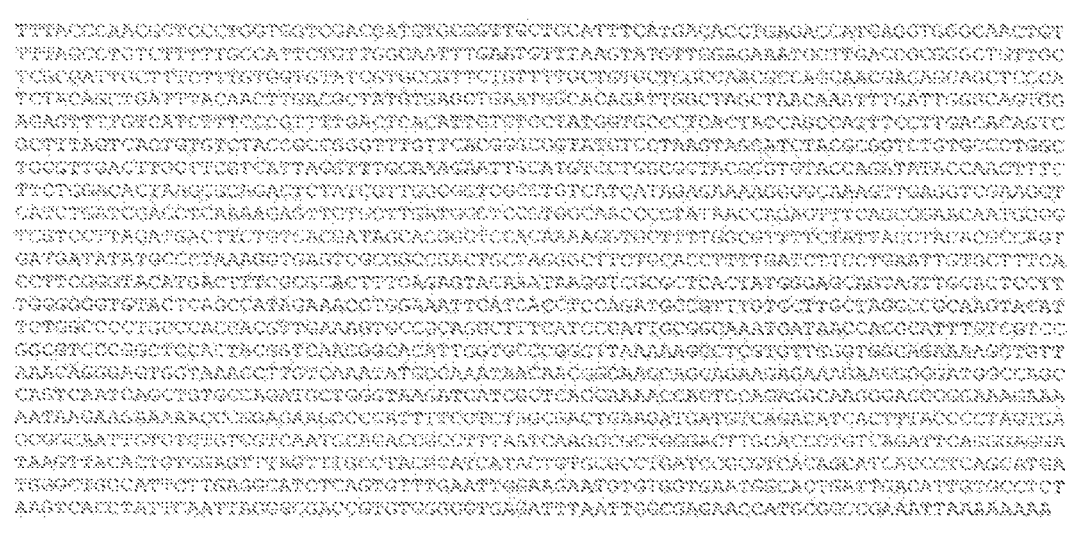
Figure 1B-2:
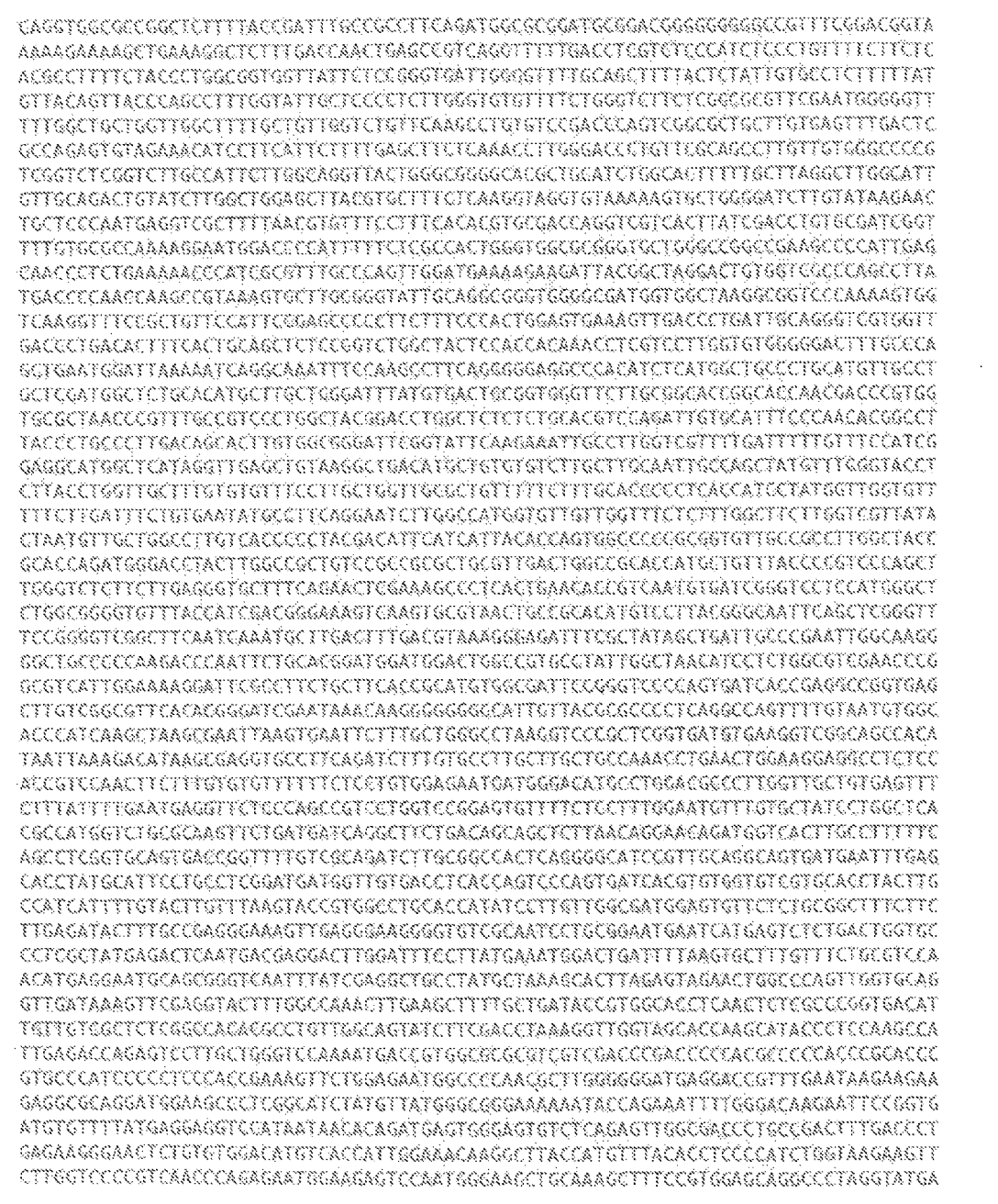
Figure 1C-2:
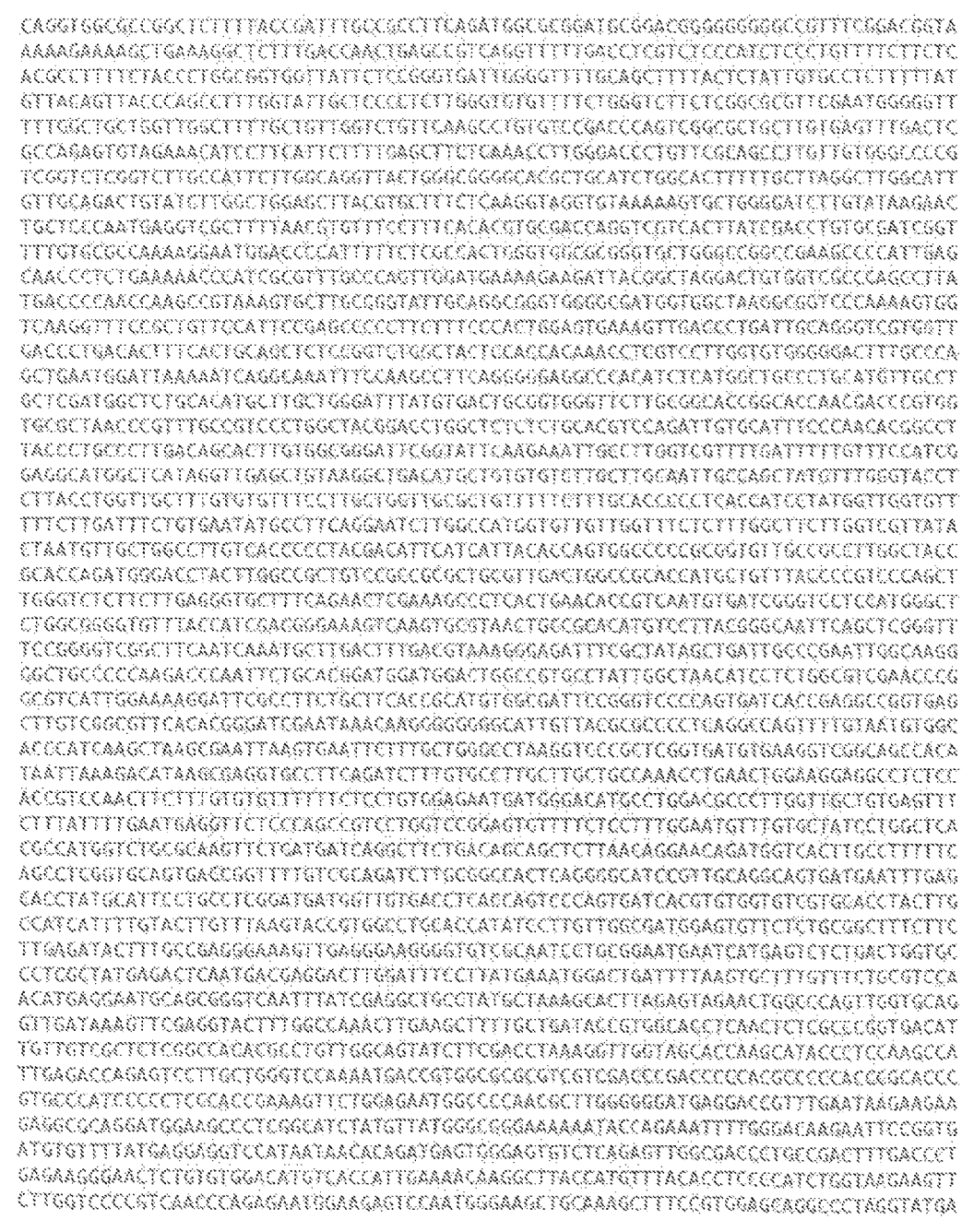
Figure 1D-2:
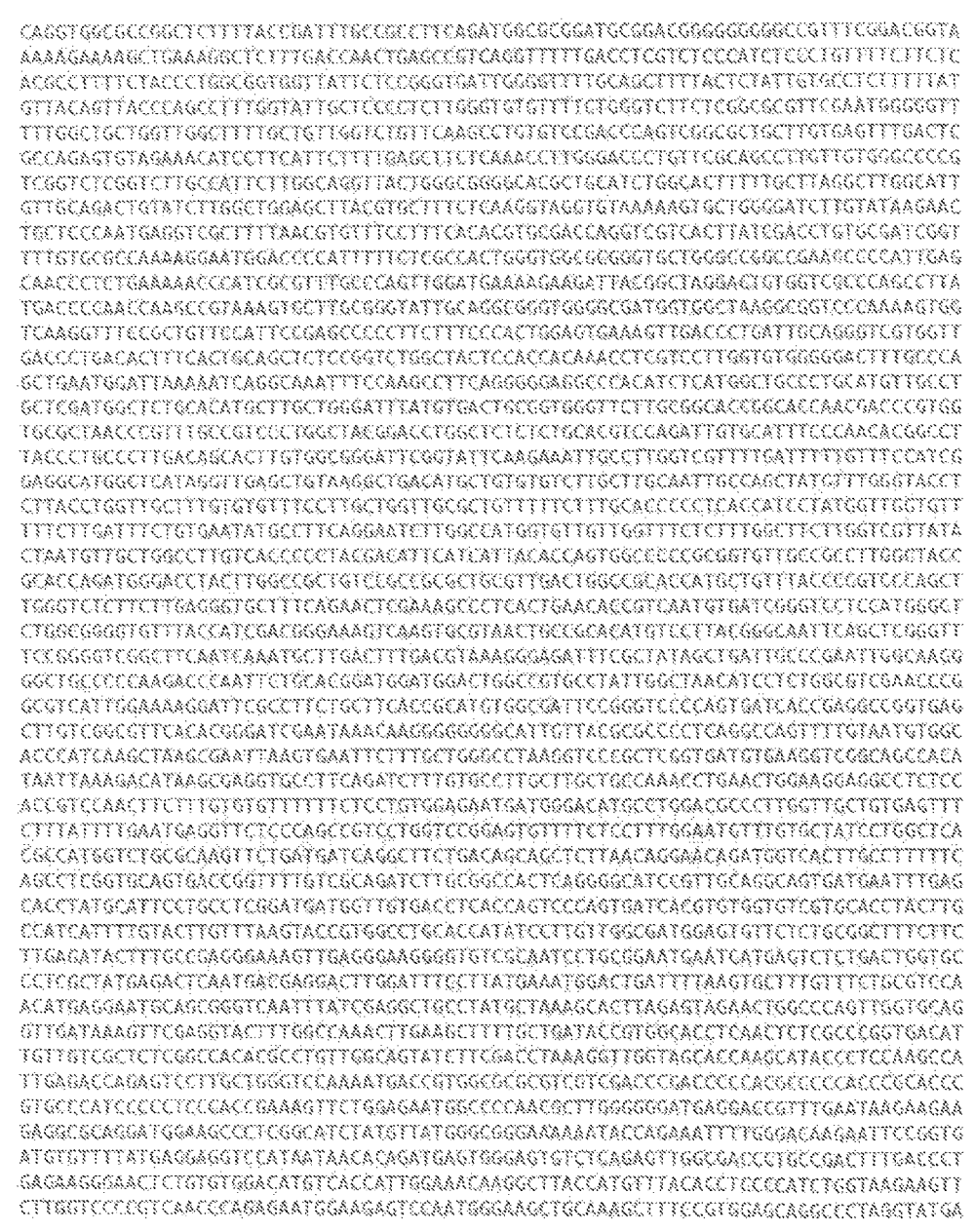
Figure 1D-3:
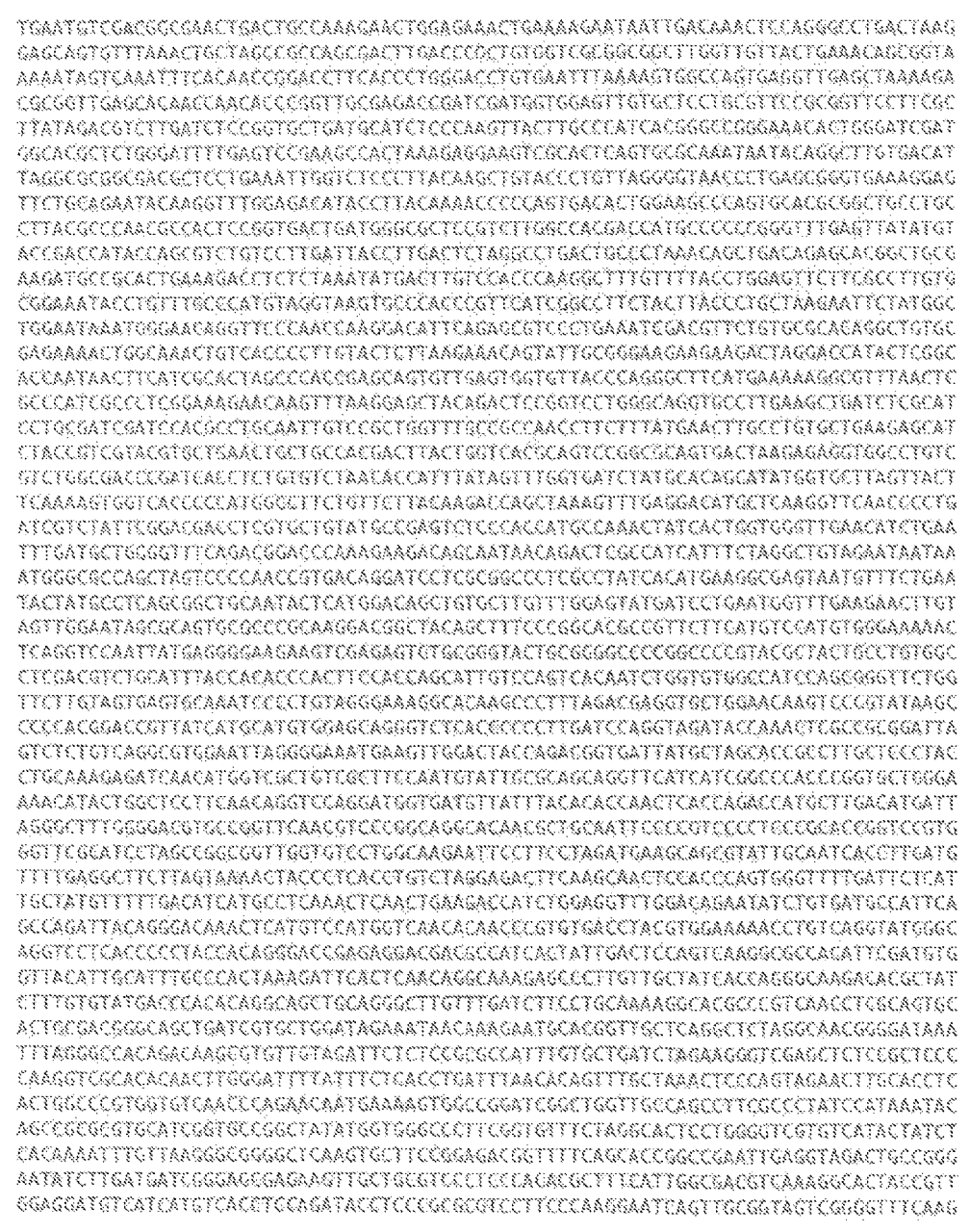
Figure 1E-2:
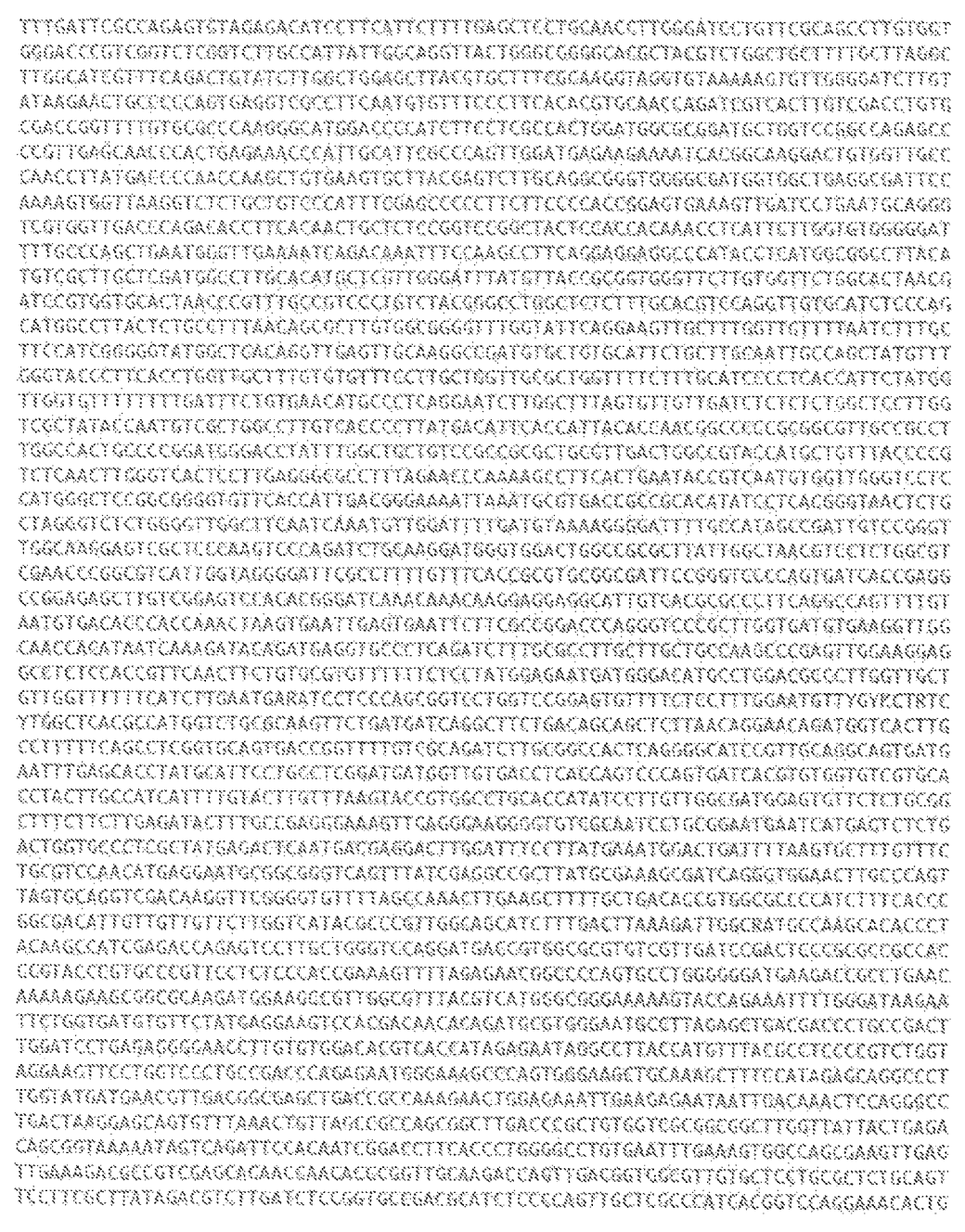
Figure 1F-3:
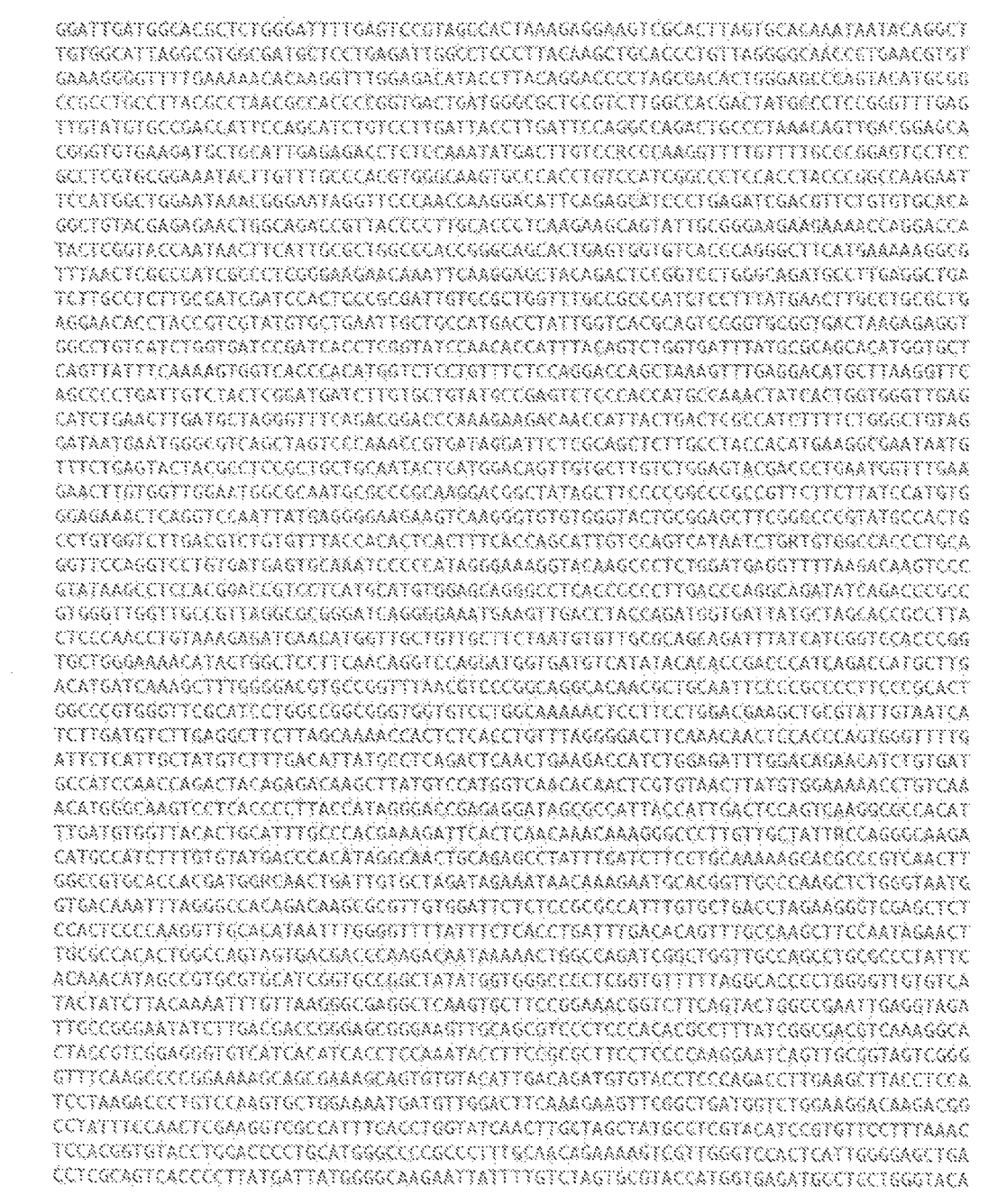
Figure 1H-2:
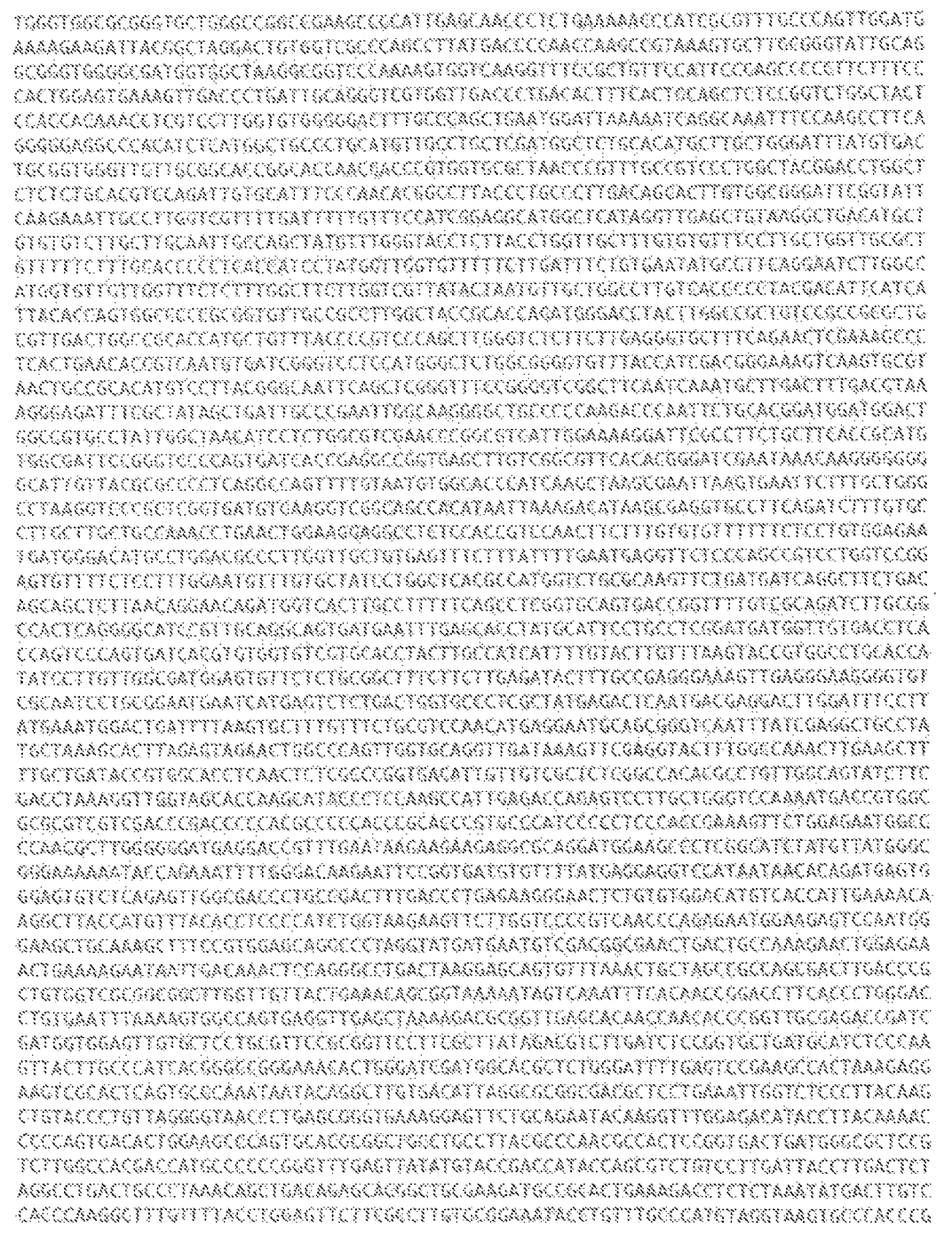
Figure 1J-1:
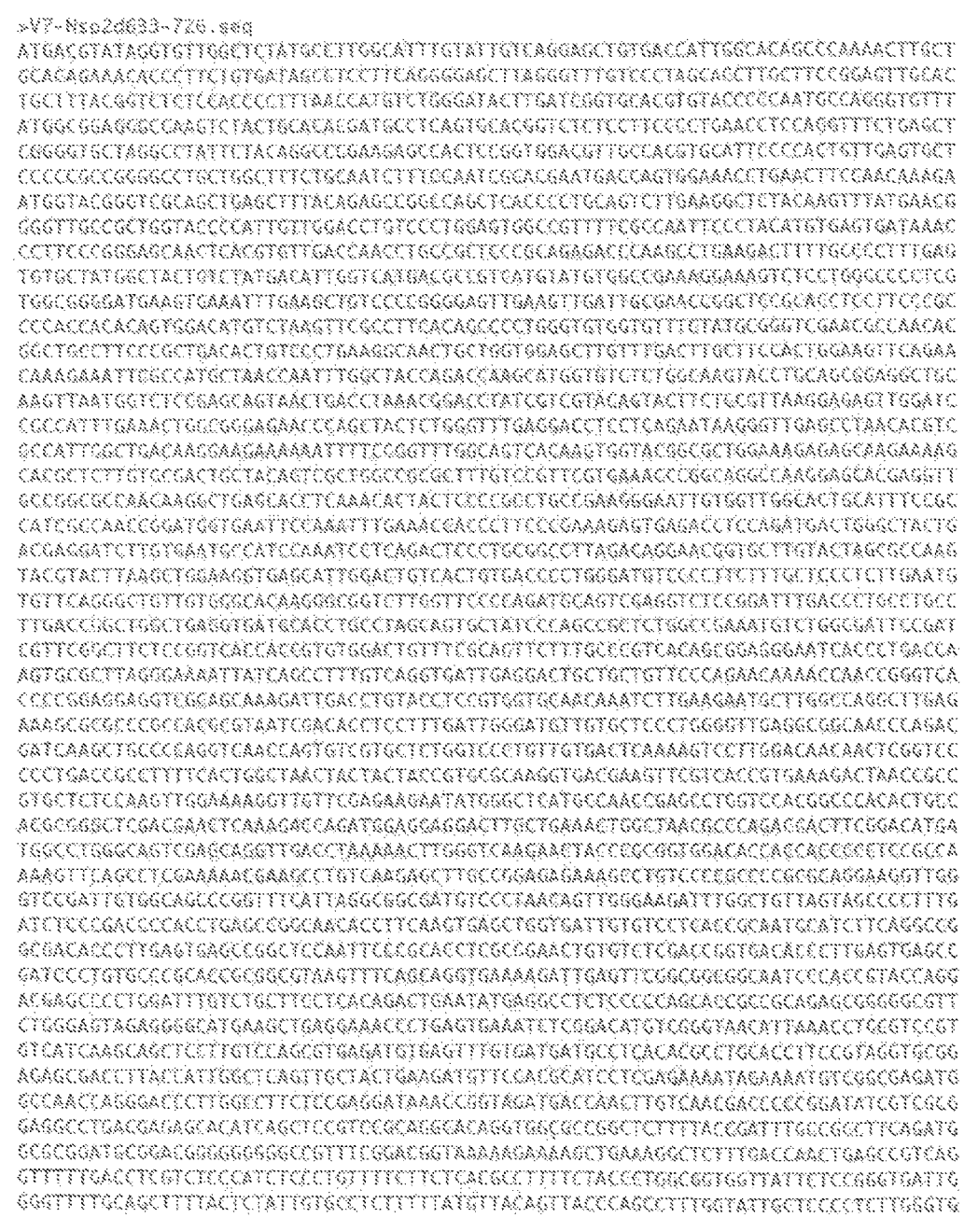
Figure 1K-2:
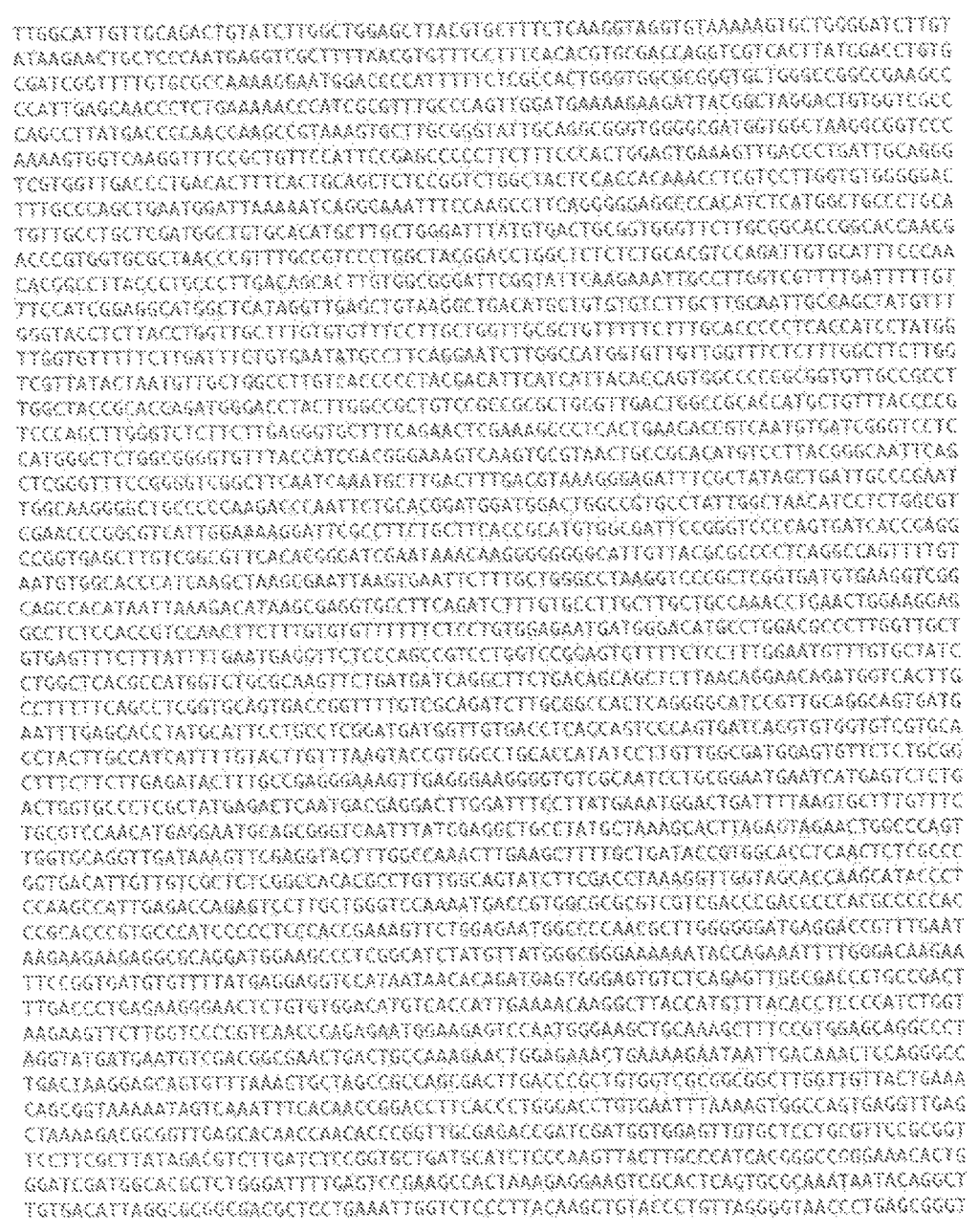
Figure 1K-4:
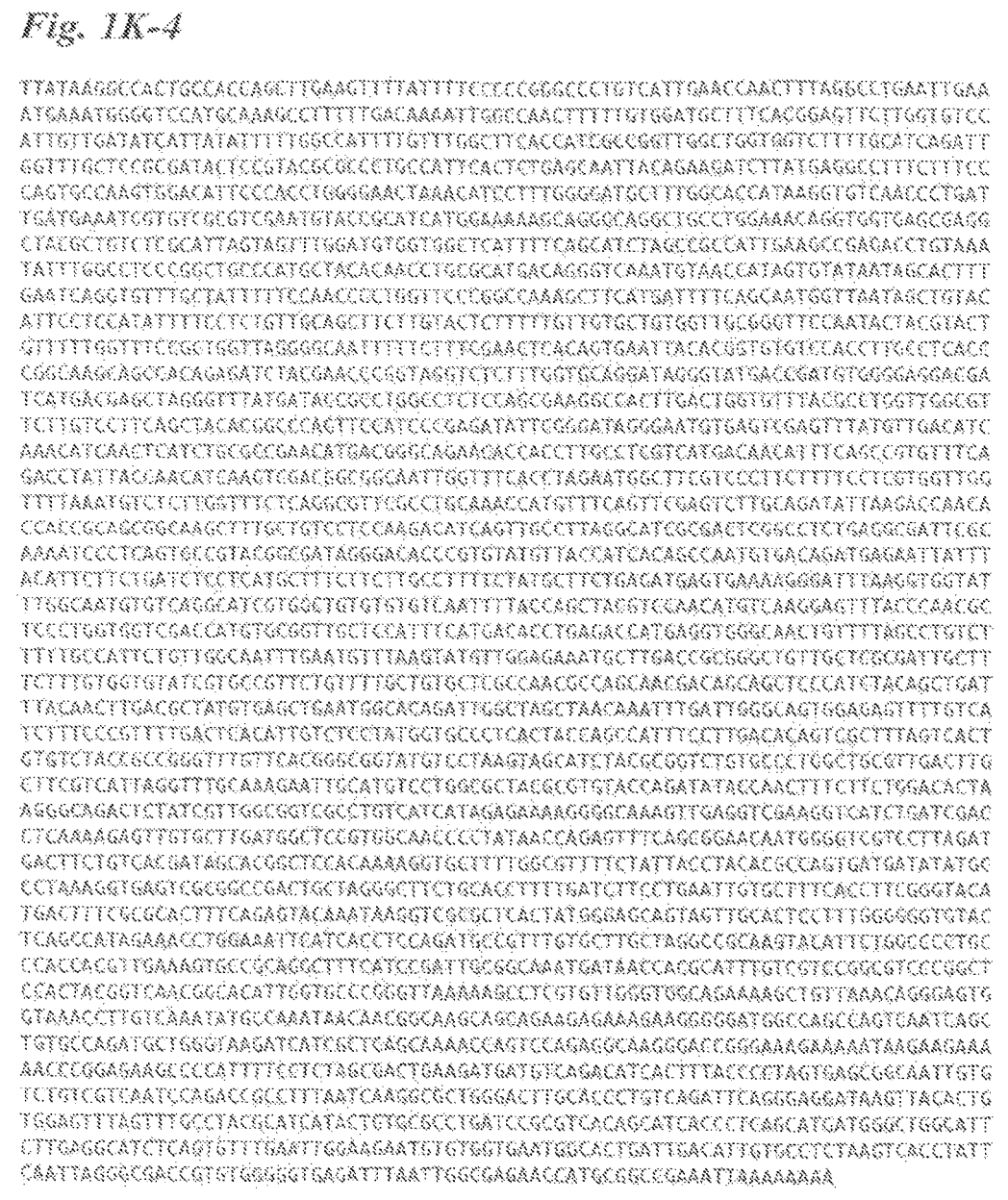
Figure 1L-2:
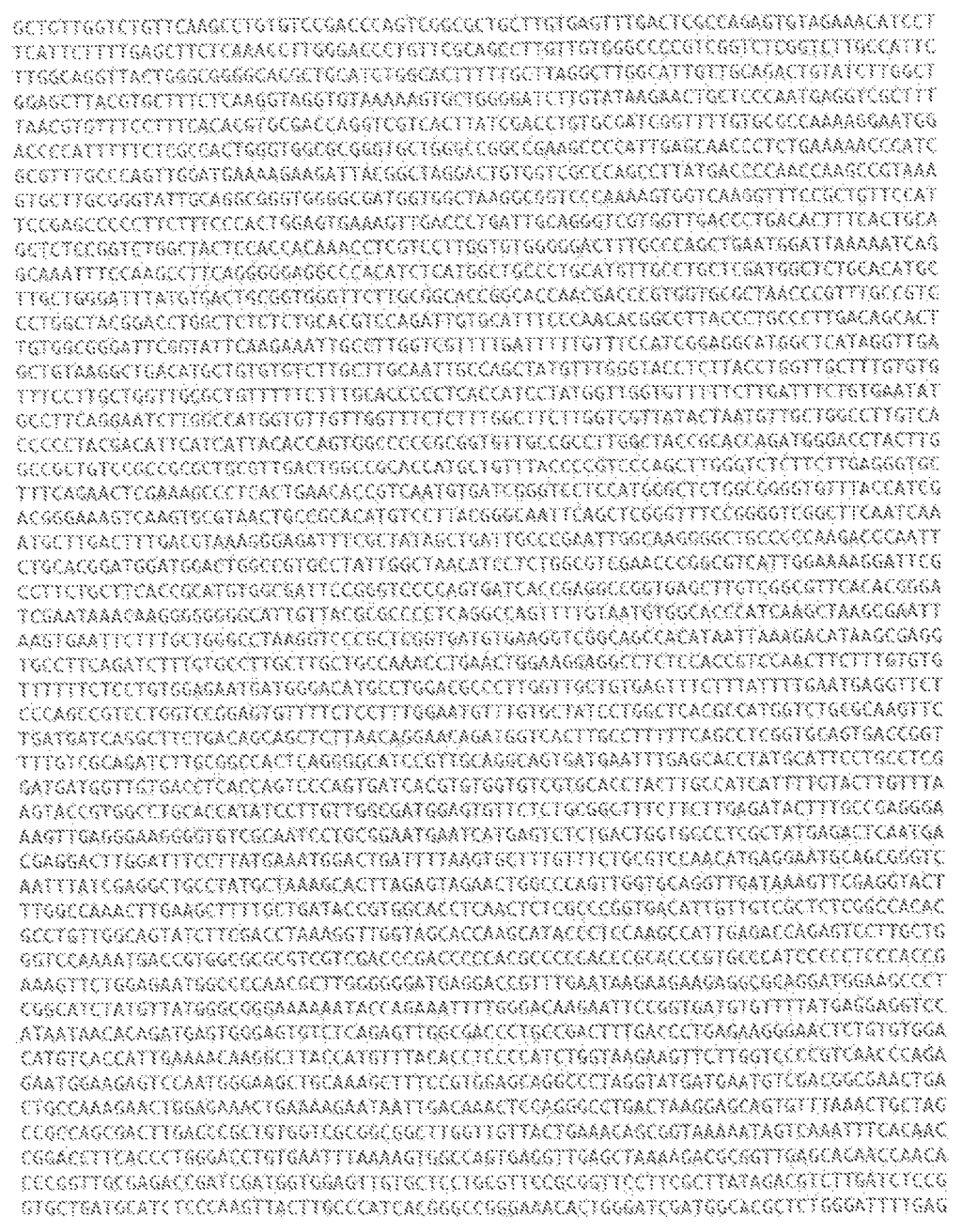
Figure 1M-2:
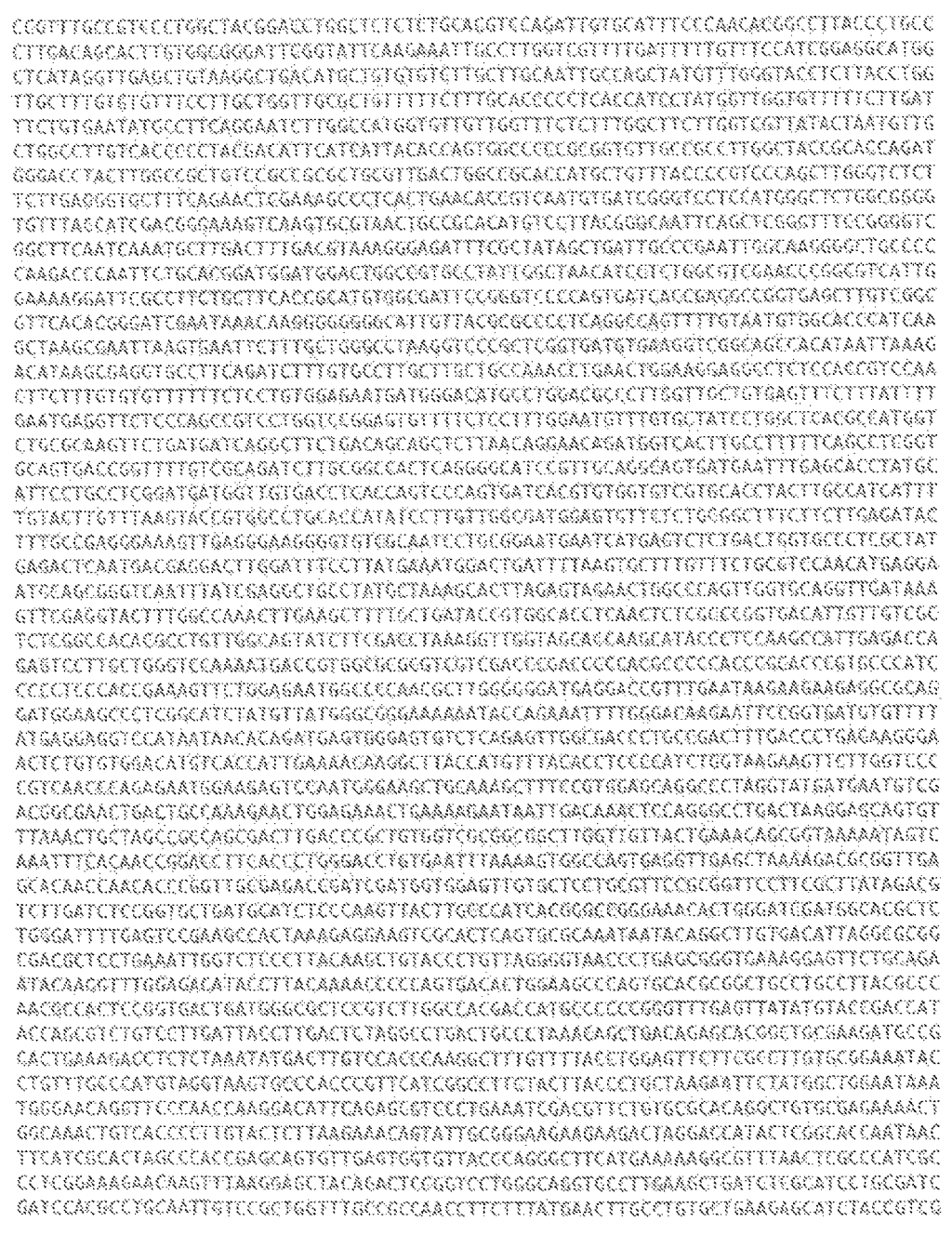
Figure 1M-3:
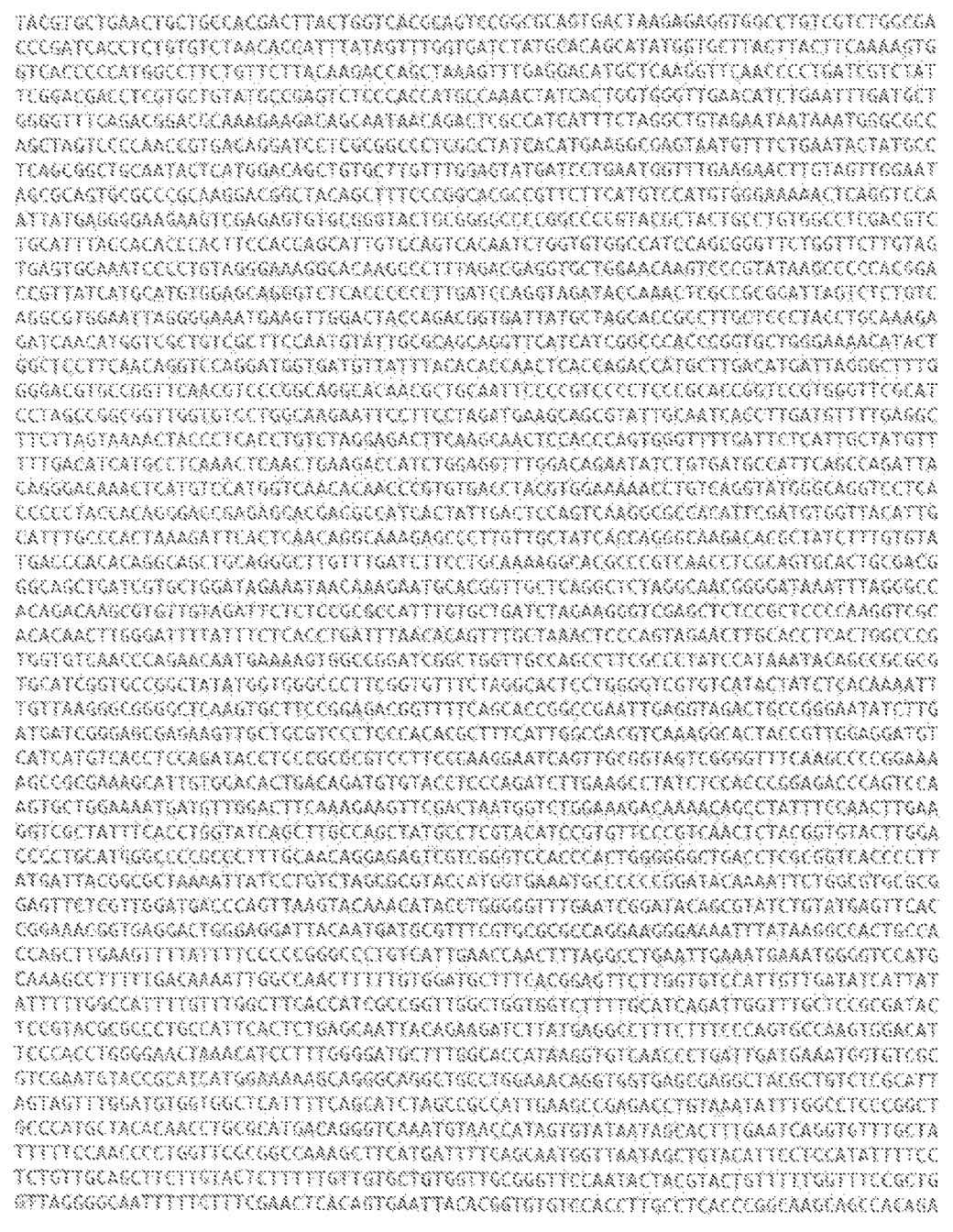

FIGS. 1A-1 to 1A-4. Nucleotide sequence (SEQ ID NO:1) of infectious polynucleotide VR-V7 (also referred to herein as V6G7475A). FIGS. 1B-1 to B-5. Nucleotide sequence (SEQ ID NO:2) of infectious polynucleotide VR-V5. FIGS. 1C-1 to 1C-5. Nucleotide sequence (SEQ ID NO:3) of infectious polynucleotide VR-V5G7475A. FIGS. 1D-1 to 1D-5. Nucleotide sequence (SEQ ID NO:4) of infectious polynucleotide VR-V6. FIGS. 1E-1 to 1E-4. Nucleotide sequence (SEQ ID NO:5) of infectious polynucleotide MN184A. FIGS. 1F-1 to 1F-4. Nucleotide sequence (SEQ ID NO:6) of infectious polynucleotide MN184B. FIGS. 1G-1 to 1G-4. Nucleotide sequence (SEQ ID NO:7) of infectious polynucleotide Nsp2 Δ324-434. FIGS. 1H-1 to 1H-4. Nucleotide sequence (SEQ ID NO:8) of infectious polynucleotide Nsp2 Δ324-523. FIGS. 1I-1 to 1I-4. Nucleotide sequence (SEQ ID NO:9) of infectious polynucleotide Nsp2 Δ543-632. FIGS. 1J-1 to 1J-4. Nucleotide sequence (SEQ ID NO:10) of infectious polynucleotide Nsp2 Δ633-726. FIGS. 1K-1 to 1K-4. Nucleotide sequence (SEQ ID NO:11) of infectious polynucleotide Nsp2 Δ543-726. FIGS. 1L-1 to 1L-4. Nucleotide sequence (SEQ ID NO:12) of infectious polynucleotide Nsp2 Δ727-813. FIGS. 1M-1 to 1M-4. Nucleotide sequence (SEQ ID NO:13) of infectious polynucleotide Nsp2 Δ324-726.

FIG. 2. Assembly of full-length clones of PRRSV strain VR-2332. The 15.4 genome was amplified in four sections (I-IV) that incorporated unique restriction enzyme cleavage sites present in viral cDNA (FseI, AvrII, BsrGI) or added to the PRRSV sequence at the 5' and 3' ends by insertion mutagenesis (SphI, Pac I respectively). A T7 polymerase promoter and 2 nontemplated G residues and a T residue preceded the viral sequence. The pOK12 vector (24) was modified to include a PacI site and a hepatitis delta ribozyme downstream of a poly adensine tail of 50 nucleotides.

FIG. 3. Schematic of nucleotide changes of infectious clones or swine progeny. Diagram of the PRRSV genome organization is presented under which are full genome comparisons. Putative nonstructural protein cleavages are depicted above ORF1a and 1b, represented by downward arrows. Signature motifs are identified below ORF1a and 1b, with upward arrows indicating their placement in the PRRSV genome [papain-like cysteine protease α and β (PCPα, PCPβ); cysteine protease (CP); serine/3C protease (SP/3CP); polymerase (POL); cysteine/histidine rich (C/H); helicase (Hel); *Xenopus laevis* homolog poly(U)-specific endoribonuclease (XendoU); Ivanov et al., *Proc. Natl. Acad. Sci. USA*, 101:12694-12699 (2004); Ziebuhr et al., *J. Gen. Virol*, 81:853-879 (2000)]. Nucleotide differences are represented by vertical bars. 1. wt strain VR-2332 (U87392) compared to VR-2332 derived vaccine (Ingelvac® MLV or RespPRRS, AF066183). 2. wt strain VR-2332 compared to pVR-V6G7475A. 3. pVR-V5 compared to in vivo passaged V5-1-P3 (Sw612). 4. wt strain VR-2332 compared to Sw612. Detailed nucleotide changes are listed in Tables 4 and 5.

FIG. 4. Seroconversion of swine after PRRSV infection. Growing swine were infected with native wt strain VR-2332 (□), Ingelvac® MLV (X), V5-1 P3 (○) or remained uninfected (■). At days indicated, serum samples were taken and tested by IDEXX Elisa for indication of seroconversion by anti-PRRSV antibodies to the nucleocapsid protein.

FIG. 5A. Plaque assays on P3 progeny (first lineage) of all infectious clones as well as wt strain VR-2332 revealed different plaque sizes. FIG. 5B. Progeny of V5-1 P3 after growth in swine (Sw612) produced plaques similar to wt strain VR-2332.

FIG. 6A. Plaque assays on P3 progeny (second lineage) of all infectious clones as well as wt strain VR-2332 displayed plaque sizes that were different from first lineage virus preparations. FIG. 6B. Titers of P4 virus indicate infectious clone progeny were not replicating as wt strain VR-2332 or Sw612 virus in spite of having similar plaque size.

FIG. 12. Nsp2 amino acid sequence alignment of divergent PRRSV. The completely conserved putative cysteine protease catalytic residues (Cys and His) are identified by stars and the boxed amino acids signify protease sequence conservation within PRRSV and EAV. The proposed cleavage sites are identified by filled arrows (↓); additional possible cleavage sites are indicated by a hashed arrow; signal peptide, solid grey box; transmembrane regions, shown in hashed black boxes; potential N-glycosylation sites, indicated by an asterisk (*). The figure derivation and color scheme were described in the FIG. 10 legend. Nsp2 amino acid sequences from the following GenBank full-length sequences were used for comparison: VR-2332 (SEQ ID NO: 74), Ingelvac MLV (SEQ ID NO: 75), 01NP1.2 (DQ056373) (SEQ ID NO: 76), PL97-1 (SEQ ID NO: 77), PA-8 (SEQ ID NO: 79), SP (SEQ ID NO: 78), BJ-4 (SEQ ID NO: 80), HN1 (SEQ ID NO: 81), 16244B (SEQ ID NO: 82), HB-1 (SEQ ID NO: 87), HB-2 (SEQ ID NO: 84), CH-1a (SEQ ID NO: 83), P129 (SEQ ID NO: 85), JA142 (SEQ ID NO: 86), SDPRRS-01-08 (A Y375474) (SEQ ID NO: 88), EuroPRRSV (SEQ ID NO: 89), Lelystad (SEQ ID NO:90), MN184A (SEQ ID NO:72), MN184B (SEQ ID NO:73).

FIG. 13. Nucleotide differences between PRRSV strains and VR-2332 infectious clones. Only positions where nucleotide differences were noted are shown. Nucleotides that are represented in strain VR-2332 are shown in unshaded boxes. Light shaded boxes represent nucleotide differences that are unique to the infectious clone, medium shaded boxes highlight those nucleotides that are also seen in Ingelvac® MLV, and boxes that are shaded black indicate swine unique nucleotides. Regions that were not sequenced are indicated by a slash.

FIG. 14. Amino acid differences between PRRSV strains and VR-2332 infectious clones. Only positions where nucleotide differences were noted are shown with corresponding amino acid position within the identified genomic region. Amino acids that are represented in strain VR-2332 are shown in unshaded boxes and infectious clone amino acid identities with VR-2332 are represented by blank boxes. Text in each individual box represent silent or amino acid changes due to nucleotide differences shown in Table 2. Light shaded boxes represent nucleotide differences that are unique to the infectious clone, medium shaded boxes highlight those nucleotides that are also seen in Ingelvac® MLV, and boxes that are shaded black indicate swine unique nucleotides. Amino acids separated by slashes indicate ORF2a/ORF2b amino acid numbers. Regions that were not sequenced are indicated by a slash.

DETAILED DESCRIPTION OF ILLUSTRATIVE EMBODIMENTS

Figure 2:
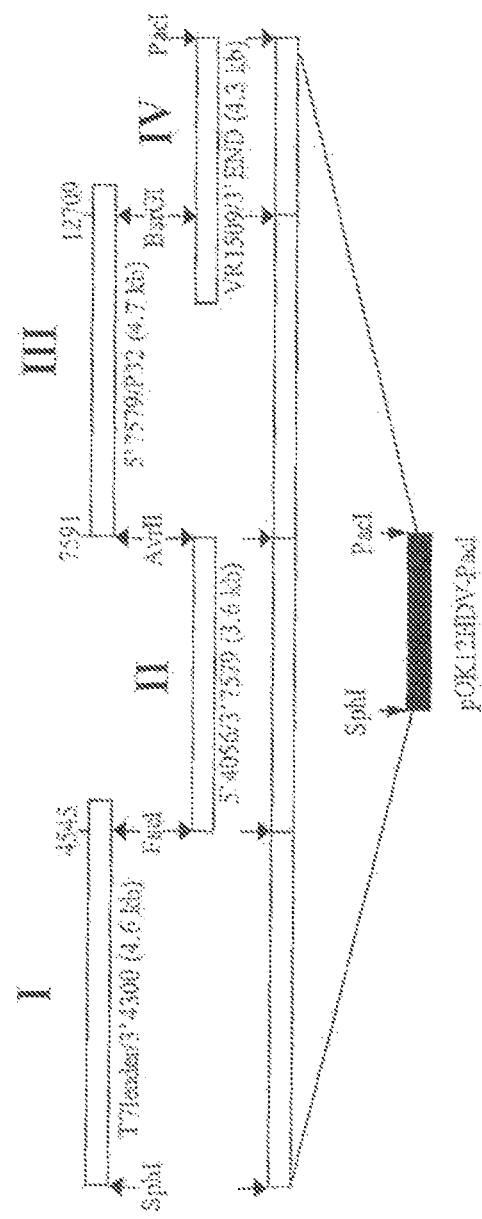

The present invention includes infectious clones of the Porcine reproductive and respiratory syndrome virus (PRRSV) VR-2332. As used herein, the term "infectious clone" is a polynucleotide having two components; a vector sequence that replicates in a prokaryotic host cell, and a second polynucleotide referred to herein as an infectious polynucleotide. When transcribed in vitro to yield an RNA polynucleotide and introduced into a permissive cell, the infectious polynucleotide replicates (as an RNA) and produces infectious virus particles. Thus, an infectious polynucleotide can be present in a vector as a DNA, as an RNA in a virus particle, or as an isolated DNA or RNA. The term "polynucleotide" refers to a polymeric form of nucleotides of any length, either ribonucleotides or deoxynucleotides, and includes both double- and single-stranded DNA and RNA. Unless otherwise noted, a polynucleotide includes the complement thereof. The nucleotide sequence of the complement of a polynucleotide can be easily determined by a person of skill in the art. A polynucleotide may include nucleotide sequences having different functions, including for instance coding sequences, and non-coding sequences such as regulatory sequences and/or untranslated regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

If naturally occurring, a polynucleotide is preferably isolated, more preferably, purified. An "isolated" compound, such as a polynucleotide, polypeptide, or virus particle, is one that is separate and discrete from its natural environment. A "purified" compound is one that is at least 60% free, preferably 75% free, and most preferably 90% free from other components with which they are naturally associated. Compounds such as polynucleotides and polypeptides that are produced outside the organism in which they naturally occur, e.g., through chemical or recombinant means, are considered to be isolated and purified by definition, since they were never present in a natural environment.

An example of an infectious polynucleotide of the present invention includes the infectious polynucleotide VR-V7 (SEQ ID NO:1). VR-V7 is also referred to herein as V6G7475A. Other examples of infectious polynucleotides of the present invention include VR-V5 (SEQ ID NO:2), VR-V5G7475A (SEQ ID NO:3), and VR-V6 (SEQ ID NO:4). It should be noted that while SEQ ID NOs:1, 2, 3, 4, 5, 6 and other virus nucleotide sequences are disclosed herein as a DNA sequence, the present invention contemplates the corresponding RNA sequence, and RNA and DNA complements thereof, as well.

Other infectious polynucleotides of the present invention have a polynucleotide sequence having structural similarity to a reference polynucleotide. Reference polynucleotides include SEQ ID NO:1, SEQ ID NO:2, SEQ ID NO:3, SEQ ID NO:4, SEQ ID NO:5, SEQ ID NO:6, the European prototype strain of PRRS virus, Lelystad (Genbank accession number M96262; SEQ ID NO:14), and the North American prototype strain of PRRS virus, VR-2332 (Genbank accession number U87392; SEQ ID NO:15). The similarity is referred to as "percent identity" and is determined by aligning the residues of the two polynucleotides (i.e., the nucleotide sequence of a candidate infectious polynucleotide and the nucleotide sequence of the reference polynucleotide) to optimize the number of identical nucleotides along the lengths of their sequences; gaps in either or both sequences are permitted in making the alignment in order to optimize the number of shared nucleotides, although the nucleotides in each sequence must nonetheless remain in their proper order. In some aspects of the present invention the gap (also referred to as a deletion) is present in the candidate infectious polynucleotide sequence. A candidate infectious polynucleotide is the polynucleotide that has the nucleotide sequence being compared to the reference polynucleotide. A candidate infectious polynucleotide can be isolated from an animal, such as a pig infected with PRRSV, isolated from a cultured cell line, or can be produced using recombinant techniques, or chemically or enzymatically synthesized. Two nucleotide sequences can be compared using any of the commercially available computer algorithms routinely used to produce alignments of nucleotide sequences. Preferably, two nucleotide sequences are compared using the GAP program of the GCG Wisconsin Package (Accelrys, Inc.) version 10.3 (2001). The GAP program uses the algorithm of Needleman et al. (*J. Mol. Biol.*, 48:443-453 (1970)) to find the alignment of two complete sequences that maximizes the number of matches and minimizes the number of gaps. Preferably, the default values for all GAP search parameters are used, including scoring matrix=NewsgapDNA.cmp, gap weight=50, length weight=3, average match=10, average mismatch=0. In the comparison of two nucleotide sequences using the GAP search algorithm, structural similarity is referred to as "percent identity." Preferably, a polynucleotide has structural similarity with a reference polynucleotide of at least 88%, at least 89%, at least 90%, at least 91%, at least 92%, at least 93%, at least 94%, at least 95%, at least 96%, at least 97%, at least 98%, or at least 99% identity when the structural similarity is determined using the GAP program.

Whether a polynucleotide is an infectious polynucleotide can be determined by inserting into a vector a candidate infectious polynucleotide, transcribing the candidate infectious polynucleotide in vitro, transfecting a permissive cell with the resulting RNA molecules, and detecting progeny viral RNA, progeny viral nucleocapsid protein, detecting infectious virus particles, or a combination thereof. The vector preferably has the characteristics of being low copy number and remains stable after insertion of large (e.g., 15 kb) inserts. An example of a suitable vector is pOK and pOK12 (GenBank Accession AF223639, Vieira et al., *Gene*, 100:189-194 (1991)), and other vectors having these characteristics are known and available. In the vector the candidate infectious polynucleotide is immediately downstream of a promoter. Useful promoters are those that can be induced to yield high levels of transcription, such as a T7 RNA polymerase promoter, for example TAATACGACTCACTATA (SEQ ID NO:16), or the RNA polymerase promoters SP6 and T3. Transcription of the candidate infectious polynucleotide typically includes restriction endonuclease digestion of the vector to make it linear, and producing RNA transcripts by use of routine and well known in vitro transcription methods. Kits for in vitro transcription are commercially available (for instance, mMessage mMachine, available from Ambion, Austin, Tex.).

After in vitro transcription the RNA is purified using routine methods and then used to transfect a permissive cell. Examples of permissive cells include, for instance, BHK-21 (which allows one round of virus particle production), CL-2621, MA-104 (ATCC CRL-2378), MARC-145 (Kim et al., *Arch. Virol.*, 133:477-483 (1993)), cell lines cloned from these cell lines, or primary porcine alveolar macrophages. Methods for efficiently transfecting cells include the use of 1,2-dimyristyloxypropyl-3-dimethyl-hydroxy ethyl ammonium bromide and cholesterol (DMRIE-C), and other commercially available products, preferably, DMRIE-C. Methods for efficiently transfecting primary porcine alveolar macrophages are known to the art (Groot Bramel-Verheige et al., *Virol.*, 278:380-389 (2000)). Generally, 2 to 3 micrograms of RNA can be used for transfection, but lower and higher amounts may be used. After a suitable period of time, the presence of progeny viral RNA can be detected by, for instance, reverse transcriptase-polymerase chain reaction (RT-PCR). Likewise, progeny viral nucleocapsid protein can be detected by, for instance, nucleocapsid specific antibody. Further, whether the virus particles produced by cells transfected with a candidate infectious polynucleotide will infect another cell can be detected by exposing uninfected permissive cells to supernatant from infected cells. Optionally, cytopathic effect (CPE) may be observed. A candidate infectious polynucleotide is considered to be an infectious polynucleotide when it produces progeny viral RNA, progeny viral proteins (nucleocapsid, membrane, GP5, and others), and infects other permissive cells.

In some aspects of the present invention an infectious polynucleotide includes a deletion of nucleotides encoding non-structural protein 2 (nsp2), one of several (12 predicted) polypeptides present in the polyprotein encoded by ORF1. In a PRRS virus, and infectious polynucleotides thereof, the nucleotides encoding the first amino acid of nsp2 can be determined by identifying the cleavage site of papain-like protease 1 beta, predicted to be after the ORF1 amino acid glycine at position 383 in VR-2332.

With respect to identifying the nucleotides encoding the last amino acid of nsp2, the exact nsp2 C-terminal cleavage site of the ORF1a-encoded polyprotein has not been empirically determined, thus the nucleotides corresponding to the 3' end of the coding region are unknown. However, two predictions of the C-terminal cleavage site have been proposed, one Gly|Gly (where the vertical line between the two glycine residues indicates the cleavage location) at amino acid 980 in VR-2332, and the other at amino acid 1197 in VR-2332. In alignment of all available PRRSV sequences, there are several completely conserved Gly|Gly doublets within this protein that may also be the nsp2 C terminal cleavage site of the polyprotein (amino acids 646, 980, 1116, 1196, 1197, in VR-2332. The locations of the Gly|Gly doublets in the other viruses and infectious polynucleotides can be identified by comparison to the sequences of nsp2 and the Gly|Gly doublets disclosed in FIG. 12. Present studies suggest that there may be at least 3 cleavage sites in nsp2, corresponding to amino acid 980, 116, 1196 or 1197.

The nsp2 polypeptide includes a highly conserved chymotrypsin-like cysteine protease domain (identified as CP in FIG. 3 and PL2 in FIG. 9) present at the N-terminus, and 3-4 predicted transmembrane domains near the C terminus of nsp2 (where the number of transmembrane domains varies depending on the location of the C-terminal cleavage site). Typically, deletion of the nucleotides encoding the amino acids of the PL2 domain or all of the predicted transmembrane domains results in a polynucleotide that can replicate in permissive cells but will not produce infectious virus particles. Thus, an infectious clone of the present invention does not typically include deletion of the entire PL2 domain or all of the predicted transmembrane domains.

The nucleotides encoding the chymotrypsin-like cysteine protease domain are nucleotides 1474 to 1776 of VR-V7 (SEQ ID NO:1), nucleotides 1474 to 1776 of VR2332 (Genbank accession number U87392), and nucleotides 1482 to 1784 of Lelystad (Genbank accession number M96262). The location of a chymotrypsin-like cysteine protease domain in the nucleotide sequence of other PRRS viruses can be identified by aligning the amino acid sequence of the nsp2 polypeptide encoded by a PRRS virus with the amino acid sequence alignment disclosed in FIG. 12, and determining which nucleotides encode those amino acids that line up with the chymotrypsin-like cysteine protease domain. Alternatively, the amino acid sequences of nsp2 polypeptides of other PRRS viruses can be identified by aligning the amino acid sequence of the nsp2 polypeptide encoded by a PRRS virus with the amino acid sequence of nsp2 polypeptides produced by other arteriviruses, such as equine arteritis virus (EAV) and lactate dehydrogenase-elevating virus (LDV).

The nucleotides encoding the predicted transmembrane domains of VR-V7 (SEQ ID NO:1), VR-2332 (Genbank accession number U87392), and Lelystad (Genbank accession number M96262) are shown in Table 1.

TABLE 1

Nsp2 nucleotides encoding predicted transmembrane domains.

|  | VR-V7 | VR-2332 | Lelystad |
| --- | --- | --- | --- |
| Transmembrane domain I | 881 to 901 | 881 to 901 | 761 to 781 |
| Transmembrane domain II | 913 to 934 | 913 to 934 | 793 to 814 |
| Transmembrane domain III | 963 to 980 | 963 to 980 | 843 to 860 |
| Transmembrane domain IV | 985 to 1003 | 985 to 1003 | 865 to 883 |

Figure 12:
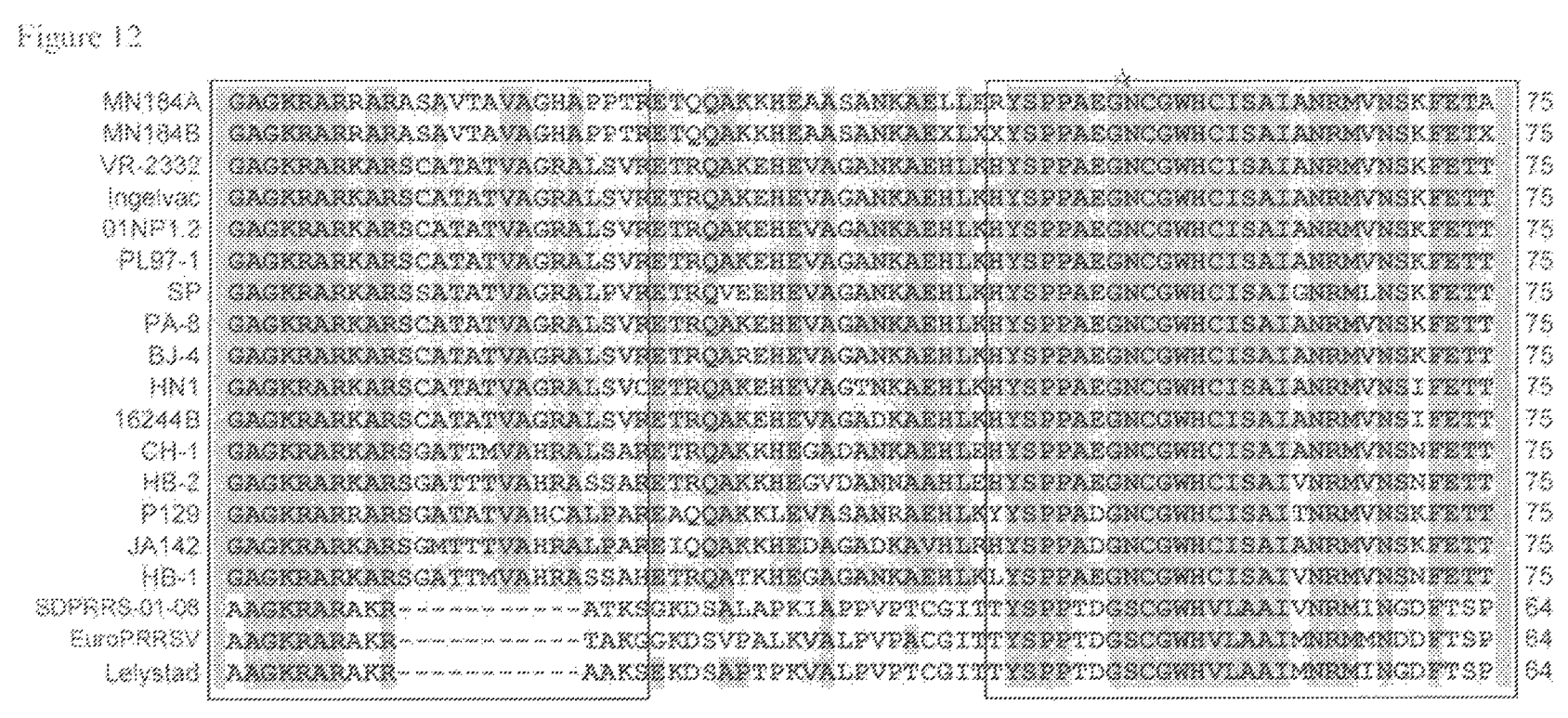
Figure 12:
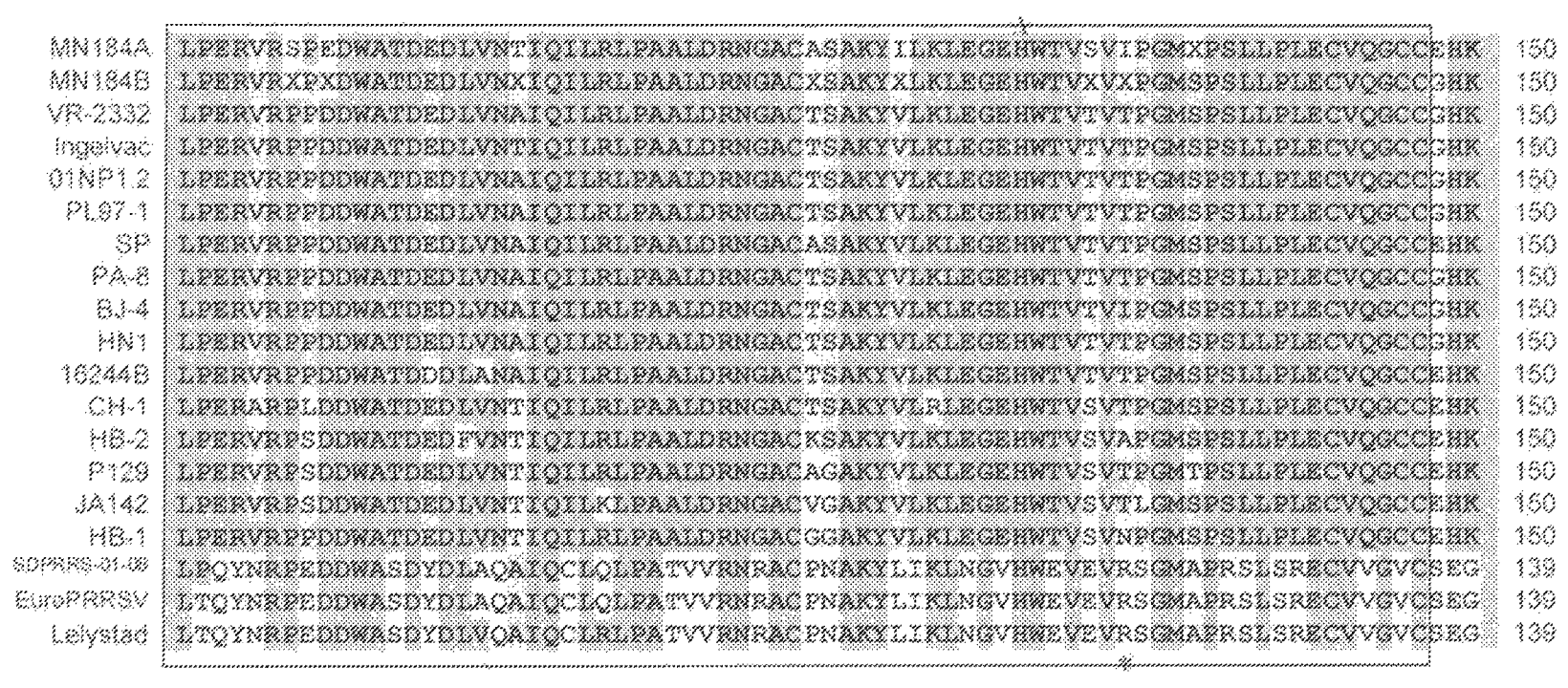
Figure 12:
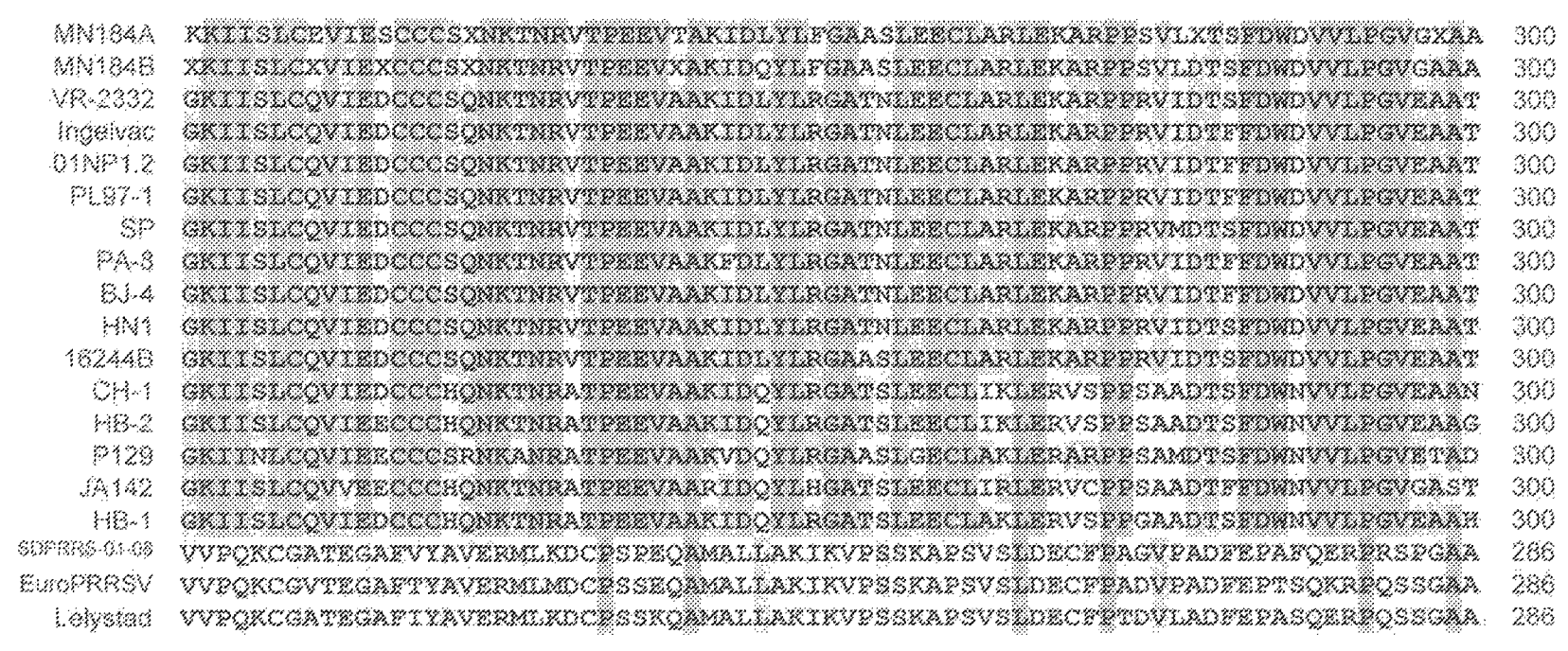
Figure 12:
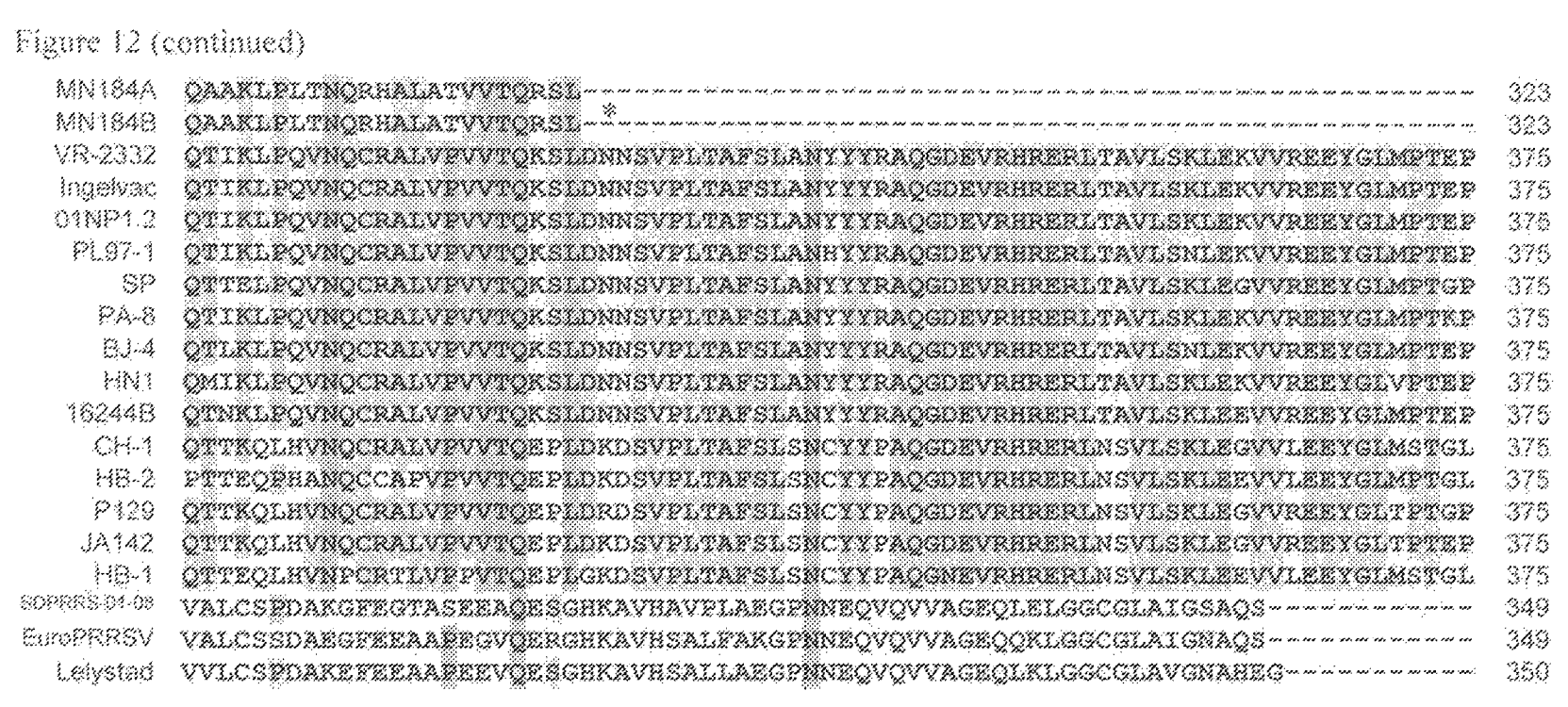
Figure 12:
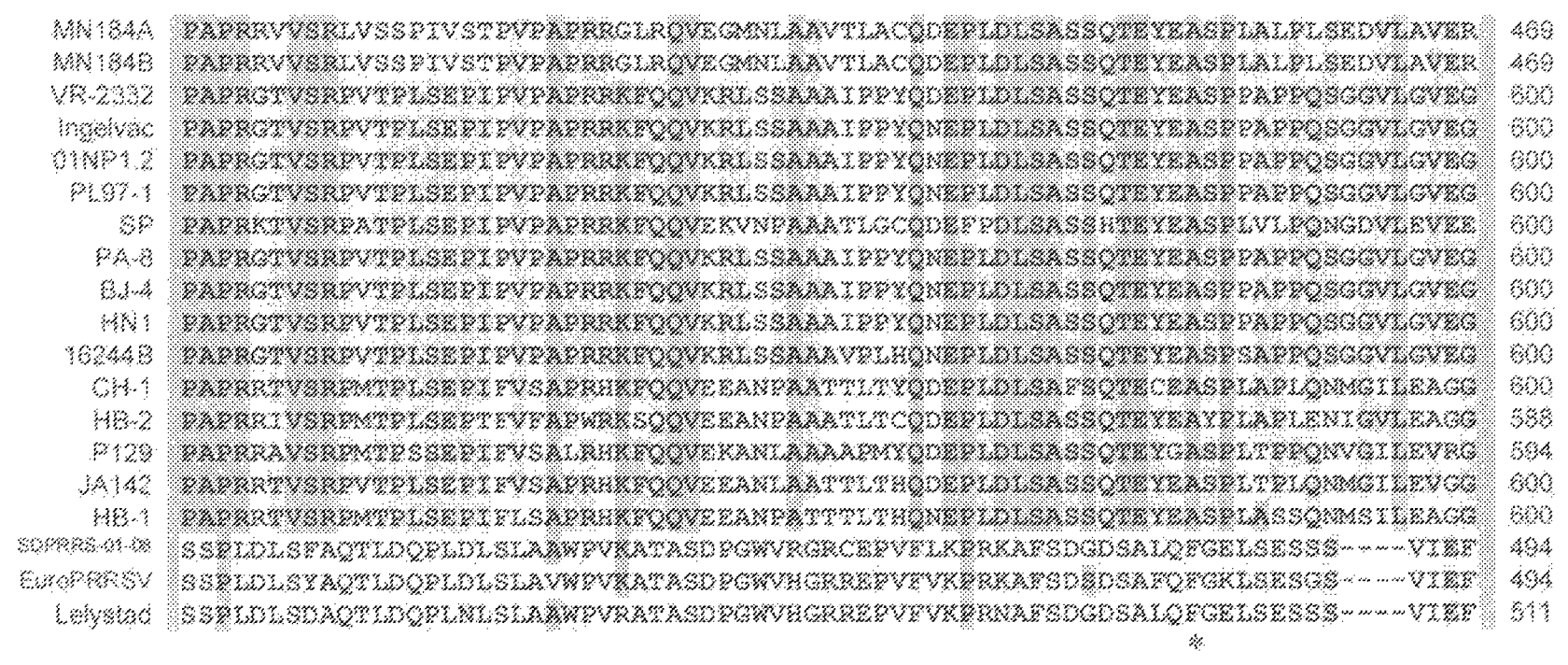
Figure 12:
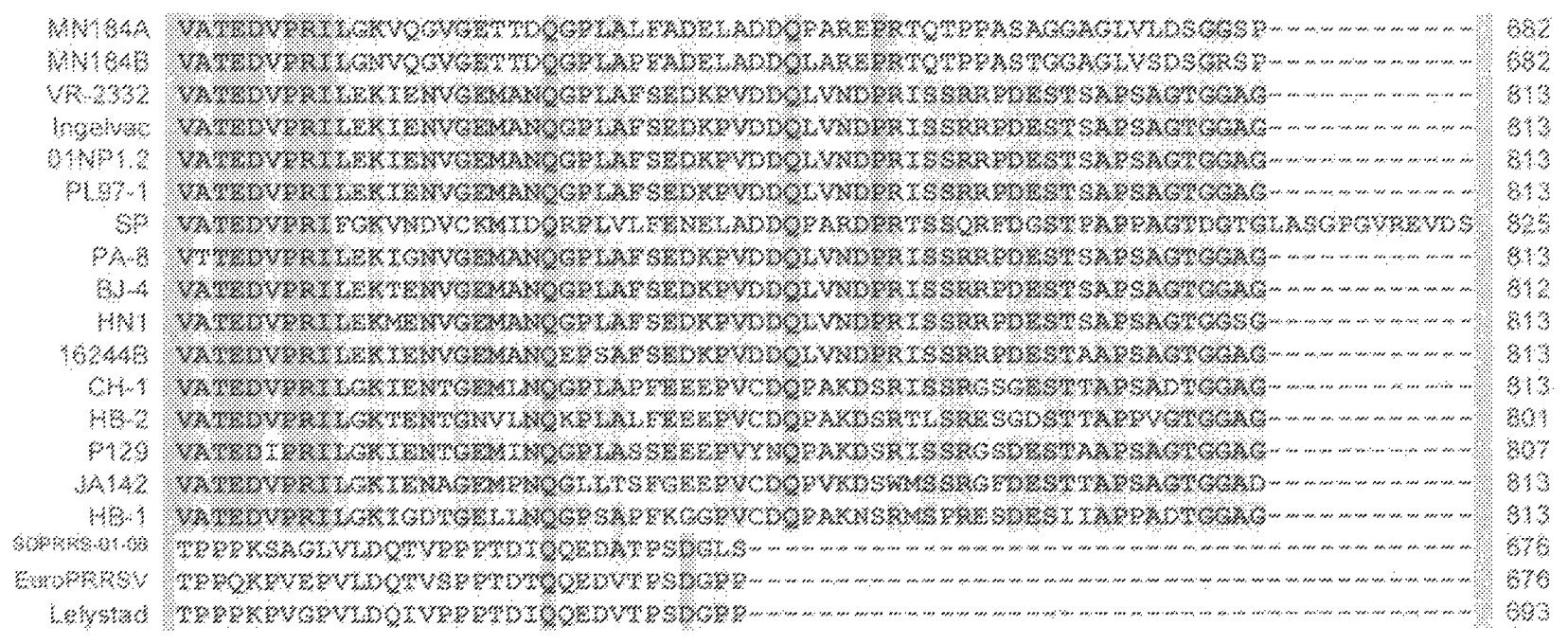
Figure 12:
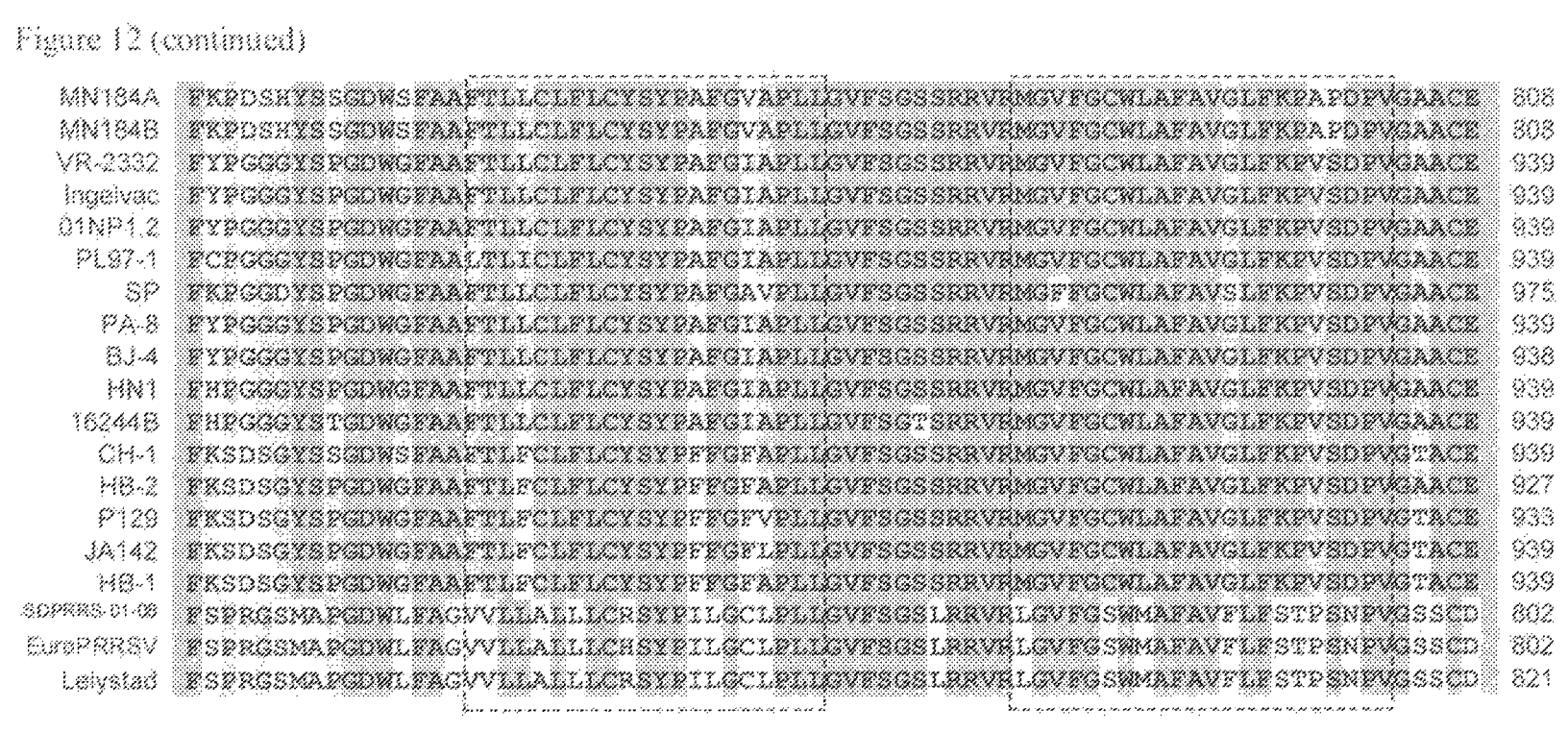
Figure 12:
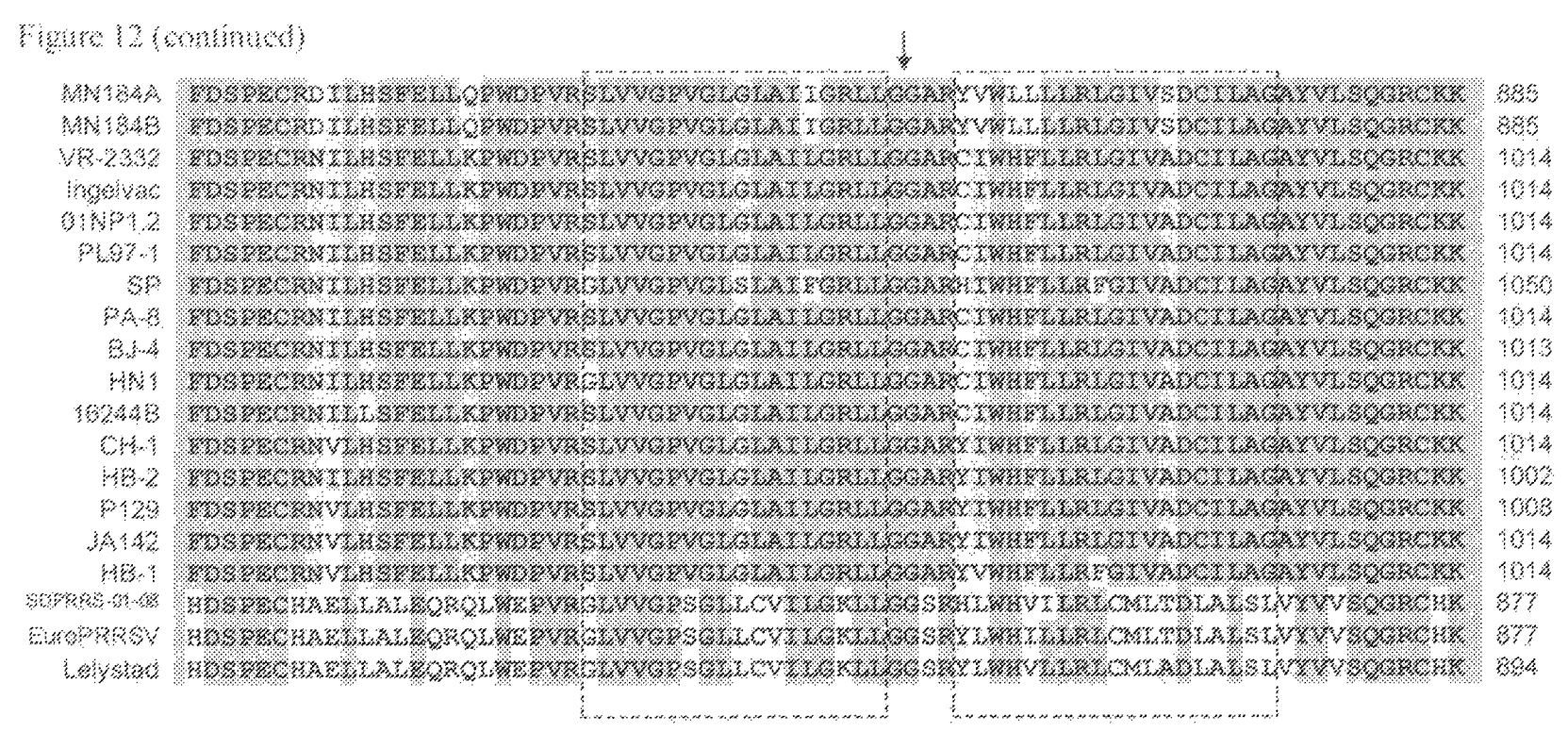
Figure 12:
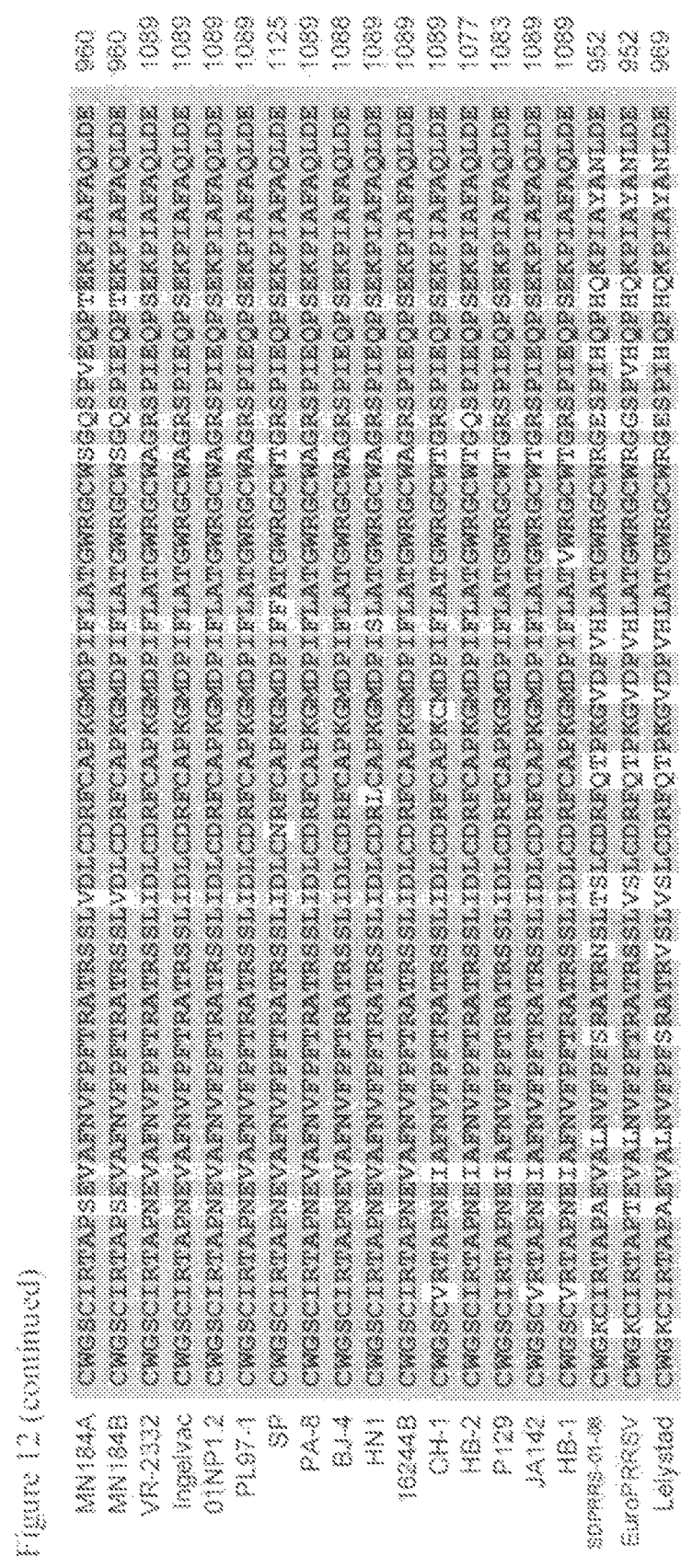
Figure 12:
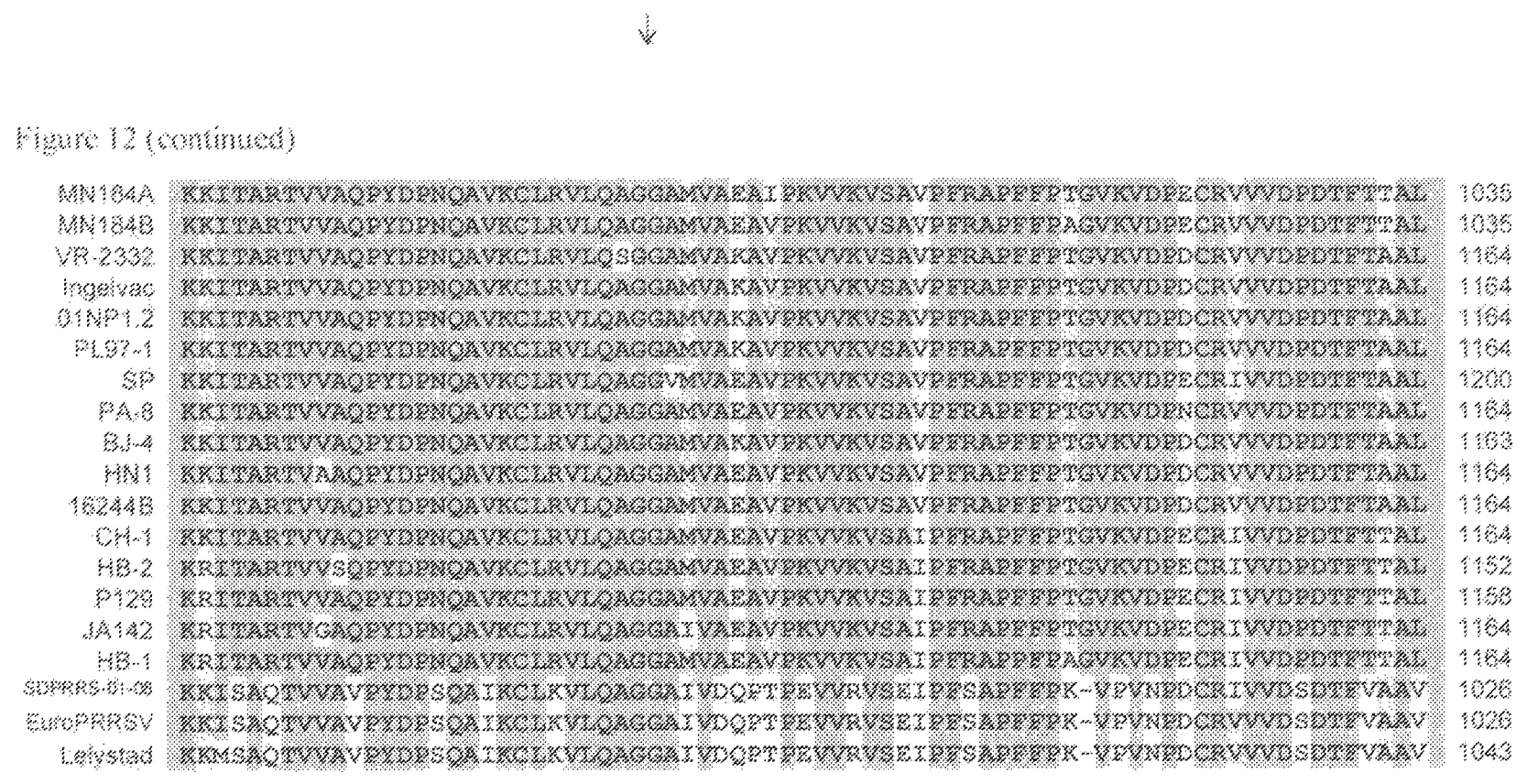

The location of the transmembrane domains in the nucleotide sequence of other PRRS viruses can be identified by aligning the amino acid sequence of the nsp2 polypeptide encoded by a PRRS virus with the amino acid sequence alignment disclosed in FIG. 12, and determining which nucleotides encode those amino acids that line up with the transmembrane domains. Alternatively, the location of the transmembrane domains can be identified with a computer algorithm, such as the PredictProtein algorithm as described by Rost et al. (*Nucleic Acids Res.*, 32 (Web Server issue): W321-326 (2004), or the TMHMM algorithm as described by Krogh et al. (*J. Mol. Biol.*, 305:567-580 (2001)) and available through the World Wide Web.

The deletion present in infectious polynucleotides of the present invention is typically between the nucleotides encoding the chymotryp sin-like cysteine protease domain and the nucleotides encoding the transmembrane domains, and does not result in a frameshift in the reading frame of ORF1. As discussed above, the deletion typically does not include all the nucleotides encoding the chymotrypsin-like cysteine protease domain, all the nucleotides encoding the transmembrane domains, or the combination thereof. In some aspects, for instance when the infectious polynucleotide has structural similarity with SEQ ID NO:1, the 5' boundary of a deletion is at nucleotide 2305, nucleotide 2205, nucleotide 2105, or nucleotide 2062, and the 3' boundary of a deletion is at nucleotide 3774, nucleotide 3804, nucleotide 3834, or nucleotide 3864. In other aspects, for instance when the infectious polynucleotide has structural similarity with SEQ ID NO:14, the 5' boundary of a deletion is at nucleotide 2304, nucleotide 2204, nucleotide 2104, or nucleotide 2061, and the 3' boundary of a deletion is at nucleotide 3455, nucleotide 3495, nucleotide 3525, or nucleotide 3545. The deletion can be at least 39 nucleotides, 48 nucleotides, or 57 nucleotides. In some aspects, the deletion can be at least 267 nucleotides, at least 276 nucleotides, or at least 285 nucleotides. In some aspects the deletion is no greater than 489 nucleotides, no greater than 459, no greater than 429, or no greater than 402 nucleotides. An infectious polynucleotide may have more than one deletion in the nsp2 region.

Examples of infectious polynucleotides derived from VR-V7 and containing a deletion are disclosed in Table 2.

TABLE 2

Infectious polynucleotides derived from VR-V7 (SEQ ID NO: 1).

| Polynucleotide* | deleted nucleotides of SEQ ID NO: 1 | amino acids of ORF1 deleted | viral titlers (PFU/ml) | Summary of phenotype** |
|---|---|---|---|---|
| Nsp2 Δ 180-323 | 1876-2304 | 563-705 | – | nonviable |
| Nsp2 Δ 242-323 | 2056-2304 | 623-705 | – | nonviable |
| Nsp2 Δ 324-434 | 2305-2637 | 706-816 | +($\sim 10^5$) | small plaque size |
| Nsp2 Δ 324-523 | 2305-2904 | 706-905 | +($\sim 10^5$-$10^6$) | intermediate |
| Nsp2 Δ 543-632 | 2962-3231 | 925-1014 | +($\sim 10^5$) | small plaque size |
| Nsp2 Δ 633-726 | 3232-3513 | 1015-1108 | +($\sim 10^5$) | small plaque size |
| Nsp2 Δ 543-726 | 2962-3513 | 925-1108 | +($\sim 10^5$) | small plaque size |
| Nsp2 Δ 727-813 | 3514-3774 | 1109-1195 | +($\sim 10^5$) | small plaque size |
| Nsp2 Δ 324-726 | 2305-3513 | 706-1108 | +($\sim 10^{1-2}$) | ND |
| Nsp2 Δ 324-813 | 2305-3774 | 706-1195 | – | nonviable |
| Nsp2 Δ 727-845 | 3514-3870 | 1109-1227 | – | nonviable |
| Nsp2 Δ 324-845 | 2305-3870 | 706-1227 | – | nonviable |

*the deletion refers to the amino acids of nsp2 that are deleted, e.g., in the virus Nsp2 Δ180-323, amino acids 180-323 of nsp2 are deleted.
**plaque size is relative to plaques produced by wildtype VR-2332.

An infectious polynucleotide containing a deletion can include an exogenous polynucleotide inserted in place of the deletion. An "exogenous" polynucleotide refers to a foreign nucleotide sequence, i.e., a nucleotide sequence that is not normally present in a PRRS virus or an infectious clone thereof. The exogenous polynucleotide can, and preferably does encode a polypeptide. Suitable exogenous polynucleotides include those encoding a detectable marker, e.g., a molecule that is easily detected by various methods. Examples include fluorescent polypeptides (e.g., green, yellow, blue, or red fluorescent proteins), luciferase, chloramphenicol acetyl transferase, and other molecules (such as c-myc, flag, 6×his, HisGln (HQ) metal-binding peptide, and V5 epitope) detectable by their fluorescence, enzymatic activity or immunological properties, and are typically useful when detected in a cell, for instance, a cultured cell, or a tissue sample that has been removed from an animal. Other exogenous polynucleotides that can be used are those encoding polypeptides expressed by other entities, such as cells and pathogens. Expression of an exogenous polynucleotide results in an infectious polynucleotide that expresses foreign antigens. Examples of exogenous nucleotide sequences include those encoding proteins expressed by pathogens, preferably porcine pathogens, such as porcine circovirus type 2, Mycoplasma hyopneumoniae (e.g., the P46 and P65 proteins of M. hyopneumoniae), Lawsonia intracellularis (e.g., the outer membrane proteins of L. intracellularis), the ORF5 of different strains of PRRSV, and Streptococcus suis (e.g., the 38-kDa protein of S. suis). The nsp2 polypeptide has B-cell epitopes and is expected to be immunogenic. Inclusion of foreign epitopes in an nsp2 polypeptide is expected to result in an immune response to the foreign epitopes. Additional examples of exogenous polynucleotides include those encoding biological response modifiers, such as, for example, IFN-α, IFN-γ, IL-12, IL-2, TNF-α, and IL-6.

The exogenous polynucleotide is inserted into the deletion region such that it is in frame with the open reading frame encoding nsp1α and nsp1β, and more than one exogenous polynucleotide can be inserted in tandem, for instance, nucleotide sequences encoding three c-myc epitopes can be present. The total size of the infectious polynucleotide containing an exogenous polynucleotide inserted in the place of the deletion is typically no greater than 16,000 bases, no greater than 15,800 bases, no greater than 15,600 bases, no greater than 15,400 bases, or no greater than 15,200 bases (including the poly A tail). An insertion can be present in an infectious polynucleotide having the Nsp2 Δ324-434, Nsp2 Δ324-523, Nsp2 Δ543-632, Nsp2 Δ633-726, Nsp2 Δ543-726, Nsp2 Δ727-813, or Nsp2 Δ324-726 deletion, preferably, the Nsp2 Δ324-434, Nsp2 Δ543-632, Nsp2 Δ633-726, Nsp2 Δ543-726, Nsp2 Δ727-813, or Nsp2 Δ324-726 deletion. Preferred examples of infectious clones containing an exogenous polynucleotide in the location of a deletion include an infectious polynucleotide having the Nsp2 Δ324-434 deletion containing a coding region encoding a 238 amino acid green fluorescent protein, an infectious polynucleotide having the Nsp2 Δ543-632 deletion containing a coding region encoding a 238 amino acid green fluorescent protein, an infectious polynucleotide having the Nsp2 Δ324-434 deletion containing a coding region encoding a 10 amino acid c-myc epitope (EQKLISEEDL, SEQ ID NO:17), an infectious polynucleotide having the Nsp2 Δ324-434 deletion containing a coding region encoding a 10 amino acid c-myc epitope, and an infectious polynucleotide having the Nsp2 Δ324-726 or Nsp2 Δ543-726 deletions each containing a coding region encoding tandem repeat of the 10 amino acid c-myc epitope.

An infectious polynucleotide is typically present in a vector, and the combination of infectious polynucleotide and vector is referred to as an infectious clone, which is made through reverse genetics. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard recombinant DNA techniques known in the art (see, e.g., Sambrook et al., *Molecular Cloning: A Laboratory Manual*, Cold Spring Harbor Laboratory Press (1989)). A vector can provide for further cloning (amplification of the polynucleotide), i.e., a cloning vector, or for expression of the polypeptide encoded by the coding region, i.e., an expression vector, or the combination thereof. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Preferably, a vector suitable for use as part of an infectious clone is both a cloning vector and an expression vector. Useful vectors have a low copy number in a host cell. Suitable host cells for cloning or expressing the vectors herein are prokaryote or eukaryotic cells. Preferably the host cell secretes minimal amounts of proteolytic enzymes. Suitable prokaryotes include eubacteria, such as gram-negative organisms, for example, *E. coli* or *S. typhimurium*. Examplary host cells useful for making, manipulating, and maintaining an infectious clone are DH-5a, DH-1 (ATCC 33849), and AG-1, preferably, DH-1 or AG-1.

A vector includes regulatory sequences operably linked to the infectious polynucleotide. The term "operably linked" refers to a juxtaposition of components such that they are in a relationship permitting them to function in their intended manner. A regulatory sequence is "operably linked" to an infectious polynucleotide of the present invention when it is joined in such a way that expression of the coding region is achieved under conditions compatible with the regulatory sequence. Typically, a promoter is one that provides for high specificity binding of an RNA polymerase, and such promoters include T7, SP6, and T3. Typically the promoter is situated immediately upstream of the first nucleotide of the infectious polynucleotide. Preferably, a GGT is inserted between the promoter and the first nucleotide of the infectious polynucleotide. Optionally and preferably the vector also contains a hepatitis delta virus ribozyme downstream of the poly A region.

The vector optionally, and preferably, includes one or more selection marker sequences, which typically encode a molecule that inactivates or otherwise detects or is detected by a compound in the growth medium. For example, the inclusion of a selection marker sequence can render the transformed cell resistant to an antibiotic, or it can confer compound-specific metabolism on the transformed cell. Examples of a selection marker sequence are sequences that confer resistance to kanamycin, ampicillin, chloramphenicol, tetracycline, and neomycin.

When producing a deletion of nucleotides encoding an nsp2 polypeptide in an infectious clone, standard recombinant DNA techniques known in the art can be used (see, e.g., Sambrook et al., *Molecular Cloning: A Laboratory Manual*, Cold Spring Harbor Laboratory Press (1989)). As the skilled person will recognize, it is standard practice during construction of an infectious clone (and when construction deletions in an infectious clone) to verify by nucleotide sequence analysis the presence of expected nucleotide sequences, such as deletions or other alterations and the absence of other mutations. Likewise, when a candidate infectious polynucleotide is tested to determine if it is infectious, it is standard practice to verify by nucleotide sequence analysis the absence of contaminating wild-type virus.

The present invention also includes isolated infectious polynucleotides disclosed at SEQ ID NO:5 and SEQ ID NO:6, and infectious polynucleotides having structural similarity to SEQ ID NO:5 or SEQ ID NO:6. Methods for determining structural similarity are described herein. Preferably, an infectious polynucleotide of this aspect of the present invention has structural similarity to SEQ ID NO:5 or SEQ ID NO:6 of at least 88%, at least 89%, at least 90%, at least 91%, at least 92%, at least 93%, at least 94%, at least 95%, at least 96%, at least 97%, at least 98%, or at least 99%. A polynucleotide having structural similarity to SEQ ID NO:5 or SEQ ID NO:6 is considered to be an infectious polynucleotide if, when present in a virus particle and exposed to permissive cells, the polynucleotide replicates in the permissive cells and produces infectious virus particles.

The present invention also includes isolated virus particles. As used herein, the terms "virus particle" and "viral particle" are used interchangeably and refer to a polynucleotide of the present invention surrounded by an envelope. A virus particle of the present invention can, when added to a permissive cultured cell, replicate to result in the production of more viral particles.

A virus particle can be grown by passage in vivo or in cell culture. Passage in vivo includes inoculating a pig (Faaberg et al., U.S. Pat. No. 7,041,443). Passage in cell culture includes exposing cultured cells to the virus particle and incubating the cells under conditions suitable for the virus to reproduce and produce more virus particles. Preferably, the cultured cells are not an immortalized or transformed cell line (i.e., the cells are not able to divide indefinitely). Preferably, primary porcine alveolar macrophages are used for passage in cell culture (Faaberg et al., U.S. Pat. No. 7,041,443).

A virus of the present invention can be inactivated, i.e., rendered incapable of reproducing in vivo and/or in cell culture. Methods of inactivation are known to the art and include, for instance, treatment of a virus particle of the invention with a standard chemical inactivating agent such as an aldehyde reagent including formalin, acetaldehyde and the like; reactive acidic alcohols including cresol, phenol and the like; acids such as benzoic acid, benzene sulfonic acid and the like; lactones such as beta propiolactone and caprolactone; and activated lactams, carbodiimides and carbonyl diheteroaromatic compounds such as carbonyl diimidazole. Irradiation such as with ultraviolet and gamma irradiation can also be used to inactivate the virus.

Also included in the present invention are attenuated virus particles (i.e., viruses having reduced ability to cause the symptoms of mystery swine disease in pigs), and methods of making an attenuated virus particle. Methods of producing an attenuated virus are known to the art. Typically, a virus of the present invention is passaged, i.e., used to infect a cell in culture, allowed to reproduce, and then harvested. This process is repeated until the virulence of the virus in pigs is decreased. For instance, the virus can be passaged 10 times in cell culture, and then the virulence of the virus measured. If virulence has not decreased, the virus that was not injected into the animal is passaged an additional 10 times in cell culture. This process is repeated until virulence is decreased. In general, virulence is measured by inoculation of pigs with virus, and evaluating the presence of clinical symptoms and/or $LD_{50}$ (see, for instance, Halbur et al., *J. Vet. Diagn. Invest.*, 8:11-20 (1996), Halbur et al., *Vet. Pathol.*, 32:200-204 (1995), and Park et al., *Am. J. Vet. Res.*, 57:320-323 (1996)). Preferably, virulence is decreased so the attenuated virus does not cause the death of animals, and preferably does not cause clinical symptoms of the disease.

Typically, a cell culture useful for producing an attenuated virus of the present invention includes cells of non-porcine mammal origin. Examples of non-porcine mammal cell cultures include, for instance, the cell line MA-104 (ATCC CRL-2378), the cell line MARC-145 (Kim et al., *Arch. Viral.*, 133:477-483 (1993)), and the cell line CL-2621 (Baustita et al., *J. Vet. Diagn. Invest.*, 5:163-165 (1993)). Preferably, a mixed cell culture is used for producing an attenuated virus particle of the present invention. In a mixed cell culture there are at least two types of cells present. Preferably, a mixed cell culture includes an immortalized or transformed cell line and a primary cell culture. A mixed cell culture is particularly useful when a virus reproduces slowly, or not at all, in an immortalized or transformed cell line. Preferred examples of an immortalized or transformed cell line for use in a mixed cell culture include, for example, the cell line MARC-145 (Kim et al., *Arch. Virol.*, 133:477-483 (1993)), and the cell line MA-104 (ATCC CRL-2378). Preferably, primary cell cultures for use in a mixed cell culture are porcine in origin. A preferred example of a primary cell culture for use in a mixed cell culture is primary porcine alveolar macrophages.

The present invention further includes the polypeptides encoded by the nsp2 coding regions present in the polynucleotides disclosed in Table 2, including those that are viable. Also included in the present invention are antibodies, including monoclonal and polyclonal antibodies, that specifically bind a polypeptide encoded by the nsp2 coding regions present in the polynucleotides disclosed in Table 2. The term "antibody," unless specified to the contrary, includes fragments of whole antibodies which retain their binding activity for a target antigen. Such fragments include Fv, F(ab') and $F(ab')_2$ fragments, as well as single chain antibodies (scFv). As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets. As used herein, the term "polypeptide: antibody complex" refers to the complex that results when an antibody specifically binds to a polypeptide, or a subunit or analog thereof. In some aspects, an antibody of the present invention include those that do not specifically bind to a full length nsp2 polypeptide encoded by VR-2332 (e.g., Genbank accession number U87392, ORF1 amino acids 384-1363 (also see Allende et al., *J. Gen. Virol.,* 80:307-315 (1999) or ORF1 amino acids 384-1580 (also see Ziebuhr et al., *J. Gen. Virol.,* 81:853-879 (2000)). Such antibodies can be identified using routine methods known in the art.

Antibodies of the present invention can be prepared using the intact polypeptide. Optionally, an nsp2 polypeptide described herein can be covalently bound or conjugated to a carrier polypeptide to improve the immunological properties of the polypeptide. Useful carrier polypeptides are known in the art.

The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. Briefly, spleen cells from an animal immunized with a desired antigen are immortalized, commonly by fusion with a myeloma cell (see, for example, *Antibodies: A Laboratory Manual*, Harlow et al., eds., Cold Spring Harbor Laboratory Press: Cold Spring Harbor, N.Y., (1988)). Monoclonal antibodies can be isolated and purified from hybridoma cultures by techniques well known in the art.

In some embodiments, the antibody can be recombinantly produced, for example, by phage display or by combinatorial methods. Phage display and combinatorial methods can be used to isolate recombinant antibodies that bind to a polypeptide described herein, or a biologically active subunit or analog thereof (see, for example, Ladner et al., U.S. Pat. No. 5,223,409). Such methods can be used to generate human monoclonal antibodies.

The present invention also provides compositions including an infectious polynucleotide, PRRS polynucleotide, virus particle, or antibody of the present invention. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Examples of routes of administration include perfusion and parenteral, e.g., intravenous, intradermal, subcutaneous, oral (e.g., inhalation), transdermal (topical), and transmucosal. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (i.e., an infectious polynucleotide or PRRS virus of the present invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. These compositions may also be formed into a powder or suspended in an aqueous solution such that these powders and/or solutions can be added to animal feed or to the animals' drinking water. These compositions can be suitably sweetened or flavored by various known agents to promote the uptake of the vaccine orally by the pig.

The active compounds can also be administered by any method suitable for administration of polynucleotide agents, e.g., using gene guns, bio injectors, and skin patches as well as needle-free methods such as the micro-particle DNA vaccine technology disclosed by Johnston et al. (U.S. Pat. No. 6,194,389). Additionally, intranasal delivery is possible, as described in, for instance, Hainajima et al., *Clin. Immunol. Immunopathol.*, 88:205-210 (1998). Liposomes and microencapsulation can also be used.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

Toxicity and therapeutic efficacy of such active compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in the field. The dosage of such compounds lies preferably within a range of circulating concentrations that include the $ED_{50}$ with little or no toxicity. The dosage may vary within this range depending upon the dosage form employed and the route of administration used.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polypeptide can include a single treatment or, preferably, can include a series of treatments.

The present invention includes methods for using the compositions described herein. In one aspect the invention includes methods for treating one or more symptoms of mystery swine disease in an animal that may be caused by infection by a PRRS virus. The method includes administering an effective amount of a composition of the present invention to an animal having or at risk of having mystery swine disease, or symptoms of mystery swine disease.

Treatment of mystery swine disease, or symptoms of mystery swine disease, can be prophylactic or, alternatively, can be initiated after the development of disease or symptoms thereof. As used herein, the term "symptom" refers to objective evidence in a subject of mystery swine disease. Symptoms associated with mystery swine disease and the evaluations of such symptoms are routine and known in the art. Examples of symptoms include abortion, anorexia, fever, lethargy, pneumonia, red/blue discoloration of ears, labored breathing (dyspnea), and increased respiratory rate (tachypnea). Treatment that is prophylactic, for instance, initiated before a subject manifests symptoms of a condition caused by a PRRS virus, is referred to herein as treatment of a subject that is "at risk" of developing the disease or symptoms thereof. Typically, an animal "at risk" is an animal present in an area where animals having the disease or symptoms thereof have been diagnosed and/or is likely to be exposed to a PRRS virus. Accordingly, administration of a composition can be performed before, during, or after the occurrence of the conditions described herein. Treatment initiated after the development of a condition may result in decreasing the severity of the symptoms of one of the conditions, or completely removing the symptoms.

In some aspects, the methods typically include administering to an animal a composition including an effective amount of a virus particle of the present invention. An "effective amount" is an amount effective to prevent the manifestation of symptoms of mystery swine disease, decrease the severity of the symptoms of the disease, and/or completely remove the symptoms. Typically, the effective amount is an amount that results in a humoral and/or cellular immune response that protects the animal during future exposure to a PRRS virus. The virus particle used in the composition may contain an infectious polynucleotide that has a deletion as described herein. Optionally, the infectious polynucleotide also includes an exogenous polynucleotide present at the location of the deletion. An advantage of using a virus particle having a deletion (or an exogenous polynucleotide present in the location of the deletion) is it can be easily distinguished from other PRRS viruses, including wild type PRRS viruses present in the field. The virus particle can be identified by isolation of the virus from an animal followed, for instance, by sequencing, restriction enzyme digestion, or PCR-based amplification of specific nucleotides. Such a "marked" virus particle is often referred to in the art as a marker vaccine.

In other aspects of the present invention the infectious clones and/or infectious polynucleotides described herein can be used to investigate viable gene insertions, to investigate alternative expressed RNA or proteins other than full length virus, to investigate viral recombination, and to investigate immunogenic properties of full-length nsp2 as relative to truncated nsp2.

EXAMPLES

Example 1

Full-length cDNA clones of North American porcine reproductive and respiratory syndrome virus (PRRSV) prototype VR-2332 strain were developed, with each progressive version possessing less nucleotide changes than prior versions when compared to wt strain VR-2332. Progeny virus of each infectious clone was recovered and analyzed for nucleotide sequence verification, in vitro growth rate and plaque size. Progeny from one infectious clone confirmed robust in vivo replication, seen by the appearance of a-PRRSV antibodies at the same rate as wt virus. Northern blot analysis of the in vivo progeny also revealed that defective subgenomic RNA species, termed heteroclites (uncommon forms), were present along with full-length genomes. Concurrent northern blot analysis of a passage series of infected MA-104 cell cultures revealed that recombinant virus only gradually gained a profile of both full-length and heteroclite RNA similar to the RNA species seen in in vivo infection.

Materials and Methods

Cells and viral strains. MA-104 cells or its descendent MARC-145 cells (ATCC CRL-11171), an African green monkey kidney epithelial cell line which supports PRRSV replication (Meng et al., *J. Vet. Diagn. Invest.*, 8:374-81 (1996)), were maintained in Eagle's minimal essential medium (EMEM) (JRH Biosciences 56416), supplemented with 1 mg/ml $NaHCO_3$ and 10% fetal bovine serum (FBS), at 37° C. with 5% $CO_2$. The cultured cells were transfected with RNA or infected with virus when monolayer growth had reached 70-80% confluency. PRRSV North American prototype strains VR-2332 and Ingelvac® MLV have been described previously (Yuan et al., *Virus Res.*, 79:189-200 (2001)). Strain VR-2332 grows to equivalent titers on both cell lines.

Viral RNA purification. Viral RNA (vRNA) was purified as described. (Chen et al., *J. Gen. Virol.*, 75:925-930 (1994); Yuan et al., *Virus Res.*, 79:189-200 (2001)). Briefly, supernatant from MARC-145 cells infected with VR-2332 was harvested on day 4 post-infection (p.i.). After removal of cellular debris by centrifugation at 12,000 rpm, the supernatants were layered onto a 2 ml 0.5 M sucrose cushion and centrifuged at 76,000×g for 4 hours. The pelleted virions were resuspended in 0.5 ml LES (0.1 M LiCl/5 mM EDTA/ 1.0% SDS) and further digested by addition of 100 µg proteinase K at 56° C. to remove all protein. After 10 minutes of incubation, vRNA was extracted several times with acid phenol and phenol/chloroform and then precipitated in 70% v/v ethanol. Pelleted vRNA was immediately resuspended into 50 µl $H_2O$ or RNase-free TE buffer (10 mM Tris-HCl, 1 mM EDTA, pH 8.0) and stored at −80° C.

Construction of full-length viral cDNA. cDNA synthesis was performed with Enhanced Avian HS RT-PCR Kit (Sigma, HSRT-100). Eight PCR primers (Table 3) were used to amplify four overlapping cDNA fragments covering the complete VR-2332 genome (FIG. 2). The cycling conditions were 94° C. for 2 minutes, then 35 cycles of 94° C. for 15 seconds, 68° C. for 4-5 seconds, followed by 68° C. for 5 minutes. Each PCR fragment was purified with the QIAEX II Gel Extraction Kit (Qiagen) and cloned into pCR®2.1-TOPO® vector with TOPO TA Cloning® Kit (Invitrogen K450001). Plasmids representing each fragment were submitted for nucleotide sequence analysis. The fragments with the minimum nucleotide mutations compared to parental VR-2332 sequence (GenBank submission number U87392) were used to assemble the full-length cDNA, as shown in FIG. 2. In each overlap region, a unique restriction enzyme site was utilized to join flanking fragments. Four digested fragments, representing full-length genomic sequence, were precisely assembled stepwise into a modified low copy plasmid vector (pOK12HDV-PacI). The vector was modified to include the HDV ribozyme by inserting a 244 bp SmaI to SacII fragment containing the HDV antigenome ribozyme and a T7 RNA polymerase terminator sequence from Transcription vector 2.0 (Johnson et al., *J. Virol.*, 71:3323-3327 (1997); Pattnaik et al., *Cell*, 69:1011-1020 (1992)) into the corresponding sites in pOK12 (Vieira et al., *Gene*, 100:189-194 (1991)). The NcoI restriction enzyme site in this 244 bp fragment was replaced with a unique PacI site by oligonucleotide mutation with primer sets 5'pOK12HDV-2157/3'pOK12HDV-257 and 5'pOK12HDV-257/polyA-modified (Table 3), followed by fusion PCR. In the full-length cDNA clones, viral genomic sequence was preceded by the T7 RNA polymerase promoter, 1 or 2 G residues and a T residue, and followed by a polyadenylic acid tail of 50 nucleotides. Assembled clones were propagated in the DH5α strain of *Eschericia coli* and then submitted for full-genome nucleotide sequence confirmation.

TABLE 3

Oligonucleotide primers used in this study. Forward primers are indicated with a slash (/) after the designator, reverse primers are preceded by a slash. Inserted restriction enzyme sites are shown in underlined italics.

| Primer | Genome Position* | Sequence |
| --- | --- | --- |
| Cloning: | | |
| T7Leader-VR long/ | 1-31 | 5'-ACAT*GCATGC*TTAATACGACTCACTATAGTATGACGTATAGGTGTTGGCTCTATGCCTTGG (SEQ ID NO: 18) |
| /3'-4300 | 4617-4635 | 5'-CTGGGCGACCACAGTCCTA (SEQ ID NO: 19) |
| 5'-4056-AscII | 4055-4080 | 5'-CTTCTC*GGCGCGCC*CGAATGGGAGT (SEQ ID NO: 20) |
| /3'-7579 | 7578-7603 | 5'-TCATCATA*CCTAGGG*CCTGCTCCACG (SEQ ID NO: 21) |
| 5'-7579/ | 7578-7603 | 5'-CGTGGAGCAGG*CCCTAGG*TATGATGA (SEQ ID NO: 22) |
| /P32 | 13293-13310 | 5'-TGCAGGCGAACGCCTGAG (SEQ ID NO: 23) |
| VR1509/ | 11938-11958 | 5'-GTGAGGACTGGGAGGATTACA (SEQ ID NO: 24) |
| /3'end-FL | 15405-15411 | 5'-GTCT*TTAATTAA*CTAG(T)$_{30}$AATTTCG (SEQ ID NO: 25) |
| Mutagenesis: | | |
| 5'-pOK12HDV-2S7/(SpbI, PacI) | pOK12HDV-PacI 257-282 | 5'-GAT*GCATGCCATTAATTAA*GGGTCGGC (SEQ ID NO: 26) |

TABLE 3-continued

Oligonucleotide primers used in this study. Forward primers are indicated with
a slash (/) after the designator, reverse primers are preceded by a slash. Inserted
restriction enzyme sites are shown in underlined italics.

| Primer | Genome Position* | Sequence |
| --- | --- | --- |
| 13'-pOK12HDV-257(SpbI, PacI) | pOK12DV-PacI 257-282 | 5'-GCCGACCC*TTAATTAA*TG*GCATGC*ATC (SEQ ID NO: 27) |
| T7leader-VR-2G/ | 1-5 | 5'-ACATGCATGCTTAATACGACTCACTATAGGTATGAC (SEQ ID NO: 28) |
| 7475G2A/ | 7453-7477 | 5'-5Phos/CTGTGTGGACATGTCACCATTGAA (SEQ ID NO: 29) |
| 13860C2T/ | 13843-13867 | 5'-5Phos/GTGTATCGTGCCGTTCTGTTTTGCT (SEQ ID NO: 30) |
| 14979A2G/ | 14958-14982 | 5'-5Phos/CAGATGCTGGGTAAGATCATCGCTC (SEQ ID NO: 31) |
| Northern Blot Analyses: | | |
| /3'-UTR | 15298-15336 | 5'-GCACAATGTCAATCAGTGCCATTCACCACACATTCT TCC (SEQ ID NO: 32) |
| /1a-p222 | 221-261 | 5'-TAGACTTGGCCCTCCGCCATAAACACCCTGGCATTG GGGGT (SEQ ID NO: 33) |

*Genome position is based on GenBank Submission U87392

Modification and sequence analysis of full-length cDNA clones. QuikChange® Multi Site-Directed Mutagenesis Kit (Stratagene) was used to modify all zcDNA clones from pVR-V4 to pVR-V6G7475A. The complete genomic cDNA plasmid inserts were then submitted to the University of Minnesota Advanced Genetic Analysis Center (AGAC) for nucleotide sequence analysis with appropriate sequencing primers (Table 3). Sequence differences between pVR-V4 through pVR-V6G7475A, as well as to those of parental VR-2332, its corresponding attenuated vaccine strain, Ingelvac® MLV, and pVR-HN, the first infectious clone of VR-2332, are listed in FIG. 13 (Nelsen et al., *J. Virol.*, 73:270-80 (1999); Yuan et al., *Virus Res.*, 79:189-200 (2001); Nielsen et al., *J. Virol.*, 77:3702-3711 (2003)).

Figure 13:
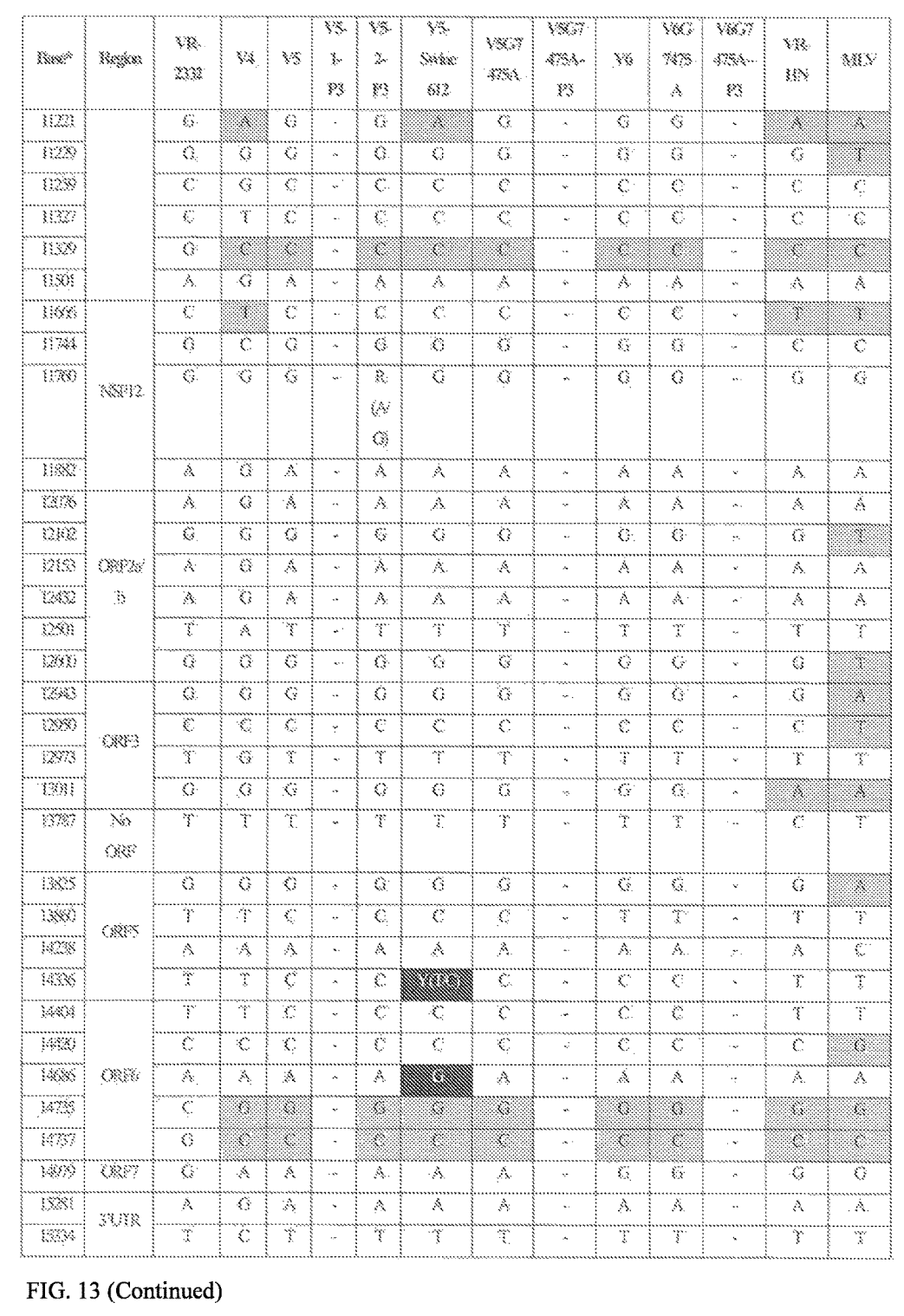

FIG. 13. Nucleotide differences between PRRSV strains and VR-2332 infectious clones. Only positions where nucleotide differences were noted are shown. Nucleotides that are represented in strain VR-2332 are shown in unshaded boxes. Light shaded boxes represent nucleotide differences that are unique to the infectious clone, medium shaded boxes highlight those nucleotides that are also seen in Ingelvac® MLV, and boxes that are shaded black indicate swine unique nucleotides. Regions that were not sequenced are indicated by a slash.

* The negative bases refer to those nucleotides present in the RNA after transcription and derived from the RNA polymerase promoter immediately upstream of the infectious polynucleotide. These promoter-derived nucleotides are typically no longer present in an infectious polynucleotide after it has been passaged 9 times.

In vitro transcription. The full-length cDNA clone was linearized by cleavage with PacI, which cuts downstream of the poly(A) tail. Capped [m$^7$G(5')ppp(5')G cap analog] RNA transcripts were produced using the mMESSAGE MACHINE™ Kit (Ambion) and an optimized 2:1 ratio of methylated cap analogue to GTP. Approximately 50 to 60 μg of RNA was generated from 2 μg of DNA template in a 20 μl of reaction mixture. Increasing the ratio of cap analogue to GTP substantially reduced the RNA yield. The RNA was subsequently purified by acid phenol-chloroform followed by isopropanol precipitation and resuspended in nuclease-free TE buffer (pH 8.0). RNA was evaluated for quality by size comparison with wild-type VR-2332 viral RNA on a 1% glyoxal denaturing agarose gel, and quantified by spectrophotometry at $OD_{260}$.

MARC-145 cell transfection. A modified transfection procedure was generated based on the approached described by Nielsen (Nielsen et al., (*J. Virol.*, 77:3702-3711 (2003)). For transfection, MARC-145 cells were seeded onto six-well plates (2-3×10$^5$ cells/well) in 3 ml of complete medium [EMEM supplemented with 10% fetal bovine serum (FBS)] and then incubated at 37° C., 5% $CO_2$ for 20-24 hours until approximately 80% confluent (Collins et al., *J. Vet. Diagn. Invest.*, 4:117-126 (1992)). 4 μg of in vitro transcribed RNA diluted in 500 μl Opti-MEM® I Reduced Serum Medium (Invitrogen) and 2 μl of 1,2-dimyristyloxypropyl-3-dimethyl-hydroxy ethyl ammonium bromide and cholesterol (DMRIE-C; Invitrogen) diluted in 1 ml Opti-MEM® medium were combined and vortexed briefly. The MARC-145 cells were washed once with 2 ml Opti-MEM® medium and then immediately overlayed with the lipid:RNA complex solution. DMRIE-C without RNA (2 μl) was used as a negative control and DMRIE-C with 10-100 ng strain (wild type) wt VR-2332 purified viral RNA was used as a positive control. After 4 hours of exposure to the lipid:RNA complexes, the monolayers were washed and fresh complete medium (EMEM with 10% FBS) was added. Supernatants from transfected cells were monitored daily for appearance of cytopathic effect (CPE) and passaged onto fresh MARC-145 at 72-96 hours posttransfection.

Detection of progeny viral RNA. To detect progeny viral RNA, cell culture supernatant from transfected and infected MARC-145 cells were harvested. RNA was isolated with QiaAmp viral RNA Kit (Qiagen). RT-PCR was performed with select primer pairs, specific to the VR-2332 strain nucleotides that were indicative of infectious clone mutated residues (Table 3). Confirmation of infectious clone progeny was obtained by nucleotide sequence verification of clone specific nucleotides present in the RT-PCR products.

Detection of progeny viral nucleocapsid protein. Indirect immunofluorescence assays (IFA) were used to detect viral protein expression in in vitro transcript RNA transfected, or progeny virus infected, MARC-145 cells prepared on coverslips. Infected cells were fixed in 3.7% paraformaldehyde with phosphate buffered saline (PBS), pH 7.5, at room temperature for 10 minutes. The fixed cells were washed with PBS, incubated at 37° C. for 45 minutes in PRRSV nucleocapsid protein specific monoclonal antibody SDOW17 (Magar et al., *Can. J. Vet Res.*, 59:232-234 (1995)) and further incubated with goat anti-mouse immunoglobulin G (IgG) conjugated with fluorescein isothiocyanate at 37° C. for another 45 minutes (1:100 dilution) (Sigma). The coverslips were washed with PBS, mounted to a slide using gel mount oil, and observed under a fluorescence microscope.

Viral plaque assay. MARC-145 cell monolayers on six-well plates were infected with cell supernatant (in 10-fold dilutions) from transfected or infected MARC-145 cells by incubation at room temperature for 1 hour. Infected monolayers were subsequently washed once with fresh EMEM/10% FBS, overlaid immediately with sterile 1% SeaPlaque Agarose (BioWhittaker Molecular Applications, Rockland, Me.) in 1×MEM (Sigma M4144)/10% FBS/2% (w/v) $NaHCO_3$/1× glutamine/1× nonessential amino acids/10 mM HEPES/2% (v/v) gentamycin, and incubated at 37° C./5% $CO_2$, inverted, for 5 days. After careful removal of the agarose, cells were stained with 5% crystal violet in 20% ethanol for 10-30 minutes for visualization of plaque size.

Viral growth curve. MARC-145 monolayers in T-75 flasks were inoculated with either parental or recombinant PRRSV diluted in serum-free EMEM at a multiplicity of infection (MOI) of 0.001. After 1 hour attachment at room temperature with gentle mixing, the inocula were removed and the monolayers washed three times with serum-free EMEM. After washing, 4 ml complete medium was added and the flasks were subsequently incubated for up to 5 days at 37° C., 5% $CO_2$. Aliquots (0.5 ml) were harvested immediately after the addition of medium (0 hour time point) and at 24, 48, 72, 96 and 120 hours and stored at −80° C. Serial dilutions of the samples were used to infect fresh MARC-145 cells and the cells then processed as described above. After removal of the agarose, plaques were visualized and counted. Growth curve results were expressed as PFU/ml.

In vivo inoculation of progeny virus. Ten 4-week-old pigs of mixed breed and sex from a PRRSV-seronegative herd were divided into three groups, each consisting of two animals. The first group received $10^{3.5}$ 50% tissue culture infectious dose ($TCID_{50}$) of cloned virus (pVR-V5, third passage on MARC-145 cells) per ml, the second group received $10^{5.4}$ $TCID_{50}$ per ml of the parental virus strain VR-2332 (fourth passage on MARC-145 cells), and the third group was mock inoculated with EMEM. All of the animals received 2 ml of inoculum by intramuscular injection. The animals were kept in separate rooms throughout the experiment and observed daily for clinical signs. All pigs were euthanized on day 28 postinfection. To recover virus, individual serum samples were diluted 5-fold with incomplete EMEM and placed on fresh MARC-145 monolayers for 1 to 2 hours at room temperature with gentle agitation. The inocula were then removed and complete EMEM was added. Infected cells were incubated at 37° C., 5% $CO_2$ and observed daily. Once CPE was evident, infected cell supernatants were frozen at −80° C. until further characterized.

Northern Blot Analysis. pVR-V6G7475A transcripts were transfected into MA104 cells and then passaged onto fresh cells for several passages. For subsequent northern blot analysis, supernatants from passage 1 (P1), P3, P6, P8 and P10 were diluted 1:50 and then used to infect cells (1 ml/T75 flask) on the same day. At the same time, infected swine serum was diluted 10-fold and then used (1 ml) to infect a separate T75 flask. Cytopathic effect was seen on day 3 p.i. for all flasks. Intracellular RNA was extracted using a RNeasy Midi kit (Qiagen) and electrophoresed (15 µg/sample) on a glyoxal denaturing gel as described previously (Nelsen et al., *J. Virol.*, 73:270-80 (1999)). pVR-V6G7475A transcript RNA (100 ng) was run as a control. After RNA transfer to 0.45 micron MagnaGraph Nylon Transfer Membrane (Osmonics), the membrane was probed with labeled oligonucleotide/1a-p222, end labeled with $\gamma$-$^{32}$P-ATP (Amersham) using polynucleotide kinase (Promega) as described previously (Nelsen et al., *J Virol.*, 73:270-80 (1999)).

Nucleic acid sequence analysis of progeny virus. 5'- and 3'-rapid amplification of cDNA ends (RACE) was performed with SMART™ RACE cDNA Amplification Kit (BD Bioscience) or 5' or 3'-Full Race Core Set (TaKaRa Bio Inc) on viral RNA isolated with the QIAmp® Viral RNA Mini Kit (Qiagen). The remaining nucleotide sequence was determined from RT-PCR products of primer pairs developed to cover the entire genome of strain VR-2332 (Table 3), as described previously (Yuan et al., *Virus Res.*, 79:189-200 (2001)). The products were submitted for nucleic acid sequence determination at the Advanced Genetic Analysis Center at the University of Minnesota. Complete viral sequence with at least three fold coverage was initially assembled with the SeqMan suite of the Lasergene® sequence analysis software (DNASTAR, Inc.), and further analyzed using GCG Wisconsin Package Version 10.3 software (Accelrys Inc.). Strain VR-2332 (GenBank Accession U87392) strain Ingelvac® MLV (GenBank Accession AF066183) and cDNA clone pVR-HN (GenBank Accession AY150564; Nielsen et al., *J. Virol.*, 77:3702-3711 (2003)) were used in all nucleotide comparisons to recombinant virus strains.

Results

Modification of pOK12 Vector. pOK12 (GenBank Accession AF223639; Vieira et al., *Gene*, 100:189-194 (1991)), a low copy cloning vector, was modified by digestion with SmaI (enzyme site at 273 bp in pOK12) and SalI (site at 307 bp) and inserting the 244 bp SmaI-SalI fragment of Vector 2.0 (7) containing the hepatitis delta virus (HDV) ribozyme. The vector (pOK12HDV) was then further modified by mutagenesis of an existing KpnI site (p0K12HDV site at 273 bp) to insert a PacI restriction enzyme site through the use of the primer pair 5'-p0K12HDV-257SphIPacI/3'-pOK12HDV-257SphIPacI. The HDV ribozyme was added to provide for effective cleavage precisely at the 3'end of the polyA tract. Studies revealed that the modification was not necessary to obtaining infectious progeny virus.

Construction of full-length cDNA clones. The cloning strategy is depicted in FIG. 2. Four overlapping genome fragments were amplified from purified VR-2332 viral RNA by RT-PCR using the primer pairs indicated (FIG. 2, Table 3). Each fragment was individually cloned into the pCR®2.1-TOPO® vector to generate intermediate clone pCR-SphI-FseI (segment I), pCR-FseI-AvrII (segment II), pCRAvrII-BsrGI (segment III), and pCR-BsrGI-PacI (segment IV). The cDNA clones were then digested with two unique restriction enzymes, as indicated by the clone name. Four fragments were gel-purified and stepwise ligated to vector pOK12HDV-PacI to generate a full-length cDNA clone of PRRSV (pVR-V4). In the full-length cDNA clone, viral genomic sequence was driven by T7 RNA polymerase promoter and followed by polyadenylic acid tail of 50 nucleotides. RNA transcripts of clone pVR-V4 did not display typical PRRSV infectivity when transfected into permissive cells, although viral RNA could be detected over several passages. When compared to strain VR-2332, a total of 45 nucleotide mutations (FIG. 13) leading to 21 amino acid changes were detected (FIG. 14), although several mutations were the same as previously identified in Ingelvac® MLV (Yuan et al., *Virus Res.*, 61:87-98 (1999)).

FIG. 14. Amino acid differences between PRRSV strains and VR-2332 infectious clones. Only positions where nucleotide differences were noted are shown with corresponding amino acid position within the identified genomic region. Amino acids that are represented in strain VR-2332 are shown in unshaded boxes and infectious clone amino acid identities with VR-2332 are represented by blank boxes. Text in each individual box represent silent or amino acid changes due to nucleotide differences shown in Table 2. Light shaded boxes represent nucleotide differences that are unique to the infectious clone, medium shaded boxes highlight those nucleotides that are also seen in Ingelvac® MLV, and boxes that are shaded black indicate swine unique nucleotides. Amino acids separated by slashes indicate ORF2a/ORF2b amino acid numbers. Regions that were not sequenced are indicated by a slash.

Because many mutations in pVR-V4 occurred in the critical region encoding putative helicase, polymerase and other Nidovirus motifs (FIG. 3, FIG. 13), additional clones of genomic segment III (pCR-AvrII-BsrGI) were generated and sequenced in their entirety. After replacing segment III of pVR-V4 with the most sequence accurate fragment obtained, we again determined the nucleotide sequence of the entire genomic full-length clone (pVR-V5). Except for the replaced region and for four spontaneous mutations (nucleotides 1595, 13860, 14336, and 14404), these two genomic clones were identical (FIG. 13). Sequence analysis of pVR-V5 showed that this clone harbored a total of 23 mutations compared to strain VR-2332. Of these 23 changes, only 8 nucleotide mutations coded for a change in amino acid and five of the amino acid residue mutations were identical to Ingelvac® MLV and thus not predicted to adversely effect in vitro replication (FIG. 13).

Clone pVR-V6 was derived from site-directed mutagenesis of genome segment IV to repair nucleotides 13860 and 14979 using primers 13860C2T/and 14979A2G/, respectively. Mutation of these two nucleotides would correct amino acid residue 25 of GP5 (L→F) and residue 31 of the nucleocapsid protein (T→A). Sequence analysis of clone pVR-V6 confirmed that the nucleotides had been corrected back to wild-type (wt) VR-2332 nucleotides and had not resulted in any other nucleotide changes elsewhere in the genome when compared to pVR-V5 (Tables 4 and 5). Finally, site-directed mutagenesis on genome segment III using oligomer 7475G2A was completed on both pVR-V5 and pVR-V6 in order to correct an alteration from wt VR-2332 at nt 7475. The change of G→A at nt 7475 resulted in a glycine (G) at ORF1 amino acid 2429 in the two recombinant clones to the glutamic acid (E) seen in the parental VR-2332 viral strain. The final two clones, pVR-V5G7475A and pVR-V6G7475A were again sequenced in their entirety and found to have only (nt 7475) altered from the original recombinant plasmids pVR-V5 and pVR-V6, respectively (FIG. 14). pVR-V6G7475A thus contains 11 nucleotide and no amino acid changes from strain VR-2332, besides those also seen in Ingelvac® MLV.

Figure 3:
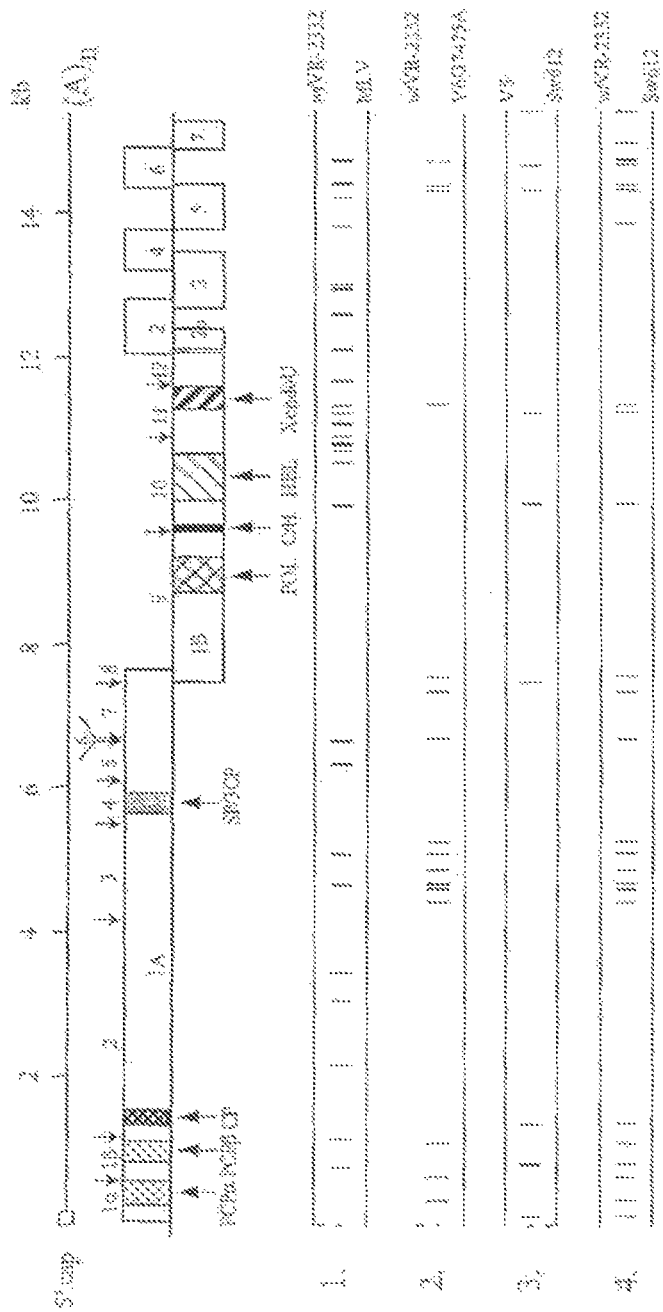

As can be seen schematically in FIG. 3 for the final construct (pVR-V6G7475A), and detailed in Tables 4 and 5, all full-length clones still possess nucleotide changes scattered throughout the genome, primarily in the poorly defined regions of ORF1. However, the large cluster of ORF1b nucleotide changes that presumably prevented pVR-V4 from completing viral replication were repaired in later versions of the full-length genome clones. Only one nucleotide mutation (nt 11329 coding for G3739A mutation) remained in ORF1b of pVR-V5 and later clones, and this mutation does not prevent Ingelvac® MLV from infecting and replicating efficiently in cultured cells. Tables 4 and 5 also display the residue information for the previously published infectious clone, pVR-HN (Nielsen et al., *J. Virol.*, 77:3702-3711 (2003)), shown to replicate in animals. There is a substantial increase in the number of residues in pVR-HN (15 nucleotides) that directly display the sequence of Ingelvac® MLV over the final construct, pVR-V6G7475A (7 nucleotides).

Characterization of recombinant virus. Full-length RNA transcripts of each cDNA clone were produced. MARC-145 cell transfection with the cDNA transcripts or wt VR-2332 viral RNA (vRNA) resulted in CPE, characterized by cell clumping followed by lysis, at 48 to 72 hours post transfection. CPE caused by the recombinant transcripts were delayed and somewhat distinct compared to that induced by wt VR2332 vRNA in which CPE presents as vigorous aggregation, detachment, and disruption. At 96 hours post-transfection, most of the cells transfected with VR-2332 vRNA had undergone lysis and detached from the plate, whereas less severe CPE was apparent in cells transfected with the cloned in vitro derived RNA transcripts.

Virus (P0) was harvested from the transfected cells and an aliquot (10 μl diluted to 1 ml in culture medium) was used to infect MARC-145 cells for progeny virus amplification. After CPE was detected, virus (P1) was again harvested and an aliquot used for reinfection of MARC-145 cells. Recombinant virus in the cell supernatant (P2) was utilized for purification of viral RNA, which was then used to obtain RT-PCR fragments with primer pairs 5'-6800/3'-ORF1b (nt 6796-7614) and P51/05P4 (nt 13757-14341). The PCR fragments obtained were submitted for nucleotide sequence analysis to confirm that the infectivity seen was due to transfected full-length RNA transcripts of the infectious construct and not a result of contamination due to wt virus. Nucleotide mutations at residues 7329, 7475, 7554, and 13860 nucleotide differences were seen in progeny virus from pVR-V5, and 7329, 7554, and 13860 were detected in virus from pVR-V5G7475A. Similarly, mutations at residues 7329, 7475, and 7554 were detected in pVR-V6 progeny and mutations at 7329 and 7554 were detected in virus resulting from pVR-V6G7475A (Tables 4 and 5). Corresponding mutations were not seen in P2 virus from wt vRNA transfections.

Immunofluorescence analysis of recombinant viruses. Direct immunofluorescence assays were used to detect the expression of PRRSV nucleocapsid protein in infected MARC-145 cells. All cells infected by recombinant virus transcripts (P2 and on) as well as vRNA were positive by this method. Massive nucleolar accumulation of the nucleocapsid protein was readily apparent, as previously reported by Rowland et al. (*Virus Res.*, 64:1-12 (1999)).

Figure 4:
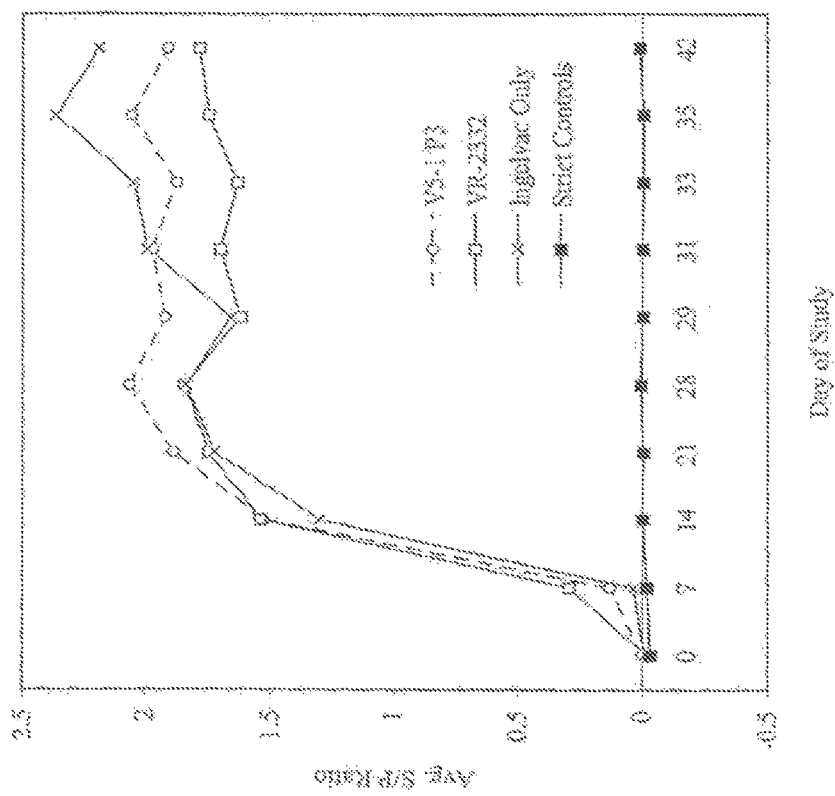

In vivo infection with pVR-V5 derived recombinant virus. Recombinant viruses recovered from P3 of MARC-145 cells transfected with RNA transcripts of cDNA clone pVR-V5 were inoculated into young swine in parallel with wt VR-2332, vaccine virus Ingelvac® MLV and saline (negative control). Blood samples were collected on 0, 3, 5, 7, 14, 21 and 28 days p.i. and analyzed for seroconversion by HerdChek PRRS 2XR ELISA (IDEXX) and for virus recovery. At day 28, all infected animals had seroconverted with approximately the same kinetics, revealing that pVR-V5 recombinant viruses replicated well in vivo (FIG. 4). Clinical signs were absent from all animals during the course of the experiment, but this was not unexpected as wt strain VR-2332 often does not produce overt disease in young swine and results in enlarged lymph nodes only transiently, typically at day 14 p.i.

A serum sample from one animal infected with progeny of pVR-V5 (Sw612), taken at 14 days p.i., was used to infect fresh MARC-145 monolayers for recovery of in vivo passaged recombinant virus. As described previously, the virus derived from in vitro transfection of clone pVR-V5 RNA transcripts caused only minimal CPE (evidenced by aggregation of infected cells) while virus recovered from day 14 serum of the test animal caused typical CPE (cell aggregation, detachment, and disruption) at 96 hours postinfection. This suggested that a shift in viral genotype or phenotype had occurred while pVR-V5 replicated in vivo.

In order to elucidate the reason for the apparent change in phenotype, full-genome sequence analysis was completed on virus recovered from one pig (Sw612) and then passaged once in MARC-145 cells to amplify the Sw612 progeny (FIG. 3, Tables 4 and 5). When compared to the virus used to infect swine, pVR-V5, 17 infectious cDNA clone-specific nucleotide changes were retained in Sw612, some of which are also seen in Ingelvac® MLV (7/17 nucleotides). The two non-viral G residues followed by a T residue present at the 5' end of the original pVR-V5 clone transcript were not seen in the virus derived from in vivo infection. Degeneracy was seen at nucleotide positions 9958 (R), 14336 (Y) and 15411 (Y). The wt VR2332-like nucleotide (G) at position 9958 showed degeneracy with an Ingelvac® MLV-like nucleotide (A). This change results in a mutation of a glycine residue to a glutamic acid residue, respectively (Table 2). At position 14336, degeneracy was detected as an infectious clone-specific base (C) and a wt VR-2332-specific base (T), which reflected a silent mutation. Another mutation (nt 7475) occurred in which a G residue had reverted to the wt residue A. However, there were another 5 nucleotide differences (nt 102, 827, 1379, 14686 and 15411) not seen in any of the other viruses in this study. Nucleotide 102 is located in the leader sequence, thought not be translated. However, if the leader sequence were translated, the encoded ORF (VR-2332 nucleotides 1-100) would be extended by one amino acid residue (W). The mutations at residues 827 and 1379 led to mutations in ORF1a, in both cases resulting in an amino acid change of wt VR-2332 encoded alanine for a Sw612 valine The guanine residue at nt 7475 of pVRV5 had mutated to wt adenine. This resulted in a G3294A non-conservative amino acid mutation, which lies in ORF1a predicted protease cleavage product NSP7 and this genomic region has no defined function to date. Nucleotide 14686, located in ORF6, showed a change from a wt VR-2332 guanine to an alanine in Sw612, which still encodes the amino acid glycine. The other unique nucleotide change occurred at the very 3' end of the viral sequence (nt 15411), before the start of the polyA tail. In this case, a previously conserved thymine residue revealed degeneracy with a cytosine residue. These genetic changes, although informative, did not immediately reveal the cause(s) of the change in growth phenotype observed. However, it did reveal the errant nature of PRRSV replication in vivo and suggests that a moderately different viral genomic sequence from wt VR-2332 was able to replicate efficiently (FIG. 3).

Comparison of viral plaque size. Plaque size determinations of the recombinant viruses as well as wt VR-2332 were completed in parallel on MARC-145 cells at 120 hours p.i. (FIG. 5A). Strain VR-2332 formed plaques that averaged 3 mm in size, while passage 3 progeny of pVR-HN cDNA clone formed slightly smaller plaques (2.5 mm average). In contrast, only pinpoint plaques were obtained from recombinant viruses derived from pVR-V5 and pVR-V6, and these were only readily apparent through microscopic examination (FIG. 5A). Recombinant virus recovered from clones pVRV5G7475A and pVR-V6G7475A formed, on average, 1 5 mm and 2 mm plaques respectively. However, in another assay, the plaques produced by the viral progeny (Sw612) recovered from in vivo infection of VR-FLV5 derived recombinant virus were much larger, approximately equal in both size and number as those derived from wt VR2332 (FIG. 5B).

Only minimal volumes of the cell supernatants containing each recombinant virus remained. Therefore, in order to fully examine the role of nucleotide change in determining plaque size, we transfected fresh RNA transcripts produced from pVR-V5, pVR-V6, pVR-V5G7475A and pVR-V6G7475A into MARC-145 cells (termed second lineage). Passage 3 progeny viruses of each infectious clone at 5 days post-infection were again analyzed for plaque size in comparison to wt VR-2332, VR—HN and Sw612 viruses. In contrast to the previous plaque assay, all plaque sizes appeared similar, with the recombinant viruses obtained from pVR-V5, pVR-V6, pVR-V5G7475A only slightly smaller than the in vivo derived wt VR-2332, Sw612 and pVR-V6G7475A viruses (FIG. 6A). The recombinant viruses, however, were not yet directly mimicking authentic viral infection as shown by the approximately 10-fold lower viral titers when compared to wt VR-2332 or to pVR-V5 recombinant virus that had been passaged through swine (Sw612) (FIG. 6B).

Nucleotide Sequence Analysis of First and Second Lineage Virus Preparations. Limited nucleotide sequence analysis (due to virus stock limitation) of passage 3 pVRV5-derived virus inoculated into swine (V5-1-P3) and complete nucleotide sequence analysis of passage 3 pVR-V5-derived virus obtained above (V5-2-P3) were completed in order to reveal the genetic reason for the plaque size discrepancies. Such analyses revealed that the two independently prepared V5 viruses differed in sequence at the 5' end (FIG. 13). The virus that had produced pinpoint plaques (V5-1-P3) had no extraneous 5'-end nucleotides, as shown in the nucleotide sequence of wt strain VR-2332, while that producing larger plaques (V5-2-P3) possessed 4 non-templated thymidine residues at the 5' terminus (FIG. 13). The remaining V5-1-P3 viral nucleotide sequence we could obtain exactly matched that of V5-2-P3 virus, as well as that of the parental clone. However, complete sequence analysis of V5-2-P3 virus revealed that the virus displayed nucleotide degeneracy at several genomic sites. Similar findings were obtained when analyzing limited regions of second lineage viruses VR-FLV5G7475A-P3 and VR-FLV6G7475A-P3. These last two infectious clone progeny displayed different 5'-termini as well as exhibiting degeneracy in sequence.

Figures 7A, 7B:
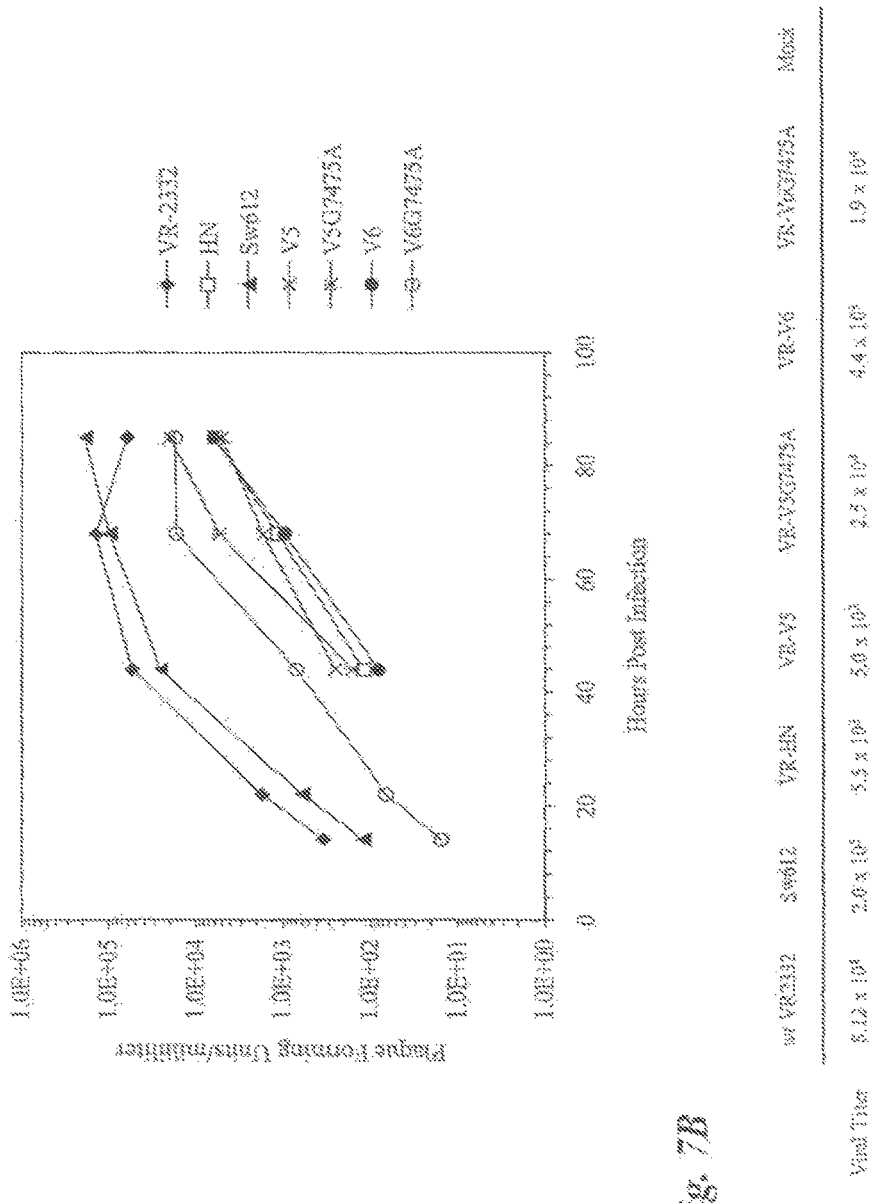
FIG. 7A is a graphical representation of the P3 progeny of wt strain VR-2332 (♦), Sw612 (▲), pVR-HN (□), pVR-V5 (X), pVR-V5G7475A(*), pVR-V6 (●), pVR-V6G7475A (○) were simultaneously examined for one step growth kinetics as outlined in Example 1. wt strain VR-2332 and Sw612 viruses replicated to approximately 10-fold higher titers at all time points. pVR-V6G7475A, with no amino acid changes from native virus or vaccine, produced virus that replicated to a higher titer at all time points than all other infectious clone progeny.
FIG. 7B. Companion table to FIG. 7A, showing the final titer for each virus preparation.

Viral Growth Curves. Simultaneous one-step viral growth curve determinations were completed using MARC-145 cells and passage 3 viruses (second lineage) (FIG. 7A-B). The recombinant viruses recovered from pVR-V5, pVR-V5G7475A, pVR-V6, and pVR-V6G7475A and pVR-HN displayed similar one-step viral growth rates, but their peaks of replication were all significantly lower than wt strain VR-2332 and Sw612, the in vivo progeny of pVR-V5. Also, the replication rates of the recombinant virus preparations derived from pVR-V5, pVR-V6 and pVR-HN were somewhat decreased as compared to the virus derived from pVR-V5G7475A and pVR-V6G7475A. The last two infectious clones code for as little as 13 and 11 nucleotide differences, respectively, resulting in 2 and zero amino acid changes, from wt VR-2332 sequence besides the changes seen in Ingelvac® MLV. These data then reveal that viruses with as little as 11 nucleotide changes from wt VR-2332 and its attenuated offspring Ingelvac® MLV are somehow impaired in replication. Correspondingly, the resultant titers of wt VR-2332 and Sw612 viruses were approximately 6-15 fold higher than that of the recombinant viruses that had not been passaged in swine (FIG. 7A-B).

Figure 8:
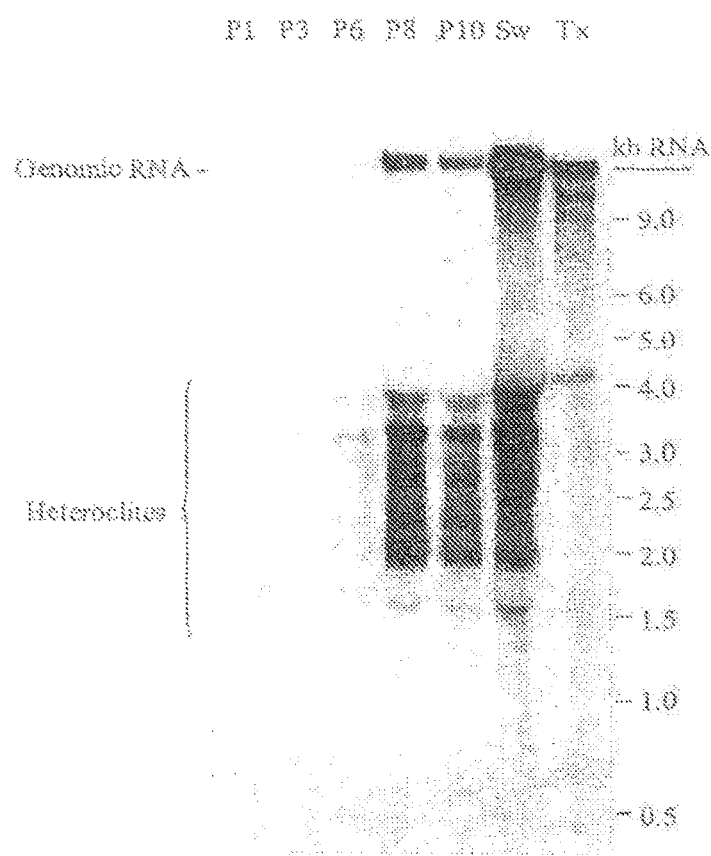
FIG. 8. Northern blot analysis of different progeny passages of pVR-V6G7475A as well as Sw612 and the initial in vitro transcript reveals heteroclites are produced as early as P1 and, along with genomic RNA, are more abundant with passage. However, transcript RNA (Tx) does not contain readily detectable heteroclite species.

Northern analyses of vRNA. PRRSV defective sgRNA species, identified previously as heteroclite subgenomic RNAs (latin: uncommon forms), have been shown to be a constituent of PRRSV infection and cannot be separated from full-length viral genomes by standard methods such as cultured cell passage at low multiplicities of infection or sucrose gradient centrifugation (Yuan et al., *Virology,* 275: 158-169; 30 (2000); Yuan et al., *Virus Res.,* 105:75-87 (2004)). To explore whether or not PRRSV heteroclites are produced during in vitro transcription of full-length cDNA genome clones or appear after subsequent transfection/infection, northern blot analysis was completed. The full-length RNA transcript and passages 1, 3, 6, 8 and 10 of the virus produced from transfected MA-104 cells were used to inoculate flesh T-75 flasks of MA-104 cells with 10 µl supernatant diluted 1:100, as well as Sw612 serum diluted 1:10 (2 ml total/flask). After 4 days, intracellular PRRSV RNA was harvested and 15 µg of each preparation was separated by electrophoresis through a denaturing agarose gel and transferred to a nylon membrane. After RNA cross-linking, the membrane was hybridized with a $^{32}$P-radiolabeled probe complementary to the 5' end of ORF1a that selects for full-length VR-2332 genomes as well as heteroclites (/1a-222; 29). As shown in FIG. 8, the RNA transcript is mostly a single band, migrating as full-length vRNA, while PRRSV RNA species from passage 1 and later migrate as both full-length and subgenomic-sized species previously identified as heteroclites. In addition, the strength of hybridization increases over passage. Since the virus was harvested from an equal volume of infected cell supernatant at the same time point, this observation suggests that the vRNA becomes more efficient at replication over time. Lastly, when comparing virus generated from Sw612 with the cell culture generated virus, the RNA banding pattern is indistinguishable, strongly suggesting that the defective RNA species are readily formed and replicated in vitro as well as in vivo and thus are a natural part of PRRSV infection.

DISCUSSION

In theory, an infectious cDNA clone of a virus should be identical to the parental sequence in order to generate a reverse genetic system that mimics wild-type infection. Considerable effort was exerted to reproduce a fully faithful PRRSV strain VR-2332 genome, yet due to unpredictable spontaneous mutations at several sites, we have not yet been successful at deriving an infectious clone that has no differences from the wt strain VR-2332 sequenced in our laboratory. High fidelity DNA polymerases, used in this study, are available to decrease artificial mutations, but such mutation cannot be avoided during reverse transcription (Malet et al., *J. Virol. Methods,* 109:161-70 (2003)). In addition, the fact that PRRSV exhibits astonishing viral evolution and strain variation (Chang et al., *J. Virol.,* 76:4750-6 (2002); Murtaugh et al., *Adv. Exp. Med. Biol.,* 440:787-94 (1998); Yoon et al., *Adv. Exp. Med. Biol.,* 494:25-30 (2001)) recombines readily at high frequency to result in intergenic recombinants between strains (Yuan et al., *Virus Res.,* 61:87-98 (1999)), undergoes intragenic recombination to form PRRSV subgenomic RNAs and heteroclites (Nelsen et al., *J. Virol.,* 73:270-80 (1999); Yuan et al., *Virology,* 275:158-169 (2000); Yuan et al., *Virus Research,* 105:75-87 (2004)) and often displays nucleotide degeneracy at unpredictable nucleotide sites in field isolates serve to make this initial goal time-consuming and of negligible gain. An infectious DNA construct possessing as little as 11 nucleotide mutations, as compared to strain VR-2332, outside of domains known to be involved in viral replication (5' and 3' ends, ORF1b) was thought sufficient for wt virus production and the downstream goals of infectious clone use for pathogenesis queries and structure:function studies. pVR-HN is more similar to Ingelvac® MLV in the region of the virus encoding the helicase motif (NSP 10). Further pathogenic comparison of these two infectious clones may shed light on the differences between the parental strain, VR-2332, and its vaccine strain offspring, Ingelvac® MLV.

Valuable information can be derived from the construction and evaluation of the infectious clones for PRRSV strain VR-2332. First of all, PRRSV strain VR-2332 cannot tolerate all mutations for survival. Particular nucleotide or amino acid mutations may help or hinder viral replication, and the challenge is to ascertain which are lethal to survival. In clone pVR-V4, which did not produce infectious virions, there were total of forty-two nucleotide differences from wt parental strain VR-2332. In these forty-two nucleotide changes, several nucleotides result in silent mutations (20 residues) or exist in other known PRRSV strains (9 amino acid residue mutations directly mimic Ingelvac® MLV) allowed prediction that these changes may be non-lethal for virus replication. Eleven nucleotide changes leading to 12 amino acid changes and two 3'UTR nucleotide mutations, each not seen in Ingelvac® MLV, were thus predicted to be lethal to PRRSV strain VR-2332. In pVR-V5 and later constructs, 19 changes were corrected, including several silent mutations and 9 aberrant amino acid changes not seen in the genome of Ingelvac® MLV and 8 other changes seen in the vaccine strain. This lead to the first evidence that the constructs were infectious, although in pVR-V5 two amino acid mutations were still present, one of which was altered through site directed mutagenesis to produce pVR-V6. The remaining amino acid change was repaired in pVR-V5G7475A and pVR-V6G7475A, although these clones still harbor silent mutations that are not found in strain VR-2332 and the derived vaccine strain.

Several unique observations were obtained from this study. First of all, each lineage of produced virus may result in a unique 5' terminal sequence that was not detected in wt strain VR-2332. We also cannot yet correlate plaque size with nucleotide sequence. Secondly, we saw unique nucleotide changes after replication in swine, which may reflect the inherent nature of the PRRSV polymerase. All nucleotide changes were transitional in nature and did not exhibit a bias (5 A/G and 4 C/T). Although the G A reversion at nucleotide 7475 was seen after in vivo passage, we could not correlate this site with the subsequent increased plaque size because other non-templated changes had occurred. In addition, full-genome sequence analyses of passage 3 of a V5-derived virus that produced larger plaques (V5-2-P3) revealed a different 5'terminal sequence from the pinpoint plaque-producing V5 virus used to infect swine (V5-1-P3). However, we can conclude that the mutations were not lethal to virus replication because this virus, after passage in swine, produced wt-sized plaques on MARC-145 cells ad grew at almost the same rate as the parental virus (FIGS. 5A, 6 and 7).

Of considerable interest is the fact that sequence analysis of the third in vitro passage of V5, V5G7475A and V6G7475A seemed to suggest that the PRRSV replicase complex allows frequent transitions, and infrequent transversions, to occur while undergoing viral replication. This may reflect a viral replicase that has evolved so that it may generate new genetic forms of a PRRSV genome and then assess their competence amid other variants, resulting in an optimally "fit" virus. These observations have also been noted during PRRSV sequential passage in vivo (Chang et al., *J. Virol.*, 76:4750-63 (2002)). Present sequencing efforts are to examine the full-length genomes of later passages, when a more robust replication is detected. Finally, it is now clear that PRRSV strain VR-2332 replicase readily synthesizes heteroclites at the same time it is producing full-length vRNA. This prototype strain, isolated and characterized in 1992, may be unique in the gradual acquisition of replication fitness, as other investigators producing infectious clones of more recent strain have not observed the same effect (Truong et al., *Virology*, 325:308-319 (2004)). The role of heteroclite formation and the concomitant appearance of vigorous viral replication suggest that there is an advantageous role for heteroclites in PRRSV evolution.

Example 2

Many virulent isolates of a seemingly novel PRRSV were recently identified in the State of Minnesota, USA. ORF5 nucleotide sequence analysis and comparison to the University of Minnesota Veterinary Diagnostic Laboratory PRRSV database (>5000 isolates) revealed that the isolates were of Type 2 lineage, but were significantly different than previous isolates. Furthermore, they were most closely related to those isolates previously seen in Canada in the early 1990s (Mardassi et al., *J. Gen. Virol.*, 75:681-685 (1994)) and in the State of Minnesota in 1998. Restriction fragment length polymorphism (RFLP) analysis of ORF5 also demonstrated that they belonged to the same group of viruses as these early cases, known as 1-8-4 isolates (Wesley et al., *J. Vet. Diagn. Invest.*, 10:140-144 (1998)) and were thus named MN184 isolates. Because of the striking dissimilarity with all but one previously isolated MN PRRSV isolate, two of these new isolates were amplified just one time on porcine alveolar macrophages (PAM), the host cell, and full-length genome analyses was completed on the viruses, designated as MN184A and MN184B. These two isolates were collected at different times from two separate farms.

Materials and Methods

To sequence the MN184 isolates, viral RNA (vRNA) was extracted from PRRSV infected cell supernatant with QIAmp® Viral RNA Mini Kit (Qiagen, Valencia, Calif.)) and RT-PCR was performed (Qiagen® OneStep RT-PCR Kit). Primers (available on request) were designed based on the published sequences of different strains of PRRSV deposited in GenBank as well as newly generated MN184 sequence. The 5' nucleotide sequence of the two PRRSV isolates was derived using the 5'-Full RACE Core Kit (TaKaRa Bio, Madison, Wis.). 3'-RACE was performed with SMART™ RACE cDNA Amplification Kit (Clontech, Mountain View, Calif.). RT-PCR products were gel purified (QIAquick®, Qiagen), cloned into the pGEM-T Vector (Promega, Madison, Wis.) and 3 to 5 clones for each RT-PCR product were chosen for sequencing. The nucleotide sequence determination was completed in both directions with the PCR specific primers or the vector encoded SP6 and T7 promoter primers. The products were submitted to the Advanced Genetic Analysis Center at the University of Minnesota for sequence determination with an ABI 377 automated DNA fragment analyzer. A quality sequence representing at least three-fold genome coverage was obtained. Sequence data was assembled and analyzed by using the GeneTool sequence analysis program (BioTools Inc., Edmonton, Alberta Calif.) and Lasergene (DNASTAR, Madison, Wis.).

Multiple sequence alignments were generated with CLUSTALX (Thompson et al., *Nucleic Acids Res.*, 24:4876-4882 (1997)) or Wisconsin Package Version 10.3 (Accelrys Inc., San Diego, Calif.). Full-length PRRSV sequences were aligned using ClustalX (version 1.83.1; IUB DNA weight matrix, gap penalty 15.00, gap length penalty 6.66). The resulting alignment was further analyzed using the Wisconsin Package Version 10.3 Distances Program (Jukes-Cantor distance method, partial matches due to degenerate symbols considered). For FIG. 10, sequences were aligned with the Pileup program of the Wisconsin Package (Blosum62 Scoring Matrix, Gap Weight=8, Length Weight=2, Weighted Ends). The alignment was scored for redundancy and colored for percent identity using Jalview (Clamp et al., *Bioinformatics*, 12:426-427 (2004)) and then transferred to Adobe Photoshop® CS, version 8.0, for grayscale transformation. For FIG. 11, sequences were aligned with the Pileup program of the Wisconsin Package (Blosum62 Scoring Matrix, Gap Weight=8, Length Weight=2, Weighted Ends). For FIG. 12, a signal peptide was predicted using the SignalP server (Bendtsen et al., *J. Mol. Biol.*, 340:783-795 (2004)). Transmembrane regions were derived by PHDhtm (Rost et al., *Protein Sci.*, 5:1704-1718 (1996)) and potential N-glycosylation sites were identified by PROSITE (Bairoch et al., *Nucleic Acids Res.*, 25:217-221 (1997)) using the PredictProtein server (Rost et al., *Nucleic Acids Res.*, 32:W321-W326 (2003)). Sequences were aligned with the Pileup program of the Wisconsin Package (Blosum62 Scoring Matrix, Gap Weight=8, Length Weight=2, Weighted Ends).

Results

Genomic alignment demonstrated that these two PRRSV were quite distinct (>14.5% nucleotide dissimilarity) from other North American Type 2 full-length sequenced genomes, yet comparison with Type 1 (European) full-length sequences confirmed that the isolates were solely of Type 2 genotype origin as they were only approximately 59% similar at the nucleotide level to both EuroPRRSV and Lelystad strains. Strikingly, these Type 2 MN184 isolates represented the shortest PRRSV genomes detected to date (15019 nucleotides, not including the poly A tail). In addition, no specific area was discerned that suggested that these isolates were derived from viral recombination between Type 1 and Type 2 strains.

Figure 9A:
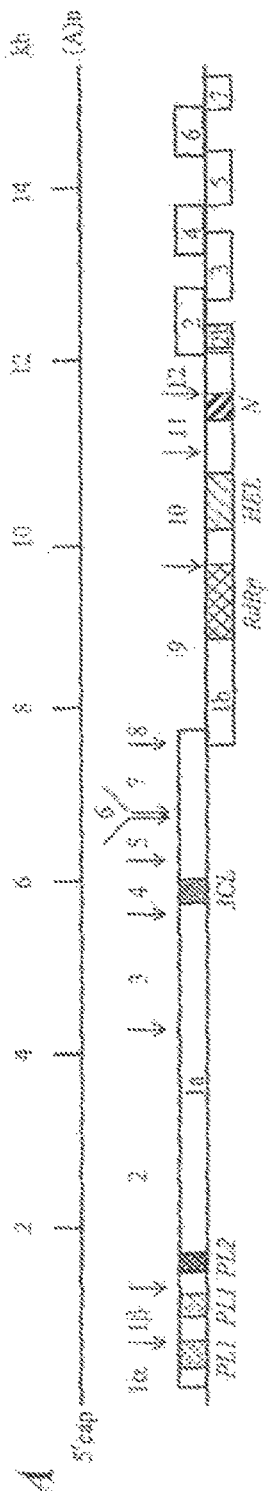
FIG. 9A. Diagrammatic representation of the PRRSV genome. Putative nonstructural protein cleavages are depicted above ORF1a and 1b, represented by downward arrows. Signature motifs are identified below ORF1a and 1b, indicating their placement in the PRRSV genome [papain-like cysteine protease α and β (PL1); cysteine protease (PL2); serine/3C protease (3CL); polymerase (RdRp); helicase (Hel); *Xenopus laevis* homolog poly(U)-specific endoribonuclease (N); Ziebuhr et al., 2000; Ivanov et al., 2004; Gorbalenya et al., 2006].
Figure 9B:
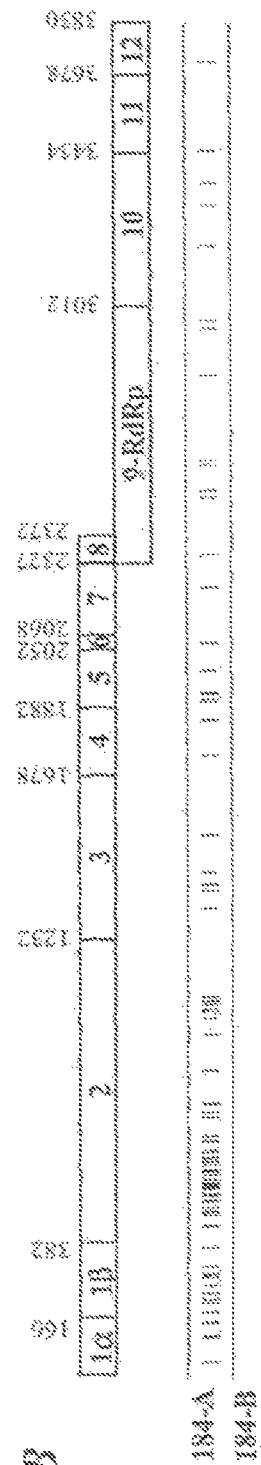
FIG. 9B. Schematic diagram of the comparison of ORF1 protein (replicase) of MN184A and MN184B and putative processing. The degeneracy seen in nsp2 is included in the comparison.
Figure 9C:
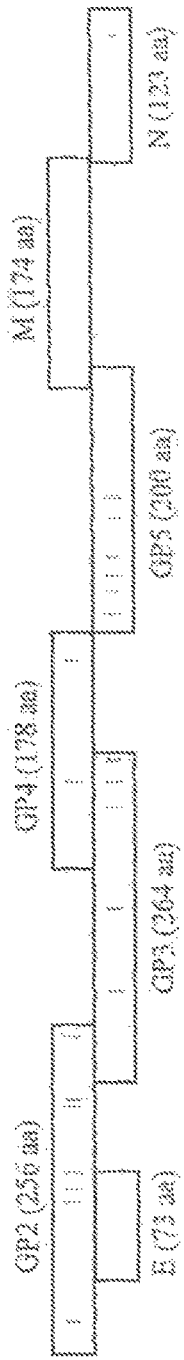
FIG. 9C. Schematic diagram of the comparison of ORF2-7 proteins of MN184A and MN184B.

Full-length sequence analysis revealed that the two MN184 isolates were actually genetically distinct. They shared 98.0% nucleotide similarity or 2% difference. This percentage of dissimilarity was unexpected due to their sudden simultaneous appearance in Minnesota, with no clear recent related isolate seen in our PRRSV database at that time. Table 6 presents the detailed nucleotide and amino acid comparison between the two isolates and FIG. 9 depicts the amino acid differences seen between these two strains. Both of these isolates possessed nucleotide degeneracy in several regions of the genome, predominantly in the predicted nsp2 region of ORF1 (Table 6). The fact that nucleotide degeneracy was seen in these isolates suggested that PRRSV can be made up of several individual species, often referred to as a swarm of related but distinct viral sequences, within infected animals.

TABLE 6

Detailed analysis of individual PRRSV genomic regions and translated proteins, and number of degenerate bases detected in each region. Degeneracy is defined as more than one nucleotide detected for a particular base on separate trace files of three or more trace files.

| Region | Bases | Nucleotide length | % Nucleotide Similarity | % Nucleotide Identity | Number of Degenerate Bases (184A/184B) | Amino Acid Length | % Amino Acid Similarity | % Amino Acid Identity |
|---|---|---|---|---|---|---|---|---|
| 5' UTR | 1-190 | 190 | 99.5 | 98.9 | 1/0 | — | — | — |
| ORF1A | 191-7309 | 7119 | 98.5 | 96.7 | 16/109 | 2372 | 96.8 | 96.5 |
| NSP1a | 191-688 | 498 | 98.8 | 98.5 | 1/0 | 166 | 97.6 | 97.6 |
| NSP1b | 689-1339 | 651 | 98.3 | 97.5 | 2/3 | 217 | 97.2 | 95.9 |
| NSP2 | 1340-3886 | 2547 | 98.0 | 94.6 | 10/76 | 849 | 94.2 | 94.2 |
| NSP3 | 3887-5224 | 1338 | 98.7 | 98.7 | 0/0 | 446 | 99.3 | 98.9 |
| NSP4 | 5225-5836 | 612 | 98.5 | 96.4 | 0/13 | 204 | 97.1 | 97.1 |
| NSP5 | 5837-6346 | 510 | 99.2 | 95.3 | 3/17 | 170 | 97.1 | 97.1 |
| NSP6 | 6347-6394 | 48 | 100.0 | 100.0 | 0/0 | 16 | 100 | 100 |
| NSP7 | 6395-7171 | 777 | 99.3 | 99.3 | 0/0 | 259 | 99.6 | 99.2 |
| NSP8 | 7172-7309 | 138 | 99.3 | 99.3 | 0/0 | 46 | 97.6 | 97.6 |
| ORF1B | 7306-11679 | 4374 | 99.2 | 98.9 | 5/4 | 1457 | 99.5 | 99.2 |
| NSP9 | 7288-9225 | 1938 | 98.9 | 98.8 | 1/1 | 646 | 99.4 | 98.9 |
| NSP10 | 9226-10548 | 1323 | 99.3 | 98.9 | 3/3 | 441 | 99.8 | 99.3 |
| NSP11 | 10549-11217 | 669 | 99.3 | 99.3 | 0/0 | 223 | 99.5 | 99.5 |
| NSP12 | 11218-11679 | 462 | 99.6 | 99.4 | 1/0 | 153 | 99.3 | 99.3 |
| ORF2a/GP2 | 11681-12451 | 771 | 99.0 | 98.3 | 1/0 | 222 | 98.0 | 97.3 |
| ORF2b/E | 11686-11907 | 222 | 99.6 | 99.6 | 0/0 | 73 | 100 | 100 |
| ORF3/GP3 | 12304-13068 | 765 | 98.6 | 98.6 | 0/0 | 254 | 97.6 | 97.6 |
| ORF4/GP4 | 12849-13385 | 537 | 98.5 | 98.5 | 0/0 | 178 | 98.9 | 98.9 |
| ORF5/GP5 | 13396-13998 | 603 | 97.8 | 97.7 | 1/0 | 200 | 96.5 | 96.5 |
| ORF6/M | 13983-14507 | 525 | 99.6 | 97.4 | 0/0 | 174 | 100 | 100 |
| ORF7/N | 14497-14868 | 372 | 98.9 | 98.9 | 0/0 | 123 | 97.6 | 97.6 |
| 3' UTR | 14869-15019 | 151 | 100 | 98.0 | 1/1 | — | — | — |

In order to more closely pinpoint the individual regions of these MN184 isolates that showed the most dissimilarity from other PRRSV strains and to assign the region(s) accounting for the difference in Type 2 viral genome length, these two isolates were compared to the sequence of the prototype Type 2 strain VR-2332. The differences between the two isolates could again be discerned, with isolate MN184B possessing slightly increased similarity to strain VR-2332 than isolate MN184A. The nucleotide and amino acid comparisons to VR-2332 showed individual MN184 isolate regions varied from 81.5-94.7% and 78.4-100%, respectively, but the regions corresponding to ORF5 (86.4-86.7% and 87.0-87.5%, respectively) predicted nsp1β3 (83.8-84.0% and 84.8-85.4%, respectively, and nsp2 (81.5-85.5% and 78.4-79.5%, respectively) were the most variable. Most interesting was that only the predicted nsp2 genomic region showed a difference in nucleotide length and that both MN184 isolates possessed the same nsp2 deletion, detailed below. The comparison also revealed that the 5' and 3' UTR's were the most conserved regions of the genome (94.7% and 94.0%, respectively), indicating sequence conservation in important regions for viral replication and transcription.

Figure 10:
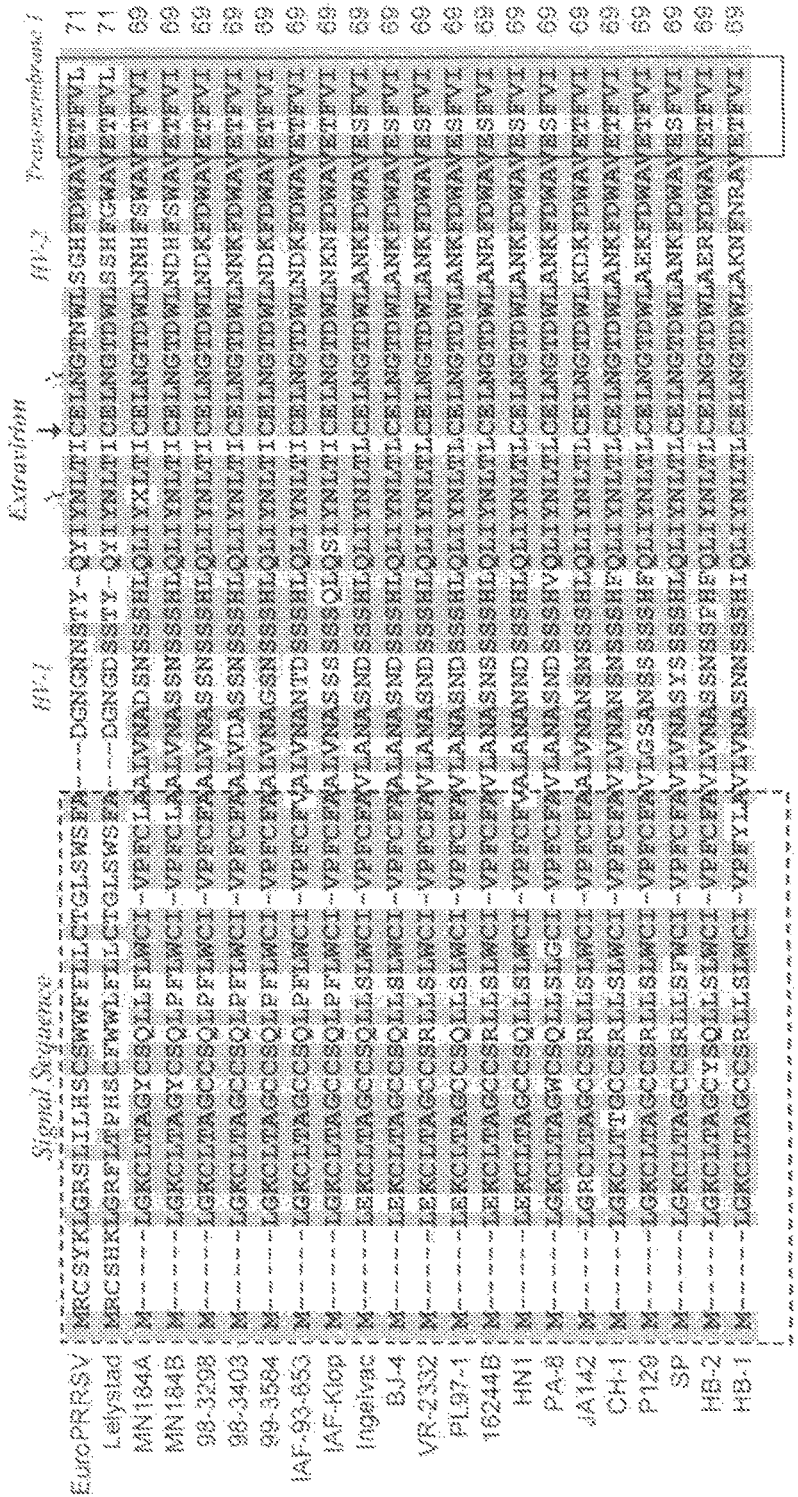
FIG. 10. ORF5 amino acid sequence alignment of divergent PRRSV. Dark grey boxes indicate high amino acid conservation (>80%; between 16 and 19 residues are identical), medium grey (>60%; between 12 and 15 residues are identical), lighter grey (>40%; between 8 and 11 residues are identical) and unshaded (<40%; less than 8 residues are identical) boxes identify less conserved residues. The dashed region indicates the putative signal sequence, the boxed regions identify the proposed transmembrane regions, the hypervariable regions are indicated (HV-1 and HV-2), and the proposed orientation of the protein in the virion is identified in bold italics. The conserved cysteine residue that is proposed to interact with the M protein is identified by the downward arrow (↓). The two conserved putative N-glycosylation sites are identified by stars and hypervariable region 1 contains strain/isolate specific N-glycosylation sites (NxS/T). ORF5 amino acid sequences from the following GenBank full-length sequences were used for comparison: VR-2332 (U87392) (SEQ ID NO: 45), Ingelvac MLV (AF066183) (SEQ ID NO: 43), PL97-1 (A Y58524) (SEQ ID NO: 46), PA-8 (AF176348) (SEQ ID NO: 49), SP (AF184212) (SEQ ID NO: 53), BJ-4 (AF331831) (SEQ ID NO: 44), HN1 (AY457635) (SEQ ID NO: 48), 16244B (AF046869) (SEQ ID NO: 47), HB-1 (AY150312) (SEQ ID NO: 55), HB-2 (AY262352) (SEQ ID NO: 54), CH-1a (AY032626) (SEQ ID NO: 51), P129 (AF494042) (SEQ ID NO: 52), JA142 (AY424271) (SEQ ID NO: 50), EuroPRRSV (AY366525) (SEQ ID NO: 34), Lelystad (M96262) (SEQ ID NO: 35), IAF-93-653 (U64931) (SEQ ID NO: 41), IAF-Klop (AY184209) (SEQ ID NO: 42), 98-3298 (DQ306877) (SEQ ID NO: 38), 98-3403 (DQ306878) (SEQ ID NO: 39), 99-3584 (DQ306879) (SEQ ID NO: 40), MN184A (SEQ ID NO:36), MN184B (SEQ ID NO:37).

ORF5 encodes a heterogeneous PRRSV structural protein (GP5) and is often used for PRRSV diagnostic identification (Kapur et al., *J. Gen. Virol.*, 77:1271-1276 (1996)). GP5 is a predicted three transmembrane protein with an endodomain and ectodomain. The 30 amino acid ectodomain is composed of a short highly conserved domain usually containing at least two N-glycosylation sites bounded by two hypervariable regions. The highly conserved domain of this 30 amino acid region has been shown to code for the viral attachment epitope in Type 2 strains (Plagemann, *Virology*, 290:11-20 (2001); Ostrowski et al., *J. Virol.*, 76:4241-4250 (2002); Plagemann et al., *Arch. Virol.*, 147: 2327-2347 (2002)). GP5 of the same set of full-length genomes, as well as the original RFLP184 isolates identified in Canada (IAF-93-653, IAF-Klop) and in 1998-1999 in Minnesota (98-3298, 98-3403, 99-3584) were aligned (FIG. 10). The alignment of PRRSV GP5 revealed amino acid identities ranging from 82.5% to 87.7% between the new MN184 isolates and other non-RFLP184 Type 2 strains. Interestingly, the amino acid differences between the new MN184 isolates and the older RFLP184 isolates were quite large (5.7%-12.2%) and thus we detected no clear origin of the new RFLP 184 virus. The limited alignment shows that most of the amino acid differences observed were found in the hypervariable regions (FIG. 10). The two conserved N-glycosylation sites were maintained in the MN184 isolates, except for detected nucleotide degeneracy coding for amino acid 44 in isolate MN184B.

Figure 11:
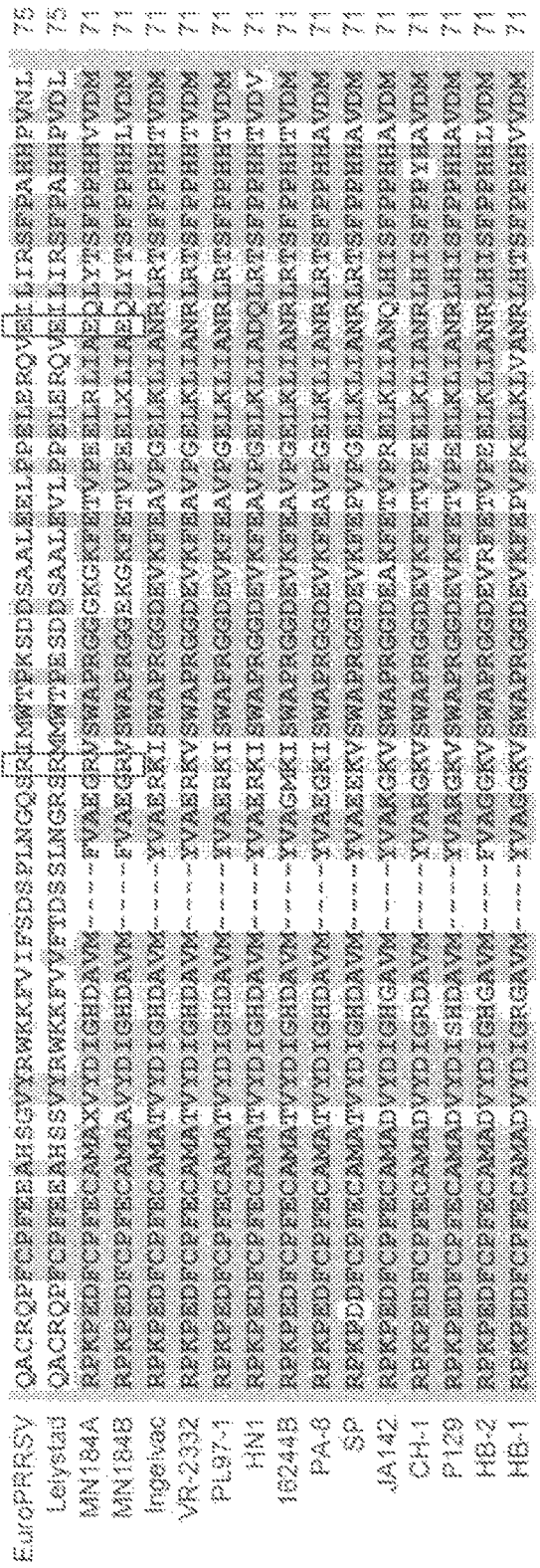
FIG. 11. Nsp1β amino acid sequence alignment of divergent PRRSV. The figure derivation and color scheme was described in the FIG. 10 legend. The two completely conserved putative catalytic residues are identified by stars and the boxed amino acids identify MN184 sequence conservation with Type 1 isolates and EAV. The proposed cleavage site is identified by the downward arrow (↓). The following sequences were used for comparison: VR-2332 (SEQ ID NO: 61), Ingelvac MLV (SEQ ID NO: 60), PL97-1 (SEQ ID NO: 62), PA-8 (SEQ ID NO: 65), SP (SEQ ID NO: 66), HN1 (SEQ ID NO: 63), 16244B (SEQ ID NO: 64), HB-1 (SEQ ID NO: 71), HB-2 (SEQ ID NO: 70), CH-1a (SEQ ID NO: 68), P129 (SEQ ID NO: 69), JA142 (SEQ ID NO: 67), EuroPRRSV (SEQ ID NO: 56), Lelystad (SEQ ID NO: 57), MN184A (SEQ ID NO:58), MN184B (SEQ ID NO:59).

Nsp1β encodes a papain-like cysteine protease (den Boon et al., *J Virol.*, 69:4500-4505 (1995)). An amino acid alignment of the MN184 isolates with a non-redundant set of available Type 2 nsp1β (3 sequences as well as Type 1 strains EuroPRRSV and Lelystad was completed (FIG. 11). The nsp1β protein possesses a number of completely conserved amino acids, and the proposed catalytic residues were maintained in all sequenced genomes (den Boon et al., *J. Virol.*, 69:4500-4505 (1995)). The alignment, ordered by amino acid similarity, indicates that the MN184 isolates are more similar to Type 1 strains than the other sequenced full-length Type 2 sequences. In particular, five amino acids (boxed in FIG. 11) directly mimic the Type 1 strains However, the amino acids that were conserved in the other non-redundant Type 2 sequences were also mostly conserved in the MN184 isolates, but scattered amino acids and the amino acid similarity (84.8-85.4%) revealed a more divergent Type 2 protein than had been evidenced to date.

Thus, the alignment further defines maintained residues of nsp113 that may be critical to the replication cycle of PRRSV.

An amino acid alignment of non-redundant sequences of nsp2, ordered by pairwise identity, is shown in FIG. 12. A highly conserved chymotrypsin-like cysteine protease (PL2) domain is present at the N-terminus, previously predicted by alignment with equine arteritis virus (EAV) nsp2 (Snijder et al., *J. Gen. Virol.*, 79:961979 (1998); Ziebuhr et al., *J Gen. Virol.*, 81:853-879 (2000)). There are 3-4 predicted transmembrane domains near the C terminus of this protein (McGuffin et al., *Bioinforinatics*, 16:404-405 (2000)), but the exact C terminal cleavage site has not been empirically determined. Two predictions of the C-terminal cleavage site have been proposed, one GIG at VR-2332 nsp2 amino acid 980 (Allende et al., *J. Gen. Virol.*, 80:307-315 (1999)) and the other at amino acid 1197 (Ziebuhr et al., *J. Gen. Virol.*, 81:853-879 (2000)), but there are several completely conserved GIG doublets within this protein (VR-23332 nsp2 amino acids 646, 980, 1116, 1196, 1197; downward arrows in FIG. 12). Prior work had also shown that the predicted nsp2 protein is proline rich and contains multiple potential B-cell epitopes (Oleksiewicz et al., *J. Virol.*, 75:3277-3290 (2001); Fang et al., *Virus Res.*, 100:229-235 (2004); Ropp et al., *J. Virol.*, 78:3684-3703 (2004)). The large middle region of PRRSV nsp2 (VR-2332 nsp2 amino acids 148-880) has no assigned function but is highly variable in length. Furthermore, the length difference between sequenced Type 1 and Type 2 strains of PRRSV has been mapped to this variable middle region of nsp2 (FIG. 12). Until now, sequenced Type 1 genomes have been shown to be 313-364 bases shorter than most Type 2 PRRSV (Meulenberg et al., *Virology*, 192:62-72 (1993); Fang et al., *Virus Res.*, 100:229-235 (2004), Ropp et al., *J. Virol.*, 78:3684-3703 (2004)). However, the multiple sequence alignment established that the MN184 genome contains the shortest predicted nsp2 to date (2547 bp), 393 bp shorter than prototype Type 2 strain VR-2332. Furthermore, it contained three discontinuous deletions in the translated protein with deletion sizes consisting of 111, 1 and 19 amino acids, respectively, corresponding to the amino acid positions in PRRSV strain VR-2332 nsp2 of 324-434, 486 and 505-523, respectively (FIG. 12). The three deletions resulted in the loss of several proline residues and predicted B-cell epitopes. Besides these deletions, significant alterations in nsp2 amino acid sequence from other Type 2 strains were also seen, sometimes corresponding to the Type 1 amino acid seen at the same relative position (FIG. 12). Comparison of the nsp2 predicted protein of the two PRRSV genotypes demonstrated that the amino acid identity within Type 2 viruses ranged from 66% to 99% and from 88-90% within Type 1 viruses, but differed greatly between genotypes (<45% similarity). In particular, the MN184 isolates displayed 66-80% amino acid identity to all Type 2 nsp2 predicted proteins and only 43-45% identity to Type 1 strains. When surveying the multiple sequence alignment in FIG. 12, we also noted that all instances of insertion or deletion in both genotypes occurred in this hypervariable middle region. To this point, Shen et al. (*Arch. Virol.*, 145:871-883 (2000)) first reported that PRRSV North American Type 2 strain SP has a unique insertion of 36 aa relative to the position between aa 813 and 814 of PRRSV VR-2332 nsp2. Another investigator found a unique 12 aa deletion at position 466-477 in PRRSV isolate HB-2(sh)/2002 nsp2 (Gao et al., *Arch. Virol.*, 149:1341-1351 (2004)). A 17 aa deletion occurred in newly identified European-like PRRSV isolates when compared to strain LV (Fang et al., *Virus Res.*, 100; 229-235 (2004); Ropp et al., *J Virol.*, 78:3684-3703 (2004)). The instances of mutation did not consistently occur along the same stretch of amino acids, although the deletions seen between the MN184 isolates and other Type 2 viruses encompass most of the largest deletion detected between Type 1 and other Type 2 PRRSV. All of these data suggested that the nsp2 ORF contains a conserved protease motif and predicted transmembrane spanning regions that may be necessary for replication of PRRSV, but is highly susceptible to mutation in the large middle section.

The sudden appearance of field isolates of PRRSV in Minnesota reflecting the 184 RFLP pattern is still a mystery, but the consequences of this event are even now being realized. The Minnesota Veterinary Diagnostic Laboratory now performs routine sequencing on similar 184 RFLP isolates from approximately one fourth of the total number of ORF5 sequence requests. In addition, the 184 RFLP pattern has now been detected not only in Minnesota, but in Iowa, Wisconsin, South Dakota, Kansas, Missouri, Illinois, Nebraska, Kentucky, Oklahoma and Wyoming as well. We chose to derive the full-length sequences from two isolates because of the need to understand if this could be more than a single virus type and the fact that the swine herd diagnosed with isolate MN184A presented with a milder case of PRRS than the herd infected with isolate MN184B, as reported by the attending pathologist. The strains have not been inoculated into naive animals to verify the case presentations, but it is interesting to note that isolate MN184B had many more nucleotide degeneracies detected when analyzing the genome and this might reflect the severity of the disease reported.

This genome analysis increased our understanding of the immense nucleotide and amino acid sequence variation that exists in the field. Factors driving this variation may be related to the way swine are now managed, the interstate and international transport of swine and boar semen, the intermixing of different PRRSV isolates within herds and the nature of the virus itself. Full genome sequence generation also allows us to monitor where on the genome variation is tolerated and which regions are more conserved. As a result of this study, as well as a previous publication (Ropp et al., *J. Virol.*, 78:3684-3703 (2004)), a picture is emerging that indicates nsp2, nsp1β and ORF5 are extraordinarily versatile proteins.

This study has also provided clear evidence that nsp2 size can no longer be used to differentiate between the two PRRSV genotypes. The novel finding that nsp2 evolved to display a Type 2 genome with three discontinuous deletions, leading to the shortest genome to date (15,019 kb), suggests that PRRSV may be evolving to eliminate dispensable genomic regions and make the genome more compact. Finally, although the significance of genetic variations in PRRSV can only be surmised at present, the evolutionary change seen in ORF5, nsp1β and nsp2 should reasonably be related to the biological fitness of PRRSV during selection pressure.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated polynucleotide comprising a sequence having at least 88% identity to SEQ ID NO: 5, wherein the polynucleotide contains at least one deletion each of at least 57 consecutive nucleotides in a region corresponding to nucleotide 2061 to nucleotide 3864, and wherein the polynucleotide further comprises an exogenous polynucleotide present in the deletion.

2. An isolated polynucleotide comprising a sequence having at least 88% identity to SEQ ID NO: 6, wherein the polynucleotide contains at least one deletion each of at least 57 consecutive nucleotides in a region corresponding to nucleotide 2061 to nucleotide 3864, and wherein the polynucleotide further comprises an exogenous polynucleotide present in the deletion.

3. The isolated polynucleotide of claim 1, wherein the polynucleotide replicates and produces infectious virus particles when introduced into a cell.

4. The isolated infectious polynucleotide of claim 2, wherein the polynucleotide replicates and produces infectious virus particles when introduced into a cell.

5. The isolated polynucleotide of claim 1, wherein the exogenous polynucleotide encodes a detectable marker.

6. The isolated polynucleotide of claim 2, wherein the exogenous polynucleotide encodes a detectable marker.

7. The isolated polynucleotide of claim 1, further comprising two or more at least 57 consecutive nucleotide deletions in a region corresponding to nucleotide 2061 to nucleotide 3864.

8. The isolated polynucleotide of claim 2, further comprising two or more at least 57 consecutive nucleotide deletions in a region corresponding to nucleotide 2061 to nucleotide 3864.

* * * * *

SEQUENCE LISTING

```
<160> NUMBER OF SEQ ID NOS: 90

<210> SEQ ID NO 1
<211> LENGTH: 15419
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 1
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta ccccaatgc cagggtgttt      240 atggcggagg gccaagtcta ctgcacacga tgcctcagtg cacggtctct ccttccctg      300 aacctccagg tttctgagct cggggtgcta ggcctattct acaggcccga agagccactc     360
cggtggacgt tgccacgtgc attccccact gttgagtgct ccccgccgg ggcctgctgg      420 ctttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtacccca ttgttggacc tgtccctgga     600
gtggccgttt tcgccaattc cctacatgtg agtgataaac ccttcccggg agcaactcac     660
gtgttgacca acctgccgct cccgcagaga cccaagcctg aagacttttg cccctttgag     720
tgtgctatgg ctactgtcta tgacattggt catgacgccg tcatgtatgt ggccgaaagg     780
aaagtctcct gggcccctcg tggcgggat gaagtgaaat ttgaagctgt ccccggggag     840
ttgaagttga ttgcgaaccg gctccgcacc tccttcccgc cccaccacac agtggacatg     900
tctaagttcg ccttcacagc ccctgggtgt ggtgtttcta tgcgggtcga acgccaacac     960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt tgaggacct cctcagaata    1260 agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaaccggg aggccaagga gcacgaggtt    1440
gccggcgcca acaaggctga gcacctcaaa cactactccc cgcctgccga agggaattgt    1500
```

```
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgaccctgg gatgtcccct     1740 tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca agttggaaaa ggttgttcga gaagaatatg gctcatgcc aaccgagcct     2460 ggtccacggc ccacactgcc acgcgggctc gacgaactca agaccagat ggaggaggac     2520 ttgctgaaac tggctaacgc ccagacgact tcggacatga tggcctgggc agtcgagcag    2580
gttgacctaa aaacttgggt caagaactac ccgcggtgga caccaccacc cctccgcca    2640 aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttg atctcccgac cccacctgag     2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggcgtt    3120 ctggagtag aggggcatga agctgaggaa accctgagtg aaatctcgga catgtcgggt     3180
aacattaaac ctgcgtccgt gtcatcaagc agctccttgt ccagcgtgag aatcacacgc    3240
ccaaaatact cagctcaagc catcatcgac tcgggcgggc cctgcagtgg catctccaa    3300 gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg     3720 cggaggcctg acgagagcac atcagctccg tccgcaggca caggtggcgc cggctctttt    3780
accgatttgc cgccttcaga tggcgcggat gcggacgggg ggggccgtt tcggacggta     3840
```

```
aaaagaaaag ctgaaaggct cttttgaccaa ctgagccgtc aggttttga cctcgtctcc    3900
catctccctg ttttcttctc acgccttttc taccctggcg gtggttattc tccgggtgat    3960
tggggttttg cagcttttac tctattgtgc ctcttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tcctttcaca    4440
cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgatttt gtttccatcg gaggcatggc tcataggttg    5220
agctgtaagg ctgacatgct gtgtgtcttg cttgcaattg ccagctatgt ttgggtacct    5280
cttacctggt tgctttgtgt gtttccttgc tggttgcgct ttttctctt gcaccccctc    5340
accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460
accccctacg acattcatca ttacaccagt ggccccgcg gtgttgccgc cttggctacc    5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc    5940
gccttctgct tcaccgcatg tggcgattcc ggtccccag tgatcaccga ggccggtgag    6000
cttgtcggcg ttcacacggg atcgaataaa caagggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atcttgtgc cttgcttgct gccaaacctg aactggaagg aggcctctcc    6240
```

```
accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact ttgccgaggg aaagttgagg aaggggtgt cgcaatcctg cggaatgaat     6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt tgctgatac cgtggcacct     7020 caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc ccaacgcttg gggggatgag    7260
gaccgtttga ataagaagaa gaggcgcagg atggaagccc tcggcatcta tgttatgggc    7320
gggaaaaaat accagaaatt ttgggacaag aattccggtg atgtgtttta tgaggaggtc    7380
cataataaca cagatgagtg ggagtgtctc agagttggcg accctgccga ctttgaccct    7440
gagaagggaa ctctgtgtgg acatgtcacc attgaaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga aacagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaagagg    8040 aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gcccctaaaca gctgacagag cacggctgcg    8400
aagatgccgc actgaaagac ctctctaaat atgacttgtc cacccaaggc tttgtttac     8460 ctggagttct tcgccttgtg cggaaatacc tgttgccca tgtaggtaag tgcccacccg    8520
ttcatcggcc ttctacttac cctgctaaga attctatggc tggaataaat gggaacaggt    8580
```

```
tcccaaccaa ggacattcag agcgtccctg aaatcgacgt tctgtgcgca caggctgtgc    8640
gagaaaactg gcaaactgtc acccttgta  ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat  ggccttctgt tcttacaaga ccagctaaag tttgaggaca    9180
tgctcaaggt tcaacccctg atcgtctatt cggacgacct cgtgctgtat gccgagtctc    9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag  acgaggtgct ggaacaagtc ccgtataagc    9840
ccccacggac cgttatcatg catgtggagc agggtctcac ccccttgat  ccaggtagat    9900
accaaaactcg ccgcggatta gtctctgtca ggcgtggaat taggggaaat gaagttggac    9960
taccagacgg tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc cctcccgca  ccggtccgtg ggttcgcatc ctagccggcg   10260
gttggtgtcc tggcaagaat tccttcctag atgaagcagc gtattgcaat caccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taagattca  ctcaacaggc   10680
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgtttgtaga tctctccgcg   10920
ccatttgtgc tgatctagaa gggtcgagct ctccgctccc caaggtcgca cacaacttgg   10980
```

```
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggct gacctcgcgg   11760 tcaccccta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttattttc ccccgggccc tgtcattgaa ccaactttag   12060
gcctgaattg aaatgaaatg gggtccatgc aaagcctttt tgacaaaatt ggccaacttt   12120
ttgtggatgc tttcacggag ttcttggtgt ccattgttga tatcattata tttttggcca   12180
ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tccttgggg   12360 atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta aatatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact ctttttgttg tgctgtggtt gcgggttcca   12780
atactacgta ctgtttttgg tttccgctgg ttaggggcaa ttttctttc gaactcacag   12840 tgaattacac ggtgtgtcca ccttgcctca cccggcaagc agccacagag atctacgaac   12900
ccggtaggtc tctttggtgc aggatagggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
accaacatca gtcgacggc ggcaattggt ttcacctaga atggcttcgt cccttctttt   13260
cctcgtggtt ggttttaaat gtctcttggt ttctcaggcg ttcgcctgca aaccatgttt   13320
```

```
cagttcgagt cttgcagata ttaagaccaa caccaccgca gcggcaagct tgctgtcct   13380 ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
gtgtgtcaat tttaccagct acgtccaaca tgtcaaggag tttacccaac gctccctggt   13680
ggtcgaccat gtgcggttgc tccatttcat gacacctgag accatgaggt gggcaactgt   13740
tttagcctgt cttttttgcca ttctgttggc aatttgaatg tttaagtatg ttggagaaat   13800
gcttgaccgc gggctgttgc tcgcgattgc tttctttgtg gtgtatcgtg ccgttctgtt   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catctttccc gttttgactc acattgtctc ctatggtgcc ctcactacca   14040
gccatttcct tgacacagtc gctttagtca ctgtgtctac cgccgggttt gttcacgggc   14100
ggtatgtcct aagtagcatc tacgcggtct gtgccctggc tgcgttgact tgcttcgtca   14160
ttaggtttgc aaagaattgc atgtcctggc gctacgcgtg taccagatat accaactttc   14220
ttctggacac aagggcaga ctctatcgtt ggcggtcgcc tgtcatcata gagaaaaggg   14280
gcaaagttga ggtcgaaggt catctgatcg acctcaaaag agttgtgctt gatggctccg   14340
tggcaacccc tataaccaga gtttcagcgg aacaatgggg tcgtccttag atgacttctg   14400
tcacgatagc acggctccac aaaaggtgct tttggcgttt tctattacct acacgccagt   14460
gatgatatat gccctaaagg tgagtcgcgg ccgactgcta gggcttctgc accttttgat   14520
cttcctgaat tgtgctttca ccttcgggta catgactttc gcgcactttc agagtacaaa   14580
taaggtcgcg ctcactatgg agcagtagt tgcactcctt tgggggtgt actcagccat   14640 agaaacctgg aaattcatca cctccagatg ccgtttgtgc ttgctaggcc gcaagtacat   14700
tctggcccct gcccaccacg ttgaaagtgc cgcaggcttt catccgattg cggcaaatga   14760
taaccacgca tttgtcgtcc ggcgtcccgg ctccactacg gtcaacgca cattggtgcc   14820 cgggttaaaa agcctcgtgt tgggtggcag aaaagctgtt aaacaggag tggtaaacct   14880 tgtcaaatat gccaaataac aacggcaagc agcagaagag aaagaagggg gatgccagc   14940 cagtcaatca gctgtgccag atgctgggta agatcatcgc tcagcaaaac cagtccagag   15000
gcaagggacc gggaaagaaa aataagaaga aaacccgga gaagcccat tttcctctag   15060 cgactgaaga tgatgtcaga catcactta cccctagtga gcggcaattg tgtctgtcgt   15120
caatccagac cgccttaat caaggcgctg ggacttgcac cctgtcagat tcagggagga   15180
taagttacac tgtggagttt agtttgccta cgcatcatac tgtgcgcctg atccgcgtca   15240
cagcatcacc ctcagcatga tgggctggca ttcttgaggc atctcagtgt ttgaattgga   15300
agaatgtgtg gtgaatggca ctgattgaca ttgtgcctct aagtcaccta ttcaattagg   15360
gcgaccgtgt gggggtgaga tttaattggc gagaaccatg cggccgaaat taaaaaaaa   15419
```

<210> SEQ ID NO 2
<211> LENGTH: 15458
<212> TYPE: DNA
<213> ORGANISM: Artificial Sequence
<220> FEATURE:
<223> OTHER INFORMATION: Porcine reproductive and respiratory syndrome
      virus

```
<400> SEQUENCE: 2
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg gccaagtcta ctgcacacga tgcctcagtg cacggtctct ccttcccctg     300
aacctccagg tttctgagct cggggtgcta ggcctattct acaggcccga agagccactc     360
cggtggacgt tgccacgtgc attccccact gttgagtgct ccccgccgg ggcctgctgg      420
ctttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtacccca ttgttggacc tgtccctgga     600
gtggccgttt tcgccaattc cctacatgtg agtgataaac ccttcccggg agcaactcac     660
gtgttgacca acctgccgct cccgcagaga cccaagcctg aagacttttg cccctttgag     720
tgtgctatgg ctactgtcta tgacattggt catgacgccg tcatgtatgt ggccgaaagg     780
aaagtctcct gggcccctcg tggcggggat gaagtgaaat ttgaagctgt ccccggggag     840
ttgaagttga ttgcgaaccg gctccgcacc tccttcccgc cccaccacac agtggacatg     900
tctaagttcg ccttcacagc ccctgggtgt ggtgtttcta tgcgggtcga acgccaacac     960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt ttgaggacct cctcagaata    1260
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg tgcttgtac tagcgccaag     1680
tacgtactta agctggaagg tgagcattgg actgtcactg tgaccgctgg gatgtcccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca cccgaggaga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgc caacccagac gatcaagctg ccccaggtca accagtgtcg tgctctggtc    2280
cctgttgtga ctcaaaagtc cttggacaac aactcggtcc ccctgaccgc cttttcactg    2340
```

```
gctaactact actaccgtgc gcaaggtgac gaagttcgtc accgtgaaag actaaccgcc    2400
gtgctctcca agttggaaaa ggttgttcga gaagaatatg ggctcatgcc aaccgagcct    2460
ggtccacggc ccacactgcc acgcgggctc gacgaactca aagaccagat ggaggaggac    2520
ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggcgtt    3120 ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgcccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg    3720 cggaggcctg acgagagcac atcagctccg tccgcaggca caggtggcgc cggctctttt    3780
accgatttgc cgccttcaga tggcgcggat gcggacgggg ggggccgtt tcggacggta    3840 aaaagaaaag ctgaaaggct ctttgaccaa ctgagccgtc aggttttttga cctcgtctcc    3900 catctccctg ttttcttctc acgccttttc taccctggcg gtggttattc tccgggtgat    3960 tgggggttttg cagcttttac tctattgtgc ctctttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tccttttcaca    4440 cgtgcgacca ggtcgtcact tatcgacctg tgcgatcggt tttgtgcgcc aaaaggaatg    4500 gacccccattt ttctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
```

```
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgtcttg cttgcaattg ccagctatgt ttgggtacct    5280
cttacctggt tgctttgtgt gtttccttgc tggttgcgct gttttctttt gcacccctc    5340 accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460 acccctacg acattcatca ttacaccagt ggccccgcg tgttgccgc cttggctacc    5520 gcaccagatg gaacctactt ggccgctgtc cgccgcgctg cgttgactgg ccgcaccatg    5580
ctgtttaccc cgtcccagct tgggtctctt cttgagggtg cttttcagaac tcgaaagccc    5640 tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc    5940 gccttctgct tcaccgcatg tggcgattcc gggtccccag tgatcaccga ggccggtgag    6000
cttgtcggcg ttcacacggg atcgaataaa cagggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttcttgtgt gttttttctc ctgtggagaa tgatgggaca tgcctggacg    6300
cccttggttg ctgtgagttt cttttatttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact tgccgagggg aaagttgagg gaagggggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
```

```
gacctaaagg ttggtagcac caagcatacc ctccaagcca ttgagaccag agtccttgct   7140
gggtccaaaa tgaccgtggc gcgcgtcgtc gacccgaccc ccacgccccc acccgcaccc   7200
gtgcccatcc ccctcccacc gaaagttctg gagaatggcc ccaacgcttg gggggatgag   7260
gaccgtttga ataagaagaa gaggcgcagg atggaagccc tcggcatcta tgttatgggc   7320
gggaaaaaat accagaaatt ttgggacaag aattccggtg atgtgtttta tgaggaggtc   7380
cataataaca cagatgagtg ggagtgtctc agagttggcg accctgccga ctttgaccct   7440
gagaagggaa ctctgtgtgg acatgtcacc attggaaaca aggcttacca tgtttacacc   7500
tccccatctg gtaagaagtt cttggtcccc gtcaacccag agaatggaag agtccaatgg   7560
gaagctgcaa agcttttccgt ggagcaggcc ctaggtatga tgaatgtcga cggcgaactg   7620
actgccaaag aactggagaa actgaaaaga ataattgaca aactccaggg cctgactaag   7680
gagcagtgtt taaactgcta gccgccagcg acttgacccg ctgtggtcgc ggcggcttgg   7740
ttgttactga aacagcggta aaatagtca aatttcacaa ccggaccttc accctgggac   7800
ctgtgaattt aaaagtggcc agtgaggttg agctaaaaga cgcggttgag cacaaccaac   7860
acccggttgc gagaccgatc gatggtggag ttgtgctcct gcgttccgcg gttccttcgc   7920
ttatagacgt cttgatctcc ggtgctgatg catctcccaa gttacttgcc catcacgggc   7980
cgggaaacac tgggatcgat ggcacgctct gggattttga gtccgaagcc actaaagagg   8040
aagtcgcact cagtgcgcaa ataatacagg cttgtgacat taggcgcggc gacgctcctg   8100
aaattggtct cccttacaag ctgtaccctg ttaggggtaa ccctgagcgg gtgaaaggag   8160
ttctgcagaa tacaaggttt ggagacatac cttacaaaac ccccagtgac actggaagcc   8220
cagtgcacgc ggctgcctgc cttacgccca acgccactcc ggtgactgat gggcgctccg   8280
tcttggccac gaccatgccc cccgggtttg agttatatgt accgaccata ccagcgtctg   8340
tccttgatta ccttgactct aggcctgact gccctaaaca gctgacagag cacggctgcg   8400
aagatgccgc actgaaagac ctctctaaat atgacttgtc cacccaaggc tttgttttac   8460
ctggagttct tcgccttgtg cggaaatacc tgtttgccca tgtaggtaag tgcccacccg   8520
ttcatcggcc ttctacttac cctgctaaga attctatggc tggaataaat gggaacaggt   8580
tcccaaccaa ggacattcag agcgtccctg aaatcgacgt tctgtgcgca caggctgtgc   8640
gagaaaactg gcaaactgtc accccttgta ctcttaagaa acagtattgc gggaagaaga   8700
agactaggac catactcggc accaataact tcatcgcact agcccaccga gcagtgttga   8760
gtggtgttac ccagggcttc atgaaaaagg cgtttaactc gcccatcgcc ctcggaaaga   8820
acaagtttaa ggagctacag actccggtcc tgggcaggtg ccttgaagct gatctcgcat   8880
cctgcgatcg atccacgcct gcaattgtcc gctggtttgc cgccaacctt ctttatgaac   8940
ttgcctgtgc tgaagagcat ctaccgtcgt acgtgctgaa ctgctgccac gacttactgg   9000
tcacgcagtc cggcgcagtg actaagagag gtggcctgtc gtctggcgac ccgatcacct   9060
ctgtgtctaa caccatttat agtttggtga tctatgcaca gcatatggtg cttagttact   9120
tcaaaagtgg tcacccccat ggccttctgt tcttacaaga ccagctaaag tttgaggaca   9180
tgctcaaggt tcaaccctg atcgtctatt cggacgacct cgtgctgtat gccgagtctc   9240
ccaccatgcc aaactatcac tggtgggttg aacatctgaa tttgatgctg gggtttcaga   9300
cggacccaaa aagacagca ataacagact cgcatcatt tctaggctgt agaataataa   9360
atgggcgcca gctagtcccc aaccgtgaca ggatcctcgc ggccctcgcc tatcacatga   9420
```

```
aggcgagtaa tgtttctgaa tactatgcct cagcggctgc aatactcatg gacagctgtg   9480
cttgtttgga gtatgatcct gaatggtttg aagaacttgt agttggaata gcgcagtgcg   9540
cccgcaagga cggctacagc tttcccggca cgccgttctt catgtccatg tgggaaaaac   9600
tcaggtccaa ttatgagggg aagaagtcga gagtgtgcgg gtactgcggg gccccggccc   9660
cgtacgctac tgcctgtggc ctcgacgtct gcatttacca cacccacttc caccagcatt   9720
gtccagtcac aatctggtgt ggccatccag cgggttctgg ttcttgtagt gagtgcaaat   9780
cccctgtagg gaaaggcaca agcccttag acgaggtgct ggaacaagtc ccgtataagc   9840
ccccacggac cgttatcatg catgtggagc agggtctcac ccccttgat ccaggtagat   9900 accaaactcg ccgcggatta gtctctgtca ggcgtggaat taggggaaat gaagttggac   9960
taccagacgg tgattatgct agcaccgcct tgctccctac ctgcaaagag atcaacatgg  10020
tcgctgtcgc ttccaatgta ttgcgcagca ggttcatcat cggcccaccc ggtgctggga  10080
aaacatactg gctccttcaa caggtccagg atggtgatgt tatttacaca ccaactcacc  10140
agaccatgct tgacatgatt agggcttggg gacgtgccg gttcaacgtc ccggcaggca  10200
caacgctgca attccccgtc ccctcccgca ccggtccgtg ggttcgcatc ctagccggcg  10260
gttggtgtcc tggcaagaat tccttcctag atgaagcagc gtattgcaat cacccttgatg  10320 ttttgaggct tcttagtaaa actaccctca cctgtctagg agacttcaag caactccacc  10380
cagtgggttt tgattctcat tgctatgttt ttgacatcat gcctcaaact caactgaaga  10440
ccatctggag gtttggacag aatatctgtg atgccattca gccagattac agggacaaac  10500
tcatgtccat ggtcaacaca acccgtgtga cctacgtgga aaaacctgtc aggtatgggc  10560
aggtcctcac cccctaccac agggaccgag aggacgacgc catcactatt gactccagtc  10620
aaggcgccac attcgatgtg gttacattgc atttgcccac taaagattca ctcaacaggc  10680
aaagagccct tgttgctatc accagggcaa gacacgctat cttgtgtat gacccacaca  10740 ggcagctgca gggcttgttt gatcttcctg caaaaggcac gcccgtcaac ctcgcagtgc  10800
actgcgacgg gcagctgatc gtgctggata gaaataacaa agaatgcacg gttgctcagg  10860
ctctaggcaa cggggataaa tttagggcca cagacaagcg tgttgtagat tctctccgcg  10920
ccatttgtgc tgatctagaa gggtcgagct ctccgctccc caaggtcgca cacaacttgg  10980
gattttattt ctcacctgat ttaacacagt ttgctaaact cccagtagaa cttgcacctc  11040
actggcccgt ggtgtcaacc cagaacaatg aaaagtggcc ggatcggctg gttgccagcc  11100
ttcgccctat ccataaatac agccgcgcgt gcatcggtgc cggctatatg gtgggccctt  11160
cggtgtttct aggcactcct ggggtcgtgt catactatct cacaaaattt gttaagggcg  11220
gggctcaagt gcttccggag acggttttca gcaccggccg aattgaggta gactgccggg  11280
aatatcttga tgatcgggag cgagaagttg ctgcgtccct cccacacgct ttcattggcg  11340
acgtcaaagg cactaccgtt ggaggatgtc atcatgtcac ctccagatac ctcccgcgcg  11400
tccttcccaa ggaatcagtt gcggtagtcg gggtttcaag cccggaaaa gccgcgaaag  11460 cattgtgcac actgacagat gtgtacctcc cagatcttga agcctatctc cacccggaga  11520
cccagtccaa gtgctggaaa atgatgttgg acttcaaaga agttcgacta atggtctgga  11580
aagacaaaac agcctatttc caacttgaag gtcgctattt cacctggtat cagcttgcca  11640
gctatgcctc gtacatccgt gttcccgtca actctacggt gtacttggac ccctgcatgg  11700
gccccgccct ttgcaacagg agagtcgtcg ggtccaccca ctgggggct gacctcgcgg  11760 tcacccctta tgattacggc gctaaaatta tcctgtctag cgcgtaccat ggtgaaatgc  11820
```

```
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag tttattttc ccccgggccc tgtcattgaa ccaactttag   12060
gcctgaattg aaatgaaatg gggtccatgc aaagcctttt tgacaaaatt ggccaacttt   12120
ttgtggatgc tttcacggag ttcttggtgt ccattgttga tatcattata ttttggcca   12180 ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta atatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact ctttttgttg tgctgtggtt gcgggttcca   12780
atactacgta ctgttttggg tttccgctgg ttaggggcaa ttttttcttc gaactcacag   12840
tgaattacac ggtgtgtcca ccttgcctca cccggcaagc agccacagag atctacgaac   12900
ccggtaggtc tctttggtgc aggatagggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct ttgctgtcct   13380
ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
gtgtgtcaat tttaccagct acgtccaaca tgtcaaggag tttacccaac gctccctggt   13680
ggtcgaccat gtgcggttgc tccatttcat gacacctgag accatgaggt gggcaactgt   13740
tttagcctgt cttttttgcca ttctgttggc aatttgaatg tttaagtatg ttggagaaat   13800
gcttgaccgc gggctgttgc tcgcgattgc tttctttgtg gtgtatcgtg ccgttctgtc   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catctttccc gttttgactc acattgtctc ctatggtgcc ctcactacca   14040
gccatttcct tgcacagtc gctttagtca ctgtgtctac cgccgggttt gttcacgggc   14100
ggtatgtcct aagtagcatc tacgcggtct gtgccctggc tgcgttgact tgcttcgtca   14160
```

-continued

```
ttaggtttgc aaagaattgc atgtcctggc gctacgcgtg taccagatat accaactttc  14220
ttctggacac taagggcaga ctctatcgtt ggcggtcgcc tgtcatcata gagaaaaggg  14280
gcaaagttga ggtcgaaggt catctgatcg acctcaaaag agttgtgctt gatggctccg  14340
tggcaacccc tataaccaga gtttcagcgg aacaatgggg tcgtccttag atgacttctg  14400
tcacgatagc acggctccac aaaaggtgct tttggcgttt tctattacct acacgccagt  14460
gatgatatat gccctaaagg tgagtcgcgg ccgactgcta gggcttctgc accttttgat  14520
cttcctgaat tgtgctttca ccttcgggta catgactttc gcgcactttc agagtacaaa  14580
taaggtcgcg ctcactatgg gagcagtagt tgcactcctt tggggggtgt actcagccat  14640
agaaacctgg aaattcatca cctccagatg ccgtttgtgc ttgctaggcc gcaagtacat  14700
tctggcccct gcccaccacg ttgaaagtgc cgcaggcttt catccgattg cggcaaatga  14760
taaccacgca tttgtcgtcc ggcgtcccgg ctccactacg gtcaacggca cattggtgcc  14820
cgggttaaaa agcctcgtgt tgggtggcag aaaagctgtt aaacagggag tggtaaacct  14880
tgtcaaatat gccaaataac aacggcaagc agcagaagag aaagaagggg gatggccagc  14940
cagtcaatca gctgtgccag atgctgggta agatcatcac tcagcaaaac cagtccagag  15000
gcaagggacc gggaaagaaa aataagaaga aaaacccgga gaagccccat tttcctctag  15060
cgactgaaga tgatgtcaga catcacttta cccctagtga gcggcaattg tgtctgtcgt  15120
caatccagac cgcctttaat caaggcgctg ggacttgcac cctgtcagat tcagggagga  15180
taagttacac tgtggagttt agtttgccta cgcatcatac tgtgcgcctg atccgcgtca  15240
cagcatcacc ctcagcatga tgggctggca ttcttgaggc atctcagtgt ttgaattgga  15300
agaatgtgtg gtgaatggca ctgattgaca ttgtgcctct aagtcaccta ttcaattagg  15360
gcgaccgtgt gggggtgaga tttaattggc gagaaccatg cggccgaaat taaaaaaaaa  15420
aaaaaaaaaa aaaaaaaaaa aaaaaaaaaa aaaaaaaa                          15458
```

<210> SEQ ID NO 3
<211> LENGTH: 15460
<212> TYPE: DNA
<213> ORGANISM: Artificial Sequence
<220> FEATURE:
<223> OTHER INFORMATION: Porcine reproductive and respiratory syndrome virus

<400> SEQUENCE: 3

```
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta cccccaatgc cagggtgttt    240
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct cccccgccgg ggcctgctgg    420
ctttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg ggttgccgc  tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagacttttg cccctttgag    720
```

```
tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgacccctgg gatgtcccct   1740
tctttgctcc ctcttgaatg tgttcagggc tgttgtgggc gcaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg   2340 gctaactact actaccgtgc gcaaggtgac gaagttcgtc accgtgaaag actaaccgcc   2400
gtgctctcca agttggaaaa ggttgttcga gaagaatatg ggctcatgcc aaccgagcct   2460
ggtccacggc ccacactgcc acgcgggctc gacgaactca agaccagat ggaggaggac    2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agcccctttg atctcccgac cccacctgag   2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatcctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct ccccccagcac cgccgcagag cggggggcgtt   3120
```

```
ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg     3720
cggaggcctg acgagagcac atcagctccg tccgcaggca caggtggcgc cggctctttt    3780
accgatttgc cgccttcaga tggcgcggat gcggacgggg gggggccgtt tcggacggta    3840
aaaagaaaag ctgaaaggct cttttgaccaa ctgagccgtc aggttttga cctcgtctcc     3900
catctccctg ttttcttctc acgccttttc taccctggcg gtggttattc tccgggtgat    3960
tggggttttg cagcttttac tctattgtgc ctcttttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tccttcaca     4440
cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag gtcgtggtt     4800
gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgaccgtgg     5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgtcttg cttgcaattg ccagctatgt ttgggtacct    5280
cttacctggt tgctttgtgt gttttccttgc tggttgcgct gttttctttt gcacccctc    5340
accatcctat ggtggtgtt tttcttgatt tctgtgaata tgccttcagg aatcttggcc     5400
atggtgttgt tggtttctct ttggcttctt ggtcgttata ctaatgttgc tggccttgtc    5460
```

```
acccccctacg acattcatca ttacaccagt ggccccgcg gtgttgccgc cttggctacc    5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc     5940 gccttctgct tcaccgcatg tggcgattcc gggtccccag tgatcaccga ggccggtgag    6000
cttgtcggcg ttcacacggg atcgaataaa caaggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgcctttttc    6480
agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact tgccgagggg aaagttgagg aagggggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt tgctgatac cgtggcacct    7020 caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc caacgcttg ggggatgag     7260 gaccgtttga ataagaagaa gaggcgcagg atggaagccc tcggcatcta tgttatgggc    7320
gggaaaaaat accagaaatt ttgggacaag aattccggtg atgtgtttta tgaggaggtc    7380
cataataaca cagatgagtg ggagtgtctc agagttggcg accctgccga ctttgaccct    7440
gagaagggaa ctctgtgtgg acatgtcacc attgaaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga aacagcggta aaaatagtca aatttcacaa ccggaccttc accctgggac    7800
ctgtgaattt aaaagtggcc agtgaggttg agctaaaaga cgcggttgag cacaaccaac    7860
```

```
acccggttgc gagaccgatc gatggtggag ttgtgctcct gcgttccgcg gttccttcgc   7920
ttatagacgt cttgatctcc ggtgctgatg catctcccaa gttacttgcc catcacgggc   7980
cgggaaacac tgggatcgat ggcacgctct gggattttga gtccgaagcc actaaagagg   8040
aagtcgcact cagtgcgcaa ataatacagg cttgtgacat taggcgcggc gacgctcctg   8100
aaattggtct cccttacaag ctgtaccctg ttaggggtaa ccctgagcgg gtgaaaggag   8160
ttctgcagaa tacaaggttt ggagacatac cttacaaaac ccccagtgac actggaagcc   8220
cagtgcacgc ggctgcctgc cttacgccca acgccactcc ggtgactgat gggcgctccg   8280
tcttggccac gaccatgccc cccgggtttg agttatatgt accgaccata ccagcgtctg   8340
tccttgatta ccttgactct aggcctgact gccctaaaca gctgacagag cacggctgcg   8400
aagatgccgc actgaaagac ctctctaaat atgacttgtc cacccaaggc tttgttttac   8460
ctggagttct tcgccttgtg cggaaatacc tgtttgccca tgtaggtaag tgcccacccg   8520
ttcatcggcc ttctacttac cctgctaaga attctatggc tggaataaat gggaacaggt   8580
tcccaaccaa ggacattcag agcgtccctg aaatcgacgt tctgtgcgca caggctgtgc   8640
gagaaaactg gcaaactgtc ccccttgta ctcttaagaa acagtattgc gggaagaaga   8700
agactaggac catactcggc accaataact tcatcgcact agcccaccga gcagtgttga   8760
gtggtgttac ccagggcttc atgaaaaagg cgtttaactc gcccatcgcc ctcggaaaga   8820
acaagtttaa ggagctacag actccggtcc tgggcaggtg ccttgaagct gatctcgcat   8880
cctgcgatcg atccacgcct gcaattgtcc gctggtttgc cgccaacctt ctttatgaac   8940
ttgcctgtgc tgaagagcat ctaccgtcgt acgtgctgaa ctgctgccac gacttactgg   9000
tcacgcagtc cggcgcagtg actaagagag gtggcctgtc gtctggcgac ccgatcacct   9060
ctgtgtctaa caccatttat agtttggtga tctatgcaca gcatatggtg cttagttact   9120
tcaaaagtgg tcaccccat ggccttctgt tcttacaaga ccagctaaag tttgaggaca   9180
tgctcaaggt tcaaccctg atcgtctatt cggacgacct cgtgctgtat gccgagtctc   9240
ccaccatgcc aaactatcac tggtgggttg aacatctgaa tttgatgctg gggtttcaga   9300
cggacccaaa gaagacagca ataacagact cgccatcatt tctaggctgt agaataataa   9360
atgggcgcca gctagtcccc aaccgtgaca ggatcctcgc ggccctcgcc tatcacatga   9420
aggcgagtaa tgtttctgaa tactatgcct cagcggctgc aatactcatg gacagctgtg   9480
cttgtttgga gtatgatcct gaatggtttg aagaacttgt agttggaata gcgcagtgcg   9540
cccgcaagga cggctacagc tttcccggca cgccgttctt catgtccatg tgggaaaaac   9600
tcaggtccaa ttatgagggg aagaagtcga gagtgtgcgg gtactgcggg gccccggccc   9660
cgtacgctac tgcctgtggc ctcgacgtct gcatttacca cacccacttc caccagcatt   9720
gtccagtcac aatctggtgt ggccatccag cgggttctgg ttcttgtagt gagtgcaaat   9780
cccctgtagg gaaaggcaca agccctttag acgaggtgct ggaacaagtc ccgtataagc   9840
ccccacggac cgttatcatg catgtggagc agggtctcac ccccttgat ccaggtagat   9900
accaaactcg ccgcggatta gtctctgtca ggcgtggaat taggggaaat gaagttggac   9960
taccagacgg tgattatgct agcaccgcct tgctccctac ctgcaaagag atcaacatgg  10020
tcgctgtcgc ttccaatgta ttgcgcagca ggttcatcat cggcccaccc ggtgctggga  10080
aaacatactg gctccttcaa caggtccagg atggtgatgt tatttacaca ccaactcacc  10140
agaccatgct tgacatgatt agggctttgg ggacgtgccg gttcaacgtc ccggcaggca  10200
```

```
caacgctgca attccccgtc ccctcccgca ccggtccgtg ggttcgcatc ctagccggcg    10260
gttggtgtcc tggcaagaat tccttcctag atgaagcagc gtattgcaat caccttgatg    10320
ttttgaggct tcttagtaaa actaccctca cctgtctagg agacttcaag caactccacc    10380
cagtgggttt tgattctcat tgctatgttt ttgacatcat gcctcaaact caactgaaga    10440
ccatctggag gtttggacag aatatctgtg atgccattca gccagattac agggacaaac    10500
tcatgtccat ggtcaacaca acccgtgtga cctacgtgga aaaacctgtc aggtatgggc    10560
aggtcctcac cccctaccac agggaccgag aggacgacgc catcactatt gactccagtc    10620
aaggcgccac attcgatgtg gttacattgc atttgcccac taaagattca ctcaacaggc    10680
aaagagccct tgttgctatc accagggcaa gacacgctat ctttgtgtat gacccacaca    10740
ggcagctgca gggcttgttt gatcttcctg caaaaggcac gcccgtcaac ctcgcagtgc    10800
actgcgacgg gcagctgatc gtgctggata gaaataacaa agaatgcacg gttgctcagg    10860
ctctaggcaa cggggataaa tttagggcca cagacaagcg tgttgtagat tctctccgcg    10920
ccatttgtgc tgatctagaa gggtcgagct ctccgctccc caaggtcgca cacaacttgg    10980 gattttatt ctcacctgat ttaacacagt ttgctaaact cccagtagaa cttgcacctc    11040
actggcccgt ggtgtcaacc cagaacaatg aaaagtggcc ggatcggctg gttgccagcc    11100
ttcgccctat ccataaatac agccgcgcgt gcatcggtgc cggctatatg gtgggcccttt    11160 cggtgtttct aggcactcct ggggtcgtgt catactatct cacaaaattt gttaagggcg    11220
gggctcaagt gcttccggag acggttttca gcaccggccg aattgaggta gactgccggg    11280
aatatcttga tgatcgggag cgagaagttg ctgcgtccct cccacacgct ttcattggcg    11340
acgtcaaagg cactaccgtt ggaggatgtc atcatgtcac ctccagatac ctcccgcgcg    11400
tccttcccaa ggaatcagtt gcggtagtcg gggtttcaag ccccgaaaaa gccgcgaaag    11460
cattgtgcac actgacagat gtgtacctcc cagatcttga agcctatctc cacccggaga    11520
cccagtccaa gtgctggaaa atgatgttgg acttcaaaga agttcgacta atggtctgga    11580
aagacaaaac agcctatttc caacttgaag gtcgctattt cacctggtat cagcttgcca    11640
gctatgcctc gtacatccgt gttcccgtca actctacggt gtacttggac ccctgcatgg    11700
gccccgccct ttgcaacagg agagtcgtcg ggtccaccca ctgggggget gacctcgcgg    11760 tcacccctta tgattacggc gctaaaatta tcctgtctag cgcgtaccat ggtgaaatgc    11820
cccccggata caaaattctg gcgtgcgcgg agttctcgtt ggatgaccca gttaagtaca    11880
aacatacctg ggggtttgaa tcggatacag cgtatctgta tgagttcacc ggaaacggtg    11940
aggactggga ggattacaat gatgcgtttc gtgcgcgcca ggaagggaaa atttataagg    12000
ccactgccac cagcttgaag ttttatttt ccccgggccc tgtcattgaa ccaactttag    12060
gcctgaattg aaatgaaatg gggtccatgc aaagccttt tgacaaaatt ggccaacttt    12120
ttgtggatgc tttcacggag ttcttggtgt ccattgttga tatcattata ttttggcca    12180 ttttgtttgg cttcaccatc gccggttggc tgtggtctt ttgcatcaga ttggtttgct    12240
ccgcgatact ccgtacgcgc cctgccattc actctgagca attacagaag atcttatgag    12300
gcctttcttt cccagtgcca agtggacatt cccacctggg gaactaaaca tccttttggg    12360
atgctttggc accataaggt gtcaaccctg attgatgaaa tggtgtcgcg tcgaatgtac    12420
cgcatcatgg aaaaagcagg gcaggctgcc tggaaacagg tggtgagcga ggctacgctg    12480
tctcgcatta gtagtttgga tgtggtggct catttcagc atctagccgc cattgaagcc    12540
gagacctgta aatatttggc ctcccggctg cccatgctac acaacctgcg catgacaggg    12600
```

```
tcaaatgtaa ccatagtgta taatagcact ttgaatcagg tgtttgctat ttttccaacc  12660
cctggttccc ggccaaagct tcatgatttt cagcaatggt taatagctgt acattcctcc  12720
atattttcct ctgttgcagc ttcttgtact cttttttgttg tgctgtggtt gcgggttcca  12780
atactacgta ctgttttttgg tttccgctgg ttagggggcaa ttttctttc gaactcacag  12840 tgaattacac ggtgtgtcca ccttgcctca cccggcaagc agccacagag atctacgaac  12900
ccggtaggtc tctttggtgc aggatagggt atgaccgatg tggggaggac gatcatgacg  12960
agctagggtt tatgataccg cctggcctct ccagcgaagg ccacttgact ggtgtttacg  13020
cctggttggc gttcttgtcc ttcagctaca cggcccagtt ccatcccgag atattcggga  13080
tagggaatgt gagtcgagtt tatgttgaca tcaaacatca actcatctgc gccgaacatg  13140
acgggcagaa caccaccttg cctcgtcatg acaacatttc agccgtgttt cagacctatt  13200
accaacatca agtcgacggc ggcaattggt ttcacctaga atggcttcgt cccttctttt  13260
cctcgtggtt ggttttaaat gtctcttggt ttctcaggcg ttcgcctgca aaccatgttt  13320
cagttcgagt cttgcaaata ttaagaccaa caccaccgca gcggcaagct ttgctgtcct  13380
ccaagacatc agttgcctta ggcatcgcga ctcggcctct gaggcgattc gcaaaatccc  13440
tcagtgccgt acggcgatag ggacacccgt gtatgttacc atcacagcca atgggacaga  13500
tgagaattat ctacattctt ctgatctcct catgctttct tcttgccttt tctatgcttc  13560
tgagatgagt gaaaagggat ttaaggtggt atttggcaat gtgtcaggca tcgtggctgt  13620
gtgtgtcaat tttaccagct acgtccaaca tgtcaaggag tttacccaac gctccctggt  13680
ggtcgaccat gtgcggttgc tccatttcat gacacctgag accatgaggt gggcaactgt  13740
tttagcctgt cttttttgcca ttctgttggc aatttgaatg tttaagtatg ttggagaaat  13800
gcttgaccgc gggctgttgc tcgcgattgc tttctttgtg gtgtatcgtg ccgttctgtc  13860
ttgctgtgct cgccaacgcc agcaacgaca gcagctccca tctacagctg atttacaact  13920
tgacgctatg tgagctgaat ggcacagatt ggctagctaa caaatttgat tgggcagtgg  13980
agagttttgt catctttccc gttttgactc acattgtctc ctatggtgcc ctcactacca  14040
gccatttcct tgacacagtc gctttagtca ctgtgtctac cgccgggttt gttcacgggc  14100
ggtatgtcct aagtagcatc tacgcggtct gtgccctggc tgcgttgact tgcttcgtca  14160
ttaggtttgc aaagaattgc atgtcctggc gctacgcgtg taccagatat accaactttc  14220
ttctggacac taagggcaga ctctatcgtt ggcggtcgcc tgtcatcata gagaaagggg  14280
gcaaagttga ggtcgaaggt catctgatcg acctcaaaag agttgtgctt gatggctccg  14340
tggcaacccc tataaccaga gtttcagcgg aacaatgggg tcgtccttag atgacttctg  14400
tcacgatagc acggctccac aaaaggtgct tttggcgttt tctattacct acacgccagt  14460
gatgatatat gccctaaagg tgagtcgcgg ccgactgcta gggcttctgc accttttgat  14520
cttcctgaat tgtgctttca ccttcgggta catgactttc gcgcactttc agagtacaaa  14580
taaggtcgcg ctcactatgg gagcagtagt tgcactcctt tgggggtgt actcagccat  14640 agaaacctgg aaattcatca cctccagatg ccgtttgtgc ttgctaggcc gcaagtacat  14700
tctgccccct gcccaccacg ttgaaagtgc cgcaggcttt catccgattg cggcaaatga  14760
taaccacgca tttgtcgtcc ggcgtcccgg ctccactacg gtcaacggca cattggtgcc  14820
cgggttaaaa agcctcgtgt tgggtggcag aaaagctgtt aaacagggag tggtaaacct  14880
tgtcaaatat gccaaataac aacggcaagc agcagaagag aaagaagggg gatggccagc  14940
```

-continued

| | |
|---|---|
| cagtcaatca gctgtgccag atgctgggta agatcatcac tcagcaaaac cagtccagag | 15000 |
| gcaagggacc gggaaagaaa aataagaaga aaaacccgga gaagcccat tttcctctag | 15060 |
| cgactgaaga tgatgtcaga catcacttta ccctagtga gcggcaattg tgtctgtcgt | 15120 |
| caatccagac cgccttaat caaggcgctg gacttgcac cctgtcagat tcagggagga | 15180 |
| taagttacac tgtggagttt agtttgccta cgcatcatac tgtgcgcctg atccgcgtca | 15240 |
| cagcatcacc ctcagcatga tgggctggca ttcttgaggc atctcagtgt ttgaattgga | 15300 |
| agaatgtgtg gtgaatggca ctgattgaca ttgtgcctct aagtcaccta ttcaattagg | 15360 |
| gcgaccgtgt gggggtgaga tttaattggc gagaaccatg cggccgaaat taaaaaaaaa | 15420 |
| aaaaaaaaaa aaaaaaaaaa aaaaaaaaaa aaaaaaccc | 15460 |

<210> SEQ ID NO 4
<211> LENGTH: 15456
<212> TYPE: DNA
<213> ORGANISM: Artificial Sequence
<220> FEATURE:
<223> OTHER INFORMATION: Porcine reproductive and respiratory syndrome
    virus

<400> SEQUENCE: 4

| | |
|---|---|
| atgacgtata ggtgttggct ctatgccttg gcatttgtat tgtcaggagc tgtgaccatt | 60 |
| ggcacagccc aaaacttgct gcacagaaac acccttctgt gatagcctcc ttcaggggag | 120 |
| cttagggttt gtccctagca ccttgcttcc ggagttgcac tgctttacgg tctctccacc | 180 |
| cctttaacca tgtctgggat acttgatcgg tgcacgtgta ccccaatgc cagggtgttt | 240 |
| atggcggagg gccaagtcta ctgcacacga tgcctcagtg cacggtctct ccttcccctg | 300 |
| aacctccagg tttctgagct cggggtgcta ggcctattct acaggcccga agagccactc | 360 |
| cggtggacgt tgccacgtgc attccccact gttgagtgct cccccgccgg ggcctgctgg | 420 |
| ctttctgcaa tctttccaat cgcacgaatg accagtggaa acctgaactt ccaacaaaga | 480 |
| atggtacggg tcgcagctga gctttacaga gccggccagc tcacccctgc agtcttgaag | 540 |
| gctctacaag tttatgaacg gggttgccgc tggtacccca ttgttggacc tgtccctgga | 600 |
| gtggccgttt tcgccaattc cctacatgtg agtgataaac ccttcccggg agcaactcac | 660 |
| gtgttgacca acctgccgct cccgcagaga cccaagcctg aagactttg ccccttgag | 720 |
| tgtgctatgg ctactgtcta tgacattggt catgacgccg tcatgtatgt ggccgaaagg | 780 |
| aaagtctcct gggcccctcg tggcggggat gaagtgaaat tgaagctgt ccccggggag | 840 |
| ttgaagttga ttgcgaaccg gctccgcacc tccttcccgc ccaccacac agtggacatg | 900 |
| tctaagttcg ccttcacagc ccctgggtgt ggtgtttcta tgcgggtcga acgccaacac | 960 |
| ggctgccttc ccgctgacac tgtccctgaa ggcaactgct ggtggagctt gtttgacttg | 1020 |
| cttccactgg aagttcagaa caaagaaatt cgccatgcta accaatttgg ctaccagacc | 1080 |
| aagcatggtg tctctggcaa gtacctgcag cggaggctgc aagttaatgg tctccgagca | 1140 |
| gtaactgacc taaacggacc tatcgtcgta cagtacttct ccgttaagga gagttggatc | 1200 |
| cgccatttga aactggcggg agaacccagc tactctgggt ttgaggacct cctcagaata | 1260 |
| agggttgagc ctaacacgtc gccattggct gacaaggaag aaaaaatttt ccggtttggc | 1320 |
| agtcacaagt ggtacggcgc tggaaagaga gcaagaaaag cacgctcttg tgcgactgct | 1380 |
| acagtcgctg gccgcgcttt gtccgttcgt gaaacccggc aggccaagga gcacgaggtt | 1440 |
| gccggcgcca acaaggctga gcacctcaaa cactactccc cgcctgccga agggaattgt | 1500 |

-continued

```
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgaccctgg gatgtcccct     1740 tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagccttg tcaggtgatt    2040 gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca ccagtgtcg tgctctggtc     2280 cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca gttggaaaa ggttgttcga gaagaatatg ggctcatgcc aaccgagcct    2460
ggtccacggc ccacactgcc acgcgggctc gacgaactca agaccagat ggaggaggac     2520 ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggggcgtt   3120 ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg    3720 cggaggcctg acgagagcac atcagctccg tccgcaggca caggtggcgc cggctctttt    3780
accgatttgc cgccttcaga tggcgcggat gcggacgggg gggggccgtt tcggacggta    3840
aaaagaaaag ctgaaaggct ctttgaccaa ctgagccgtc aggttttga cctcgtctcc    3900
```

```
catctccctg ttttcttctc acgccttttc taccctggcg gtggttattc tccgggtgat    3960
tggggttttg cagcttttac tctattgtgc ctcttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggcccg tcggtctcgg tcttgccatt     4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tcctttcaca    4440
cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag gtcgtggtt     4800 gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgtcttg cttgcaattg ccagctatgt ttgggtacct    5280
cttacctggt tgctttgtgt gttttccttgc tggttgcgct gttttcttt gcacccctc     5340 accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460 acccctacg acattcatca ttacaccagt ggccccgcg gtgttgccgc cttggctacc      5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cggcaattc agctcgggtt     5760 tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc     5940 gccttctgct tcaccgcatg tggcgattcc gggtccccag tgatcaccga ggccggtgag    6000
cttgtcggcg ttcacacggg atcgaataaa caagggggg gcattgttac gcgcccctca     6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
```

```
accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact ttgccgaggg aaagttgagg aagggggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccgtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc cctcccacc gaaagttctg agaatggcc caacgcttg ggggatgag    7260 gaccgtttga ataagaagaa gaggcgcagg atggaagccc tcggcatcta tgttatgggc    7320
gggaaaaaat accagaaatt tgggacaag aattccggtg atgtgtttta tgaggaggtc    7380
cataataaca cagatgagtg ggagtgtctc agagttggcg accctgccga ctttgaccct    7440
gagaagggaa ctctgtgtgg acatgtcacc attggaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga acagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttagggtaa ccctgagcgg gtgaaaggag    8160
ttctgcagaa tacaaggttt ggagacatac cttacaaaac ccccagtgac actgaagcc    8220 cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
```

```
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaaccctg atcgtctatt cggacgacct cgtgctgtat gccgagtctc    9240
ccaccatgcc aaactatcac tggtgggttg aacatctgaa tttgatgctg gggtttcaga    9300
cggacccaaa aagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg acagctgtg    9480 cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780 ccctgtagg gaaaggcaca agccctttag acgaggtgct ggaacaagtc ccgtataagc    9840 cccacggac cgttatcatg catgtggagc agggtctcac ccccttgat ccaggtagat    9900 accaaactcg ccgcggatta gtctctgtca ggcgtggaat taggggaaat gaagttggac    9960
taccagacgg tgattatgct agcaccgcct tgctccctac ctgcaaagag atcaacatgg    10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggctttgg ggacgtgccg gttcaacgtc ccggcaggca    10200
caacgctgca attccccgtc ccctcccgca ccggtccgtg ggttcgcatc ctagccggcg    10260
gttggtgtcc tggcaagaat tccttcctag atgaagcagc gtattgcaat caccttgatg    10320
ttttgaggct tcttagtaaa actaccctca cctgtctagg agacttcaag caactccacc    10380
cagtgggttt tgattctcat tgctatgttt ttgacatcat gcctcaaact caactgaaga    10440
ccatctggag gttggacag atatctgtg atgccattca gccagattac agggacaaac    10500
tcatgtccat ggtcaacaca acccgtgtga cctacgtgga aaaacctgtc aggtatgggc    10560
aggtcctcac cccctaccac agggaccgag aggacgacgc catcactatt gactccagtc    10620
aaggcgccac attcgatgtg gttacattgc atttgcccac taaagattca ctcaacaggc    10680
aaagagccct tgttgctatc accagggcaa gacacgctat ctttgtgtat gacccacaca    10740
ggcagctgca gggcttgttt gatcttcctg caaaaggcac gcccgtcaac ctcgcagtgc    10800
actgcgacgg gcagctgatc gtgctggata gaaataacaa agaatgcacg gttgctcagg    10860
ctctaggcaa cggggataaa tttagggcca cagacaagcg tgtttagat tctctccgcg    10920 ccatttgtgc tgatctagaa gggtcgagct ctccgctccc caaggtcgca cacaacttgg    10980
```

```
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag cccgggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760 tcacccctta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttattttc ccccgggccc tgtcattgaa ccaactttag   12060
gcctgaattg aaatgaaatg gggtccatgc aaagcctttt tgacaaaatt ggccaacttt   12120
ttgtggatgc tttcacggag ttcttggtgt ccattgttga tatcattata ttttttggcca  12180 ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tccttttggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta atatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact cttttttgttg tgctgtggtt gcgggttcca   12780
atactacgta ctgtttttgg tttccgctgg ttaggggcaa ttttttctttc gaactcacag   12840 tgaattacac ggtgtgtcca ccttgcctca cccggcaagc agccacagag atctacgaac   12900
ccggtaggtc tctttggtgc aggataggggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct tgctgtcct   13380
```

-continued

```
ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttgcca ttctgttggc aatttgaatg tttaagtatg ttggagaaat    13800
gcttgaccgc gggctgttgc tcgcgattgc tttctttgtg gtgtatcgtg ccgttctgtt    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggctccg    14340
tggcaacccc tataaccaga gtttcagcgg aacaatgggg tcgtccttag atgacttctg    14400
tcacgatagc acggctccac aaaaggtgct tttggcgttt tctattacct acacgccagt    14460
gatgatatat gccctaaagg tgagtcgcgg ccgactgcta gggcttctgc acctttgat    14520 cttcctgaat tgtgctttca ccttcgggta catgactttc gcgcactttc agagtacaaa    14580
taaggtcgcg ctcactatgg gagcagtagt tgcactcctt tgggggtgt actcagccat    14640 agaaacctgg aaattcatca cctccagatg ccgtttgtgc ttgctaggcc gcaagtacat    14700
tctggcccct gcccaccacg ttgaaagtgc cgcaggcttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcgc tcagcaaaac cagtccagag    15000
gcaagggacc gggaaagaaa ataagaagaa aaacccggag aagccccat tttcctctag    15060 cgactgaaga tgatgtcaga catcacttta cccctagtga gcggcaattg tgtctgtcgt    15120
caatccagac cgcctttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat taaaaaaaaa    15420
aaaaaaaaaa aaaaaaaaaa aaaaaaaaaa aaaaaa                              15456
```

<210> SEQ ID NO 5
<211> LENGTH: 15019
<212> TYPE: DNA
<213> ORGANISM: Artificial Sequence
<220> FEATURE:
<223> OTHER INFORMATION: Porcine reproductive and respiratory syndrome
    virus, strain MN184A -continued

```
<220> FEATURE:
<221> NAME/KEY: misc_feature
<222> LOCATION: (654)..(654)
<223> OTHER INFORMATION: S = C or G
<220> FEATURE:
<221> NAME/KEY: misc_feature
<222> LOCATION: (735)..(735)
<223> OTHER INFORMATION: M = A or C
<220> FEATURE:
<221> NAME/KEY: misc_feature
<222> LOCATION: (745)..(745)
<223> OTHER INFORMATION: Y = C or T
<220> FEATURE:
<221> NAME/KEY: misc_feature
<222> LOCATION: (1627)..(1627)
<223> OTHER INFORMATION: R = A or G
<220> FEATURE:
<221> NAME/KEY: misc_feature
<222> LOCATION: (1642)..(1642)
<223> OTHER INFORMATION: Y = C or T
<220> FEATURE:
<221> NAME/KEY: misc_feature
<222> LOCATION: (1736)..(1736)
<223> OTHER INFORMATION: Y = C or T
<220> FEATURE:
<221> NAME/KEY: misc_feature
<222> LOCATION: (1987)..(1987)
<223> OTHER INFORMATION: R = A or G
<220> FEATURE:
<221> NAME/KEY: misc_feature
<222> LOCATION: (2061)..(2061)
<223> OTHER INFORMATION: R = A or G
<220> FEATURE:
<221> NAME/KEY: misc_feature
<222> LOCATION: (2161)..(2161)
<223> OTHER INFORMATION: R = A or G
<220> FEATURE:
<221> NAME/KEY: misc_feature
<222> LOCATION: (2186)..(2186)
<223> OTHER INFORMATION: R = A or G
<220> FEATURE:
<221> NAME/KEY: misc_feature
<222> LOCATION: (2228)..(2228)
<223> OTHER INFORMATION: R = A or G
<220> FEATURE:
<221> NAME/KEY: misc_feature
<222> LOCATION: (2293)..(2293)
<223> OTHER INFORMATION: Y = C or T
<220> FEATURE:
<221> NAME/KEY: misc_feature
<222> LOCATION: (3407)..(3407)
<223> OTHER INFORMATION: R = A or G
<220> FEATURE:
<221> NAME/KEY: misc_feature
<222> LOCATION: (5992)..(5992)
<223> OTHER INFORMATION: Y = C or T
<220> FEATURE:
<221> NAME/KEY: misc_feature
<222> LOCATION: (5994)..(5994)
<223> OTHER INFORMATION: Y = C or T
      R = A or G
<220> FEATURE:
<221> NAME/KEY: misc_feature
<222> LOCATION: (5995)..(5995)
<223> OTHER INFORMATION: K= G or T
<220> FEATURE:
<221> NAME/KEY: misc_feature
<222> LOCATION: (5998)..(5998)
<223> OTHER INFORMATION: R = A or G
<220> FEATURE:
<221> NAME/KEY: misc_feature
<222> LOCATION: (6001)..(6001)
<223> OTHER INFORMATION: Y = C or T
<220> FEATURE:
<221> NAME/KEY: misc_feature
<222> LOCATION: (6704)..(6704)
<223> OTHER INFORMATION: R = A or G
<220> FEATURE:
<221> NAME/KEY: misc_feature
```

<222> LOCATION: (8811)..(8811)
<223> OTHER INFORMATION: Y = C or T
<220> FEATURE:
<221> NAME/KEY: misc_feature
<222> LOCATION: (9777)..(9777)
<223> OTHER INFORMATION: R = A or G
<220> FEATURE:
<221> NAME/KEY: misc_feature
<222> LOCATION: (11935)..(11935)
<223> OTHER INFORMATION: Y = C or T
<220> FEATURE:
<221> NAME/KEY: misc_feature
<222> LOCATION: (13527)..(13527)
<223> OTHER INFORMATION: M = A or C
<220> FEATURE:
<221> NAME/KEY: misc_feature
<222> LOCATION: (14133)..(14133)
<223> OTHER INFORMATION: Y = C or T
<220> FEATURE:
<221> NAME/KEY: misc_feature
<222> LOCATION: (14947)..(14947)
<223> OTHER INFORMATION: Y = C or T

<400> SEQUENCE: 5

```
atgacgtata ggtgttggct ctatgccacg acatttgtat tgtcaggagc tgtgaccact      60
ggcacagccc aaagcttgct gcacagaaac acccttctgt gacggcctcc ttcaggggag     120
tttaggggtt tatccctagc accttgtttc tggagttgca ctgctttacg gtctctccac     180
ccctttaacc atgtctggga ttcttgatcg gtgcacgtgc accccaatg ccagggtgtt     240
tatggcagag ggccaagtct actgcacacg atgtctcagt gcacggtccc tccttcccct     300
gaatctccaa gtccctgagc tcggagtgtt gggcttgttt tataggcccg aagagccgct     360
ccggtggacg ttgccacgcg cattccccac tgttgagtgc tcccctgctg gggcttgttg     420
gctttctgca atttttccaa ttgcacgaat gaccagtgga aacctgaact ttcaacaaag     480
attagtgcgg gtcgcagctg agctttacaa agccggctgc ctcaccccta tagtcctaaa     540
gaatctacaa gtctatgaac ggggttgccg atggtacccc atcgttggac ctgtccctgg     600
agttgccgtt ttcgccaact ccctacatgt gagtgataga cctttcccag gggstactca     660
cgtgctaacc aacctgccgc tcccgcagag acctaagcct gaagattttt gccccttga    720
gtgtgctatg gctgmcgtct atgayattgg tcatgacgcc gttatgttcg tggccgaagg     780
gagagtctcc tgggctccgc gtggtggggg aaaaggaaaa tttgaaactg ttcccgagga     840
gttgaggttg attgcagagc aactttatac ctccttcccg ccccaccacg tggtggacat     900
gtcgaaattc accttacgg cccctgagtg tggtgcttcc atgcgagtcg aacgccatta     960
tggctgcctc cccgccggca ctgtccctga cggcaattgc tggtggagtt tgtttagctc    1020
gctcccattg gaaatccagt acaaagaaat tcgccacgcc acccaatttg ctatcaaac    1080
taagcatggc gttgctggca agtacctaca gcggaggctg caagttaatg gtctccgagc    1140
agtggttgac tcgaatggac ctatcgtcat acagtacttc tctgttaagg agagctggat    1200
ccgccacgtg aaactggcgg aagagtttga ctaccctggg tttgaggatc tcctcaggat    1260
aagagtcgag cccaacacgt tgccattgtc caacaaggac gagaaaatct tccggtttgg    1320
tgggtgcaag tggtacggtg ctgggaagag ggcaaggagg gcacgtgcaa gtgcagtcac    1380
cgcagtcgcc ggtcacgctc cgcctactcg tgaaacccag caagccaaga acacgaggc    1440
tgctagtgcc aacaaggctg agcttcttga acgctactcc ccgcctgctg aagggaattg    1500
cggctggcac tgtatttccg ccatcgccaa tcggatggta aattctaagt ttgagactgc    1560
ccttcccgaa agagtgagat ccccagaaga ctgggctact gatgaggatc ttgtgaatac    1620
```

```
tatccaratc ctcaggctcc cygcggcctt agacaggaac ggcgcctgtg caagcgccaa    1680
gtacatcctt aagctggaag gtgagcactg gactgtttca gtgattcccg gaatgycccc    1740
ttccttgctc ccccttgaat gcgttcaggg ttgctgtgag cataagggta atcttggttc    1800
tccgaacgcg gtcggggttt ttggattcga ccctgccagc cttgaccgac ttgctggggt    1860
gatgcacctg cccagcagtg ccatcccagc cgctctggcc gagttgtctg gcgaccttga    1920
tcgtccaact tccccggccg ccactgtgtg gactgtctcg cagttttatg ctcgtcatag    1980
tggaggrgag catcctgatc aaaagtgttt aaaaaaaatt atcagtctct gtgaggtgat    2040
cgagagttgt tgctgttctc rgaacaaaac taaccgggtc accccggaag aggtcacagc    2100
aaagattgat ctgtacccttt ttggtgcagc aagtcttgaa gaatgcttgg ccaggcttga    2160
raaagctcgc ccgccaagcg tattaracac ctcctttgat tgggatgttg tgctccctgg    2220
tgttgggrcg gctgctcaag cagcaaaact gcccctcacc aaccagcgtc acgtctagc     2280
cactgttgtg acycaaaggt ctttgccgaa atttcaacct cgaaaagcgg agtctgtcaa    2340
gagcctacca gagagcaggc cactccctgc cccgcgcaaa aagattaggt ccaggtgtgg    2400
tagtccgatt tcattgggcg gcaatctccc tgacagccag aaagacttgg ccggtggttc    2460
ctttgatttc ccaaccctac ctgagttggt ggtaagctcg agtgagtctg tgcctgtccc    2520
tgcaccgcgc agggttgtgt cccgattagt gtcgtctccg atagtgtcga cccctgtgcc    2580
cgcaccacga cgtgggcttc ggcaggtgga gggaatgaat ttggcggcag tgactctagc    2640
gtgccaggac gagcccctcg atttgtctgc gtcctcgcag actgaatatg aggcgtcccc    2700
cttggcattg ccgctgagtg aggatgtcct ggcggtggag agacgagaag ttgaagaagt    2760
cctgagcgga atatcgggca tgtcagatga catcaggttg gcgcccgtgt catcaagtag    2820
ctccctgtca agcatagaga tcacgcgtcc aaagtactca gctcaagcca tcattaactc    2880
aggtgggccc tgttgtgggc acctccagga ggtgaaagag aaataccctta atgtgatgcg    2940
tgaggcatgt gatgcgacca agcttgatga ccctgccacg caagaatggc tttcccgtat    3000
gtgggatagg gtagacatgc taacctggcg caaacgtcc atttttcagg cgcctttcac     3060
cttggctgac aagtttaagt ccctcccgaa gatgatactc gaaacaccgc cgccctaccc    3120
ttgtgggttt gtgatgatgc cccgcacgcc tgcaccttct gtaggtgcgg agagcgacct    3180
caccgttggc tcagttgcta ctgaagatgt cccgcgcatt ctcgggaagg tacaaggtgt    3240
tggcgaaacg accgaccagg gaccccttggc actcttcgca gatgaattgg cagatgacca    3300
acctgctaga gaaccccgga cacaaacccc tcctgcaagc gcaggtggcg ccggcttagt    3360
tttggattct ggagggtcgc cggagctcac tgacctgccg cttccaracg gtacagacgc    3420
gggcggaggg ggaccgttac acacggtcaa gaagaaagct gagaggtgct ttgaccagct    3480
gagccgtcgg gttttttgaca ttgtctccca tctccctgtc ttcttctcac gccttttcaa    3540
gcctgacagt cactactctt cgggtgactg gagttttgca gcttttactt tattgtgcct    3600
ctttctatgt tacagttacc cggcctttgg tgttgctccc ctattgggtg tatttttctgg   3660
gtcttctcgg cgcgttcgca tgggggtttt tggctgctgg ttggctttcg ctgttggttt    3720
gttcaagcct gcacccgacc cagtcggtgc tgcttgtgag tttgattcgc cagagtgtag    3780
agacatcctt cattctttg agctcctgca accttgggat cctgttcgca gccttgtggt    3840
gggacccgtc ggtctcggtc ttgccattat tggcaggtta ctgggcgggg cacgctacgt    3900
ctggctgctt ttgcttaggc ttggcatcgt ttcagactgt atcttggctg gagcttacgt    3960
gctttcgcaa ggtaggtgta aaaagtgttg gggatcttgt ataagaactg ccccagtga    4020
```

```
ggtcgccttc aatgtgtttc ccttcacacg tgcaaccaga tcgtcacttg tcgacctgtg    4080
cgaccggttt tgtgcgccca agggcatgga ccccatcttc ctcgccactg gatggcgcgg    4140
atgctggtcc ggccagagcc ccgttgagca acccactgag aaacccattg cattcgccca    4200
gttggatgag aagaaaatca cggcaaggac tgtggttgcc caaccttatg accccaacca    4260
agctgtgaag tgcttacgag tcttgcaggc gggtggggcg atggtggctg aggcgattcc    4320
aaaagtggtt aaggtctctg ctgtcccatt tcgagccccc ttcttcccca ccggagtgaa    4380
agttgatcct gaatgcaggg tcgtggttga cccagacacc ttcacaactg ctctccggtc    4440
cggctactcc accacaaacc tcattcttgg tgtgggggat tttgcccagc tgaatgggtt    4500
gaaaatcaga caaatttcca agccttcagg aggaggccca tacctcatgg cggccttaca    4560
tgtcgcttgc tcgatggcct tgcacatgct cgttgggatt tatgttaccg cggtgggttc    4620
ttgtggttct ggcactaacg atccgtggtg cactaacccg tttgccgtcc ctgtctacgg    4680
gcctggctct ctttgcacgt ccaggttgtg catctcccag catggcctta ctctgccttt    4740
aacagcgctt gtggcggggt ttggtattca ggaagttgct ttggttgttt taatctttgc    4800
ttccatcggg ggtatggctc acaggttgag ttgcaaggcc gatgtgctgt gcattctgct    4860
tgcaattgcc agctatgttt gggtaccctt cacctggttg cttttgtgtgt tccttgctg    4920 gttgcgctgg ttttctttgc atcccctcac cattctatgg ttggtgtttt tttgatttc    4980 tgtgaacatg ccctcaggaa tcttggcttt agtgttgttg atctctctct ggctccttgg    5040
tcgctatacc aatgtcgctg gccttgtcac cccttatgac attcaccatt acaccaacgg    5100
ccccccgcgg cgttgccgcct tggccactgc cccggatggg acctatttgg ctgctgtccg    5160
ccgcgctgcg ttgactggcc gtaccatgct gtttaccccg tctcaacttg ggtcactcct    5220
tgagggcgcc tttagaaccc aaaagccttc actgaatacc gtcaatgtgg ttgggtcctc    5280
catgggctcc ggcggggtgt tcaccattga cgggaaaatt aaatgcgtga ccgccgcaca    5340
tatcctcacg ggtaactctg ctagggtctc tgggggttggc ttcaatcaaa tgttggattt    5400
tgatgtaaaa ggggattttg ccatagccga ttgtccgggt tggcaaggag tcgctcccaa    5460
gtcccagatc tgcaaggatg ggtggactgg ccgcgcttat tggctaacgt cctctggcgt    5520
cgaacccggc gtcattggta ggggattcgc cttttgtttc accgcgtgcg gcgattccgg    5580
gtccccagtg atcaccgagg ccggagagct tgtcggagtc cacacgggat caaacaaaca    5640
aggaggaggc attgtcacgc gcccttcagg ccagttttgt aatgtgacac ccaccaaact    5700
aagtgaattg agtgaattct tcgccggacc cagggtcccg cttggtgatg tgaaggttgg    5760
caaccacata atcaaagata cagatgaggt gccctcagat cttttgcgcct tgcttgctgc    5820 caagcccgag ttggaaggag gcctctccac cgttcaactt ctgtgcgtgt tttttctcct    5880
atggagaatg atgggacatg cctggacgcc cttggttgct gttggttttt tcatcttgaa    5940
tgaratcctc ccagcggtcc tggtccggag tgttttctcc tttggaatgt tygykctrtc    6000
ytggctcacg ccatggtctg cgcaagttct gatgatcagg cttctgacag cagctcttaa    6060
caggaacaga tggtcacttg ccttttttcag cctcggtgca gtgaccggtt ttgtcgcaga    6120
tcttgcggcc actcagggc atccgttgca ggcagtgatg aatttgagca cctatgcatt    6180
cctgcctcgg atgatggttg tgacctcacc agtcccagtg atcacgtgtg tgtcgtgca    6240 cctacttgcc atcattttgt acttgtttaa gtaccgtggc ctgcaccata tccttgttgg    6300
cgatggagtg ttctctgcgg cttttcttctt gagatacttt gccgagggaa agttgaggga    6360
```

```
aggggtgtcg caatcctgcg gaatgaatca tgagtctctg actggtgccc tcgctatgag    6420
actcaatgac gaggacttgg atttccttat gaaatggact gattttaagt gctttgtttc    6480
tgcgtccaac atgaggaatg cggcgggtca gtttatcgag gccgcttatg cgaaagcgat    6540
cagggtggaa cttgcccagt tagtgcaggt cgacaaggtt cggggtgttt tagccaaact    6600
tgaagctttt gctgacaccg tggcgcccca tctttcaccc ggcgacattg ttgttgttct    6660
tggtcatacg cccgttggca gcatctttga cttaaagatt ggcratgcca agcacaccct    6720
acaagccatc gagaccagag tccttgctgg gtccaggatg accgtggcgc gtgtcgttga    6780
tccgactccc gcgccgccac ccgtacccgt gcccgttcct ctcccaccga agttttaga    6840 gaacggcccc agtgcctggg gggatgaaga ccgcctgaac aaaaagaagc ggcgcaagat    6900
ggaagccgtt ggcgtttacg tcatgggcgg gaaaaagtac cagaaatttt gggataagaa    6960
ttctggtgat gtgttctatg aggaagtcca cgacaacaca gatgcgtggg aatgccttag    7020
agctgacgac cctgccgact ggatcctga gggggaacc ttgtgtggac acgtcaccat    7080
agagaatagg ccttaccatg tttacgcctc cccgtctggt aggaagttcc tggtccctgc    7140
cgacccagag aatgggaaag cccagtggga agctgcaaag cttccatag agcaggccct   7200 tggtatgatg aacgttgacg gcgagctgac cgccaaagaa ctggagaaat tgaagagaat    7260
aattgacaaa ctccagggcc tgactaagga gcagtgttta aactgttagc cgccagcggc    7320
ttgacccgct gtggtcgcgg cggcttggtt attactgaga cagcggtaaa aatagtcaga    7380
ttccacaatc ggaccttcac cctggggcct gtgaatttga agtggccag cgaagttgag    7440 ttgaaagacg ccgtcgagca caaccaacac ccggttgcaa gaccagttga cggtggcgtt    7500
gtgctcctgc gctctgcagt tccttcgctt atagacgtct tgatctccgg tgccgacgca    7560
tctccccagt tgctcgccca tcacggtcca ggaaacactg ggattgatgg cacgctctgg    7620
gattttgagt ccgtagccac taaagaggaa gtcgcactta gtgcacaaat aatacaggct    7680
tgtggcatta ggcgtggcga tgctcctgag attggcctcc cttacaagct gcaccctgtt    7740
agggacaacc ctgaacgtgt aaaagggtt ttgaaaaaca caaggtttgg agacatacct    7800
tacaagaccc ctagcgacac tgggagccca gtacatgcgg ccgcctgcct tacgcctaat    7860
gccaccccgg tgactgatgg gcgctccgtc ttggccacga ctatgccctc cgggtttgag    7920
ttgtatgtgc cgaccattcc agcgtctgtc cttgattacc ttgattccag gccagactgc    7980
cctaaacagt tgacggagca cgggtgtgaa aatgctgcat tgagagacct ctccaaatat    8040
gacttgtcca cccaaggttt tgttttgccc ggagtcctcc gcctcgtgcg gaaatacttg    8100
tttgcccacg tgggcaagtg cccacctgtc catcggccct ccacctaccc ggccaagaat    8160
tccatggctg gaataaacgg gaataggttc ccgaccaagg acattcagag catccctgag    8220
atcgacgttc tgtgtgcaca ggctgtacga gagaactggc agaccgttac cccttgcacc    8280
ctcaagaagc agtattgcgg gaagaagaaa accaggacca tactcggtac caataacttc    8340
attgcgctgg cccaccgggc agcactgagt ggtgtcaccc agggcttcat gaaaaggcg    8400 tttaactcgc ccatcgccct cgggaagaac aaattcaagg agctacagac tccggtcctg    8460
ggcagatgtc ttgaggctga tcttgcctct tgcgatcggt ccactcccgc gattgtccgc    8520
tggtttgccg cccatctcct ttatgaactt gcctgcgctg aggagcacct accgtcgtat    8580
gtgctgaatt gctgccatga cctattggtc acgcagtccg gtgcggtgac taagagaggt    8640
ggcctgtcat ctggtgatcc gatcacctct gtatccaaca ccatttacag tctggtaatt    8700
tatgcgcagc acatggtgct cagttacttc aaaagtggtc acccacatgg tctcctgtat    8760
```

```
ctccaggacc agctaaagtt tgaggacatg cttaaggttc agcccctgat ygtctactcg    8820
gatgatcttg tgctgtatgc cgagtccccc accatgccaa actaccactg gtgggttgag    8880
catctgaact tgatgctagg gtttcagacg gacccaaaga agacaaccat tactgactcg    8940
ccatcttttc tgggctgtag gataatgaat gggcgtcagc tagtcccaaa ccgtgacagg    9000
attctcgcag ctcttgccta ccacatgaag gcgaataatg tttctgagta ctacgcctcc    9060
gctgctgcaa tactcatgga cagttgtgct tgtctggagt acgaccctga atggtttgaa    9120
gaacttgtgg ttggaatggc gctatgcgcc cgcaaggacg gctatagctt ccccggcccg    9180
ccgttcttct tatccatgtg ggagaaactt aagtccaatt atgaggggaa gaagtcaagg    9240
gtatgtgggt actgcggagc ttcggccccg tatgccactg cctgtggtct tgacgtctgt    9300
gtttaccaca ctcactttca ccagcattgt ccagtcataa tctggtgtgg ccaccctgca    9360
ggttccaggt cctgtgatga gtgcaaatcc cccatgggga aaggcacaag ccctctggat    9420
gaggttttga gacaagtccc gtataagcct ccacggaccg tcctcatgca tgtggagcag    9480
ggcctcaccc cccttgaccc aggcagatat cagacccgcc gtgggttggt tgccgttagg    9540
cgcgggatca ggggaaatga agttgaccta ccagatggtg attatgctag caccgcctta    9600
ctcccaacct gtaaagagat caacatggtt gctgttgctt ctaatgtgtt gcgcagcaga    9660
tttatcatcg gtccacccgg tgctgggaaa acatactggc tccttcaaca ggtccaggat    9720
ggtgatgtca tatacacacc gacccatcag accatgcttg acatgatcaa gctttrggg    9780 acgtgccggt ttaacgtccc ggcaggcaca acgctgcaat tccccgtccc ctcccgcacc    9840
ggtccgtggg ttcgcatcct ggccggcggg tggtgtcctg gcaaaaactc cttcctggac    9900
gaagctgcgt attgtaatca tcttgatgtc ttgaggcttc ttagcaaaac cactctcacc    9960
tgtttggggg acttcaaaca actccaccca gtgggttttg attctcattg ctatgtcttt   10020
gacattatgc ctcagactca attgaagacc atctggagat ttggacagaa catctgtgat   10080
gccatccaac cagactacag agacaagctt atgtccatgg tcaacacaac tcgtgtaact   10140
tatgtggaaa aacctgtcaa atatgggcaa gtcctcaccc cttaccatag ggaccgagag   10200
gatagcgcca ttaccattga ctccagtcaa ggcgccacat ttgatgtggt tacactgcat   10260
ttgcccacga aagattcact caacaaacaa agggcccttg ttgctattac cagggcaaga   10320
catgccatct ttgtgtatga cccatatagg caactgcaga gcctatttga tcttcctgca   10380
aaaagcacgc ccgtcaactt ggccgtgcac cacgatgggc aactgattgt gctagataga   10440
aataacaaag aatgcacggt tgcccaagct ctgggtaatg gtgacaaatt tagggccaca   10500
gacaagcgcg ttgtggattc tctccgcgcc atttgtgctg acctagaagg gtcgagctct   10560
ccactcccca aggttgcaca taatttgggg ttttatttct cacctgattt gatacagttt   10620
gccaagcttc caatagaact tgcgccacac tggccagtag tgacgaccca agacaataaa   10680
aactggccag atcggctggt tgccagccta cgccctattc acaaacatag ccgtgcgtgt   10740
atcggtgccg gctatatggt gggcccctcg gtgttttag gcacccctgg ggttgtgtca   10800
tactatctta caaaatttgt taagggcgag gctcaagtgc ttcggaaaac ggtcttcagt   10860
accggccgaa ttgaggtgga ttgccgggaa tatcttgacg accgggagcg ggaagttgca   10920
gcgtccctcc cacacgcctt tatcggcgac gtcaaaggca ctaccgtcgg agggtgtcat   10980
cacatcacct ccaaatacct tccgcgcttc ctccccaagg aatcagttgc ggtagtcggg   11040
gtttcaagcc ccggaaaagc agcgaaagca gtgtgtacat tgacagatgt gtacctccca   11100
```

```
gaccttgaag cttacctcca tcctaagacc ctgtccaagt gctggaaaat gatgttggac    11160
ttcaaagaag ttcggctgat ggtctggaag gacaagacgg cctatttcca actcgaaggt    11220
cgccatttca cctggtatca acttgctagc tatgcctcgt acatccgtgt tcctttaaac    11280
tccacggtgt acctggaccc ctgcatgggc cccgcccttt gcaacagaaa agttgttggg    11340
tccactcatt ggggagctga cctcgcagtc accccttatg attatggggc aagaattatt    11400
ttgtctagtg cgtaccatgg tgagatgcct cctgggtaca agattctggc gtgcgcggag    11460
ttctcgctgg acgacccagt cagatacaag cacacttggg ggtttgagtc ggatacagcg    11520
tacttgtacg agttcactgg aaacggtgag gactgggagg attataacga cgcgtttcgt    11580
gcgcgacaga aggaaagat ttacaaggcc actgccacca gcctgaagtt ccattttcct     11640
ccgggtcata ccgttgaacc aactttgggc ctagactgaa atgaaatggg ggctgtgcag    11700
agcctatttg ataaaattgg ccaactgttt gtggacgctt tcacggagtt cttggtgtcc    11760
attgttgata tcatcatatt tttgccatt tgttcggct tcacaatcgc cggttggctg      11820
gtggtctttt gcatcagatt ggtttgctcc gcgatactcc gttcgcgctc tgccgttcac    11880
cctgagcaat tacagaagat cctatgaggc atttctctcc cagtgccgga cggayattcc    11940
cacctgggga actaaacatc ccttggggat gctctggcac cacaaggtgt cgaccctaat    12000
tgatgaaatg gtgtcgcgtc gaatgtaccg catcatggaa caagcagggc aggctgcctg    12060
gaaacaggtg gtgaccgagg caacgttgtc tcgtattagt agcttggatg tggtggctca    12120
tttccagcac cttgccgcca tagaagccga gacttgtaaa tacttggcct cccggctgcc    12180
aatgctgcac aacctgcgca tgacagggtc aaatgtaacc atagtgtata atagctctct    12240
agaacaggtg tttgctgttt tcccgaccct cagttcccgg ccaaagcttc atgattttcg    12300
gcaatggcta atagctgtgc attcctccat attctcttct gttgcggctt cctgtacccct    12360 tttcgtcgtg ctgtggttgc ggcttccaat aatacgtact gttttggtt tccactggtt     12420 aggggcaatt tttccttcga gctcacagtg aactacacgg tgtgtcctcc ctgcctcacc    12480
cggcaggcgg ccgcagagat ctacgaacct agtgggtctc tttggtgcag gatagggcac    12540
gatcgatgct cggaggacga tcacgacgag ctaggatttc tggtgccgcc tggcctctcc    12600
agcgaaggcc acttgaccag tgtttacgcc tggttggcgt tcttgtcctt cagttacacg    12660
gcccagtttc accccgagat attcgggata gggaatgtga gtaaagttta tgttgacatc    12720
aagcatcaat ttatttgcgc tgttcatgac gggcaaaaca ccaccttgcc tcgccatgac    12780
aacgtctcag ccgtgttcca gacttattac cagcatcagg tcgacggcgg caattggttt    12840
cacctggaat ggctgcgccc cttcttctcc tcctggttgg ttttgaacgt ctcttggttt    12900
ctcaggcgtt cgcctgtaag ccgtgtttca gttcgagtct ctcagacatt aagaccaaca    12960
ccaccgcagc tgcaggcttt gctgtcctcc aagacatcag ttgtcttagg catggccact    13020
cgtcctctga ggcgactcgc aaaagccgtc aatgtcgcac ggcgatagga acgcccgtat    13080
acattactgt cacagccaat gtaacagatg agaattattt gcattcctct gaccttctca    13140
tgctttcctc ttgcctttc tacgcttccg agatgagtga aaagggattt gaagtgatat     13200
ttggcaatgt gtcaggcata gtggctgtgt gtgtcaactt taccagctat gtccaacatg    13260
tcaaggagtt cacccagcgc tccttggtgg ttgaccatgt gcggttactt cattttatga    13320
cacctgagac tatgaggtgg gcgaccgttt tagcctgtct ttttgccatt ctgttggcca    13380
tttgaatgtt cagatatgtt ggggaaatgc ttgaccgcgg gctattgctc gcaattgctt    13440
tttttgtggt gtatcgtgcc gttctgtctt gctgcgctcg tcaacgccga cagcaacagc    13500
```

```
agctcccatt tacagttgat ttataamtta acgatatgtg agctgaatgg cacagactgg   13560
ctgaacaatc attttagttg ggcagtggag actttcgtta tctttcctgt gttgactcat   13620
attgtttcct acggcgccct cactaccagc cacctccttg acacggtcgg cctgatcact   13680
gtgtccaccg ccgatactg ccataagcgg tatgtcttga gtagcatcta tgctgtctgc   13740
gccctggctg cgctgatttg cttcgtcatc aggttgacga aaaattgtat gtcctggcgc   13800
tactcatgta ccagatatac caactttctt ctggacacca agggcagact ctatcgctgg   13860
cggtcacccg tcatcataga gaaaaggggt aaaattgagg ttggaggtga cctgatcgac   13920
ctcaagagag ttgtgcttga tggttccgcg gcaaccctg taaccaaagt ttcagcggaa   13980
caatggggtc gtccttagac gacttctgca atgacagcac ggctccacaa aaggtgatct   14040
tggcatttc tatcacctac acaccagtga tgatatatgc cctaaaggtg agtcgtggcc   14100
ggctgctagg gcttttacac cttttgattt ttytaaactg tgcttttacc ttcgggtata   14160
tgacatttgt gcactttcag agcacaaaca gagttgcact cactatggga gcagtagtcg   14220
cgctcctttg ggggtgtac tcagctatag aaacctggaa attcatcact tccagatgcc   14280
gtttgtgctt gctaggccgc aagtacattc tggcccctgc ccaccacgtt gagagtgccg   14340
caggctttca tccgattgcg gcaagtgata accacgcatt tgtcgtccgg cgtcccggtt   14400
ccactacggt taacggcaca ttggtgcccg ggttgaaaag cctcgtgttg ggtggcagaa   14460
gagctgtcaa acggggagtg gtaaaacctcg ttaaatatgc caaataacaa cggcaggcag   14520
cagaagaaaa agaaagggga cggccagcca gtcaatcagc tgtgccaaat gttgggcagg   14580
atcatcgccc agcaaaacca gtccagaggt aagggaccgg ggaagaaaag taagaagaaa   14640
agcccggaga agccccattt tcctctcgcg actgaagatg acgttagaca tcacttcacc   14700
cctagtgagc ggcaattgtg tctgtcgtca atccagactg cctttaacca aggcgctgga   14760
acttgtaccc tgtcggattc agggagaata agttacgctg tggagtttag tttgcctacg   14820
catcatactg tgcgcctaat tcgcgtcaca gcatcaccct cagcatgatg agctggcatt   14880
cttgagacat cccagtgttt gaattggaag gatgtgtggt gaatggcact gattgatatt   14940
gtgcctytaa gtcacctatt caattagggc gaccgtatgg gggtaatatt taattggcgt   15000
gaaccatgcg gccgaaatt                                                 15019
```

<210> SEQ ID NO 6  
<211> LENGTH: 15019  
<212> TYPE: DNA  
<213> ORGANISM: Artificial Sequence
<220> FEATURE:
<223> OTHER INFORMATION: Porcine reproductive and respiratory syndrome virus, strain MN184B
<220> FEATURE:
<221> NAME/KEY: misc_feature
<222> LOCATION: (1540)..(1540)
<223> OTHER INFORMATION: R = A or G
<220> FEATURE:
<221> NAME/KEY: misc_feature
<222> LOCATION: (1546)..(1546)
<223> OTHER INFORMATION: Y = C or T
<220> FEATURE:
<221> NAME/KEY: misc_feature
<222> LOCATION: (1549)..(1549)
<223> OTHER INFORMATION: R = C or A
<220> FEATURE:
<221> NAME/KEY: misc_feature
<222> LOCATION: (1558)..(1558)
<223> OTHER INFORMATION: Y = C or T
<220> FEATURE:
<221> NAME/KEY: misc_feature

```
<222> LOCATION: (1559)..(1559)
<223> OTHER INFORMATION: R = C or A
<220> FEATURE:
<221> NAME/KEY: misc_feature
<222> LOCATION: (2110)..(2110)
<223> OTHER INFORMATION: Y = C or T
<220> FEATURE:
<221> NAME/KEY: misc_feature
<222> LOCATION: (2161)..(2161)
<223> OTHER INFORMATION: R = C or A
<220> FEATURE:
<221> NAME/KEY: misc_feature
<222> LOCATION: (2186)..(2186)
<223> OTHER INFORMATION: R = C or A
<220> FEATURE:
<221> NAME/KEY: misc_feature
<222> LOCATION: (5389)..(5389)
<223> OTHER INFORMATION: R = C or A
<220> FEATURE:
<221> NAME/KEY: misc_feature
<222> LOCATION: (5687)..(5687)
<223> OTHER INFORMATION: R = C or A
<220> FEATURE:
<221> NAME/KEY: misc_feature
<222> LOCATION: (5694)..(5694)
<223> OTHER INFORMATION: Y = C or T
<220> FEATURE:
<221> NAME/KEY: misc_feature
<222> LOCATION: (5698)..(5698)
<223> OTHER INFORMATION: R = C or A
<220> FEATURE:
<221> NAME/KEY: misc_feature
<222> LOCATION: (5699)..(5699)
<223> OTHER INFORMATION: Y = C or T
<220> FEATURE:
<221> NAME/KEY: misc_feature
<222> LOCATION: (5704)..(5704)
<223> OTHER INFORMATION: Y = C or T
<220> FEATURE:
<221> NAME/KEY: misc_feature
<222> LOCATION: (5710)..(5710)
<223> OTHER INFORMATION: R = C or A
<220> FEATURE:
<221> NAME/KEY: misc_feature
<222> LOCATION: (5722)..(5722)
<223> OTHER INFORMATION: Y = C or T
<220> FEATURE:
<221> NAME/KEY: misc_feature
<222> LOCATION: (5724)..(5724)
<223> OTHER INFORMATION: Y = C or T
<220> FEATURE:
<221> NAME/KEY: misc_feature
<222> LOCATION: (5728)..(5728)
<223> OTHER INFORMATION: R = C or A
<220> FEATURE:
<221> NAME/KEY: misc_feature
<222> LOCATION: (5733)..(5733)
<223> OTHER INFORMATION: R = C or A
<220> FEATURE:
<221> NAME/KEY: misc_feature
<222> LOCATION: (5743)..(5743)
<223> OTHER INFORMATION: Y = C or T
<220> FEATURE:
<221> NAME/KEY: misc_feature
<222> LOCATION: (5749)..(5749)
<223> OTHER INFORMATION: Y = C or T
<220> FEATURE:
<221> NAME/KEY: misc_feature
<222> LOCATION: (6511)..(6511)
<223> OTHER INFORMATION: R = C or A
<220> FEATURE:
<221> NAME/KEY: misc_feature
<222> LOCATION: (6523)..(6523)
<223> OTHER INFORMATION: Y = C or T
<220> FEATURE:
<221> NAME/KEY: misc_feature
<222> LOCATION: (8050)..(8050)
<223> OTHER INFORMATION: R = C or A
<220> FEATURE:
```

```
<221> NAME/KEY: misc_feature
<222> LOCATION: (9345)..(9345)
<223> OTHER INFORMATION: R = C or A
<220> FEATURE:
<221> NAME/KEY: misc_feature
<222> LOCATION: (10309)..(10309)
<223> OTHER INFORMATION: R = C or A
<220> FEATURE:
<221> NAME/KEY: misc_feature
<222> LOCATION: (10419)..(10419)
<223> OTHER INFORMATION: R = C or A
<220> FEATURE:
<221> NAME/KEY: misc_feature
<222> LOCATION: (14947)..(14947)
<223> OTHER INFORMATION: Y = C or T
<220> FEATURE:
<221> NAME/KEY: misc_feature
<222> LOCATION: (15018)..(15018)
<223> OTHER INFORMATION: Y = C or T

<400> SEQUENCE: 6
atgacgtata ggtgttggct ctatgccacg acatttgtat tgtcaggagc tgtgaccact      60
ggcacagccc aaagcttgct gcacagaaac acccttctgt gacggcctcc ttcaggggag     120
tttaggggtt tgtccctagc accttgtttc tggagttgca ctgctttacg gtctctccac     180 cccttaacc atgtctggga ttcttgatcg gtgcacgtgc accccaatg ccagggtgtt       240 tatggcagag ggccaagtct actgcacacg atgtctcagt gcacggtccc tccttcccct    300
gaatctccaa gtctctgagc tcggagtgtt gggcttgttt tataggcctg aagagccgct    360
ccggtggacg ttgccacgcg cattccccac tgttgagtgc tcccctgctg gggcttgttg    420
gctttctgca atttttccaa ttgcacgaat gaccagtgga aacctgaact ttcaacaaag    480
attagtgcgg gtcgcagctg agctttacaa agccggctgc ctcaccccta cagtcctaaa    540
gagtctacaa gtctatgaac ggggttgccg ctggtacccc atcgttggac ctgtccctgg    600
agttgccgtt ttcgccaact ccctacatgt gagtgataga cctttcccag gtgctactca    660
cgtgctaacc aacctgccgc tcccgcagag acctaagcct gaagattttt gccccttga     720 gtgtgctatg gctgccgtct atgacattgg tcatgacgcc gttatgttcg tggccgaagg    780
gagagtctct tgggctccgc gtggtgggga aaaaggaaaa tttgaaactg ttcccgagga    840
gttggggttg attgcagagc aactttatac ctccttcccg ccccaccact tggtggacat    900
gtcgaaattc acctttacgg ccccctgagtg tggtgcttcc atgcgagtcg aacgccagta    960
tggctgcctc cccgctggca ctgtccctga cggcaattgc tggtggagct tgtttagctc   1020
gctcccattg gaagtccagt ataaagaaat tcgctacgcc acccaatttg gctatcaaac   1080
taagcatggc gttgctggca agtacctaca gcggaggctg caaattaatg gtctccgagc   1140
agtggttgac tcgaatggac ccatcgtcat acagtacttc tctgttaagg agagctggat   1200
ccgccacgtg aaactggcgg aagagtttga ctaccctggg tttgaggatc tcctcaggat   1260
aagagtcgag cccaacacgt tgccattgtc caacaaggac gagaaaatct ccggttttgg   1320
tgggtgcaag tggtacggtg ctgggaagag ggcaaggagg gcacgtgcaa gtgcagtcac   1380
cgcagtcgcc ggtcacgctc cgcctactcg tgaaacccag caagccaaga aacacgaagc   1440
tgctagtgcc aacaaggctg agcttcttga acgctactcc ccgcctgctg aagggaattg   1500
cggctggcac tgtatctccg ccatcgccaa ccggatggtr aattcyaart ttgaaacyrc   1560
ccttcccgaa agagtgagac ctccagatga ctgggctact gacgaggatc ttgtgaatgc   1620
catccaaatc ctcagactcc ctgcggcctt agacaggaac ggtgcttgta ctagcgccaa   1680
gtacgtactt aagctggaag gtgagcattg gactgtcact gtgacccctg ggatgtcccc   1740
```

```
ttctttgctc cctcttgaat gtgttcaggg ctgttgtggg cacaaggcg gtcttggttc    1800 cccagatgca gtcgaggtct ccggatttga ccctgcctgc cttgaccggc tggctgaggt    1860
gatgcacctg cctagcagtg ctatcccagc cgctctggcc gaaatgtctg gcgattccga    1920
tcgttcggct tctccggtca ccaccgtgtg gactgtttcg cagttctttg cccgtcacag    1980
cggagggaat caccctgacc aagtgcgctt agggaaaatt atcagccttt gtcaggtgat    2040
tgaggactgc tgctgttccc agaacaaaac caaccgggtc accccggagg aggtcgcagc    2100
aaagattgay cagtaccttt ttggtgcagc aagtcttgaa gaatgcttgg ccaggcttga    2160
raaagctcgc ccgccaagcg tattaracac ctcctttgat tgggatgttg tgctccctgg    2220
tgtcggggcg gctgctcaag cagcaaaact gcccctcacc aaccagcgtc acgctctagc    2280
cactgttgtg actcaaaggt ctttgccgaa atttcaacct cgaaaagcgg agtctgtcaa    2340
gagcctacca gagagcaggc cctccctgc cccgcgcaaa aagattgggt ccaggtgtgg    2400
tagtccgatt tcattgggcg gcaatctccc tgacagccgg gaagacttgg ccggtggttc    2460
ctttgatttc ccaaccctac ctgagttggt ggcaagctcg agcgagcctg tgcctgtccc    2520
tgcaccgcgc agggttgtgt cccgattagt gtcgtctccg atagtgtcga cccctgtgcc    2580
cgcaccacga cgtgggcttc ggcaggtgga gggaatgaat ttggcggcgg tgactctagc    2640
gtgccaggac gagcccctcg atttgtctgc gtcctcgcag actgaatatg aggcgtcccc    2700
cttggcattg ccgctgagtg aggatgtcct ggcggtggag agacgagaag ttgaagaagt    2760
cctgagcgga atatcgggca tgccagatga catcaggttg gcgcccgtgt catcaagtag    2820
ctccctgtca agcatagaga tcacacgtcc aaagtactca gctcaagcca tcattaactc    2880
aggtgggccc tgttgtgggc acctccagga ggtaaaagag aaataccta atgtgatgcg    2940 tgaggcatgt gatgcgacca gcttgatga ccctgccacg caagaatggc tttcccgcat    3000
gtgggatagg gtagacatgc taacctggcg caacacgtcc attttcagg cgcctttcac    3060 cttggctgac aagtttaaga ccctcccgaa gatgatactc gaaacaccgc cgccctaccc    3120
ttgtgggttt gtgatgatgc cccgcacgcc tgcaccttct gtaggtgcgg agagcgacct    3180
caccgttggc tcagttgcta ctgaggatgt cccgcgcatt ctcgggaatg tacaaggtgt    3240
tggcgaaacg accgaccagg gacccttggc accttcgca gacgaattgg cagatgacca    3300
acttgctaga gaaccccgga cacaaacccc tcctgcaagc acaggtggcg ccggcttggt    3360
ttcggattct ggaaggtcgc cggagctcac tgacctgccg ctttcaaacg gtacagacgc    3420
gggcggaggg gggccgttac acacggtcaa gaagaaagct gagaggtgct ttgaccagct    3480
gagccgtcgg gttttttgaca ttgtctccca tctccctgtt ttcttctcac gccttttcaa    3540
gcctgacagt cactactctt cgggtgactg gagttttgca gcttttactt tattgtgcct    3600
ctttctatgt tacagttacc cagcctttgg tgttgctccc ctattgggtg tattttctgg    3660
gtcttctcgg cgcgttcgca tggggtttt tggctgctgg ttggcttttcg ctgttggttt    3720 gttcaagcct gcacccgacc cagtcggtgc tgcttgtgag tttgattcgc cagagtgtag    3780
agacatcctt cattcttttg agcttctgca accttgggac cctgttcgca gccttgtggt    3840
ggggcccgtc ggtctcggtc ttgccattat tggcaggtta ctgggcgggg cacgctacgt    3900
ctggctgctt ttgcttaggc ttggcatcgt ttcagactgt atcttggctg gagcttatgt    3960
gctttcgcaa ggtaggtgta aaagtgttg gggatcttgt ataagaactg ctcccagtga    4020
ggtcgccttc aatgtgtttc ccttcacacg tgcaaccaga tcgtcacttg tcgacctgtg    4080
```

-continued

```
cgaccggttt tgtgcgccca agggcatgga ccccatcttc ctcgccactg gatggcgcgg       4140
atgttggtcc ggccagagcc ccattgagca acccactgag aaacccattg cgttcgccca       4200
gttggatgaa aagaaaatca cggcaaggac tgtggttgcc caaccttatg accccaacca       4260
agctgtgaag tgcttacgag tcttgcaggc gggtggggcg atggtggctg aggcggttcc       4320
aaaagtggtt aaggtctctg ctgtcccatt tcgagccccc ttcttccccg ccggagtgaa       4380
agttgatcct gaatgcaggg tcgtggttga cccagacacc ttcacaactg ctctccggtc       4440
cggctactcc accacaaacc tcattcttgg tatgggggat tttgcccaac tgaatgggtt       4500
gaaaatcaga caaatttcca agccttcagg aggtggtcca tacctcatgg cggccttaca       4560
tgtcgcttgc tcgatggcct tgcacatgct cgttgggatt tatgttaccg cggtgggttc       4620
ttgtggttct ggcactaacg atccgtggtg cactaacccg tttgccgtcc ctgtctacgg       4680
gcctggctct ctttgcacgt ccaggttgtg catctcccag catggcctta ctctgccttt       4740
aacagcgctt gtggcggggt ttggcattca ggaagttgct ttggttgttt taatcttttac      4800
ttccatcggg ggtatggctc acaggttgag ctgcaaggcc gatgtgctgt gtattctgct       4860
tgcaattgcc agctatgttt gggtacccct cacctggttg cttttgtgtgt ttccttgctg      4920
gttgcgctgg ttttctttgc atcccctcac cattctatgg ttggtgtttt tcttgatttc       4980
tgtgaacatg ccctcaggaa tcttggcttt agtgttgttg atctctctct ggctccttgg       5040
tcgctatacc aatgtcgctg gccttgtcac cccttatgac attcaccatt acaccaacgg       5100
cccccgcggc gttgccgcct tggccactgc cccggatggg acctatttgg ctgctgtccg       5160
ccgcgctgcg ttgactggcc gcaccatgct gtttaccccg tctcaacttg gtcactcct       5220
tgagggcgcc tttagaaccc aaaagccttc actgaatacc gtcaatgtgg ttgggtcctc       5280
catgggctcc ggcggggtgt tcaccattga cgggaaaatt aagtgcgtga ccgccgcaca       5340
tatcctcacg ggtaactctg ctagggtctc tggggttggc ttcaatcara tgttggattt       5400
tgatgtaaaa gggattttg ccatagccga ttgtccgggt tggcagggag tcgctcccaa        5460
gtcccagttc tgcaaggatg ggtggactgg ccgcgcttat tggctaacgt cctctggcgt       5520
cgaaccggc gtcattggta ggggattcgc cttttgtttc accgcgtgcg gcgattccgg        5580
gtccccagtg atcaccgagg ccggagagct tgtcggagtc cacacgggat caaacaaaca       5640
aggaggaggc attgtcacgc gcccttcagg ccagttttgt aatgtgrcac ccaycaaryt       5700
aagygaattr agtgaattct tygcyggrcc targgtcccg ctyggtgayg tgaaggtcgg       5760
cagccacata attaaagaca taagcgaggt gccttcagat cttttgtgcct tgcttgctgc      5820
caaacctgaa ctgaaggag gcctctccac cgtccaactt ctttgtgtgt tttttctcct       5880
gtggagaatg atgggacatg cctggacgcc cttggttgct gtgagtttct ttattttgaa       5940
tgaggttctc ccagccgtcc tggtccggag tgttttctcc tttggaatgt tgtgctatc       6000
ctggctcacg ccatggtctg cgcaagttct gatgatcagg cttctgacag cagctcttaa      6060
caggaacaga tggtcacttg cctttttcag cctcggtgca gtgaccggtt ttgtcgcaga       6120
tcttgcggcc actcaggggc atccgttgca ggcagtgatg aatttgagca cctatgcatt      6180
cctgcctcgg atgatggttg tgacctcacc agtcccagtg atcacgtgtg tgtcgtgca       6240
cctacttgcc atcattttgt acttgtttaa gtaccgtggc ctgcaccata tccttgttgg       6300
cgatggagtg ttctctgcgg cttttcttct gagatacttt gccgagggaa agttgagga       6360
aggggtgtcg caatcctgcg gaatgaatca tgagtctctg actggtgccc tcgctatgag       6420
actcaatgac gaggacttgg atttccttat gaaatggact gattttaagt gctttgtttc       6480
```

```
tgcgtccaac atgaggaatg cagcgggtca rtttatcgag gcygcctatg cgaaagcgat    6540
cagggtggaa cttgcccagt tagtgcaggt cgacaaggtt cggggtgttt tagccaaact    6600
tgaagctttt gctgacaccg tggcgcccca tctttcaccc ggcgacattg ttgttgttct    6660
tggtcatacg cccgttggca gcatctttga cttaaagatt ggcaatgcca agcacaccct    6720
acaagccatc gagaccagag tccttgctgg gtccaggatg accgtggcgc gtgtcgttga    6780
tccgactccc gcgccgccac ccgtacccgt gcccgttcct ctcccaccga agtttttaga    6840
gaacggcccc agtgcctggg gggatgaaga ccgcctgaac aaaagaagc ggcgcaagat     6900 ggaagccgtt ggcatttacg ttatgggcgg gaaaaagtac cagaaatttt gggataagaa    6960
ttctggtgat gtgttctatg aggaagtcca cgacaacaca gatgcgtggg aatgccttag    7020
agctgacgac cccgccgact tggatcctga gggggaacc ttgtgtggac acgtcaccat      7080
agagaatagg ccttaccatg tttatgcctc cccgtctggt aggaagttcc tggtccctgc    7140
cgacccagag aatgggaaag cccagtggga agctgcaaag cttccatgg agcaggccct     7200 tggtatgatg aacgttgacg gcgagctgac cgccaagaa ctggagaaat tgaagagaat     7260
aattgacaaa ctccagggcc tgactaagga gcagtgttta aactgttagc cgccagcggc    7320
ttgacccgct gtggtcgcgg cggcttggtt attactgaga cagcggtaaa aatagtcaga    7380
ttccacaatc ggaccttcac cctggggcct gtgaatttga agtggccag cgaagttgag     7440 ttgaaagacg ccgtcgagca caaccaacac ccggttgcaa gaccagttga cggtggcgtt    7500
gtgctcctgc gctctgcagt tccttcgctt atagacgtct tgatctccgg tgccgacgca    7560 tctcccagt tgctcgccca tcacgggcca ggaaacactg ggattgatgg cacgctctgg     7620 gatttgagt ccgtagccac taagaggaa gtcgcactta gtgcacaaat aatacaggct      7680
tgtggcatta ggcgtggcga tgctcctgag attggcctcc cttacaagct gcaccctgtt    7740 agggcaacc ctgaacgtgt gaaggggtt ttgaaaaaca caaggtttgg agacatacct      7800
tacaggaccc ctagcgacac tgggagccca gtacatgcgg ccgcctgcct tacgcctaac    7860
gccaccccgg tgactgatgg cgctccgtc ttggccacga ctatgccctc cgggtttgag     7920
ttgtatgtgc cgaccattcc agcatctgtc cttgattacc ttgattccag gccagactgc    7980
cctaaacagt tgacggagca cgggtgtgaa gatgctgcat tgagagacct ctccaaatat    8040
gacttgtccr cccaaggttt tgttttgccc ggagtcctcc gcctcgtgcg gaaatacttg    8100
tttgcccacg tgggcaagtg cccacctgtc catcggccct ccacctaccc ggccaagaat    8160
tccatggctg gaataaacgg gaataggttc ccaaccaagg acattcagag catccctgag    8220
atcgacgttc tgtgtgcaca ggctgtacga gagaactggc agaccgttac cccttgcacc    8280
ctcaagaagc agtattgcgg gaagaagaaa accaggacca tactcggtac caataacttc    8340
attgcgctgg cccaccgggc agcactgagt ggtgtcaccc agggcttcat gaaaaaggcg    8400
tttaactcgc ccatcgccct cgggaagaac aaattcaagg agctacagac tccggtcctg    8460
ggcagatgcc ttgaggctga tcttgcctct tgcgatcgat ccactccgc gattgtccgc      8520 tggtttgccg cccatctcct ttatgaactt gcctgcgctg aggaacacct accgtcgtat    8580
gtgctgaatt gctgccatga cctattggtc acgcagtccg gtgcggtgac taagagaggt    8640
ggcctgtcat ctggtgatcc gatcacctcg gtatccaaca ccatttacag tctggtgatt    8700
tatgcgcagc acatggtgct cagttatttc aaaagtggtc acccacatgg tctcctgttt    8760
ctccaggacc agctaaagtt tgaggacatg cttaaggttc agcccctgat tgtctactcg    8820
```

```
gatgatcttg tgctgtatgc cgagtctccc accatgccaa actatcactg gtgggttgag    8880
catctgaact tgatgctagg gtttcagacg gacccaaaga agacaaccat tactgactcg    8940
ccatcttttc tgggctgtag gataatgaat gggcgtcagc tagtcccaaa ccgtgatagg    9000
attctcgcag ctcttgccta ccacatgaag gcgaataatg tttctgagta ctacgcctcc    9060
gctgctgcaa tactcatgga cagttgtgct tgtctggagt acgaccctga atggtttgaa    9120
gaacttgtgg ttggaatggc gcaatgcgcc cgcaaggacg gctatagctt ccccggcccg    9180
ccgttcttct tatccatgtg ggagaaactc aggtccaatt atgagggaa gaagtcaagg     9240 gtgtgtgggt actgcggagc ttcggccccg tatgccactg cctgtggtct tgacgtctgt    9300
gtttaccaca ctcactttca ccagcattgt ccagtcataa tctgrtgtgg ccaccctgca    9360
ggttccaggt cctgtgatga gtgcaaatcc cccataggga aaggtacaag ccctctggat    9420
gaggttttaa gacaagtccc gtataagcct ccacggaccg tcctcatgca tgtggagcag    9480
ggcctcaccc cccttgaccc aggcagatat cagacccgcc gtgggttggt tgccgttagg    9540
cgcgggatca ggggaaatga agttgaccta ccagatggtg attatgctag caccgcctta    9600
ctcccaacct gtaaagagat caacatggtt gctgttgctt ctaatgtgtt gcgcagcaga    9660
tttatcatcg gtccacccgg tgctgggaaa acatactggc tccttcaaca ggtccaggat    9720
ggtgatgtca tatacacacc gacccatcag accatgcttg acatgatcaa agctttgggg    9780
acgtgccggt ttaacgtccc ggcaggcaca acgctgcaat tccccgcccc ttcccgcact    9840
ggcccgtggg ttcgcatcct ggccggcggg tggtgtcctg gcaaaaactc cttcctggac    9900
gaagctgcgt attgtaatca tcttgatgtc ttgaggcttc ttagcaaaac cactctcacc    9960
tgtttagggg acttcaaaca actccaccca gtgggttttg attctcattg ctatgtcttt    10020
gacattatgc ctcagactca actgaagacc atctggagat ttggacagaa catctgtgat    10080
gccatccaac cagactacag agacaagctt atgtccatgg tcaacacaac tcgtgtaact    10140
tatgtggaaa aacctgtcaa acatgggcaa gtcctcaccc cttaccatag ggaccgagag    10200
gatagcgcca ttaccattga ctccagtcaa ggcgccacat ttgatgtggt tacactgcat    10260
ttgcccacga aagattcact caacaaacaa agggcccttg ttgctattrc cagggcaaga    10320
catgccatct ttgtgtatga cccacatagg caactgcaga gcctatttga tcttcctgca    10380
aaaagcacgc ccgtcaactt ggccgtgcac cacgatggrc aactgattgt gctagataga    10440
aataacaaag aatgcacggt tgcccaagct ctgggtaatg gtgacaaatt tagggccaca    10500
gacaagcgcg ttgtggattc tctccgcgcc atttgtgctg acctagaagg gtcgagctct    10560
ccactcccca aggttgcaca taatttgggg ttttatttct cacctgattt gacacagttt    10620
gccaagcttc caatagaact tgcgccacac tggccagtag tgacgaccca agacaataaa    10680
aactggccag atcggctggt tgccagcctg cgccctattc acaaacatag ccgtgcgtgc    10740 atcggtccg gctatatggt gggccctcg tgttttttag gcacccctgg ggttgtgtca    10800
tactatctta caaaatttgt taagggcgag gctcaagtgc ttccggaaac ggtcttcagt    10860
actggccgaa ttgaggtaga ttgccgggaa tatcttgacg accgggagcg ggaagttgca    10920
gcgtccctcc cacacgcctt tatcggcgac gtcaaaggca ctaccgtcgg agggtgtcat    10980
cacatcacct ccaaatacct tccgcgcttc ctccccaagg aatcagttgc ggtagtcggg    11040
gtttcaagcc ccggaaaagc agcgaaagca gtgtgtacat tgacagatgt gtacctccca    11100
gaccttgaag cttacctcca tcctaagacc ctgtccaagt gctggaaaat gatgttggac    11160
ttcaaagaag ttcggctgat ggtctggaag gacaagacgg cctatttcca actcgaaggt    11220
```

```
cgccatttca cctggtatca acttgctagc tatgcctcgt acatccgtgt tcctttaaac    11280
tccacggtgt acctggaccc ctgcatgggc cccgcccttt gcaacagaaa agtcgttggg    11340
tccactcatt ggggagctga cctcgcagtc accccttatg attatggggc aagaattatt    11400
ttgtctagtg cgtaccatgg tgagatgcct cctgggtaca agattctggc gtgcgcggag    11460
ttctcgctgg acgacccagt cagatacaag cacacttggg ggtttgagtc ggatacagcg    11520
tacttgtacg agttcactgg aaacggtgag gactgggagg attataacga cgcgtttcgt    11580
gcgcgacaga aaggaaagat ttacaaggcc actgccacca gcctgaagtt ccattttcct    11640
ccgggtcata ccgttgaacc aactttgggc ttagactgaa atgaaatggg ggctgtgcag    11700
agcctatttg ataaaattgg ccaactgttt gtggacgctt tcacggagtt cttggtatcc    11760
attgttgata tcatcatatt tttggccatt ttgttcggct tcacaatcgc cggttggctg    11820
gtggtctttt gcatcagatt ggtttgctcc gcgatactcc gttcgcgctc tgccgttcac    11880
cctgagcaat tacagaagat cctatgaggc atttctctcc cagtgccgga cggacattcc    11940
cacctgggga actaaacatc ccttggggat gctctggcac cacaaggtgt cgaccctaat    12000
tgatgaaatg gtgtcgcgtc gaatgtaccg caccatggaa caagcagggc aggctgcctg    12060
gagacaggtg gtgaccgagg caacgttgtc tcgtattagt aacttggatg tggtggctca    12120
tttccagcac cttgccgcca tagaagccga gacttgtaaa tacttggcct cccggctgcc    12180
aatgctgcac aacctgcgca tgacagggtc aaatgtaacc atagtgtata atagctctct    12240
agaacaggtg tttgctattt tcccgaccct cgattcccgg ccaaagcttc atgattttcg    12300
gcaatggcta atagctgtgc attcctccat attctcttct gttgcggctt cctgtaccct    12360
tttcgtcgtg ctgtggttgc ggcttccaat aatacgtact gtttttggtt tccactggtc    12420
aggggcaatt tttccttcga gctcacagtg aactacacgg tgtgtcctcc ctgcctcacc    12480
cggcaggcgg ccgcagagat ctacgaacct ggtgggtctc tttggtgcag gatagggcac    12540
gatcgatgct cggaggacga tcacgacgag ctaggatttc tggtgccgcc tggcctctcc    12600
agcgaaggcc acttgaccag tgtttacgcc tggttggcgt tcttgtcctt cagttacacg    12660
gcccagtttc accccgagat attcggaata gggaatgtga gccaagttta tgttgacatc    12720
aagcatcaat ttatttgtgc tgttcatgac gggcaaaaca ccaccttgcc tcgccatgac    12780
aacgtctcag ccgtgttcca gacttattac cagcatcagg tcgacggcgg caattggttt    12840
cacctggaat ggctgcgccc cttcttctcc tcctggttgg ttttgaacgt ctcttggttt    12900
ctcaggcgtt cgcctgtaag ccgtgtttca gttcgagtct ttcagacatt aagaccaaca    12960
ccaccgcagc tgcaggcttt gctgtcctcc aagacatcag ctgtcttagg catggccact    13020
cgtcctctga ggcgactcgc aaaggccgcc aatgccgcac ggcgatagga acgcccgtat    13080
acattactgt cacagccaat gtaacagatg agaattattt gcattcctct gaccttctca    13140
tgctttcctc ttgccttttc tacgcttccg agatgagtga aaaggatttt gaggtgatat    13200
ttggcaatgt gtcaggcata gtggctgtgt gtgtcaactt taccagctat gtccaacatg    13260
ttaaggagtt cacccagcgc tccttggtgg ttgaccatgt gcggttactt cattttgtga    13320
cacctgagac tatgaggtgg cgaccgtttt tagcctgtct ttttgccatt ctgttggcca    13380
tttgaatgtt cagatatgtt ggggaaatgc ttgaccgcgg gctattgctc gcaattgcct    13440
tttttgtggt gtatcgtgcc gttctgtctt gctgcgctcg tcaacgccag cagcaacagc    13500
agctcccact tacagttgat ttataactta acgatatgtg agctgaatgg cacagactgg    13560
```

-continued

```
ctgaatgatc attttagttg ggcagtggag actttcgtta tctttcctgt gttgactcac    13620
attgtttcct acggcgccct cactaccagc cacttccttg acacggtcgg cctgatcact    13680
gtgtccaccg ccggatacta ccatgcgcgg tatgtcttga gtagcatcta tgccgtctgc    13740
gccctggctg cgctgatttg cttcgtcatc aggttgacga aaaattgtat gtcctggcgc    13800
tactcatgta ccagatatac caactttctt ctggacacca agggcagact ctatcgctgg    13860
cggtcacccg tcatcataga gaaaaggggt aaaattgagg ttggaggtga cctgatcgac    13920
ctcaagagag ttgtgcttga tggctccgcg gcaacccctg taaccaaagt tcagcggaa     13980
caatggggtc gtccttagac gacttctgca atgacagcac ggctccacaa aaggtgatct    14040
tggcattttc tatcacctac actccagtga tgatatatgc cctaaaggtg agtcgtggcc    14100
ggctgctagg gcttttacac ctttttgattt ttctaaactg tgcttttacc ttcgggtata   14160
tgacatttgt gcactttcag agcacaaaca gagttgcact cactatggga gcagtagtcg    14220
cgctcctttg ggggtgtac tcagctatag aaacctggaa attcatcact tccagatgcc     14280
gtttgtgctt gctaggccgc aagtacattc tggcccctgc ccaccacgtt gagagtgccg    14340
caggctttca tccgattgcg gcaagtgata accacgcatt tgtcgtccgg cgtcccggtt    14400
ccactacggt taacggcaca ttggttcccg ggttgaaaag cctcgtgttg ggtggcagaa    14460
gagctgtcaa acggggagtg gtaaacctcg ttaaatatgc caaataacaa cggcaggcag    14520
cagaagaaga agaaaggga cggccagcca gtcaatcagc tgtgccaaat gttgggcagg    14580
atcatcgccc agcaaaacca gtccagaggt aagggaccgg ggaagaaaag taagaagaaa    14640
agcctggaga agccccattt tcctctcgcg actgaagatg acgttagaca tcacttcacc    14700
cctagtgagc ggcaattgtg tctgtcgtca atccagactg cctttaacca aggcgctgga    14760
acttgtaccc tgtcggattc agggagaata agttacactg cggagtttag tttgcctacg    14820
catcatactg tgcgcctaat tcgcgtcaca gcatcaccct cagcatgatg agctggcatt    14880
cttgagacat cccagtgttt gaattggaag gatgtgtggt gaatggcact gattgatatt    14940
gtgcctytaa gtcacctatt caattagggc gaccgtatgg gggtaatatt taattggcgt    15000
gaaccatgcg gccgaaayt                                                15019
```

<210> SEQ ID NO 7
<211> LENGTH: 15086
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 7

```
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtcccctagca ccttgcttcc ggagttgcac tgcttacgg tctctccacc     180
ccttttaacca tgtctgggat acttgatcgg tgcacgtgta cccccaatgc cagggtgttt    240
atggcggagg ccaagtcta ctgcacacga tgcctcagtg cacggtctct ccttcccctg     300
aacctccagg tttctgagct cggggtgcta ggcctattct acaggcccga agagccactc    360
cggtggacgt tgccacgtgc attccccact gttgagtgct ccccgccgg ggcctgctgg     420
ctttctgcaa tcttttccaat cgcacgaatg accagtggaa acctgaactt ccaacaaaga    480
atggtacggg tcgcagctga gctttacaga gccggccagc tcacccctgc agtcttgaag    540
```

-continued

```
gctctacaag tttatgaacg gggttgccgc tggtacccca ttgttggacc tgtccctgga      600
gtggccgttt tcgccaattc cctacatgtg agtgataaac ccttcccggg agcaactcac      660
gtgttgacca acctgccgct cccgcagaga cccaagcctg aagactttg ccctttgag       720
tgtgctatgg ctactgtcta tgacattggt catgacgccg tcatgtatgt ggccgaaagg     780
aaagtctcct gggcccctcg tggcggggat gaagtgaaat ttgaagctgt ccccggggag     840
ttgaagttga ttgcgaaccg gctccgcacc tccttcccgc ccaccacac agtggacatg      900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga actggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta cacaggaacg gtgcttgtac tagcgccaag   1680
tacgtactta agctggaagg tgagcattgg actgtcactg tgaccctgg gatgtcccct   1740
tctttgctcc ctcttgaatg tgttcaggc gtgtggc acaagggcgg tcttggttcc     1800
ccagatgcag tcgaggtctc cggatttgac cctgcctgcc ttgaccggct ggctgaggtg   1860
atgcacctgc tagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caaccagac gatcaagctg ccccaggtca accagtgtcg tgctctggtc   2280
cctgttgtga ctcaaaagtc cttgccaaaa gttcagcctc gaaaaacgaa gcctgtcaag   2340
agcttgccgg agagaaagcc tgtccccgcc ccgcgcagga aggttgggtc cgattgtggc   2400
agcccggttt cattaggcgg cgatgtccct aacagttggg aagatttggc tgttagtagc   2460
cccttttgatc tcccgacccc acctgagccg gcaacacctt caagtgagct ggtgattgtg   2520
tcctcaccgc aatgcattct caggccggcg acacccttga gtgagccggc tccaattccc   2580
gcacctcgcg gaactgtgtc tcgaccggtg acacccttga gtgagccgat ccctgtgccc   2640
gcaccgcggg gtaagtttca gcaggtgaaa agattgagtt cggcggcggc aatcccaccg   2700
taccaggacg agcccctgga tttgtctgct tcctcacaga ctgaatatga ggcctctccc   2760
ccagcaccgc cgcagagcgg ggcgttctg ggagtagagg ggcatgaagc tgaggaaacc   2820
ctgagtgaaa tctcggacat gtcgggtaac attaaacctg cgtccgtgtc atcaagcagc   2880
tccttgtcca gcgtgagaat cacacgccca aaatactcag ctcaagccat catcgactcg   2940
```

```
ggcgggccct gcagtgggca tctccaagag gtaaaggaaa catgccttag tgtcatgcgc    3000
gaggcatgtg atgcgactaa gcttgatgac cctgctacgc aggaatggct ttctcgcatg    3060
tgggatcggg tggacatgct gacttggcgc aacacgtctg tttaccaggc gatttgcacc    3120
ttagatggca ggttaaagtt cctcccaaaa atgatactcg agacaccgcc gccctatccg    3180
tgtgagtttg tgatgatgcc tcacacgcct gcaccttccg taggtgcgga gagcgacctt    3240
accattggct cagttgctac tgaagatgtt ccacgcatcc tcgagaaaat agaaaatgtc    3300
ggcgagatgg ccaaccaggg acccttggcc ttctccgagg ataaaccggt agatgaccaa    3360
cttgtcaacg acccccggat atcgtcgcgg aggcctgacg agagcacatc agctccgtcc    3420
gcaggcacag gtggcgccgg ctcttttacc gatttgccgc cttcagatgg cgcggatgcg    3480 gacgggggggg ggccgtttcg gacggtaaaa agaaaagctg aaaggctctt tgaccaactg    3540
agccgtcagg ttttgacct cgtctcccat ctccctgttt tcttctcacg cctttctac     3600 cctggcggtg gttattctcc gggtgattgg ggttttgcag cttttactct attgtgcctc    3660 ttttttatgtt acagttaccc agcctttggt attgctcccc tcttgggtgt gttttctggg   3720
tcttctcggc gcgttcgaat gggggttttt ggctgctggt tggcttttgc tgttggtctg    3780
ttcaagcctg tgtccgaccc agtcggcgct gcttgtgagt ttgactcgcc agagtgtaga    3840
aacatccttc attcttttga gcttctcaaa ccttgggacc ctgttcgcag ccttgttgtg    3900
ggccccgtcg gtctcggtct tgccattctt ggcaggttac tgggcggggc acgctgcatc    3960
tggcactttt tgcttaggct tggcattgtt gcagactgta tcttggctgg agcttacgtg    4020 cttttctcaag gtaggtgtaa aaagtgctgg ggatcttgta taagaactgc tcccaatgag   4080
gtcgctttta acgtgtttcc tttcacacgt gcgaccaggt cgtcacttat cgacctgtgc    4140
gatcggtttt gtgcgccaaa aggaatggac cccattttc tcgccactgg gtggcgcggg     4200
tgctgggccg gccgaagccc cattgagcaa ccctctgaaa acccatcgc gtttgcccag     4260 ttggatgaaa agaagattac ggctaggact gtggtcgccc agccttatga ccccaaccaa    4320
gccgtaaagt gcttgcgggt attgcaggcg ggtggggcga tggtggctaa ggcggtccca    4380
aaagtggtca aggtttccgc tgttccattc cgagcccct tctttcccac tggagtgaaa     4440
gttgaccctg attgcagggt cgtggttgac cctgacactt tcactgcagc tctccggtct    4500
ggctactcca ccacaaaacct cgtccttggt gtggggggact tgcccagct gaatggatta    4560 aaaatcaggc aaatttccaa gccttcaggg ggaggcccac atctcatggc tgccctgcat    4620
gttgcctgct cgatggctct gcacatgctt gctgggattt atgtgactgc ggtgggttct    4680
tgcggcaccg gcaccaacga cccgtggtgc gctaacccgt ttgccgtccc tggctacgga    4740
cctggctctc tctgcacgtc cagattgtgc atttcccaac acggccttac cctgcccttg    4800
acagcacttg tggcgggatt cggtattcaa gaaattgcct tggtcgtttt gattttgtt     4860 tccatcggag gcatggctca taggttgagc tgtaaggctg acatgctgtg tgtcttgctt    4920
gcaattgcca gctatgtttg ggtacctctt acctggttgc tttgtgtgtt ccttgctgg     4980 ttgcgctgtt tttctttgca cccctcacc atcctatggt tggtgttttt cttgatttct     5040
gtgaatatgc cttcaggaat cttggccatg gtgttgttgg tttctctttg gcttcttggt    5100
cgttatacta atgttgctgg ccttgtcacc ccctacgaca ttcatcatta caccagtggc    5160
ccccgcggtg ttgccgcctt ggctaccgca ccagatggga cctacttggc cgctgtccgc    5220
cgcgctgcgt tgactggccg caccatgctg tttacccgt cccagcttgg gtctcttctt     5280
```

```
gagggtgctt tcagaactcg aaagccctca ctgaacaccg tcaatgtgat cgggtcctcc    5340
atgggctctg gcggggtgtt taccatcgac gggaaagtca agtgcgtaac tgccgcacat    5400
gtccttacgg gcaattcagc tcgggtttcc ggggtcggct tcaatcaaat gcttgacttt    5460
gacgtaaagg gagatttcgc tatagctgat tgcccgaatt ggcaaggggc tgcccccaag    5520
acccaattct gcacggatgg atggactggc cgtgcctatt ggctaacatc ctctggcgtc    5580
gaacccggcg tcattggaaa aggattcgcc ttctgcttca ccgcatgtgg cgattccggg    5640
tccccagtga tcaccgaggc cggtgagctt gtcggcgttc acacgggatc gaataaacaa    5700
ggggggggca ttgttacgcg cccctcaggc cagttttgta atgtggcacc catcaagcta    5760
agcgaattaa gtgaattctt tgctgggcct aaggtcccgc tcggtgatgt gaaggtcggc    5820
agccacataa ttaaagacat aagcgaggtg ccttcagatc tttgtgcctt gcttgctgcc    5880
aaacctgaac tggaaggagg cctctccacc gtccaacttc tttgtgtgtt ttttctcctg    5940
tggagaatga tgggacatgc ctggacgccc ttggttgctg tgagtttctt tattttgaat    6000
gaggttctcc cagccgtcct ggtccggagt gttttctcct ttggaatgtt tgtgctatcc    6060
tggctcacgc catggtctgc gcaagttctg atgatcaggc ttctgacagc agctcttaac    6120
aggaacagat ggtcacttgc cttttcagc tcggtgcag tgaccggttt tgtcgcagat      6180
cttgcggcca ctcaggggca tccgttgcag gcagtgatga atttgagcac ctatgcattc    6240
ctgcctcgga tgatggttgt gacctcacca gtcccagtga tcacgtgtgg tgtcgtgcac    6300
ctacttgcca tcattttgta cttgtttaag taccgtggcc tgcaccatat ccttgttggc    6360
gatgagtgt tctctgcggc tttcttcttg agatactttg ccgagggaaa gttgagggaa     6420
ggggtgtcgc aatcctgcgg aatgaatcat gagtctctga ctggtgccct cgctatgaga    6480
ctcaatgacg aggacttgga tttccttatg aaatggactg attttaagtg ctttgtttct    6540
gcgtccaaca tgaggaatgc agcgggtcaa tttatcgagg ctgcctatgc taaagcactt    6600
agagtagaac tggcccagtt ggtgcaggtt gataaagttc gaggtacttt ggccaaactt    6660
gaagcttttg ctgataccgt ggcacctcaa ctctcgcccg gtgacattgt tgtcgctctc    6720
ggccacacgc ctgttggcag tatcttcgac ctaaaggttg gtagcaccaa gcataccctc    6780
caagccattg agaccagagt ccttgctggg tccaaaatga ccgtggcgcg cgtcgtcgac    6840
ccgaccccca cgcccccacc cgcacccgtg cccatccccc tcccaccgaa agttctggag    6900
aatggcccca acgcttgggg ggatgaggac cgtttgaata agaagaagag cgcaggatg     6960
gaagccctcg gcatctatgt tatgggcggg aaaaaatacc agaaattttg ggacaagaat    7020
tccggtgatg tgttttatga ggaggtccat aataacacag atgagtggga gtgtctcaga    7080
gttggcgacc ctgccgactt tgaccctgag aagggaactc tgtgtggaca tgtcaccatt    7140
gaaaacaagg cttaccatgt ttacacctcc ccatctggta agaagttctt ggtccccgtc    7200
aacccagaga atggaagagt ccaatgggaa gctgcaaagc tttccgtgga gcaggcccta    7260
ggtatgatga atgtcgacgg cgaactgact gccaagaac tggagaaact gaaaagaata     7320
attgacaaac tccagggcct gactaaggag cagtgtttaa actgctagcc gccagcgact    7380
tgacccgctg tggtcgcggc ggcttggttg ttactgaaac agcggtaaaa atagtcaaat    7440
ttcacaaccg gaccttcacc ctgggacctg tgaatttaaa agtggccagt gaggttgagc    7500
taaaagacgc ggttgagcac aaccaacacc cggttgcgag accgatcgat ggtggagttg    7560
tgctcctgcg ttccgcggtt ccttcgctta tagacgtctt gatctccggt gctgatgcat    7620
ctcccaagtt acttgcccat cacgggccgg gaaacactgg gatcgatggc acgctctggg    7680
```

```
attttgagtc cgaagccact aaagaggaag tcgcactcag tgcgcaaata atacaggctt    7740
gtgacattag gcgcggcgac gctcctgaaa ttggtctccc ttacaagctg taccctgtta    7800
ggggtaaccc tgagcgggtg aaaggagttc tgcagaatac aaggtttgga gatataccttt   7860
acaaaacccc cagtgacact ggaagcccag tgcacgcggc tgcctgcctt acgcccaacg    7920
ccactccggt gactgatggg cgctccgtct tggccacgac catgccccccc gggtttgagt   7980
tatatgtacc gaccatacca gcgtctgtcc ttgattacct tgactctagg cctgactgcc    8040
ctaaacagct gacagagcac ggctgcgaag atgccgcact gaaagacctc tctaaatatg    8100
acttgtccac ccaaggcttt gttttacctg gagttcttcg ccttgtgcgg aaatacctgt    8160
ttgcccatgt aggtaagtgc ccacccgttc atcggccttc tacttaccct gctaagaatt    8220
ctatggctgg aataaatggg aacaggttcc caaccaagga cattcagagc gtccctgaaa    8280
tcgacgttct gtgcgcacag gctgtgcgag aaaactggca aactgtcacc ccttgtactc    8340
ttaagaaaca gtattgcggg aagaagaaga ctaggaccat actcggcacc aataacttca    8400
tcgcactagc ccaccgagca gtgttgagtg tgttaccca gggcttcatg aaaaaggcgt     8460
ttaactcgcc catcgccctc ggaaagaaca agtttaagga gctacagact ccggtcctgg    8520
gcaggtgcct tgaagctgat ctcgcatcct gcgatcgatc cacgcctgca attgtccgct    8580
ggtttgccgc caaccttctt tatgaacttg cctgtgctga agagcatcta ccgtcgtacg    8640
tgctgaactg ctgccacgac ttactggtca cgcagtccgg cgcagtgact aagagaggtg    8700
gcctgtcgtc tggcgacccg atcacctctg tgtctaacac catttatagt ttggtgatct    8760
atgcacagca tatggtgctt agttacttca aaagtggtca ccccccatggc cttctgttct   8820
tacaagacca gctaaagttt gaggacatgc tcaaggttca accctgatc gtctattcgg     8880
acgacctcgt gctgtatgcc gagtctccca ccatgccaaa ctatcactgg tgggttgaac    8940
atctgaattt gatgctgggg tttcagacgg acccaaagaa gacagcaata acagactcgc    9000
catcattctct aggctgtaga ataataaatg gcgccagct agtccccaac cgtgacagga    9060
tcctcgcggc cctcgcctat cacatgaagg cgagtaatgt ttctgaatac tatgcctcag    9120
cggctgcaat actcatggac agctgtgctt gtttggagta tgatcctgaa tggtttgaag    9180
aacttgtagt tggaatagcg cagtgcgccc gcaaggacgg ctacagcttt cccggcacgc    9240
cgttcttcat gtccatgtgg gaaaaactca ggtccaatta tgaggggaag aagtcgagag    9300
tgtgcgggta ctgcgggcc ccggccccgt acgctactgc ctgtggcctc gacgtctgca    9360
tttaccacac ccacttccac cagcattgtc cagtcacaat ctggtgtggc catccagcgg    9420
gttctggttc ttgtagtgag tgcaaatccc ctgtagggaa aggcacaagc cctttagacg    9480
aggtgctgga acaagtcccg tataagcccc acggaccgt tatcatgcat gtggagcagg    9540
gtctcacccc ccttgatcca ggtagatacc aaactcgccg cggattagtc tctgtcaggc    9600
gtggaattag gggaaatgaa gttggactac cagacggtga ttatgctagc accgccttgc    9660
tccctacctg caaagagatc aacatggtcg ctgtcgcttc caatgtattg cgcagcaggt    9720
tcatcatcgg cccaccgggt gctgggaaaa catactggct ccttcaacag gtccaggatg    9780
gtgatgttat ttacacacca actcaccaga ccatgcttga catgattagg gctttgggga    9840
cgtgccggtt caacgtcccg gcaggcacaa cgctgcaatt ccccgtcccc tcccgcaccg    9900
gtccgtgggt tcgcatccta gccggcggtt ggtgtcctgg caagaattcc ttcctagatg    9960
aagcagcgta ttgcaatcac cttgatgttt tgaggcttct tagtaaaact accctcacct   10020
```

```
gtctaggaga cttcaagcaa ctccacccag tgggttttga ttctcattgc tatgtttttg   10080
acatcatgcc tcaaactcaa ctgaagacca tctggaggtt tggacagaat atctgtgatg   10140
ccattcagcc agattacagg gacaaactca tgtccatggt caacacaacc cgtgtgacct   10200
acgtggaaaa acctgtcagg tatgggcagg tcctcacccc ctaccacagg gaccgagagg   10260
acgacgccat cactattgac tccagtcaag gcgccacatt cgatgtggtt acattgcatt   10320
tgcccactaa agattcactc aacaggcaaa gagcccttgt tgctatcacc agggcaagac   10380
acgctatctt tgtgtatgac ccacacaggc agctgcaggg cttgtttgat cttcctgcaa   10440
aaggcacgcc cgtcaacctc gcagtgcact gcgacgggca gctgatcgtg ctggatagaa   10500
ataacaaaga atgcacggtt gctcaggctc taggcaacgg ggataaattt agggccacag   10560
acaagcgtgt tgtagattct ctccgcgcca tttgtgctga tctagaaggg tcgagctctc   10620
cgctccccaa ggtcgcacac aacttgggat tttatttctc acctgattta acacagtttg   10680
ctaaactccc agtagaactt gcacctcact ggcccgtggt gtcaacccag aacaatgaaa   10740
agtggccgga tcggctggtt gccagccttc gccctatcca taaatacagc cgcgcgtgca   10800
tcggtgccgg ctatatggtg ggcccttcgg tgtttctagg cactcctggg gtcgtgtcat   10860
actatctcac aaaatttgtt aagggcgggg ctcaagtgct tccggagacg ttttcagca   10920 ccggccgaat tgaggtagac tgccgggaat atcttgatga tcgggagcga gaagttgctg   10980
cgtccctccc acacgctttc attggcgacg tcaaaggcac taccgttgga ggatgtcatc   11040
atgtcacctc cagataccct ccgcgcgtcc ttcccaagga atcagttgcg gtagtcgggg   11100
tttcaagccc cggaaaagcc gcgaaagcat tgtgcacact gacagatgtg tacctcccag   11160
atcttgaagc ctatctccac ccggagaccc agtccaagtg ctggaaaatg atgttggact   11220
tcaaagaagt tcgactaatg gtctggaaag acaaaacagc ctatttccaa cttgaaggtc   11280
gctatttcac ctggtatcag cttgccagct atgcctcgta catccgtgtt cccgtcaact   11340
ctacggtgta cttggacccc tgcatggggc ccgccctttg caacaggaga gtcgtcgggt   11400
ccacccactg gggggctgac ctcgcggtca ccccttatga ttacggcgct aaaattatcc   11460
tgtctagcgc gtaccatggt gaaatgcccc ccggatacaa aattctggcg tgcgcggagt   11520
tctcgttgga tgacccagtt aagtacaaac atacctgggg gtttgaatcg gatacagcgt   11580
atctgtatga gttcaccgga aacggtgagg actgggagga ttacaatgat gcgtttcgtg   11640
cgcgccagga agggaaaatt tataaggcca ctgccaccag cttgaagttt tattttcccc   11700
cgggccctgt cattgaacca actttaggcc tgaattgaaa tgaaatgggg tccatgcaaa   11760 gccttttga caaaattggc caacttttg tggatgcttt cacggagttc ttggtgtcca   11820
ttgttgatat cattatattt ttggccattt tgtttggctt caccatcgcc ggttggctgg   11880
tggtcttttg catcagattg gtttgctccg cgatactccg tacgcgccct gccattcact   11940
ctgagcaatt acagaagatc ttatgaggcc tttctttccc agtgccaagt ggacattccc   12000
acctggggaa ctaaacatcc tttggggatg ctttggcacc ataaggtgtc aaccctgatt   12060
gatgaaatgg tgtcgcgtcg aatgtaccgc atcatggaaa aagcagggca ggctgcctgg   12120
aaacaggtgg tgagcgaggc tacgctgtct cgcattagta gtttggatgt ggtggctcat   12180
tttcagcatc tagccgccat tgaagccgag acctgtaaat atttggcctc ccggctgccc   12240
atgctacaca acctgcgcat gacagggtca aatgtaacca tagtgtataa tagcactttg   12300
aatcaggtgt ttgctatttt tccaacccct ggttcccggc caaagcttca tgattttcag   12360
caatggttaa tagctgtaca ttcctccata ttttcctctg ttgcagcttc ttgtactctt   12420
```

```
tttgttgtgc tgtggttgcg ggttccaata ctacgtactg tttttggttt ccgctggtta    12480
ggggcaattt ttctttcgaa ctcacagtga attacacggt gtgtccacct tgcctcaccc    12540
ggcaagcagc cacagagatc tacgaacccg gtaggtctct ttggtgcagg atagggtatg    12600
accgatgtgg ggaggacgat catgacgagc tagggtttat gataccgcct ggcctctcca    12660
gcgaaggcca cttgactggt gtttacgcct ggttggcgtt cttgtccttc agctacacgg    12720
cccagttcca tcccgagata ttcgggatag ggaatgtgag tcgagtttat gttgacatca    12780
aacatcaact catctgcgcc gaacatgacg ggcagaacac caccttgcct cgtcatgaca    12840
acatttcagc cgtgtttcag acctattacc aacatcaagt cgacggcggc aattggtttc    12900
acctagaatg gcttcgtccc ttcttttcct cgtggttggt tttaaatgtc tcttggtttc    12960
tcaggcgttc gcctgcaaac catgtttcag ttcgagtctt gcagatatta agaccaacac    13020
caccgcagcg gcaagctttg ctgtcctcca agacatcagt tgccttaggc atcgcgactc    13080
ggcctctgag gcgattcgca aaatccctca gtgccgtacg gcgatagggA cacccgtgta    13140
tgttaccatc acagccaatg tgacagatga gaattattta cattcttctg atctcctcat    13200
gctttcttct tgccttttct atgcttctga gatgagtgaa aagggattta aggtggtatt    13260
tggcaatgtg tcaggcatcg tggctgtgtg tgtcaatttt accagctacg tccaacatgt    13320
caaggagttt acccaacgct ccctggtggt cgaccatgtg cggttgctcc atttcatgac    13380
acctgagacc atgaggtggg caactgtttt agcctgtctt tttgccattc tgttggcaat    13440
ttgaatgttt aagtatgttg gagaaatgct tgaccgcggg ctgttgctcg cgattgcttt    13500
ctttgtggtg tatcgtgccg ttctgttttg ctgtgctcgc caacgccagc aacgacagca    13560
gctcccatct acagctgatt tacaacttga cgctatgtga gctgaatggc acagattggc    13620
tagctaacaa atttgattgg gcagtggaga gttttgtcat cttttcccgtt ttgactcaca    13680 ttgtctccta tggtgccctc actaccagcc atttccttga cacagtcgct ttagtcactg    13740
tgtctaccgc cgggtttgtt cacgggcggt atgtcctaag tagcatctac gcggtctgtg    13800
ccctggctgc gttgacttgc ttcgtcatta ggttttgcaaa gaattgcatg tcctggcgct    13860
acgcgtgtac cagatatacc aactttcttc tggacactaa gggcagactc tatcgttggc    13920
ggtcgcctgt catcatagag aaaaggggca agttgaggt cgaaggtcat ctgatcgacc    13980
tcaaaagagt tgtgcttgat ggctccgtgg caaccctat aaccagagtt tcagcggaac    14040 aatgggggtcg tccttagatg acttctgtca cgatagcacg gctccacaaa aggtgctttt    14100
ggcgttttct attacctaca cgccagtgat gatatatgcc ctaaaggtga gtcgcggccg    14160
actgctaggg cttctgcacc ttttgatctt cctgaattgt gctttcacct tcgggtacat    14220
gactttcgcg cactttcaga gtacaaataa ggtcgcgctc actatgggag cagtagttgc    14280
actcctttgg ggggtgtact cagccataga aacctggaaa ttcatcacct ccagatgccg    14340
tttgtgcttg ctaggccgca agtacattct ggccctgcc caccacgttg aaagtgccgc    14400 aggcttttcat ccgattgcgg caaatgataa ccacgcattt gtcgtccggc gtcccggctc    14460
cactacggtc aacggcacat tggtgcccgg gttaaaaagc ctcgtgttgg gtggcagaaa    14520
agctgttaaa caggagtgg taaaccttgt caaatatgcc aaataacaac ggcaagcagc    14580
agaagagaaa gaaggggggat ggccagccag tcaatcagct gtgccagatg ctgggtaaga    14640
tcatcgctca gcaaaaccag tccagaggca agggaccggg aaagaaaaat aagaagaaaa    14700
acccggagaa gccccatttt cctctagcga ctgaagatga tgtcagacat cactttaccc    14760
```

| | |
|---|---:|
| ctagtgagcg gcaattgtgt ctgtcgtcaa tccagaccgc ctttaatcaa ggcgctggga | 14820 |
| cttgcaccct gtcagattca gggaggataa gttacactgt ggagtttagt ttgcctacgc | 14880 |
| atcatactgt gcgcctgatc cgcgtcacag catcaccctc agcatgatgg gctggcattc | 14940 |
| ttgaggcatc tcagtgtttg aattggaaga atgtgtggtg aatggcactg attgacattg | 15000 |
| tgcctctaag tcacctattc aattagggcg accgtgtggg ggtgagattt aattggcgag | 15060 |
| aaccatgcgg ccgaaattaa aaaaaa | 15086 |

<210> SEQ ID NO 8
<211> LENGTH: 14819
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 8

| | |
|---|---:|
| atgacgtata ggtgttggct ctatgccttg gcatttgtat tgtcaggagc tgtgaccatt | 60 |
| ggcacagccc aaaacttgct gcacagaaac acccttctgt gatagcctcc ttcaggggag | 120 |
| cttagggttt gtccctagca ccttgcttcc ggagttgcac tgctttacgg tctctccacc | 180 |
| cctttaacca tgtctgggat acttgatcgg tgcacgtgta cccccaatgc caggtgtttt | 240 |
| atggcggagg ccaagtcta ctgcacacga tgcctcagtg cacggtctct ccttcccctg | 300 |
| aacctccagg tttctgagct cggggtgcta ggcctattct acaggcccga agagccactc | 360 |
| cggtggacgt tgccacgtgc attcccact gttgagtgct ccccgccgg ggcctgctgg | 420 |
| cttcctgcaa tctttccaat cgcacgaatg accagtggaa acctgaactt ccaacaaaga | 480 |
| atggtacggg tcgcagctga gctttacaga gccggccagc tcacccctgc agtcttgaag | 540 |
| gctctacaag tttatgaacg gggttgccgc tggtacccca ttgttggacc tgtccctgga | 600 |
| gtggccgttt cgccaattc cctacatgtg agtgataaac ccttcccggg agcaactcac | 660 |
| gtgttgacca acctgccgct cccgcagaga cccaagcctg aagacttttg ccccttgag | 720 |
| tgtgctatgg ctactgtcta tgacattggt catgacgccg tcatgtatgt ggccgaaagg | 780 |
| aaagtctcct gggcccctcg tggcggggat gaagtgaaat ttgaagctgt ccccggggag | 840 |
| ttgaagttga ttgcgaaccg gctccgcacc tccttcccgc ccaccacac agtggacatg | 900 |
| tctaagttcg ccttcacagc ccctgggtgt ggtgtttcta gcgggtcga acgccaacac | 960 |
| ggctgccttc ccgctgacac tgtccctgaa ggcaactgct ggtggagctt gtttgacttg | 1020 |
| cttccactgg aagttcagaa caaagaaatt cgccatgcta accaatttgg ctaccagacc | 1080 |
| aagcatggtg tctctggcaa gtacctgcag cggaggctgc aagttaatgg tctccgagca | 1140 |
| gtaactgacc taaacggacc tatcgtcgta cagtacttct ccgttaagga gagttggatc | 1200 |
| cgccatttga aactggcggg agaacccagc tactctgggt ttgaggacct cctcagaata | 1260 |
| agggttgagc ctaacacgtc gccattggct gacaaggaag aaaaaatttt ccggtttggc | 1320 |
| agtcacaagt ggtacggcgc tggaaagaga gcaagaaaag cacgctcttg tgcgactgct | 1380 |
| acagtcgctg gccgcgcttt gtccgttcgt gaaacccggc aggccaagga gcacgaggtt | 1440 |
| gccggcgcca acaaggctga gcacctcaaa cactactccc cgcctgccga agggaattgt | 1500 |
| ggttggcact gcatttccgc catcgccaac cggatggtga attccaaatt tgaaaccacc | 1560 |
| cttccccgaaa gagtgagacc tccagatgac tgggctactg acgaggatct tgtgaatgcc | 1620 |
| atccaaatcc tcagactccc tgcggcctta gacaggaacg gtgcttgtac tagcgccaag | 1680 |

```
tacgtactta agctggaagg tgagcattgg actgtcactg tgacccctgg gatgtcccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttgccaatt cccgcacctc gcggaactgt gtctcgaccg    2340
gtgacaccct tgagtgagcc gatccctgtg cccgcaccgc ggcgtaagtt tcagcaggtg    2400
aaaagattga gttcggcggc ggcaatccca ccgtaccagg acgagcccct ggatttgtct    2460
gcttcctcac agactgaata tgaggcctct cccccagcac cgccgcagag cggggggcgtt    2520 ctgggagtag aggggcatga agctgaggaa accctgagtg aaatctcgga catgtcgggt    2580
aacattaaac ctgcgtccgt gtcatcaagc agctccttgt ccagcgtgag aatcacacgc    2640
ccaaaatact cagctcaagc catcatcgac tcgggcgggc cctgcagtgg gcatctccaa    2700
gaggtaaagg aaacatgcct tagtgtcatg cgcgaggcat gtgatgcgac taagcttgat    2760
gaccctgcta cgcaggaatg gctttctcgc atgtgggatc gggtggacat gctgacttgg    2820
cgcaacacgt ctgtttacca ggcgatttgc accttagatg gcaggttaaa gttcctccca    2880
aaaatgatac tcgagacacc gccgcccttt ccgtgtgagt ttgtgatgat gcctcacacg    2940
cctgcacctt ccgtaggtgc ggagagcgac cttaccattg gctcagttgc tactgaagat    3000
gttccacgca tcctcgagaa aatagaaaat gtcggcgaga tggccaacca gggacccttg    3060
gccttctccg aggataaacc ggtagatgac caacttgtca acgaccccg gatatcgtcg    3120 cggaggcctg acgagagcac atcagctccg tccgcaggca caggtggcgc cggctctttt    3180
accgatttgc cgccttcaga tggcgcggat gcggacgggg ggggccgtt tcggacggta    3240 aaaagaaaag ctgaaaggct cttttgaccaa ctgagccgtc aggttttttga cctcgtctcc    3300 catctccctg ttttcttctc acgcctttttc taccctggcg gtggttattc tccgggtgat    3360 tggggtttg cagcttttac tctattgtgc ctcttttttat gttacagtta cccagccttt    3420
ggtattgctc ccctcttggg tgtgttttct gggtcttctc ggcgcgttcg aatgggggtt    3480
tttggctgct ggttggcttt tgctgttggt ctgttcaagc ctgtgtccga cccagtcggc    3540
gctgcttgtg agtttgactc gccagagtgt agaaacatcc ttcattcttt tgagcttctc    3600
aaaccttggg accctgttcg cagccttgtt gtgggcccg tcggtctcgg tcttgccatt    3660
cttggcaggt tactgggcgg ggcacgctgc atctggcact ttttgcttag gcttggcatt    3720
gttgcagact gtatcttggc tggagcttac gtgctttctc aaggtaggtg taaaaagtgc    3780
tggggatctt gtataagaac tgctcccaat gaggtcgctt ttaacgtgtt tcctttcaca    3840
cgtgcgacca ggtcgtcact tatcgacctg tgcgatcggt tttgtgcgcc aaaaggaatg    3900 gacccccattt ttctcgccac tgggtggcgc gggtgctggg ccggccgaag ccccattgag    3960
caaccctctg aaaaacccat gcgctttgcc cagttggatg aaaagaagat tacggctagg    4020
actgtggtcg cccagcctta tgaccccaac caagccgtaa agtgcttgcg ggtattgcag    4080
```

```
gcgggtgggg cgatggtggc taaggcggtc ccaaaagtgg tcaaggtttc cgctgttcca   4140
ttccgagccc ccttctttcc cactggagtg aaagttgacc ctgattgcag ggtcgtggtt   4200
gaccctgaca ctttcactgc agctctccgg tctggctact ccaccacaaa cctcgtcctt   4260
ggtgtggggg actttgccca gctgaatgga ttaaaaatca ggcaaatttc caagccttca   4320
gggggaggcc cacatctcat ggctgccctg catgttgcct gctcgatggc tctgcacatg   4380
cttgctggga tttatgtgac tgcggtgggt tcttgcggca ccggcaccaa cgacccgtgg   4440
tgcgctaacc cgtttgccgt ccctggctac ggacctggct ctctctgcac gtccagattg   4500
tgcatttccc aacacggcct taccctgccc ttgacagcac ttgtggcggg attcggtatt   4560
caagaaattg ccttggtcgt tttgattttt gtttccatcg gaggcatggc tcataggttg   4620
agctgtaagg ctgacatgct gtgtgtcttg cttgcaattg ccagctatgt ttgggtacct   4680
cttacctggt tgctttgtgt gttccttgc tggttgcgct gttttcttt gcacccctc    4740 accatcctat ggtggtgtt tttcttgatt tctgtaata tgccttcagg aatcttggcc    4800
atggtgttgt tggtttctct ttggcttctt ggtcgttata ctaatgttgc tggccttgtc   4860 acccctacg acattcatca ttacaccagt ggccccgcg gtgttgccgc cttggctacc    4920
gcaccagatg ggacctactt ggccgctgtc cgccgcgctg cgttgactgg ccgcaccatg   4980
ctgtttaccc cgtcccagct tgggtctctt cttgagggtg ctttcagaac tcgaaagccc   5040
tcactgaaca ccgtcaatgt gatcgggtcc tccatgggct ctggcggggt gtttaccatc   5100
gacgggaaag tcaagtgcgt aactgccgca catgtcctta cgggcaattc agctcggggtt  5160 tccggggtcg gcttcaatca aatgcttgac tttgacgtaa agggagattt cgctatagct   5220
gattgcccga attggcaagg ggctgccccc aagacccaat tctgcacgga tggatggact   5280
ggccgtgcct attggctaac atcctctggc gtcgaacccg cgtcattgg aaaaggattc    5340 gccttctgct tcaccgcatg tggcgattcc gggtccccag tgatcaccga ggccggtgag   5400
cttgtcggcg ttcacacggg atcgaataaa caaggggggg gcattgttac gcgcccctca   5460 ggccagttt gtaatgtggc acccatcaag ctaagcgaat taagtgaatt ctttgctggg    5520
cctaaggtcc cgctcggtga tgtgaaggtc ggcagccaca taattaaaga cataagcgag   5580
gtgccttcag atctttgtgc cttgcttgct gccaaacctg aactggaagg aggcctctcc   5640
accgtccaac ttctttgtgt gtttttctc ctgtggagaa tgatgggaca tgcctggacg    5700
cccttggttg ctgtgagttt ctttattttg aatgaggttc tcccagccgt cctggtccgg   5760
agtgttttct cctttggaat gtttgtgcta tcctggctca cgccatggtc tgcgcaagtt   5820
ctgatgatca ggcttctgac agcagctctt aacaggaaca gatggtcact tgcctttttc   5880
agcctcggtg cagtgaccgg ttttgtcgca gatcttgcgg ccactcaggg gcatccgttg   5940
caggcagtga tgaatttgag cacctatgca ttcctgcctc ggatgatggt tgtgacctca   6000
ccagtcccag tgatcacgtg tggtgtcgtg cacttacttg ccatcatttt gtacttgttt   6060
aagtaccgtg gcctgcacca tatccttgtt ggcgatggag tgttctctgc ggctttcttc   6120
ttgagatact tgccgagggg aaagttgagg aagggggtgt cgcaatcctg cggaatgaat   6180
catgagtctc tgactggtgc cctcgctatg agactcaatg acgaggactt ggatttcctt   6240
atgaaatgga ctgattttaa gtgctttgtt tctgcgtcca acatgaggaa tgcagcgggt   6300
caatttatcg aggctgccta tgctaaagca cttagagtag aactggccca gttggtgcag   6360
gttgataaag ttcgaggtac tttggccaaa cttgaagctt ttgctgatac cgtggcacct   6420
```

```
caactctcgc ccggtgacat tgttgtcgct ctcggccaca cgcctgttgg cagtatcttc    6480
gacctaaagg ttggtagcac caagcatacc ctccaagcca ttgagaccag agtccttgct    6540
gggtccaaaa tgaccgtggc gcgcgtcgtc gacccgaccc ccacgccccc acccgcaccc    6600
gtgcccatcc ccctcccacc gaaagttctg gagaatggcc ccaacgcttg ggggatgag    6660
gaccgtttga ataagaagaa gaggcgcagg atggaagccc tcggcatcta tgttatgggc    6720
gggaaaaaat accagaaatt ttgggacaag aattccggtg atgtgtttta tgaggaggtc    6780
cataataaca cagatgagtg ggagtgtctc agagttggcg accctgccga ctttgaccct    6840
gagaagggaa ctctgtgtgg acatgtcacc attgaaaaca aggcttacca tgtttacacc    6900
tccccatctg gtaagaagtt cttggtcccc gtcaacccag agaatggaag agtccaatgg    6960
gaagctgcaa agctttccgt ggagcaggcc ctaggtatga tgaatgtcga cggcgaactg    7020
actgccaaag aactggagaa actgaaaaga ataattgaca aactccaggg cctgactaag    7080
gagcagtgtt taaactgcta gccgccagcg acttgacccg ctgtggtcgc ggcggcttgg    7140
ttgttactga aacagcggta aaatagtca aatttcacaa ccggaccttc accctgggac    7200
ctgtgaattt aaaagtggcc agtgaggttg agctaaaaga cgcggttgag cacaaccaac    7260
acccggttgc gagaccgatc gatggtggag ttgtgctcct gcgttccgcg gttccttcgc    7320
ttatagacgt cttgatctcc ggtgctgatg catctcccaa gttacttgcc catcacgggc    7380
cgggaaacac tgggatcgat ggcacgctct gggattttga gtccgaagcc actaagagg    7440
aagtcgcact cagtgcgcaa ataatacagg cttgtgacat taggcgcggc gacgctcctg    7500
aaattggtct cccttacaag ctgtaccctg ttaggggtaa ccctgagcgg gtgaaaggag    7560
ttctgcagaa tacaaggttt ggagacatac cttacaaaac ccccagtgac actggaagcc    7620
cagtgcacgc ggctgcctgc cttacgccca acgccactcc ggtgactgat gggcgctccg    7680
tcttggccac gaccatgccc cccgggtttg agttatatgt accgaccata ccagcgtctg    7740
tccttgatta ccttgactct aggcctgact gccctaaaca gctgacagag cacggctgcg    7800
aagatgccgc actgaaagac ctctctaaat atgacttgtc cacccaaggc tttgttttac    7860
ctggagttct tcgccttgtg cggaaatacc tgtttgccca tgtaggtaag tgcccacccg    7920
ttcatcggcc ttctacttac cctgctaaga attctatggc tggaataaat gggaacaggt    7980
tcccaaccaa ggacattcag agcgtccctg aaatcgacgt tctgtgcgca caggctgtgc    8040
gagaaaactg gcaaactgtc accccttgta ctcttaagaa acagtattgc gggaagaaga    8100
agactaggac catactcggc accaataact tcatcgcact agcccaccga gcagtgttga    8160
gtggtgttac ccagggcttc atgaaaaagg cgtttaactc gcccatcgcc ctcggaaaga    8220
acaagtttaa ggagctacag actccggtcc tgggcaggtg ccttgaagct gatctcgcat    8280
cctgcgatcg atccacgcct gcaattgtcc gctggtttgc cgccaacctt ctttatgaac    8340
ttgcctgtgc tgaagagcat ctaccgtcgt acgtgctgaa ctgctgccac gacttactgg    8400
tcacgcagtc cggcgcagtg actaagagag gtggcctgtc gtctggcgac ccgatcacct    8460
ctgtgtctaa caccatttat agtttggtga tctatgcaca gcatatggtg cttagttact    8520
tcaaaagtgg tcaccccccat ggccttctgt tcttacaaga ccagctaaag tttgaggaca    8580
tgctcaaggt tcaacccctg atcgtctatt cggacgacct cgtgctgtat gccgagtctc    8640
ccaccatgcc aaactatcac tggtgggttg aacatctgaa tttgatgctg ggttttcaga    8700
cggacccaaa aagacagca ataacagact cgccatcatt tctaggctgt agaataataa    8760
atgggcgcca gctagtcccc aaccgtgaca ggatcctcgc ggccctcgcc tatcacatga    8820
```

```
aggcgagtaa tgtttctgaa tactatgcct cagcggctgc aatactcatg acagctgtg    8880
cttgttttgga gtatgatcct gaatggtttg aagaacttgt agttggaata gcgcagtgcg   8940
cccgcaagga cggctacagc tttcccggca cgccgttctt catgtccatg tgggaaaaac   9000
tcaggtccaa ttatgagggg aagaagtcga gagtgtgcgg gtactgcggg gccccggccc   9060
cgtacgctac tgcctgtggc ctcgacgtct gcatttacca cacccacttc caccagcatt   9120
gtccagtcac aatctggtgt ggccatccag cgggttctgg ttcttgtagt gagtgcaaat   9180
cccctgtagg gaaaggcaca agcccttag acgaggtgct ggaacaagtc cgtataagc    9240
ccccacggac cgttatcatg catgtggagc agggtctcac ccccttgat ccaggtagat    9300
accaaactcg ccgcggatta gtctctgtca ggcgtggaat taggggaaat gaagttggac   9360
taccagacgg tgattatgct agcaccgcct tgctccctac ctgcaaagag atcaacatgg   9420
tcgctgtcgc ttccaatgta ttgcgcagca ggttcatcat cggcccaccc ggtgctggga   9480
aaacatactg gctccttcaa caggtccagg atggtgatgt tatttacaca ccaactcacc   9540
agaccatgct tgacatgatt agggctttgg ggacgtgccg gttcaacgtc ccggcaggca   9600
caacgctgca attccccgtc ccctcccgca ccggtccgtg ggttcgcatc ctagccggcg   9660
gttggtgtcc tggcaagaat tccttcctag atgaagcagc gtattgcaat caccttgatg   9720
ttttgaggct tcttagtaaa actaccctca cctgtctagg agacttcaag caactccacc   9780
cagtgggttt tgattctcat tgctatgttt ttgacatcat gcctcaaact caactgaaga   9840
ccatctggag gtttggacag aatatctgtg atgccattca gccagattac agggacaaac   9900
tcatgtccat ggtcaacaca acccgtgtga cctacgtgga aaaacctgtc aggtatgggc   9960
aggtcctcac ccctaccac agggaccgag aggacgacgc catcactatt gactccagtc   10020
aaggcgccac attcgatgtg gttacattgc atttgcccac taaagattca ctcaacaggc   10080
aaagagccct tgttgctatc accagggcaa gacacgctat cttgtgtat gacccacaca   10140
ggcagctgca gggcttgttt gatcttcctg caaaaggcac gcccgtcaac ctcgcagtgc   10200
actgcgacgg gcagctgatc gtgctggata gaaataacaa agaatgcacg gttgctcagg   10260
ctctaggcaa cggggataaa tttagggcca cagacaagcg tgttgtagat tctctccgcg   10320
ccatttgtgc tgatctagaa gggtcgagct ctccgctccc caaggtcgca cacaacttgg   10380
gattttattt ctcacctgat ttaacacagt ttgctaaact cccagtagaa cttgcacctc   10440
actggcccgt ggtgtcaacc cagaacaatg aaaagtggcc ggatcggctg gttgccagcc   10500
ttcgcccctat ccataaatac agccgcgcgt gcatcggtgc cggctatatg gtgggccctt   10560
cggtgtttct aggcactcct ggggtcgtgt catactatct cacaaaattt gttaagggcg   10620
gggctcaagt gcttccggag acggttttca gcaccggccg aattgaggta gactgccggg   10680
aatatcttga tgatcgggag cgagaagttg ctgcgtccct cccacacgct ttcattggcg   10740
acgtcaaagg cactaccgtt ggaggatgtc atcatgtcac ctccagatac ctcccgcgcg   10800
tccttcccaa ggaatcagtt gcggtagtcg gggtttcaag ccccggaaaa gccgcgaaag   10860
cattgtgcac actgacagat gtgtacctcc cagatcttga agcctatctc cacccggaga   10920
cccagtccaa gtgctggaaa atgatgttgg acttcaaaga agttcgacta atggtctgga   10980
aagacaaaac agcctatttc caacttgaag gtcgctattt cacctggtat cagcttgcca   11040
gctatgcctc gtacatccgt gttcccgtca actctacggt gtacttggac ccctgcatgg   11100
gccccgccct ttgcaacagg agagtcgtcg ggtccaccca ctgggggct gacctcgcgg   11160
```

```
tcacccctta tgattacggc gctaaaatta tcctgtctag cgcgtaccat ggtgaaatgc    11220
cccccggata caaaattctg gcgtgcgcgg agttctcgtt ggatgaccca gttaagtaca    11280
aacatacctg ggggtttgaa tcggatacag cgtatctgta tgagttcacc ggaaacggtg    11340
aggactggga ggattacaat gatgcgtttc gtgcgcgcca ggaagggaaa atttataagg    11400
ccactgccac cagcttgaag ttttattttc ccccgggccc tgtcattgaa ccaactttag    11460
gcctgaattg aaatgaaatg gggtccatgc aaagcctttt tgacaaaatt ggccaacttt    11520
ttgtggatgc tttcacggag ttcttggtgt ccattgttga tatcattata tttttggcca    11580
ttttgtttgg cttcaccatc gccggttggc tggtggtctt ttgcatcaga ttggtttgct    11640
ccgcgatact ccgtacgcgc cctgccattc actctgagca attacagaag atcttatgag    11700
gcctttcttt cccagtgcca agtggacatt cccacctggg gaactaaaca tcctttgggg    11760
atgctttggc accataaggt gtcaaccctg attgatgaaa tggtgtcgcg tcgaatgtac    11820
cgcatcatgg aaaaagcagg gcaggctgcc tggaaacagg tggtgagcga ggctacgctg    11880
tctcgcatta gtagtttgga tgtggtggct cattttcagc atctagccgc cattgaagcc    11940
gagacctgta aatatttggc ctcccggctg cccatgctac acaacctgcg catgacaggg    12000
tcaaatgtaa ccatagtgta taatagcact ttgaatcagg tgtttgctat ttttccaacc    12060
cctggttccc ggccaaagct tcatgatttt cagcaatggt taatagctgt acattcctcc    12120
atattttcct ctgttgcagc ttcttgtact cttttttgttg tgctgtggtt gcgggttcca    12180
atactacgta ctgtttttgg tttccgctgg ttaggggcaa ttttttctttc gaactcacag    12240 tgaattacac ggtgtgtcca ccttgcctca cccggcaagc agccacagag atctacgaac    12300
ccggtaggtc tctttggtgc aggatagggt atgaccgatg tggggaggac gatcatgacg    12360
agctagggtt tatgataccg cctggcctct ccagcgaagg ccacttgact ggtgtttacg    12420
cctggttggc gttcttgtcc ttcagctaca cggcccagtt ccatcccgag atattcggga    12480
tagggaatgt gagtcgagtt tatgttgaca tcaaacatca actcatctgc gccgaacatg    12540
acgggcagaa caccaccttg cctcgtcatg acaacatttc agccgtgttt cagacctatt    12600
accaacatca agtcgacggc ggcaattggt ttcacctaga atggcttcgt cccttctttt    12660
cctcgtggtt ggttttaaat gtctcttggt ttctcaggcg ttcgcctgca aaccatgttt    12720
cagttcgagt cttgcagata ttaagaccaa caccaccgca gcggcaagct ttgctgtcct    12780
ccaagacatc agttgcctta ggcatcgcga ctcggcctct gaggcgattc gcaaaatccc    12840
tcagtgccgt acggcgatag ggacacccgt gtatgttacc atcacagcca atgtgacaga    12900
tgagaattat ttacattctt ctgatctcct catgctttct tcttgccttt tctatgcttc    12960
tgagatgagt gaaaagggat ttaaggtggt atttggcaat gtgtcaggca tcgtggctgt    13020
gtgtgtcaat tttaccagct acgtccaaca tgtcaaggag tttacccaac gctccctggt    13080
ggtcgaccat gtgcggttgc tccatttcat gacacctgag accatgaggt gggcaactgt    13140
tttagcctgt cttttttgcca ttctgttggc aatttgaatg tttaagtatg ttggagaaat    13200
gcttgaccgc gggctgttgc tcgcgattgc tttctttgtg gtgtatcgtg ccgttctgtt    13260
ttgctgtgct cgccaacgcc agcaacgaca gcagctccca tctacagctg atttacaact    13320
tgacgctatg tgagctgaat ggcacagatt ggctagctaa caaatttgat tgggcagtgg    13380
agagttttgt catctttccc gttttgactc acattgtctc ctatggtgcc ctcactacca    13440
gccatttcct tgacacagtc gctttagtca ctgtgtctac cgccgggttt gttcacgggc    13500
ggtatgtcct aagtagcatc tacgcggtct gtgccctggc tgcgttgact tgcttcgtca    13560
```

```
ttaggtttgc aaagaattgc atgtcctggc gctacgcgtg taccagatat accaactttc   13620
ttctggacac taagggcaga ctctatcgtt ggcggtcgcc tgtcatcata gagaaaaggg   13680
gcaaagttga ggtcgaaggt catctgatcg acctcaaaag agttgtgctt gatggctccg   13740
tggcaacccc tataaccaga gtttcagcgg aacaatgggg tcgtccttag atgacttctg   13800
tcacgatagc acggctccac aaaaggtgct tttggcgttt tctattacct acacgccagt   13860
gatgatatat gccctaaagg tgagtcgcgg ccgactgcta gggcttctgc acctttgat   13920
cttcctgaat tgtgctttca ccttcgggta catgactttc gcgcactttc agagtacaaa   13980
taaggtcgcg ctcactatgg gagcagtagt tgcactcctt tgggggtgt actcagccat   14040
agaaacctgg aaattcatca cctccagatg ccgtttgtgc ttgctaggcc gcaagtacat   14100
tctgcccct gcccaccacg ttgaaagtgc gcaggcttt catccgattg cggcaaatga   14160
taaccacgca tttgtcgtcc ggcgtcccgg ctccactacg gtcaacggca cattggtgcc   14220
cgggttaaaa agcctcgtgt tgggtggcag aaaagctgtt aaacaggag tggtaaacct   14280
tgtcaaatat gccaaataac aacggcaagc agcagaagag aaagaagggg gatggccagc   14340
cagtcaatca gctgtgccag atgctgggta agatcatcgc tcagcaaaac cagtccagag   14400
gcaagggacc gggaaagaaa aataagaaga aaaacccgga gagcccat tttcctctag   14460
cgactgaaga tgatgtcaga catcacttta ccccctagtga gcggcaattg tgtctgtcgt   14520
caatccagac cgccttta aaggcgctg ggacttgcac cctgtcagat tcagggagga   14580
taagttacac tgtggagttt agtttgccta cgcatcatac tgtgcgcctg atccgcgtca   14640
cagcatcacc ctcagcatga tgggctggca ttcttgaggc atctcagtgt ttgaattgga   14700
agaatgtgtg gtgaatggca ctgattgaca ttgtgcctct aagtcaccta ttcaattagg   14760
gcgaccgtgt gggggtgaga tttaattggc gagaaccatg cggccgaaat taaaaaaaa   14819
```

<210> SEQ ID NO 9
<211> LENGTH: 15149
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 9

```
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta cccccaatgc cagggtgttt    240
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct ccccgccgg ggcctgctgg    420
ctttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt cgccaattc cctacatgtg agtgataaac ccttcccggg agcaactcac    660
gtgttgacca acctgccgct cccgcagaga cccaagccta agacttttg ccccttgag    720
tgtgctatgg ctactgtcta tgacattggt catgacgccg tcatgtatgt ggccgaaagg    780
```

```
aaagtctcct gggcccctcg tggcggggat gaagtgaaat ttgaagctgt ccccggggag    840
ttgaagttga ttgcgaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccctgg gatgtccct    1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca gtgcgcttta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc ccctgaccgc cttttcactg   2340
gctaactact actaccgtgc gcaaggtgac gaagttcgtc accgtgaaag actaaccgcc   2400
gtgctctcca gttggaaaa ggttgttcga gaagaatatg ggctcatgcc aaccgagcct   2460
ggtccacggc ccacactgcc acgcgggctc gacgaactca agaccagat ggaggaggac    2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttg atctcccgac cccacctgag    2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatcacacgc ccaaaatact cagctcaagc catcatcgac   3000
tcgggcgggc cctgcagtgg gcatctccaa gaggtaaagg aaacatgcct tagtgtcatg   3060
cgcgaggcat gtgatgcgac taagcttgat gaccctgcta cgcaggaatg gctttctcgc   3120
```

```
atgtgggatc gggtggacat gctgacttgg cgcaacacgt ctgtttacca ggcgatttgc    3180
accttagatg gcaggttaaa gttcctccca aaaatgatac tcgagacacc gccgccctat    3240
ccgtgtgagt ttgtgatgat gcctcacacg cctgcacctt ccgtaggtgc ggagagcgac    3300
cttaccattg gctcagttgc tactgaagat gttccacgca tcctcgagaa aatagaaaat    3360
gtcggcgaga tggccaacca gggacccttg gccttctccg aggataaacc ggtagatgac    3420
caacttgtca acgaccccg gatatcgtcg cggaggcctg acgagagcac atcagctccg    3480
tccgcaggca caggtggcgc cggctctttt accgatttgc cgccttcaga tggcgcggat    3540
gcggacgggg gggggccgtt tcggacggta aaagaaaag ctgaaaggct ctttgaccaa    3600
ctgagccgtc aggttttga cctcgtctcc catctccctg ttttcttctc acgccttttc    3660
taccctggcg gtggttattc tccgggtgat tgggttttg cagcttttac tctattgtgc    3720
ctctttttat gttacagtta cccagccttt ggtattgctc ccctcttggg tgtgttttct    3780
gggtcttctc ggcgcgttcg aatgggggtt tttggctgct ggttggcttt tgctgttggt    3840
ctgttcaagc ctgtgtccga cccagtcggc gctgcttgtg agtttgactc gccagagtgt    3900
agaaacatcc ttcattcttt tgagcttctc aaaccttggg accctgttcg cagccttgtt    3960
gtgggccccg tcggtctcgg tcttgccatt cttggcaggt tactgggcgg ggcacgctgc    4020
atctggcact ttttgcttag gcttggcatt gttgcagact gtatcttggc tggagcttac    4080
gtgctttctc aaggtaggtg taaaaagtgc tggggatctt gtataagaac tgctcccaat    4140
gaggtcgctt ttaacgtgtt tcctttcaca cgtgcgacca ggtcgtcact tatcgacctg    4200
tgcgatcggt tttgtgcgcc aaaaggaatg gaccccattt ttctcgccac tgggtggcgc    4260
gggtgctggg ccggccgaag ccccattgag caaccctctg aaaaacccat cgcgtttgcc    4320
cagttggatg aaaagaagat tacggctagg actgtggtcg cccagcctta tgaccccaac    4380
caagccgtaa agtgcttgcg ggtattgcag gcgggtgggg cgatggtggc taaggcggtc    4440
ccaaaagtgg tcaaggtttc cgctgttcca ttccgagccc ccttctttcc cactggagtg    4500
aaagttgacc ctgattgcag ggtcgtggtt gaccctgaca cttcactgc agctctccgg    4560 tctggctact ccaccacaaa cctcgtcctt ggtgtggggg actttgccca gctgaatgga    4620
ttaaaaatca ggcaaatttc caagccttca gggaggcc cacatctcat ggctgccctg    4680
catgttgcct gctcgatggc tctgcacatg cttgctggga tttatgtgac tgcggtgggt    4740
tcttgcggca ccggcaccaa cgacccgtgg tgcgctaacc cgtttgccgt ccctggctac    4800
ggacctggct ctctctgcac gtccagattg tgcatttccc aacacggcct taccctgccc    4860
ttgacagcac ttgtggcggg attcggtatt caagaaattg ccttggtcgt tttgatttt    4920 gtttccatcg gaggcatggc tcataggttg agctgtaagg ctgacatgct gtgtgtcttg    4980
cttgcaattg ccagctatgt ttgggtacct cttacctggt tgctttgtgt gtttccttgc    5040
tggttgcgct tttttctttt gcaccccctc accatcctat ggttggtgtt tttcttgatt    5100
tctgtgaata tgccttcagg aatcttggcc atggtgttgt tggtttctct ttggcttctt    5160
ggtcgttata ctaatgttgc tggccttgtc acccctacg acattcatca ttacaccagt    5220 ggccccgcg tgttgccgc cttggctacc gcaccagatg gaacctactt ggccgctgtc    5280
cgccgcgctg cgttgactgg ccgcaccatg ctgtttaccc cgtcccagct tgggtctctt    5340
cttgagggtg ctttcagaac tcgaaagccc tcactgaaca ccgtcaatgt gatcgggtcc    5400
tccatgggct ctgcggggt gtttaccatc gacgggaaag tcaagtgcgt aactgccgca    5460
catgtcctta cgggcaattc agctcgggtt tccggggtcg gcttcaatca aatgcttgac    5520
```

```
tttgacgtaa agggagattt cgctatagct gattgcccga attggcaagg ggctgccccc    5580
aagacccaat tctgcacgga tggatggact ggccgtgcct attggctaac atcctctggc    5640
gtcgaacccg gcgtcattgg aaaaggattc gccttctgct tcaccgcatg tggcgattcc    5700
gggtccccag tgatcaccga ggccggtgag cttgtcggcg ttcacacggg atcgaataaa    5760
caaggggggg gcattgttac gcgcccctca ggccagtttt gtaatgtggc acccatcaag    5820
ctaagcgaat taagtgaatt ctttgctggg cctaaggtcc cgctcggtga tgtgaaggtc    5880
ggcagccaca taattaaaga cataagcgag gtgccttcag atctttgtgc cttgcttgct    5940
gccaaacctg aactgaagg aggcctctcc accgtccaac ttctttgtgt gttttttctc     6000
ctgtggagaa tgatgggaca tgcctggacg cccttggttg ctgtgagttt ctttattttg    6060
aatgaggttc tcccagccgt cctggtccga agtgttttct cctttggaat gtttgtgcta    6120
tcctggctca cgccatggtc tgcgcaagtt ctgatgatca ggcttctgac agcagctctt    6180
aacaggaaca gatggtcact tgccttttc agcctcggtg cagtgaccgg ttttgtcgca     6240
gatcttgcgg ccactcaggg gcatccgttg caggcagtga tgaatttgag cacctatgca    6300
ttcctgcctc ggatgatggt tgtgacctca ccagtcccag tgatcacgtg tggtgtcgtg    6360
cacctacttg ccatcatttt gtacttgttt aagtaccgtg gcctgcacca tatccttgtt    6420
ggcgatggag tgttctctgc ggcttttctc ttgagatact ttgccgaggg aaagttgagg    6480
gaaggggtgt cgcaatcctg cggaatgaat catgagtctc tgactggtgc cctcgctatg    6540
agactcaatg acgaggactt ggatttcctt atgaaatgga ctgattttaa gtgctttgtt    6600
tctgcgtcca acatgaggaa tgcagcgggt caatttatcg aggctgccta tgctaaagca    6660
cttagagtag aactggccca gttggtgcag gttgataaag ttcgaggtac tttggccaaa    6720
cttgaagctt ttgctgatac cgtggcacct caactctcgc ccggtgacat tgttgtcgct    6780
ctcggccaca cgcctgttgg cagtatcttc gacctaaagg ttggtagcac caagcatacc    6840
ctccaagcca ttgagaccag agtccttgct gggtccaaaa tgaccgtggc gcgcgtcgtc    6900
gacccgaccc ccacgccccc acccgcaccc gtgcccatcc cctcccacc gaaagttctg     6960
gagaatggcc ccaacgcttg gggggatgag gaccgtttga ataagaagaa gaggcgcagg    7020
atggaagccc tcggcatcta tgttatgggc gggaaaaaat accagaaatt ttgggacaag    7080
aattccggtg atgtgtttta tgaggaggtc cataataaca cagatgagtg ggagtgtctc    7140
agagttggcg accctgccga ctttgacccc tgagaaggga actctgtgtgg acatgtcacc   7200
attgaaaaca aggcttacca tgtttacacc tccccatctg gtaagaagtt cttggtcccc    7260
gtcaacccag agaatggaag agtccaatgg gaagctgcaa agctttccgt ggagcaggcc    7320
ctaggtatga tgaatgtcga cggcgaactg actgccaaag aactggagaa actgaaaaga    7380
ataattgaca aactccaggg cctgactaag gagcagtgtt taaactgcta gccgccagcg    7440
acttgacccg ctgtggtcgc ggcggcttgg ttgttactga acagcggta aaaatagtca     7500
aatttcacaa ccggaccttc accctgggac ctgtgaattt aaaagtggcc agtgaggttg    7560
agctaaaaga cgcggttgag cacaaccaac acccggttgc gagaccgatc gatggtggag    7620
ttgtgctcct gcgttccgcg gttccttcgc ttatagacgt cttgatctcc ggtgctgatg    7680
catctcccaa gttacttgcc catcacgggc cgggaaacac tgggatcgat ggcacgctct    7740
gggattttga gtccgaagcc actaaagagg aagtcgcact cagtgcgcaa ataatacagg    7800
cttgtgacat taggcgcggc gacgctcctg aaattggtct cccttacaag ctgtaccctg    7860
```

```
ttaggggtaa ccctgagcgg gtgaaaggag ttctgcagaa tacaaggttt ggagacatac    7920
cttacaaaac ccccagtgac actggaagcc cagtgcacgc ggctgcctgc cttacgccca    7980
acgccactcc ggtgactgat gggcgctccg tcttggccac gaccatgccc cccgggtttg    8040
agttatatgt accgaccata ccagcgtctg tccttgatta ccttgactct aggcctgact    8100
gccctaaaca gctgacagag cacggctgcg aagatgccgc actgaaagac ctctctaaat    8160
atgacttgtc cacccaaggc tttgttttac ctggagttct tcgccttgtg cggaaatacc    8220
tgtttgccca tgtaggtaag tgcccacccg ttcatcggcc ttctacttac cctgctaaga    8280
attctatggc tggaataaat gggaacaggt tcccaaccaa ggacattcag agcgtccctg    8340
aaatcgacgt tctgtgcgca caggctgtgc gagaaaactg gcaaactgtc ccccttgta    8400 ctcttaagaa acagtattgc gggaagaaga agactaggac catactcggc accaataact    8460
tcatcgcact agcccaccga gcagtgttga gtggtgttac ccagggcttc atgaaaaagg    8520
cgtttaactc gcccatcgcc ctcggaaaga acaagtttaa ggagctacag actccggtcc    8580
tgggcaggtg ccttgaagct gatctcgcat cctgcgatcg atccacgcct gcaattgtcc    8640
gctggtttgc cgccaacctt ctttatgaac ttgcctgtgc tgaagagcat ctaccgtcgt    8700
acgtgctgaa ctgctgccac gacttactgg tcacgcagtc cggcgcagtg actaagagag    8760
gtggcctgtc gtctggcgac ccgatcacct ctgtgtctaa caccatttat agtttggtga    8820
tctatgcaca gcatatggtg cttagttact tcaaaagtgg tcaccccat ggccttctgt    8880 tcttacaaga ccagctaaag tttgaggaca tgctcaaggt tcaacccctg atcgtctatt    8940
cggacgacct cgtgctgtat gccgagtctc ccaccatgcc aaactatcac tggtgggttg    9000
aacatctgaa tttgatgctg gggtttcaga cggacccaaa gaagacagca ataacagact    9060
cgccatcatt tctaggctgt agaataataa atgggcgcca gctagtcccc aaccgtgaca    9120
ggatcctcgc ggccctcgcc tatcacatga aggcgagtaa tgtttctgaa tactatgcct    9180
cagcggctgc aatactcatg gacagctgtg cttgtttgga gtatgatcct gaatggtttg    9240
aagaacttgt agttggaata gcgcagtgcg cccgcaagga cggctacagc tttcccggca    9300
cgccgttctt catgtccatg tgggaaaaac tcaggtccaa ttatgagggg aagaagtcga    9360
gagtgtgcgg gtactgcggg gccccggccc cgtacgctac tgcctgtggc ctcgacgtct    9420
gcatttacca cacccacttc caccagcatt gtccagtcac aatctggtgt ggccatccag    9480
cgggttctgg ttcttgtagt gagtgcaaat cccctgtagg gaaaggcaca agcccttag    9540 acgaggtgct ggaacaagtc ccgtataagc ccccacggac cgttatcatg catgtggagc    9600
agggtctcac ccccccttgat ccaggtagat accaaactcg ccgcggatta gtctctgtca    9660
ggcgtggaat tagggaaat gaagttggac taccagacgg tgattatgct agcaccgcct    9720
tgctccctac ctgcaaagag atcaacatgg tcgctgtcgc ttccaatgta ttgcgcagca    9780
ggttcatcat cggcccaccc ggtgctggga aaacatactg gctccttcaa caggtccagg    9840
atggtgatgt tatttacaca ccaactcacc agaccatgct tgacatgatt agggctttgg    9900
ggacgtgccg gttcaacgtc ccggcaggca aacgctgca attccccgtc cctcccgca    9960 ccggtccgtg ggttcgcatc ctagccgcg gttggtgtcc tggcaagaat tccttcctag   10020
atgaagcagc gtattgcaat caccttgatg ttttgaggct tctagtaaa actaccctca   10080 cctgtctagg agacttcaag caactccacc cagtgggttt tgattctcat tgctatgttt   10140
ttgacatcat gcctcaaact caactgaaga ccatctggag gttggacag aatatctgtg   10200 atgccattca gccagattac agggacaaac tcatgtccat ggtcaacaca accgtgtga   10260
```

```
cctacgtgga aaaacctgtc aggtatgggc aggtcctcac cccctaccac agggaccgag    10320
aggacgacgc catcactatt gactccagtc aaggcgccac attcgatgtg gttacattgc    10380
atttgcccac taaagattca ctcaacaggc aaagagccct tgttgctatc accagggcaa    10440
gacacgctat ctttgtgtat gacccacaca ggcagctgca gggcttgttt gatcttcctg    10500
caaaaggcac gcccgtcaac ctcgcagtgc actgcgacgg gcagctgatc gtgctggata    10560
gaaataacaa agaatgcacg gttgctcagg ctctaggcaa cggggataaa tttagggcca    10620
cagacaagcg tgttgtagat tctctccgcg ccatttgtgc tgatctagaa gggtcgagct    10680
ctccgctccc caaggtcgca cacaacttgg gattttattt ctcacctgat ttaacacagt    10740
ttgctaaact cccagtagaa cttgcacctc actggcccgt ggtgtcaacc cagaacaatg    10800
aaaagtggcc ggatcggctg gttgccagcc ttcgccctat ccataaatac agccgcgcgt    10860
gcatcggtgc cggctatatg gtgggcccct cggtgtttct aggcactcct ggggtcgtgt    10920
catactatct cacaaaattt gttaagggcg gggctcaagt gcttccggag acggttttca    10980
gcaccggccg aattgaggta gactgccggg aatatcttga tgatcgggag cgagaagttg    11040
ctgcgtccct cccacacgct ttcattggcg acgtcaaagg cactaccgtt ggaggatgtc    11100
atcatgtcac ctccagatac ctcccgcgcg tccttcccaa ggaatcagtt gcggtagtcg    11160
gggtttcaag ccccggaaaa gccgcgaaag cattgtgcac actgacagat gtgtacctcc    11220
cagatcttga agcctatctc cacccggaga cccagtccaa gtgctggaaa atgatgttgg    11280
acttcaaaga agttcgacta atggtctgga aagacaaaac agcctatttc caacttgaag    11340 gtcgctatt cacctggtat cagcttgcca gctatgcctc gtacatccgt gttcccgtca    11400
actctacggt gtacttggac ccctgcatgg gccccgccct ttgcaacagg agagtcgtcg    11460
ggtccaccca ctgggggct gacctcgcgg tcaccccctta tgattacggc gctaaaatta    11520
tcctgtctag cgcgtaccat ggtgaaatgc ccccccggata caaaattctg gcgtgcgcgg    11580
agttctcgtt ggatgaccca gttaagtaca aacatacctg ggggtttgaa tcggatacag    11640
cgtatctgta tgagttcacc ggaaacggtg aggactggga ggattacaat gatgcgtttc    11700
gtgcgcgcca ggaagggaaa atttataagg ccactgccac cagcttgaag ttttattttc    11760
ccccgggccc tgtcattgaa ccaactttag gcctgaattg aaatgaaatg gggtccatgc    11820
aaagcctttt tgacaaaatt ggccaacttt ttgtggatgc tttcacgag ttcttggtgt    11880 ccattgttga tatcattata ttttggcca ttttgtttgg cttccaccatc gccggttggc    11940 tggtggtctt ttgcatcaga ttggtttgct ccgcgatact ccgtacgcgc cctgccattc    12000
actctgagca attacagaag atcttatgag gcctttcttt cccagtgcca agtggacatt    12060
cccacctggg gaactaaaca tccttttggg atgctttggc accataaggt gtcaaccctg    12120
attgatgaaa tggtgtcgcg tcgaatgtac cgcatcatgg aaaaagcagg gcaggctgcc    12180
tggaaacagg tggtgagcga ggctacgctg tctcgcatta gtagttga tgtggtggct    12240 cattttcagc atctagccgc cattgaagcc gagacctgta atatttggc ctcccggctg    12300 cccatgctac acaacctgcg catgacaggg tcaaatgtaa ccatagtgta taatagcact    12360
ttgaatcagg tgtttgctat ttttccaacc cctggttccc ggccaaagct tcatgatttt    12420
cagcaatggt taatagctgt acattcctcc atattttcct ctgttgcagc ttcttgtact    12480 cttttttgttg tgctgtggtt gcgggttcca atactacgta ctgttttttgg tttccgctgg    12540 ttaggggcaa ttttttctttc gaactcacag tgaattacac ggtgtgtcca ccttgcctca    12600
```

```
cccggcaagc agccacagag atctacgaac ccggtaggtc tctttggtgc aggatagggt    12660
atgaccgatg tggggaggac gatcatgacg agctagggtt tatgataccg cctggcctct    12720
ccagcgaagg ccacttgact ggtgtttacg cctggttggc gttcttgtcc ttcagctaca    12780
cggcccagtt ccatcccgag atattcggga tagggaatgt gagtcgagtt tatgttgaca    12840
tcaaacatca actcatctgc gccgaacatg acgggcagaa caccaccttg cctcgtcatg    12900
acaacatttc agccgtgttt cagacctatt accaacatca agtcgacggc ggcaattggt    12960
ttcacctaga atggcttcgt cccttctttt cctcgtggtt ggttttaaat gtctcttggt    13020
ttctcaggcg ttcgcctgca aaccatgttt cagttcgagt cttgcagata ttaagaccaa    13080
caccaccgca gcggcaagct ttgctgtcct ccaagacatc agttgcctta ggcatcgcga    13140
ctcggcctct gaggcgattc gcaaaatccc tcagtgccgt acggcgatag ggacacccgt    13200
gtatgttacc atcacagcca atgtgacaga tgagaattat ttacattctt ctgatctcct    13260
catgctttct tcttgccttt tctatgcttc tgagatgagt gaaaagggat ttaaggtggt    13320
atttggcaat gtgtcaggca tcgtggctgt gtgtgtcaat tttaccagct acgtccaaca    13380
tgtcaaggag tttacccaac gctccctggt ggtcgaccat gtgcggttgc tccatttcat    13440
gacacctgag accatgaggt gggcaactgt tttagcctgt cttttttgcca ttctgttggc    13500 aatttgaatg tttaagtatg ttggagaaat gcttgaccgc gggctgttgc tcgcgattgc    13560
tttctttgtg gtgtatcgtg ccgttctgtt ttgctgtgct cgccaacgcc agcaacgaca    13620
gcagctccca tctacagctg atttacaact tgacgctatg tgagctgaat ggcacagatt    13680
ggctagctaa caaatttgat tgggcagtgg agagttttgt catctttccc gttttgactc    13740
acattgtctc ctatggtgcc ctcactacca gccatttcct tgacacagtc gctttagtca    13800
ctgtgtctac cgccgggttt gttcacgggc ggtatgtcct aagtagcatc tacgcggtct    13860
gtgccctggc tgcgttgact tgcttcgtca ttaggtttgc aaagaattgc atgtcctggc    13920
gctacgcgtg taccagatat accaactttc ttctggacac taagggcaga ctctatcgtt    13980
ggcggtcgcc tgtcatcata gagaaaaggg gcaaagttga ggtcgaaggt catctgatcg    14040
acctcaaaag agttgtgctt gatggctccg tggcaacccc tataaccaga gtttcagcgg    14100
aacaatgggg tcgtccttag atgacttctg tcacgatagc acggctccac aaaaggtgct    14160
tttggcgttt tctattacct acacgccagt gatgatatat gccctaaagg tgagtcgcgg    14220
ccgactgcta gggcttctgc accttttgat cttcctgaat tgtgctttca ccttcgggta    14280
catgactttc gcgcacttc agagtacaaa taaggtcgcg ctcactatgg gagcagtagt    14340
tgcactcctt tggggggtgt actcagccat agaaacctgg aaattcatca cctccagatg    14400
ccgtttgtgc ttgctaggcc gcaagtacat tctggcccct gcccaccacg ttgaaagtgc    14460
cgcaggcttt catccgattg cggcaaatga taaccacgca tttgtcgtcc ggcgtcccgg    14520
ctccactacg gtcaacggca cattggtgcc cgggttaaaa agcctcgtgt tgggtggcag    14580
aaaagctgtt aaacagggag tggtaaacct tgtcaaatat gccaaataac aacggcaagc    14640
agcagaagag aaagaagggg gatggccagc cagtcaatca gctgtgccag atgctgggta    14700
agatcatcgc tcagcaaaac cagtccagag gcaagggacc gggaaagaaa ataagaagaa    14760
aaacccggag aagccccat tttcctctag cgactgaaga tgatgtcaga catcactta    14820 cccctagtga gcggcaattg tgtctgtcgt caatccagac cgcctttaat caaggcgctg    14880
ggacttgcac cctgtcagat tcaggaggga taagttacac tgtggagttt agtttgccta    14940
cgcatcatac tgtgcgcctg atccgcgtca cagcatcacc ctcagcatga tgggctggca    15000
```

-continued

| | |
|---|---|
| ttcttgaggc atctcagtgt ttgaattgga agaatgtgtg gtgaatggca ctgattgaca | 15060 |
| ttgtgcctct aagtcaccta ttcaattagg gcgaccgtgt gggggtgaga tttaattggc | 15120 |
| gagaaccatg cggccgaaat taaaaaaaa | 15149 |

<210> SEQ ID NO 10
<211> LENGTH: 15137
<212> TYPE: DNA
<213> ORGANISM: Artificial Sequence
<220> FEATURE:
<223> OTHER INFORMATION: Porcine reproductive and respiratory syndrome virus -continued

```
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttgacaaca aactcggtcc ccctgaccgc cttttcactg    2340
gctaactact actaccgtgc gcaaggtgac gaagttcgtc accgtgaaag actaaccgcc    2400
gtgctctcca agttggaaaa ggttgttcga agaatatg ggctcatgcc aaccgagcct      2460
ggtccacggc ccacactgcc acgcgggctc gacgaactca agaccagat ggaggaggac     2520
ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agcccctttg atctcccgac ccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggcgtt    3120
ctggagtag aggggcatga agctgaggaa accctgagtg aaatctcgga catgtcgggt     3180
aacattaaac ctgcgtccgt gtcatcaagc agctccttgt ccagcgtgag atgtgagttt    3240
gtgatgatgc ctcacacgcc tgcaccttcc gtaggtgcgg agagcgacct taccattggc    3300
tcagttgcta ctgaagatgt tccacgcatc ctcgagaaaa tagaaaatgt cggcgagatg    3360
gccaaccagg gacccttggc cttctccgag gataaaccgg tagatgacca acttgtcaac    3420
gaccccggga tatcgtcgcg gaggcctgac gagagcacat cagctccgtc cgcaggcaca    3480
ggtggcgccg gctctttac cgatttgccg ccttcagatg gcgcggatgc ggacgggggg     3540
gggccgtttc ggacggtaaa aagaaaagct gaaaggctct tgaccaact gagccgtcag     3600
gtttttgacc tcgtctccca tctccctgtt ttcttctcac gccttttcta ccctggcggt    3660
ggttattctc cgggtgattg gggttttgca gcttttactc tattgtgcct cttttatgt     3720
tacagttacc cagcctttgg tattgctccc ctcttgggtg tgttttctgg gtcttctcgg    3780
cgcgttcgaa tggggttttt ggctgctgg ttggcttttg ctgttggtct gttcaagcct    3840
gtgtccgacc cagtcggcgc tgcttgtgag tttgactcgc cagagtgtag aaacatcctt    3900
cattcttttg agcttctcaa acctgggac cctgttcgca gccttgttgt gggcccgtc      3960
ggtctcggtc ttgccattct tggcaggtta ctgggcgggg cacgctgcat ctggcacttt    4020
ttgcttaggc ttggcattgt tgcagactgt atcttggctg gagcttacgt gctttctcaa    4080
ggtaggtgta aaaagtgctg gggatcttgt ataagaactg ctcccaatga ggtcgctttt    4140
aacgtgtttc ctttcacacg tgcgaccagg tcgtcactta tcgacctgtg cgatcggttt    4200
```

```
tgtgcgccaa aaggaatgga ccccattttt ctcgccactg ggtggcgcgg gtgctgggcc      4260
ggccgaagcc ccattgagca accctctgaa aaacccatcg cgtttgccca gttggatgaa      4320
aagaagatta cggctaggac tgtggtcgcc cagccttatg accccaacca agccgtaaag      4380
tgcttgcggg tattgcaggc gggtggggcg atggtggcta aggcggtccc aaaagtggtc      4440
aaggtttccg ctgttccatt ccgagccccc ttctttccca ctggagtgaa agttgaccct      4500
gattgcaggg tcgtggttga ccctgacact ttcactgcag ctctccggtc tggctactcc      4560
accacaaacc tcgtccttgg tgtgggggac tttgcccagc tgaatggatt aaaaatcagg      4620
caaatttcca agccttcagg gggaggccca catctcatgg ctgccctgca tgttgcctgc      4680
tcgatggctc tgcacatgct tgctgggatt tatgtgactg cggtgggttc ttgcggcacc      4740
ggcaccaacg accccgtggtg cgctaacccg tttgccgtcc ctggctacgg acctggctct      4800
ctctgcacgt ccagattgtg catttcccaa cacggcctta ccctgccctt gacagcactt      4860
gtggcgggat tcggtattca agaaattgcc ttggtcgttt tgattttgt ttccatcgga       4920
ggcatggctc ataggttgag ctgtaaggct gacatgctgt gtgtcttgct tgcaattgcc      4980
agctatgttt gggtacctct tacctggttg ctttgtgtgt ttccttgctg gttgcgctgt      5040
tttctttgc accccctcac catcctatgg ttggtgtttt tcttgatttc tgtgaatatg       5100
ccttcaggaa tcttggccat ggtgttgttg gtttctcttt ggcttcttgg tcgttatact      5160
aatgttgctg gccttgtcac cccctacgac attcatcatt acaccagtgg ccccgcggt      5220
gttgccgcct tggctaccgc accagatggg acctacttgg ccgctgtccg ccgcgctgcg      5280
ttgactggcc gcaccatgct gtttaccccg tcccagcttg ggtctcttct tgagggtgct      5340
ttcagaactc gaaagccctc actgaacacc gtcaatgtga tcgggtcctc catgggctct      5400
ggcggggtgt ttaccatcga cgggaaagtc aagtgcgtaa ctgccgcaca tgtccttacg      5460
ggcaattcag ctcgggtttc cggggtcggc ttcaatcaaa tgcttgactt tgacgtaaag      5520
ggagatttcg ctatagctga ttgcccgaat tggcaagggg ctgcccccaa gacccaattc      5580
tgcacggatg gatggactgg ccgtgcctat tggctaacat cctctggcgt cgaacccggc      5640
gtcattggaa aaggattcgc cttctgcttc accgcatgtg gcgattccgg gtccccagtg      5700
atcaccgagg ccggtgagct tgtcggcgtt cacacgggat cgaataaaca aggggggggc      5760
attgttacgc gcccctcagg ccagtttttgt aatgtggcac ccatcaagct aagcgaatta      5820
agtgaattct ttgctgggcc taaggtcccg ctcggtgatg tgaaggtcgg cagccacata      5880
attaaagaca taagcgaggt gccttcagat cttgtgcct tgcttgctgc caaacctgaa       5940
ctggaaggag gcctctccac cgtccaactt cttttgtgtg ttttttctcct gtggagaatg     6000
atgggacatg cctggacgcc cttggttgct gtgagtttct ttattttgaa tgaggttctc      6060
ccagccgtcc tggtccggag tgttttctcc tttggaatgt ttgtgctatc ctggctcacg      6120
ccatggtctg cgcaagttct gatgatcagg cttctgacag cagctcttaa caggaacaga      6180
tggtcacttg cctttttcag cctcggtgca gtgaccggtt ttgtcgcaga tcttgcggcc      6240
actcaggggc atccgttgca ggcagtgatg aatttgagca cctatgcatt cctgcctcgg      6300
atgatggttt tgacctcacc agtcccagtg atcacgtgtg tgtcgtgca cctacttgcc       6360
atcatttgt acttgtttaa gtaccgtggc ctgcaccata tccttgttgg cgatggagtg      6420
ttctctgcgg ctttcttctt gagatacttt gccgagggaa agttgaggga aggggtgtcg      6480
caatcctgcg gaatgaatca tgagtctctg actggtgccc tcgctatgag actcaatgac      6540
gaggacttgg atttccttat gaaatggact gattttaagt gctttgtttc tgcgtccaac      6600
```

```
atgaggaatg cagcgggtca atttatcgag gctgcctatg ctaaagcact tagagtagaa   6660
ctggcccagt tggtgcaggt tgataaagtt cgaggtactt tggccaaact tgaagctttt   6720
gctgataccg tggcacctca actctcgccc ggtgacattg ttgtcgctct cggccacacg   6780
cctgttggca gtatcttcga cctaaaggtt ggtagcacca agcatacoct ccaagccatt   6840 gagaccagag tccttgctgg gtccaaaatg accgtggcgc gcgtcgtcga cccgaccccc   6900
acgcccccac ccgcacccgt gcccatcccc ctcccaccga aagttctgga gaatggcccc   6960
aacgcttggg gggatgagga ccgtttgaat aagaagaaga ggcgcaggat ggaagccctc   7020
ggcatctatg ttatgggcgg gaaaaaatac cagaaatttt gggacaagaa ttccggtgat   7080
gtgttttatg aggaggtcca taataacaca gatgagtggg agtgtctcag agttggcgac   7140
cctgccgact ttgaccctga aagggaact ctgtgtggac atgtcaccat tgaaaacaag   7200
```

```
cctgccgact ttgaccctga aagggaact  ctgtgtggac atgtcaccat tgaaaacaag   7200
gcttaccatg tttacacctc cccatctggt aagaagttct tggtcccegt caacccagag   7260 aatggaaagag tccaatggga agctgcaaag ctttccgtgg agcaggccct aggtatgatg   7320
aatgtcgacg gcgaactgac tgccaaagaa ctggagaaac tgaaaagaat aattgacaaa   7380
ctccagggcc tgactaagga gcagtgttta aactgctagc cgccagcgac ttgacccgct   7440
gtggtcgcgg cggcttggtt gttactgaaa cagcggtaaa aatagtcaaa tttcacaacc   7500
ggaccttcac cctgggacct gtgaatttaa aagtggccag tgaggttgag ctaaagacg   7560 cggttgagca caaccaacac ccggttgcga gaccgatcga tggtggagtt gtgctcctgc   7620
gttccgcggt tccttcgctt atagacgtct tgatctccgg tgctgatgca tctcccaagt   7680
tacttgccca tcacgggccg ggaaacactg ggatcgatgg cacgctctgg gattttgagt   7740
ccgaagccac taagaggaa gtcgcactca gtgcgcaaat aatacaggct tgtgacatta   7800
ggcgcggcga cgctcctgaa attggtctcc cttacaagct gtaccctgtt aggggtaacc   7860
ctgagcgggt gaaaggagtt ctgcagaata caaggtttgg agacatacct tacaaaaccc   7920
ccagtgacac tggaagccca gtgcacgcgg ctgcctgcct tacgcccaac gccactccgg   7980
tgactgatgg gcgctccgtc ttggccacga ccatgccccc cgggtttgag ttatatgtac   8040
cgaccatacc agcgtctgtc cttgattacc ttgactctag gcctgactgc cctaaacagc   8100
tgacagagca cggctgcgaa gatgccgcac tgaaagacct ctctaaatat gacttgtcca   8160
cccaaggctt tgttttacct ggagttcttc gccttgtgcg gaaatacctg tttgcccatg   8220
taggtaagtg cccacccgtt catcggcctt ctacttaccc tgctaagaat tctatggctg   8280
gaataaatgg gaacaggttc ccaaccaagg acattcagag cgtccctgaa atcgacgttc   8340
tgtgcgcaca ggctgtgcga gaaaactggc aaactgtcac ccttgtact cttaagaaac   8400 agtattgcgg gaagaagaag actaggacca tactcggcac caataacttc atcgcactag   8460
cccaccgagc agtgttgagt ggtgttaccc agggcttcat gaaaaaggcg tttaactcgc   8520
ccatcgccct cggaaagaac aagtttaagg agctacagac tccggtcctg ggcaggtgcc   8580
ttgaagctga tctcgcatcc tgcgatcgat ccacgcctgc aattgtccgc tggtttgccg   8640
ccaaccttct ttatgaactt gcctgtgctg aagagcatct accgtcgtac gtgctgaact   8700
gctgccacga cttactggtc acgcagtccg gcgcagtgac taagagaggt ggcctgtcgt   8760
ctggcgaccc gatcacctct gtgtctaaca ccatttatag tttggtgatc tatgcacagc   8820
atatggtgct tagttacttc aaaagtggtc accccatgg ccttctgttc ttacaagacc   8880
agctaaagtt tgaggacatg ctcaaggttc aaccctgat cgtctattcg gacgacctcg   8940
```

```
tgctgtatgc cgagtctccc accatgccaa actatcactg gtgggttgaa catctgaatt    9000
tgatgctggg gtttcagacg gacccaaaga agacagcaat aacagactcg ccatcatttc    9060
taggctgtag aataataaat gggcgccagc tagtccccaa ccgtgacagg atcctcgcgg    9120
ccctcgccta tcacatgaag gcgagtaatg tttctgaata ctatgcctca gcggctgcaa    9180
tactcatgga cagctgtgct tgtttggagt atgatcctga atggtttgaa gaacttgtag    9240
ttggaatagc gcagtgcgcc cgcaaggacg gctacagctt tcccggcacg ccgttcttca    9300
tgtccatgtg ggaaaaactc aggtccaatt atgaggggaa gaagtcgaga gtgtgcgggt    9360
actgcggggc cccggccccg tacgctactg cctgtggcct cgacgtctgc atttaccaca    9420
cccacttcca ccagcattgt ccagtcacaa tctggtgtgg ccatccagcg ggttctggtt    9480
cttgtagtga gtgcaaatcc cctgtaggga aggcacaag cccttagac gaggtgctgg      9540
aacaagtccc gtataagccc ccacggaccg ttatcatgca tgtggagcag ggtctcaccc    9600
cccttgatcc aggtagatac caaactcgcc gcggattagt ctctgtcagg cgtggaatta    9660
ggggaaatga agttggacta ccagacgtg attatgctag caccgccttg ctccctacct     9720
gcaaagagat caacatggtc gctgtcgctt ccaatgtatt gcgcagcagg ttcatcatcg    9780
gcccacccgg tgctgggaaa acatactggc tccttcaaca ggtccaggat ggtgatgtta    9840
tttacacacc aactcaccag accatgcttg acatgattag ggctttgggg acgtgccggt    9900
tcaacgtccc ggcaggcaca acgctgcaat tccccgtccc ctcccgcacc ggtccgtggg    9960
ttcgcatcct agccggcggt tggtgtcctg gcaagaattc cttcctagat gaagcagcgt    10020
attgcaatca ccttgatgtt ttgaggcttc ttagtaaaac tacccctcacc tgtctaggag   10080
acttcaagca actccaccca gtgggttttg attctcattg ctatgttttt gacatcatgc    10140
ctcaaactca actgaagacc atctggaggt ttggacagaa tatctgtgat gccattcagc    10200
cagattacag ggacaaactc atgtccatgg tcaacacaac ccgtgtgacc tacgtggaaa    10260
aacctgtcag gtatgggcag gtcctcaccc cctaccacag ggaccgagag gacgacgcca    10320
tcactattga ctccagtcaa ggcgccacat cgatgtggt tacattgcat ttgcccacta      10380
aagattcact caacaggcaa agagcccttg ttgctatcac cagggcaaga cacgctatct    10440
ttgtgtatga cccacacagg cagctgcagg gcttgtttga tcttcctgca aaaggcacgc    10500
ccgtcaacct cgcagtgcac tgcgacgggc agctgatcgt gctggataga aataacaaag    10560
aatgcacggt tgctcaggct ctaggcaacg gggataaatt tagggccaca gacaagcgtg    10620
ttgtagattc tctccgcgcc atttgtgctg atctagaagg gtcgagctct ccgctcccca    10680
aggtcgcaca caacttggga tttttatttct cacctgattt aacacagttt gctaaactcc    10740
cagtagaact tgcacctcac tggcccgtgg tgtcaaccca gaacaatgaa aagtggccgg    10800
atcggctggt tgccagcctt cgccctatcc ataaatacag ccgcgcgtgc atcggtgccg    10860
gctatatggt gggcccttcg gtgtttctag gcactcctgg ggtcgtgtca tactatctca    10920
caaaatttgt taagggcggg gctcaagtgc ttccggagac ggttttcagc accggccgaa    10980
ttgaggtaga ctgccgggaa tatcttgatg atcgggagcg agaagttgct gcgtccctcc    11040
cacacgcttt cattggcgac gtcaaaggca ctaccgttgg aggatgtcat catgtcacct    11100
ccagatacct cccgcgcgtc cttcccaagg aatcagttgc ggtagtcggg gtttcaagcc    11160
ccggaaaagc cgcgaaagca ttgtgcacac tgacagatgt gtacctccca gatcttgaag    11220
cctatctcca cccggagacc cagtccaagt gctggaaaat gatgttggac ttcaaagaag    11280
ttcgactaat ggtctggaaa gacaaaacag cctatttcca acttgaaggt cgctatttca    11340
```

```
cctggtatca gcttgccagc tatgcctcgt acatccgtgt tcccgtcaac tctacggtgt   11400
acttggaccc ctgcatgggc cccgcccttt gcaacaggag agtcgtcggg tccacccact   11460 gggggggctga cctcgcggtc accccttatg attacggcgc taaaattatc ctgtctagcg   11520
cgtaccatgg tgaaatgccc cccggataca aaattctggc gtgcgcggag ttctcgttgg   11580
atgacccagt taagtacaaa catacctggg ggtttgaatc ggatacagcg tatctgtatg   11640
agttcaccgg aaacggtgag gactgggagg attacaatga tgcgtttcgt gcgcgccagg   11700
aagggaaaat ttataaggcc actgccacca gcttgaagtt ttattttccc ccgggccctg   11760
tcattgaacc aactttaggc ctgaattgaa atgaaatggg gtccatgcaa agccttttg    11820 acaaaattgg ccaacttttt gtggatgctt tcacggagtt cttggtgtcc attgttgata   11880
tcattatatt tttggccatt ttgtttggct tcaccatcgc cggttggctg gtggtctttt   11940
gcatcagatt ggtttgctcc gcgatactcc gtacgcgccc tgccattcac tctgagcaat   12000
tacagaagat cttatgaggc ctttctttcc cagtgccaag tggacattcc cacctgggga   12060
actaaacatc ctttggggat gctttggcac cataaggtgt caaccctgat tgatgaaatg   12120
gtgtcgcgtc gaatgtaccg catcatggaa aaagcagggc aggctgcctg gaaacaggtg   12180
gtgagcgagg ctacgctgtc tcgcattagt agtttggatg tggtggctca ttttcagcat   12240
ctagccgcca ttgaagccga gacctgtaaa tatttggcct cccggctgcc catgctacac   12300
aacctgcgca tgacagggtc aaatgtaacc atagtgtata atagcacttt gaatcaggtg   12360
tttgctattt ttccaacccc tggttccgg ccaaagcttc atgattttca gcaatggtta   12420
atagctgtac attcctccat attttcctct gttgcagctt cttgtactct ttttgttgtg   12480
ctgtggttgc gggttccaat actacgtact gttttttggtt tccgctggtt agggcaatt   12540 tttctttcga actcacagtg aattacacgg tgtgtccacc ttgcctcacc cggcaagcag   12600
ccacagagat ctacgaaccc ggtaggtctc tttggtgcag gatagggtat gaccgatgtg   12660
gggaggacga tcatgacgag ctagggttta tgataccgcc tggcctctcc agcgaaggcc   12720
acttgactgg tgtttacgcc tggttggcgt tcttgtcctt cagctacacg gcccagttcc   12780
atcccgagat attcgggata gggaatgtga gtcgagttta tgttgacatc aaacatcaac   12840
tcatctgcgc cgaacatgac gggcagaaca ccaccttgcc tcgtcatgac aacatttcag   12900
ccgtgtttca gacctattac caacatcaag tcgacggcgg caattggttt cacctagaat   12960
ggcttcgtcc cttctttcc tcgtggttgg ttttaaatgt ctcttggttt ctcaggcgtt    13020
cgcctgcaaa ccatgtttca gttcgagtct tgcagatatt aagaccaaca ccaccgcagc   13080
ggcaagcttt gctgtcctcc aagacatcag ttgccttagg catcgcgact cggcctctga   13140
ggcgattcgc aaaatccctc agtgccgtac ggcgataggg acaccgtgt atgttaccat    13200 cacagccaat gtgacagatg agaattattt acattcttct gatctcctca tgctttcttc   13260
ttgccttttc tatgcttctg agatgagtga aaagggattt aaggtggtat ttggcaatgt   13320
gtcaggcatc gtggctgtgt gtgtcaattt taccagctac gtccaacatg tcaaggagtt   13380
tacccaacgc tccctggtgg tcgaccatgt gcggttgctc catttcatga cacctgagac   13440
catgaggtgg gcaactgttt tagcctgtct ttttgccatt ctgttggcaa tttgaatgtt   13500
taagtatgtt ggagaaatgc ttgaccgcgg gctgttgctc gcgattgctt tctttgtggt   13560
gtatcgtgcc gttctgtttt gctgtgctcg ccaacgccag caacgacagc agctcccatc   13620
tacagctgat ttacaacttg acgctatgtg agctgaatgg cacagattgg ctagctaaca   13680
```

-continued

```
aatttgattg ggcagtggag agttttgtca tctttcccgt tttgactcac attgtctcct    13740
atggtgccct cactaccagc catttccttg acacagtcgc tttagtcact gtgtctaccg    13800
ccgggtttgt tcacgggcgg tatgtcctaa gtagcatcta cgcggtctgt gccctggctg    13860
cgttgacttg cttcgtcatt aggttttgca agaattgcat gtcctggcgc tacgcgtgta    13920
ccagatatac caactttctt ctggacacta agggcagact ctatcgttgg cggtcgcctg    13980
tcatcataga gaaaagggc aaagttgagg tcgaaggtca tctgatcgac ctcaaaagag     14040
ttgtgcttga tggctccgtg gcaaccccta taaccagagt ttcagcggaa caatggggtc    14100
gtccttagat gacttctgtc acgatagcac ggctccacaa aaggtgcttt tggcgttttc    14160
tattacctac acgccagtga tgatatatgc cctaaaggtg agtcgcggcc gactgctagg    14220
gcttctgcac ctttgatct tcctgaattg tgctttcacc ttcgggtaca tgactttcgc      14280
gcactttcag agtacaaata aggtcgcgct cactatggga gcagtagttg cactcctttg    14340
ggggtgtac tcagccatag aaacctggaa attcatcacc tccagatgcc gtttgtgctt      14400
gctaggccgc aagtacattc tggcccctgc ccaccacgtt gaaagtgccg caggctttca    14460
tccgattgcg gcaaatgata accacgcatt tgtcgtccgg cgtcccggct ccactacggt    14520
caacggcaca ttggtgcccg ggttaaaaag cctcgtgttg ggtggcagaa aagctgttaa    14580
acagggagtg gtaaaccttg tcaaatatgc caaataacaa cggcaagcag cagaagagaa    14640
agaaggggga tggccagcca gtcaatcagc tgtgccagat gctgggtaag atcatcgctc    14700
agcaaaacca gtccagaggc aagggaccgg gaaagaaaaa taagaagaaa acccgggaga    14760
agccccattt tcctctagcg actgaagatg atgtcagaca tcactttacc cctagtgagc    14820
ggcaattgtg tctgtcgtca atccagaccg cctttaatca aggcgctggg acttgcaccc    14880
tgtcagattc aggaggata agttacactg tggagtttag tttgcctacg catcatactg     14940
tgcgcctgat ccgcgtcaca gcatcaccct cagcatgatg ggctggcatt cttgaggcat    15000
ctcagtgttt gaattggaag aatgtgtggt gaatggcact gattgacatt gtgcctctaa    15060
gtcacctatt caattagggc gaccgtgtgg gggtgagatt taattggcga gaaccatgcg    15120
gccgaaatta aaaaaaa                                                   15137
```

<210> SEQ ID NO 11
<211> LENGTH: 14867
<212> TYPE: DNA
<213> ORGANISM: Artificial Sequence
<220> FEATURE:
<223> OTHER INFORMATION: Porcine reproductive and respiratory syndrome virus

<400> SEQUENCE: 11

```
atgacgtata ggtgttggct ctatgccttg gcatttgtat tgtcaggagc tgtgaccatt       60
ggcacagccc aaaacttgct gcacagaaac acccttctgt gatagcctcc ttcaggggag     120
cttagggttt gtccctagca ccttgcttcc ggagttgcac tgcttacgg tctctccacc      180
ccttttaacca tgtctgggat acttgatcgg tgcacgtgta cccccaatgc cagggtgttt    240
atggcggagg ccaagtcta ctgcacacga tgcctcagtg cacggtctct ccttcccctg      300
aacctccagg tttctgagct cggggtgcta ggcctattct acaggcccga agagccactc    360
cggtggacgt tgccacgtgc attccccact gttgagtgct ccccgccgg ggcctgctgg     420
ctttctgcaa tctttccaat cgcacgaatg accagtggaa acctgaactt ccaacaaga     480
atggtacggg tcgcagctga gctttacaga gccggccagc tcacccctgc agtcttgaag    540
```

```
gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagactttg ccccttgag     720 tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc ccaccacac agtggacatg     900 tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg tgcttgtac tagcgccaag   1680 tacgtactta agctggaagg tgagcattgg actgtcactg tgaccctgg gatgtcccct   1740 tctttgctcc ctcttgaatg tgttcaggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg   2340 gctaactact actaccgtgc gcaaggtgac gaagttcgtc accgtgaaag actaaccgcc   2400
gtgctctcca gttggaaaaa ggttgttcga gaagaatatg gctcatgcc aaccgagcct   2460 ggtccacggc ccacactgcc acgcgggctc gacgaactca agaccagat ggaggaggac   2520 ttgctgaaac tggctaacgc ccagacgact tcggacatga tggcctgggc agtcgagcag   2580
gttgacctaa aaacttgggt caagaactac ccgcggtgga caccaccacc cctccgcca    2640 aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttg atctcccgac cccacctgag   2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
```

```
gtgacaccct tgagtgagcc gtgtgagttt gtgatgatgc ctcacacgcc tgcaccttcc      3000
gtaggtgcgg agagcgacct taccattggc tcagttgcta ctgaagatgt tccacgcatc      3060
ctcgagaaaa tagaaaatgt cggcgagatg gccaaccagg gacccttggc cttctccgag      3120
gataaaccgg tagatgacca acttgtcaac gaccccggga tatcgtcgcg gaggcctgac      3180
gagagcacat cagctccgtc cgcaggcaca ggtggcgccg gctcttttac cgatttgccg      3240
ccttcagatg gcgcggatgc ggacgggggg gggccgtttc ggacggtaaa aagaaaagct      3300
gaaaggctct ttgaccaact gagccgtcag gttttgacc tcgtctccca tctccctgtt       3360
ttcttctcac gccttttcta ccctggcggt ggttattctc cgggtgattg gggttttgca      3420
gcttttactc tattgtgcct cttttatgt tacagttacc cagcctttgg tattgctccc       3480
ctcttgggtg tgttttctgg gtcttctcgg cgcgttcgaa tgggggtttt tggctgctgg      3540
ttggcttttg ctgttggtct gttcaagcct gtgtccgacc cagtcggcgc tgcttgtgag      3600
tttgactcgc cagagtgtag aaacatcctt cattcttttg agcttctcaa accttgggac      3660
cctgttcgca gccttgttgt gggccccgtc ggtctcggtc ttgccattct tggcaggtta      3720
ctgggcgggg cacgctgcat ctggcacttt ttgcttaggc ttggcattgt tgcagactgt      3780
atcttggctg gagcttacgt gctttctcaa ggtaggtgta aaaagtgctg gggatcttgt      3840
ataagaactg ctcccaatga ggtcgctttt aacgtgtttc ctttcacacg tgcgaccagg      3900
tcgtcactta tcgacctgtg cgatcggttt tgtgcgccaa aaggaatgga ccccattttt      3960
ctcgccactg ggtggcgcgg gtgctgggcc ggccgaagcc ccattgagca accctctgaa      4020
aaacccatcg cgtttgccca gttggatgaa aagaagatta cggctaggac tgtggtcgcc      4080
cagccttatg accccaacca agccgtaaag tgcttgcggg tattgcaggc gggtggggcg      4140
atggtggcta aggcggtccc aaaagtggtc aaggtttccg ctgttccatt ccgagccccc      4200
ttctttccca ctggagtgaa agttgaccct gattgcaggg tcgtggttga ccctgacact      4260
ttcactgcag ctctccggtc tggctactcc accacaaacc tcgtccttgg tgtgggggac      4320
tttgcccagc tgaatggatt aaaaatcagg caaatttcca agccttcagg gggaggccca      4380
catctcatgg ctgccctgca tgttgcctgc tcgatggctc tgcacatgct tgctgggatt      4440
tatgtgactg cggtgggttc ttgcggcacc ggcaccaacg accgtggtg cgctaacccg      4500
tttgccgtcc ctggctacgg acctggctct ctctgcacgt ccagattgtg catttcccaa      4560
cacggcctta ccctgccctt gacagcactt gtggcgggat tcggtattca agaaattgcc      4620
ttggtcgttt tgattttgt ttccatcgga ggcatggctc ataggttgag ctgtaaggct       4680
gacatgctgt gtgtcttgct tgcaattgcc agctatgttt gggtacctct tacctggttg      4740
ctttgtgtgt ttccttgctg gttgcgctgt ttttcttgc acccctcac catcctatgg        4800
ttggtgtttt tcttgatttc tgtgaatatg ccttcaggaa tcttggccat ggtgttgttg      4860
gtttctcttt ggcttcttgg tcgttatact aatgttgctg gccttgtcac ccctacgac       4920
attcatcatt acaccagtgg ccccgcggt gttgccgcct tggctaccgc accagatggg       4980
acctacttgg ccgctgtccg ccgcgctgcg ttgactggcc gcaccatgct gtttaccccg      5040
tcccagcttg ggtctcttct tgagggtgct ttcagaactc gaaagccctc actgaacacc      5100
gtcaatgtga tcgggtcctc catgggctct ggcggggtgt ttaccatcga cgggaaagtc      5160
aagtgcgtaa ctgccgcaca tgtccttacg ggcaattcag ctcgggtttc cggggtcggc      5220
ttcaatcaaa tgcttgactt tgacgtaaag ggagatttcg ctatagctga ttgcccgaat      5280
```

```
tggcaagggg ctgcccccaa gacccaattc tgcacggatg gatggactgg ccgtgcctat    5340
tggctaacat cctctggcgt cgaacccggc gtcattggaa aaggattcgc cttctgcttc    5400
accgcatgtg gcgattccgg gtccccagtg atcaccgagg ccggtgagct tgtcggcgtt    5460
cacacgggat cgaataaaca aggggggggc attgttacgc gcccctcagg ccagttttgt    5520
aatgtggcac ccatcaagct aagcgaatta agtgaattct ttgctgggcc taaggtcccg    5580
ctcggtgatg tgaaggtcgg cagccacata attaaagaca taagcgaggt gccttcagat    5640 cttttgtgcct tgcttgctgc caaacctgaa ctggaaggag gcctctccac cgtccaactt    5700 cttttgtgtgt ttttctcct gtggagaatg atgggacatg cctggacgcc cttggttgct    5760
gtgagtttct ttattttgaa tgaggttctc ccagccgtcc tggtccggag tgttttctcc    5820
tttggaatgt ttgtgctatc ctggctcacg ccatggtctg cgcaagttct gatgatcagg    5880
cttctgacag cagctcttaa caggaacaga tggtcacttg ccttttttcag cctcggtgca    5940 gtgaccggtt ttgtcgcaga tcttgcggcc actcaggggc atccgttgca ggcagtgatg    6000
aatttgagca cctatgcatt cctgcctcgg atgatggttg tgacctcacc agtcccagtg    6060
atcacgtgtg gtgtcgtgca cctacttgcc atcattttgt acttgtttaa gtaccgtggc    6120
ctgcaccata tccttgttgg cgatggagtg ttctctgcgg cttctcttctt gagatacttt    6180 gccgagggaa agttgaggga aggggtgtcg caatcctgcg gaatgaatca tgagtctctg    6240
actggtgccc tcgctatgag actcaatgac gaggacttgg atttccttat gaaatggact    6300
gattttaagt gctttgtttc tgcgtccaac atgaggaatg cagcgggtca atttatcgag    6360
gctgcctatg ctaaagcact tagagtagaa ctggcccagt tggtgcaggt tgataaagtt    6420
cgaggtactt tggccaaact tgaagctttt gctgataccg tggcacctca actctcgccc    6480
ggtgacattg ttgtcgctct cggccacacg cctgttggca gtatcttcga cctaaaggtt    6540
ggtagcacca agcatacccct ccaagccatt gagaccagag tccttgctgg gtccaaaatg    6600
accgtggcgc gcgtcgtcga cccgaccccc acgcccccac ccgcaccgt gcccatcccc    6660 ctcccaccga aagttctgga gaatggcccc aacgcttggg gggatgagga ccgtttgaat    6720
aagaagaaga ggcgcaggat ggaagccctc ggcatctatg ttatgggcgg gaaaaaatac    6780
cagaaatttt gggacaagaa ttccggtgat gtgttttatg aggaggtcca taataacaca    6840
gatgagtggg agtgtctcag agttggcgac cctgccgact ttgaccctga aagggaact    6900 ctgtgtggac atgtcaccat tgaaaacaag gcttaccatg tttacacctc cccatctggt    6960
aagaagttct tggtccccgt caacccagag aatggaagag tccaatggga agctgcaaag    7020 cttttccgtgg agcaggccct aggtatgatg aatgtcgacg gcgaactgac tgccaaagaa    7080
ctggagaaac tgaaaagaat aattgacaaa ctccagggcc tgactaagga gcagtgttta    7140
aactgctagc cgccagcgac ttgacccgct gtggtcgcgg cggcttggtt gttactgaaa    7200
cagcggtaaa aatagtcaaa tttcacaacc ggaccttcac cctgggacct gtgaatttaa    7260
aagtggccag tgaggttgag ctaaaagacg cggttgagca caaccaacac ccggttgcga    7320
gaccgatcga tggtggagtt gtgctcctgc gttccgcggt tccttcgctt atagacgtct    7380
tgatctccgg tgctgatgca tctcccaagt tacttgccca tcacgggccg ggaaacactg    7440
ggatcgatgg cacgctctgg gattttgagt ccgaagccac taaagaggaa gtcgcactca    7500
gtgcgcaaat aatacaggct tgtgacatta ggcgcggcga cgctcctgaa attggtctcc    7560
cttacaagct gtaccctgtt aggggtaacc ctgagcgggt gaaggagtt ctgcagaata    7620 caaggtttgg agacatacct tacaaaaccc ccagtgacac tggaagccca gtgcacgcgg    7680
```

-continued

```
ctgcctgcct tacgcccaac gccactccgg tgactgatgg gcgctccgtc ttggccacga   7740
ccatgccccc cgggtttgag ttatatgtac cgaccatacc agcgtctgtc cttgattacc   7800
ttgactctag gcctgactgc cctaaacagc tgacagagca cggctgcgaa gatgccgcac   7860
tgaaagacct ctctaaatat gacttgtcca cccaaggctt tgttttacct ggagttcttc   7920
gccttgtgcg gaaatacctg tttgcccatg taggtaagtg cccacccgtt catcggcctt   7980
ctacttaccc tgctaagaat tctatggctg gaataaatgg gaacaggttc ccaaccaagg   8040
acattcagag cgtccctgaa atcgacgttc tgtgcgcaca ggctgtgcga gaaaactggc   8100
aaactgtcac cccttgtact cttaagaaac agtattgcgg gaagaagaag actaggacca   8160
tactcggcac caataacttc atcgcactag cccaccgagc agtgttgagt ggtgttaccc   8220
agggcttcat gaaaaggcg tttaactcgc ccatcgccct cggaaagaac aagtttaagg   8280
agctacagac tccggtcctg ggcaggtgcc ttgaagctga tctcgcatcc tgcgatcgat   8340
ccacgcctgc aattgtccgc tggtttgccg ccaaccttct ttatgaactt gcctgtgctg   8400
aagagcatct accgtcgtac gtgctgaact gctgccacga cttactggtc acgcagtccg   8460
gcgcagtgac taagagaggt ggcctgtcgt ctggcgaccc gatcacctct gtgtctaaca   8520
ccatttatag tttggtgatc tatgcacagc atatggtgct tagttacttc aaaagtggtc   8580
accccccatgg ccttctgttc ttacaagacc agctaaagtt tgaggacatg ctcaaggttc   8640
aaccctgat cgtctattcg gacgacctcg tgctgtatgc cgagtctccc accatgccaa   8700
actatcactg gtgggttgaa catctgaatt tgatgctggg gtttcagacg gacccaaaga   8760
agacagcaat aacagactcg ccatcatttc taggctgtag aataataaat gggcgccagc   8820
tagtccccaa ccgtgacagg atcctcgcgg ccctcgccta tcacatgaag gcgagtaatg   8880
tttctgaata ctatgcctca gcggctgcaa tactcatgga cagctgtgct tgtttggagt   8940
atgatcctga atggtttgaa gaacttgtag ttggaatagc gcagtgcgcc cgcaaggacg   9000
gctacagctt tccccggcacg ccgttcttca tgtccatgtg ggaaaaactc aggtccaatt   9060
atgaggggaa gaagtcgaga gtgtgcgggt actgcggggc cccggccccg tacgctactg   9120
cctgtggcct cgacgtctgc atttaccaca cccacttcca ccagcattgt ccagtcacaa   9180
tctggtgtgg ccatccagcg ggttctggtt cttgtagtga gtgcaaatcc cctgtaggga   9240
aaggcacaag ccctttagac gaggtgctgg aacaagtccc gtataagccc cacggaccg   9300
ttatcatgca tgtggagcag ggtctcaccc cccttgatcc aggtagatac caaactcgcc   9360
gcggattagt ctctgtcagg cgtggaatta ggggaaatga agttggacta ccagacggtg   9420
attatgctag caccgccttg ctccctacct gcaaagagat caacatggtc gctgtcgctt   9480
ccaatgtatt gcgcagcagg ttcatcatcg gcccacccgg tgctgggaaa acatactggc   9540
tccttcaaca ggtccaggat ggtgatgtta tttacacacc aactcaccag accatgcttg   9600
acatgattag ggctttgggg acgtgccggt tcaacgtccc ggcaggcaca acgctgcaat   9660
tccccgtccc ctcccgcacc ggtccgtggg ttcgcatcct agccggcggt tggtgtcctg   9720
gcaagaattc cttcctagat gaagcagcgt attgcaatca ccttgatgtt ttgaggcttc   9780
ttagtaaaac taccctcacc tgtctaggag acttcaagca actccaccca gtgggttttg   9840
attctcattg ctatgttttt gacatcatgc ctcaaactca actgaagacc atctggaggt   9900
ttggacagaa tatctgtgat gccattcagc cagattacag ggacaaactc atgtccatgg   9960
tcaacacaac ccgtgtgacc tacgtggaaa aacctgtcag gtatgggcag gtcctcaccc  10020
```

```
cctaccacag ggaccgagag gacgacgcca tcactattga ctccagtcaa ggcgccacat   10080
tcgatgtggt tacattgcat ttgcccacta aagattcact caacaggcaa agagcccttg   10140
ttgctatcac cagggcaaga cacgctatct ttgtgtatga cccacacagg cagctgcagg   10200
gcttgtttga tcttcctgca aaaggcacgc ccgtcaacct cgcagtgcac tgcgacgggc   10260
agctgatcgt gctggataga aataacaaag aatgcacggt tgctcaggct ctaggcaacg   10320
gggataaatt tagggccaca gacaagcgtg ttgtagattc tctccgcgcc atttgtgctg   10380
atctagaagg gtcgagctct ccgctcccca aggtcgcaca caacttggga ttttatttct   10440
cacctgattt aacacagttt gctaaactcc cagtagaact tgcacctcac tggcccgtgg   10500
tgtcaaccca gaacaatgaa aagtggccgg atcggctggt tgccagcctt cgccctatcc   10560
ataaatacag ccgcgcgtgc atcggtgccg gctatatggt gggcccttcg gtgtttctag   10620
gcactcctgg ggtcgtgtca tactatctca caaaatttgt taagggcggg gctcaagtgc   10680
ttccggagac ggttttcagc accggccgaa ttgaggtaga ctgccgggaa tatcttgatg   10740
atcgggagcg agaagttgct gcgtcccctcc cacacgcttt cattggcgac gtcaaaggca   10800
ctaccgttgg aggatgtcat catgtcacct ccagataacct cccgcgcgtc cttcccaagg   10860
aatcagttgc ggtagtcggg gttttcaagcc ccggaaaagc cgcgaaagca ttgtgcacac   10920
tgacagatgt gtacctccca gatcttgaag cctatctcca cccggagacc cagtccaagt   10980
gctggaaaat gatgttggac ttcaaagaag ttcgactaat ggtctggaaa gacaaaacag   11040
cctatttcca acttgaaggt cgctatttca cctggtatca gcttgccagc tatgcctcgt   11100
acatccgtgt tcccgtcaac tctacggtgt acttggaccc ctgcatgggc cccgcccttt   11160
gcaacaggag agtcgtcggg tccacccact gggggggctga cctcgcggtc accccttatg   11220 attacgcgc taaaattatc ctgtctagcg cgtaccatgg tgaaatgccc cccggataca   11280
aaattctggc gtgcgcggag ttctcgttgg atgacccagt taagtacaaa catacctggg   11340
ggtttgaatc ggatacagcg tatctgtatg agttcaccgg aaacggtgag gactgggagg   11400
attacaatga tgcgtttcgt gcgcgccagg aagggaaaat ttataaggcc actgccacca   11460
gcttgaagtt ttattttccc ccgggccctg tcattgaacc aactttaggc ctgaattgaa   11520
atgaaatggg gtccatgcaa agccttttg acaaaattgg ccaacttttt gtggatgctt   11580
tcacggagtt cttggtgtcc attgttgata tcattatatt tttggccatt ttgtttggct   11640
tcaccatcgc cggttggctg gtggtctttt gcatcagatt ggtttgctcc gcgatactcc   11700
gtacgcgccc tgccattcac tctgagcaat tacagaagat cttatgaggc ctttctttcc   11760
cagtgccaag tggacattcc cacctgggga actaaacatc ctttggggat gctttggcac   11820
cataaggtgt caaccctgat tgatgaaatg gtgtcgcgtc gaatgtaccg catcatggaa   11880
aaagcagggc aggctgcctg gaaacaggtg gtgagcgagg ctacgctgtc tcgcattagt   11940
agtttggatg tggtggctca ttttcagcat ctagccgcca ttgaagccga gacctgtaaa   12000
tatttggcct cccggctgcc catgctacac aacctgcgca tgacagggtc aaatgtaacc   12060
atagtgtata atagcacttt gaatcaggtg tttgctattt ttccaacccc tggttcccgg   12120
ccaaagcttc atgattttca gcaatggtta atagctgtac attcctccat attttcctct   12180
gttgcagctt cttgtactct ttttgttgtg ctgtggttgc gggttccaat actacgtact   12240
gtttttggtt tccgctggtt aggggcaatt tttctttcga actcacagtg aattacacgg   12300
tgtgtccacc ttgcctcacc cggcaagcag ccacagagat ctacgaaccc ggtaggtctc   12360
tttggtgcag gatagggtat gaccgatgtg gggaggacga tcatgacgag ctagggttta   12420
```

```
tgataccgcc tggcctctcc agcgaaggcc acttgactgg tgtttacgcc tggttggcgt   12480
tcttgtcctt cagctacacg gcccagttcc atcccgagat attcgggata gggaatgtga   12540
gtcgagttta tgttgacatc aaacatcaac tcatctgcgc cgaacatgac gggcagaaca   12600
ccaccttgcc tcgtcatgac aacatttcag ccgtgtttca gacctattac caacatcaag   12660
tcgacggcgg caattggttt cacctagaat ggcttcgtcc cttcttttcc tcgtggttgg   12720
tttaaatgt ctcttggttt ctcaggcgtt cgcctgcaaa ccatgtttca gttcgagtct   12780
tgcagatatt aagaccaaca ccaccgcagc ggcaagcttt gctgtcctcc aagacatcag   12840
ttgccttagg catcgcgact cggcctctga ggcgattcgc aaaatccctc agtgccgtac   12900
ggcgataggg acaccegtgt atgttaccat cacagccaat gtgacagatg agaattattt   12960
acattcttct gatctcctca tgctttcttc ttgccttttc tatgcttctg agatgagtga   13020
aaagggattt aaggtggtat ttggcaatgt gtcaggcatc gtggctgtgt gtgtcaattt   13080
taccagctac gtccaacatg tcaaggagtt tacccaacgc tccctggtgg tcgaccatgt   13140
gcggttgctc catttcatga cacctgagac catgaggtgg gcaactgttt tagcctgtct   13200
ttttgccatt ctgttggcaa tttgaatgtt taagtatgtt ggagaaatgc ttgaccgcgg   13260
gctgttgctc gcgattgctt tctttgtggt gtatcgtgcc gttctgtttt gctgtgctcg   13320
ccaacgccag caacgacagc agctcccatc tacaacttg acgctatgtg   13380
agctgaatgg cacagattgg ctagctaaca aatttgattg ggcagtggag agttttgtca   13440
tctttcccgt tttgactcac attgtctcct atggtgccct cactaccagc catttccttg   13500
acacagtcgc tttagtcact gtgtctaccg ccgggtttgt tcacgggcgg tatgtcctaa   13560
gtagcatcta cgcggtctgt gccctggctg cgttgacttg cttcgtcatt aggtttgcaa   13620
agaattgcat gtcctggcgc tacgcgtgta ccagatatac caactttctt ctggacacta   13680
agggcagact ctatcgttgg cggtcgcctg tcatcataga gaaaggggc aaagttgagg   13740
tcgaaggtca tctgatcgac ctcaaaagag ttgtgcttga tggctccgtg gcaacccta   13800
taaccagagt ttcagcggaa caatggggtc gtccttagat gacttctgtc acgatagcac   13860
ggctccacaa aaggtgcttt tggcgttttc tattacctac acgccagtga tgatatatgc   13920
cctaaaggtg agtcgcggcc gactgctagg gcttctgcac cttttgatct tcctgaattg   13980
tgctttcacc ttcgggtaca tgactttcgc gcactttcag agtacaaata aggtcgcgct   14040
cactatggga gcagtagttg cactccttg ggggtgtac tcagccatag aaacctggaa   14100
attcatcacc tccagatgcc gtttgtgctt gctaggccgc aagtacattc tggcccctgc   14160
ccaccacgtt gaaagtgccg caggctttca tccgattgcg gcaaatgata accacgcatt   14220
tgtcgtccgg cgtcccggct ccactacggt caacggcaca ttggtgcccg ggttaaaaag   14280
cctcgtgttg ggtggcagaa aagctgttaa acagggagtg gtaaaccttg tcaaatatgc   14340
caaataacaa cggcaagcag cagaagagaa agaagggga tggccagcca gtcaatcagc   14400
tgtgccagat gctgggtaag atcatcgctc agcaaaacca gtccagaggc aagggaccgg   14460
gaaagaaaaa taagaagaaa aacccggaga gccccatt tcctctagcg actgaagatg   14520
atgtcagaca tcactttacc cctagtgagc ggcaattgtg tctgtcgtca atccagaccg   14580
ccttaatca aggcgctggg acttgcaccc tgtcagattc agggaggata agttacactg   14640
tggagtttag tttgcctacg catcatactg tgcgcctgat ccgcgtcaca gcatcaccct   14700
cagcatgatg ggctggcatt cttgaggcat ctcagtgttt gaattggaag aatgtgtggt   14760
```

```
gaatggcact gattgacatt gtgcctctaa gtcacctatt caattagggc gaccgtgtgg    14820
gggtgagatt taattggcga gaaccatgcg gccgaaatta aaaaaaa                  14867

<210> SEQ ID NO 12
<211> LENGTH: 15158
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 12
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg gccaagtcta ctgcacacga tgcctcagtg cacggtctct ccttcccctg     300
aacctccagg tttctgagct cggggtgcta ggcctattct acaggcccga gagccactc      360 cggtggacgt tgccacgtgc attccccact gttgagtgct ccccgccgg ggcctgctgg      420 ctttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtacccca ttgttggacc tgtccctgga     600
gtggccgttt tcgccaattc cctacatgtg agtgataaac ccttcccggg agcaactcac     660
gtgttgacca acctgccgct cccgcagaga cccaagcctg aagacttttg cccctttgag     720
tgtgctatgg ctactgtcta tgacattggt catgacgccg tcatgtatgt ggccgaaagg     780
aaagtctcct gggcccctcg tggcggggat gaagtgaaat ttgaagctgt ccccggggag     840
ttgaagttga ttgcgaaccg gctccgcacc tccttcccgc cccaccacac agtggacatg     900
tctaagttcg ccttcacagc ccctgggtgt ggtgtttcta tgcgggtcga acgccaacac     960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt ttgaggacct cctcagaata    1260
agggttgagc taacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg tgcttgtac tagcgccaag    1680 tacgtactta agctggaagg tgagcattgg actgtcactg tgacccctgg gatgtcccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
```

```
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca agttggaaaa ggttgttcga gaagaatatg gctcatgcc aaccgagcct     2460 ggtccacggc ccacactgcc acgcgggctc gacgaactca agaccagat ggaggaggac      2520 ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agcccctttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggggcgtt    3120 ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgcccttat ccgtctttta ccgatttgcc gccttcagat    3540
ggcgcggatg cggacggggg ggggccgttt cggacggtaa aaagaaaagc tgaaaggctc    3600
tttgaccaac tgagccgtca ggttttgac ctcgtctccc atctccctgt tttcttctca     3660
cgccttttct accctggcgg tggttattct ccgggtgatt ggggttttgc agcttttact    3720
ctattgtgcc tcttttatg ttacagttac ccagcctttg gtattgctcc cctcttgggt     3780
gtgttttctg ggtcttctcg gcgcgttcga atgggggttt ttggctgctg gttggcttt     3840 gctgttggtc tgttcaagcc tgtgtccgac ccagtcggcg ctgcttgtga gtttgactcg    3900
ccagagtgta gaaacatcct tcattctttt gagcttctca aaccttggga ccctgttcgc    3960
agccttgttg tgggccccgt cggtctcggt cttgccattc ttggcaggtt actgggcggg    4020
gcacgctgca tctggcactt tttgcttagg cttggcattg ttgcagactg tatcttggct    4080
ggagcttacg tgctttctca aggtaggtgt aaaaagtgct ggggatcttg tataagaact    4140
gctcccaatg aggtcgcttt taacgtgttt ccttttcacac gtgcgaccag gtcgtcactt    4200
atcgacctgt gcgatcggtt ttgtgcgcca aaaggaatgg accccatttt tctcgccact    4260
gggtggcgcg ggtgctgggc cggccgaagc cccattgagc aaccctctga aaaacccatc    4320
```

```
gcgtttgccc agttggatga aaagaagatt acggctagga ctgtggtcgc ccagccttat    4380
gaccccaacc aagccgtaaa gtgcttgcgg gtattgcagg cgggtggggc gatggtggct    4440
aaggcggtcc caaaagtggt caaggtttcc gctgttccat tccgagcccc cttctttccc    4500
actggagtga agttgaccc tgattgcagg gtcgtggttg accctgacac tttcactgca    4560
gctctccggt ctggctactc caccacaaac ctcgtccttg tgtgggggga ctttgcccag    4620
ctgaatggat taaaaatcag gcaaatttcc aagccttcag ggggaggccc acatctcatg    4680
gctgccctgc atgttgcctg ctcgatggct ctgcacatgc ttgctgggat ttatgtgact    4740
gcggtgggtt cttgcggcac cggcaccaac gacccgtggt gcgctaaccc gtttgccgtc    4800
cctggctacg gacctggctc tctctgcacg tccagattgt gcatttccca acacggcctt    4860
accctgccct tgacagcact tgtggcggga ttcggtattc aagaaattgc cttggtcgtt    4920
ttgattttg tttccatcgg aggcatggct cataggttga gctgtaaggc tgacatgctg    4980
tgtgtcttgc ttgcaattgc cagctatgtt tgggtacctc ttacctggtt gctttgtgtg    5040
tttccttgct ggttgcgctg ttttttctttg caccccctca ccatcctatg gttggtgttt    5100
ttcttgattt ctgtgaatat gccttcagga atcttggcca tggtgttgtt ggtttctctt    5160
tggcttcttg gtcgttatac taatgttgct ggccttgtca ccccctacga cattcatcat    5220
tacaccagtg gccccgcgg tgttgccgcc ttggctaccg caccagatgg gacctacttg    5280
gccgctgtcc gccgcgctgc gttgactggc cgcaccatgc tgtttacccc gtcccagctt    5340
gggtctcttc ttgagggtgc tttcagaact cgaaagccct cactgaacac cgtcaatgtg    5400
atcgggtcct ccatgggctc tggcggggtg tttaccatcg acgggaaagt caagtgcgta    5460
actgccgcac atgtccttac gggcaattca gctcgggttt ccggggtcgg cttcaatcaa    5520
atgcttgact ttgacgtaaa gggagatttc gctatagctg attgcccgaa ttggcaaggg    5580
gctgccccca gacccaatt ctgcacggat ggatggactg gccgtgccta ttggctaaca    5640
tcctctggcg tcgaacccgg cgtcattgga aaaggattcg ccttctgctt caccgcatgt    5700
ggcgattccg ggtccccagt gatcaccgag gccggtgagc ttgtcggcgt tcacacggga    5760
tcgaataaac aagggggggg cattgttacg cgccctcag gccagttttg taatgtggca    5820
cccatcaagc taagcgaatt aagtgaattc tttgctgggc ctaaggtccc gctcggtgat    5880
gtgaaggtcg gcagccacat aattaaagac ataagcgagg tgccttcaga tctttgtgcc    5940
ttgcttgctg ccaaacctga actggaagga ggcctctcca ccgtccaact tctttgtgtg    6000
ttttttctcc tgtggagaat gatgggacat gcctggacgc ccttggttgc tgtgagtttc    6060
tttatttga atgaggttct cccagccgtc ctggtccgga gtgttttctc ctttggaatg    6120
tttgtgctat cctggctcac gccatggtct gcgcaagttc tgatgatcag gcttctgaca    6180
gcagctctta acaggaacag atggtcactt gccttttca gcctcggtgc agtgaccggt    6240
tttgtcgcag atcttgcggc cactcagggg catccgttgc aggcagtgat gaatttgagc    6300
acctatgcat tcctgcctcg gatgatggtt gtgacctcac cagtcccagt gatcacgtgt    6360
ggtgtcgtgc acctacttgc catcattttg tacttgttta agtaccgtgg cctgcaccat    6420
atccttgttg gcgatggagt gttctctgcg gctttcttct tgagatactt tgccgaggga    6480
aagttgaggg aaggggtgtc gcaatcctgc ggaatgaatc atgagtctct gactggtgcc    6540
ctcgctatga gactcaatga cgaggacttg gatttcctta tgaaatggac tgattttaag    6600
tgctttgttt ctgcgtccaa catgaggaat gcagcgggtc aatttatcga ggctgcctat    6660
```

```
gctaaagcac ttagagtaga actggcccag ttggtgcagg ttgataaagt tcgaggtact    6720
ttggccaaac ttgaagcttt tgctgatacc gtggcacctc aactctcgcc cggtgacatt    6780
gttgtcgctc tcggccacac gcctgttggc agtatcttcg acctaaaggt tggtagcacc    6840
aagcataccc tccaagccat tgagaccaga gtccttgctg gtccaaaat gaccgtggcg     6900 cgcgtcgtcg acccgacccc cacgccccca cccgcacccg tgcccatccc cctcccaccg    6960
aaagttctgg agaatggccc caacgcttgg ggggatgagg accgtttgaa taagaagaag    7020
aggcgcagga tggaagccct cggcatctat gttatgggcg ggaaaaaata ccagaaattt    7080
tgggacaaga attccggtga tgtgttttat gaggaggtcc ataataacac agatgagtgg    7140
gagtgtctca gagttggcga ccctgccgac tttgaccctg agaagggaac tctgtgtgga    7200
catgtcacca ttgaaaacaa ggcttaccat gtttacacct ccccatctgg taagaagttc    7260
ttggtccccg tcaacccaga gaatggaaga gtccaatggg aagctgcaaa gctttccgtg    7320
gagcaggccc taggtatgat gaatgtcgac ggcgaactga ctgccaaaga actggagaaa    7380
ctgaaaagaa taattgacaa actccagggc ctgactaagg agcagtgttt aaactgctag    7440
ccgccagcga cttgacccgc tgtggtcgcg gcggcttggt tgttactgaa acagcggtaa    7500
aaatagtcaa atttcacaac cggaccttca ccctgggacc tgtgaattta aaagtggcca    7560
gtgaggttga gctaaaagac gcggttgagc acaaccaaca cccggttgcg agaccgatcg    7620
atggtggagt tgtgctcctg cgttccgcgg ttccttcgct tatagacgtc ttgatctccg    7680
gtgctgatgc atctcccaag ttacttgccc atcacgggcc gggaaacact gggatcgatg    7740
gcacgctctg ggattttgag tccgaagcca ctaaagagga agtcgcactc agtgcgcaaa    7800
taatacaggc ttgtgacatt aggcgcggcg acgctcctga aattggtctc ccttacaagc    7860
tgtaccctgt taggggtaac cctgagcggg tgaaaggagt tctgcagaat acaaggtttg    7920
gagacatacc ttacaaaacc cccagtgaca ctggaagccc agtgcacgcg gctgcctgcc    7980
ttacgcccaa cgccactccg gtgactgatg gcgctccgt cttggccacg accatgcccc    8040
ccgggtttga gttatatgta ccgaccatac cagcgtctgt ccttgattac cttgactcta    8100
ggcctgactg ccctaaacag ctgacagagc acggctgcga agatgccgca ctgaaagacc    8160
tctctaaata tgacttgtcc acccaaggct ttgttttacc tggagttctt cgccttgtgc    8220
ggaaatacct gtttgcccat gtaggtaagt gcccacccgt tcatcggcct tctacttacc    8280
ctgctaagaa ttctatggct ggaataaatg gaacaggtt cccaaccaag gacattcaga    8340
gcgtccctga aatcgacgtt ctgtgcgcac aggctgtgcg agaaaactgg caaactgtca    8400
ccccttgtac tcttaagaaa cagtattgcg ggaagaagaa gactaggacc atactcggca    8460
ccaataactt catcgcacta gcccaccgag cagtgttgag tggtgttacc cagggcttca    8520
tgaaaaaggc gtttaactcg cccatcgccc tcggaaagaa caagtttaag gagctacaga    8580
ctccggtcct gggcaggtgc cttgaagctg atctcgcatc ctgcgatcga tccacgcctg    8640
caattgtccg ctggtttgcc gccaaccttc tttatgaact tgcctgtgct gaagagcatc    8700
taccgtcgta cgtgctgaac tgctgccacg acttactggt cacgcagtcc ggcgcagtga    8760
ctaagagagg tggcctgtcg tctggcgacc cgatcacctc tgtgtctaac accatttata    8820
gtttggtgat ctatgcacag catatggtgc ttagttactt caaaagtggt cacccccatg    8880
gccttctgtt cttacaagac cagctaaagt ttgaggacat gctcaaggtt caaccctga    8940 tcgtctattc ggacgacctc gtgctgtatg ccgagtctcc caccatgcca aactatcact    9000
ggtgggttga acatctgaat ttgatgctgg ggtttcagac ggacccaaag aagacagcaa    9060
```

```
taacagactc gccatcattt ctaggctgta gaataataaa tgggcgccag ctagtcccca    9120
accgtgacag gatcctcgcg gccctcgcct atcacatgaa ggcgagtaat gtttctgaat    9180
actatgcctc agcggctgca atactcatgg acagctgtgc ttgtttggag tatgatcctg    9240
aatggtttga agaacttgta gttggaatag cgcagtgcgc ccgcaaggac ggctacagct    9300
ttcccggcac gccgttcttc atgtccatgt gggaaaaact caggtccaat tatgagggga    9360
agaagtcgag agtgtgcggg tactgcgggg ccccggcccc gtacgctact gcctgtggcc    9420
tcgacgtctg catttaccac acccacttcc accagcattg tccagtcaca atctggtgtg    9480
gccatccagc gggttctggt tcttgtagtg agtgcaaatc ccctgtaggg aaaggcacaa    9540 gcccttaga cgaggtgctg gaacaagtcc cgtataagcc cccacggacc gttatcatgc    9600
atgtggagca gggtctcacc ccccttgatc caggtagata ccaaactcgc cgcggattag    9660
tctctgtcag gcgtggaatt aggggaaatg aagttggact accagacggt gattatgcta    9720
gcaccgcctt gctccctacc tgcaaagaga tcaacatggt cgctgtcgct tccaatgtat    9780
tgcgcagcag gttcatcatc ggcccacccg gtgctgggaa acatactgg ctccttcaac     9840 aggtccagga tggtgatgtt atttacacac caactcacca gaccatgctt gacatgatta    9900
gggctttggg gacgtgccgg ttcaacgtcc cggcaggcac aacgctgcaa ttccccgtcc    9960
cctcccgcac cggtccgtgg gttcgcatcc tagccggcgg ttggtgtcct ggcaagaatt    10020
ccttcctaga tgaagcagcg tattgcaatc accttgatgt tttgaggctt cttagtaaaa    10080
ctaccctcac ctgtctagga gacttcaagc aactccaccc agtgggtttt gattctcatt    10140
gctatgtttt tgacatcatg cctcaaactc aactgaagac catctggagg tttggacaga    10200
atatctgtga tgccattcag ccagattaca gggacaaact catgtccatg gtcaacacaa    10260
cccgtgtgac ctacgtggaa aaacctgtca ggtatgggca ggtcctcacc ccctaccaca    10320
gggaccgaga ggacgacgcc atcactattg actccagtca aggcgccaca ttcgatgtgg    10380
ttacattgca tttgcccact aaagattcac tcaacaggca aagagccctt gttgctatca    10440
ccagggcaag acacgctatc tttgtgtatg acccacacag gcagctgcag ggcttgtttg    10500
atcttcctgc aaaaggcacg cccgtcaacc tcgcagtgca ctgcgacggg cagctgatcg    10560
tgctggatag aaataacaaa gaatgcacgg ttgctcaggc tctaggcaac ggggataaat    10620
ttagggccac agacaagcgt gttgtagatt ctctccgcgc catttgtgct gatctagaag    10680
ggtcgagctc tccgctcccc aaggtcgcac acaacttggg attttatttc tcacctgatt    10740
taacacagtt tgctaaactc ccagtagaac ttgcacctca ctggcccgtg gtgtcaaccc    10800
agaacaatga aaagtggccg gatcggctgg ttgccagcct tcgccctatc cataaataca    10860
gccgcgcgtg catcggtgcc ggctatatgg tgggcccttc ggtgtttcta ggcactcctg    10920
gggtcgtgtc atactatctc acaaaatttg ttaagggcgg ggctcaagtg cttccggaga    10980
cggttttcag caccggccga attgaggtag actgccggga atatcttgat gatcgggagc    11040
gagaagttgc tgcgtccctc ccacacgctt tcattggcga cgtcaaaggc actaccgttg    11100
gaggatgtca tcatgtcacc tccagatacc tcccgcgcgt ccttcccaag gaatcagttg    11160
cggtagtcgg ggtttcaagc cccggaaaag ccgcgaaagc attgtgcaca ctgacagatg    11220
tgtacctccc agatcttgaa gcctatctcc acccggagac ccagtccaag tgctggaaaa    11280
tgatgttgga cttcaaagaa gttcgactaa tggtctggaa agacaaaaca gcctatttcc    11340
aacttgaagg tcgctatttc acctggtatc agcttgccag ctatgcctcg tacatccgtg    11400
```

```
ttcccgtcaa ctctacggtg tacttggacc cctgcatggg ccccgccctt tgcaacagga    11460
gagtcgtcgg gtccaccac tgggggctg acctcgcggt caccccttat gattacggcg      11520
ctaaaattat cctgtctagc gcgtaccatg gtgaaatgcc ccccggatac aaaattctgg    11580
cgtgcgcgga gttctcgttg gatgacccag ttaagtacaa acatacctgg gggtttgaat    11640
cggatacagc gtatctgtat gagttcaccg gaaacggtga ggactgggag gattacaatg    11700
atgcgtttcg tgcgcgccag gaagggaaaa tttataaggc cactgccacc agcttgaagt    11760 tttatttttcc cccgggccct gtcattgaac caactttagg cctgaattga aatgaaatgg    11820
ggtccatgca aagccttttt gacaaaattg gccaactttt tgtggatgct ttcacggagt    11880
tcttggtgtc cattgttgat atcattatat ttttggccat tttgtttggc ttcaccatcg    11940
ccggttggct ggtggtcttt tgcatcagat tggtttgctc cgcgatactc cgtacgcgcc    12000
ctgccattca ctctgagcaa ttacagaaga tcttatgagg cctttctttc ccagtgccaa    12060
gtggacattc ccacctgggg aactaaacat cctttgggga tgctttggca ccataaggtg    12120
tcaaccctga ttgatgaaat ggtgtcgcgt cgaatgtacc gcatcatgga aaaagcaggg    12180
caggctgcct ggaaacaggt ggtgagcgag gctacgctgt ctcgcattag tagtttggat    12240
gtggtggctc attttcagca tctagccgcc attgaagccg agacctgtaa atatttggcc    12300
tcccggctgc ccatgctaca caacctgcgc atgacagggt caaatgtaac catagtgtat    12360
aatagcactt tgaatcaggt gtttgctatt tttccaaccc ctggttcccg gccaaagctt    12420
catgattttc agcaatggtt aatagctgta cattcctcca tattttcctc tgttgcagct    12480
tcttgtactc tttttgttgt gctgtggttg cgggttccaa tactacgtac tgttttggt     12540 ttccgctggt tagggcaat ttttctttcg aactcacagt gaattacacg gtgtgtccac     12600
cttgcctcac ccggcaagca gccacagaga tctacgaacc cggtaggtct ctttggtgca    12660
ggatagggta tgaccgatgt ggggaggacg atcatgacga gctagggttt atgataccgc    12720
ctggcctctc cagcgaaggc cacttgactg gtgtttacgc ctggttggcg ttcttgtcct    12780
tcagctacac ggcccagttc catcccgaga tattcgggat agggaatgtg agtcgagttt    12840
atgttgacat caaacatcaa ctcatctgcg ccgaacatga cggcagaac accaccttgc     12900 ctcgtcatga caacatttca gccgtgtttc agacctatta ccaacatcaa gtcgacggcg    12960
gcaattggtt tcacctagaa tggcttcgtc ccttcttttc ctcgtggttg gttttaaatg    13020
tctcttggtt tctcaggcgt tcgcctgcaa accatgtttc agttcgagtc ttgcagatat    13080
taagaccaac accaccgcag cggcaagctt tgctgtcctc caagacatca gttgccttag    13140
gcatcgcgac tcggcctctg aggcgattcg caaaatccct cagtgccgta cggcgatagg    13200
gacacccgtg tatgttacca tcacagccaa tgtgacagat gagaattatt tacattcttc    13260
tgatctcctc atgctttctt cttgccttt ctatgcttct gagatgagtg aaaagggatt     13320
taaggtggta tttggcaatg tgtcaggcat cgtggctgtg tgtgtcaatt ttaccagcta    13380
cgtccaacat gtcaaggagt ttacccaacg ctccctggtg gtcgaccatg tgcggttgct    13440
ccatttcatg acacctgaga ccatgaggtg ggcaactgtt ttagcctgtc tttttgccat    13500
tctgttggca atttgaatgt ttaagtatgt tggagaaatg cttgaccgcg ggctgttgct    13560
cgcgattgct ttctttgtgg tgtatcgtgc cgttctgttt tgctgtgctc gccaacgcca    13620
gcaacgacag cagctcccat ctacagctga tttacaactt gacgctatgt gagctgaatg    13680
gcacagattg gctagctaac aaatttgatt gggcagtgga gagttttgtc atctttcccg    13740
ttttgactca cattgtctcc tatggtgccc tcactaccag ccatttcctt gacacagtcg    13800
```

```
ctttagtcac tgtgtctacc gccgggtttg ttcacgggcg gtatgtccta agtagcatct    13860
acgcggtctg tgcccctggct gcgttgactt gcttcgtcat taggtttgca aagaattgca    13920
tgtcctggcg ctacgcgtgt accagatata ccaactttct tctggacact aagggcagac    13980
tctatcgttg gcggtcgcct gtcatcatag agaaaagggg caaagttgag gtcgaaggtc    14040
atctgatcga cctcaaaaga gttgtgcttg atggctccgt ggcaaccct  ataaccagag    14100 tttcagcgga caatgggt  cgtccttaga tgacttctgt cacgatagca cggctccaca    14160
aaaggtgctt ttggcgtttt ctattaccta cacgccagtg atgatatatg ccctaaaggt    14220
gagtcgcggc cgactgctag ggcttctgca cctttgatc ttcctgaatt gtgctttcac    14280
cttcgggtac atgactttcg cgcactttca gagtacaaat aaggtcgcgc tcactatggg    14340
agcagtagtt gcactccttt gggggtgta  ctcagccata gaaacctgga aattcatcac    14400
ctccagatgc cgtttgtgct tgctaggccg caagtacatt ctggcccctg cccaccacgt    14460
tgaaagtgcc gcaggctttc atccgattgc ggcaaatgat aaccacgcat tgtcgtccg    14520 gcgtcccggc tccactacgg tcaacggcac attggtgccc gggttaaaaa gcctcgtgtt    14580
gggtggcaga aaagctgtta aacagggagt ggtaaacctt gtcaaatatg ccaaataaca    14640
acggcaagca gcagaagaga aagaaggggg atggccagcc agtcaatcag ctgtgccaga    14700
tgctgggtaa gatcatcgct cagcaaaacc agtccagagg caagggaccg ggaaagaaaa    14760
ataagaagaa aaacccggag aagccccatt ttcctctagc gactgaagat gatgtcagac    14820
atcactttac ccctagtgag cggcaattgt gtctgtcgtc aatccagacc gcctttaatc    14880
aaggcgctgg gacttgcacc ctgtcagatt cagggaggat aagttacact gtggagttta    14940
gtttgcctac gcatcatact gtgcgcctga tccgcgtcac agcatcaccc tcagcatgat    15000
gggctggcat tcttgaggca tctcagtgtt tgaattggaa gaatgtgtgg tgaatggcac    15060
tgattgacat tgtgcctcta agtcacctat tcaattaggg cgaccgtgtg ggggtgagat    15120
ttaattggcg agaaccatgc ggccgaaatt aaaaaaaa                             15158
```

<210> SEQ ID NO 13
<211> LENGTH: 14210
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 13

```
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta ccccccaatgc cagggtgttt    240 atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attcccccact gttgagtgct ccccgccgg  ggcctgctgg    420 cttttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt tcgccaattc cctacatgtg agtgataaac ccttcccggg agcaactcac    660
```

```
gtgttgacca acctgccgct cccgcagaga cccaagcctg aagacttttg cccctttgag      720
tgtgctatgg ctactgtcta tgacattggt catgacgccg tcatgtatgt ggccgaaagg      780
aaagtctcct gggcccctcg tggcggggat gaagtgaaat ttgaagctgt ccccggggag      840
ttgaagttga ttgcgaaccg gctccgcacc tccttcccgc ccaccacac agtggacatg       900 tctaagttcg ccttcacagc ccctgggtgt ggtgtttcta tgcgggtcga acgccaacac     960
ggctgccttc ccgctgacac tgtccctgaa ggcaactgct ggtggagctt gtttgacttg     1020
cttccactgg aagttcagaa caaagaaatt cgccatgcta accaatttgg ctaccagacc     1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt ttgaggacct cctcagaata     1260
agggttgagc ctaacacgtc gccattggct gacaaggaag aaaaaatttt ccggtttggc     1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt     1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag    1680
tacgtactta agctggaagg tgagcattgg actgtcactg tgaccctggg gatgtcccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat   1920
cgttcggctt ctccggtcac caccgtgtgg actgttcgc agttctttgc ccgtcacagc     1980
ggagggaatc accctgacca gtgcgcttta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc   2280
cctgttgtga ctcaaaagtc cttgtgtgag tttgtgatga tgcctcacac gcctgcacct    2340
tccgtaggtg cggagagcga ccttaccatt ggctcagttg ctactgaaga tgttccacgc    2400
atcctcgaga aaatagaaaa tgtcggcgag atggccaacc agggacccctt ggccttctcc   2460 gaggataaac cggtagatga ccaacttgtc aacgaccccc ggatatcgtc gcggaggcct    2520
gacgagagca catcagctcc gtccgcaggc acaggtggcg ccggctcttt taccgatttg    2580
ccgccttcag atggcgcgga tgcggacggg gggggccgt ttcggacggt aaaaagaaaa     2640
gctgaaaggc tctttgacca actgagccgt caggttttg acctcgtctc ccatctccct     2700
gttttcttct cacgccttt ctaccctggc ggtggttatt ctccgggtga ttggggtttt    2760 gcagcttta ctctattgtg cctcttttta tgttacagtt acccagcctt tggtattgct    2820
cccctcttgg gtgtgttttc tgggtcttct cggcgcgttc gaatgggggt ttttggctgc  2880
tggttggctt ttgctgttgg tctgttcaag cctgtgtccg acccagtcgg cgctgcttgt   2940
gagtttgact cgccagagtg tagaaacatc cttcattctt ttgagcttct caaaccttgg   3000
```

```
gaccctgttc gcagccttgt tgtgggcccc gtcggtctcg gtcttgccat tcttggcagg    3060
ttactgggcg gggcacgctg catctggcac ttttttgctta ggcttggcat tgttgcagac    3120
tgtatcttgg ctggagctta cgtgctttct caaggtaggt gtaaaaagtg ctggggatct    3180
tgtataagaa ctgctcccaa tgaggtcgct tttaacgtgt ttcctttcac acgtgcgacc    3240
aggtcgtcac ttatcgacct gtgcgatcgg ttttgtgcgc caaaggaat ggaccccatt    3300 tttctcgcca ctgggtggcg cgggtgctgg gccggccgaa gccccattga gcaaccctct    3360
gaaaaaccca tcgcgtttgc ccagttggat gaaaagaaga ttacggctag gactgtggtc    3420
gcccagcctt atgaccccaa ccaagccgta aagtgcttgc gggtattgca ggcgggtggg    3480
gcgatggtgg ctaaggcggt cccaaaagtg gtcaaggttt ccgctgttcc attccgagcc    3540
cccttctttc ccactggagt gaaagttgac cctgattgca gggtcgtggt tgaccctgac    3600
actttcactg cagctctccg gtctggctac tccaccacaa acctcgtcct tggtgtgggg    3660
gactttgccc agctgaatgg attaaaaatc aggcaaattt ccaagccttc aggggaggc    3720 ccacatctca tggctgccct gcatgttgcc tgctcgatgg ctctgcacat gcttgctggg    3780
atttatgtga ctgcggtggg ttcttgcggc accggcacca acgacccgtg gtgcgctaac    3840
ccgtttgccg tccctggcta cggacctggc tctctctgca cgtccagatt gtgcatttcc    3900
caacacggcc ttaccctgcc cttgacagca cttgtggcgg gattcggtat tcaagaaatt    3960
gccttggtcg ttttgatttt tgtttccatc ggaggcatgg ctcataggtt gagctgtaag    4020
gctgacatgc tgtgtgtctt gcttgcaatt gccagctatg tttgggtacc tcttacctgg    4080
ttgctttgtg tgtttccttg ctggttgcgc tgttttcctt tgcaccccct caccatccta    4140
tggttggtgt ttttcttgat ttctgtgaat atgccttcag gaatcttggc catggtgttg    4200
ttggtttctc tttggcttct tggtcgttat actaatgttg ctggccttgt caccccctac    4260
gacattcatc attacaccag tggccccccgc ggtgttgccg ccttggctac cgcaccagat    4320
gggacctact tggccgctgt ccgccgcgct gcgttgactg gccgcaccat gctgtttacc    4380
ccgtcccagc ttgggtctct tcttgagggt gctttcagaa ctcgaaagcc ctcactgaac    4440
accgtcaatg tgatcgggtc ctccatgggc tctgccgggg tgtttaccat cgacgggaaa    4500
gtcaagtgcg taactgccgc acatgtcctt acgggcaatt cagctcgggt ttccggggtc    4560
ggcttcaatc aaatgcttga ctttgacgta aagggagatt tcgctatagc tgattgcccg    4620
aattggcaag gggctgcccc caagacccaa ttctgcacgg atggatggac tggccgtgcc    4680
tattggctaa catcctctgg cgtcgaaccc ggcgtcattg gaaaaggatt cgccttctgc    4740
ttcaccgcat gtggcgattc cgggtcccca gtgatcaccg aggccggtga gcttgtcggc    4800
gttcacacgg gatcgaataa acaagggggg ggcattgtta cgcgccctcg aggccagttt    4860
tgtaatgtgg cacccatcaa gctaagcgaa ttaagtgaat ctttgctgg gcctaaggtc    4920 ccgctcggtg atgtgaaggt cggcagccac ataattaaag acataagcga ggtgccttca    4980
gatctttgtg ccttgcttgc tgccaaacct gaactggaag gaggcctctc caccgtccaa    5040
cttctttgtg tgttttttct cctgtggaga atgatgggac atgcctggac gcccttggtt    5100
gctgtgagtt tctttatttt gaatgaggtt ctcccagccg tcctggtccg gagtgttttc    5160
tcctttggaa tgtttgtgct atcctggctc acgccatggt ctgcgcaagt tctgatgatc    5220
aggcttctga cagcagctct taacaggaac agatggtcac ttgcctttt cagcctcggt    5280 gcagtgaccg gttttgtcgc agatcttgcg gccactcagg ggcatccgtt gcaggcagtg    5340
atgaatttga gcacctatgc attcctgcct cggatgatgg ttgtgacctc accagtccca    5400
```

```
gtgatcacgt gtggtgtcgt gcacctactt gccatcattt tgtacttgtt taagtaccgt   5460
ggcctgcacc atatccttgt tggcgatgga gtgttctctg cggctttctt cttgagatac   5520
tttgccgagg gaaagttgag ggaaggggtg tcgcaatcct gcggaatgaa tcatgagtct   5580
ctgactggtg ccctcgctat gagactcaat gacgaggact tggatttcct tatgaaatgg   5640
actgatttta agtgctttgt ttctgcgtcc aacatgagga atgcagcggg tcaatttatc   5700
gaggctgcct atgctaaagc acttagagta gaactggccc agttggtgca ggttgataaa   5760
gttcgaggta ctttggccaa acttgaagct tttgctgata ccgtggcacc tcaactctcg   5820
cccggtgaca ttgttgtcgc tctcggccac acgcctgttg gcagtatctt cgacctaaag   5880
gttggtagca ccaagcatac cctccaagcc attgagacca gagtccttgc tgggtccaaa   5940
atgaccgtgg cgcgcgtcgt cgacccgacc cccacgcccc cacccgcacc cgtgcccatc   6000
cccctcccac cgaaagttct ggagaatggc cccaacgctt gggggatga ggaccgtttg    6060
aataagaaga gaggcgcag gatggaagcc ctcggcatct atgttatggg cgggaaaaaa    6120
taccagaaat tttgggacaa gaattccggt gatgtgtttt atgaggaggt ccataataac   6180
acagatgagt gggagtgtct cagagttggc gaccctgccg actttgaccc tgagaaggga   6240
actctgtgtg gacatgtcac cattgaaaac aaggcttacc atgtttacac ctccccatct   6300
ggtaagaagt tcttggtccc cgtcaaccca gagaatggaa gagtccaatg gaagctgca    6360
aagctttccg tggagcaggc cctaggtatg atgaatgtcg acggcgaact gactgccaaa   6420
gaactggaga aactgaaaag aataattgac aaactccagg gcctgactaa ggagcagtgt   6480
ttaaactgct agccgccagc gacttgaccc gctgtggtcg cggcggcttg ttgttactg    6540
aaacagcggt aaaatagtc aaatttcaca accggacctt caccctggga cctgtgaatt    6600
taaaagtggc cagtgaggtt gagctaaaag acgcggttga gcacaaccaa cacccggttg   6660
cgagaccgat cgatggtgga gttgtgctcc tgcgttccgc ggttccttcg cttatagacg   6720
tcttgatctc cggtgctgat gcatctccca agttacttgc ccatcacggg ccgggaaaca   6780
ctgggatcga tggcacgctc tgggatttg agtccgaagc cactaaagag gaagtcgcac    6840
tcagtgcgca aataatacag gcttgtgaca ttaggcgcgg cgacgctcct gaaattggtc   6900
tcccttacaa gctgtaccct gttaggggta accctgagcg ggtgaaagga gttctgcaga   6960
atacaaggtt tggagacata ccttacaaaa ccccagtga cactgaaagc ccagtgcacg    7020
cggctgcctg ccttacgccc aacgccactc cggtgactga tgggcgctcc gtcttggcca   7080
cgaccatgcc ccccgggttt gagttatatg taccgaccat accagcgtct gtccttgatt   7140
accttgactc taggcctgac tgccctaaac agctgacaga gcacggctgc gaagatgccg   7200
cactgaaaga cctctctaaa tatgacttgt ccacccaagg ctttgtttta cctggagttc   7260
ttcgccttgt gcggaaatac ctgtttgccc atgtaggtaa gtgcccaccc gttcatcggc   7320
cttctactta ccctgctaag aattctatgg ctggaataaa tgggaacagg ttcccaacca   7380
aggacattca gagcgtccct gaaatcgacg ttctgtgcgc acaggctgtg cgagaaaact   7440
ggcaaactgt caccccttgt actcttaaga acagtattg cgggaagaag aagactagga    7500
ccatactcgg caccaataac ttcatcgcac tagcccaccg agcagtgttg agtggtgtta   7560
cccagggctt catgaaaaag gcgtttaact cgcccatcgc cctcggaaag aacaagttta   7620
aggagctaca gactccggtc ctgggcaggt gccttgaagc tgatctcgca tcctgcgatc   7680
gatccacgcc tgcaattgtc cgctggtttg ccgccaacct tctttatgaa cttgcctgtg   7740
```

```
ctgaagagca tctaccgtcg tacgtgctga actgctgcca cgacttactg gtcacgcagt    7800
ccggcgcagt gactaagaga ggtggcctgt cgtctggcga cccgatcacc tctgtgtcta    7860
acaccattta tagtttggtg atctatgcac agcatatggt gcttagttac ttcaaaagtg    7920
gtcaccccca tggccttctg ttcttacaag accagctaaa gtttgaggac atgctcaagg    7980
ttcaacccct gatcgtctat tcggacgacc tcgtgctgta tgccgagtct cccaccatgc    8040
caaactatca ctggtgggtt gaacatctga atttgatgct ggggtttcag acggacccaa    8100
agaagacagc aataacagac tcgccatcat ttctaggctg tagaataata aatgggcgcc    8160
agctagtccc caaccgtgac aggatcctcg cggccctcgc ctatcacatg aaggcgagta    8220
atgtttctga atactatgcc tcagcggctg caatactcat ggacagctgt gcttgtttgg    8280
agtatgatcc tgaatggttt gaagaacttg tagttggaat agcgcagtgc gcccgcaagg    8340
acggctacag ctttcccggc acgccgttct tcatgtccat gtgggaaaaa ctcaggtcca    8400
attatgaggg gaagaagtcg agagtgtgcg ggtactgcgg ggccccggcc ccgtacgcta    8460
ctgcctgtgg cctcgacgtc tgcatttacc acacccactt ccaccagcat tgtccagtca    8520
caatctggtg tggccatcca gcgggttctg gttcttgtag tgagtgcaaa tcccctgtag    8580
ggaaaggcac aagccccttta gacgaggtgc tggaacaagt cccgtataag cccccacgga    8640
ccgttatcat gcatgtggag cagggtctca ccccccttga tccaggtaga taccaaactc    8700
gccgcggatt agtctctgtc aggcgtggaa ttaggggaaa tgaagttgga ctaccagacg    8760
gtgattatgc tagcaccgcc ttgctcccta cctgcaaaga gatcaacatg gtcgctgtcg    8820
cttccaatgt attgcgcagc aggttcatca tcggcccacc cggtgctggg aaaacatact    8880
ggctccttca acaggtccag gatggtgatg ttatttacac accaactcac cagaccatgc    8940
ttgacatgat tagggctttg gggacgtgcc ggttcaacgt cccggcaggc acaacgctgc    9000
aattccccgt ccccctcccgc accggtccgt gggttcgcat cctagccggc ggttggtgtc    9060
ctggcaagaa ttccttccta gatgaagcag cgtattgcaa tcaccttgat gttttgaggc    9120
ttcttagtaa aactacccctc acctgtctag gagacttcaa gcaactccac ccagtgggtt    9180
ttgattctca ttgctatgtt tttgacatca tgcctcaaac tcaactgaag accatctgga    9240
ggtttggaca gaatatctgt gatgccattc agccagatta cagggacaaa ctcatgtcca    9300
tggtcaacac aacccgtgtg acctacgtgg aaaaacctgt caggtatggg caggtcctca    9360 cccccctacca cagggaccga gaggacgacg ccatcactat tgactccagt caaggcgcca    9420
cattcgatgt ggttacattg catttgccca ctaaagattc actcaacagg caaagagccc    9480
ttgttgctat caccagggca agacacgcta tctttgtgta tgacccacac aggcagctgc    9540
agggcttgtt tgatcttcct gcaaaaggca cgcccgtcaa cctcgcagtg cactgcgacg    9600
ggcagctgat cgtgctggat agaaataaca agaatgcac ggttgctcag gctctaggca    9660
acggggataa atttagggcc acagacaagc gtgttgtaga ttctctccgc gccatttgtg    9720
ctgatctaga agggtcgagc tctccgctcc ccaaggtcgc acacaacttg ggattttatt    9780
tctcacctga tttaacacag tttgctaaac tcccagtaga acttgcacct cactggcccg    9840
tggtgtcaac ccagaacaat gaaaagtggc cggatcggct ggttgccagc cttcgcccta    9900
tccataaata cagccgcgcg tgcatcggtg ccggctatat ggtgggccct tcggtgtttc    9960
taggcactcc tggggtcgtg tcatactatc tcacaaaatt tgttaagggc ggggctcaag   10020
tgcttccgga gacggttttc agcaccgcc gaattgaggt agactgccgg gaatatcttg    10080
atgatcggga gcgagaagtt gctgcgtccc tcccacacgc tttcattggc gacgtcaaag   10140
```

```
gcactaccgt tggaggatgt catcatgtca cctccagata cctcccgcgc gtccttccca    10200
aggaatcagt tgcggtagtc ggggtttcaa gccccggaaa agccgcgaaa gcattgtgca    10260
cactgacaga tgtgtacctc ccagatcttg aagcctatct ccacccggag acccagtcca    10320
agtgctggaa aatgatgttg gacttcaaag aagttcgact aatggtctgg aaagacaaaa    10380
cagcctattt ccaacttgaa ggtcgctatt tcacctggta tcagcttgcc agctatgcct    10440
cgtacatccg tgttcccgtc aactctacgg tgtacttgga ccctgcatg ggccccgccc     10500 tttgcaacag gagagtcgtc gggtccaccc actgggggc tgacctcgcg gtcacccctt      10560
atgattacgg cgctaaaatt atcctgtcta gcgcgtacca tggtgaaatg ccccccggat    10620
acaaaattct ggcgtgcgcg gagttctcgt tggatgaccc agttaagtac aaacatacct    10680
gggggtttga atcggataca gcgtatctgt atgagttcac cggaaacggt gaggactggg    10740
aggattacaa tgatgcgttt cgtgcgcgcc aggaagggaa aatttataag gccactgcca    10800
ccagcttgaa gttttatttt ccccgggcc ctgtcattga accaacttta ggcctgaatt      10860
gaaatgaaat ggggtccatg caaagccttt ttgacaaaat tggccaactt tttgtggatg    10920
ctttcacgga gttcttggtg tccattgttg atatcattat attttttggcc attttgtttg     10980 gcttcaccat cgccggttgg ctggtggtct tttgcatcag attggtttgc tccgcgatac    11040
tccgtacgcg ccctgccatt cactctgagc aattacagaa gatcttatga ggcctttctt    11100
tcccagtgcc aagtggacat tcccacctgg ggaactaaac atcctttggg gatgctttgg    11160
caccataagg tgtcaaccct gattgatgaa atggtgtcgc gtcgaatgta ccgcatcatg    11220
gaaaaagcag ggcaggctgc ctggaaacag gtggtgagcg aggctacgct gtctcgcatt    11280
agtagtttgg atgtggtggc tcattttcag catctagccg ccattgaagc cgagacctgt    11340
aaatatttgg cctcccggct gcccatgcta cacaacctgc gcatgacagg gtcaaatgta    11400
accatagtgt ataatagcac tttgaatcag gtgtttgcta ttttccaac ccctggttcc     11460 cggccaaagc ttcatgattt tcagcaatgg ttaatagctg tacattcctc catattttcc    11520
tctgttgcag cttcttgtac tctttttgtt gtgctgtggt tgcgggttcc aatactacgt    11580
actgtttttg gtttccgctg gttaggggca attttttcttt cgaactcaca gtgaattaca    11640
cggtgtgtcc accttgcctc acccggcaag cagccacaga gatctacgaa cccggtaggt    11700
ctctttggtg caggataggg tatgaccgat gtggggagga cgatcatgac gagctagggt    11760
ttatgatacc gcctggcctc tccagcgaag gccacttgac tggtgtttac gcctggttgg    11820
cgttcttgtc cttcagctac acggcccagt tccatcccga gatattcggg ataggggaatg   11880 tgagtcgagt ttatgttgac atcaaacatc aactcatctg cgccgaacat gacgggcaga    11940
acaccacctt gcctcgtcat gacaacattt cagccgtgtt tcagacctat taccaacatc    12000
aagtcgacgg cggcaattgg tttcacctag aatggcttcg tccccttcttt tcctcgtggt    12060 tggttttaaa tgtctcttgg tttctcaggc gttcgcctgc aaaccatgtt tcagttcgag    12120
tcttgcagat attaagacca acaccaccgc agcggcaagc tttgctgtcc tccaagacat    12180
cagttgcctt aggcatcgcg actcggcctc tgaggcgatt cgcaaaatcc ctcagtgccg    12240
tacggcgata gggacacccg tgtatgttac catcacagcc aatgtgacag atgagaatta    12300
tttacattct tctgatctcc tcatgctttc ttcttgcctt ttctatgctt ctgagatgag    12360
tgaaaaggga tttaaggtgg tatttggcaa tgtgtcaggc atcgtggctg tgtgtgtcaa    12420
ttttaccagc tacgtccaac atgtcaagga gtttacccaa cgctccctgg tggtcgacca    12480
```

```
tgtgcggttg ctccatttca tgacacctga gaccatgagg tgggcaactg tttttagcctg    12540 tcttttttgcc attctgttgg caatttgaat gtttaagtat gttggagaaa tgcttgaccg    12600
cgggctgttg ctcgcgattg ctttctttgt ggtgtatcgt gccgttctgt tttgctgtgc    12660
tcgccaacgc cagcaacgac agcagctccc atctacagct gatttacaac ttgacgctat    12720
gtgagctgaa tggcacagat tggctagcta acaaatttga ttgggcagtg gagagttttg    12780
tcatctttcc cgttttgact cacattgtct cctatggtgc cctcactacc agccatttcc    12840
ttgacacagt cgctttagtc actgtgtcta ccgccgggtt tgttcacggg cggtatgtcc    12900
taagtagcat ctacgcggtc tgtgccctgg ctgcgttgac ttgcttcgtc attaggtttg    12960
caaagaattg catgtcctgg cgctacgcgt gtaccagata taccaacttt cttctggaca    13020
ctaagggcag actctatcgt tggcggtcgc ctgtcatcat agagaaaagg ggcaaagttg    13080
aggtcgaagg tcatctgatc gacctcaaaa gagttgtgct tgatggctcc gtggcaaccc    13140
ctataaccag agtttcagcg gaacaatggg gtcgtcctta gatgacttct gtcacgatag    13200
cacggctcca caaaaggtgc ttttggcgtt ttctattacc tacacgccag tgatgatata    13260
tgccctaaag gtgagtcgcg gccgactgct agggcttctg cacctttga tcttcctgaa    13320 ttgtgctttc accttcgggt acatgacttt cgcgcacttt cagagtacaa ataaggtcgc    13380
gctcactatg ggagcagtag ttgcactcct ttgggggtg tactcagcca tagaaacctg    13440
gaaattcatc acctccagat gccgtttgtg cttgctaggc cgcaagtaca ttctggcccc    13500
tgcccaccac gttgaaagtg ccgcaggctt tcatccgatt gcggcaaatg ataaccacgc    13560
atttgtcgtc cggcgtcccg gctccactac ggtcaacggc acattggtgc ccgggttaaa    13620
aagcctcgtg ttgggtggca gaaaagctgt taaacaggga gtggtaaacc ttgtcaaata    13680
tgccaaataa caacggcaag cagcagaaga gaaagaaggg ggatggccag ccagtcaatc    13740
agctgtgcca gatgctgggt aagatcatcg ctcagcaaaa ccagtccaga ggcaagggac    13800
cgggaaagaa aaataagaag aaaaacccgg agaagcccca tttttcctcta gcgactgaag    13860 atgatgtcag acatcacttt acccctagtg agcggcaatt gtgtctgtcg tcaatccaga    13920
ccgcctttaa tcaaggcgct gggacttgca ccctgtcaga ttcagggagg ataagttaca    13980
ctgtggagtt tagtttgcct acgcatcata ctgtgcgcct gatccgcgtc acagcatcac    14040
cctcagcatg atgggctggc attcttgagg catctcagtg tttgaattgg aagaatgtgt    14100
ggtgaatggc actgattgac attgtgcctc taagtcacct attcaattag ggcgaccgtg    14160
tgggggtgag atttaattgg cgagaaccat gcggccgaaa ttaaaaaaaa               14210
```

<210> SEQ ID NO 14
<211> LENGTH: 15111
<212> TYPE: DNA
<213> ORGANISM: Porcine Reproductive and Respiratory Syndrome Virus
<220> FEATURE:
<221> NAME/KEY: misc_feature
<223> OTHER INFORMATION: Lelystad strain
<300> PUBLICATION INFORMATION:
<308> DATABASE ACCESSION NUMBER: Genbank/M96262.2
<309> DATABASE ENTRY DATE: 2000-11-08
<313> RELEVANT RESIDUES IN SEQ ID NO: (1)..(15111)

<400> SEQUENCE: 14

```
atgatgtgta gggtattccc cctacataca cgacacttct agtgtttgtg taccttggag      60
gcgtgggtac agccccgccc cacccctggg cccctgttct agcccaacag gtatccttct     120
ctctcggggc gagtgcgccg cctgctgctc ccttgcagcg ggaaggacct cccgagtatt     180
```

```
tccggagagc acctgcttta cgggatctcc acccttttaac catgtctggg acgttctccc      240
ggtgcatgtg cacccccggct gcccgggtat tttggaacgc cggccaagtc ttttgcacac      300
ggtgtctcag tgcgcggtct cttctctctc cagagcttca ggacactgac ctcggtgcag      360
ttggcttgtt ttacaagcct agggacaagc ttcactggaa agtccctatc ggcatccctc      420
aggtggaatg tactccatcc gggtgctgtt ggctctcagc tgttttccct ttggcgcgta      480
tgacctccgg caatcacaac ttcctccaac gacttgtgaa ggttgctgat gttttgtacc      540
gtgacggttg cttggcacct cgacaccttc gtgaactcca agtttacgag cgcggctgca      600
actggtaccc gatcacgggg cccgtgcccg ggatgggttt gtttgcgaac tccatgcacg      660
tatccgacca gccgttccct ggtgccaccc atgtgttgac taactcgcct ttgcctcaac      720
aggcttgtcg gcagccgttc tgtccatttg aggaggctca ttctagcgtg tacaggtgga      780
agaaatttgt ggttttcacg gactcctccc tcaacggtcg atctcgcatg atgtggacgc      840
cggaatccga tgattcagcc gccctggagg tactaccgcc tgagttagaa cgtcaggtcg      900
aaatcctcat tcggagtttt cctgctcatc accctgtcga cctggccgac tgggagctca      960
ctgagtcccc tgagaacggt ttttccttca acacgtctca ttcttgcggt caccttgtcc     1020
agaaccccga cgtgtttgat ggcaagtgct ggctctcctg cttttttgggc cagtcggtcg     1080
aagtgcgctg ccatgaggaa catctagctg acgccttcgg ttaccaaacc aagtggggcg     1140
tgcatggtaa gtacctccag cgcaggcttc aagttcgcgg cattcgtgct gtagtcgatc     1200
ctgatggtcc cattcacgtt gaagcgctgt cttgcccccca gtcttggatc aggcacctga     1260
ctctggatga tgatgtcacc ccaggattcg ttcgcctgac atcccttcgc attgtgccga     1320
acacagagcc taccacttcc cggatctttc ggtttggagc gcataagtgg tatggcgctg     1380
ccggcaaacg ggctcgtgct aagcgtgccg ctaaaagtga aaggattcg gctcccaccc      1440
ccaaggttgc cctgccggtc cccacctgtg gaattaccac ctactctcca ccgacagacg     1500
ggtcttgtgg ttggcatgtc cttgccgcca taatgaaccg gatgataaat ggtgacttca     1560
cgtcccctct gactcagtac aacagaccag aggatgattg ggcttctgat tatgatcttg     1620
ttcaggcgat tcaatgtcta cgactgcctg ctaccgtggt tcggaatcgc gcctgtcctta     1680
acgccaagta ccttataaaa cttaacggag ttcactggga ggtagaggtg aggtctggaa     1740
tggctcctcg ctccctttct cgtgaatgtg tggttggcgt ttgctctgaa ggctgtgtcg     1800
caccgcctta ccagcagac gggctaccta aacgtgcact cgaggccttg gcgtctgctt      1860
acagactacc ctccgattgt gttagctctg gtattgctga ctttcttgct aatccacctc     1920
ctcaggaatt ctggaccctc gacaaaatgt tgacctcccc gtcaccagag cggtccggct     1980
tctctagttt gtataaatta ctattagagg ttgttccgca aaaatgcggt gccacggaag     2040
gggcttttcat ctatgctgtt gagaggatgt tgaaggattg tccgagctcc aaacaggcca     2100
tggccccttct ggcaaaaaatt aaagttccat cctcaaaggc cccgtctgtg tccctggacg     2160
agtgtttccc tacggatgtt ttagccgact tcgagccagc atctcaggaa aggccccaaa     2220
gttccggcgc tgctgttgtc ctgtgttcac cggatgcaaa agagttcgag gaagcagccc     2280
cggaagaagt tcaagagagt ggccacaagg ccgtccactc tgcactcctt gccgagggtc     2340
ctaacaatga gcaggtacag gtggttgccg gtgagcaact gaagctcggc ggttgtggtt     2400
tggcagtcgg gaatgctcat gaaggtgctc tggtctcagc tggtctaatt aacctggtag     2460
gcgggaattt gtccccctca gaccccatga aagaaaacat gctcaatagc cgggaagacg     2520
aaccactgga tttgtcccaa ccagcaccag cttccacaac gaccccttgtg agagagcaaa     2580
```

```
cacccgacaa cccaggttct gatgccggtg ccctccccgt caccgttcga gaatttgtcc    2640
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacggtagg cgcgagcctg    2820
tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaaccccca gccaccaggg agtggctcga caaaatgtgg gataggggtgg   3180 acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360
cccccccaaa accggttggg ccagtgcttg accagatcgt ccctccgcct acggatatcc    3420
agcaagaaga tgtcaccccc tccgatgggc caccccatgc gccggatttt cctagtcgag    3480
tgagcacggg cggagttgg aaaggcctta tgctttccgg cacccgtctc gcggggtcta    3540
tcagccagcg ccttatgaca tgggttttg aagttttctc ccacctccca gcttttatgc    3600
tcacactttt ctcgccgcgg ggctctatgg ctccaggtga ttggttgttt gcaggtgtcg    3660
ttttacttgc tctcttgctc tgtcgttctt acccgatact cggatgcctt cccttattgg    3720
gtgtcttttc tggttctttg cggcgtgttc gtctgggtgt ttttggttct tggatggctt    3780
ttgctgtatt tttattctcg actccatcca acccagtcgg ttcttcttgt gaccacgatt    3840
cgccggagtg tcatgctgag cttttggctc ttgagcagcg ccaactttgg gaacctgtgc    3900
gcggccttgt ggtcggcccc tcaggcctct tatgtgtcat tcttggcaag ttactcggtg    3960
ggtcacgtta tctctggcat gttctcctac gtttatgcat gcttgcagat ttggcccttt    4020
ctcttgttta tgtggtgtcc cagggggcgtt gtcacaagtg ttggggaaag tgtataagga    4080
cagctcctgc ggaggtggct cttaatgtat ttccttctc gcgcgccacc cgtgtctctc    4140
ttgtatcctt gtgtgatcga ttccaaacgc caaaaggggg tgatcctgtg cacttggcaa    4200
cgggttggcg cgggtgctgg cgtggtgaga gccccatcca tcaaccacac caaaagccca    4260
tagcttatgc caatttggat gaaagaaaa tgtctgccca acggtggtt gctgtcccat    4320 acgatcccag tcaggctatc aaatgcctga agttctgca ggcgggaggg gccatcgtgg    4380
accagcctac acctgaggtc gttcgtgtgt ccgagatccc cttctcagcc ccattttcc    4440 caaaagttcc agtcaaccca gattgcaggg ttgtggtaga ttcggacact tttgtggctg    4500
cggttcgctg cggttactcg acagcacaac tggttctggg ccggggcaac tttgccaagt    4560
taaatcagac ccccccccagg aactctatct ccaccaaaac gactggtggg gcctcttaca    4620
cccttgctgt ggctcaagtg tctgcgtgga ctcttgttca tttcatcctc ggtctttggt    4680
tcacatcacc tcaagtgtgt ggccgaggaa ccgctgaccc atggtgttca atccttttt    4740 catatcctac ctatggcccc ggagttgtgt gctcctctcg actttgtgtg tctgccgacg    4800
gggtcaccct gccattgttc tcagccgtgg cacaactctc cggtagagag gtggggatttt    4860 ttattttggt gctcgtctcc ttgactgctt tggcccaccg catggctctt aaggcagaca    4920
```

```
tgttagtggt cttttcggct ttttgtgctt acgcctggcc catgagctcc tggttaatct    4980
gcttctttcc tatactcttg aagtgggtta cccttcaccc tcttactatg ctttgggtgc    5040
actcattctt ggtgttttgt ctgccagcag ccggcatcct ctcactaggg ataactggcc    5100
ttctttgggc aattggccgc tttacccagg ttgccggaat tattacacct tatgacatcc    5160
accagtacac ctctgggcca cgtggtgcag ctgctgtggc cacagcccca gaaggcactt    5220
atatggccgc cgtccggaga gctgctttaa ctgggcgaac tttaatcttc accccgtctg    5280
cagttggatc ccttctcgaa ggtgctttca ggactcataa accctgcctt aacaccgtga    5340
atgttgtagg ctcttccctt ggttccggag gggttttcac cattgatggc agaagaactg    5400
tcgtcactgc tgcccatgtg ttgaacggcg acacagctag agtcaccggc gactcctaca    5460
accgcatgca cactttcaag accaatggtg attatgcctg gtcccatgct gatgactggc    5520
agggcgttgc ccctgtggtc aaggttgcga aggggtaccg cggtcgtgcc tactggcaaa    5580
catcaactgg tgtcgaaccc ggtatcattg gggaagggtt cgccttctgt tttactaact    5640
gcggcgattc ggggtcaccc gtcatctcag aatctggtga tcttattgga atccacaccg    5700
gttcaaacaa acttggttct ggtcttgtga caacccctga aggggagacc tgcaccatca    5760
aagaaaccaa gctctctgac cttttccagac attttgcagg cccaagcgtt cctcttgggg    5820
acattaaatt gagtccggcc atcatccctg atgtaacatc cattccgagt gacttggcat    5880
cgctcctagc ctccgtccct gtagtggaag gcggcctctc gaccgttcaa cttttgtgtg    5940 tcttttcct tctctggcgc atgatgggcc atgcctggac acccattgtt gccgtgggct    6000 tcttttgct gaatgaaatt cttccagcag ttttggtccg agccgtgttt tcttttgcac    6060
tctttgtgct tgcatgggcc accccctggt ctgcacaggt gttgatgatt agactcctca    6120
cggcatctct caaccgcaac aagctttctc tggcgttcta cgcactcggg ggtgtcgtcg    6180
gtttggcagc tgaaatcggg acttttgctg gcagattgtc tgaattgtct caagctctttt   6240 cgacatactg cttcttacct agggtccttg ctatgaccag ttgtgttccc accatcatca    6300
ttggtggact ccataccctc ggtgtgattc tgtggttatt caaataccgg tgcctccaca    6360
acatgctggt tggtgatggg agttttttcaa gcgccttctt cctacggtat tttgcagagg    6420
gtaatctcag aaaaggtgtt tcacagtcct gtggcatgaa taacgagtcc ctaacggctg    6480
ctttagcttg caagttgtca caggctgacc ttgattttttt gtccagctta acgaacttca    6540
agtgctttgt atctgcttca aacatgaaaa atgctgccgg ccagtacatt gaagcagcgt    6600
atgccaaggc cctgcgccaa gagttggcct ctctagttca gattgacaaa atgaaaggag    6660
ttttgtccaa gctcgaggcc tttgctgaaa cagccacccc gtcccttgac ataggtgacg    6720
tgattgttct gctggggcaa catcctcacg gatccatcct cgatattaat gtggggactg    6780
aaaggaaaac tgtgtccgtg caagagaccc ggagcctagg cggctccaaa ttcagtgttt    6840
gtactgtcgt gtccaacaca cccgtggacg ccttgaccgg catcccactc cagacaccaa    6900
cccctctttt tgagaatggt ccgcgtcatc gcagcgagga agacgatctt aaagtcgaga    6960
ggatgaagaa acactgtgta tccctcggct tccacaacat caatggcaaa gtttactgca    7020
aaatttggga caagtctacc ggtgacacct tttacgcgga tgattcccgg tacacccaag    7080
accatgcttt tcaggacagg tcagccgact acagagacag ggactatgag ggtgtgcaaa    7140
ccacccccca cagggattt gatccaaagt ctgaaacccc tgttggcact gttgtgatcg    7200
gcggtattac gtataacagg tatctgatca aaggtaagga ggttctggtc cccaagcctg    7260
acaactgcct tgaagctgcc aagctgtccc ttgagcaagc tctcgctggg atgggccaaa    7320
```

```
cttgcgacct tacagctgcc gaggtggaaa agctaaagcg catcattagt caactccaag    7380
gtttgaccac tgaacaggct ttaaactgtt agccgccagc ggcttgaccc gctgtggccg    7440
cggcggccta gttgtgactg aaacggcggt aaaattata aaataccaca gcagaacttt    7500
caccttaggc cctttagacc taaaagtcac ttccgaggtg gaggtaaaga aatcaactga    7560
gcagggccac gctgttgtgg caaacttatg ttccggtgtc atcttgatga gacctcaccc    7620
accgtccctt gtcgacgttc ttctgaaacc cggacttgac acaatacccg gcattcaacc    7680
agggcatggg gccgggaata tgggcgtgga cggttctatt tgggattttg aaaccgcacc    7740
cacaaaggca gaactcgagt tatccaagca aataatccaa gcatgtgaag ttaggcgcgg    7800
ggacgccccg aacctccaac tcccttacaa gctctatcct gttagggggg atcctgagcg    7860
gcataaaggc cgccttatca ataccaggtt tggagattta ccttacaaaa ctcctcaaga    7920
caccaagtcc gcaatccacg cggcttgttg cctgcacccc aacggggccc ccgtgtctga    7980
tggtaaatcc acactaggta ccactcttca acatggtttc gagctttatg tccctactgt    8040
gccctatagt gtcatggagt accttgattc acgccctgac ccccttttta tgtgtactaa    8100
acatggcact tccaaggctg ctgcagagga cctccaaaaa tacgacctat ccacccaagg    8160
atttgtcctg cctggggtcc tacgcctagt acgcagattc atctttggcc atattggtaa    8220
ggcgccgcca ttgttcctcc catcaaccta tcccgccaag aactctatgg cagggatcaa    8280
tggccagagg ttcccaacaa aggacgttca gagcatacct gaaattgatg aaatgtgtgc    8340
ccgcgctgtc aaggagaatt ggcaaactgt gacaccttgc accctcaaga aacagtactg    8400
ttccaagccc aaaaccagga ccatcctggg caccaacaac tttattgcct tggctcacag    8460
atcggcgctc agtggtgtca cccaggcatt catgaagaag gcttggaagt ccccaattgc    8520
cttggggaaa aacaaattca aggagctgca ttgcactgtc gccggcaggt gtcttgaggc    8580
cgacttggcc tcctgtgacc gcagcacccc cgccattgta agatggtttg ttgccaacct    8640
cctgtatgaa cttgcaggat gtgaagagta cttgcctagc tatgtgctta attgctgcca    8700
tgacctcgtg gcaacacagg atggtgcctt cacaaaacgc ggtggcctgt cgtccgggga    8760
ccccgtcacc agtgtgtcca caccgtata ttcactggta atttatgccc agcacatggt    8820
attgtcggcc ttgaaaatgg gtcatgaaat tggtcttaag ttcctcgagg aacagctcaa    8880
gttcgaggac ctccttgaaa ttcagccat gttggtatac tctgatgatc ttgtcttgta    8940
cgctgaaaga cccacatttc ccaattacca ctggtgggtc gagcaccttg acctgatgct    9000
gggtttcaga acgacccaa agaaaaccgt cataactgat aaacccagct tcctcggctg    9060
cagaattgag gcagggcgac agctagtccc caatcgcgac cgcatcctgg ctgctcttgc    9120
atatcacatg aaggcgcaga acgcctcaga gtattatgcg tctgctgccg caatcctgat    9180
ggattcatgt gcttgcattg accatgaccc tgagtggtat gaggacctca tctgcggtat    9240
tgcccggtgc gcccgccagg atggttatag cttcccaggt ccggcatttt tcatgtccat    9300
gtgggagaag ctgagaagtc ataatgaagg gaagaaattc cgccactgcg gcatctgcga    9360
cgccaaagcc gactatgcgt ccgcctgtgg gcttgatttg tgtttgttcc attcgcactt    9420
tcatcaacac tgccctgtca ctctgagctg cggtcaccat gccggttcaa aggaatgttc    9480
gcagtgtcag tcacctgttg gggctggcag atcccctctt gatgccgtgc taaaacaaat    9540
tccatacaaa cctcctcgta ctgtcatcat gaaggtgggt aataaaacaa cggccctcga    9600
tccggggagg taccagtccc gtcgaggtct cgttgcagtc aagaggggta ttgcaggcaa    9660
```

```
tgaagttgat ctttctgatg gggactacca agtggtgcct cttttgccga cttgcaaaga   9720
cataaacatg gtgaaggtgg cttgcaatgt actactcagc aagttcatag tagggccacc   9780
aggttccgga aagaccacct ggctactgag tcaagtccag gacgatgatg tcatttacac   9840
acccacccat cagactatgt ttgatatagt cagtgctctc aaagtttgca ggtattccat   9900
tccaggagcc tcaggactcc ctttcccacc acctgccagg tccgggccgt gggttaggct   9960
tattgccagc gggcacgtcc ctggccgagt atcatacctc gatgaggctg gatattgtaa  10020
tcatctggac attcttagac tgcttttcaa aacacccctt gtgtgtttgg gtgaccttca  10080
gcaacttcac cctgtcggct ttgattccta ctgttatgtg ttcgatcaga tgcctcagaa  10140
gcagctgacc actatttaca gatttggccc taacatctgc gcagccatcc agccttgtta  10200
cagggagaaa cttgaatcta aggctaggaa cactagggtg gttttttacca cccggcctgt  10260 ggcctttggt caggtgctga caccatacca taaagatcgc atcggctctg cgataaccat  10320
agattcatcc caggggggcca ccttttgatat tgtgacattg catctaccat cgccaaagtc  10380
cctaaataaa tcccgagcac ttgtagccat cactcgggca agacacgggt tgttcattta  10440
tgaccctcat aaccagctcc aggagttttt caacttaacc cctgagcgca ctgattgtaa  10500
ccttgtgttc agccgtgggg atgagctggt agttctgaat gcggataatg cagtcacaac  10560
tgtagcgaag gcccttgaga caggtccatc tcgatttcga gtatcagacc cgaggtgcaa  10620
gtctctctta gccgcttgtt cggccagtct ggaagggagc tgtatgccac taccgcaagt  10680
ggcacataac ctgggggtttt acttttcccc ggacagtcca acatttgcac ctctgccaaa  10740
agagttggcg ccacattggc cagtggttac ccaccagaat aatcgggcgt ggcctgatcg  10800
acttgtcgct agtatgcgcc caattgatgc ccgctacagc aagccaatgg tcggtgcagg  10860
gtatgtggtc gggccgtcca ccttttcttgg tactcctggt gtggtgtcat actatctcac  10920
actatacatc aggggtgagc cccaggcctt gccagaaaca ctcgtttcaa cagggcgtat  10980
agccacagat tgtcgggagt atctcgacgc ggctgaggaa gaggcagcaa aagaactccc  11040
ccacgcattc attggcgatg tcaaaggtac cacggttggg gggtgtcatc acattacatc  11100
aaaataccta cctaggtccc tgcctaagga ctctgttgcc gtagttggag taagttcgcc  11160
cggcagggct gctaaagccg tgtgcactct caccgatgtg tacctccccg aactccggcc  11220
atatctgcaa cctgagacgg catcaaaatg ctggaaactc aaattagact tcagggacgt  11280
ccgactaatg gtctggaaag gagccaccgc ctatttccag ttggaagggc ttacatggtc  11340
ggcgctgccc gactatgcca ggtttattca gctgcccaag gatgccgttg tatacattga  11400
tccgtgtata ggaccggcaa cagccaaccg taaggtcgtg cgaaccacag actggcgggc  11460
cgacctggca gtgacaccgt atgattacgg tgcccagaac attttgacaa cagcctggtt  11520
cgaggacctc gggccgcagt ggaagatttt gggggttgcag ccctttaggc gagcatttgg  11580
ctttgaaaac actgaggatt gggcaatcct tgcacgccgt atgaatgacg caaggacta  11640 cactgactat aactggaact gtgttcgaga acgcccacac gccatctacg ggcgtgctcg  11700
tgaccatacg tatcattttg ccctggcac agaattgcag gtagagctag gtaaaccccg  11760
gctgccgcct gggcaagtgc cgtgaattcg gggtgatgca atgggtcac tgtggagtaa  11820 aatcagccag ctgttcgtgg acgccttcac tgagttcctt gttagtgtgg ttgatattgc  11880
cattttcctt gccatactgt ttggggttcac cgtcgcagga tggttactgg tctttcttct  11940
cagagtggtt tgctccgcgc ttctccgttc gcgctctgcc attcactctc ccgaactatc  12000
gaaggtccta tgaaggcttg ttgcccaact gcagaccgga tgtcccacaa tttgcagtca  12060
```

```
agcacccatt gggtatgttt tggcacatgc gagtttccca cttgattgat gagatggtct   12120
ctcgtcgcat ttaccagacc atggaacatt caggtcaagc ggcctggaag caggtggttg   12180
gtgaggccac tctcacgaag ctgtcagggc tcgatatagt tactcatttc caacacctgg   12240
ccgcagtgga ggcggattct tgccgctttc tcagctcacg actcgtgatg ctaaaaaatc   12300
ttgccgttgg caatgtgagc ctacagtaca acaccacgtt ggaccgcgtt gagctcatct   12360
tccccacgcc aggtacgagg cccaagttga ccgatttcag acaatggctc atcagtgtgc   12420
acgcttccat ttttccctct gtggcttcat ctgttacctt gttcatagtg ctttggcttc   12480
gaattccagc tctacgctat gttttttggtt tccattggcc cacggcaaca catcattcga   12540
gctgaccatc aactacacca tatgcatgcc ctgttctacc agtcaagcgg ctcgccaaag   12600
gctcgagccc ggtcgtaaca tgtggtgcaa aatagggcat gacaggtgtg aggagcgtga   12660
ccatgatgag ttgttaatgt ccatcccgtc cgggtacgac aacctcaaac ttgagggtta   12720
ttatgcttgg ctggcttttt tgtccttttc ctacgcggcc caattccatc cggagttgtt   12780
cgggataggg aatgtgtcgc gcgtcttcgt ggacaagcga caccagttca tttgtgccga   12840
gcatgatgga cacaattcaa ccgtatctac cggacacaac atctccgcat tatatgcggc   12900
atattaccac caccaaatag acgggggcaa ttggttccat ttggaatggc tgcggccact   12960
cttttcttcc tggctggtgc tcaacatatc atggtttctg aggcgttcgc ctgtaagccc   13020
tgtttctcga cgcatctatc agatattgag accaacacga ccgcggctgc cggtttcatg   13080
gtccttcagg acatcaattg tttccgacct cacggggtct cagcagcgca agagaaaatt   13140
tccttcggaa agtcgtccca atgtcgtgaa gccgtcggta ctccccagta catcacgata   13200
acggctaacg tgaccgacga atcatacttg tacaacgcgg acctgctgat gctttctgcg   13260
tgccttttct acgcctcaga aatgagcgag aaaggcttca aagtcatctt tgggaatgtc   13320
tctggcgttg tttctgcttg tgtcaatttc acagattatg tggcccatgt gacccaacat   13380
acccagcagc atcatctggt aattgatcac attcggttgc tgcatttcct gacaccatct   13440
gcaatgaggt gggctacaac cattgcttgt ttgttcgcca ttctcttggc aatatgagat   13500
gttctcacaa attgggcgt ttcttgactc cgcactcttg cttctggtgg cttttttgc    13560 tgtgtaccgg cttgtcctgg tccttttgccg atggcaacgg cgacagctcg ataccaat    13620 acatatataa cttgacgata tgcgagctga atgggaccga ctggttgtcc agccattttg   13680
gttgggcagt cgagaccttt gtgctttacc cggttgccac tcatatcctc tcactgggtt   13740
ttctcacaac aagccatttt tttgacgcgc tcggtctcgg cgctgtatcc actgcaggat   13800
ttgttggcgg gcggtacgta ctctgcagcg tctacggcgc ttgtgctttc gcagcgttcg   13860
tatgttttgt catccgtgct gctaaaaatt gcatggcctg ccgctatgcc cgtacccggt   13920
ttaccaactt cattgtggac gaccggggga gagttcatcg atggaagtct ccaatagtgg   13980
tagaaaaatt gggcaaagcc gaagtcgatg gcaacctcgt caccatcaaa catgtcgtcc   14040 tcgaagggt taaagctcaa cccttgacga ggacttcggc tgagcaatgg gaggcctaga    14100 cgattttgc aacgatccta tcgccgcaca aaagctcgtg ctagccttta gcatcacata    14160
cacacctata atgatatacg cccttaaggt gtcacgcggc cgactcctgg ggctgttgca   14220
catcctaata tttctgaact gttcctttac attcggatac atgacatatg tgcattttca   14280
atccaccaac cgtgtcgcac ttaccctggg ggctgttgtc gcccttctgt ggggtgttta   14340
cagcttcaca gagtcatgga agtttatcac ttccagatgc agattgtgtt gccttggccg   14400
```

```
gcgatacatt ctggcccctg cccatcacgt agaaagtgct gcaggtctcc attcaatctc    14460
agcgtctggt aaccgagcat acgctgtgag aaagcccgga ctaacatcag tgaacggcac    14520
tctagtacca ggacttcgga gcctcgtgct gggcggcaaa cgagctgtta aacgaggagt    14580
ggttaacctc gtcaagtatg gccggtaaaa accagagcca gaagaaaaag aaaagtacag    14640
ctccgatggg gaatggccag ccagtcaatc aactgtgcca gttgctgggt gcaatgataa    14700
agtcccagcg ccagcaacct aggggaggac aggccaaaaa gaaaaagcct gagaagccac    14760
attttcccct ggctgctgaa gatgacatcc ggcaccacct cacccagact gaacgctccc    14820
tctgcttgca atcgatccag acggctttca atcaaggcgc aggaactgcg tcgctttcat    14880
ccagcgggaa ggtcagtttt caggttgagt ttatgctgcc ggttgctcat acagtgcgcc    14940
tgattcgcgt gacttctaca tccgccagtc agggtgcaag ttaatttgac agtcaggtga    15000
atggccgcga ttggcgtgtg gcctctgagt cacctattca attgggcga tcacatgggg    15060 gtcatactta atcaggcagg aaccatgtga ccgaaattaa aaaaaaaaa a             15111
```

<210> SEQ ID NO 15
<211> LENGTH: 15411
<212> TYPE: DNA
<213> ORGANISM: Porcine Reproductive and Respiratory Syndrome Virus
<220> FEATURE:
<221> NAME/KEY: misc_feature
<223> OTHER INFORMATION: Strain VR-2332
<300> PUBLICATION INFORMATION:
<308> DATABASE ACCESSION NUMBER: Genbank/U87392.3
<309> DATABASE ENTRY DATE: 2000-11-17
<313> RELEVANT RESIDUES IN SEQ ID NO: (1)..(15411)

<400> SEQUENCE: 15

```
atgacgtata ggtgttggct ctatgccttg gcatttgtat tgtcaggagc tgtgaccatt      60
ggcacagccc aaaacttgct gcacagaaac acccttctgt gatagcctcc ttcagggag     120 cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg ccaagtctca ctgcacacga tgcctcagtg cacggtctct ccttcccctg     300
aacctccaag tttctgagct cggggtgcta ggcctattct acaggcccga agagccactc     360
cggtggacgt tgccacgtgc attccccact gttgagtgct ccccgccgg ggcctgctgg     420 cttttctgcaa tctttccaat cgcacgaatg accagtggaa acctgaactt ccaacaaaga   480
atggtacggg tcgcagctga gctttacaga gccggccagc tcacccctgc agtcttgaag    540
gctctacaag tttatgaacg gggttgccgc tggtacccca ttgttggacc tgtccctgga     600
gtggccgttt cgccaattc cctacatgtg agtgataaac ctttcccggg agcaactcac      660
gtgttgacca acctgccgct cccgcagaga cccaagcctg aagactttg cccctttgag     720 tgtgctatgg ctactgtcta tgacattggt catgacgccg tcatgtatgt ggccgaaagg    780
aaagtctcct gggcccctcg tggcgggat gaagtgaaat ttgaagctgt ccccggggag    840
ttgaagttga ttgcgaaccg gctccgcacc tccttcccgc ccaccacac agtggacatg      900 tctaagttcg ccttcacagc ccctgggtgt ggtgtttcta gcgggtcga acgccaacac      960 ggctgccttc ccgctgacac tgtccctgaa ggcaactgct ggtggagctt gtttgacttg    1020
cttccactgg aagttcagaa caaagaaatt cgccatgcta accaatttgg ctaccagacc   1080
aagcatggtg tctctggcaa gtacctacag cggaggctgc aagttaatgg ctccgagca    1140 gtaactgacc taaacggacc tatcgtcgta cagtacttct ccgttaagga gagttggatc    1200
```

-continued

```
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccccctgg gatgtcccct   1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca atcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg   2340
gctaactact actaccgtgc gcaaggtgac gaagttcgtc accgtgaaag actaaccgcc   2400
gtgctctcca agttggaaaa ggttgttcga gaagaatatg ggctcatgcc aaccgagcct   2460
ggtccacggc ccacactgcc acgcgggctc gacgaactca agaccagat ggaggaggac   2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agcccctttg atctcccgac ccacctgag    2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt    3120
ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg catctccaa    3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc acccttagatg gcaggttaaa gttcctccca   3480
aaaatgatac tcgagacacc gccgcccat ccgtgtgagt ttgtgatgat gcctcacacg    3540
cctgcacctt ccgtaggtgc ggagagcgac cttaccattg gctcagttgc tactgaagat   3600
```

```
gttccacgca tcctcgagaa aatagaaaat gtcggcgaga tggccaacca gggacccttg    3660
gccttctccg aggataaacc ggtagatgac caacttgtca acgaccccg gatatcgtcg      3720 cggaggcctg acgagagcac atcagctccg tccgcaggca caggtggcgc cggctctttt    3780
accgatttgc cgccttcaga tggcgcggat gcggacgggg gggggccgtt tcggacggta    3840
aaaagaaaag ctgaaaggct ctttgaccaa ctgagccgtc aggttttga cctcgtctcc      3900 catctccctg ttttcttctc acgccttttc taccctggcg gtggttattc tccgggtgat    3960
tggggttttg cagcttttac tctattgtgc ctcttttat gttacagtta cccagccttt     4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcctaat gaggtcgctt ttaacgtgtt tcctttcaca    4440
cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaaacccat cgcgtttgcc caattggatg aaaagaagat tacggctagg    4620
actgtggtcg cccagcctta tgaccccaac caagccgtaa agtgcttgcg ggtattgcag    4680
tcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860
ggtgtagggg actttgcccca gctgaatgga ttaaaaatca ggcaaattc caagccttca    4920 gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggcc tctctgcac gtccaggttg     5100 tgcatttccc aacacggcct taccctgccc ttgacagcac ttgtggcggg attcggtatt    5160
caagaaattg ccttggtcgt tttgatttt gtttccatcg gaggcatggc tcataggttg      5220
agctgtaagg ctgacatgct gtgtgttttg cttgcaattg ccagctatgt ttgggtacct    5280
cttacctggt tgctttgtgt gttcccttgc tggttgcgct gtttctcttt gcacccctc     5340 accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460
accccctacg acattcatca ttacaccagt ggcccccgcg tgttgccgc cttggctacc    5520 gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatgact    5880 ggccgtgcct attggctaac atcctctggc gtcgaacccg gcgtcattgg aaaaggattc    5940
```

```
gccttctgct tcaccgcatg tggcgattcc gggtccccag tgatcaccga ggccggtgag    6000
cttgtcggcg ttcacacggg atcgaataaa caagggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttctttgtgt gttttttctc ctgtggagaa tgatgggaca tgcctggacg    6300
cccttggttg ctgtgagttt cttttatttttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480
agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcccgcacca tatccttgtt ggcgatgagt gttctctgc ggctttcttc    6720
ttgagatact ttgccgaggg aaagttgagg gaaggggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc caacgcttg ggggatgag    7260
gaccgtttga ataagaagaa gaggcgcagg atggaagccc tcggcatcta tgttatgggc    7320
gggaaaaagt accagaaatt ttgggacaag aattccggtg atgtgtttta tgaggaggtc    7380
cataataaca cagatgagtg ggagtgtctc agagttggcg accctgccga cttttgaccct    7440
gagaagggaa ctctgtgtgg acatgtcacc attgaaaaca aggcttacca tgtttacacc    7500
tccccatctg gtaagaagtt cttggtcccc gtcaacccag agaatggaag agttcaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga acagcggta aaaatagtca aatttcacaa ccggaccttc acctggggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
```

```
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaaccccctg atcgtctatt cggacgacct cgtgctgtat gccgagtctc    9240
ccaccatgcc aaactatcac tggtgggttg aacatctgaa tttgatgctg ggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
ccccctgtagg gaaaggcaca agcccttag acgaggtgct ggaacaagtc ccgtataagc    9840
ccccacggac cgttatcatg catgtggagc agggtctcac ccccccttgat ccaggtagat    9900
accaaactcg ccgcggatta gtctctgtca ggcgtggaat taggggaaat gaagttggac    9960
taccagacgg tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc ccctcccgca ccggtccgtg ggttcgcatc ctagccggcg   10260
gttggtgtcc tggcaagaat tccttcctag atgaagcagc gtattgcaat cacccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taaagattca ctcaacaggc   10680
```

```
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacggt ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760 tcacccctta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttatttcc ccccgggccc tgtcattgaa ccaactttag   12060
gcctgaattg aaatgaaatg gggtccatgc aaagcctttt tgacaaaatt ggccaacttt   12120
ttgtggatgc tttcacggag ttcttggtgt ccattgttga tatcattata tttttggcca   12180
ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta atatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact ctttttgttg tgctgtggtt gcgggttcca   12780
atactacgta ctgttttggg tttccgctgg ttagggcaa ttttcttc gaactcacag   12840 tgaattacac ggtgtgtcca ccttgcctca cccggcaagc agccacagag atctacgaac   12900
ccggtaggtc tctttggtgc aggatagggt atgaccgatg tggggaggac gatcatgacg   12960
agctagggtt tatgataccg cctggcctct ccagcgaagg ccactgact ggtgtttacg   13020 cctggttggc gttcttgtcc ttcagctaca cggcccagtt ccatcccgag atattcggga   13080
```

```
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttttgcca ttctgttggc aatttgaatg tttaagtatg ttggagaaat    13800
gcttgaccgc gggctgttgc tcgcgattgc tttctttgtg gtgtatcgtg ccgttctgtt    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggttccg    14340
tggcaacccc tataaccaga gtttcagcgg aacaatgggg tcgtccttag atgacttctg    14400
tcatgatagc acggctccac aaaaggtgct tttggcgttt tctattacct acacgccagt    14460
gatgatatat gccctaaagg tgagtcgcgg ccgactgcta gggcttctgc acctttttgat    14520 cttcctgaat tgtgctttca ccttcgggta catgactttc gcgcactttc agagtacaaa    14580
taaggtcgcg ctcactatgg gagcagtagt tgcactcctt tggggggtgt actcagccat    14640
agaaacctgg aaattcatca cctccagatg ccgtttgtgc ttgctaggcc gcaagtacat    14700
tctggcccct gcccaccacg ttgaaagtgc cgcacggttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaataacc aacggcaagc agcagaagag aaagaagggg gatggccagc    14940
cagtcaatca gctgtgccag atgctgggta agatcatcgc tcagcaaaac cagtccagag    15000
gcaagggacc gggaaagaaa aataagaaga aaaacccgga gaagcccat tttcctctag    15060 cgactgaaga tgatgtcaga catcacttta ccccctagtga gcggcaattg tgtctgtcgt    15120
caatccagac cgcctttaat caaggcgctg gacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat t    15411
```

<210> SEQ ID NO 16
<211> LENGTH: 17
<212> TYPE: DNA
<213> ORGANISM: Artificial Sequence
<220> FEATURE:
<223> OTHER INFORMATION: Synthetic Promoter

<400> SEQUENCE: 16
taatacgact cactata                                              17

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 17

Glu Gln Lys Leu Ile Ser Glu Glu Asp Leu
1               5                   10

<210> SEQ ID NO 18
<211> LENGTH: 61
<212> TYPE: DNA
<213> ORGANISM: Artificial Sequence
<220> FEATURE:
<223> OTHER INFORMATION: Synthetic Primer

<400> SEQUENCE: 18
acatgcatgc ttaatacgac tcactatagt atgacgtata ggtgttggct ctatgccttg    60
g                                                                   61

<210> SEQ ID NO 19
<211> LENGTH: 19
<212> TYPE: DNA
<213> ORGANISM: Artificial Sequence
<220> FEATURE:
<223> OTHER INFORMATION: Synthetic Primer

<400> SEQUENCE: 19
ctgggcgacc acagtccta                                            19

<210> SEQ ID NO 20
<211> LENGTH: 25
<212> TYPE: DNA
<213> ORGANISM: Artificial Sequence
<220> FEATURE:
<223> OTHER INFORMATION: Synthetic Primer

<400> SEQUENCE: 20
cttctcggcg cgcccgaatg ggagt                                     25

<210> SEQ ID NO 21
<211> LENGTH: 26
<212> TYPE: DNA
<213> ORGANISM: Artificial Sequence
<220> FEATURE:
<223> OTHER INFORMATION: Synthetic Primer

<400> SEQUENCE: 21
tcatcatacc tagggcctgc tccacg                                    26

<210> SEQ ID NO 22
<211> LENGTH: 26
<212> TYPE: DNA

```
<213> ORGANISM: Artificial Sequence
<220> FEATURE:
<223> OTHER INFORMATION: Synthetic Primer

<400> SEQUENCE: 22
cgtggagcag gccctaggta tgatga                                          26

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
tgcaggcgaa cgcctgag                                                   18

<210> SEQ ID NO 24
<211> LENGTH: 21
<212> TYPE: DNA
<213> ORGANISM: Artificial Sequence
<220> FEATURE:
<223> OTHER INFORMATION: Synthetic Primer

<400> SEQUENCE: 24
gtgaggactg ggaggattac a                                               21

<210> SEQ ID NO 25
<211> LENGTH: 53
<212> TYPE: DNA
<213> ORGANISM: Artificial Sequence
<220> FEATURE:
<223> OTHER INFORMATION: Synthetic Primer

<400> SEQUENCE: 25
gtctttaatt aactagtttt tttttttttt tttttttttt tttttaatt tcg             53

<210> SEQ ID NO 26
<211> LENGTH: 27
<212> TYPE: DNA
<213> ORGANISM: Artificial Sequence
<220> FEATURE:
<223> OTHER INFORMATION: Synthetic Primer

<400> SEQUENCE: 26
gatgcatgcc attaattaag ggtcggc                                         27

<210> SEQ ID NO 27
<211> LENGTH: 27
<212> TYPE: DNA
<213> ORGANISM: Artificial Sequence
<220> FEATURE:
<223> OTHER INFORMATION: Synthetic Primer

<400> SEQUENCE: 27
gccgaccctt aattaatggc atgcatc                                         27

<210> SEQ ID NO 28
<211> LENGTH: 36
<212> TYPE: DNA
<213> ORGANISM: Artificial Sequence
<220> FEATURE:
<223> OTHER INFORMATION: Synthetic Primer

<400> SEQUENCE: 28
acatgcatgc ttaatacgac tcactatagg tatgac                               36
```

<210> SEQ ID NO 29
<211> LENGTH: 25
<212> TYPE: DNA
<213> ORGANISM: Artificial Sequence
<220> FEATURE:
<223> OTHER INFORMATION: Synthetic Primer

<400> SEQUENCE: 29
ctgtgtggac atgtcaccat tgaaa                                            25

<210> SEQ ID NO 30
<211> LENGTH: 25
<212> TYPE: DNA
<213> ORGANISM: Artificial Sequence
<220> FEATURE:
<223> OTHER INFORMATION: Synthetic Primer

<400> SEQUENCE: 30
gtgtatcgtg ccgttctgtt ttgct                                            25

<210> SEQ ID NO 31
<211> LENGTH: 25
<212> TYPE: DNA
<213> ORGANISM: Artificial Sequence
<220> FEATURE:
<223> OTHER INFORMATION: Synthetic Primer

<400> SEQUENCE: 31
cagatgctgg gtaagatcat cgctc                                            25

<210> SEQ ID NO 32
<211> LENGTH: 39
<212> TYPE: DNA
<213> ORGANISM: Artificial Sequence
<220> FEATURE:
<223> OTHER INFORMATION: Synthetic Primer

<400> SEQUENCE: 32
gcacaatgtc aatcagtgcc attcaccaca cattcttcc                             39

<210> SEQ ID NO 33
<211> LENGTH: 41
<212> TYPE: DNA
<213> ORGANISM: Artificial Sequence
<220> FEATURE:
<223> OTHER INFORMATION: Synthetic Primer

<400> SEQUENCE: 33
tagacttggc cctccgccat aaacaccctg gcattggggg t                          41

<210> SEQ ID NO 34
<211> LENGTH: 201
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 34

Met Arg Cys Ser Tyr Lys Leu Gly Arg Ser Leu Ile Leu His Ser Cys
1               5                   10                  15

Ser Trp Trp Phe Phe Leu Leu Cys Thr Gly Leu Ser Trp Ser Phe Ala
20 25 30

Asp Gly Asn Gly Asn Asn Ser Thr Tyr Gln Tyr Ile Tyr Asn Leu Thr

```
                  35                  40                  45
Ile Cys Glu Leu Asn Gly Thr Asn Trp Leu Ser Gly His Phe Asp Trp
 50                  55                  60

Ala Val Glu Thr Phe Val Leu Tyr Pro Val Val Thr His Ile Leu Ser
 65                  70                  75                  80

Leu Gly Phe Leu Thr Thr Ser His Phe Phe Asp Ala Leu Gly Leu Gly
                     85                  90                  95

Ala Val Ser Thr Ala Gly Phe Ile Asp Gly Arg Tyr Val Leu Ser Ser
                    100                 105                 110

Ile Tyr Gly Ala Cys Ala Phe Ala Ala Phe Val Cys Phe Val Ile Arg
            115                 120                 125

Ala Ala Lys Asn Cys Met Ala Cys Arg Tyr Ala Arg Thr Arg Phe Thr
        130                 135                 140

Asn Phe Ile Val Asp Asp Arg Gly Gly Val His Arg Trp Lys Ser Pro
145                 150                 155                 160

Ile Val Val Glu Lys Leu Gly Lys Ala Asp Ile Asp Gly Ser Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200

<210> SEQ ID NO 35
<211> LENGTH: 201
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 35

Met Ar

Arg Thr Ser Ala Glu Gln Trp Glu Ala
        195                 200

<210> SEQ ID NO 36
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)
<220> FEATURE:
<221> NAME/KEY: MISC_FEATURE
<222> LOCATION: (44)..(44)
<223> OTHER INFORMATION: X = Xaa
<220> FEATURE:
<221> NAME/KEY: MISC_FEATURE
<222> LOCATION: (44)..(44)
<223> OTHER INFORMATION: Xaa = variable or unknown amino acid

<400> SEQUENCE: 36

Met Leu Gly Lys Cys Leu Thr Ala Gly Tyr Cys Ser Gln Leu Leu Phe
1               5                   10                  15

Leu Trp Cys Ile Val Pro Phe Cys Leu Ala Ala Leu Val Asn Ala Asp
            20                  25                  30

Ser Asn Ser Ser Ser His Leu Gln Leu Ile Tyr Xaa Leu Thr Ile Cys
        35                  40                  45

Glu Leu Asn Gly Thr Asp Trp Leu Asn Asn His Phe Ser Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Leu Leu Asp Thr Val Gly Leu Ile Thr Val
                85                  90                  95

Ser Thr Ala Gly Tyr Cys His Lys Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Ile Glu Val Gly Gly Asp Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Gly Arg Pro
        195                 200

<210> SEQ ID NO 37
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 37

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Ser
            20                  25                  30

Ser Asn Ser Ser Ser His Leu Gln Leu Ile Tyr Asn Leu Thr Ile Cys

```
                35                  40                  45
Glu Leu Asn Gly Thr Asp Trp Leu Asn Asp His Phe Ser Trp Ala Val
 50                  55                  60
Glu Thr Phe Val Ile Phe Pro Val Leu Thr His Ile Val Ser Tyr Gly
 65                  70                  75                  80
Ala Leu Thr Thr Ser His Phe Leu Asp Thr Val Gly Leu Ile Thr Val
                 85                  90                  95
Ser Thr Ala Gly Tyr Tyr His Ala Arg Tyr Val Leu Ser Ser Ile Tyr
                100                 105                 110
Ala Val Cys Ala Leu Ala Ala Leu Ile Cys Phe Val Ile Arg Leu Thr
                115                 120                 125
Lys Asn Cys Met Ser Trp Arg Tyr Ser Cys Thr Arg Tyr Thr Asn Phe
                130                 135                 140
Leu Leu Asp Thr Lys Gly Arg Leu Tyr Arg Trp Arg Ser Pro Val Ile
145                 150                 155                 160
Ile Glu Lys Arg Gly Lys Ile Glu Val Gly Gly Asp Leu Ile Asp Leu
                165                 170                 175
Lys Arg Val Val Leu Asp Gly Ser Ala Ala Thr Pro Val Thr Lys Val
                180                 185                 190
Ser Ala Glu Gln Trp Gly Arg Pro
                195                 200

<210> SEQ ID NO 38
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 38

Met Leu Gly Lys Cys Leu Thr Ala Gly Cys Cys Ser Gln Leu Pro Phe
  1               5                  10                  15
Leu Trp Cys Ile Val Pro Phe Cys Phe Ala Ala Leu Val Asn Ala Ser
                 20                  25                  30
Ser Asn Ser Ser Ser His Leu Gln Leu Ile Tyr Asn Leu Thr Ile Cys
                 35                  40                  45
Glu Leu Asn Gly Thr Asp Trp Leu Asn Asp Lys Phe Asp Trp Ala Val
 50                  55                  60
Glu Thr Phe Val Ile Phe Pro Val Leu Thr His Ile Val Ser Tyr Gly
 65                  70                  75                  80
Ala Leu Thr Thr Ser His Phe Leu Asp Thr Val Gly Leu Val Thr Val
                 85                  90                  95
Ser Thr Ala Gly Tyr Tyr His Gly Arg Tyr Val Leu Ser Ser Ile Tyr
                100                 105                 110
Ala Val Cys Ala Leu Ala Ala Leu Ile Cys Phe Val Ile Arg Leu Thr
                115                 120                 125
Lys Asn Cys Met Ser Trp Arg Tyr Ser Cys Thr Arg Tyr Thr Asn Phe
                130                 135                 140
Leu Leu Asp Thr Lys Gly Arg Leu Tyr Arg Trp Arg Ser Pro Val Ile
145                 150                 155                 160
Ile Glu Lys Gly Gly Lys Val Glu Val Glu Gly His Leu Ile Asp Leu
                165                 170                 175
Lys Arg Val Val Leu Asp Gly Ser Ala Ala Thr Pro Val Thr Lys Val
                180                 185                 190
```

```
Ser Ala Glu Arg Trp Gly Arg Pro
            195                 200
```

<210> SEQ ID NO 39
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 39

```
Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asp Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asn Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Val Ile Arg Leu Thr
            115                 120                 125

Lys Asn Cys Met Ser Trp Arg Tyr Ser Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Arg Trp Gly Arg Pro
            195                 200
```

<210> SEQ ID NO 40
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 40

```
Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Gly
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp Lys Phe Asp Trp Ala Val
    50                  55                  60

Glu Thr Phe Val Ile Phe Pro Val Leu Thr His Ile Val Ser Tyr Gly
65                  70                  75                  80
```

-continued

Ala Leu Thr Thr Ser His Phe Leu Asp Thr Val Gly Leu Val Thr Val
                    85                  90                  95

Ser Thr Ala Gly Tyr Tyr His Arg Arg Tyr Val Leu Ser Ser Ile Tyr
            100                 105                 110

Ala Val Cys Ala Leu Ala Ala Leu Ile Cys Phe Val Ile Arg Leu Thr
            115                 120                 125

Lys Asn Cys Met Ser Trp Arg Tyr Ser Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Arg Trp Gly Arg Pro
            195                 200

<210> SEQ ID NO 41
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 41

Met Leu Gly Lys Cys Leu Thr Ala Gly Cys Cys Ser Gln Leu Pro Phe
1               5                   10                  15

Leu Trp Cys Ile Val Pro Phe Cys Phe Val Ala Leu Val Asn Ala Asn
            20                  25                  30

Thr Asp Ser Ser Ser His Leu Gln Leu Ile Tyr Asn Leu Thr Ile Cys
        35                  40                  45

Glu Leu Asn Gly Thr Asp Trp Leu Asn Asp Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                    85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Ala Ile Arg Leu Thr
            115                 120                 125

Lys Asn Cys Met Ser Trp Arg Tyr Ser Cys Thr Arg Tyr Thr Asn Phe
        130                 135                 140

Leu Leu Asp Thr Lys Gly Lys Leu Tyr Arg Trp Arg Ser Pro Val Ile
145                 150                 155                 160

Ile Glu Arg Gln Gly Lys Val Glu Val Glu Gly His Leu Ile Asp Leu
                165                 170                 175

Lys Arg Val Val Leu Asp Gly Ser Ala Ala Thr Pro Val Thr Arg Val
            180                 185                 190

Ser Ala Glu Arg Trp Gly Arg Pro
            195                 200

<210> SEQ ID NO 42
<211> LENGTH: 200
<212> TYPE: PRT
<213> ORGANISM: Artificial Sequence

```
<220> FEATURE:
<223> OTHER INFORMATION: Porcine reproductive and respiratory syndrome
      virus; open reading frame 5 (ORF5)

<400> SEQUENCE: 42

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
                20                  25                  30

Ser Ser Ser Ser Ser Gln Leu Ser Ile Tyr Asn Leu Thr Ile Cys
            35                  40                  45

Glu Leu Asn Gly Thr Asp Trp Leu Asn Lys Asn Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Tyr Val Leu Ser Ser Val Tyr
            100                 105                 110

Ala Val Cys Ala Leu Ala Ala Leu Ile Cys Phe Val Ile Arg Leu Thr
            115                 120                 125

Lys Asn Cys Met Ser Trp Arg Tyr Ser Cys Thr Arg Tyr Thr Asn Phe
130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Cys Arg Pro
            195                 200

<210> SEQ ID NO 43
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 43

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
                20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
            115                 120                 125
```

-continued

```
Lys Asn Cys Met Ser Trp Arg Tyr Ala Cys Thr Arg Tyr Thr Asn Phe
            130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
            195                 200

<210> SEQ ID NO 44
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 44

Met Leu Glu Lys Cys Leu Thr Ala Gly Cys Cys Ser Gln Leu Leu Ser
1               5                   10                  15

Leu Trp Cys Ile Val Pro Phe Cys Phe Ala Ala Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Cys Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
            130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
            195                 200

<210> SEQ ID NO 45
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 45

Met Leu Glu Lys Cys Leu Thr Ala Gly Cys Cys Ser Arg Leu Leu Ser
1               5                   10                  15
```

```
Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
            115                 120                 125

Lys Asn Cys Met Ser Trp Arg Tyr Ala Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
            195                 200

<210> SEQ ID NO 46
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 46

Met Leu Glu L

```
                165                 170                 175

Lys Arg Val Val Leu Asp Gly Ser Val Ala Thr Pro Ile Thr Arg Val
                180                 185                 190

Ser Ala Glu Gln Trp Gly Arg Pro
        195                 200

<210> SEQ ID NO 47
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 47

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
                20                  25                  30

Asn Ser Ser Ser Ser His Leu Gln Leu Ile Tyr Asn Leu Thr Leu Cys
            35                  40                  45

Glu Leu Asn Gly Thr Asp Trp Leu Ala Asn Arg Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
        195                 200

<210> SEQ ID NO 48
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 48

Met Leu Glu Lys Cys Leu Thr Ala Gly Cys Cys Ser Gln Leu Leu Ser
1               5                   10                  15

Leu Trp Cys Ile Val Pro Phe Cys Phe Val Ala Leu Ala Asn Ala Asn
                20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
```

```
                  50                  55                  60
Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
                100                 105                 110

Ala Ala Cys Ala Leu Ala Ala Leu Thr Cys Phe Val Ile Arg Leu Ala
                115                 120                 125

Lys Asn Cys Met Ser Trp Arg Tyr Ala Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
            195                 200

<210> SEQ ID NO 49
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 49

Met Leu Gly Lys Cys Leu Thr Ala Gly Trp Cys Ser Gln Leu Leu Ser
 1               5                  10                  15

Leu Gly Cys Ile Val Pro Phe Cys Phe Ala Val Leu Ala Asn Ala Ser
                20                  25                  30

Asn Asp Ser Ser Ser His Val Gln Leu Ile Tyr Asn Leu Thr Leu Cys
            35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
                100                 105                 110

Ala Val Cys Ala Leu Ala Ala Leu Thr Cys Phe Val Ile Arg Phe Ala
                115                 120                 125

Lys Asn Cys Met Ser Trp Arg Tyr Ala Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
            195                 200
```

<210> SEQ ID NO 50
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 50

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Lys Asp Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 51
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 51

Met Leu Gly Lys Cys Leu Thr Thr Gly Cys Cys Ser Arg Leu Leu Ser
1               5                   10                  15

Leu Trp Cys Ile Val Pro Phe Cys Phe Ala Val Leu Val Asn Ala Asn
            20                  25                  30

Ser Asn Ser Ser Ser His Phe Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
            115                 120                 125

Lys Asn Cys Met Ser Trp Arg Tyr Ser Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
            195                 200

<210> SEQ ID NO 52
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 52

Met Leu Gly Lys Cys Leu Thr Ala Gly Cys Cys Ser Arg Leu Leu Ser
1               5                   10                  15

Leu Trp Cys Ile Val Pro Phe Cys Phe Ala Val Leu Gly Ser Ala Asn
            20                  25                  30

Ser Ser Ser Ser Ser His Phe Gln Leu Ile Tyr Asn Leu Thr Leu Cys
        35                  40                  45

Glu Leu Asn Gly Thr Asp Trp Leu Ala Glu Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
            115                 120                 125

Lys Asn Cys Met Ser Trp Arg Tyr Ser Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
            195                 200

<210> SEQ ID NO 53
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 53

Met Leu Gly Lys Cys Leu Thr Ala Gly Cys Cys Ser Arg Leu Leu Ser
1               5                   10                  15

Phe Trp Cys Ile Val Pro Phe Cys Phe Ala Val Leu Val Asn Ala Ser
            20                  25                  30

Tyr Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Ser His Leu Ile Asp Leu
                165                 170                 175

Lys Arg Val Val Leu Asp Gly Ser Ala Ala Thr Pro Leu Thr Arg Val
            180                 185                 190

Ser Ala Glu Gln Trp Gly Arg Pro
        195                 200

<210> SEQ ID NO 54
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 54

Met Leu Gly Lys Cys Leu Thr Ala Gly Cys Tyr Ser Gln Leu Leu Ser
1               5                   10                  15

Leu Trp Cys Ile Val Pro Phe Cys Phe Ala Val Leu Val Asn Ala Ser
            20                  25                  30

Ser Asn Ser Ser Pro His Phe Gln Leu Ile Tyr Asn Leu Thr Leu Cys
        35                  40                  45

Glu Leu Asn Gly Thr Asp Trp Leu Ala Glu Arg Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Phe Tyr His Arg Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 55
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 55

Met Leu Gly Lys Cys Leu Thr Ala Gly Cys Cys Ser Arg Leu Leu Ser
1               5                   10                  15

Leu Trp Cys Ile Val Pro Phe Tyr Leu Ala Val Leu Val Asn Ala Ser
            20                  25                  30

Asn Asn Ser Ser Ser His Ile Gln Leu Ile Tyr Asn Leu Thr Leu Cys
        35                  40                  45

Glu Leu Asn Gly Thr Asp Trp Leu Ala Lys Asn Phe Asn Arg Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Arg Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Lys Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 56
<211> LENGTH: 219
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 56

Gln Ala Cys Arg Gln Pro Phe Cys Pro Phe Glu Glu Ala His Ser Gly
1               5                   10                  15

Val Tyr Arg Trp Lys Lys Phe Val Ile Phe Ser Asp Ser Pro Leu Asn
            20                  25                  30

Gly Gln Ser Arg Ile Met Trp Thr Pro Lys Ser Asp Asp Ser Ala Ala
            35                  40                  45

Leu Glu Glu Leu Pro Pro Leu Glu Arg Gln Val Glu Ile Leu Ile
 50                  55                  60

Arg Ser Phe Pro Ala His His Pro Val Asn Leu Ala Asp Trp Glu Leu
 65                  70                  75                  80

Thr Gly Ser Pro Glu Asn Gly Phe Ser Phe Asn Thr Ser His Ser Cys
                 85                  90                  95

Gly His Leu Val Arg Asn Ser Asn Val Phe Asp Gly Lys Cys Trp Leu
                100                 105                 110

Thr Cys Phe Leu Gly Gln Ser Val Glu Val Arg Cys His Glu Glu His
                115                 120                 125

Leu Ala Asn Ala Phe Gly Tyr Gln Thr Lys Trp Gly Val His Gly Lys
130                 135                 140

Tyr Leu Gln Arg Arg Leu Gln Val Arg Gly Ile Arg Ala Val Val Asp
145                 150                 155                 160

Pro Asp Gly Pro Ile His Val Glu Ala Leu Ser Cys Ser Gln Ser Trp
                165                 170                 175

Ile Arg His Leu Thr Leu Asn Asp Asp Val Thr Pro Gly Phe Val Arg
                180                 185                 190

Leu Thr Ser Ile Arg Ile Val Pro Asn Thr Glu Pro Thr Thr Ser Gln
                195                 200                 205

Ile Phe Arg Phe Gly Ala His Lys Trp Tyr Gly
210                 215

<210> SEQ ID NO 57
<211> LENGTH: 219
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 57

Gln Ala Cys Arg Gln Pro Phe Cys Pro Phe Glu Glu Ala His Ser Ser
 1               5                  10                  15

Val Tyr Arg Trp Lys Lys Phe Val Val Phe Thr Asp Ser Ser Leu Asn
                20                  25                  30

Gly Arg Ser Arg Met Met Trp Thr Pro Glu Ser Asp Asp Ser Ala Ala
            35                  40                  45

Leu Glu Val Leu Pro Pro Glu Leu Glu Arg Gln Val Glu Ile Leu Ile
 50                  55                  60

Arg Ser Phe Pro Ala His His Pro Val Asp Leu Ala Asp Trp Glu Leu
 65                  70                  75                  80

Thr Glu Ser Pro Glu Asn Gly Phe Ser Phe Asn Thr Ser His Ser Cys
                 85                  90                  95

Gly His Leu Val Gln Asn Pro Asp Val Phe Asp Gly Lys Cys Trp Leu
                100                 105                 110

Ser Cys Phe Leu Gly Gln Ser Val Glu Val Arg Cys His Glu Glu His
                115                 120                 125

Leu Ala Asp Ala Phe Gly Tyr Gln Thr Lys Trp Gly Val His Gly Lys
130                 135                 140

Tyr Leu Gln Arg Arg Leu Gln Val Arg Gly Ile Arg Ala Val Val Asp
145                 150                 155                 160

Pro Asp Gly Pro Ile His Val Glu Ala Leu Ser Cys Pro Gln Ser Trp

```
                    165                 170                 175

Ile Arg His Leu Thr Leu Asp Asp Val Thr Pro Gly Phe Val Arg
        180                 185                 190

Leu Thr Ser Leu Arg Ile Val Pro Asn Thr Glu Pro Thr Thr Ser Arg
            195                 200                 205

Ile Phe Arg Phe Gly Ala His Lys Trp Tyr Gly
        210                 215

<210> SEQ ID NO 58
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta
<220> FEATURE:
<221> NAME/KEY: MOD_RES
<222> LOCATION: (16)..(16)
<223> OTHER INFORMATION: Xaa = variable or unknown amino acid

<400> SEQUENCE: 58

Arg Pro Lys Pro Glu Asp Phe Cys Pro Phe Glu Cys Ala Met Ala Xaa
1               5                   10                  15

Val Tyr Asp Ile Gly His Asp Ala Val Met Phe Val Ala Glu Gly Arg
            20                  25                  30

Val Ser Trp Ala Pro Arg Gly Gly Lys Gly Lys Phe Glu Thr Val
        35                  40                  45

Pro Glu Glu Leu Arg Leu Ile Ala Glu Gln Leu Tyr Thr Ser Phe Pro
    50                  55                  60

Pro His His Val Val Asp Met Ser Lys Phe Thr Phe Thr Ala Pro Glu
65                  70                  75                  80

Cys Gly Ala Ser Met Arg Val Glu Arg His Tyr Gly Cys Leu Pro Ala
                85                  90                  95

Gly Thr Val Pro Asp Gly Asn Cys Trp Trp Ser Leu Phe Ser Ser Leu
            100                 105                 110

Pro Leu Glu Ile Gln Tyr Lys Glu Ile Arg His Ala Thr Gln Phe Gly
        115                 120                 125

Tyr Gln Thr Lys His Gly Val Ala Gly Lys Tyr Leu Gln Arg Arg Leu
    130                 135                 140

Gln Val Asn Gly Leu Arg Ala Val Val Asp Ser Asn Gly Pro Ile Val
145                 150                 155                 160

Ile Gln Tyr Phe Ser Val Lys Glu Ser Trp Ile Arg His Val Lys Leu
                165                 170                 175

Ala Glu Glu Phe Asp Tyr Pro Gly Phe Glu Asp Leu Leu Arg Ile Arg
            180                 185                 190

Val Glu Pro Asn Thr Leu Pro Leu Ser Asn Lys Asp Glu Lys Ile Phe
        195                 200                 205

Arg Phe Gly Gly Cys Lys Trp Tyr Gly
    210                 215

<210> SEQ ID NO 59
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta
<220> FEATURE:
<221> NAME/KEY: MOD_RES
<222> LOCATION: (53)..(53)
```

<223> OTHER INFORMATION: Xaa = variable or unknown amino acid
<220> FEATURE:
<221> NAME/KEY: MOD_RES
<222> LOCATION: (198)..(198)
<223> OTHER INFORMATION: Xaa = variable or unknown amino acid

<400> SEQUENCE: 59

```
Arg Pro Lys Pro Glu Asp Phe Cys Pro Phe Glu Cys Ala Met Ala Ala
1               5                   10                  15

Val Tyr Asp Ile Gly His Asp Ala Val Met Phe Val Ala Glu Gly Arg
            20                  25                  30

Val Ser Trp Ala Pro Arg Gly Gly Glu Lys Gly Lys Phe Glu Thr Val
        35                  40                  45

Pro Glu Glu Leu Xaa Leu Ile Ala Glu Gln Leu Tyr Thr Ser Phe Pro
    50                  55                  60

Pro His His Leu Val Asp Met Ser Lys Phe Thr Phe Thr Ala Pro Glu
65                  70                  75                  80

Cys Gly Ala Ser Met Arg Val Glu Arg Gln Tyr Gly Cys Leu Pro Ala
                85                  90                  95

Gly Thr Val Pro Asp Gly Asn Cys Trp Trp Ser Leu Phe Ser Ser Leu
            100                 105                 110

Pro Leu Glu Val Gln Tyr Lys Glu Ile Arg Tyr Ala Thr Gln Phe Gly
        115                 120                 125

Tyr Gln Thr Lys His Gly Val Ala Gly Lys Tyr Leu Gln Arg Arg Leu
    130                 135                 140

Gln Ile Asn Gly Leu Arg Ala Val Val Asp Ser Asn Gly Pro Ile Val
145                 150                 155                 160

Ile Gln Tyr Phe Ser Val Lys Glu Ser Trp Ile Arg His Val Lys Leu
                165                 170                 175

Ala Glu Glu Phe Asp Tyr Pro Gly Phe Glu Asp Leu Leu Arg Ile Arg
            180                 185                 190

Val Glu Pro Asn Thr Xaa Pro Leu Ser Asn Lys Asp Glu Lys Ile Phe
        195                 200                 205

Arg Phe Gly Gly Cys Lys Trp Tyr Gly
    210                 215
```

<210> SEQ ID NO 60
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 60

```
Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
                85                  90                  95
```

Asp Thr Val Pro Glu Gly Asn Cys Trp Trp Ser Leu Phe Asp Leu Leu
                100                 105                 110

Pro Leu Glu Val Gln Asn Lys Glu Ile Arg His Ala Asn Gln Phe Gly
            115                 120                 125

Tyr Gln Thr Lys His Gly Val Ser Gly Lys Tyr Leu Gln Arg Arg Leu
        130                 135                 140

Gln Val Asn Gly Leu Arg Ala Val Thr Asp Leu Asn Gly Pro Ile Val
145                 150                 155                 160

Val Gln Tyr Phe Phe Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Glu Lys Ile Phe
        195                 200                 205

Arg Phe Gly Ser His Lys Trp Tyr Gly
        210                 215

<210> SEQ ID NO 61
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 61

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
            20                  25                  30

Val Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg His Ala Asn Gln Phe Gly
        115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Leu Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Glu Lys Ile Phe
        195                 200                 205

Arg Phe Gly Ser His Lys Trp Tyr Gly
    210                 215

<210> SEQ ID NO 62

<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 62

Arg Pro Lys Pro Glu Asp Phe Cys Pro Phe Glu Cys Ala Met Ala

```
Asp Thr Val Pro Glu Gly Asn Cys Trp Trp Ser Leu Phe Asp Leu Leu
            100                 105                 110

Pro Leu Glu Val Lys Asn Lys Glu Ile Arg His Ala Asn Gln Phe Gly
            115                 120                 125

Tyr Gln Thr Lys His Gly Val Ser Gly Lys Tyr Leu Gln Arg Arg Leu
130                 135                 140

Gln Val Asn Gly Leu Arg Ala Val Thr Asp Pro Asn Gly Pro Ile Val
145                 150                 155                 160

Val Gln Tyr Phe Ser Val Lys Glu Ser Trp Ile Arg His Leu Arg Leu
                165                 170                 175

Ala Gly Glu Pro Ser Tyr Pro Gly Phe Glu Asp Leu Leu Arg Ile Arg
            180                 185                 190

Val Glu Pro Asn Thr Ser Pro Leu Ala Asp Lys Glu Glu Lys Ile Phe
            195                 200                 205

Arg Phe Gly Ser His Lys Trp Tyr Gly
            210                 215

<210> SEQ ID NO 64
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 64

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Gly Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
50                  55                  60

Pro His His Ala Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asp Lys Glu Ile Arg His Ala Asn Gln Phe Gly
            115                 120                 125

Tyr Gln Thr Lys His Gly Val Ser Gly Lys Tyr Leu Gln Arg Arg Leu
130                 135                 140

Gln Val Asn Gly Leu Arg Ala Val Thr Asp Ser Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asn Thr Glu Gly Lys Ile Phe
            195                 200                 205

Arg Phe Gly Ser His Lys Trp Tyr Gly
            210                 215
```

<210> SEQ ID NO 65
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 65

```
Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Gly Met Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Leu Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg Tyr Ala Asn Gln Phe Gly
        115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Leu Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Lys Ile Phe
        195                 200                 205

Arg Phe Gly Ser His Lys Trp Tyr Gly
    210                 215
```

<210> SEQ ID NO 66
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 66

```
Arg Pro Lys Pro Asp Asp Phe Cys Pro Phe Glu Cys Ala Met Ala Thr
1               5                   10                  15

Val Tyr Asp Ile Gly His Asp Ala Val Met Tyr Val Ala Glu Glu Lys
            20                  25                  30

Val Ser Trp Ala Pro Arg Gly Gly Asp Glu Val Lys Phe Glu Pro Val
        35                  40                  45

Pro Gly Glu Leu Lys Leu Ile Ala Asn Arg Leu Arg Thr Ser Phe Pro
    50                  55                  60

Pro His His Ala Val Asp Met Ser Lys Phe Thr Phe Thr Ala Pro Gly
65                  70                  75                  80

Arg Gly Val Ser Met Arg Val Glu Arg Gln His Gly Cys Leu Pro Ala
```

```
                85                  90                  95
Asp Thr Val Pro Glu Gly Asn Cys Trp Trp Ser Leu Phe Asn Leu Leu
            100                 105                 110

Pro Leu Glu Val Gln Asn Lys Glu Ile Arg His Ala Gly Gln Phe Gly
            115                 120                 125

Tyr Gln Thr Lys His Gly Val Ser Gly Lys Tyr Leu Gln Arg Arg Leu
            130                 135                 140

Gln Val Asn Gly Leu Arg Ala Val Thr Asp Leu Asn Gly Pro Ile Val
145                 150                 155                 160

Val Gln Cys Phe Ser Val Lys Glu Ser Trp Ile Arg His Leu Lys Leu
                165                 170                 175

Ala Glu Glu Pro Ser Tyr Pro Gly Phe Glu Asp Leu Leu Arg Ile Arg
            180                 185                 190

Val Glu Pro Asn Thr Ser Pro Leu Ala Asp Lys Asp Glu Lys Ile Phe
            195                 200                 205

Arg Phe Gly Asn His Lys Trp Tyr Gly
            210                 215

<210> SEQ ID NO 67
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 67

Arg Pro Lys Pro Glu Asp Phe Cys Pro Phe Glu Cys Ala Met Ala Asp
1               5                   10                  15

Val Tyr Asp Ile Gly His Gly Ala Val Met Tyr Val Ala Lys Gly Lys
            20                  25                  30

Val Ser Trp Ala Pro Arg Gly Gly Asp Glu Ala Lys Phe Glu Thr Val
        35                  40                  45

Pro Arg Glu Leu Lys Leu Ile Ala Asn Gln Leu His Ile Ser Phe Pro
50                  55                  60

Pro His His Ala Val Asp Met Ser Lys Phe Val Phe Ile Ala Pro Gly
65                  70                  75                  80

Ser Gly Val Ser Met Arg Val Glu Cys Pro His Gly Cys Leu Pro Ala
                85                  90                  95

Asn Thr Val Pro Glu Gly Asn Cys Trp Trp Arg Leu Phe Asp Ser Leu
            100                 105                 110

Pro Leu Asp Val Gln Asn Lys Glu Ile Arg Arg Ala Asn Gln Phe Gly
            115                 120                 125

Tyr Gln Thr Lys His Gly Val Ala Gly Lys Tyr Leu Gln Arg Arg Leu
            130                 135                 140

Gln Ala Asn Gly Leu Arg Ala Val Thr Asp Thr Asp Gly Pro Ile Val
145                 150                 155                 160

Val Gln Tyr Phe Ser Val Arg Glu Ser Trp Ile Arg His Phe Arg Leu
                165                 170                 175

Ala Glu Glu Pro Ser Leu Pro Gly Phe Glu Asp Leu Leu Arg Ile Arg
            180                 185                 190

Val Glu Pro Asn Thr Ser Pro Leu Ser Asp Lys Gly Gly Lys Ile Phe
            195                 200                 205

Arg Phe Gly Ser His Lys Trp Tyr Gly
            210                 215
```

<210> SEQ ID NO 68
<211> LENGTH: 217
<212> TYPE: PRT
<213> ORGANISM: Artificial Sequence
<220> FEATURE:
<223> OTHER INFORMATION: Porcine reproductive and respiratory syndrome virus; Nsp1 beta

<400> SEQUENCE: 68

```
Arg Pro Lys Pro Glu Asp Phe Cys Pro Phe Glu Cys Ala Met Ala Asp
  1               5                  10                  15

Val Tyr Asp Ile Gly Arg Asp Ala Val Met Tyr Val Ala Arg Gly Lys
             20                  25                  30

Val Ser Trp Ala Pro Arg Gly Gly Asp Glu Val Lys Phe Glu Thr Val
         35                  40                  45

Pro Glu Glu Leu Lys Leu Ile Ala Asn Arg Leu His Ile Ser Phe Pro
     50                  55                  60

Pro Tyr His Ala Val Asp Met Ser Lys Phe Ala Phe Ile Ala Pro Gly
 65                  70                  75                  80

Ser Gly Val Ser Leu Arg Val Glu Tyr Gln His Gly Cys Leu Pro Ala
                 85                  90                  95

Asp Thr Val Pro Glu Gly Asn Cys Trp Trp Arg Leu Phe Asp Leu Leu
            100                 105                 110

Pro Pro Glu Val Gln Asn Lys Glu Ile Arg Tyr Ala Asn Gln Phe Gly
        115                 120                 125

Tyr Gln Thr Lys His Gly Val Pro Gly Lys Tyr Leu Gln Arg Arg Leu
    130                 135                 140

Gln Val Asn Gly Leu Arg Ala Val Thr Asp Thr His Gly Pro Ile Val
145                 150                 155                 160

Ile Gln Tyr Phe Ser Val Glu Glu Ser Trp Ile Arg His Phe Arg Leu
                165                 170                 175

Ala Gly Glu Pro Ser Leu Pro Gly Phe Glu Asp Leu Leu Arg Ile Arg
            180                 185                 190

Val Glu Pro Asn Thr Ser Pro Leu Ala Glu Lys Asp Gly Lys Ile Phe
        195                 200                 205

Arg Phe Gly Ser His Lys Trp Tyr Gly
    210                 215
```

<210> SEQ ID NO 69
<211> LENGTH: 217
<212> TYPE: PRT
<213> ORGANISM: Artificial Sequence
<220> FEATURE:
<223> OTHER INFORMATION: Porcine reproductive and respiratory syndrome virus; Nsp1 beta

<400> SEQUENCE: 69

```
Arg Pro Lys Pro Glu Asp Phe Cys Pro Phe Glu Cys Ala Met Ala Asp
  1               5                  10                  15

Val Tyr Asp Ile Ser His Asp Ala Val Met Tyr Val Ala Arg Gly Lys
             20                  25                  30

Val Ser Trp Ala Pro Arg Gly Gly Asp Glu Val Lys Phe Glu Thr Val
         35                  40                  45

Pro Glu Glu Leu Lys Leu Ile Ala Asn Arg Leu His Ile Ser Phe Pro
     50                  55                  60

Pro His His Ala Val Asp Met Ser Glu Phe Ala Phe Ile Ala Pro Gly
 65                  70                  75                  80
```

```
Ser Gly Val Ser Leu Arg Val Glu His Gln His Gly Cys Leu Pro Ala
                85                  90                  95

Asp Thr Val Pro Glu Gly Asn Cys Trp Trp Cys Leu Phe Asp Leu Leu
            100                 105                 110

Pro Pro Glu Val Gln Asn Lys Glu Ile Arg Arg Ala Asn Gln Phe Gly
        115                 120                 125

Tyr Gln Thr Lys His Gly Val Pro Gly Lys Tyr Leu Gln Arg Arg Leu
    130                 135                 140

Gln Val Asn Gly Leu Arg Ala Val Thr Asp Thr Asp Gly Pro Ile Val
145                 150                 155                 160

Val Gln Tyr Phe Ser Val Arg Glu Ser Trp Ile Arg His Phe Arg Leu
                165                 170                 175

Ala Glu Glu Pro Ser Leu Pro Gly Phe Glu Asp Leu Leu Arg Ile Arg
            180                 185                 190

Val Glu Pro Asn Thr Ser Pro Leu Gly Gly Lys Gly Glu Lys Ile Phe
        195                 200                 205

Arg Phe Gly Ser His Lys Trp Tyr Gly
    210                 215

<210> SEQ ID NO 70
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 70

Arg Pro Lys Pro Glu Asp Phe Cys Pro Phe Glu Cys Ala Met Ala Asp
1               5                   10                  15

Val Tyr Asp Ile Gly His Gly Ala Val Met Phe Val Ala Gly Gly Lys
            20                  25                  30

Val Ser Trp Ala Pro Arg Gly Gly Asp Glu Val Arg Phe Glu Thr Val
        35                  40                  45

Pro Glu Glu Leu Lys Leu Ile Ala Asn Arg Leu His Ile Ser Phe Pro
    50                  55                  60

Pro His His Leu Val Asp Met Ser Lys Phe Ala Phe Ile Val Pro Gly
65                  70                  75                  80

Ser Gly Val Ser Leu Arg Val Glu His Gln His Gly Cys Leu Pro Ala
                85                  90                  95

Asp Ile Val Pro Lys Gly Asn Cys Trp Trp Cys Leu Phe Asp Leu Leu
            100                 105                 110

Pro Pro Gly Val Gln Asn Arg Glu Ile Arg Tyr Ala Asn Gln Phe Gly
        115                 120                 125

Tyr Gln Thr Lys His Gly Val Ser Gly Lys Tyr Leu Gln Arg Arg Leu
    130                 135                 140

Gln Ile Asn Gly Leu Arg Ala Val Thr Asp Thr His Gly Pro Ile Val
145                 150                 155                 160

Val Gln Tyr Phe Ser Val Lys Glu Ser Trp Ile Arg His Phe Arg Leu
                165                 170                 175

Ala Gly Glu Pro Ser Leu Pro Gly Phe Glu Asp Leu Leu Arg Ile Arg
            180                 185                 190

Val Glu Ser Asn Thr Ser Pro Leu Ala Asp Lys Asp Glu Lys Ile Phe
        195                 200                 205

Arg Phe Gly Ser His Lys Trp Tyr Gly
    210                 215
```

<210> SEQ ID NO 71
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 71

Arg Pro Lys Pro Glu Asp Phe Cys Pro Phe Glu Cys Ala Met Ala Asp
1               5                   10                  15

Val Tyr Asp Ile Gly Arg Gly Ala Val Met Tyr Val Ala Gly Gly Lys
            20                  25                  30

Val Ser Trp Ala Pro Arg Gly Gly Asp Glu Val Lys Phe Glu Pro Val
        35                  40                  45

Pro Lys Glu Leu Lys Leu Val Ala Asn Arg Leu His Thr Ser Phe Pro
    50                  55                  60

Pro His His Val Val Asp Met Ser Lys Phe Thr Phe Met Thr Pro Gly
65                  70                  75                  80

Ser Gly Val Ser Met Arg Val Glu Tyr Gln Tyr Gly Cys Leu Pro Ala
                85                  90                  95

Asp Thr Val Pro Glu Gly Asn Cys Trp Trp Arg Leu Phe Asp Leu Leu
            100                 105                 110

Pro Pro Glu Val Gln Asn Lys Glu Ile Arg His Ala Asn Gln Phe Gly
        115                 120                 125

Tyr Gln Thr Lys His Gly Val Pro Gly Lys Tyr Leu Gln Arg Arg Leu
    130                 135                 140

Gln Val Asn Gly Leu Arg Ala Val Thr Asp Thr His Gly Pro Ile Val
145                 150                 155                 160

Ile Gln Tyr Phe Ser Val Lys Glu Ser Trp Ile Arg His Leu Lys Pro
                165                 170                 175

Val Glu Glu Pro Ser Leu Pro Gly Phe Glu Asp Leu Leu Arg Ile Arg
            180                 185                 190

Val Glu Pro Asn Thr Ser Pro Leu Ala Gly Lys Asn Glu Lys Ile Phe
        195                 200                 205

Arg Phe Gly Ser His Lys Trp Tyr Gly
    210                 215

<210> SEQ ID NO 72
<211> LENGTH: 1066
<212> TYPE: PRT
<213> ORGANISM: Artificial Sequence
<220> FEATURE:
<223> OTHER INFORMATION: Porcine reproductive and respiratory syndrome
      virus; Nsp2
<220> FEATURE:
<221> NAME/KEY: MOD_RES
<222> LOCATION: (134)..(134)
<223> OTHER INFORMATION: Xaa = variable or unknown amino acid
<220> FEATURE:
<221> NAME/KEY: MOD_RES
<222> LOCATION: (242)..(242)
<223> OTHER INFORMATION: Xaa = variable or unknown amino acid
<220> FEATURE:
<221> NAME/KEY: MOD_RES
<222> LOCATION: (284)..(284)
<223> OTHER INFORMATION: Xaa = variable or unknown amino acid
<220> FEATURE:
<221> NAME/KEY: MOD_RES
<222> LOCATION: (298)..(298)
<223> OTHER INFORMATION: Xaa = variable or unknown amino acid
<220> FEATURE:

```
<221> NAME/KEY: MOD_RES
<222> LOCATION: (691)..(691)
<223> OTHER INFORMATION: Xaa = variable or unknown amino acid

<400> SEQUENCE: 72
```

Gly Ala Gly Lys Arg Ala Arg Arg Ala Arg Ala Ser Ala Val Thr Ala
1               5                   10                  15

Val Ala Gly His Ala Pro Pro Thr Arg Glu Thr Gln Gln Ala Lys Lys
            20                  25                  30

His Glu Ala Ala Ser Ala Asn Lys Ala Glu Leu Leu Glu Arg Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Ala Leu Pro Glu Arg Val
65              70                  75                  80

Arg Ser Pro Glu Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Ala
            100                 105                 110

Ser Ala Lys Tyr Ile Leu Lys Leu Glu Gly Glu His Trp Thr Val Ser
        115                 120                 125

Val Ile Pro Gly Met Xaa Pro Ser Leu Leu Pro Leu Glu Cys Val Gln
    130                 135                 140

Gly Cys Cys Glu His Lys Gly Asn Leu Gly Ser Pro Asn Ala Val Gly
145                 150                 155                 160

Val Phe Gly Phe Asp Pro Ala Ser Leu Asp Arg Leu Ala Gly Val Met
            165                 170                 175

His Leu Pro Ser Ser Ala Ile Pro Ala Ala Leu Ala Glu Leu Ser Gly
        180                 185                 190

Asp Leu Asp Arg Pro Thr Ser Pro Ala Ala Thr Val Trp Thr Val Ser
    195                 200                 205

Gln Phe Tyr Ala Arg His Ser Gly Gly Glu His Pro Asp Gln Lys Cys
    210                 215                 220

Leu Lys Lys Ile Ile Ser Leu Cys Glu Val Ile Glu Ser Cys Cys Cys
225                 230                 235                 240

Ser Xaa Asn Lys Thr Asn Arg Val Thr Pro Glu Glu Val Thr Ala Lys
            245                 250                 255

Ile Asp Leu Tyr Leu Phe Gly Ala Ala Ser Leu Glu Glu Cys Leu Ala
        260                 265                 270

Arg Leu Glu Lys Ala Arg Pro Pro Ser Val Leu Xaa Thr Ser Phe Asp
    275                 280                 285

Trp Asp Val Val Leu Pro Gly Val Gly Xaa Ala Ala Gln Ala Ala Lys
    290                 295                 300

Leu Pro Leu Thr Asn Gln Arg His Ala Leu Ala Thr Val Val Thr Gln
305                 310                 315                 320

Arg Ser Leu Pro Lys Phe Gln Pro Arg Lys Ala Glu Ser Val Lys Ser
            325                 330                 335

Leu Pro Glu Ser Arg Pro Leu Pro Ala Pro Arg Lys Lys Ile Arg Ser
        340                 345                 350

Arg Cys Gly Ser Pro Ile Ser Leu Gly Gly Asn Leu Pro Asp Ser Gln
    355                 360                 365

Glu Asp Leu Ala Gly Gly Ser Phe Asp Phe Pro Thr Leu Pro Glu Leu
    370                 375                 380

Val Val Ser Ser Ser Glu Ser Val Pro Val Pro Ala Pro Arg Arg Val

```
            385                 390                 395                 400
        Val Ser Arg Leu Val Ser Ser Pro Ile Val Ser Thr Pro Val Pro Ala
                        405                 410                 415
        Pro Arg Arg Gly Leu Arg Gln Val Glu Gly Met Asn Leu Ala Ala Val
                        420                 425                 430
        Thr Leu Ala Cys Gln Asp Glu Pro Leu Asp Leu Ser Ala Ser Ser Gln
                        435                 440                 445
        Thr Glu Tyr Glu Ala Ser Pro Leu Ala Leu Pro Leu Ser Glu Asp Val
                        450                 455                 460
        Leu Ala Val Glu Arg Arg Glu Val Glu Val Leu Ser Gly Ile Ser
        465                 470                 475                 480
        Gly Met Ser Asp Asp Ile Arg Leu Ala Pro Val Ser Ser Ser Ser
                            485                 490                 495
        Leu Ser Ser Ile Glu Ile Thr Arg Pro Lys Tyr Ser Ala Gln Ala Ile
                        500                 505                 510
        Ile Asn Ser Gly Gly Pro Cys Cys Gly His Leu Gln Glu Val Lys Glu
                        515                 520                 525
        Lys Tyr Leu Asn Val Met Arg Glu Ala Cys Asp Ala Thr Lys Leu Asp
                        530                 535                 540
        Asp Pro Ala Thr Gln Glu Trp Leu Ser Arg Met Trp Asp Arg Val Asp
        545                 550                 555                 560
        Met Leu Thr Trp Arg Asn Thr Ser Ile Phe Gln Ala Pro Phe Thr Leu
                            565                 570                 575
        Ala Asp Lys Phe Lys Ser Leu Pro Lys Met Ile Leu Glu Thr Pro Pro
                        580                 585                 590
        Pro Tyr Pro Cys Gly Phe Val Met Met Pro Arg Thr Pro Ala Pro Ser
                        595                 600                 605
        Val Gly Ala Glu Ser Asp Leu Thr Val Gly Ser Val Ala Thr Glu Asp
                        610                 615                 620
        Val Pro Arg Ile Leu Gly Lys Val Gln Gly Val Gly Glu Thr Thr Asp
        625                 630                 635                 640
        Gln Gly Pro Leu Ala Leu Phe Ala Asp Glu Leu Ala Asp Asp Gln Pro
                            645                 650                 655
        Ala Arg Glu Pro Arg Thr Gln Thr Pro Pro Ala Ser Ala Gly Gly Ala
                        660                 665                 670
        Gly Leu Val Leu Asp Ser Gly Gly Ser Pro Glu Leu Thr Asp Leu Pro
                        675                 680                 685
        Leu Pro Xaa Gly Thr Asp Ala Gly Gly Gly Pro Leu His Thr Val
                        690                 695                 700
        Lys Lys Lys Ala Glu Arg Cys Phe Asp Gln Leu Ser Arg Arg Val Phe
        705                 710                 715                 720
        Asp Ile Val Ser His Leu Pro Val Phe Phe Ser Arg Leu Phe Lys Pro
                            725                 730                 735
        Asp Ser His Tyr Ser Ser Gly Asp Trp Ser Phe Ala Ala Phe Thr Leu
                        740                 745                 750
        Leu Cys Leu Phe Leu Cys Tyr Ser Tyr Pro Ala Phe Gly Val Ala Pro
                        755                 760                 765
        Leu Leu Gly Val Phe Ser Gly Ser Arg Arg Val Arg Met Gly Val
                        770                 775                 780
        Phe Gly Cys Trp Leu Ala Phe Ala Val Gly Leu Phe Lys Pro Ala Pro
        785                 790                 795                 800
        Asp Pro Val Gly Ala Ala Cys Glu Phe Asp Ser Pro Glu Cys Arg Asp
                            805                 810                 815
```

```
Ile Leu His Ser Phe Glu Leu Gln Pro Trp Asp Pro Val Arg Ser
            820                 825                 830

Leu Val Val Gly Pro Val Gly Leu Gly Leu Ala Ile Ile Gly Arg Leu
835                 840                 845

Leu Gly Gly Ala Arg Tyr Val Trp Leu Leu Leu Arg Leu Gly Ile
850                 855                 860

Val Ser Asp Cys Ile Leu Ala Gly Ala Tyr Val Leu Ser Gln Gly Arg
865                 870                 875                 880

Cys Lys Lys Cys Trp Gly Ser Cys Ile Arg Thr Ala Pro Ser Glu Val
                885                 890                 895

Ala Phe Asn Val Phe Pro Phe Thr Arg Ala Thr Arg Ser Ser Leu Val
                900                 905                 910

Asp Leu Cys Asp Arg Phe Cys Ala Pro Lys Gly Met Asp Pro Ile Phe
                915                 920                 925

Leu Ala Thr Gly Trp Arg Gly Cys Trp Ser Gly Gln Ser Pro Val Glu
            930                 935                 940

Gln Pro Thr Glu Lys Pro Ile Ala Phe Ala Gln Leu Asp Glu Lys Lys
945                 950                 955                 960

Ile Thr Ala Arg Thr Val Val Ala Gln Pro Tyr Asp Pro Asn Gln Ala
                965                 970                 975

Val Lys Cys Leu Arg Val Leu Gln Ala Gly Gly Ala Met Val Ala Glu
                980                 985                 990

Ala Ile Pro Lys Val Val Lys Val  Ser Ala Val Pro Phe  Arg Ala Pro
            995                 1000                1005

Phe Phe Pro Thr Gly Val Lys  Val Asp Pro Glu Cys  Arg Val Val
    1010                1015                1020

Val Asp Pro Asp Thr Phe Thr  Thr Ala Leu Arg Ser  Gly Tyr Ser
    1025                1030                1035

Thr Thr Asn Leu Ile Leu Gly  Val Gly Asp Phe Ala  Gln Leu Asn
    1040                1045                1050

Gly Leu Lys Ile Arg Gln Ile  Ser Lys Pro Ser Gly  Gly
    1055                1060                1065
```

<210> SEQ ID NO 73
<211> LENGTH: 1066
<212> TYPE: PRT
<213> ORGANISM: Artificial Sequence
<220> FEATURE:
<223> OTHER INFORMATION: Porcine reproductive and respiratory syndrome
      virus; Nsp2
<220> FEATURE:
<221> NAME/KEY: MOD_RES
<222> LOCATION: (43)..(43)
<223> OTHER INFORMATION: Xaa = variable or unknown amino acid
<220> FEATURE:
<221> NAME/KEY: MOD_RES
<222> LOCATION: (45)..(46)
<223> OTHER INFORMATION: Xaa = variable or unknown amino acid
<220> FEATURE:
<221> NAME/KEY: MOD_RES
<222> LOCATION: (75)..(75)
<223> OTHER INFORMATION: Xaa = variable or unknown amino acid
<220> FEATURE:
<221> NAME/KEY: MOD_RES
<222> LOCATION: (82)..(82)
<223> OTHER INFORMATION: Xaa = variable or unknown amino acid
<220> FEATURE:
<221> NAME/KEY: MOD_RES
<222> LOCATION: (84)..(84)
<223> OTHER INFORMATION: Xaa = variable or unknown amino acid
<220> FEATURE:
<221> NAME/KEY: MOD_RES

```
<222> LOCATION: (95)..(95)
<223> OTHER INFORMATION: Xaa = variable or unknown amino acid
<220> FEATURE:
<221> NAME/KEY: MOD_RES
<222> LOCATION: (112)..(112)
<223> OTHER INFORMATION: Xaa = variable or unknown amino acid
<220> FEATURE:
<221> NAME/KEY: MOD_RES
<222> LOCATION: (117)..(117)
<223> OTHER INFORMATION: Xaa = variable or unknown amino acid
<220> FEATURE:
<221> NAME/KEY: MOD_RES
<222> LOCATION: (128)..(128)
<223> OTHER INFORMATION: Xaa = variable or unknown amino acid
<220> FEATURE:
<221> NAME/KEY: MOD_RES
<222> LOCATION: (130)..(130)
<223> OTHER INFORMATION: Xaa = variable or unknown amino acid
<220> FEATURE:
<221> NAME/KEY: MOD_RES
<222> LOCATION: (174)..(174)
<223> OTHER INFORMATION: Xaa = variable or unknown amino acid
<220> FEATURE:
<221> NAME/KEY: MOD_RES
<222> LOCATION: (190)..(190)
<223> OTHER INFORMATION: Xaa = variable or unknown amino acid
<220> FEATURE:
<221> NAME/KEY: MOD_RES
<222> LOCATION: (194)..(194)
<223> OTHER INFORMATION: Xaa = variable or unknown amino acid
<220> FEATURE:
<221> NAME/KEY: MOD_RES
<222> LOCATION: (197)..(198)
<223> OTHER INFORMATION: Xaa = variable or unknown amino acid
<220> FEATURE:
<221> NAME/KEY: MOD_RES
<222> LOCATION: (201)..(202)
<223> OTHER INFORMATION: Xaa = variable or unknown amino acid
<220> FEATURE:
<221> NAME/KEY: MOD_RES
<222> LOCATION: (218)..(218)
<223> OTHER INFORMATION: Xaa = variable or unknown amino acid
<220> FEATURE:
<221> NAME/KEY: MOD_RES
<222> LOCATION: (223)..(224)
<223> OTHER INFORMATION: Xaa = variable or unknown amino acid
<220> FEATURE:
<221> NAME/KEY: MOD_RES
<222> LOCATION: (226)..(226)
<223> OTHER INFORMATION: Xaa = variable or unknown amino acid
<220> FEATURE:
<221> NAME/KEY: MOD_RES
<222> LOCATION: (233)..(233)
<223> OTHER INFORMATION: Xaa = variable or unknown amino acid
<220> FEATURE:
<221> NAME/KEY: MOD_RES
<222> LOCATION: (237)..(237)
<223> OTHER INFORMATION: Xaa = variable or unknown amino acid
<220> FEATURE:
<221> NAME/KEY: MOD_RES
<222> LOCATION: (242)..(242)
<223> OTHER INFORMATION: Xaa = variable or unknown amino acid
<220> FEATURE:
<221> NAME/KEY: MOD_RES
<222> LOCATION: (254)..(254)
<223> OTHER INFORMATION: Xaa = variable or unknown amino acid

<400> SEQUENCE: 73

Gly Ala Gly Lys Arg Ala Arg Arg Ala Arg Ala Ser Ala Val Thr Ala
1               5                   10                  15

Val Ala Gly His Ala Pro Pro Thr Arg Glu Thr Gln Gln Ala Lys Lys
            20                  25                  30

His Glu Ala Ala Ser Ala Asn Lys Ala Glu Xaa Leu Xaa Xaa Tyr Ser
        35                  40                  45

Pro Pro Ala Glu Gly Asn Cys Gly Trp His Cys Ile Ser Ala Ile Ala
```

-continued

```
             50                  55                  60
Asn Arg Met Val Asn Ser Lys Phe Glu Thr Xaa Leu Pro Glu Arg Val
 65                  70                  75                  80
Arg Xaa Pro Xaa Asp Trp Ala Thr Asp Glu Asp Leu Val Asn Xaa Ile
                     85                  90                  95
Gln Ile Leu Arg Leu Pro Ala Ala Leu Asp Arg Asn Gly Ala Cys Xaa
                100                 105                 110
Ser Ala Lys Tyr Xaa Leu Lys Leu Glu Gly Glu His Trp Thr Val Xaa
                115                 120                 125
Val Xaa Pro Gly Met Ser Pro Ser Leu Leu Pro Leu Glu Cys Val Gln
130                 135                 140
Gly Cys Cys Gly His Lys Gly Leu Gly Ser Pro Asp Ala Val Glu
145                 150                 155                 160
Val Ser Gly Phe Asp Pro Ala Cys Leu Asp Arg Leu Ala Xaa Val Met
                165                 170                 175
His Leu Pro Ser Ser Ala Ile Pro Ala Ala Leu Ala Glu Xaa Ser Gly
                180                 185                 190
Asp Xaa Asp Arg Xaa Xaa Ser Pro Xaa Xaa Thr Val Trp Thr Val Ser
    195                 200                 205
Gln Phe Tyr Ala Arg His Ser Gly Gly Xaa His Pro Asp Gln Xaa Xaa
210                 215                 220
Leu Xaa Lys Ile Ile Ser Leu Cys Xaa Val Ile Glu Xaa Cys Cys Cys
225                 230                 235                 240
Ser Xaa Asn Lys Thr Asn Arg Val Thr Pro Glu Glu Val Xaa Ala Lys
                245                 250                 255
Ile Asp Gln Tyr Leu Phe Gly Ala Ala Ser Leu Glu Glu Cys Leu Ala
                260                 265                 270
Arg Leu Glu Lys Ala Arg Pro Pro Ser Val Leu Asp Thr Ser Phe Asp
                275                 280                 285
Trp Asp Val Val Leu Pro Gly Val Gly Ala Ala Gln Ala Ala Lys
                290                 295                 300
Leu Pro Leu Thr Asn Gln Arg His Ala Leu Ala Thr Val Val Thr Gln
305                 310                 315                 320
Arg Ser Leu Pro Lys Phe Gln Pro Arg Lys Ala Glu Ser Val Lys Ser
                325                 330                 335
Leu Pro Glu Ser Arg Pro Leu Pro Ala Pro Arg Lys Lys Ile Gly Ser
                340                 345                 350
Arg Cys Gly Ser Pro Ile Ser Leu Gly Gly Asn Leu Pro Asp Ser Arg
                355                 360                 365
Glu Asp Leu Ala Gly Gly Ser Phe Asp Phe Pro Thr Leu Pro Glu Leu
                370                 375                 380
Val Ala Ser Ser Ser Glu Pro Val Pro Val Ala Pro Arg Arg Val
385                 390                 395                 400
Val Ser Arg Leu Val Ser Ser Pro Ile Val Ser Thr Pro Val Pro Ala
                405                 410                 415
Pro Arg Arg Gly Leu Arg Gln Val Glu Gly Met Asn Leu Ala Ala Val
                420                 425                 430
Thr Leu Ala Cys Gln Asp Glu Pro Leu Asp Leu Ser Ala Ser Ser Gln
                435                 440                 445
Thr Glu Tyr Glu Ala Ser Pro Leu Ala Leu Pro Leu Ser Glu Asp Val
                450                 455                 460
Leu Ala Val Glu Arg Arg Glu Val Glu Glu Val Leu Ser Gly Ile Ser
465                 470                 475                 480
```

```
Gly Met Pro Asp Asp Ile Arg Leu Ala Pro Val Ser Ser Ser Ser
            485                 490                 495

Leu Ser Ser Ile Glu Ile Thr Arg Pro Lys Tyr Ser Ala Gln Ala Ile
        500                 505                 510

Ile Asn Ser Gly Gly Pro Cys Cys Gly His Leu Gln Glu Val Lys Glu
        515                 520                 525

Lys Tyr Leu Asn Val Met Arg Glu Ala Cys Asp Ala Thr Lys Leu Asp
        530                 535                 540

Asp Pro Ala Thr Gln Glu Trp Leu Ser Arg Met Trp Asp Arg Val Asp
545                 550                 555                 560

Met Leu Thr Trp Arg Asn Thr Ser Ile Phe Gln Ala Pro Phe Thr Leu
                565                 570                 575

Ala Asp Lys Phe Lys Thr Leu Pro Lys Met Ile Leu Glu Thr Pro Pro
                580                 585                 590

Pro Tyr Pro Cys Gly Phe Val Met Met Pro Arg Thr Pro Ala Pro Ser
                595                 600                 605

Val Gly Ala Glu Ser Asp Leu Thr Val Gly Ser Val Ala Thr Glu Asp
            610                 615                 620

Val Pro Arg Ile Leu Gly Asn Val Gln Gly Val Gly Thr Thr Asp
625                 630                 635                 640

Gln Gly Pro Leu Ala Pro Phe Ala Asp Glu Leu Ala Asp Gln Leu
                645                 650                 655

Ala Arg Glu Pro Arg Thr Gln Thr Pro Pro Ala Ser Thr Gly Gly Ala
                660                 665                 670

Gly Leu Val Ser Asp Ser Gly Arg Ser Pro Glu Leu Thr Asp Leu Pro
            675                 680                 685

Leu Ser Asn Gly Thr Asp Ala Gly Gly Gly Pro Leu His Thr Val
            690                 695                 700

Lys Lys Lys Ala Glu Arg Cys Phe Asp Gln Leu Ser Arg Arg Val Phe
705                 710                 715                 720

Asp Ile Val Ser His Leu Pro Val Phe Phe Ser Arg Leu Phe Lys Pro
                725                 730                 735

Asp Ser His Tyr Ser Ser Gly Asp Trp Ser Phe Ala Ala Phe Thr Leu
                740                 745                 750

Leu Cys Leu Phe Leu Cys Tyr Ser Tyr Pro Ala Phe Gly Val Ala Pro
                755                 760                 765

Leu Leu Gly Val Phe Ser Gly Ser Ser Arg Arg Val Arg Met Gly Val
            770                 775                 780

Phe Gly Cys Trp Leu Ala Phe Ala Val Gly Leu Phe Lys Pro Ala Pro
785                 790                 795                 800

Asp Pro Val Gly Ala Cys Glu Phe Asp Ser Pro Glu Cys Arg Asp
                805                 810                 815

Ile Leu His Ser Phe Glu Leu Leu Gln Pro Trp Asp Pro Val Arg Ser
                820                 825                 830

Leu Val Val Gly Pro Val Gly Leu Gly Leu Ala Ile Ile Gly Arg Leu
            835                 840                 845

Leu Gly Gly Ala Arg Tyr Val Trp Leu Leu Leu Arg Leu Gly Ile
            850                 855                 860

Val Ser Asp Cys Ile Leu Ala Gly Ala Tyr Val Leu Ser Gln Gly Arg
865                 870                 875                 880

Cys Lys Lys Cys Trp Gly Ser Cys Ile Arg Thr Ala Pro Ser Glu Val
                885                 890                 895
```

```
Ala Phe Asn Val Phe Pro Phe Thr Arg Ala Thr Arg Ser Ser Leu Val
            900             905             910

Asp Leu Cys Asp Arg Phe Cys Ala Pro Lys Gly Met Asp Pro Ile Phe
        915             920             925

Leu Ala Thr Gly Trp Arg Gly Cys Trp Ser Gly Gln Ser Pro Ile Glu
    930             935             940

Gln Pro Thr Glu Lys Pro Ile Ala Phe Ala Gln Leu Asp Glu Lys Lys
945             950             955             960

Ile Thr Ala Arg Thr Val Val Ala Gln Pro Tyr Asp Pro Asn Gln Ala
            965             970             975

Val Lys Cys Leu Arg Val Leu Gln Ala Gly Gly Ala Met Val Ala Glu
        980             985             990

Ala Val Pro Lys Val Val Lys Val  Ser Ala Val Pro Phe  Arg Ala Pro
        995             1000             1005

Phe Phe  Pro Ala Gly Val  Lys Val Asp Pro Glu Cys  Arg Val Val
    1010             1015             1020

Val Asp  Pro Asp Thr Phe  Thr Thr Ala Leu Arg Ser  Gly Tyr Ser
    1025             1030             1035

Thr Thr  Asn Leu Ile Leu Gly  Met Gly Asp Phe Ala  Gln Leu Asn
    1040             1045             1050

Gly Leu  Lys Ile Arg Gln Ile  Ser Lys Pro Ser Gly  Gly
    1055             1060             1065

<210> SEQ ID NO 74
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 74

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190
```

```
Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Ser Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Lys Leu Glu Lys Val Val Arg Glu Glu Tyr
        355                 360                 365

Gly Leu Met Pro Thr Glu Pro Gly Pro Arg Pro Thr Leu Pro Arg Gly
    370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Ser Asp
    450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Glu Pro
                485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
        515                 520                 525

Arg Gly Thr Val Ser Arg Pro Val Thr Pro Leu Ser Glu Pro Ile Pro
    530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asp Glu Pro Leu Asp Leu Ser Ala
                565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
        595                 600                 605
```

```
Glu Ile Ser Asp Met Ser Gly Asn Ile Lys Pro Ala Ser Val Ser Ser
610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Tyr Gln Ala Ile
690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
        755                 760                 765

Met Ala Asn Gln Gly Pro Leu Ala Phe Ser Glu Asp Lys Pro Val Asp
770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Ala Gly Ser Phe Thr
                805                 810                 815

Asp Leu Pro Pro Ser Asp Gly Ala Asp Ala Asp Gly Gly Pro Phe
            820                 825                 830

Arg Thr Val Lys Arg Lys Ala Glu Arg Leu Phe Asp Gln Leu Ser Arg
        835                 840                 845

Gln Val Phe Asp Leu Val Ser His Leu Pro Val Phe Phe Ser Arg Leu
850                 855                 860

Phe Tyr Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Gly Ser Ser Arg Arg Val Arg
            900                 905                 910

Met Gly Val Phe Gly Cys Trp Leu Ala Phe Ala Val Gly Leu Phe Lys
        915                 920                 925

Pro Val Ser Asp Pro Val Gly Ala Ala Cys Glu Phe Asp Ser Pro Glu
930                 935                 940

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile Leu Ala Gly Ala Tyr Val Leu Ser
        995                 1000                1005

Gln Gly Arg Cys Lys Lys Cys Trp Gly Ser Cys Ile Arg Thr Ala
    1010                1015                1020

Pro Asn Glu Val Ala Phe Asn Val Phe Pro Phe Thr Arg Ala Thr
```

-continued

```
                1025                1030                1035

Arg Ser Ser Leu Ile Asp Leu Cys Asp Arg Phe Cys Ala Pro Lys
        1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Glu Lys Pro Ile Ala
1070                1075                1080

Phe Ala Gln Leu Asp Glu Lys Lys Ile Thr Ala Arg Thr Val Val
        1085                1090                1095

Ala Gln Pro Tyr Asp Pro Asn Gln Ala Val Lys Cys Leu Arg Val
    1100                1105                1110

Leu Gln Ser Gly Gly Ala Met Val Ala Lys Ala Val Pro Lys Val
1115                1120                1125

Val Lys Val Ser Ala Val Pro Phe Arg Ala Pro Phe Phe Pro Thr
        1130                1135                1140

Gly Val Lys Val Asp Pro Asp Cys Arg Val Val Val Asp Pro Asp
    1145                1150                1155

Thr Phe Thr Ala Ala Leu Arg Ser Gly Tyr Ser Thr Thr Asn Leu
1160                1165                1170

Val Leu Gly Val Gly Asp Phe Ala Gln Leu Asn Gly Leu Lys Ile
        1175                1180                1185

Arg Gln Ile Ser Lys Pro Ser Gly Gly
    1190                1195

<210> SEQ ID NO 75
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 75

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175
```

```
His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
            195                 200                 205

Gln Phe Phe Ala Arg His Ser Gly Gly Asn His Pro Asp Gln Val Arg
            210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
            245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
            275                 280                 285

Trp Asp Val Val Leu Pro Gly Val Glu Ala Ala Thr Gln Thr Ile Lys
            290                 295                 300

Leu Pro Gln Val Asn Gln Cys Arg Ala Leu Val Pro Val Thr Gln
305                 310                 315                 320

Lys Ser Leu Asp Asn Asn Ser Val Pro Leu Thr Ala Phe Ser Leu Ala
            325                 330                 335

Asn Tyr Tyr Arg Ala Gln Gly Asp Glu Val Arg His Arg Glu Arg
            340                 345                 350

Leu Thr Ala Val Leu Ser Lys Leu Glu Lys Val Val Arg Glu Glu Tyr
            355                 360                 365

Gly Leu Met Pro Thr Glu Pro Gly Pro Arg Pro Thr Leu Pro Arg Gly
370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
            405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
            435                 440                 445

Pro Glu Arg Lys Pro Val Pro Ala Pro Arg Arg Lys Val Gly Ser Asp
450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
            485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
            515                 520                 525

Arg Gly Thr Val Ser Arg Pro Val Thr Pro Leu Ser Glu Pro Ile Pro
            530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
            565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
```

-continued

```
                595                 600                 605
Glu Ile Ser Asp Met Ser Gly Asn Ile Lys Pro Ala Ser Val Ser Ser
            610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Val Tyr Gln Ala Ile
            690                 695                 700

Cys Thr Leu Asn Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
            755                 760                 765

Met Ala Asn Gln Gly Pro Leu Ala Phe Ser Asp Lys Pro Val Asp
770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Ala Gly Ser Phe Thr
                805                 810                 815

Asp Leu Pro Pro Ser Asp Gly Ala Asp Ala Asp Gly Gly Pro Phe
            820                 825                 830

Arg Thr Val Lys Arg Lys Ala Glu Arg Leu Phe Asp Gln Leu Ser Arg
            835                 840                 845

Gln Val Phe Asp Leu Val Ser His Leu Pro Val Phe Phe Ser Arg Leu
850                 855                 860

Phe Tyr Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
            900                 905                 910

Met Gly Val Phe Gly Cys Trp Leu Ala Phe Ala Val Gly Leu Phe Lys
            915                 920                 925

Pro Val Ser Asp Pro Val Gly Ala Ala Cys Glu Phe Asp Ser Pro Glu
930                 935                 940

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile  Leu Ala Gly Ala Tyr  Val Leu Ser
            995                 1000                1005

Gln Gly  Arg Cys Lys Lys Cys  Trp Gly Ser Cys Ile  Arg Thr Ala
        1010                1015                1020
```

-continued

```
Pro Asn Glu Val Ala Phe Asn Val Phe Pro Phe Thr Arg Ala Thr
    1025                1030                1035

Arg Ser Ser Leu Ile Asp Leu Cys Asp Arg Phe Cys Ala Pro Lys
    1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Lys Pro Ile Ala
    1070                1075                1080

Phe Ala Gln Leu Asp Glu Lys Lys Ile Thr Ala Arg Thr Val Val
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Lys Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asp Cys Arg Val Val Val Asp Pro Asp
    1145                1150                1155

Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 76
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 76

Gly Ala Gly Lys Arg Ala Arg Lys Ala Arg Ser Cys Ala Thr Ala
1               5                   10                  15

Val Ala Gly Arg Ala Leu Ser Val Arg Glu Thr Arg Gln Ala Lys Glu
                20                  25                  30

His Glu Val Ala Gly Ala Asn Lys Ala Glu His Leu Lys His Tyr Ser
            35                  40                  45

Pro Pro Ala Glu Gly Asn Cys Gly Trp His Cys Ile Ser Ala Ile Ala
        50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
```

-continued

```
                165                 170                 175
His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
            245                 250                 255

Ile Asp Leu Tyr Leu Arg Gly Ala Thr Asn Leu Glu Glu Cys Leu Ala
        260                 265                 270

Arg Leu Glu Lys Ala Arg Pro Pro Arg Val Ile Asp Thr Phe Phe Asp
    275                 280                 285

Trp Asp Val Val Leu Pro Gly Val Glu Ala Ala Thr Gln Thr Ile Lys
290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
            325                 330                 335

Asn Tyr Tyr Tyr Arg Ala Gln Gly Asp Glu Val Arg His Arg Glu Arg
        340                 345                 350

Leu Thr Ala Val Leu Ser Lys Leu Glu Lys Val Val Arg Glu Glu Tyr
    355                 360                 365

Gly Leu Met Pro Thr Glu Pro Gly Pro Arg Pro Thr Leu Pro Arg Gly
370                 375                 380

Leu Asp Glu Leu Lys Ala Gln Met Glu Glu Asp Leu Leu Lys Leu Ala
385                 390                 395                 400

Asn Ala Gln Thr Thr Ser Asp Met Met Ala Trp Ala Val Glu Gln Val
            405                 410                 415

Asp Leu Lys Thr Trp Val Lys Asn Tyr Pro Arg Trp Thr Pro Pro Pro
        420                 425                 430

Pro Pro Pro Lys Val Gln Pro Arg Lys Thr Lys Pro Val Lys Ser Leu
    435                 440                 445

Pro Glu Arg Lys Pro Val Pro Ala Pro Arg Arg Lys Val Gly Ser Asp
450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
            485                 490                 495

Ala Thr Pro Ser Ser Glu Leu Val Ile Val Ser Ser Pro Gln Cys Ile
        500                 505                 510

Phe Arg Pro Ala Thr Pro Leu Ser Glu Pro Ala Pro Ile Pro Ala Pro
    515                 520                 525

Arg Gly Thr Val Ser Arg Pro Val Thr Pro Leu Ser Glu Pro Ile Pro
530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
            565                 570                 575

Ser Ser Gln Thr Glu Tyr Glu Ala Ser Pro Pro Ala Pro Pro Gln Ser
        580                 585                 590
```

Gly Gly Val Leu Gly Val Glu Gly His Glu Ala Glu Thr Leu Ser
        595                 600                 605
Glu Ile Ser Asp Met Ser Gly Asn Ile Lys Pro Ala Ser Val Ser Ser
610                 615                 620
Ser Ser Ser Leu Ser Ser Val Arg Ile Thr Arg Pro Lys Tyr Ser Ala
625                 630                 635                 640
Gln Ala Ile Ile Asp Ser Gly Gly Pro Cys Ser Gly His Leu Gln Glu
            645                 650                 655
Val Lys Glu Thr Cys Leu Ser Val Met Arg Glu Ala Cys Asp Ala Thr
                660                 665                 670
Lys Leu Asp Asp Pro Ala Thr Gln Glu Trp Leu Ser Arg Met Trp Asp
            675                 680                 685
Arg Val Asp Met Leu Thr Trp Arg Asn Thr Ser Val Tyr Gln Ala Ile
            690                 695                 700
Cys Thr Leu Asp Gly Arg Leu Lys Phe Leu Pro Lys Met Ile Leu Glu
705                 710                 715                 720
Thr Pro Pro Pro Tyr Pro Cys Glu Phe Val Met Met Pro His Thr Pro
                725                 730                 735
Ala Pro Ser Val Gly Ala Glu Ser Asp Leu Thr Ile Gly Ser Val Ala
                740                 745                 750
Thr Glu Asp Val Pro Arg Ile Leu Glu Lys Ile Glu Asn Val Gly Glu
            755                 760                 765
Met Ala Asn Gln Gly Pro Leu Ala Phe Ser Glu Asp Lys Pro Val Asp
770                 775                 780
Asp Gln Leu Val Asn Asp Pro Arg Ile Ser Ser Arg Arg Pro Asp Glu
785                 790                 795                 800
Ser Thr Ser Ala Pro Ser Ala Gly Thr Gly Gly Ala Gly Ser Phe Thr
                805                 810                 815
Asp Leu Pro Pro Ser Asp Gly Ala Asp Ala Asp Gly Gly Pro Phe
                820                 825                 830
Arg Thr Val Lys Arg Lys Ala Glu Arg Leu Phe Asp Gln Leu Ser Arg
            835                 840                 845
Gln Val Phe Asp Leu Val Ser His Leu Pro Val Phe Phe Ser Arg Leu
    850                 855                 860
Phe Tyr Pro Gly Gly Gly Tyr Ser Pro Gly Asp Trp Gly Phe Ala Ala
865                 870                 875                 880
Phe Thr Leu Leu Cys Leu Phe Leu Cys Tyr Ser Tyr Pro Ala Phe Gly
            885                 890                 895
Ile Ala Pro Leu Leu Gly Val Phe Gly Ser Ser Arg Arg Val Arg
            900                 905                 910
Met Gly Val Phe Gly Cys Trp Leu Ala Phe Ala Val Gly Leu Phe Lys
            915                 920                 925
Pro Val Ser Asp Pro Val Gly Ala Ala Cys Glu Phe Asp Ser Pro Glu
            930                 935                 940
Cys Arg Asn Ile Leu His Ser Phe Glu Leu Leu Lys Pro Trp Asp Pro
945                 950                 955                 960
Val Arg Ser Leu Val Val Gly Pro Val Gly Leu Gly Leu Ala Ile Leu
                965                 970                 975
Gly Arg Leu Leu Gly Gly Ala Arg Cys Ile Trp His Phe Leu Leu Arg
            980                 985                 990
Leu Gly Ile Val Ala Asp Cys Ile Leu Ala Gly Ala Tyr Val Leu Ser
            995                 1000                1005

-continued

```
Gln Gly Arg Cys Lys Lys Cys Trp Gly Ser Cys Ile Arg Thr Ala
    1010                1015                1020

Pro Asn Glu Val Ala Phe Asn Val Phe Pro Phe Thr Arg Ala Thr
    1025                1030                1035

Arg Ser Ser Leu Ile Asp Leu Cys Asp Arg Phe Cys Ala Pro Lys
    1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Glu Lys Pro Ile Ala
    1070                1075                1080

Phe Ala Gln Leu Asp Glu Lys Lys Ile Thr Ala Arg Thr Val Val
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Lys Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asp Cys Arg Val Val Val Asp Pro Asp
    1145                1150                1155

Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 77
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 77

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160
```

```
Val Ser Gly Phe Asp Pro Ala Cys Leu Asp Arg Leu Ala Glu Val Met
                165                 170                 175
His Leu Pro Ser Ser Ala Ile Pro Ala Ala Leu Ala Glu Met Ser Gly
            180                 185                 190
Asp Ser Asp Arg Ser Ala Ser Pro Val Thr Thr Val Trp Thr Val Ser
            195                 200                 205
Gln Phe Phe Ala Arg His Ser Gly Asn His Pro Asp Gln Val Arg
    210                 215                 220
Leu Gly Lys Ile Leu Ser Leu Cys Gln Val Ile Glu Asp Cys Cys Cys
225                 230                 235                 240
Ser Gln Asn Lys Thr Asn Arg Val Thr Pro Glu Glu Val Ala Ala Lys
                245                 250                 255
Ile Asp Leu Tyr Leu Arg Gly Ala Thr Asn Leu Glu Glu Cys Leu Ala
                260                 265                 270
Arg Leu Glu Lys Ala Arg Pro Arg Val Ile Asp Thr Phe Phe Asp
    275                 280                 285
Trp Asp Val Val Leu Pro Gly Val Glu Ala Ala Thr Gln Thr Ile Lys
    290                 295                 300
Leu Pro Gln Val Asn Gln Cys Arg Ala Leu Val Pro Val Thr Gln
305                 310                 315                 320
Lys Ser Leu Asp Asn Asn Ser Val Pro Leu Thr Ala Phe Ser Leu Ala
                325                 330                 335
Asn His Tyr Tyr Arg Ala Gln Gly Asp Glu Val Arg His Arg Glu Arg
                340                 345                 350
Leu Thr Ala Val Leu Ser Asn Leu Glu Lys Val Val Arg Glu Glu Tyr
                355                 360                 365
Gly Leu Met Pro Thr Glu Pro Gly Pro Arg Pro Thr Leu Pro Arg Gly
    370                 375                 380
Leu Asp Glu Leu Lys Asp Gln Met Glu Glu Asp Leu Leu Lys Leu Ala
385                 390                 395                 400
Asn Ala Gln Thr Thr Ser Asp Met Met Ala Trp Ala Val Glu Gln Val
                405                 410                 415
Asp Leu Lys Thr Trp Val Lys Asn Tyr Pro Arg Trp Thr Pro Pro
                420                 425                 430
Pro Pro Pro Lys Val Gln Pro Arg Lys Thr Lys Pro Val Lys Ser Leu
            435                 440                 445
Pro Glu Arg Lys Pro Val Pro Ala Pro Arg Arg Lys Val Gly Ser Asp
    450                 455                 460
Cys Gly Ser Pro Val Ser Leu Gly Gly Asp Val Pro Asn Ser Trp Glu
465                 470                 475                 480
Asp Leu Ala Val Ser Ser Pro Phe Asp Leu Pro Thr Pro Glu Pro
                485                 490                 495
Ala Thr Pro Ser Ser Glu Leu Val Ile Val Ser Ser Pro Gln Cys Ile
            500                 505                 510
Phe Arg Pro Ala Thr Pro Leu Ser Glu Pro Ala Pro Ile Pro Ala Pro
        515                 520                 525
Arg Gly Thr Val Ser Arg Pro Val Thr Pro Leu Ser Glu Pro Ile Pro
        530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
```

```
Ser Ser Gln Thr Glu Tyr Glu Ala Ser Pro Pro Ala Pro Pro Gln Ser
            580                 585                 590

Gly Gly Val Leu Gly Val Glu Gly His Glu Ala Glu Glu Thr Leu Ser
        595                 600                 605

Glu Ile Ser Asp Met Ser Gly Asn Ile Lys Pro Ala Ser Val Ser Ser
    610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Pro Cys Ser Gly His Leu Gln Glu
                645                 650                 655

Val Lys Glu Ala Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Tyr Gln Ala Ile
    690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
        755                 760                 765

Met Ala Asn Gln Gly Pro Leu Ala Phe Ser Glu Asp Lys Pro Val Asp
    770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Gly Ala Gly Phe Phe Thr
                805                 810                 815

Asp Leu Pro Pro Ser Asp Gly Ala Asp Ala Asp Gly Gly Gly Pro Phe
            820                 825                 830

Arg Thr Val Lys Arg Lys Ala Glu Arg Leu Phe Asp Gln Leu Ser Arg
        835                 840                 845

Gln Val Phe Asp Leu Val Ser His Leu Pro Val Phe Phe Ser Arg Leu
    850                 855                 860

Phe Cys Pro Gly Gly Gly Tyr Ser Pro Gly Asp Trp Gly Phe Ala Ala
865                 870                 875                 880

Leu Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
            900                 905                 910

Met Gly Val Phe Gly Cys Trp Leu Ala Phe Ala Val Gly Leu Phe Lys
        915                 920                 925

Pro Val Ser Asp Pro Val Gly Ala Ala Cys Glu Phe Asp Ser Pro Glu
    930                 935                 940

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile  Leu Ala Gly Ala Tyr  Val Leu Ser
```

```
                995              1000             1005

Gln  Gly  Arg  Cys  Lys  Lys  Cys  Trp  Gly  Ser  Cys  Ile  Arg  Thr  Ala
          1010                 1015                 1020

Pro  Asn  Glu  Val  Ala  Phe  Asn  Val  Phe  Pro  Phe  Thr  Arg  Ala  Thr
     1025                 1030                 1035

Arg  Ser  Ser  Leu  Ile  Asp  Leu  Cys  Asp  Arg  Phe  Cys  Ala  Pro  Lys
     1040                 1045                 1050

Gly  Met  Asp  Pro  Ile  Phe  Leu  Ala  Thr  Gly  Trp  Arg  Gly  Cys  Trp
     1055                 1060                 1065

Ala  Gly  Arg  Ser  Pro  Ile  Glu  Gln  Pro  Ser  Glu  Lys  Pro  Ile  Ala
     1070                 1075                 1080

Phe  Ala  Gln  Leu  Asp  Glu  Lys  Lys  Ile  Thr  Ala  Arg  Thr  Val  Val
     1085                 1090                 1095

Ala  Gln  Pro  Tyr  Asp  Pro  Asn  Gln  Ala  Val  Lys  Cys  Leu  Arg  Val
     1100                 1105                 1110

Leu  Gln  Ala  Gly  Gly  Ala  Met  Val  Ala  Lys  Ala  Val  Pro  Lys  Val
     1115                 1120                 1125

Val  Lys  Val  Ser  Ala  Val  Pro  Phe  Arg  Ala  Pro  Phe  Phe  Pro  Thr
     1130                 1135                 1140

Gly  Val  Lys  Val  Asp  Pro  Asp  Cys  Arg  Val  Val  Val  Asp  Pro  Asp
     1145                 1150                 1155

Thr  Phe  Thr  Ala  Ala  Leu  Arg  Ser  Gly  Tyr  Ser  Thr  Thr  Asn  Leu
     1160                 1165                 1170

Val  Leu  Gly  Val  Gly  Asp  Phe  Ala  Gln  Leu  Asn  Gly  Leu  Lys  Ile
     1175                 1180                 1185

Arg  Gln  Ile  Ser  Lys  Pro  Ser  Gly  Gly
     1190                 1195
```

<210> SEQ ID NO 78
<211> LENGTH: 1233
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 78

```
Gly  Ala  Gly  Lys  Arg  Ala  Arg  Lys  Ala  Arg  Ser  Ser  Ala  Thr  Ala  Thr
1                   5                   10                  15

Val  Ala  Gly  Arg  Ala  Leu  Pro  Val  Arg  Glu  Thr  Arg  Gln  Val  Glu  Glu
               20                  25                  30

His  Glu  Val  Ala  Gly  Ala  Asn  Lys  Ala  Glu  His  Leu  Lys  His  Tyr  Ser
           35                  40                  45

Pro  Pro  Ala  Glu  Gly  Asn  Cys  Gly  Trp  His  Cys  Ile  Ser  Ala  Ile  Gly
50                  55                  60

Asn  Arg  Met  Leu  Asn  Ser  Lys  Phe  Glu  Thr  Thr  Leu  Pro  Glu  Arg  Val
65                  70                  75                  80

Arg  Pro  Pro  Asp  Asp  Trp  Ala  Thr  Asp  Glu  Asp  Leu  Val  Asn  Ala  Ile
                85                  90                  95

Gln  Ile  Leu  Arg  Leu  Pro  Ala  Ala  Leu  Asp  Arg  Asn  Gly  Ala  Cys  Ala
            100                 105                 110

Ser  Ala  Lys  Tyr  Val  Leu  Lys  Leu  Glu  Gly  Glu  His  Trp  Thr  Val  Thr
        115                 120                 125

Val  Thr  Pro  Gly  Met  Ser  Pro  Ser  Leu  Leu  Pro  Leu  Glu  Cys  Val  Gln
    130                 135                 140
```

```
Gly Cys Cys Glu His Lys Gly Gly Leu Gly Ser Pro Asp Ala Val Glu
145                 150                 155                 160

Val Phe Gly Phe Asp Pro Ala Cys Leu Asp Trp Leu Ala Glu Val Met
            165                 170                 175

His Leu Pro Ser Asn Ala Ile Pro Ala Ala Leu Ala Glu Met Ser Gly
            180                 185                 190

Asp Ser Asn Arg Pro Ala Ser Pro Val Thr Thr Val Trp Thr Val Ser
            195                 200                 205

Gln Phe Leu Ala Arg His Gly Gly Asn His Pro Asp Gln Ile Arg
    210                 215                 220

Leu Gly Lys Ile Ile Ser Leu Cys Gln Val Ile Glu Asp Cys Cys
225                 230                 235                 240

Ser Gln Asn Lys Thr Asn Arg Val Thr Pro Glu Glu Val Ala Ala Lys
            245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Met Asp Thr Ser Phe Asp
    275                 280                 285

Trp Asp Val Val Leu Pro Gly Val Glu Ala Ala Thr Gln Thr Thr Glu
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Lys Leu Glu Gly Val Val Arg Glu Glu Tyr
            355                 360                 365

Gly Leu Met Pro Thr Gly Pro Gly Pro Arg Pro Thr Leu Pro Arg Gly
            370                 375                 380

Leu Asp Glu Leu Lys Asp Gln Met Glu Val Asp Leu Leu Lys Leu Ala
385                 390                 395                 400

Asn Ala Gln Met Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Ile Val Gln Pro Arg Lys Thr Lys Leu Val Lys Ser Leu
            435                 440                 445

Pro Glu Ser Lys Pro Val Pro Ala Pro Arg Arg Lys Val Arg Ser Asp
    450                 455                 460

Cys Asp Cys Pro Thr Leu Ser Gly Asn Asn Leu Pro Asp Ser Trp Glu
465                 470                 475                 480

Asp Leu Ala Val Gly Cys Pro Ser Asp Leu Pro Thr Ser Pro Glu Pro
                485                 490                 495

Val Thr Pro Leu Ser Glu Pro Ala Ser Val Ser Ala Pro Arg Arg Ser
            500                 505                 510

Phe Arg Pro Val Lys Pro Leu Ser Glu Pro Val Pro Val Pro Ala Pro
            515                 520                 525

Arg Lys Thr Val Ser Arg Pro Ala Thr Pro Leu Ser Glu Pro Ile Pro
            530                 535                 540

Val Pro Ala Pro Arg Arg Lys Phe Gln Gln Val Glu Lys Val Asn Pro
545                 550                 555                 560

Ala Ala Ala Thr Leu Gly Cys Gln Asp Glu Phe Pro Asp Leu Ser Ala
```

-continued

```
                565                 570                 575
Ser Ser His Thr Glu Tyr Glu Ala Ser Pro Leu Val Leu Pro Gln Asn
            580                 585                 590
Gly Asp Val Leu Glu Val Glu Arg Glu Ala Glu Glu Ile Leu Ser
        595                 600                 605
Gly Ile Ser Asp Ile Leu Asp Ala Ile Lys Pro Ala Ser Ala Ser Ser
    610                 615                 620
Ser Ser Ser Leu Ser Ser Val Ala Ile Thr Arg Pro Lys Tyr Ser Ala
625                 630                 635                 640
Gln Ala Ile Ile Asp Ser Gly Pro Tyr Ser Gly His Leu Gln Glu
            645                 650                 655
Val Lys Glu Thr Cys Leu Ser Ile Met Ser Glu Ala Cys Asp Val Thr
            660                 665                 670
Lys Leu Asp Asp Pro Ala Thr Gln Glu Trp Leu Ser Arg Met Trp Asp
            675                 680                 685
Arg Val Asp Met Leu Thr Trp Arg Asn Thr Ser Val His Gln Ala Ser
        690                 695                 700
Arg Thr Leu Asp Asp Asp Phe Lys Phe Leu Pro Lys Met Ile Leu Glu
705                 710                 715                 720
Thr Pro Pro Pro Tyr Pro Cys Gly Phe Val Met Met Pro Arg Thr Pro
                725                 730                 735
Ala Pro Ser Val Gly Ala Glu Ser Asp Leu Thr Ile Gly Ser Val Ala
            740                 745                 750
Thr Glu Asp Val Pro Arg Ile Phe Gly Lys Val Asn Asp Val Cys Lys
            755                 760                 765
Met Ile Asp Gln Arg Pro Leu Val Leu Phe Glu Asn Glu Leu Ala Asp
    770                 775                 780
Asp Gln Pro Ala Arg Asp Pro Arg Thr Ser Ser Gln Arg Phe Asp Gly
785                 790                 795                 800
Ser Thr Pro Ala Pro Pro Ala Gly Thr Asp Gly Thr Gly Leu Ala Ser
            805                 810                 815
Gly Pro Gly Val Arg Glu Val Asp Ser Cys Glu Ala Ser Ser Thr Glu
        820                 825                 830
Lys Ile Glu Gln Pro Phe Val Leu Asn Gly Gly Ala Ser Thr Gln Ala
    835                 840                 845
Ser Thr Phe Thr Asn Leu Pro Pro Gly Gly Ile Asp Ala Gly Gly
    850                 855                 860
Ser Gly Pro Leu Gln Thr Val Arg Lys Lys Ala Glu Arg Phe Asp
865                 870                 875                 880
Leu Leu Ser Arg Gln Val Phe Asn Leu Val Ser His Leu Pro Val Phe
            885                 890                 895
Phe Ser Arg Leu Phe Lys Pro Gly Gly Asp Tyr Ser Pro Gly Asp Trp
            900                 905                 910
Gly Phe Ala Ala Phe Thr Leu Leu Cys Leu Phe Leu Cys Tyr Ser Tyr
            915                 920                 925
Pro Ala Phe Gly Ala Val Pro Leu Leu Gly Val Phe Ser Gly Ser Ser
    930                 935                 940
Arg Arg Val Arg Met Gly Phe Gly Cys Trp Leu Ala Phe Ala Val
945                 950                 955                 960
Ser Leu Phe Lys Pro Val Ser Asp Pro Val Gly Ala Ala Cys Glu Phe
            965                 970                 975
Asp Ser Pro Glu Cys Arg Asn Ile Leu His Ser Phe Glu Leu Leu Lys
            980                 985                 990
```

```
Pro Trp Asp Pro Val Arg Gly Leu Val Val Gly Pro Val Gly Leu Ser
        995                 1000                1005

Leu Ala Ile Phe Gly Arg Leu Leu Gly Gly Ala Arg His Ile Trp
        1010                1015                1020

His Phe Leu Leu Arg Phe Gly Ile Val Ala Asp Cys Ile Leu Ala
        1025                1030                1035

Gly Ala Tyr Val Leu Ser Gln Gly Arg Cys Lys Lys Cys Trp Gly
        1040                1045                1050

Ser Cys Ile Arg Thr Ala Pro Asn Glu Val Ala Phe Asn Val Phe
        1055                1060                1065

Pro Phe Thr Arg Ala Thr Arg Ser Ser Leu Ile Asp Leu Cys Asn
        1070                1075                1080

Arg Phe Cys Ala Pro Lys Gly Met Asp Pro Ile Phe Phe Ala Thr
        1085                1090                1095

Gly Trp Arg Gly Cys Trp Thr Gly Arg Ser Pro Ile Glu Gln Pro
        1100                1105                1110

Ser Glu Lys Pro Ile Ala Phe Ala Gln Leu Asp Glu Lys Lys Ile
        1115                1120                1125

Thr Ala Arg Thr Val Val Ala Gln Pro Tyr Asp Pro Asn Gln Ala
        1130                1135                1140

Val Lys Cys Leu Arg Val Leu Gln Ala Gly Gly Val Met Val Ala
        1145                1150                1155

Glu Ala Val Pro Lys Val Val Lys Val Ser Ala Val Pro Phe Arg
        1160                1165                1170

Ala Pro Phe Phe Pro Thr Gly Val Lys Val Asp Pro Glu Cys Arg
        1175                1180                1185

Ile Val Val Asp Pro Asp Thr Phe Thr Ala Ala Leu Arg Ser Gly
        1190                1195                1200

Tyr Ser Thr Thr Asn Leu Val Leu Gly Val Gly Asp Phe Ala Gln
        1205                1210                1215

Leu Asn Gly Leu Lys Ile Arg Gln Ile Ser Lys Pro Ser Gly Gly
        1220                1225                1230

<210> SEQ ID NO 79
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 79

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
                20                  25                  30

His Glu Val Ala Gly Ala Asn Lys Ala Glu His Leu Lys His Tyr Ser
            35                  40                  45

Pro Pro Ala Glu Gly Asn Cys Gly Trp His Cys Ile Ser Ala Ile Ala
        50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
```

-continued

```
                100             105             110
Ser Ala Lys Tyr Val Lys Leu Glu Gly Glu His Trp Thr Val Thr
            115             120             125
Val Thr Pro Gly Met Ser Pro Ser Leu Leu Pro Leu Glu Cys Val Gln
130             135             140
Gly Cys Cys Gly His Lys Gly Gly Leu Gly Ser Pro Asp Ala Val Glu
145             150             155             160
Val Ser Gly Phe Asp Pro Ala Cys Leu Asp Arg Leu Ala Glu Val Met
            165             170             175
His Leu Pro Ser Ser Ala Ile Pro Ala Ala Leu Ala Glu Met Ser Gly
            180             185             190
Asp Ser Asp Arg Ser Ala Ser Pro Val Thr Thr Val Trp Thr Val Ser
            195             200             205
Gln Phe Phe Ala Arg His Ser Gly Gly Asn His Pro Asp Gln Val Arg
            210             215             220
Leu Gly Lys Ile Ile Ser Leu Cys Gln Val Ile Glu Asp Cys Cys Cys
225             230             235             240
Ser Gln Asn Lys Thr Asn Arg Val Thr Pro Glu Glu Val Ala Ala Lys
            245             250             255
Phe Asp Leu Tyr Leu Arg Gly Ala Thr Asn Leu Glu Glu Cys Leu Ala
            260             265             270
Arg Leu Glu Lys Ala Arg Pro Pro Arg Val Ile Asp Thr Phe Phe Asp
            275             280             285
Trp Asp Val Val Leu Pro Gly Val Glu Ala Ala Thr Gln Thr Ile Lys
            290             295             300
Leu Pro Gln Val Asn Gln Cys Arg Ala Leu Val Pro Val Val Thr Gln
305             310             315             320
Lys Ser Leu Asp Asn Asn Ser Val Pro Leu Thr Ala Phe Ser Leu Ala
            325             330             335
Asn Tyr Tyr Tyr Arg Ala Gln Gly Asp Glu Val Arg His Arg Glu Arg
            340             345             350
Leu Thr Ala Val Leu Ser Lys Leu Glu Lys Val Val Arg Glu Glu Tyr
            355             360             365
Gly Leu Met Pro Thr Lys Pro Gly Pro Arg Pro Thr Leu Pro Arg Gly
            370             375             380
Leu Asp Glu Leu Lys Asp Gln Met Glu Glu Asp Leu Leu Lys Leu Ala
385             390             395             400
Asn Ala Gln Thr Thr Ser Asp Met Met Ala Trp Ala Ala Glu Gln Val
            405             410             415
Asp Leu Lys Thr Trp Val Lys Asn Tyr Pro Arg Trp Thr Pro Pro Pro
            420             425             430
Pro Ser Pro Lys Val Gln Leu Arg Lys Thr Lys Pro Val Lys Ser Leu
            435             440             445
Pro Lys Arg Lys Pro Val Pro Ala Pro Arg Arg Lys Val Gly Ser Asp
            450             455             460
Cys Gly Ser Pro Val Ser Leu Gly Gly Asp Val Pro Asn Ser Trp Glu
465             470             475             480
Asp Leu Ala Val Ser Ser Pro Phe Asp Leu Pro Thr Pro Glu Pro
            485             490             495
Ala Ile Pro Ser Ser Glu Leu Val Ile Val Ser Ser Pro Gln Cys Ile
            500             505             510
Phe Arg Pro Ala Thr Pro Leu Ser Glu Pro Ala Pro Ile Pro Ala Pro
            515             520             525
```

-continued

```
Arg Gly Thr Val Ser Arg Pro Val Thr Pro Leu Ser Glu Pro Ile Pro
        530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
Ser Ser Gln Thr Glu Tyr Glu Ala Ser Pro Ala Pro Pro Gln Ser
            580                 585                 590
Gly Gly Val Leu Gly Val Glu Gly His Glu Ala Glu Thr Leu Ser
        595                 600                 605
Glu Ile Ser Asp Met Ser Gly Asn Ile Lys Pro Ala Ser Val Ser Ser
    610                 615                 620
Ser Ser Ser Leu Ser Ser Val Arg Ile Thr Arg Pro Lys Tyr Ser Ala
625                 630                 635                 640
Gln Ala Ile Ile Asp Ser Gly Gly Pro Cys Ser Gly His Leu Gln Glu
                645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
        675                 680                 685
Arg Val Asp Met Leu Thr Trp Arg Asn Thr Ser Val Tyr Gln Val Ile
690                 695                 700
Cys Thr Leu Asp Gly Met Leu Lys Phe Leu Pro Lys Met Ile Leu Glu
705                 710                 715                 720
Thr Pro Pro Pro Tyr Pro Cys Glu Phe Val Met Met Pro His Thr Pro
                725                 730                 735
Ala Pro Ser Val Gly Ala Glu Ser Asp Leu Thr Ile Gly Ser Val Thr
            740                 745                 750
Thr Glu Asp Val Pro Arg Ile Leu Glu Lys Ile Gly Asn Val Gly Glu
        755                 760                 765
Met Ala Asn Gln Gly Pro Leu Ala Phe Ser Glu Asp Lys Pro Val Asp
    770                 775                 780
Asp Gln Leu Val Asn Asp Pro Arg Ile Ser Ser Arg Pro Asp Glu
785                 790                 795                 800
Ser Thr Ser Ala Pro Ser Ala Gly Thr Gly Ala Gly Ser Phe Thr
                805                 810                 815
Asp Leu Pro Pro Ser Asp Gly Ala Asp Ala Asp Gly Gly Pro Phe
            820                 825                 830
Arg Thr Val Lys Arg Lys Ala Glu Arg Leu Phe Asp Gln Leu Ser Arg
        835                 840                 845
Gln Val Phe Asp Leu Val Ser His Leu Pro Val Phe Phe Ser Arg Leu
    850                 855                 860
Phe Tyr Pro Gly Gly Gly Tyr Ser Pro Gly Asp Trp Gly Phe Ala Ala
865                 870                 875                 880
Phe Thr Leu Leu Cys Leu Phe Leu Cys Tyr Ser Tyr Pro Ala Phe Gly
                885                 890                 895
Ile Ala Pro Leu Leu Gly Val Phe Ser Gly Ser Ser Arg Arg Val Arg
            900                 905                 910
Met Gly Val Phe Gly Cys Trp Leu Ala Phe Ala Val Gly Leu Phe Lys
        915                 920                 925
Pro Val Ser Asp Pro Val Gly Ala Ala Cys Glu Phe Asp Ser Pro Glu
    930                 935                 940
```

```
Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile Leu Ala Gly Ala Tyr Val Leu Ser
        995                 1000                1005

Gln Gly Arg Cys Lys Lys Cys Trp Gly Ser Cys Ile Arg Thr Ala
    1010                1015                1020

Pro Asn Glu Val Ala Phe Asn Val Phe Pro Phe Thr Arg Ala Thr
    1025                1030                1035

Arg Ser Ser Leu Ile Asp Leu Cys Asp Arg Phe Cys Ala Pro Lys
    1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Glu Lys Pro Ile Ala
    1070                1075                1080

Phe Ala Gln Leu Asp Glu Lys Lys Ile Thr Ala Arg Thr Val Val
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Glu Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asn Cys Arg Val Val Val Asp Pro Asp
    1145                1150                1155

Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 80
<211> LENGTH: 1196
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 80

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Arg Glu
                20                  25                  30

His Glu Val Ala Gly Ala Asn Lys Ala Glu His Leu Lys His Tyr Ser
            35                  40                  45

Pro Pro Ala Glu Gly Asn Cys Gly Trp His Cys Ile Ser Ala Ile Ala
        50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95
```

```
Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
            115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
            195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
    275                 280                 285

Trp Asp Val Val Leu Pro Gly Val Glu Ala Ala Thr Gln Thr Ile Lys
            290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Asn Leu Glu Lys Val Val Arg Glu Glu Tyr
    355                 360                 365

Gly Leu Met Pro Thr Glu Pro Gly Pro Arg Pro Thr Leu Pro Arg Gly
            370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
    435                 440                 445

Pro Glu Arg Lys Pro Val Pro Ala Pro Arg Arg Lys Val Gly Ser Asp
        450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Leu
                485                 490                 495

Ala Thr Pro Ser Ser Glu Leu Val Ile Val Ser Ser Pro Gln Cys Ile
            500                 505                 510
```

```
Phe Arg Pro Ala Thr Pro Leu Ser Glu Pro Ala Pro Ile Pro Ala Pro
        515                 520                 525
Arg Gly Thr Val Ser Arg Pro Val Thr Pro Leu Ser Glu Pro Ile Pro
    530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
Ser Ser Gln Thr Glu Tyr Glu Ala Ser Pro Pro Ala Pro Gln Ser
            580                 585                 590
Gly Gly Val Leu Gly Val Glu Gly His Glu Ala Glu Glu Thr Leu Ser
        595                 600                 605
Glu Ile Ser Asp Met Ser Gly Asn Ile Lys Pro Ala Ser Val Ser Ser
    610                 615                 620
Ser Ser Ser Leu Ser Ser Val Arg Ile Thr Arg Pro Lys Tyr Ser Ala
625                 630                 635                 640
Gln Ala Ile Ile Asp Ser Gly Gly Pro Cys Ser Gly His Leu Gln Glu
                645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
        675                 680                 685
Arg Val Asp Met Leu Thr Cys Asn Thr Ser Val Tyr Gln Ala Ile Cys
    690                 695                 700
Thr Leu Asp Gly Arg Leu Lys Phe Leu Pro Lys Leu Ile Leu Glu Thr
705                 710                 715                 720
Pro Pro Pro Tyr Pro Cys Glu Phe Val Met Met Pro His Thr Pro Ala
                725                 730                 735
Pro Ser Val Gly Ala Glu Ser Asp Leu Thr Ile Gly Ser Val Ala Thr
            740                 745                 750
Glu Asp Val Pro Arg Ile Leu Glu Lys Thr Glu Asn Val Gly Glu Met
        755                 760                 765
Ala Asn Gln Gly Pro Leu Ala Phe Ser Glu Asp Lys Pro Val Asp Asp
    770                 775                 780
Gln Leu Val Asn Asp Pro Arg Ile Ser Ser Arg Arg Pro Asp Glu Ser
785                 790                 795                 800
Thr Ser Ala Pro Ser Ala Gly Thr Gly Gly Ala Gly Ser Phe Thr Asp
                805                 810                 815
Leu Pro Pro Ser Asp Gly Ala Asp Ala Asp Gly Gly Pro Phe Arg
            820                 825                 830
Thr Val Lys Arg Lys Ala Glu Arg Leu Phe Asp Gln Leu Ser Arg Gln
        835                 840                 845
Val Phe Asp Leu Val Ser His Leu Pro Val Phe Phe Ser Arg Leu Phe
    850                 855                 860
Tyr Pro Gly Gly Gly Tyr Ser Pro Gly Asp Trp Gly Phe Ala Ala Phe
865                 870                 875                 880
Thr Leu Leu Cys Leu Phe Leu Cys Tyr Ser Tyr Pro Ala Phe Gly Ile
                885                 890                 895
Ala Pro Leu Leu Gly Val Phe Ser Gly Ser Arg Arg Val Arg Met
            900                 905                 910
Gly Val Phe Gly Cys Trp Leu Ala Phe Ala Val Gly Leu Phe Lys Pro
        915                 920                 925
Val Ser Asp Pro Val Gly Ala Ala Cys Glu Phe Asp Ser Pro Glu Cys
```

```
                930             935             940
Arg Asn Ile Leu His Ser Phe Glu Leu Leu Lys Pro Trp Asp Pro Val
945             950             955             960

Arg Ser Leu Val Val Gly Pro Val Gly Leu Gly Leu Ala Ile Leu Gly
                965             970             975

Arg Leu Leu Gly Gly Ala Arg Cys Ile Trp His Phe Leu Leu Arg Leu
            980             985             990

Gly Ile Val Ala Asp Cys Ile Leu Ala Gly Ala Tyr Val Leu Ser Gln
        995             1000            1005

Gly Arg Cys Lys Lys Cys Trp Gly Ser Cys Ile Arg Thr Ala Pro
    1010            1015            1020

Asn Glu Val Ala Phe Asn Val Phe Pro Phe Thr Arg Ala Thr Arg
    1025            1030            1035

Ser Ser Leu Ile Asp Leu Cys Asp Arg Phe Cys Ala Pro Lys Gly
    1040            1045            1050

Met Asp Pro Ile Phe Leu Ala Thr Gly Trp Arg Gly Cys Trp Ala
    1055            1060            1065

Gly Arg Ser Pro Ile Glu Gln Pro Ser Glu Lys Pro Ile Ala Phe
    1070            1075            1080

Ala Gln Leu Asp Glu Lys Lys Ile Thr Ala Arg Thr Val Val Ala
    1085            1090            1095

Gln Pro Tyr Asp Pro Asn Gln Ala Val Lys Cys Leu Arg Val Leu
    1100            1105            1110

Gln Ala Gly Gly Ala Met Val Ala Lys Ala Val Pro Lys Val Val
    1115            1120            1125

Lys Val Ser Ala Val Pro Phe Arg Ala Pro Phe Phe Pro Thr Gly
    1130            1135            1140

Val Lys Val Asp Pro Asp Cys Arg Val Val Val Asp Pro Asp Thr
    1145            1150            1155

Phe Thr Ala Ala Leu Arg Ser Gly Tyr Pro Thr Thr Asn Leu Val
    1160            1165            1170

Leu Gly Val Gly Asp Phe Ala Gln Leu Asn Gly Leu Lys Ile Arg
    1175            1180            1185

Gln Ile Ser Lys Pro Ser Gly Gly
    1190            1195

<210> SEQ ID NO 81
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 81

Gly Ala Gly Lys Arg Ala Arg Lys Ala Arg Ser Cys Ala Thr Ala Thr
1               5                   10                  15

Val Ala Gly Arg Ala Leu Ser Val Cys Glu Thr Arg Gln Ala Lys Glu
                20                  25                  30

His Glu Val Ala Gly Thr Asn Lys Ala Glu His Leu Lys His Tyr Ser
            35                  40                  45

Pro Pro Ala Glu Gly Asn Cys Gly Trp His Cys Ile Ser Ala Ile Ala
        50                  55                  60

Asn Arg Met Val Asn Ser Ile Phe Glu Thr Thr Leu Pro Glu Arg Val
65                  70                  75                  80
```

-continued

Arg Pro Pro Asp Asp Trp Ala Thr Asp Glu Asp Leu Val Asn Ala Ile
              85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Val Ala Ala Lys
                245                 250                 255

Ile Asp Leu Tyr Leu Arg Gly Ala Thr Asn Leu Glu Glu Cys Leu Ala
                260                 265                 270

Arg Leu Glu Lys Ala Arg Pro Pro Arg Val Ile Asp Thr Ser Phe Asp
        275                 280                 285

Trp Asp Val Val Leu Pro Gly Val Glu Ala Ala Thr Gln Met Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
                340                 345                 350

Leu Thr Ala Val Leu Ser Lys Leu Glu Lys Val Val Arg Glu Glu Tyr
            355                 360                 365

Gly Leu Val Pro Thr Glu Pro Gly Pro Gln Pro Thr Leu Pro Arg Gly
        370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Ser Asp
    450                 455                 460

Cys Gly Gly Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
                485                 490                 495

Ala Thr Pro Ser Ser Glu Leu Val Ile Val Ser Ser Pro Gln Cys Ile

```
                500             505             510
Phe Arg Pro Ala Thr Pro Leu Ser Glu Pro Ala Pro Ile Pro Ala Pro
            515             520             525

Arg Gly Thr Val Ser Arg Pro Val Thr Pro Leu Ser Glu Pro Ile Pro
            530             535             540

Val Pro Ala Pro Arg Arg Lys Phe Gln Gln Val Lys Arg Leu Ser Ser
545             550             555             560

Ala Ala Ala Ile Pro Pro Tyr Gln Asn Glu Pro Leu Asp Leu Ser Ala
            565             570             575

Ser Ser Gln Thr Glu Tyr Glu Ala Ser Pro Ala Pro Pro Gln Ser
            580             585             590

Gly Gly Val Leu Gly Val Glu Gly His Glu Ala Glu Thr Leu Ser
            595             600             605

Glu Ile Ser Asp Met Ser Gly Asn Ile Lys Pro Ala Ser Val Ser Ser
            610             615             620

Ser Ser Ser Leu Ser Ser Val Arg Val Thr Arg Pro Lys Tyr Ser Ala
625             630             635             640

Gln Ala Ile Ile Asp Ser Gly Gly Pro Cys Ser Gly His Leu Gln Glu
            645             650             655

Val Lys Glu Thr Cys Leu Ser Val Met Arg Glu Ala Cys Asp Ala Thr
            660             665             670

Lys Leu Asp Asp Pro Ala Thr Gln Glu Trp Leu Ser Arg Met Trp Asp
            675             680             685

Arg Val Asp Met Leu Thr Trp Arg Asn Thr Ser Ala Tyr Gln Ala Ile
            690             695             700

Cys Thr Leu Asp Gly Arg Leu Lys Phe Leu Pro Lys Met Ile Leu Glu
705             710             715             720

Thr Pro Pro Pro Tyr Pro Cys Glu Phe Val Met Met Pro His Thr Pro
            725             730             735

Ala Pro Ser Val Gly Ala Glu Ser Asp Leu Thr Ile Gly Ser Val Ala
            740             745             750

Thr Glu Asp Val Pro Arg Ile Leu Glu Lys Met Glu Asn Val Gly Glu
            755             760             765

Met Ala Asn Gln Gly Pro Leu Ala Phe Ser Glu Asp Lys Pro Val Asp
            770             775             780

Asp Gln Leu Val Asn Asp Pro Arg Ile Ser Ser Arg Arg Pro Asp Glu
785             790             795             800

Ser Thr Ser Ala Pro Ser Ala Gly Thr Gly Gly Ser Gly Ser Phe Thr
            805             810             815

Asp Leu Pro Pro Ser Asp Gly Ala Asp Ala Asp Gly Gly Pro Phe
            820             825             830

Arg Thr Ala Lys Arg Lys Ala Glu Arg Leu Phe Asp Gln Leu Ser Arg
            835             840             845

Gln Val Phe Asp Leu Val Ser His Leu Pro Val Phe Phe Ser Arg Leu
            850             855             860

Phe His Pro Gly Gly Gly Tyr Ser Pro Gly Asp Trp Gly Phe Ala Ala
865             870             875             880

Phe Thr Leu Leu Cys Leu Phe Leu Cys Tyr Ser Tyr Pro Ala Phe Gly
            885             890             895

Ile Ala Pro Leu Leu Gly Val Phe Ser Gly Ser Ser Arg Arg Val Arg
            900             905             910

Met Gly Val Phe Gly Cys Trp Leu Ala Phe Ala Val Gly Leu Phe Lys
            915             920             925
```

Pro Val Ser Asp Pro Val Gly Ala Ala Cys Glu Phe Asp Ser Pro Glu
          930                 935                 940

Cys Arg Asn Ile Leu His Ser Phe Glu Leu Leu Lys Pro Trp Asp Pro
945                 950                 955                 960

Val Arg Gly Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
          980                 985                 990

Leu Gly Ile Val Ala Asp Cys Ile Leu Ala Gly Ala Tyr Val Leu Ser
          995                 1000                1005

Gln Gly Arg Cys Lys Lys Cys Trp Gly Ser Cys Ile Arg Thr Ala
    1010                1015                1020

Pro Asn Glu Val Ala Phe Asn Val Phe Pro Phe Thr Arg Ala Thr
    1025                1030                1035

Arg Ser Ser Leu Ile Asp Leu Cys Asp Arg Leu Cys Ala Pro Lys
    1040                1045                1050

Gly Met Asp Pro Ile Ser Leu Ala Thr Gly Trp Arg Gly Cys Trp
    1055                1060                1065

Ala Gly Arg Ser Pro Ile Glu Gln Pro Ser Glu Lys Pro Ile Ala
    1070                1075                1080

Phe Ala Gln Leu Asp Glu Lys Lys Ile Thr Ala Arg Thr Val Ala
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Glu Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asp Cys Arg Val Val Val Asp Pro Asp
    1145                1150                1155

Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 82
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 82

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asp Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Ile Phe Glu Thr Thr Leu Pro Glu Arg Val

```
        65                  70                  75                  80
Arg Pro Pro Asp Asp Trp Ala Thr Asp Asp Leu Ala Asn Ala Ile
                85                  90                  95
Gln Ile Leu Arg Leu Pro Ala Ala Leu Asp Arg Asn Gly Ala Cys Thr
                100                 105                 110
Ser Ala Lys Tyr Val Leu Lys Leu Glu Gly Glu His Trp Thr Val Thr
                115                 120                 125
Val Thr Pro Gly Met Ser Pro Ser Leu Leu Pro Leu Glu Cys Val Gln
                130                 135                 140
Gly Cys Cys Glu His Lys Gly Leu Gly Ser Pro Asp Ala Ile Glu
145                 150                 155                 160
Val Ser Gly Phe Asp Pro Ala Cys Leu Asp Trp Leu Ala Glu Val Met
                165                 170                 175
His Leu Pro Ser Ser Ala Ile Pro Ala Ala Leu Ala Glu Met Ser Gly
                180                 185                 190
Asp Ser Asp Arg Ser Ala Ser Pro Val Thr Thr Val Trp Thr Val Ser
                195                 200                 205
Gln Phe Phe Ala Arg His Ser Gly Gly Asn His Pro Asp Gln Val Arg
                210                 215                 220
Leu Gly Lys Ile Ile Ser Leu Cys Gln Val Ile Glu Asp Cys Cys Cys
225                 230                 235                 240
Ser Gln Asn Lys Thr Asn Arg Val Thr Pro Glu Glu Val Ala Ala Lys
                245                 250                 255
Ile Asp Leu Tyr Leu Arg Gly Ala Thr Asn Leu Glu Glu Cys Leu Ala
                260                 265                 270
Arg Leu Glu Lys Ala Arg Pro Pro Arg Val Ile Asp Thr Ser Phe Asp
                275                 280                 285
Trp Asp Val Val Leu Pro Gly Val Glu Ala Ala Thr Gln Thr Asn Lys
                290                 295                 300
Leu Pro Gln Val Asn Gln Cys Arg Ala Leu Val Pro Val Thr Gln
305                 310                 315                 320
Lys Ser Leu Asp Asn Asn Ser Val Pro Leu Thr Ala Phe Ser Leu Ala
                325                 330                 335
Asn Tyr Tyr Tyr Arg Ala Gln Gly Asp Glu Val Arg His Arg Glu Arg
                340                 345                 350
Leu Thr Ala Val Leu Ser Lys Leu Glu Glu Val Arg Glu Glu Tyr
                355                 360                 365
Gly Leu Met Pro Thr Glu Pro Gly Pro Arg Pro Thr Leu Pro Arg Gly
                370                 375                 380
Leu Asp Glu Leu Lys Asp Gln Met Glu Glu Asp Leu Leu Arg Leu Ala
385                 390                 395                 400
Asn Ala Gln Ala Thr Ser Asp Met Met Ala Trp Ala Val Glu Gln Val
                405                 410                 415
Asp Leu Lys Thr Trp Val Lys Asn Tyr Pro Arg Trp Thr Pro Pro
                420                 425                 430
Pro Pro Pro Lys Val Gln Pro Arg Lys Thr Lys Pro Val Lys Ser Leu
                435                 440                 445
Pro Glu Arg Lys Pro Val Pro Ala Pro Arg Arg Lys Val Gly Pro Asp
                450                 455                 460
Cys Gly Ser Pro Val Ser Leu Gly Gly Asp Val Pro Asn Ser Trp Glu
465                 470                 475                 480
Asp Leu Ala Val Ser Ser Pro Leu Asp Leu Pro Thr Pro Pro Glu Pro
                485                 490                 495
```

```
Ala Thr Leu Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
            515                 520                 525

Arg Gly Thr Val Ser Arg Pro Val Thr Pro Leu Ser Glu Pro Ile Pro
            530                 535                 540

Val Pro Ala Pro Arg Arg Lys Phe Gln Gln Val Lys Arg Leu Ser Ser
545                 550                 555                 560

Ala Ala Ala Val Pro Leu His Gln Asn Glu Pro Leu Asp Leu Ser Ala
            565                 570                 575

Ser Ser Gln Thr Glu Tyr Glu Ala Ser Pro Ser Ala Pro Pro Gln Ser
            580                 585                 590

Gly Gly Val Leu Gly Val Glu Gly His Glu Ala Glu Glu Thr Leu Ser
            595                 600                 605

Glu Ile Ser Asp Met Ser Gly Asn Ile Lys Pro Ala Ser Val Ser Ser
            610                 615                 620

Ser Ser Ser Leu Ser Ser Val Glu Ile Thr Arg Pro Lys Tyr Ser Ala
625                 630                 635                 640

Gln Ala Ile Ile Asp Ser Gly Pro Cys Ser Gly His Leu Gln Gly
            645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Val Cys Gln Ala Ile
            690                 695                 700

Arg Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
            725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
            755                 760                 765

Met Ala Asn Gln Glu Pro Ser Ala Phe Ser Glu Asp Lys Pro Val Asp
            770                 775                 780

Asp Gln Leu Val Asn Asp Pro Arg Ile Ser Ser Arg Arg Pro Asp Glu
785                 790                 795                 800

Ser Thr Ala Ala Pro Ser Ala Gly Thr Gly Ala Gly Ser Phe Thr
            805                 810                 815

Asp Leu Pro Ser Ser Asp Gly Ala Asp Ala Asp Gly Gly Pro Phe
            820                 825                 830

Arg Thr Ala Lys Arg Lys Ala Glu Arg Leu Phe Asp Gln Leu Ser Arg
            835                 840                 845

Gln Val Phe Asp Leu Val Ser His Leu Pro Val Phe Phe Ser Arg Leu
            850                 855                 860

Phe His Pro Gly Gly Gly Tyr Ser Thr Gly Asp Trp Gly Phe Ala Ala
865                 870                 875                 880

Phe Thr Leu Leu Cys Leu Phe Leu Cys Tyr Ser Tyr Pro Ala Phe Gly
            885                 890                 895

Ile Ala Pro Leu Leu Gly Val Phe Ser Gly Thr Ser Arg Arg Val Arg
            900                 905                 910
```

Met Gly Val Phe Gly Cys Trp Leu Ala Phe Ala Val Gly Leu Phe Lys
            915                 920                 925

Pro Val Ser Asp Pro Val Gly Ala Ala Cys Glu Phe Asp Ser Pro Glu
930                 935                 940

Cys Arg Asn Ile Leu Leu Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile Leu Ala Gly Ala Tyr Val Leu Ser
            995                 1000                1005

Gln Gly Arg Cys Lys Lys Cys Trp Gly Ser Cys Ile Arg Thr Ala
        1010                1015                1020

Pro Asn Glu Val Ala Phe Asn Val Phe Pro Phe Thr Arg Ala Thr
        1025                1030                1035

Arg Ser Ser Leu Ile Asp Leu Cys Asp Arg Phe Cys Ala Pro Lys
        1040                1045                1050

Gly Met Asp Pro Ile Phe Leu Ala Thr Gly Trp Arg Gly Cys Trp
        1055                1060                1065

Ala Gly Arg Ser Pro Ile Glu Gln Pro Ser Glu Lys Pro Ile Ala
        1070                1075                1080

Phe Ala Gln Leu Asp Glu Lys Lys Ile Thr Ala Arg Thr Val Val
        1085                1090                1095

Ala Gln Pro Tyr Asp Pro Asn Gln Ala Val Lys Cys Leu Arg Val
        1100                1105                1110

Leu Gln Ala Gly Gly Ala Met Val Ala Glu Ala Val Pro Lys Val
        1115                1120                1125

Val Lys Val Ser Ala Val Pro Phe Arg Ala Pro Phe Phe Pro Thr
        1130                1135                1140

Gly Val Lys Val Asp Pro Asp Cys Arg Val Val Val Asp Pro Asp
        1145                1150                1155

Thr Phe Thr Ala Ala Leu Arg Ser Gly Tyr Ser Thr Thr Asn Leu
        1160                1165                1170

Val Leu Gly Val Gly Asp Phe Ala Gln Leu Asn Gly Leu Lys Ile
        1175                1180                1185

Arg Gln Ile Ser Lys Pro Ser Gly Gly
        1190                1195

<210> SEQ ID NO 83
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 83

Gly Ala Gly Lys Arg Ala Arg Lys Ala Arg Ser Gly Ala Thr Thr Met
1               5                   10                  15

Val Ala His Arg Ala Leu Ser Ala Arg Glu Thr Arg Gln Ala Lys Lys
                20                  25                  30

His Glu Gly Ala Asp Ala Asn Lys Ala Glu His Leu Glu His Tyr Ser
            35                  40                  45

Pro Pro Ala Glu Gly Asn Cys Gly Trp His Cys Ile Ser Ala Ile Ala
        50                  55                  60

```
Asn Arg Met Val Asn Ser Asn Phe Glu Thr Thr Leu Pro Glu Arg Ala
 65              70                  75                  80

Arg Pro Leu Asp Asp Trp Ala Thr Asp Glu Asp Leu Val Asn Thr Ile
                 85                  90                  95

Gln Ile Leu Arg Leu Pro Ala Ala Leu Asp Arg Asn Gly Ala Cys Thr
                100                 105                 110

Ser Ala Lys Tyr Val Leu Arg Leu Glu Gly Glu His Trp Thr Val Ser
            115                 120                 125

Val Thr Pro Gly Met Ser Pro Ser Leu Leu Pro Leu Glu Cys Val Gln
130                 135                 140

Gly Cys Cys Glu His Lys Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Pro Val
                180                 185                 190

Asp Ser Asn Arg Pro Ala Ser Pro Val Thr Thr Ala Trp Thr Val Ser
            195                 200                 205

Gln Phe Tyr Ala Arg His Arg Gly Gly Asn His Arg Asp Gln Val Cys
210                 215                 220

Leu Gly Lys Ile Ile Ser Leu Cys Gln Val Ile Glu Asp Cys Cys Cys
225                 230                 235                 240

His Gln Asn Lys Thr Asn Arg Ala Thr Pro Glu Val Ala Ala Lys
                245                 250                 255

Ile Asp Gln Tyr Leu Arg Gly Ala Thr Ser Leu Glu Glu Cys Leu Ile
                260                 265                 270

Lys Leu Glu Arg Val Ser Pro Pro Ser Ala Ala Asp Thr Ser Phe Asp
            275                 280                 285

Trp Asn Val Val Leu Pro Gly Val Glu Ala Ala Asn Gln Thr Thr Lys
            290                 295                 300

Gln Leu His Val Asn Gln Cys Arg Ala Leu Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
                340                 345                 350

Leu Asn Ser Val Leu Ser Lys Leu Glu Gly Val Val Leu Glu Glu Tyr
            355                 360                 365

Gly Leu Met Ser Thr Gly Leu Gly Pro Arg Pro Val Leu Pro Ser Gly
            370                 375                 380

Leu Asp Glu Leu Lys Asp Gln Met Glu Glu Asp Leu Leu Lys Leu Ala
385                 390                 395                 400

Asn Ala Gln Ala Thr Ser Glu Met Met Ala Trp Ala Ala Glu Gln Val
                405                 410                 415

Asp Leu Lys Ala Trp Val Lys Ser Tyr Pro Arg Trp Thr Pro Pro Pro
                420                 425                 430

Pro Pro Pro Arg Val Gln Pro Arg Lys Thr Lys Pro Val Lys Ser Leu
            435                 440                 445

Pro Glu Asn Lys Pro Val Pro Ala Pro Arg Arg Lys Val Gly Ser Asp
            450                 455                 460

Cys Gly Ser Pro Ile Leu Met Gly Asp Asn Val Pro Asn Gly Trp Glu
465                 470                 475                 480
```

-continued

Asp Phe Ala Val Gly Gly Pro Leu Asp Phe Pro Thr Pro Ser Glu Pro
                485                 490                 495

Met Thr Pro Leu Ser Glu Pro Val Leu Met Pro Ala Ser Gln His Ile
            500                 505                 510

Pro Arg Pro Val Thr Pro Leu Ser Gly Pro Ala Pro Val Pro Ala Pro
        515                 520                 525

Arg Arg Thr Val Ser Arg Pro Met Thr Pro Leu Ser Glu Pro Ile Phe
    530                 535                 540

Val Ser Ala Pro Arg His Lys Phe Gln Gln Val Glu Ala Asn Pro
545                 550                 555                 560

Ala Ala Thr Thr Leu Thr Tyr Gln Asp Glu Pro Leu Asp Leu Ser Ala
                565                 570                 575

Phe Ser Gln Thr Glu Cys Glu Ala Ser Pro Leu Ala Pro Leu Gln Asn
            580                 585                 590

Met Gly Ile Leu Glu Ala Gly Gly Gln Glu Ala Glu Glu Val Leu Ser
        595                 600                 605

Gly Ile Ser Asp Ile Leu Asn Asp Ile Asn Pro Ala Pro Val Ser Ser
    610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Arg
                645                 650                 655

Glu Lys Glu Ala Cys Leu Ser Ile Met Arg Glu Ala Cys Asp Ala Ala
            660                 665                 670

Lys Leu Ser Asp Pro Ala Thr Gln Glu Trp Leu Ser Arg Met Trp Asp
        675                 680                 685

Arg Val Asp Met Leu Thr Trp Arg Asn Thr Ser Ala Tyr Gln Ala Leu
    690                 695                 700

His Thr Leu Asp Gly Arg Ser Gly Phe Leu Pro Lys Met Ile Leu Glu
705                 710                 715                 720

Thr Pro Pro Pro His Pro Cys Gly Phe Val Met Leu Pro His Thr Pro
                725                 730                 735

Ala Pro Ser Val Ser Ala Lys Ser Asp Leu Thr Ile Gly Ser Val Ala
            740                 745                 750

Thr Glu Asp Val Pro Arg Ile Leu Gly Lys Ile Glu Asn Thr Gly Glu
        755                 760                 765

Met Leu Asn Gln Gly Pro Leu Ala Pro Phe Glu Glu Pro Val Cys
    770                 775                 780

Asp Gln Pro Ala Lys Asp Ser Arg Ile Ser Ser Arg Gly Ser Gly Glu
785                 790                 795                 800

Ser Thr Thr Ala Pro Ser Ala Asp Thr Gly Ala Gly Leu Phe Thr
                805                 810                 815

Asp Leu Leu Pro Ser Asp Gly Met Asp Ala Asp Gly Gly Pro Leu
            820                 825                 830

Arg Thr Val Lys Lys Lys Thr Glu Lys Leu Phe Asp Gln Leu Ser Arg
        835                 840                 845

Gln Val Phe Asn Leu Val Ser His Leu Pro Val Phe Phe Ser His Leu
    850                 855                 860

Phe Lys Ser Asp Ser Gly Tyr Ser Ser Gly Asp Trp Ser Phe Ala Ala
865                 870                 875                 880

Phe Thr Leu Phe Cys Leu Phe Leu Cys Tyr Ser Tyr Pro Phe Phe Gly
                885                 890                 895

Phe Ala Pro Leu Leu Gly Val Phe Ser Gly Ser Ser Arg Arg Val Arg

```
                    900               905               910
Met Gly Val Phe Gly Cys Trp Leu Ala Phe Ala Val Gly Leu Phe Lys
                915               920               925

Pro Val Ser Asp Pro Val Gly Thr Ala Cys Glu Phe Asp Ser Pro Glu
        930               935               940

Cys Arg Asn Val Leu His Ser Phe Glu Leu Leu Lys Pro Trp Asp Pro
945               950               955               960

Val Arg Ser Leu Val Val Gly Pro Val Gly Leu Gly Leu Ala Ile Leu
                965               970               975

Gly Arg Leu Leu Gly Gly Ala Arg Tyr Ile Trp His Phe Leu Leu Arg
            980               985               990

Leu Gly Ile Val Ala Asp Cys Ile Leu Ala Gly Ala Tyr Val Leu Ser
                995              1000              1005

Gln Gly Arg Cys Lys Lys Cys Trp Gly Ser Cys Val Arg Thr Ala
       1010              1015              1020

Pro Asn Glu Ile Ala Phe Asn Val Phe Pro Phe Thr Arg Ala Thr
       1025              1030              1035

Arg Ser Ser Leu Ile Asp Leu Cys Asp Arg Phe Cys Ala Pro Lys
       1040              1045              1050

Cys Met Asp Pro Ile Phe Leu Ala Thr Gly Trp Arg Gly Cys Trp
       1055              1060              1065

Thr Gly Arg Ser Pro Ile Glu Gln Pro Ser Glu Lys Pro Ile Ala
       1070              1075              1080

Phe Ala Gln Leu Asp Glu Lys Lys Ile Thr Ala Arg Thr Val Val
       1085              1090              1095

Ala Gln Pro Tyr Asp Pro Asn Gln Ala Val Lys Cys Leu Arg Val
       1100              1105              1110

Leu Gln Ala Gly Gly Ala Met Val Ala Glu Ala Val Pro Lys Val
       1115              1120              1125

Val Lys Val Ser Ala Ile Pro Phe Arg Ala Pro Phe Phe Pro Thr
       1130              1135              1140

Gly Val Lys Val Asp Pro Glu Cys Arg Ile Val Val Asp Pro Asp
       1145              1150              1155

Thr Phe Thr Thr Ala Leu Arg Ser Gly Tyr Ser Thr Thr Asn Leu
       1160              1165              1170

Val Leu Gly Val Gly Asp Phe Ala Gln Leu Asn Gly Leu Lys Ile
       1175              1180              1185

Arg Gln Ile Ser Lys Pro Ser Gly Gly
       1190              1195

<210> SEQ ID NO 84
<211> LENGTH: 1186
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 84

Gly Ala Gly Lys Arg Ala Arg Lys Ala Arg Ser Gly Ala Thr Thr Thr
1               5                  10                  15

Val Ala His Arg Ala Ser Ser Ala Arg Glu Thr Arg Gln Ala Lys Lys
                20                  25                  30

His Glu Gly Val Asp Ala Asn Asn Ala Ala His Leu Glu His Tyr Ser
            35                  40                  45
```

```
Pro Pro Ala Glu Gly Asn Cys Gly Trp His Cys Ile Ser Ala Ile Val
    50                  55                  60

Asn Arg Met Val Asn Ser Asn Phe Glu Thr Thr Leu Pro Glu Arg Val
 65              70                  75                      80

Arg Pro Ser Asp Asp Trp Ala Thr Asp Glu Asp Phe Val Asn Thr Ile
                 85                  90                  95

Gln Ile Leu Arg Leu Pro Ala Ala Leu Asp Arg Asn Gly Ala Cys Lys
                100                 105                 110

Ser Ala Lys Tyr Val Leu Lys Leu Glu Gly Glu His Trp Thr Val Ser
            115                 120                 125

Val Ala Pro Gly Met Ser Pro Ser Leu Leu Pro Leu Glu Cys Val Gln
130                 135                 140

Gly Cys Cys Glu His Lys Gly Leu Gly Ser Pro Asp Ala Val Glu
145                 150                 155                 160

Val Ser Gly Phe Asp Pro Thr Cys Leu Asp Arg Leu Ala Glu Val Met
                165                 170                 175

His Leu Pro Ser Ser Val Ile Pro Ala Ala Leu Ala Glu Met Ser Asn
                180                 185                 190

Asn Ser Asp Arg Pro Ala Ser Leu Val Asn Thr Ala Trp Thr Val Ser
            195                 200                 205

Gln Phe Tyr Ala Arg His Thr Gly Gly Asn His Arg Asp Gln Val Arg
    210                 215                 220

Leu Gly Lys Ile Ile Ser Leu Cys Gln Val Ile Glu Glu Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ile
            260                 265                 270

Lys Leu Glu Arg Val Ser Pro Ser Ala Ala Asp Thr Ser Phe Asp
                275                 280                 285

Trp Asn Val Val Leu Pro Gly Val Glu Ala Ala Gly Pro Thr Thr Glu
    290                 295                 300

Gln Pro His Ala Asn Gln Cys Cys Ala Pro Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Glu Val Leu Glu Glu Tyr
            355                 360                 365

Gly Leu Met Pro Thr Gly Leu Gly Pro Arg Pro Val Leu Pro Ser Gly
    370                 375                 380

Leu Asp Glu Leu Lys Asp Gln Met Glu Glu Asp Leu Leu Lys Leu Ala
385                 390                 395                 400

Asn Ala Gln Ala Thr Ser Glu Met Met Ala Leu Ala Ala Glu Gln Val
                405                 410                 415

Asp Leu Lys Ala Trp Val Lys Ser Tyr Pro Arg Trp Ile Pro Pro Pro
            420                 425                 430

Pro Pro Pro Lys Val Gln Pro Arg Arg Met Lys Pro Val Lys Ser Leu
        435                 440                 445

Pro Glu Asn Lys Pro Val Pro Ala Pro Arg Arg Lys Val Arg Ser Asp
450                 455                 460

Pro Gly Lys Ser Ile Leu Ala Val Gly Gly Pro Leu Asn Phe Ser Thr
```

```
                465                 470                 475                 480
           Pro Ser Glu Leu Val Thr Pro Leu Gly Glu Pro Val Leu Met Pro Ala
                               485                 490                 495

Ser Gln His Val Ser Arg Pro Val Thr Pro Leu Ser Glu Pro Ala Pro
                               500                 505                 510

Val Pro Ala Pro Arg Arg Ile Val Ser Arg Pro Met Thr Pro Leu Ser
                               515                 520                 525

Glu Pro Thr Phe Val Phe Ala Pro Trp Arg Lys Ser Gln Gln Val Glu
                               530                 535                 540

Glu Ala Asn Pro Ala Ala Ala Thr Leu Thr Cys Gln Asp Glu Pro Leu
           545                 550                 555                 560

Asp Leu Ser Ala Ser Ser Gln Thr Glu Tyr Glu Ala Tyr Pro Leu Ala
                               565                 570                 575

Pro Leu Glu Asn Ile Gly Val Leu Glu Ala Gly Gly Gln Glu Ala Glu
                               580                 585                 590

Glu Val Leu Ser Gly Ile Ser Asp Ile Leu Asp Asn Thr Asn Pro Ala
                               595                 600                 605

Pro Val Ser Ser Ser Ser Leu Ser Ser Val Lys Ile Thr Arg Pro
                               610                 615                 620

Lys Tyr Ser Ala Gln Ala Ile Ile Asp Ser Gly Gly Pro Cys Ser Gly
           625                 630                 635                 640

His Leu Gln Lys Glu Lys Glu Ala Cys Leu Arg Ile Met Arg Glu Ala
                               645                 650                 655

Cys Asp Ala Ala Arg Leu Gly Asp Pro Ala Thr Gln Glu Trp Leu Ser
                               660                 665                 670

His Met Trp Asp Arg Val Asp Val Leu Thr Trp Arg Asn Thr Ser Val
                               675                 680                 685

Tyr Gln Ala Phe Arg Thr Leu Asp Gly Arg Phe Gly Phe Leu Pro Lys
                               690                 695                 700

Met Ile Leu Glu Thr Pro Pro Tyr Pro Cys Gly Phe Val Met Leu
           705                 710                 715                 720

Pro His Thr Pro Thr Pro Ser Val Ser Ala Glu Ser Asp Leu Thr Ile
                               725                 730                 735

Gly Ser Val Ala Thr Glu Asp Val Pro Arg Ile Leu Gly Lys Thr Glu
                               740                 745                 750

Asn Thr Gly Asn Val Leu Asn Gln Lys Pro Leu Ala Leu Phe Glu Glu
                               755                 760                 765

Glu Pro Val Cys Asp Gln Pro Ala Lys Asp Ser Arg Thr Leu Ser Arg
           770                 775                 780

Glu Ser Gly Asp Ser Thr Thr Ala Pro Pro Val Gly Thr Gly Gly Ala
           785                 790                 795                 800

Gly Leu Pro Thr Asp Leu Pro Pro Leu Asp Gly Val Asp Ala Asp Gly
                               805                 810                 815

Gly Gly Leu Leu Arg Thr Ala Lys Gly Lys Ala Glu Arg Phe Phe Asp
                               820                 825                 830

Gln Leu Ser Arg Gln Val Phe Asn Ile Val Ser His Leu Pro Val Phe
                               835                 840                 845

Phe Ser His Leu Phe Lys Ser Asp Ser Gly Tyr Ser Pro Gly Asp Trp
           850                 855                 860

Gly Phe Ala Ala Phe Thr Leu Phe Cys Leu Phe Leu Cys Tyr Ser Tyr
           865                 870                 875                 880

Pro Phe Phe Gly Phe Ala Pro Leu Leu Gly Val Phe Ser Gly Ser Ser
                               885                 890                 895
```

Arg Arg Val Arg Met Gly Val Phe Gly Cys Trp Leu Ala Phe Ala Val
                900                 905                 910

Gly Leu Phe Lys Pro Val Ser Asp Pro Val Gly Ala Ala Cys Glu Phe
            915                 920                 925

Asp Ser Pro Glu Cys Arg Asn Ile Leu His Ser Phe Glu Leu Leu Lys
        930                 935                 940

Pro Trp Asp Pro Val Arg Ser Leu Val Val Gly Gly Pro Val Gly Leu
945                 950                 955                 960

Gly Leu Ala Ile Leu Gly Arg Leu Leu Gly Gly Ala Arg Tyr Ile Trp
                965                 970                 975

His Phe Leu Leu Arg Leu Gly Ile Val Ala Asp Cys Ile Leu Ala Gly
            980                 985                 990

Ala Tyr Val Leu Ser Gln Gly Arg Cys Lys Lys Cys Trp Gly Ser Cys
        995                 1000                1005

Ile Arg Thr Ala Pro Asn Glu Ile Ala Phe Asn Val Phe Pro Phe
    1010                1015                1020

Thr Arg Ala Thr Arg Ser Ser Leu Ile Asp Leu Cys Asp Arg Phe
    1025                1030                1035

Cys Ala Pro Lys Gly Met Asp Pro Ile Phe Leu Ala Thr Gly Trp
    1040                1045                1050

Arg Gly Cys Trp Thr Gly Gln Ser Pro Ile Glu Gln Pro Ser Glu
    1055                1060                1065

Lys Pro Ile Ala Phe Ala Gln Leu Asp Glu Lys Arg Ile Thr Ala
    1070                1075                1080

Arg Thr Val Val Ser Gln Pro Tyr Asp Pro Asn Gln Ala Val Lys
    1085                1090                1095

Cys Leu Arg Val Leu Gln Ala Gly Gly Ala Met Val Ala Glu Ala
    1100                1105                1110

Val Pro Lys Val Val Lys Val Ser Ala Ile Pro Phe Arg Ala Pro
    1115                1120                1125

Phe Phe Pro Thr Gly Val Lys Val Asp Pro Glu Cys Arg Ile Val
    1130                1135                1140

Val Asp Pro Asp Thr Phe Thr Thr Ala Leu Arg Ser Gly Tyr Ser
    1145                1150                1155

Thr Thr Asn Leu Val Leu Gly Val Gly Asp Phe Ala Gln Leu Asn
    1160                1165                1170

Gly Leu Lys Ile Arg Gln Ile Ser Lys Pro Ser Gly Gly
    1175                1180                1185

<210> SEQ ID NO 85
<211> LENGTH: 1191
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 85

Gly Ala Gly Lys Arg Ala Arg Arg Ala Arg Ser Gly Ala Thr Ala Thr
1               5                   10                  15

Val Ala His Cys Ala Leu Pro Ala Arg Glu Ala Gln Gln Ala Lys Lys
                20                  25                  30

Leu Glu Val Ala Ser Ala Asn Arg Ala Glu His Leu Lys Tyr Tyr Ser
            35                  40                  45

Pro Pro Ala Asp Gly Asn Cys Gly Trp His Cys Ile Ser Ala Ile Thr

```
              50                  55                  60
Asn Arg Met Val Asn Ser Lys Phe Glu Thr Thr Leu Pro Glu Arg Val
 65                  70                  75                  80

Arg Pro Ser Asp Asp Trp Ala Thr Asp Glu Asp Leu Val Asn Thr Ile
                     85                  90                  95

Gln Ile Leu Arg Leu Pro Ala Ala Leu Asp Arg Asn Gly Ala Cys Ala
                100                 105                 110

Gly Ala Lys Tyr Val Leu Lys Leu Glu Gly Glu His Trp Thr Val Ser
                115                 120                 125

Val Thr Pro Gly Met Thr Pro Ser Leu Leu Pro Leu Glu Cys Val Gln
                130                 135                 140

Gly Cys Cys Glu His Lys Ser Gly Leu Gly Phe Pro Asp Val Val Glu
145                 150                 155                 160

Val Ser Gly Phe Asp Pro Ala Cys Leu Asp Arg Leu Ala Glu Ile Met
                165                 170                 175

His Leu Pro Ser Ser Val Ile Pro Ala Ala Leu Ala Glu Met Ser Asp
                180                 185                 190

Asp Phe Asn Arg Leu Ala Ser Pro Ala Ala Thr Val Trp Thr Val Ser
                195                 200                 205

Gln Phe Phe Ala Arg His Arg Gly Gly Glu His Pro Asp Gln Val Cys
                210                 215                 220

Leu Gly Lys Ile Ile Asn Leu Cys Gln Val Ile Glu Glu Cys Cys
225                 230                 235                 240

Ser Arg Asn Lys Ala Asn Arg Ala Thr Pro Glu Glu Val Ala Ala Lys
                245                 250                 255

Val Asp Gln Tyr Leu Arg Gly Ala Ala Ser Leu Gly Glu Cys Leu Ala
                260                 265                 270

Lys Leu Glu Arg Ala Arg Pro Pro Ser Ala Met Asp Thr Ser Phe Asp
                275                 280                 285

Trp Asn Val Val Leu Pro Gly Val Glu Thr Ala Asp Gln Thr Thr Lys
                290                 295                 300

Gln Leu His Val Asn Gln Cys Arg Ala Leu Val Pro Val Val Thr Gln
305                 310                 315                 320

Glu Pro Leu Asp Arg Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
                340                 345                 350

Leu Asn Ser Val Leu Ser Lys Leu Glu Gly Val Val Arg Glu Glu Tyr
                355                 360                 365

Gly Leu Thr Pro Thr Gly Pro Gly Pro Arg Pro Ala Leu Pro Asn Gly
                370                 375                 380

Leu Asp Glu Leu Lys Asp Gln Met Glu Glu Asp Leu Leu Lys Leu Val
385                 390                 395                 400

Asn Ala Gln Ala Thr Ser Glu Met Met Ala Trp Ala Ala Glu Gln Val
                405                 410                 415

Asp Leu Lys Ala Trp Val Lys Asn Tyr Pro Arg Trp Thr Pro Pro Pro
                420                 425                 430

Pro Pro Pro Arg Val Gln Pro Arg Lys Thr Lys Ser Val Lys Ser Leu
                435                 440                 445

Leu Glu Asn Lys Pro Val Pro Ala Pro Arg Arg Lys Val Arg Ser Asp
                450                 455                 460

Tyr Gly Ser Pro Ile Leu Met Gly Asp Asn Val Pro Asn Gly Trp Glu
465                 470                 475                 480
```

-continued

```
Asp Ser Thr Val Gly Gly Pro Leu Asp Leu Ser Ala Pro Ser Glu Pro
            485                 490                 495

Met Thr Pro Leu Ser Glu Pro Val Leu Ile Ser Arg Pro Val Thr Ser
            500                 505                 510

Leu Ser Val Pro Ala Pro Val Pro Ala Pro Arg Arg Ala Val Ser Arg
            515                 520                 525

Pro Met Thr Pro Ser Ser Glu Pro Ile Phe Val Ser Ala Leu Arg His
530                 535                 540

Lys Phe Gln Gln Val Glu Lys Ala Asn Leu Ala Ala Ala Ala Pro Met
545                 550                 555                 560

Tyr Gln Asp Glu Pro Leu Asp Leu Ser Ala Ser Ser Gln Thr Glu Tyr
                565                 570                 575

Gly Ala Ser Pro Leu Thr Pro Pro Gln Asn Val Gly Ile Leu Glu Val
            580                 585                 590

Arg Gly Gln Glu Ala Glu Glu Val Leu Ser Glu Ile Ser Asp Ile Leu
            595                 600                 605

Asn Asp Thr Asn Pro Ala Pro Val Ser Ser Ser Ser Leu Ser Ser
            610                 615                 620

Val Arg Ile Thr Arg Pro Lys Tyr Ser Ala Gln Ala Ile Ile Asp Leu
625                 630                 635                 640

Gly Gly Pro Cys Ser Gly His Leu Gln Arg Glu Lys Glu Ala Cys Leu
                645                 650                 655

Arg Ile Met Arg Glu Ala Cys Asp Ala Ala Lys Leu Ser Asp Pro Ala
                660                 665                 670

Thr Gln Glu Trp Leu Ser Arg Met Trp Asp Arg Val Asp Met Leu Thr
            675                 680                 685

Trp Arg Asn Thr Ser Ala Tyr Gln Ala Phe Arg Thr Leu Asp Gly Arg
            690                 695                 700

Phe Gly Phe Leu Pro Lys Met Ile Leu Glu Thr Pro Pro Tyr Pro
705                 710                 715                 720

Cys Gly Phe Val Met Leu Pro His Thr Pro Ala Pro Ser Val Ser Ala
                725                 730                 735

Glu Ser Asp Leu Thr Ile Gly Ser Val Ala Thr Glu Asp Ile Pro Arg
            740                 745                 750

Ile Leu Gly Lys Ile Glu Asn Thr Gly Glu Met Ile Asn Gln Gly Pro
            755                 760                 765

Leu Ala Ser Ser Glu Glu Glu Pro Val Tyr Asn Gln Pro Ala Lys Asp
            770                 775                 780

Ser Arg Ile Ser Ser Arg Gly Ser Asp Glu Ser Thr Ala Ala Pro Ser
785                 790                 795                 800

Ala Gly Thr Gly Gly Ala Gly Leu Pro Thr Asp Leu Pro Pro Ser Asp
                805                 810                 815

Gly Val Asp Ala Asp Gly Gly Pro Leu Gln Thr Val Arg Lys Lys
                820                 825                 830

Ala Glu Arg Leu Phe Asp Gln Leu Ser Arg Gln Val Phe Asn Leu Val
                835                 840                 845

Ser His Leu Pro Val Phe Phe Ser His Leu Phe Lys Ser Asp Ser Gly
850                 855                 860

Tyr Ser Pro Gly Asp Trp Gly Phe Ala Ala Phe Thr Leu Phe Cys Leu
865                 870                 875                 880

Phe Leu Cys Tyr Ser Tyr Pro Phe Phe Gly Phe Val Pro Leu Leu Gly
                885                 890                 895
```

Val Phe Ser Gly Ser Ser Arg Arg Val Arg Met Gly Val Phe Gly Cys
             900                 905                 910

Trp Leu Ala Phe Ala Val Gly Leu Phe Lys Pro Val Ser Asp Pro Val
         915                 920                 925

Gly Thr Ala Cys Glu Phe Asp Ser Pro Glu Cys Arg Asn Val Leu His
     930                 935                 940

Ser Phe Glu Leu Leu Lys Pro Trp Asp Pro Val Arg Ser Leu Val Val
945                 950                 955                 960

Gly Pro Val Gly Leu Gly Leu Ala Ile Leu Gly Arg Leu Leu Gly Gly
                 965                 970                 975

Ala Arg Tyr Ile Trp His Phe Leu Leu Arg Leu Gly Ile Val Ala Asp
             980                 985                 990

Cys Ile Leu Ala Gly Ala Tyr Val Leu Ser Gln Gly Arg Cys Lys Lys
         995                 1000                1005

Cys Trp Gly Ser Cys Ile Arg Thr Ala Pro Asn Glu Ile Ala Phe
    1010                1015                1020

Asn Val Phe Pro Phe Thr Arg Ala Thr Arg Ser Ser Leu Ile Asp
    1025                1030                1035

Leu Cys Asp Arg Phe Cys Ala Pro Lys Gly Met Asp Pro Ile Phe
    1040                1045                1050

Leu Ala Thr Gly Trp Arg Gly Cys Trp Thr Gly Arg Ser Pro Ile
    1055                1060                1065

Glu Gln Pro Ser Glu Lys Pro Ile Ala Phe Ala Gln Leu Asp Glu
    1070                1075                1080

Lys Arg Ile Thr Ala Arg Thr Val Val Ala Gln Pro Tyr Asp Pro
    1085                1090                1095

Asn Gln Ala Val Lys Cys Leu Arg Val Leu Gln Ala Gly Gly Ala
    1100                1105                1110

Met Val Ala Glu Ala Val Pro Lys Val Val Lys Val Ser Ala Ile
    1115                1120                1125

Pro Phe Arg Ala Pro Phe Phe Pro Thr Gly Val Lys Val Asp Pro
    1130                1135                1140

Glu Cys Arg Ile Val Val Asp Pro Asp Thr Phe Thr Thr Ala Leu
    1145                1150                1155

Arg Ser Gly Tyr Ser Thr Thr Asn Leu Val Leu Gly Val Gly Asp
    1160                1165                1170

Phe Ala Gln Leu Asn Gly Leu Lys Ile Arg Gln Ile Ser Lys Pro
    1175                1180                1185

Ser Gly Gly
    1190

<210> SEQ ID NO 86
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 86

Gly Ala Gly Lys Arg Ala Arg Lys Ala Arg Ser Gly Met Thr Thr Thr
1               5                   10                  15

Val Ala His Arg Ala Leu Pro Ala Arg Glu Ile Gln Gln Ala Lys Lys
            20                  25                  30

His Glu Asp Ala Gly Ala Asp Lys Ala Val His Leu Arg His Tyr Ser
        35                  40                  45

```
Pro Pro Ala Asp Gly Asn Cys Gly Trp His Cys Ile Ser Ala Ile Ala
 50                  55                  60

Asn Arg Met Val Asn Ser Lys Phe Glu Thr Thr Leu Pro Glu Arg Val
 65                  70                  75                  80

Arg Pro Ser Asp Asp Trp Ala Thr Asp Glu Asp Leu Val Asn Thr Ile
                 85                  90                  95

Gln Ile Leu Lys Leu Pro Ala Ala Leu Asp Arg Asn Gly Ala Cys Val
            100                 105                 110

Gly Ala Lys Tyr Val Leu Lys Leu Glu Gly Glu His Trp Thr Val Ser
            115                 120                 125

Val Thr Leu Gly Met Ser Pro Ser Leu Leu Pro Leu Glu Cys Val Gln
 130                 135                 140

Gly Cys Cys Glu His Lys Ser Gly Leu Gly Pro Pro Asp Ala Val Glu
145                 150                 155                 160

Val Phe Gly Phe Asp Pro Ala Cys Leu Asp Arg Leu Ala Glu Val Met
                165                 170                 175

His Leu Pro Ser Ser Val Ile Pro Ala Ala Leu Ala Glu Met Ser Gly
            180                 185                 190

Asp Pro Asn Cys Pro Ala Ser Pro Val Thr Thr Val Trp Thr Val Ser
            195                 200                 205

Gln Phe Phe Ala Arg His Arg Gly Gly Glu His Pro Asp Gln Val Arg
 210                 215                 220

Leu Gly Lys Ile Ile Ser Leu Cys Gln Val Val Glu Glu Cys Cys Cys
225                 230                 235                 240

His Gln Asn Lys Thr Asn Arg Ala Thr Pro Glu Glu Val Ala Ala Arg
                245                 250                 255

Ile Asp Gln Tyr Leu His Gly Ala Thr Ser Leu Glu Gly Cys Leu Ile
            260                 265                 270

Arg Leu Glu Arg Val Cys Pro Pro Ser Ala Ala Asp Thr Phe Phe Asp
            275                 280                 285

Trp Asn Val Val Leu Pro Gly Val Gly Ala Ser Thr Gln Thr Thr Lys
 290                 295                 300

Gln Leu His Val Asn Gln Cys Arg Ala Leu Val Pro Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Arg Glu Glu Tyr
            355                 360                 365

Gly Leu Thr Pro Thr Glu Pro Gly Pro Arg Pro Ala Leu Pro Asn Gly
 370                 375                 380

Leu Val Glu Leu Lys Asp Gln Met Glu Glu Asp Leu Leu Lys Leu Val
385                 390                 395                 400

Asn Ala Gln Ala Thr Ser Glu Met Met Ala Trp Ala Ala Glu Gln Val
                405                 410                 415

Asp Leu Lys Ala Trp Val Lys Asn Tyr Pro Arg Trp Thr Pro Pro Pro
            420                 425                 430

Pro Pro Pro Arg Val Gln Pro Arg Lys Thr Lys Ser Val Lys Ser Leu
            435                 440                 445

Pro Gly Asn Lys Pro Val Pro Ala Pro Arg Arg Lys Val Arg Ser Asp
 450                 455                 460
```

-continued

```
Cys Gly Ser Pro Ile Leu Met Gly Asp Asn Val Pro Asp Gly Arg Glu
465                 470                 475                 480

Asp Leu Thr Val Gly Gly Pro Leu Asp Leu Ser Thr Pro Ser Glu Pro
                485                 490                 495

Met Thr Pro Leu Ser Glu Pro Ala Leu Met Pro Ala Leu Gln Tyr Ile
            500                 505                 510

Ser Arg Pro Val Thr Ser Leu Ser Val Leu Ala Pro Val Pro Ala Pro
        515                 520                 525

Arg Arg Thr Val Ser Arg Pro Val Thr Pro Leu Ser Glu Pro Ile Phe
    530                 535                 540

Val Ser Ala Pro Arg His Lys Phe Gln Gln Val Glu Glu Ala Asn Leu
545                 550                 555                 560

Ala Ala Thr Thr Leu Thr His Gln Asp Glu Pro Leu Asp Leu Ser Ala
                565                 570                 575

Ser Ser Gln Thr Glu Tyr Glu Ala Ser Pro Leu Thr Pro Leu Gln Asn
            580                 585                 590

Met Gly Ile Leu Glu Val Gly Gly Gln Glu Ala Glu Glu Val Leu Ser
        595                 600                 605

Glu Ile Ser Asp Thr Leu Asn Asp Ile Asn Pro Ala Pro Val Ser Ser
    610                 615                 620

Ser Ser Ser Leu Ser Ser Val Lys Ile Thr Arg Pro Lys His Ser Ala
625                 630                 635                 640

Gln Ala Ile Ile Asp Ser Gly Gly Pro Cys Ser Gly His Leu Arg Arg
                645                 650                 655

Glu Lys Glu Ala Cys Leu Ser Ile Met Arg Glu Ala Cys Asp Ala Ala
            660                 665                 670

Lys Leu Ser Asp Pro Ala Thr Gln Glu Trp Leu Ser Arg Met Trp Asp
        675                 680                 685

Arg Val Asp Met Leu Thr Trp Arg Asn Thr Ser Ala Tyr Gln Ala Phe
    690                 695                 700

Arg Ile Leu Asp Gly Arg Phe Glu Phe Leu Pro Lys Met Ile Leu Glu
705                 710                 715                 720

Thr Pro Pro Pro Tyr Pro Cys Gly Phe Val Met Leu Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Gly Lys Ile Glu Asn Ala Gly Glu
        755                 760                 765

Met Pro Asn Gln Gly Leu Leu Thr Ser Phe Gly Glu Glu Pro Val Cys
    770                 775                 780

Asp Gln Pro Val Lys Asp Ser Trp Met Ser Ser Arg Gly Phe Asp Glu
785                 790                 795                 800

Ser Thr Thr Ala Pro Ser Ala Gly Thr Gly Gly Ala Asp Leu Pro Thr
                805                 810                 815

Asp Leu Pro Pro Ser Asp Gly Leu Asp Ala Asp Glu Trp Gly Pro Leu
            820                 825                 830

Arg Thr Val Arg Lys Lys Ala Glu Arg Leu Phe Asp Gln Leu Ser Arg
        835                 840                 845

Gln Val Phe Asn Leu Val Ser His Leu Pro Val Phe Phe Ser His Leu
    850                 855                 860

Phe Lys Ser Asp Ser Gly Tyr Ser Pro Gly Asp Trp Gly Phe Ala Ala
865                 870                 875                 880

Phe Thr Leu Phe Cys Leu Phe Leu Cys Tyr Ser Tyr Pro Phe Phe Gly
```

885                 890                 895

Phe Val Pro Leu Leu Gly Val Phe Ser Gly Ser Arg Val Arg
                    900                 905                 910

Met Gly Val Phe Gly Cys Trp Leu Ala Phe Ala Val Gly Leu Phe Lys
                    915                 920                 925

Pro Val Ser Asp Pro Val Gly Thr Ala Cys Glu Phe Asp Ser Pro Glu
                    930                 935                 940

Cys Arg Asn Val Leu His Ser Phe Glu Leu Leu Lys Pro Trp Asp Pro
        945                 950                 955                 960

Val Arg Ser Leu Val Val Gly Pro Val Gly Leu Gly Leu Ala Ile Leu
                        965                 970                 975

Gly Arg Leu Leu Gly Gly Ala Arg Tyr Ile Trp His Phe Leu Leu Arg
                    980                 985                 990

Leu Gly Ile Val Ala Asp Cys Ile Leu Ala Gly Ala Tyr Val Leu Ser
                    995                 1000                1005

Gln Gly Arg Cys Lys Lys Cys Trp Gly Ser Cys Val Arg Thr Ala
                1010                1015                1020

Pro Asn Glu Ile Ala Phe Asn Val Phe Pro Phe Thr Arg Ala Thr
                1025                1030                1035

Arg Ser Ser Leu Ile Asp Leu Cys Asp Arg Phe Cys Ala Pro Lys
                1040                1045                1050

Gly Met Asp Pro Ile Phe Leu Ala Thr Gly Trp Arg Gly Cys Trp
                1055                1060                1065

Thr Gly Arg Ser Pro Ile Glu Gln Pro Ser Glu Lys Pro Ile Ala
                1070                1075                1080

Phe Ala Gln Leu Asp Glu Lys Arg Ile Thr Ala Arg Thr Val Gly
                1085                1090                1095

Ala Gln Pro Tyr Asp Pro Asn Gln Ala Val Lys Cys Leu Arg Val
                1100                1105                1110

Leu Gln Ala Gly Gly Ala Ile Val Ala Glu Ala Val Pro Lys Val
                1115                1120                1125

Val Lys Val Ser Ala Ile Pro Phe Arg Ala Pro Phe Phe Pro Thr
                1130                1135                1140

Gly Val Lys Val Asp Pro Glu Cys Arg Ile Val Val Asp Pro Asp
                1145                1150                1155

Thr Phe Thr Thr Ala Leu Arg Ser Gly Tyr Ser Thr Thr Asn Leu
                1160                1165                1170

Val Leu Gly Val Gly Asp Phe Ala Gln Leu Asn Gly Leu Lys Ile
                1175                1180                1185

Arg Gln Ile Ser Lys Pro Ser Gly Gly
                1190                1195

<210> SEQ ID NO 87
<211> LENGTH: 1194
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 87

Gly Ala Gly Lys Arg Ala Arg Lys Ala Arg Ser Gly Ala Thr Thr Met
1               5                   10                  15

Val Ala His Arg Ala Ser Ser His Glu Thr Arg Gln Ala Thr Lys
            20                  25                  30

-continued

His Glu Gly Ala Gly Ala Asn Lys Ala Glu His Leu Lys Leu Tyr Ser
             35                  40                  45

Pro Pro Ala Glu Gly Asn Cys Gly Trp His Cys Ile Ser Ala Ile Val
 50                  55                  60

Asn Arg Met Val Asn Ser Asn Phe Glu Thr Thr Leu Pro Glu Arg Val
 65                  70                  75                  80

Arg Pro Pro Asp Asp Trp Ala Thr Asp Glu Asp Leu Val Asn Thr Ile
             85                  90                  95

Gln Ile Leu Arg Leu Pro Ala Ala Leu Asp Arg Asn Gly Ala Cys Gly
                 100                 105                 110

Gly Ala Lys Tyr Val Leu Lys Leu Glu Gly Glu His Trp Thr Val Ser
             115                 120                 125

Val Asn Pro Gly Met Ser Pro Ser Leu Leu Pro Leu Glu Cys Val Gln
 130                 135                 140

Gly Cys Cys Glu His Lys Gly Leu Gly Ser Pro Asp Ala Val Glu
 145                 150                 155                 160

Val Ser Gly Phe Asp Pro Ala Cys Leu Asp Arg Leu Leu Gln Val Met
             165                 170                 175

His Leu Pro Ser Ser Thr Ile Pro Ala Ala Leu Ala Glu Leu Ser Asp
                 180                 185                 190

Asp Ser Asn Arg Pro Val Ser Pro Ala Ala Thr Trp Thr Val Ser
             195                 200                 205

Gln Ser Tyr Ala Arg His Arg Gly Gly Asn His His Asp Gln Val Cys
 210                 215                 220

Leu Gly Lys Ile Ile Ser Leu Cys Gln Val Ile Glu Asp Cys Cys Cys
 225                 230                 235                 240

His Gln Asn Lys Thr Asn Arg Ala Thr Pro Glu Glu Val Ala Ala Lys
                 245                 250                 255

Ile Asp Gln Tyr Leu Arg Gly Ala Thr Ser Leu Glu Glu Cys Leu Ala
             260                 265                 270

Lys Leu Glu Arg Val Ser Pro Pro Gly Ala Ala Asp Thr Ser Phe Asp
             275                 280                 285

Trp Asn Val Val Leu Pro Gly Val Glu Ala Ala His Gln Thr Thr Glu
 290                 295                 300

Gln Leu His Val Asn Pro Cys Arg Thr Leu Val Pro Pro Val Thr Glu
 305                 310                 315                 320

Pro Leu Gly Lys Asp Ser Val Pro Leu Thr Ala Phe Ser Leu Ser Asn
                 325                 330                 335

Cys Tyr Tyr Pro Ala Gln Gly Asn Glu Val Arg His Arg Glu Arg Leu
             340                 345                 350

Asn Ser Val Leu Ser Lys Leu Glu Val Val Leu Glu Glu Tyr Gly
             355                 360                 365

Leu Met Ser Thr Gly Leu Gly Pro Arg Pro Val Leu Pro Ser Gly Leu
 370                 375                 380

Asp Glu Leu Lys Asp Gln Met Glu Glu Asp Leu Leu Lys Leu Ala Asn
 385                 390                 395                 400

Thr Gln Ala Thr Ser Glu Met Met Ala Trp Ala Ala Glu Gln Val Asp
             405                 410                 415

Leu Lys Ala Trp Val Lys Ser Tyr Pro Arg Trp Thr Pro Pro Pro
             420                 425                 430

Pro Pro Arg Val Gln Pro Arg Lys Thr Lys Ser Val Lys Ser Leu Pro
 435                 440                 445

Glu Asp Lys Pro Val Pro Ala Pro Arg Arg Lys Val Arg Ser Gly Cys

```
              450                 455                 460
Gly Ser Pro Val Leu Met Gly Asp Asn Val Pro Asn Gly Ser Glu Asp
465                 470                 475                 480

Leu Thr Val Gly Gly Pro Leu Asn Phe Pro Thr Pro Ser Glu Pro Met
                485                 490                 495

Thr Pro Met Ser Glu Pro Val Leu Thr Pro Ala Leu Gln Arg Val Pro
            500                 505                 510

Lys Leu Met Thr Pro Leu Asp Gly Ser Ala Pro Val Pro Ala Pro Arg
                515                 520                 525

Arg Thr Val Ser Arg Pro Met Thr Pro Leu Ser Glu Pro Ile Phe Leu
            530                 535                 540

Ser Ala Pro Arg His Lys Phe Gln Gln Val Glu Glu Ala Asn Pro Ala
545                 550                 555                 560

Thr Thr Thr Leu Thr His Gln Asn Glu Pro Leu Asp Leu Ser Ala Ser
                565                 570                 575

Ser Gln Thr Glu Tyr Glu Ala Ser Pro Leu Ala Ser Ser Gln Asn Met
                580                 585                 590

Ser Ile Leu Glu Ala Gly Gly Gln Glu Ala Glu Glu Val Leu Ser Glu
            595                 600                 605

Ile Ser Asp Ile Leu Asn Asp Thr Ser Pro Ala Pro Val Ser Ser Ser
            610                 615                 620

Ser Ser Leu Ser Ser Val Lys Ile Thr Arg Pro Lys Tyr Ser Ala Gln
625                 630                 635                 640

Ala Ile Ile Asp Ser Gly Gly Pro Cys Ser Gly His Leu Gln Lys Glu
                645                 650                 655

Lys Glu Ala Cys Leu Ser Ile Met Arg Glu Ala Cys Asp Ala Ser Lys
            660                 665                 670

Leu Ser Asp Pro Ala Gln Glu Trp Leu Ser Arg Met Trp Asp Arg Val
            675                 680                 685

Asp Met Leu Thr Trp Arg Asn Thr Ser Ala Tyr Gln Ala Phe Arg Thr
            690                 695                 700

Leu Asn Gly Arg Phe Glu Phe Leu Pro Lys Met Ile Leu Glu Thr Pro
705                 710                 715                 720

Pro Pro His Pro Cys Gly Phe Val Met Leu Pro His Thr Pro Ala Pro
                725                 730                 735

Ser Val Ser Ala Glu Ser Asp Leu Thr Ile Gly Ser Val Ala Thr Glu
                740                 745                 750

Asp Val Pro Arg Ile Leu Gly Lys Ile Gly Asp Thr Gly Glu Leu Leu
            755                 760                 765

Asn Gln Gly Pro Ser Ala Pro Phe Lys Gly Gly Pro Val Cys Asp Gln
            770                 775                 780

Pro Ala Lys Asn Ser Arg Met Ser Pro Arg Glu Ser Asp Glu Ser Ile
785                 790                 795                 800

Ile Ala Pro Pro Ala Asp Thr Gly Gly Ala Gly Ser Phe Thr Asp Leu
                805                 810                 815

Pro Ser Ser Asp Ser Val Asp Ala Asn Gly Gly Pro Leu Arg Thr Val
            820                 825                 830

Lys Thr Lys Ala Gly Arg Leu Leu Asp Gln Leu Ser Cys Gln Val Phe
            835                 840                 845

Ser Leu Val Ser His Leu Pro Val Phe Phe Ser His Leu Phe Lys Ser
            850                 855                 860

Asp Ser Gly Tyr Ser Pro Gly Asp Trp Gly Phe Ala Ala Phe Thr Leu
865                 870                 875                 880
```

```
Phe Cys Leu Phe Leu Cys Tyr Ser Tyr Pro Phe Phe Gly Phe Ala Pro
                885                 890                 895

Leu Leu Gly Val Phe Ser Gly Ser Ser Arg Arg Val Arg Met Gly Val
            900                 905                 910

Phe Gly Cys Trp Leu Ala Phe Ala Val Gly Leu Phe Lys Pro Val Ser
        915                 920                 925

Asp Pro Val Gly Thr Ala Cys Glu Phe Asp Ser Pro Glu Cys Arg Asn
    930                 935                 940

Val Leu His Ser Phe Glu Leu Leu Lys Pro Trp Asp Pro Val Arg Ser
945                 950                 955                 960

Leu Val Val Gly Pro Val Gly Leu Gly Leu Ala Ile Leu Gly Arg Leu
                965                 970                 975

Leu Gly Gly Ala Arg Tyr Val Trp His Phe Leu Leu Arg Phe Gly Ile
            980                 985                 990

Val Ala Asp Cys Ile Leu Ala Gly Ala Tyr Val Leu Ser Gln Gly Arg
        995                 1000                1005

Cys Lys Lys Cys Trp Gly Ser Cys Val Arg Thr Ala Pro Asn Glu
    1010            1015                1020

Ile Ala Phe Asn Val Phe Pro Phe Thr Arg Ala Thr Arg Ser Ser
    1025            1030                1035

Leu Ile Asp Leu Cys Asp Arg Phe Cys Ala Pro Lys Gly Met Asp
    1040            1045                1050

Pro Ile Phe Leu Ala Thr Val Trp Arg Gly Cys Trp Thr Gly Arg
    1055            1060                1065

Ser Pro Ile Glu Gln Pro Ser Glu Lys Pro Ile Ala Phe Ala Gln
    1070            1075                1080

Leu Asp Glu Lys Arg Ile Thr Ala Arg Thr Val Val Ala Gln Pro
    1085            1090                1095

Tyr Asp Pro Asn Gln Ala Val Lys Cys Leu Arg Val Leu Gln Ala
    1100            1105                1110

Gly Gly Ala Met Val Ala Glu Ala Val Pro Lys Val Val Lys Val
    1115            1120                1125

Ser Ala Ile Pro Phe Arg Ala Pro Phe Phe Pro Ala Gly Val Lys
    1130            1135                1140

Val Asp Pro Glu Cys Arg Ile Val Val Asp Pro Asp Thr Phe Thr
    1145            1150                1155

Thr Ala Leu Arg Ser Gly Tyr Ser Thr Thr Asn Leu Val Leu Gly
    1160            1165                1170

Met Gly Asp Phe Ala Gln Leu Asn Gly Leu Lys Ile Arg Gln Ile
    1175            1180                1185

Ser Lys Pro Ser Gly Gly
    1190

<210> SEQ ID NO 88
<211> LENGTH: 1061
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 88

Ala Ala Gly Lys Arg Ala Arg Ala Lys Arg Ala Thr Lys Ser Gly Lys
1               5                   10                  15

Asp Ser Ala Leu Ala Pro Lys Ile Ala Pro Pro Val Pro Thr Cys Gly
```

```
            20                  25                  30
Ile Thr Thr Tyr Ser Pro Pro Thr Asp Gly Ser Cys Gly Trp His Val
            35                  40                  45
Leu Ala Ala Ile Val Asn Arg Met Ile Asn Gly Asp Phe Thr Ser Pro
            50                  55                  60
Leu Pro Gln Tyr Asn Arg Pro Glu Asp Asp Trp Ala Ser Asp Tyr Asp
 65                  70                  75                  80
Leu Ala Gln Ala Ile Gln Cys Leu Gln Leu Pro Ala Thr Val Val Arg
                    85                  90                  95
Asn Arg Ala Cys Pro Asn Ala Lys Tyr Leu Ile Lys Leu Asn Gly Val
                   100                 105                 110
His Trp Glu Val Glu Val Arg Ser Gly Met Ala Pro Arg Ser Leu Ser
                   115                 120                 125
Arg Glu Cys Val Val Gly Val Cys Ser Glu Gly Cys Val Ala Pro Pro
                   130                 135                 140
Tyr Pro Ala Asp Gly Leu Pro Lys Arg Ala Leu Glu Ala Leu Ala Ser
145                 150                 155                 160
Ala Tyr Arg Leu Pro Ser Asp Cys Val Ser Ser Gly Ile Ala Asp Phe
                   165                 170                 175
Leu Ala Asp Pro Pro Gln Glu Phe Trp Thr Leu Asp Lys Met Leu
                   180                 185                 190
Thr Ser Pro Ser Pro Glu Arg Ser Gly Phe Ser Ser Leu Tyr Lys Leu
                   195                 200                 205
Leu Leu Glu Val Val Pro Gln Lys Cys Gly Ala Thr Glu Gly Ala Phe
                   210                 215                 220
Val Tyr Ala Val Glu Arg Met Leu Lys Asp Cys Pro Ser Pro Glu Gln
225                 230                 235                 240
Ala Met Ala Leu Leu Ala Lys Ile Lys Val Pro Ser Ser Lys Ala Pro
                   245                 250                 255
Ser Val Ser Leu Asp Glu Cys Phe Pro Ala Gly Val Pro Ala Asp Phe
                   260                 265                 270
Glu Pro Ala Phe Gln Glu Arg Pro Arg Ser Pro Gly Ala Ala Val Ala
                   275                 280                 285
Leu Cys Ser Pro Asp Ala Lys Gly Phe Glu Gly Thr Ala Ser Glu Glu
                   290                 295                 300
Ala Gln Glu Ser Gly His Lys Ala Val His Ala Val Pro Leu Ala Glu
305                 310                 315                 320
Gly Pro Asn Asn Glu Gln Val Gln Val Val Ala Gly Glu Gln Leu Glu
                   325                 330                 335
Leu Gly Gly Cys Gly Leu Ala Ile Gly Ser Ala Gln Ser Ser Ser Asp
                   340                 345                 350
Ser Lys Arg Glu Asn Met His Asn Ser Arg Glu Asp Glu Pro Leu Asp
                   355                 360                 365
Leu Ser His Pro Ala Pro Ala Ala Thr Thr Thr Leu Val Gly Glu Gln
                   370                 375                 380
Thr Pro Asp Asn Pro Gly Ser Asp Ala Ser Ala Leu Pro Ile Ala Val
385                 390                 395                 400
Arg Gly Phe Val Pro Thr Gly Pro Ile Leu Arg His Val Glu His Cys
                   405                 410                 415
Gly Thr Glu Ser Gly Asp Ser Ser Ser Pro Leu Asp Leu Ser Phe Ala
                   420                 425                 430
Gln Thr Leu Asp Gln Pro Leu Asp Leu Ser Leu Ala Ala Trp Pro Val
                   435                 440                 445
```

-continued

```
Lys Ala Thr Ala Ser Asp Pro Gly Trp Val Arg Gly Arg Cys Glu Pro
    450                 455                 460
Val Phe Leu Lys Pro Arg Lys Ala Phe Ser Asp Gly Asp Ser Ala Leu
465                 470                 475                 480
Gln Phe Gly Glu Leu Ser Glu Ser Ser Val Ile Glu Phe Asp Gln
            485                 490                 495
Thr Lys Asp Thr Leu Val Ala Asp Ala Pro Val Asp Leu Thr Thr Ser
            500                 505                 510
Asn Glu Ala Leu Ser Ala Val Asp Pro Ser Glu Phe Val Glu Leu Arg
            515                 520                 525
Arg Pro Arg His Ser Ala Gln Ala Leu Ile Asp Arg Gly Gly Pro Leu
    530                 535                 540
Ala Asp Val His Ala Lys Ile Lys Asn Arg Val Tyr Glu Gln Cys Leu
545                 550                 555                 560
Gln Ala Cys Glu Pro Gly Ser Arg Ala Thr Pro Ala Thr Arg Glu Trp
                565                 570                 575
Leu Asp Lys Met Trp Asp Arg Val Asp Met Lys Thr Trp Arg Cys Thr
            580                 585                 590
Ser Gln Phe Gln Ala Gly Arg Ile Leu Ala Ser Leu Lys Phe Leu Pro
    595                 600                 605
Asp Met Ile Gln Asp Thr Pro Pro Val Pro Arg Lys Asn Arg Ala
    610                 615                 620
Ser Asp Asn Ala Gly Leu Lys Gln Leu Val Ala Arg Trp Asp Lys Lys
625                 630                 635                 640
Leu Ser Val Thr Pro Pro Lys Ser Ala Gly Leu Val Leu Asp Gln
                645                 650                 655
Thr Val Pro Pro Pro Thr Asp Ile Gln Gln Glu Asp Ala Thr Pro Ser
                660                 665                 670
Asp Gly Leu Ser His Ala Ser Asp Phe Ser Ser Arg Val Ser Thr Ser
            675                 680                 685
Trp Ser Trp Lys Gly Leu Met Leu Ser Gly Thr Arg Leu Ala Gly Ser
    690                 695                 700
Ala Gly Gln Arg Leu Met Thr Trp Val Phe Glu Val Tyr Ser His Leu
705                 710                 715                 720
Pro Ala Phe Ile Leu Thr Leu Phe Ser Pro Arg Gly Ser Met Ala Pro
            725                 730                 735
Gly Asp Trp Leu Phe Ala Gly Val Val Leu Ala Leu Leu Leu Cys
            740                 745                 750
Arg Ser Tyr Pro Ile Leu Gly Cys Leu Pro Leu Leu Gly Val Phe Ser
            755                 760                 765
Gly Ser Leu Arg Arg Val Arg Leu Gly Val Phe Gly Ser Trp Met Ala
    770                 775                 780
Phe Ala Val Phe Leu Phe Ser Thr Pro Ser Asn Pro Val Gly Ser Ser
785                 790                 795                 800
Cys Asp His Asp Ser Pro Glu Cys His Ala Glu Leu Leu Glu Leu Glu
                805                 810                 815
Gln Arg Gln Leu Trp Glu Pro Val Arg Gly Leu Val Val Gly Pro Ser
            820                 825                 830
Gly Leu Leu Cys Val Ile Leu Gly Lys Leu Leu Gly Gly Ser Arg His
            835                 840                 845
Leu Trp His Val Ile Leu Arg Leu Cys Met Leu Thr Asp Leu Ala Leu
    850                 855                 860
```

```
Ser Leu Val Thr Val Val Ser Gln Gly Arg Cys His Lys Cys Trp Gly
865                 870                 875                 880

Lys Cys Ile Arg Thr Ala Pro Ala Glu Val Ala Leu Asn Val Phe Pro
            885                 890                 895

Phe Ser Arg Ala Thr Arg Asn Ser Leu Thr Ser Leu Cys Asp Arg Phe
            900                 905                 910

Gln Thr Pro Lys Gly Val Asp Pro Val His Leu Ala Thr Gly Trp Arg
            915                 920                 925

Gly Cys Trp Arg Gly Glu Ser Pro Ile His Gln Pro His Gln Lys Pro
            930                 935                 940

Ile Ala Tyr Ala Asn Leu Asp Glu Lys Lys Ile Ser Ala Gln Thr Val
945                 950                 955                 960

Val Ala Val Pro Tyr Asp Pro Ser Gln Ala Ile Lys Cys Leu Lys Val
            965                 970                 975

Leu Gln Ala Gly Gly Ala Ile Val Asp Gln Pro Thr Pro Glu Val Val
            980                 985                 990

Arg Val Ser Glu Ile Pro Phe Ser Ala Pro Phe Phe Pro Lys Val Pro
            995                 1000                1005

Val Asn Pro Asp Cys Arg Ile Val Val Asp Ser Asp Thr Phe Val
    1010                1015                1020

Ala Ala Val Arg Cys Gly Tyr Ser Thr Ala Gln Leu Val Leu Gly
    1025                1030                1035

Arg Gly Asn Phe Ala Lys Leu Asn Gln Thr Pro Leu Arg Asp Ser
    1040                1045                1050

Ala Ser Thr Lys Thr Thr Gly Gly
    1055                1060

<210> SEQ ID NO 89
<211> LENGTH: 1060
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 89

Ala Ala Gly Lys Arg Ala Arg Ala Lys Arg Thr Ala Lys Gly Gly Lys
1               5                   10                  15

Asp Ser Val Pro Ala Leu Lys Val Ala Leu Pro Val Pro Ala Cys Gly
            20                  25                  30

Ile Thr Thr Tyr Ser Pro Pro Thr Asp Gly Ser Cys Gly Trp His Val
        35                  40                  45

Leu Ala Ala Ile Met Asn Arg Met Met Asn Asp Asp Phe Thr Ser Pro
50                  55                  60

Leu Thr Gln Tyr Asn Arg Pro Glu Asp Asp Trp Ala Ser Asp Tyr Asp
65                  70                  75                  80

Leu Ala Gln Ala Ile Gln Cys Leu Gln Leu Pro Ala Thr Val Val Arg
            85                  90                  95

Asn Arg Ala Cys Pro Asn Ala Lys Tyr Leu Ile Lys Leu Asn Gly Val
            100                 105                 110

His Trp Glu Val Glu Val Arg Ser Gly Met Ala Pro Arg Ser Leu Ser
        115                 120                 125

Glu Cys Val Val Gly Val Cys Ser Glu Gly Cys Val Ala Pro Pro Tyr
    130                 135                 140

Pro Ala Asp Gly Leu Pro Lys Arg Ala Leu Glu Ala Leu Ala Ser Ala
145                 150                 155                 160
```

-continued

Tyr Arg Leu Pro Ser Asp Cys Val Cys Ser Gly Ile Ala Asp Phe Leu
                165                 170                 175

Ala Asn Pro Pro Pro Gln Glu Phe Trp Thr Leu Asp Lys Met Leu Thr
            180                 185                 190

Ser Pro Ser Pro Glu Arg Ser Gly Phe Ser Ser Leu Tyr Asn Leu Leu
        195                 200                 205

Leu Glu Val Val Pro Gln Lys Cys Gly Val Thr Glu Gly Ala Phe Thr
    210                 215                 220

Tyr Ala Val Glu Arg Met Leu Met Asp Cys Pro Ser Ser Glu Gln Ala
225                 230                 235                 240

Met Ala Leu Leu Ala Lys Ile Lys Val Pro Ser Ser Lys Ala Pro Ser
                245                 250                 255

Val Ser Leu Asp Glu Cys Phe Pro Ala Asp Val Pro Ala Asp Phe Glu
            260                 265                 270

Pro Thr Ser Gln Lys Arg Pro Gln Ser Ser Gly Ala Ala Val Ala Leu
        275                 280                 285

Cys Ser Ser Asp Ala Glu Gly Phe Glu Glu Ala Ala Pro Glu Gly Val
    290                 295                 300

Gln Glu Arg Gly His Lys Ala Val His Ser Ala Leu Phe Ala Lys Gly
305                 310                 315                 320

Pro Asn Asn Glu Gln Val Gln Val Val Ala Gly Glu Gln Lys Leu
                325                 330                 335

Gly Gly Cys Gly Leu Ala Ile Gly Asn Ala Gln Ser Pro Leu Asn Ser
            340                 345                 350

Met Lys Glu Asn Met Arg Ser Ser Arg Glu Asp Glu Pro Leu Asp Leu
        355                 360                 365

Ser Gln Pro Ala Pro Val Ala Ala Thr Thr Leu Glu Arg Glu Gln Thr
    370                 375                 380

Pro Asp Asn Pro Gly Ser Asp Ala Gly Ala Leu Pro Ala Thr Val Arg
385                 390                 395                 400

Glu Ser Val Pro Thr Gly Pro Met Leu Arg His Val Glu His Cys Gly
                405                 410                 415

Thr Glu Ser Gly Asp Ser Ser Pro Leu Asp Leu Ser Tyr Ala Gln
            420                 425                 430

Thr Leu Asp Gln Pro Leu Asp Leu Ser Leu Ala Val Trp Pro Val Lys
        435                 440                 445

Ala Thr Ala Ser Asp Pro Gly Trp Val His Gly Arg Arg Glu Pro Val
    450                 455                 460

Phe Val Lys Pro Arg Lys Ala Phe Ser Asp Ser Asp Ser Ala Phe Gln
465                 470                 475                 480

Phe Gly Lys Leu Ser Glu Ser Gly Ser Val Ile Glu Phe Asp Arg Thr
                485                 490                 495

Lys Asp Ala Pro Val Val Asp Ala Pro Val Gly Ser Thr Thr Ser Asn
            500                 505                 510

Glu Ala Leu Ser Ile Ala Asp Pro Phe Glu Phe Ala Glu Leu Lys Arg
        515                 520                 525

Pro Arg Phe Ser Ala Gln Ala Leu Ile Asp Arg Gly Gly Pro Leu Ala
    530                 535                 540

Asp Val His Ala Lys Ile Lys Asn Arg Val Tyr Glu Arg Cys Leu Gln
545                 550                 555                 560

Ala Cys Glu Pro Gly Ser Arg Ala Thr Pro Ala Thr Lys Glu Trp Leu
                565                 570                 575

-continued

```
Asp Lys Met Trp Asp Arg Val Asp Met Lys Thr Trp Cys Cys Thr Ser
                580             585             590

Gln Phe Gln Ala Gly Arg Ile Leu Ala Ser Leu Lys Phe Leu Pro Asp
        595             600             605

Met Ile Gln Asp Thr Pro Pro Val Pro Arg Lys Asn Arg Ala Ser
    610             615             620

Asp Asn Ala Asp Leu Lys Gln Leu Val Ala Gln Trp Asp Arg Lys Leu
625             630             635             640

Ser Met Thr Pro Pro Gln Lys Pro Val Glu Pro Val Leu Asp Gln Thr
                645             650             655

Val Ser Pro Pro Thr Asp Thr Gln Gln Glu Asp Val Thr Pro Ser Asp
                660             665             670

Gly Pro Pro His Ala Pro Asp Phe Pro Ser Arg Val Ser Thr Gly Gly
                675             680             685

Ser Trp Lys Asp Leu Met Cys Ser Gly Thr Arg Leu Ala Gly Ser Ile
                690             695             700

Ser Gln Arg Leu Met Thr Trp Val Phe Glu Val Phe Ser His Leu Pro
705             710             715             720

Ala Phe Met Leu Thr Leu Phe Ser Pro Arg Gly Ser Met Ala Pro Gly
                725             730             735

Asp Trp Leu Phe Ala Gly Val Val Leu Ala Leu Leu Leu Cys His
                740             745             750

Ser Tyr Pro Ile Leu Gly Cys Leu Pro Leu Leu Gly Val Phe Ser Gly
                755             760             765

Ser Leu Arg Arg Val Arg Leu Gly Val Phe Gly Ser Trp Met Ala Phe
770             775             780

Ala Val Phe Leu Phe Ser Thr Pro Ser Asn Pro Val Gly Ser Ser Cys
785             790             795             800

Asp His Asp Ser Pro Glu Cys His Ala Glu Leu Leu Ala Leu Glu Gln
                805             810             815

Arg Gln Leu Trp Glu Pro Val Arg Gly Leu Val Val Gly Pro Ser Gly
                820             825             830

Leu Leu Cys Val Ile Leu Gly Lys Leu Leu Gly Gly Ser Arg Tyr Leu
                835             840             845

Trp His Ile Leu Leu Arg Leu Cys Met Leu Thr Asp Leu Ala Leu Ser
850             855             860

Leu Val Tyr Val Val Ser Gln Gly Arg Cys His Lys Cys Trp Gly Lys
865             870             875             880

Cys Ile Arg Thr Ala Pro Thr Glu Val Ala Leu Asn Val Phe Pro Phe
                885             890             895

Thr Arg Ala Thr Arg Ser Ser Leu Val Ser Leu Cys Asp Arg Phe Gln
                900             905             910

Thr Pro Lys Gly Val Asp Pro Val His Leu Ala Thr Gly Trp Arg Gly
                915             920             925

Cys Trp Arg Gly Gly Ser Pro Val His Gln Pro His Gln Lys Pro Ile
930             935             940

Ala Tyr Ala Asn Leu Asp Glu Lys Lys Ile Ser Ala Gln Thr Val Val
945             950             955             960

Ala Val Pro Tyr Asp Pro Ser Gln Ala Ile Lys Cys Leu Lys Val Leu
                965             970             975

Gln Ala Gly Gly Ala Ile Val Asp Gln Pro Thr Pro Glu Val Val Arg
                980             985             990

Val Ser Glu Ile Pro Phe Ser Ala  Pro Phe Phe Pro Lys  Val Pro Val
```

995                 1000                1005
Asn Pro Asp Cys Arg Val Val Val Asp Ser Asp Thr Phe Val Ala
    1010                1015                1020

Ala Val Arg Cys Gly Tyr Ser Thr Ala Gln Leu Val Leu Gly Gln
    1025                1030                1035

Gly Asn Phe Ala Lys Leu Asn Gln Thr Pro Pro Arg Asn Ser Thr
    1040                1045                1050

Ser Thr Lys Thr Thr Gly Gly
    1055                1060

<210> SEQ ID NO 90
<211> LENGTH: 1094
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 90

Ala Ala Gly Lys Arg Ala Arg Lys Ala Ala Lys Ser Glu Lys
1               5                   10                  15

Asp Ser Ala Pro Thr Pro Lys Val Ala Leu Pro Val Pro Thr Cys Gly
            20                  25                  30

Ile Thr Thr Tyr Ser Pro Pro Thr Asp Gly Ser Cys Gly Trp His Val
        35                  40                  45

Leu Ala Ala Ile Met Asn Arg Met Ile Asn Gly Asp Phe Thr Ser Pro
    50                  55                  60

Leu Thr Gln Tyr Asn Arg Pro Glu Asp Asp Trp Ala Ser Asp Tyr Asp
65                  70                  75                  80

Leu Val Gln Ala Ile Gln Cys Leu Arg Leu Pro Ala Thr Val Val Arg
                85                  90                  95

Asn Arg Ala Cys Pro Asn Ala Lys Tyr Leu Ile Lys Leu Asn Gly Val
            100                 105                 110

His Trp Glu Val Glu Val Arg Ser Gly Met Ala Pro Arg Ser Leu Ser
        115                 120                 125

Arg Glu Cys Val Val Gly Val Cys Ser Glu Gly Cys Val Ala Pro Pro
    130                 135                 140

Tyr Pro Ala Asp Gly Leu Pro Lys Arg Ala Leu Glu Ala Leu Ala Ser
145                 150                 155                 160

Ala Tyr Arg Leu Pro Ser Asp Cys Val Ser Ser Gly Ile Ala Asp Phe
                165                 170                 175

Leu Ala Asn Pro Pro Gln Glu Phe Trp Thr Leu Asp Lys Met Leu
            180                 185                 190

Thr Ser Pro Ser Pro Glu Arg Ser Gly Phe Ser Ser Leu Tyr Lys Leu
        195                 200                 205

Leu Leu Glu Val Val Pro Gln Lys Cys Gly Ala Thr Glu Gly Ala Phe
    210                 215                 220

Ile Tyr Ala Val Glu Arg Met Leu Lys Asp Cys Pro Ser Ser Lys Gln
225                 230                 235                 240

Ala Met Ala Leu Leu Ala Lys Ile Lys Val Pro Ser Ser Lys Gln Ala
                245                 250                 255

Met Ala Leu Leu Ala Lys Ile Lys Val Pro Ser Ser Lys Ala Pro Ser
            260                 265                 270

Val Ser Leu Asp Glu Cys Phe Pro Thr Asp Val Leu Ala Asp Phe Glu
        275                 280                 285

```
Pro Ala Ser Gln Glu Arg Pro Gln Ser Ser Gly Ala Val Val Leu
    290                 295                 300

Cys Ser Pro Asp Ala Lys Glu Phe Glu Ala Ala Pro Glu Glu Val
305                 310                 315                 320

Gln Glu Ser Gly His Lys Ala Val His Ser Ala Leu Leu Ala Glu Gly
                325                 330                 335

Pro Asn Asn Glu Gln Val Gln Val Val Ala Gly Glu Gln Leu Lys Leu
            340                 345                 350

Gly Gly Cys Gly Leu Ala Val Gly Asn Ala His Glu Gly Ala Leu Val
        355                 360                 365

Ser Ala Gly Leu Ile Asn Leu Val Gly Gly Asn Leu Ser Pro Ser Asp
    370                 375                 380

Pro Met Lys Glu Asn Met Leu Asn Ser Arg Glu Asp Glu Pro Leu Asp
385                 390                 395                 400

Leu Ser Gln Pro Ala Pro Ala Ser Thr Thr Thr Leu Val Arg Glu Gln
                405                 410                 415

Thr Pro Asp Asn Pro Gly Ser Asp Ala Gly Ala Leu Pro Val Thr Val
            420                 425                 430

Arg Glu Phe Val Pro Thr Gly Pro Ile Leu Cys His Val Glu His Cys
        435                 440                 445

Gly Thr Glu Ser Gly Asp Ser Ser Pro Leu Asp Leu Ser Asp Ala
    450                 455                 460

Gln Thr Leu Asp Gln Pro Leu Asn Leu Ser Leu Ala Ala Trp Pro Val
465                 470                 475                 480

Arg Ala Thr Ala Ser Asp Pro Gly Trp Val His Gly Arg Arg Glu Pro
                485                 490                 495

Val Phe Val Lys Pro Arg Asn Ala Phe Ser Asp Gly Asp Ser Ala Leu
            500                 505                 510

Gln Phe Gly Glu Leu Ser Glu Ser Ser Val Ile Glu Phe Asp Arg
        515                 520                 525

Thr Lys Asp Ala Pro Val Val Asp Ala Pro Val Asp Leu Thr Thr Ser
    530                 535                 540

Asn Glu Ala Leu Ser Val Val Asp Pro Phe Glu Phe Ala Glu Leu Lys
545                 550                 555                 560

Arg Pro Arg Phe Ser Ala Gln Ala Leu Ile Asp Arg Gly Gly Pro Leu
                565                 570                 575

Ala Asp Val His Ala Lys Ile Lys Asn Arg Val Tyr Glu Gln Cys Leu
            580                 585                 590

Gln Ala Cys Glu Pro Gly Ser Arg Ala Thr Pro Ala Thr Arg Glu Trp
        595                 600                 605

Leu Asp Lys Met Trp Asp Arg Val Asp Met Lys Thr Trp Arg Cys Thr
    610                 615                 620

Ser Gln Phe Gln Ala Gly Arg Ile Leu Ala Ser Leu Lys Phe Leu Pro
625                 630                 635                 640

Asp Met Ile Gln Asp Thr Pro Pro Val Pro Arg Lys Asn Arg Ala
                645                 650                 655

Ser Asp Asn Ala Gly Leu Lys Gln Leu Val Ala Gln Trp Asp Arg Lys
            660                 665                 670

Leu Ser Val Thr Pro Pro Lys Pro Val Gly Pro Val Leu Asp Gln
        675                 680                 685

Ile Val Pro Pro Thr Asp Ile Gln Gln Glu Asp Val Thr Pro Ser
    690                 695                 700

Asp Gly Pro Pro His Ala Pro Asp Phe Pro Ser Arg Val Ser Thr Gly
```

|     |     |     |     |     |     |     |     |     |     |     |     |
|-----|-----|-----|-----|-----|-----|-----|-----|-----|-----|-----|-----|
| 705 |     |     |     |     | 710 |     |     |     | 715 |     |     | 720 |
| Gly | Ser | Trp | Lys | Gly | Leu | Met | Leu | Ser | Gly | Thr | Arg | Leu | Ala | Gly | Ser |
|     |     |     |     | 725 |     |     |     |     | 730 |     |     |     |     | 735 |     |

Ile Ser Gln Arg Leu Met Thr Trp Val Phe Glu Val Phe Ser His Leu
          740                 745             750

Pro Ala Phe Met Leu Thr Leu Phe Ser Pro Arg Gly Ser Met Ala Pro
          755                 760             765

Gly Asp Trp Leu Phe Ala Gly Val Val Leu Ala Leu Leu Leu Cys
          770             775         780

Arg Ser Tyr Pro Ile Leu Gly Cys Leu Pro Leu Leu Gly Val Phe Ser
785                 790             795             800

Gly Ser Leu Arg Arg Val Arg Leu Gly Val Phe Gly Ser Trp Met Ala
                805             810             815

Phe Ala Ala Phe Leu Phe Ser Thr Pro Ser Asn Pro Val Gly Ser Ser
            820             825             830

Cys Asp His Asp Ser Pro Glu Cys His Ala Glu Leu Leu Ala Leu Glu
            835             840             845

Gln Arg Gln Leu Trp Glu Pro Val Arg Gly Leu Val Val Gly Pro Ser
850                 855             860

Gly Leu Leu Cys Val Ile Leu Gly Lys Leu Leu Gly Gly Ser Arg Tyr
865                 870             875             880

Leu Trp His Val Leu Leu Arg Leu Cys Met Leu Ala Asp Leu Ala Leu
                885             890             895

Ser Leu Val Tyr Val Val Ser Gln Gly Arg Cys His Lys Cys Trp Gly
                900             905             910

Lys Cys Ile Arg Thr Ala Pro Ala Glu Val Ala Leu Asn Val Phe Pro
            915             920             925

Phe Ser Arg Ala Thr Arg Val Ser Leu Val Ser Leu Cys Asp Arg Phe
            930             935             940

Gln Thr Pro Lys Gly Val Asp Pro Val His Leu Ala Thr Gly Trp Arg
945                 950             955             960

Gly Cys Trp Arg Gly Glu Ser Pro Ile His Gln Pro His Gln Lys Pro
                965             970             975

Ile Ala Tyr Ala Asn Leu Asp Glu Lys Lys Met Ser Ala Gln Thr Val
            980             985             990

Val Ala Val Pro Tyr Asp Pro Ser Gln Ala Ile Lys Cys Leu Lys Val
            995             1000            1005

Leu Gln Ala Gly Gly Ala Ile Val Asp Gln Pro Thr Pro Glu Val
    1010            1015            1020

Val Arg Val Ser Glu Ile Pro Phe Ser Ala Pro Phe Phe Pro Lys
    1025            1030            1035

Val Pro Val Asn Pro Asp Cys Arg Val Val Val Asp Ser Asp Thr
    1040            1045            1050

Phe Val Ala Ala Ala Val Arg Cys Gly Tyr Ser Thr Ala Gln Leu
    1055            1060            1065

Val Leu Gly Arg Gly Asn Phe Ala Lys Leu Asn Gln Thr Pro Pro
    1070            1075            1080

Arg Asn Ser Ile Ser Thr Lys Thr Thr Gly Gly
    1085            1090